US008119421B2

(12) United States Patent
Pagano et al.

(10) Patent No.: US 8,119,421 B2
(45) Date of Patent: Feb. 21, 2012

(54) METHODS TO IDENTIFY COMPOUNDS USEFUL FOR THE TREATMENT OF PROLIFERATIVE AND DIFFERENTIATIVE DISORDERS

(75) Inventors: Michele Pagano, New York, NY (US); Frank Mercurio, San Diego, CA (US); Weilin Xie, San Diego, CA (US); Antonia Lopez-Girona, San Diego, CA (US); Angelo Peschiaroli, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 12/315,862

(22) Filed: Dec. 5, 2008

(65) Prior Publication Data
US 2009/0297528 A1  Dec. 3, 2009

Related U.S. Application Data

(60) Continuation of application No. 11/106,014, filed on Apr. 13, 2005, now abandoned, which is a continuation-in-part of application No. 10/632,150, filed on Jul. 30, 2003, now abandoned, which is a division of application No. 09/385,219, filed on Aug. 27, 1999, now Pat. No. 6,720,181, said application No. 11/106,014 is a continuation-in-part of application No. 10/042,417, filed on Jan. 7, 2002, now abandoned.

(60) Provisional application No. 60/098,355, filed on Aug. 28, 1998, provisional application No. 60/118,568, filed on Feb. 3, 1999, provisional application No. 60/124,449, filed on Mar. 15, 1999.

(51) Int. Cl.
*G01N 33/566* (2006.01)
*G01N 33/53* (2006.01)
*C12Q 1/00* (2006.01)
*C12Q 1/68* (2006.01)

(52) U.S. Cl. ................. 436/501; 435/4; 435/6; 435/7.1

(58) Field of Classification Search ........................ None
See application file for complete search history.

(56) References Cited

U.S. PATENT DOCUMENTS

| | | | |
|---|---|---|---|
| 4,873,191 A | 10/1989 | Wagner et al. | |
| 5,093,246 A | 3/1992 | Cech et al. | |
| 5,519,003 A | 5/1996 | Mochly-Rosen et al. | |
| 5,981,702 A | 11/1999 | Zhang et al. | |
| 6,720,181 B1 | 4/2004 | Chiaur et al. | |
| 6,964,868 B1 | 11/2005 | Williams et al. | |
| 2002/0123082 A1 | 9/2002 | Pagano et al. | |
| 2004/0171074 A1 | 9/2004 | Orlicky et al. | |
| 2005/0214879 A1 | 9/2005 | Pagano | |
| 2005/0251871 A1 | 11/2005 | Pagano et al. | |
| 2005/0560556 | 11/2005 | Pagano | |
| 2005/0272066 A1 | 12/2005 | Pagano | |

FOREIGN PATENT DOCUMENTS

| | | |
|---|---|---|
| WO | WO 89/10134 | 11/1989 |
| WO | WO 95/21252 | 8/1995 |
| WO | WO 97/11176 | 3/1997 |
| WO | WO 99/18989 | 4/1999 |
| WO | WO 99/31252 | 6/1999 |
| WO | WO 99/38969 | 8/1999 |
| WO | WO 00/12679 | 3/2000 |
| WO | WO 0012679 A1 * | 3/2000 |
| WO | WO 00/22110 | 4/2000 |
| WO | WO 02/40717 * | 5/2002 |

OTHER PUBLICATIONS

Ngo et al., In The Protein Folding Problem and Tertiary Structure Prediction, 1994, Merz, et al., (ed.), Birkhauser, Boston, MA, pp. 433 and 492-495.*
Burgess et al., J of Cell Bio. 111:2129-2138, 1990.*
Lazar et al. Molecular and Cellular Biology 8:1247-1252, 1988.*
Bowie et al. Science, 247:1306-1310, 1990.*
Jin et al (Genes and Development 2004; 18(21):257.*
Amati et al., 1999, "Kip1 meets SKP2: new links in cell-cycle control." Nature Cell. Biol. 1:E91-E93.
Bai et al., 1996, "SKP1 connects cell cycle regulators to the ubiquitin proteolysis machinery through a novel motif, the F-box." Cell 86:263-274.
Bonaldo et al., 1996, "Normalization and subtraction: two approaches to facilitate gene discovery," Genome Res. 6(9):791-806.
Bourne et al., 1996, "Crystal structure and mutational analysis of the human CDK2 kinase complex with cell cycle-regulatory protein CksHs1." Cell. 84:863.
Brown & Pagano, 1997, "Mechanism of p53 degradation." Biochim. Biophys Acta 1332:1.
Cameron, 1997, "Recent Advances in Transgenic Technology." Review 7:263-265.

(Continued)

*Primary Examiner* — Anne M. Gussow
(74) *Attorney, Agent, or Firm* — Jones Day

(57) ABSTRACT

The present invention relates to the discovery, identification and characterization of nucleotide sequences that encode novel substrate-targeting subunits of ubiquitin ligases. The invention encompasses nucleotides encoding novel substrate-targeting subunits of ubiquitin ligases: FBP1, FBP2, FBP3, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25, transgenic mice, knock-out mice, host-cell expression systems and proteins encoded by the nucleotides of the novel substrate-targeting subunits. The present invention relates to screening assays that use novel and known substrate-targeting subunits of ubiquitin ligases to identify potential therapeutic agents such as small molecules, compounds or derivatives and analogues of the novel and known ubiquitin ligases which modulate activity of the novel and known ubiquitin ligases for the treatment of proliferative and differentiative disorders, such as cancer, major opportunistic infections, immune disorders, certain cardiovascular diseases, and inflammatory disorders. The invention further encompasses therapeutic protocols and pharmaceutical compositions designed to target ubiquitin ligases and their substrates for the treatment of proliferative and differentiative disorders.

13 Claims, 136 Drawing Sheets

OTHER PUBLICATIONS

Figure 2:
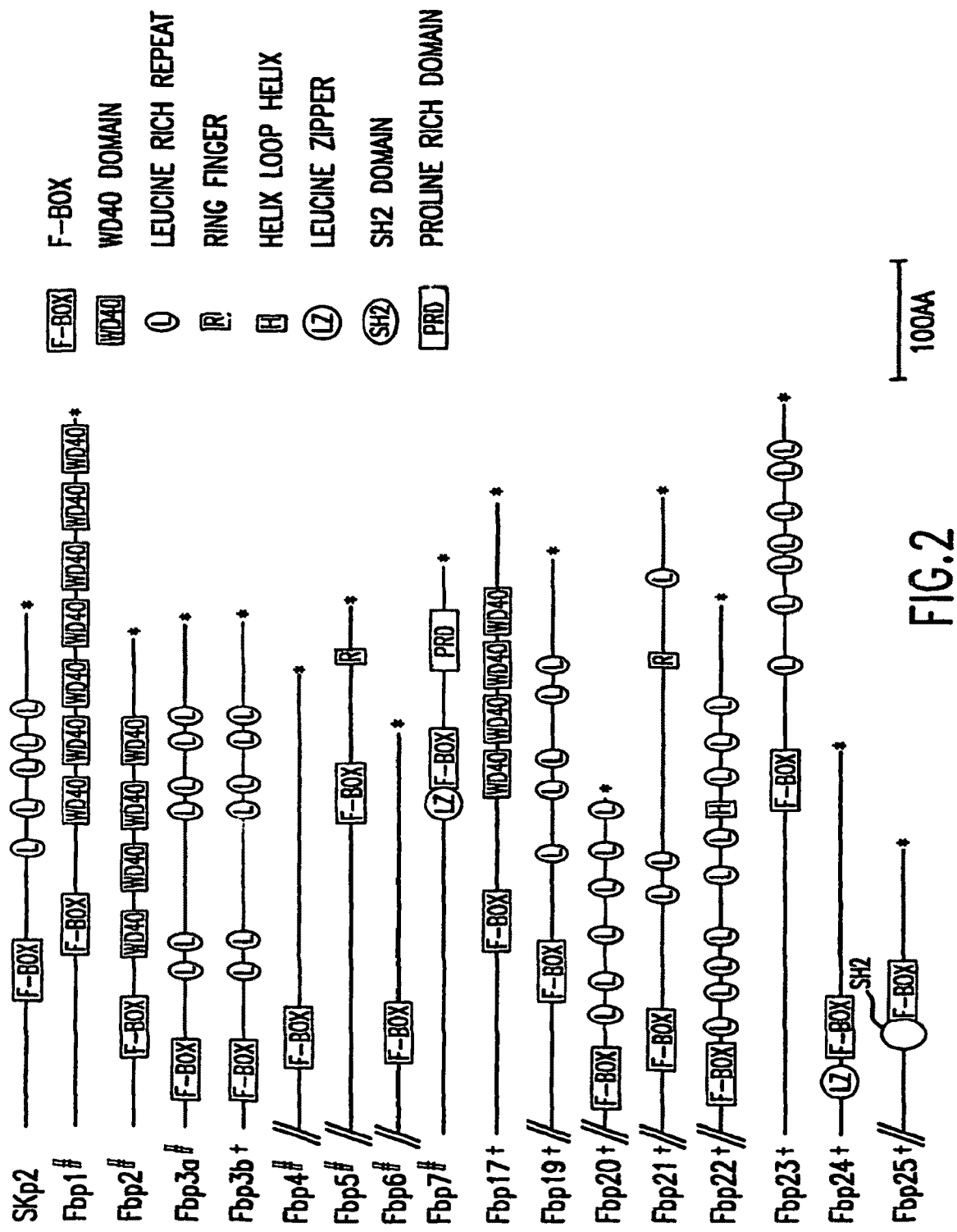

Carrano et al., 1999, "SKP2 is required for ubiquitin-mediated degradation of the CDK inhibitor p27." Nat. Cell. Biol. 1:193.
Cenciarelli et al., 1999, "Identification of a family of human F-Box proteins." Current Biol. 9:1177-1179.
Chiaur et al., 2000, "Five human genes encoding F-box proteins: chromosome, mapping, and analysis in human tumors." 88:255-258.
Ciechanover, 1994, "The ubiquitin-proteasome proteolytic pathway." Cell 79:13-21.
Ciechanover, 1998, "The ubiquitin-proteasome pathway: on protein death and cell life." EMBO J., 17:7151.
Cliff et al., 2005, "Molecular recognition via coupled folding and binding in a TPR domain." J. Mol. Biol. 346:717.
Davis et al., 2002, "Pseudosubstrate regulation of the SCF(beta-TrCP) ubiquitin ligase by hnRNP-U." Genes Dev. 16:439-451.
Deshaies, 1999, "SCF and Cullin/Ring H2-based ubiquitin ligases," Ann. Rev. Cell Dev. Biol. 15:435-67.
Espisito et al., 1997, "Prognostic role of the cell cycle inhibitor p27 in non-small cell lung cancer.," Cancer Research 57:3381-3385.
Fong & Sun, 2002, "Genetic evidence for the essential role of beta-transducin repeat-containing protein in the inducible processing of NF-kappa B2/p100." J. Biol. Chem. 277:22111.
Fuchs et al., 1999, "HOS, a human homolog of Slimb, forms an SCF complex with Skp1 and Cullin1 and targets the phoshorylation-dependent degradation of 1kappaB and beta-catenin." Oncogene 18: 2039.
Fukuchi et al., 2001, "Ligand-dependent degradation of Smad3 by a ubiquitin ligase complex of ROC1 and associated proteins."Mol. Biol. Cell. 12:1431.
Furukawa et al., 2000, "The CUL1 C-terminal sequence and ROC1 are required for efficient nuclear accumulation, NEDD8 modification, and ubiquitin ligase activity of CUL1." Mol. Cell. Biol. 20:8185.
Ganoth et al., 2001, "The cell-cycle regulatory protein Cks1 is required or SCF(Skp2)-mediated ubiquitinylation of p27." Nature Cell. Biol. 3:321-324.
Genbank Accession No. AC001226, Hawkins et al., 1997.
Genbank Accession No. AF126028, Klockars et al., 2000.
Genbank Accession No. Z43904, Auffray et al., 1994.
Gonen et al., 1999, "Identification of the Ubiquitin Carrier Proteins, E2s, Involved in Signal-induced Conjugation and Subsequent Degradation of IκBα" J. Biol. Chem. 274:14823.
Gong and Yeh, 1999, "Identification of the Activating and Conjugating Enzymes of the NEDD8 Conjugation Pathway," The Journal of Biological Chemistry, vol. 274, No. 17, pp. 12036-12042.
Hadwiger et al., 1989, "The *Saccharomyces cerevisiae* CKS1 gene, a homolog of the *Schizosaccharomyces pombe* suc1+ gene, encodes a subunit of the Cdc28 protein kinase complex." Mol. Cell. Biol. 9:2034.
Hammer et al., 1990, "Spontaneous Inflammatory Disease in Transgenic Rats Expressing HLA-B27 and Human Beta2m: An Animal Model of HLA-B27-Associated Human Disorders." Cell. 63:1099-1112.
Hart et al., 1999, "The F-box protein beta-TrCP associates with phosphorylated beta-catenin and regulates its activity in the cell." Curr. Biol. 9:207.
Hatakeyama et al., 1999, "Ubiquitin-dependent degradation of IkappaBalpha is mediated by a ubiquitin ligase Skp1/Cu1 1/F-box protein FWD1." Proc. Natl. Acad. Sci. USA 96:3859.
Hattori et al., 1999, "Molecular dissection of the interactions among IkappaBalpha, FWD1, and Skp1 required for ubiquitin-mediated proteolysis of IkappaBalpha." J. Biol. Chem. 274:29641.
Hayles et al., 1986, "Molecular dissection of the interactions among IkappaBalpha, FWD1, and Skp1 required for ubiquitin-mediated proteolysis of IkappaBalpha." Mol. Gen. Genet. 202:291.
Ho et al., 2006, "F-box proteins: the key to protein degradation" J Biomed Sci 13(2):181-91.
Hochstrasser, 1995, "Ubiquitin, proteasomes, and the regulation of intracellular protein degradation," Curr. Oop. Cell Biol. 7:215-223.
Hunter & Pines, 1994, "Cyclins and cancer. H: Cyclin D and CDK inhibitors come of age." Cell. 79:573.
Jin Jianping et al., 2004, "Systematic Analysis and nomenclature mammalian F-box proteins." Genes & Dev. 18:2573-2580.

Kaiser et al., 1998, "Cdc34 and the F-box protein Met30 are required for degradation of the Cdk-inhibitory kinase Swe1," Genes Dev. 12(16):2587-2597.
Keyomarsi et al., 1995, "Deregulation of cyclin E in breast cancer," Oncogene 11:941-950.
Kipreos & Pagano, 2000, The F-box protein family Genome Biology 1:3002.2.
Kipreos et al, 1996, "*cul-1* Is Required for Cell Cycle Exit in *C. elegans* and Identifies a Nove Gene Family" Cell. 85:829-875.
Kitagawa et al., 1999, "An F-box protein, FWD1, mediates ubiquitin-dependent proteolysis of β-catenin." EMBO J. 18:2401.
Kobe & Deisenhofer, 1994, "The leucine-rich repeat: a versatile binding motif" Trends. Biochem. Sci. 19:415-421.
Koch et al., 1991, "SH2 and SH3 domains: elements that control interactions of cytoplasmic signaling proteins." Science 252:668.
Koepp et al., 1999, "How the cyclin became a cyclin: regulated proteolysis the cell cycle," Cell. 97:431-433.
Koike et al., 2000, "Molecular cloning and genomic structure of the betaTRCP2 gene on chromosome 5q35.1." Biochem. Biophys. Res. Commun, 296:103.
Kroll et al., 1999, "Inducible degradation of IkappaBalpha by the proteasome requires interaction with the F-box protein h-betaTrCP." J. Biol. Chem. 274:7941.
Ku et al., 2002, "The zinc ion in the HNH motif of the endonuclease domain of colicin E7 is not required for DNA binding but is essential for DNA hydrolysis." Nuc. Acids. Res. 30:1670.
Kuzuya et al., 1996, "Molecular analysis of outer capsid glycoprotein (VP7) genes from two isolates of human group C rotavirus with different genome electropherotypes." J. Clin Microbiol. 34(12):3185-9.
Landshultz et al., 1988, "Molecular mechanism of inhibition of firefly luminescence by local anesthetics." Science 240:1759.
Lassot et al., 2001, "ATF4 degradation relies on a phosphorylation-dependent interaction with the SCF(betaTrCP) ubiquitin ligase." Mol. Cell. Biol. 21:2192.
Latres et al., 1999, "The human F box protein beta-Trcp associates with the Cul1/Skp1 complex and regulates the stability of beta-catenin." Oncogene 18:849.
Latres et al., 2001, "Role of the F-box protein Skp2 in lymphomagenesis." Proc. Natl. Acad. Sci. USA 98:2515.
Lloyd, 1999, "p27$^{kip1}$ A Multifunctional Cyclin-Dependent Kinase Inhibitor with Prognostic Significance in Human Cancers" Am. J. Pathol. 154:313.
Lyapina, 1998, "Human CUL1 forms an evolutionarily conserved ubiquitin ligase complex (SCF) with SKP1 and an F-box protein," Proc. Natl. Acad. Sci. USA 95:7451-7476.
Margottin et al., 1998, "A novel human WD protein, h-beta TrCp, that interacts with HIV-1 Vpu connects CD4 to the ER degradation pathway through an F-box motif." Mol. Cell. 1:565.
Marikawa & Elinson, 1998, "β-TrCP is a negative regulator of the Wnt/β-catenin signaling pathway and dorsal axis formation in Xenopus embryos" Mech. Dev. 77:75.
Montagnoli et al., 1999, "Ubiquitination of p27 is regulated by Cdk-dependent phosphorylation and trimeric complex formation." Genes Dev. 13:1181.
Mullins et al., 1993, "Transgenesis in Nonmurine Species." Hyperten. 22(4):630-633.
NCI-CGAP http://www//ncbi.nlm.nih.gov/ncicgap (National Cancer Institute, Cancer Genome Anatomy Project (CGAP), Tumor Gene Index, 1997 (three pages of NCBI-CGAP page).
Neer et al., 1994, "The ancient regulatory-protein family of WD-repeat proteins." Nature 371:297-300.
Ohta et al., 1999, "ROC1, a homolog of APC11, represents a family of cullin partners with an associated ubiquitin ligase activity." Mol. Cell. 3:535.
Ohtsubo et al., 1995, "Human cyclin E, a nuclear protein essential for the $G_1$-to-S phase transition," Cell Biol. 15:2612-2624.
Orian et al., 2000, "SCF(beta)(-TrCP) ubiquitin ligase-mediated processing of NF-kappaB p105 requires phosphorylation of its C-terminus by IkappaB kinase." EMBO J. 19:2580.
Osaka et al., 1998, "A new NEDD8-ligating system for cullin-4A" Genes Dev. 12:2263.
Pagano et al., 1992, "Association of cdk2 kinase with the transcription factor E2F during S phase." Science 255:1144.
Pagano et al., 1992, "Cyclin A is required at two points in the human cell cycle" EMBO J.: 11(3):961-971.

Pagano et al., 1995, "Role of the ubiquitin-proteasome pathway in regulating abundance of the cyclin-dependent kinase inhibitor p27." Science 269:682.
Pagano, 1993, "Regulation of the cell cycle by the cdk2 protein kinase in cultured human fibroblasts," J. Cell Bio. 121:101-111.
Pagano, 1995, "From peptide purified antibody," in Cell Cycle: Materials and Methods, M. Pagano, ed., Spring-Verlag, pp. 217-281.
Pagano, 1997, "Cell cycle regulation by the ubiquitin pathway" FASEB 11:1067.
Panchenko et al., 2004, "von Hippel-Lindau partner Jade-1 is a transcriptional co-activator associated with histone acetyltransferase activity." J. Biol. Chem. 53:56032.
Patra & Dunphy, 1988, "Xe-p9, a Xenopus Suc1/Cks protein, is essential for the Cdc2-dependent phosphorylation of the anaphase-promoting complex at mitosis." Genes Dev. 12:2549.
Patra, 1999, "The xenopus Suc1/Cks protein promotes the phosphorylation of G(2)/M regulators.." J. Biol. Chem. 274:36839.
Patton et al., 1998, "Combinatorial control in ubiquitin-dependent proteolysis: don't Skp the F-box hypothesis" Trends in Genet. 14(6):236.
Peifer, 1997, "Beta-catenin as oncogene: the smoking gun." Science 275: 1752.
Pines et al., 1996, "Cell cycle: reaching for a role for the Cks proteins." Curr. Biol. 11:1399.
Podust et al., 2000, "A Nedd8 conjugation pathway is essential for proteolytic targeting of p27Kip1 by ubiquitination." Proc. Natl. Acad. Sci USA 97:4579.
Read et al., 2000, "Nedd8 Modification of Cul-1 Activates $SCF^{\beta TrCP}$-Dependent Ubiquitination of IκBα" Mol. Cel. Biol. 20:2326.
Reynard et al., 2000, "Cks1 is required for G(1) cyclin-cyclin-dependent kinase activity in budding yeast." Mol. Cell. Biol. 20:5858.
Richardson et al., 1990, "Human cDNAs encoding homologs of the small p34Cdc28/Cdc2-associated protein of *Saccharomyces cerevisiae* and *Schizosaccharomyces pombe*." Genes Dev. 4:1332.
Rolfe et al., 1997, "The ubiquitin-mediated proteolytic pathway as a therapeutic area," Mol. Med. 75:5-17.
Rudinger et al., 1976, "Characteristics of the amino acids as components of a peptide hormone sequence." Peptide Hormones 1-7 Edited by JA Parsons, University Park Press, Baltimore.
Seamark, 1994, "Progress and Emerging Problems in Livestock Transgenesis: a Summary Perspective." 6:653-7.
Sheaff et al., 1997, "Cyclin E-CDK2 is a regulator of $p27^{Kip1}$," Genes Dev. 11:1464-1478.
Sherr & Roberts, 1995, "Inhibitors of mammalian $G_1$ cyclin-dependent kinases.," Genes Dev. 9:1149-1163.
Sherr & Roberts, 1999, "CDK inhibitors: positive and negative regulators of G1-phase progression." Genes Dev. 13:1501.
Shevchenko, et al., 1996, "Mass Spectrometric Sequencing of Proteins from Silver-Stained Polyacrylamide Gels," Anal. Chem. 68, 85-858.
Shirane et al., 1999, "Common pathway for the ubiquitination of IkappaBalpha, IkappaBbeta, and IkappaBepsilon mediated by the F-box protein FWD1." J. Biol. Chem. 274:28169.
Shteinberg & Hershko, 1999, "Role of Suc1 in the activation of the cyclosome by protein kinase Cdk1/cyclin B." Biochem. Biophys. Res. Commun. 257:12.
Singh et al., 1998, "Loss or altered subcellular localization of p27 in Barrett's associated adenocarcinoma," Cancer Research 58:1730-1735.
Skowyra et al., 1997, "F-box proteins are receptors that recruit phosphorylated substrates to the SCF ubiquitin-ligase complex." Cell. 91:209.
Spataro, 1998, "The ubiquitin-proteasome pathway in cancer," Br. J. Cancer. 77:448.
Spencer et al., 1999, "Signal-induced ubiquitination of IkappaBalpha by the F-box protein Slimb/beta-TrCP." Genes Dev. 13:284.
Spevak et al., 1993, "*Saccharomyces cerevisiae* cdc15 mutants arrested at a late stage in anaphase are rescued by Xenopus cDNAs encoding N-ras or a protein with beta-transducin repeats." Mol. Cell. Biol. 8:4953.
Sudol et al., 1996, "The WW module competes with the SH3 domain?" Trends. Biochem. 21:1.
Sun, 2006, "E3 ubiquitin ligases as cancer targets and biomarkers." Neoplasia 8(8):645-54.
Suzuki et al., 1999, "IkappaBalpha ubiquitination is catalyzed by an SCF-like complex containing Skp1, cullin-1, and two F-box/WD40-repeat proteins, betaTrCP1 and betaTrCP2." Biochem Biophys. Res. Cummun 256:127.
Tan et al., 1997, "The cell cycle inhibitor p27 is an independent marker in small ($T_{1a,b}$) invasive breast carcinomas," Cancer Research 57:1259-1263.
Tan et al., 1999, "Recruitment of a ROC1-CUL1 ubiquitin ligase by Skp1 and HOS to catalyze the ubiquitination of I kappa B alpha." Mol. Cell. 3:527.
Thomas et al., 1998, "Downregulation of p27 is associated with development of colorectal adenocarcinoma metastases," Am. J. Pathol. 153:681-687.
Tsvetkov et al., 1999, "p27(Kip1) ubiquitination and degradation is regulated by the SCF(Skp2) complex through phosphorylated Thr187 in p27."Current Biol. 661.
Winston et al., 1999, "A family of mammalian F-box proteins." Current Biol. 9:1180.
Winston et al., 1999, "The SCFbeta-TRCP-ubiquitin ligase complex associates specifically with phosphorylated destruction motifs in IkappaBalpha and beta-catenin and stimulates IkappaBalpha ubiquitination in vitro." Genes Dev. 13:270.
Wu & Ghosh, 1999, "beta-TrCP mediates the signal-induced ubiquitination of IkappaBbeta." J. Biol. Chem.274:29591.
Wu et al., 2000, "Conjugation of Nedd8 to CUL1 enhances the ability of the ROC-CUL1 complex to promote ubiquitin polymerization." J. Biol. Chem 275:32317.
www.ncbi.nlm.nih.gov (National Center tor Biotechnology Information) GenBank Accession No. AF17621 (Mus musculus leucine-rich repeat-containing F-box protein FBL3a mRNA, partial cds) Database [Online]. Accessed on Mar. 9, 2001. Released from GenBank on Dec. 6, 1999.
www.ncbi.nlm.nih.gov (National Center for Biotechnology Information) GenBank Accession No. AF129532 (*Homo sapiens* chromosome 13 F-box protein Fbl3a (FBL3A) mRNA, partial cds) Database [Online]. Accessed on Mar. 9, 2001. Released from GenBank on Oct. 31, 1999.
Yaron et al., 1998, "Identification of the receptor component of the IkappaBalpha-ubiquitin ligase." Nature 386:590.
Yeh et al., 2000, "Ubiquitin-like proteins: new wines in new bottles." Gene 248:1.
Yu et al., 1998. "Human CUL-1 associates with the SKP1/SKP2 complex and regulates p21(CIP1/WAF1) and cyclin D proteins." Proc. Natl. Acad. Sci USA 95:11324.
Yudkovsky et al., 2000, "Phosphorylation of Cdc20/fizzy negatively regulates the mammalian cyclosome/APC in the mitotic checkpoint." Biochem. Biophys. Res. Commun. 271:299.
Zachariae & Nasmyth, 1999, "Whose end is destruction: cell division and the anaphase-promoting complex," Genes Dev. 13:2039-58.
Zhang et al. 1995, "p19Skp1 and p45Skp2 are essential elements of the cyclin A-CDK2 S phase kinase." Cell 82:915.
Zhang et al., 2003, "Senescence-specific gene expression fingerprints reveal cell-type-dependent physical clustering of up-regulated chromosomal loci." Proc. Natl. Acad. Sci. 100:3251-3256.
Bowie et al., 1990, "Deciphering the message in protein sequences: tolerance to amino acid substitutions." Science. 247(4948):1306-1310.
Burgess, et al., 1990, "Possible dissociation of the heparin-binding and mitogenic activities of heparin-binding (acidic fibroblast) growth factor-1 from its receptor-binding activities by site-directed mutagenesis of a single lysine residue." J Cell Biol. 111(5 Pt 1):2129-2138.
Lazar et al., 1988, "Transforming growth factor alpha: mutation of aspartic acid 47 and leucine 48 results in different biological activities." Mol Cell Biol. 8(3):1247-1252.
Ngo et al., 1994, In The Protein Folding Problem and Tertiary Structure Prediction, Merz, et al., (ed.), Birkhauser, Boston, MA, pp. 433 and 492-495.

* cited by examiner

FIG. 1

```
          10         20         30         40         50         60
MDPAEAVLQEKALKFMNSSEREDCNNGEPPRKIIPEKNSLRQTYNSCARLCLNQETVCLA 70         80         90        100        110        120
STAMKTENCVAKTKLANGTSSMIVPKQRKLSASYEKEKELCVKYFEQWSESDQVEFVEHL 130        140        150        160        170        180
ISQMCHYQHGHINSYLKPMLQRDFITALPARGLDHIAENILSYLDAKSLCAAELVCKEWY 190        200        210        220        230        240
RVTSDGMLWKKLIERMVRTDSLWRGLAERRGWGQYLFKNKPPDGNAPPNSFYRALYPKII 250        260        270        280        290        300
QDIETIESNWRCGRHSLQRIHCRSETSKGVYCLQYDDQKIVSGLRDNTIKIWDKNTLECK 310        320        330        340        350        360
RILTGHTGSVLCLQYDERVIITGSSDSTVRVWDVNTGEMLNTLIHHCEAVLHLRFNNGMM 370        380        390        400        410        420
VTCSKDRSIAVWDMASPTDITLRRVLVGHRAAVNVVDFDDKYIVSASGDRTIKVWNTSTC 430        440        450        460        470        480
EFVRTLNGHKRGIACLQYRDRLVVSGSSDNTIRLWDIECGACLRVLEGHEELVRCIRFDN 490        500        510        520        530        540
KRIVSGAYDGKIKVWDLVAALDPRAPAGTLCLRTLVEHSGRVFRLQFDEFQIVSSSHDDT 550        560
ILIWDFLNDPAAQAEPPRSPSRTYTYISR
```

FIG. 3A

```
  10         20         30         40         50         60         70         80         90
TGCGTTGGCTGCGGCCCTGGCACCAAACGGGCGGCCCCCCGGCGAGACGCCGACCCAGTGCTGCCTCGGGATTATGGACCGGGCCGAGGCCGTGCTGC 100        110        120        130        140        150        160        170        180
AAGAGAAGGCACTCAAGTTTATGAATTCCTCAGAGAGAAGACTGTAATAATGCCGAACCCCTAGAAGAAGATAATACCAGAAGAAGAATTCACT 190        200        210        220        230        240        250        260        270        280
TAGACAGAGACATACAAACAGCTGTGCCAGACTCTGCTTAAACCAAGAAAACAGTATGTTTAGCAAGCACTCTATGAAGACTGAGAATTGTGTGCCC 290        300        310        320        330        340        350        360        370
AAAACAAAACTTGCCAATGGCCACTTCCAGTATGATTGTCCCAAGCAAGTATGAAACTCTCAGCAAGTCTATGAAAAGGAAAAGGAACTGTGTCA 380        390        400        410        420        430        440        450        460        470
AATACTTTGAGCAGTGCTCAGAGTCAGATCAAGTCGAATTTGTCGAACATCTTATATCCCAAATGTGTCATTATTACCAACATGGGCCACATAAACTC 480        490        500        510        520        530        540        550        560
GTATCTTAAACTATGCTGCAGAGAGATTTCATAACTGCTCTGCCAGCCTCCGGGATTGGATCATATGCTGAGAACATTCTGTCATACCTGAT 570        580        590        600        610        620        630        640        650
GCCAAATCACTACTATGTGCTGCTGAACTTGTGTGCCAAGGAATGGTTACCGAGTGACCTCTGATGCGCATGCTGTGGAAGAAGCTTATCGAGAGAATGG 660        670        680        690        700        710        720        730        740        750
TCACGACAGATTCTCTGTGGAGAGGCCTGGCAGAACGAAGAGGATGGGCGACAGTATTTATTCAAAAACAAACCTCCTGACGGGAATGCTCCTCC 760        770        780        790        800        810        820        830        840
CAACTCTTTTTATAGAGCACTTTATCCTAAAATTATACAAGACATTGAGACAATAGAATCTAATTGGAGATGTGAAGACATAGTTTACAGAGA 850        860        870        880        890        900        910        920        930        940
ATTCACTCGCCGAAGTGAAACAAGCAAAGGAGTTTACTCTGTTTACAGTATGATGATCAGAAAATAGTAAGGCCCCTTCGAGACAACAACAATCAAGA
```

FIG.3B

```
       950       960       970       980       990      1000      1010      1020      1030
TCTGGGATAAAAACACATTGGAATGCAAGCGAATTCTCACAGGCCATACAGGTTCAGTCCTCTGTCTCCAGTATGATGAGAGTGATCATAAC 1040      1050      1060      1070      1080      1090      1100      1110      1120
AGGATCATCGGATTCCACGGTCAGAGTGTGGGATGTAAATACAGGTGAAATGCTAAACACGTTGATTCACCATTGTGAAGCAGTTCTGCACTTG 1130      1140      1150      1160      1170      1180      1190      1200      1210      1220
CGTTTCAATAATGGCATGATGGTGACCTGCTCCAAAGATCGTTCCATTGCTGTATGGCGATATGGCCTCCCCAACTGACATTACCCTCCGGAGGG 1230      1240      1250      1260      1270      1280      1290      1300      1310
TGCTGGTCGGACACCGAGCTGCTCTCAATGTTGTAGACTTTGATGACAAGTACATTGTTTCTCCATCTGGGGATAGAACTATAAAGGTATGGAA 1320      1330      1340      1350      1360      1370      1380      1390      1400      1410
CACAGTACTGTGTAATTGTAAGGACCTTAAATGGACACAAACCAGGCATTGCCCTGTTTGCAGTACAGGCTGTAGTGAGTGGCTCA 1420      1430      1440      1450      1460      1470      1480      1490      1500
TCTGACAACACTATCAGATTATGGGACATAGAAATGTGGTCATGTTTACGAGTGTTAGAAGGCCATGAGGAATTGGTGCGTTGTATTCGATTTG 1510      1520      1530      1540      1550      1560      1570      1580      1590
ATAACAGAGGATCAGTGGGCCTATGATGAAAAATTAAAGTGTGGGATCTTGTGGCTGTCTTTGACCCCGTGCTCCTGCAGGACACT 1600      1610      1620      1630      1640      1650      1660      1670      1680      1690
CTGTCTACGGACCCTTGTGTGGAGCATTCCCGAAGAGTTTTTGCTACTACAGTTGATGAATTCCAGATTGTCAGTAGTTCACATGATGACACAATC
```

FIG.3C

```
      1700      1710      1720      1730      1740      1750      1760      1770      1780
CTCATCTGGGACTTCCTAAATGATCCAGCTGCCAAGCTGAACCCCCCGTTCCCTTCTGAACATACACCTACATCTCCAGATAAATAACCA 1790      1800      1810      1820      1830      1840      1850      1860      1870      1880
TACACTGACCTCATACTTGCCCAGGACCCATTAAAGTTCCGTATTTAACGTATCTGCCAATACCAGGATGAGCAACAACAGTAACAATCAAAC 1890      1900      1910      1920      1930      1940      1950      1960      1970
TACTGCCCAGTTTCCCTGGACTAGCCGAGGAGGAGCAGGGCTTTGAGACTCCTGTTGGGACACAGTTGGTCTGCAGTCGGCCCAGGAGGGTCTACTC 1980      1990      2000      2010      2020      2030      2040      2050      2060
AGCACAACTGACTGCTTCAGTGCTGCTATCAGAAGATGTCTTCTATCAATTGTGAATGATTGGAACTTTTAAACCTCCCCTCTCTCCTCCTTT 2070      2080      2090      2100      2110      2120      2130      2140      2150
CACCCTCTGCCACCTAGTTTTTTCCCATTGGTTCCAGACACAAAGGTGACTTATAAATATATTTAGTGTTTGCCAGAAAAAAAAA
```

FIG.3D

```
          10         20         30         40         50         60
MERKDFETWLDNISVTFLSLTDLQKNETLDHLISLSGAVQLRHLSNNLETLLKRDFLKLL 70         80         90        100        110        120
PLELSFYLLKWLDPQTLLTCCLVSKQWNKVISACTEWWQTACKNLGWQIDDSVQDALHWK 130        140        150        160        170        180
KVYLKAILRMKQLEDHEAFETSSLIGHSARVYALYYKDGLLCTGSDDLSAKLWDVSTGQC 190        200        210        220        230        240
VYGIQTHTCAAVKFDEQKLVTGSFDNTVACWEWSSGARTQHFRGHTGAVFSVDYNDELDI 250        260        270        280        290        300
LVSGSADFTVKVWALSAGTCLNTLTGHTEWVTKVVLQKCKVKSLLHSPGDYILLSADKYE 310        320        330        340        350        360
IKIWPIGREINCKCLKTLSVSEDRSICLQPRLHFDGKYIVCSSALGLYQWDFASYDILRV 370        380        390        400        410        420
IKTPEIANLALLGFGDIFALLFDNRYLYIMDLRTESLISRWPLPEYRESKRGSSFLAGEH
```

PG

FIG.4A

```
          10         20         30         40         50         60         70         80         90
ATGGAGAGAAGGACTTTGAGACATGGCTTGATAACATTTCTTTCTCTGACGGACTTGCAGAAAATGAAACTCTGGATCACC
         100        110        120        130        140        150        160        170        180
TGATTAGTCTGACTGGGGCAGTCCAGTCTCAGGCATCTCTCCAATAACCTAGAGACTCTCCTCAAGCGGACTTCCTCAAACTCCTTCCCCTGGA
         190        200        210        220        230        240        250        260        270        280
GCTCAGTTTTTATTTGTTAAAATGCCTCGATCCTCAGACTTTACTCACATGCCCTCGTCCTCTAAACAGTGGAATAAGGTGATAAGTGCCTGT
         290        300        310        320        330        340        350        360        370
ACAGAGGTGTGGCAGACTGCATGTAAAAATTTGGGCTGGCAGATAGATGATTCTGTTCAGGACGCTTTGCACTGAGGACAGTGTATGCACTTTACTTGAAGG
         380        390        400        410        420        430        440        450        460        470
CTATTTTGAGAATGAAGCAACTGGAGGACCATGAAGCCTTTGAAACCTGGTCATTAATTGGACAGAGTGCCAGAGTGTATGCACTTTACTACAA
         480        490        500        510        520        530        540        550        560
AGATGGACTTCTCTGTACAGGGTCAGATGACTTGTCTGCAAGCTGTGGGATGTGAGCACCAGGGCCAGTGGCTTTATGGCATCCAGACCCACACT
         570        580        590        600        610        620        630        640        650
TCTGCAGCGGTGAAGTTTGATGAACAGAAGCTTCCTTTGACAGCCTGGATGTGTCAGACACTCTGCCTTGCTGGAATGGAGTTCCCGAGCCAGGACCC
         660        670        680        690        700        710        720        730        740        750
AGCACTTTCGGGGGCACACGGGGGGGGGTATTTAGCGTGAACTACAATGATGAACTGGATATCTGTGGTGAGCGGGCTCuGCAGACTTCACTGTGAA
         760        770        780        790        800        810        820        830        840
AGTATGGGCTTTATCTGCTGGAGACTACTACATCCTCTCTTAAGTGCAGACAAATATGAGAGAGAAATCAACTGTAAGT
         850        860        870        880        890        900        910        920        930        940
TCTCTCTTGCACAGTCCTCTGGAGACTACTACATCCTCTCTTAAGTGCAGACAAATATGAGAGAGAAATCAACTGTAAGT
```

FIG.4B

```
      950       960       970       980       990      1000      1010      1020      1030
GCTTAAAGACATTGTCTGTCTCTGAGGATAGAAGTATCTGCCTGCTGCAGCCAAGACTTCATTTTGATGGCAAATACATGTCTGTAGTTCAGCACT 1040      1050      1060      1070      1080      1090      1100      1110      1120
TGGTCTCTACCAGTGGGACTTGGCCAGTTATGATATTCTCAGGTCATCATCAAGACTCCTGAGATAGCAAACTTGGCCTTGCTTGGCTTTGGAGAT 1130       1140      1150      1160      1170      1180      1190      1200      1210      1220
ATCTTGCCCTGCTGTTTGACAACCGCTACCTGTACATCATGACTGCGGACAGAGAGCCTGATTAGTCGGCTGGCCTCTGCCAGAGTACAGAGG 1230      1240      1250      1260      1270      1280      1290      1300      1310
AATCAAAGAGAGGCTCAAGTTCCTGCAGGCGAACATCCTGGCTGGAATGGACTGGATGGGCACAATGACACCGGCTTGGTCTCTTTGCCACCAGC 1320      1330      1340      1350      1360      1370      1380      1390      1400      1410
ATGCCTGACCACCAGTATTCACCTGGTGTTGTGGAAGGAGCACCGCTGACACCATGAGCCACCACGCTGACTGACTTTGGGTGCCGGGGCTGCG 1420      1430      1440      1450      1460      1470
GGTTTTGGGTGCACCTCTGCGGCACGCGACTGCATGAACCAAGTTCTCACCTAATGGTATCATCA
```

FIG.4C

```
         10        20        30        40        50        60
MKRGGRDSDRNSSEEGTAEKSKKLRTTNEHSQTCDWGNLLQDIILQVFKYLPLLDRAHAS 70        80        90       100       110       120
QVCRNWNQVFHMPDLWRCFEFELNQPATSYLKATHPELIKQIIKRHSNHLQYVSFKVDSS 130       140       150       160       170       180
KESAEAACDILSQLVNCSLKTLGLISTARPSFMDLPKSHFISALTVVFVNSKSLSSLKID 190       200       210       220       230       240
DTPVDDPSLKVLVANNSDTLKLLKMSSCPHVSPAGILCVADQCHGLRELALNYHLLSDEL 250       260       270       280       290       300
LLALSSEKHVRLEHLRIDVVSENPGQTHFHTIQKSSWDAFIRHSPKVNLVMYFFLYEEEF 310       320       330       340       350       360
DPFFRYEIPATHLYFGRSVSKDVLGRVGMTCPRLVELVVCANGLRPLDEELIRIAERCKN 370       380       390       400       410       420
LSAIGLGECEVSCSAFVEFVKMCGGRLSQLSIMEEVLIPDQKYSLEQIHWEVSKHLGRVW

FPDMMPTW
```

FIG. 5A

```
  10         20         30         40         50         60         70         80         90
CGGGGTGGTGTGTGGGGAAGCCGCCCCCGGCACCCAGGATGAAACGAGGAGGAAGAGATAGTGACCCGTAATTCATCAGAAGAAGGAACTGCAGA 100        110        120        130        140        150        160        170        180
GAAATCCAAGAAACTGAGGACTACAAATGAGCATTCTCAGACTGTGTGGGTAATCTCCTTCAGGACATTATTCTCCAAGTATTTAAATAT 190        200        210        220        230        240        250        260        270        280
TTGCCTCTTCTGACCCGGCCTCATGCTTCACAAGTTTGCCGAACCAGTTGCAAGCCAGGAATCCATGCCTGTGGAGATGTTTTGAATTTG 290        300        310        320        330        340        350        360        370
AACTGAATCAGCCAGCTACATCTTATTTGAAACGCTACCATCCAGAGCTGACAAACAGATTATTAAAAGACATTCAAACCATCTACAATATGT 380        390        400        410        420        430        440        450        460        470
CAGCTTCAAGGTGGACAGCAGCAAGAATCAGCTGAAGCAGCTTGATATATACTATCGCCAACTGTGTGATTGCTCTTTAAAAACACTTGGACTT 480        490        500        510        520        530        540        550        560
ATTTCAACTGCTCGACCAGCTTTATGGATTTACCAAAGTCTCACTTTATCTCTGCACTGACAGTGTGTGTCGTAAACTCCAAATCCCTGTCTT 570        580        590        600        610        620        630        640        650
CGCTTAAGATAGATGATACTCCAGTAGTAGATGAICATCCTCAAAGTACTAGTGCCAACAATAGTGATACACTCAAGCTCTTGAAAATGACCAG 660        670        680        690        700        710        720        730        740        750
CTGTCCTCATGTCTCTCCACGAGGTATCCTTGTGTGGCCTGATCAGTCAGGACTTAAGAGAACTAGCCCTGAACTACCACTTATTGAGTGAT 760        770        780        790        800        810        820        830        840
GAGTGTTACTTGGATTGCTCTCTGAAAAACATGTTCATGATTAGAACATTTGCCCATTGACATGTAGTCAGTGAGAATCCTGGACAGACACTTCC 850        860        870        880        890        900        910        920        930        940
ATACTATTCAGAAGAGTACCTTGGGATCGGATCGTTTCATCAGACATTCACCCAAAGTGAACGTAGTAGTGAGTATTTTTTTATATGAAGAAGAATTGA
```

FIG.5B

```
      950       960       970       980       990      1000      1010      1020      1030
CCCCTTCTTCTTCCCTATGAAATACCTGCCATCTGCCACCCATCATCTGTACTTTGGGAGATCAGTAGCCAAAGATGTGCTTGGCCTCTGCGGAATGACATGCCCT 1040      1050      1060      1070      1080      1090      1100      1110      1120
AGACTGGTGAACTAGTAGTCTGTGCAAATGGATTACGGCCACTTGATGAAGAGTTAATTCCATTGCAGAACGTTGCAAAAATTTGTCAGCTA 1130      1140      1150      1160      1170      1180      1190      1200      1210      1220
TTGGACTAGGGAATGTGAAGTCTCATGTAGTGCCTTTGTTGTGAAGATGTGGAAGAACATCTGGTGGCCCCTATCTCAATTATCCATTATGGAAGA 1230      1240      1250      1260      1270      1280      1290      1300      1310
AGTACTAATTCCTGACCAAAGTATAGTTTGGAGCAGATTCACTGGGAAGTGTCCAAGCATCTTGGTAGGGTGTGGTTTCCCGACGATGATGCCC 1320      1330      1340      1350      1360      1370      1380      1390      1400
ACTTGGTAAAAACTGCATGATGAATAGCCACCTTAATTCAAGCAAATGTATTATTAATTAAGTTTTATTGCTGTAAAAAAAAAAAAAAA
```

FIG.5C

```
         10         20         30         40         50         60
MKRNSLSVENKIVQLSGAAKQPKVGFYSSLNQTHTHTVLLDWGSLPHHVVLQIFQYLPLL 70         80         90        100        110        120
DRACASSVCRRWNEVFHISDLWRKFEFELNQSATSSFKSTHPDLIQQIIKKHFAHLQYVS 130        140        150        160        170        180
FKVDSSAESAEAACDILSQLVNCSIQTLGLISTAKPSFMNVSESHFVSALTVVFINSKSL 190        200        210        220        230        240
SSIKIEDTPVDDPSLKILVANNSDTLRLPKMSSCPHVSSDGILCVADRCQGLRELALNYY 250        260        270        280        290        300
ILTDELFLALSSETHVNLEHLRIDVVSENPGQIKFHAVKKHSWDALIKHSPRVNVVMHFF 310        320        330        340        350        360
LYEEEFETFFKEETPVTHLYFGRSVSKVVLGRVGLNCPRLIELVVCANDLQPLDNELICI 370        380        390        400        410        420
AEHCTNLTALGLSKCEVSCSAFIRFVRLCERRLTQLSVMEEVLIPDEDYSLDEIHTEVSK

430
YLGRVWFPDVMPLW
```

FIG.6A

```
          10        20        30        40        50        60
ACATTTTCTAATGTTTACAGAATGAAGAGGAACAGTTTATCTGTTGAGAATAAAATTGTCCAGTTGTCA 70        80        90       100       110       120       130
GGAGCAGCGAAACAGCCAAAAGTTGGGTTCTACTCTTCTCTCAACCAGACTCATACACACACGGTTCTT 140       150       160       170       180       190       200
CTAGACTGGGGGAGTTTGCCTCACCATGTAGTATTACAAATTTTTCAGTATCTTCCTTTACTAGATCGG 210       220       230       240       250       260       270
GCCTGTGCATCTTCTGTATGTAGGAGGTGGAATGAAGTTTTTCATATTTCTGACCTTTGGAGAAAGTTT 280       290       300       310       320       330       340
GAATTTGAACTGAACCAGTCAGCTACTTCATCTTTTAAGTCCACTCATCCTGATCTCATTCAGCAGATC 350       360       370       380       390       400       410
ATTAAAAAGCATTTTGCTCATCTTCAGTATGTCAGCTTTAAGGTTGACAGTAGCGCTGAGTCAGCAGAA 420       430       440       450       460       470       480
GCTGCCTGTGATATACTCTCTCAGCTGGTAAATTGTTCCATCCAGACCTTGGGCTTGATTTCAACAGCC 490       500       510       520       530       540       550
AAGCCAAGTTTCATGAATGTGTCGGAGTCTCATTTTGTGTCAGCACTTACAGTTGTTTTTATCAACTCA 560       570       580       590       600       610       620
AAATCATTATCATCAATCAAAATTGAAGATACACCAGTGGATGATCCTTCATTGAAGATTCTTGTGGCC 630       640       650       660       670       680       690
AATAATAGTGACACTCTAAGACTCCCAAAGATGAGTAGCTGTCCTCATGTTTCATCTGATGGAATTCTT 700       710       720       730       740       750
TGTGTAGCTGACCGTTGTCAAGGCCTTAGAGAACTGGCGTTGAATTATTACATCCTAACTGATGAACTT 760       770       780       790       800       810       820
 TTCCTTGCACTCTCAAGCGAGACTCATGTTAACCTTGAACATCTTCGAATTGATGTTGTGAGTGAAAAT 830       840       850       860       870       880       890
 CCTGGACAGATTAAATTTCATGCTGTTAAAAAACACAGTTGGGATGCACTTATTAAACATTCCCCTAGA 900       910       920       930       940       950       960
GTTAATGTTGTTATGCACTTCTTTCTATATGAAGAGGAATTCGAGACGTTCTTCAAAGAAGAAACCCCT
```

FIG.6B

```
       970        980        990       1000       1010       1020       1030
GTTACTCACCTTTATTTTGGTCGTTCAGTCAGCAAAGTGGTTTTAGGACGGGTAGGTCTCAACTGTCCT 1040       1050       1060       1070       1080       1090       1100
CGACTGATTGAGTTAGTGGTGTGTGCTAATGATCTTCAGCCTCTTGATAATGAACTTATTTGTATTGCT 1110       1120       1130       1140       1150       1160       1170
GAACACTGTACAAACCTAACAGCCTTGGGCCTCAGCAAATGTGAAGTTAGCTGCAGTGCCTTCATCAGG 1180       1190       1200       1210       1220       1230       1240
TTTGTAAGACTGTGTGAGAGAAGGTTAACACAGCTCTCTGTAATGGAGGAAGTTTTGATCCCTGATGAG 1250       1260       1270       1280       1290       1300       1310
GATTATAGCCTAGATGAAATTCACACTGAAGTCTCCAAATACCTGGGAAGAGTATGGTTCCCTGATGTG

1230
ATGCCTCTCTGG
```

FIG.6C

```
          10        20        30        40        50        60
MAGSEPRSGTNSPPPPFSDWGRLEAAILSGWKTFWQSVSKDRVARTTSREEVDEAASTLT 70        80        90       100       110       120
RLPIDVQLYILSFLSPHDLCQLGSTNHYWNETVRNPILWRYFLLRDLPSWSSVDWKSLPY 130       140       150       160       170       180
LQILKKPISEVSDGAFFDYMAVYLMCCPYTRRASKSSRPMYGAVTSFLHSLIIPNEPRFA 190       200       210       220       230       240
LFGPRLEQLNTSLVLSLLSSEELCPTAGLPQRQIDGIGSGVNFQLNNQHKFNILILYSTT 250       260       270       280       290       300
RKERDRAREEHTSAVNKMFSRHNEGDDRPGSRYSVIPQIQKLCEVVDGFIYVANAEAHKR 310       320       330       340       350       360
HEWQDEFSHIMAMTDPAFGSSGRPLLVLSCISQGDVKRMPCFYLAHELHLNLLNHPWLVQ 370       380       390       400       410       420
DTEAETLTGFLNGIEWILEEVESKRAR*FSFQILGTETI*NLLLRS*CEYLLSQPTLSCL 430       440       450       460       470       480
FADRLSFGQL*LLCFLYYFYFLP*INYKKRVSVLVFSPKMNL*TFFW*FLYFLSF*KY*I

L
```

FIG. 7A

```
         10        20        30        40        50        60
ATGGCGGGAAGCGAGCCGCGCAGCGGAACAAATTCGCCGCCGCCGCCCTTCAGCGACTGGGGCCGCCTG 70        80        90        100       110       120       130
GAGGCGGCCATCCTCAGCGGCTGGAAGACCTTCTGGCAGTCAGTGAGCAAGGATAGGGTGGCGCGTACG 140       150       160       170       180       190       200
ACCTCCCGGGAGGAGGTGGATGAGGCGGCCAGCACCCTGACGCGGCTGCCGATTGATGTACAGCTATAT 210       220       230       240       250       260       270
ATTTTGTCCTTTCTTTCACCTCATGATCTGTGTCAGTTGGGAAGTACAAATCATTATTGGAATGAAACT 280       290       300       310       320       330       340
GTAAGAAATCCAATTCTGTGGAGATACTTTTTGTTGAGGGATCTTCCTTCTTGGTCTTCTGTTGACTGG 350       360       370       380       390       400       410
AAGTCTCTTCCATATCTACAAATCTTAAAAAAGCCTATATCTGAGGTCTCTGATGGTGCATTTTTTGAC 420       430       440       450       460       470       480
TACATGGCAGTCTATCTAATGTGCTGTCCATACACAAGAAGAGCTTCAAAATCCAGCCGTCCTATGTAT 490       500       510       520       530       540       550
GGAGCTGTCACTTCTTTTTTTACACTCCCTGATCATTCCCAATGAACCTCGATTTGCTCTGTTTGGACCA 560       570       580       590       600       610       620
CGTTTGGAACAATTGAATACCTCTTTGGTGTTGAGCTTGCTGTCTTCAGAGGAACTTTGCCCAACAGCT 630       640       650       660       670       680       690
GGTTTGCCTCAGAGCCAGATTGATGGTATTGGATCAGGAGTCAATTTTCAGTTGAACAACCAACATAAA 700       710       720       730       740       750
TTCAACATTCTAATCTTATATTCAACTACCAGAAAGGAAAGAGATAGAGCAAGGGAAGAGCATACAAGT 760       770       780       790       800       810       820
GCAGTTAACAAGATGTTCAGTCGACACAATGAAGGTGATGATCGACCAGGAAGCCGGTACAGTGTGATT 830       840       850       860       870       880       890
CCACAGATTCAAAAACTGTGTGAAGTTGTAGATGGGTTCATCTATGTTGCAAATGCTGAAGCTCATAAA 900       910       920       930       940       950       960
AGACATGAATGGCAAGATGAATTTTCTCATATTATGGCAATGACAGATCCAGCCTTTGGGTCTTCGGGA
```

FIG.7B

```
970         980         990        1000        1010        1020        1030
AGACCATTGTTGGTTTTATCTTGTATTTCTCAAGGGGATGTAAAAAGAATGCCCTGTTTTTATTTGGCT 1040        1050        1060        1070        1080        1090        1100
CATGAGCTGCATCTGAATCTTCTAAATCACCCATGGCTGGTCCAGGATACAGAGGCTGAAACTCTGACT 1110        1120        1130        1140        1150        1160        1170
GGTTTTTTGAATGGCATTGAGTGGATTCTTGAAGAAGTGGAATCTAAGCGTGCAAGATGATTCTCTTTT 1180        1190        1200        1210        1220        1230        1240
CAGATCTTGGGAACTGAAACCATTTGAAATTTATTACTAAGGTCGTGATGTGAATATTTGCTCAGTCAG 1250        1260        1270        1280        1290        1300        1310
CCCACCTTGTCCTGCCTTTTTGCAGATAGGCTTTCATTTGGACAGCTATAACTGCTGTGTTTTTTATAT 1320        1330        1340        1350        1360        1370        1380
TATTTTTACTTTTTACCATAAATCAATTACAAGAAAAGAGTTTCAGTCCTAGTATTTAGCCCCAAAATG 1390        1400        1410        1420        1430        1440
AACCTTTAAACATTTTTTTGGTAATTTTTATATTTTCTGTCTTTTTAAAAATATTAAATTTTGG
```

FIG. 7C

```
            10         20         30         40         50         60
MSRRPCSCALRPPRCSCSASPSAVTAAGRPRPSDSCKEESSTLSVKMKCDFNCNHVHSGL 70         80         90        100        110        120
KLVKPDDIGRLVSYTPAYLEGSCKDCIKDYERLSCIGSPIVSPRIVQLETESKRLHNKEN 130        140        150        160        170        180
QHVQQTLNSTNEIEALETSRLYEDSGYSSFSLQSGLSEHEEGSLLEENFGDSLQSCLLQI 190        200        210        220        230        240
QSPDQYPNKNLLPVLHFEKVVCSTLKKNAKRNPKVDREMLKEIIARGNFRLQNIIGRKMG 250        260        270        280        290        300
LECVDILSELFRRGLRHVLATILAQLSDMDLINVSKVSTTWKKILEDDKGAFQLYSKAIQ 310        320        330        340        350        360
RVTENNNKFSPHASTREYVMFRTPLASVQKSAAQTSLKKDAQTKLSNQGDQKGSTYSRHN 370        380        390        400        410        420
EFSEVAKTLKKNESLKACIRCNSPAKYDCYLQRATCKREGCGFDYCTKCLCNYHTTKDCS 430        440
DGKLLKASCKIGPLPGTKKSKKNLRRL
```

FIG. 8A

```
  10         20         30         40         50         60         70         80         90
AGGTTGCTCAGCTGCCCCCCGAGCGGTTCCTCCACCTGAGCCAGACCACCACCTCGGTTGGCATGACCCGGCCCCCCTGCAGCTGCCGCCCTACCG 100        110        120        130        140        150        160        170        180
CCACCCCGCCTGCTCCTGCACGCCCAGCCCAGCCCCCAGCTGCAGCCCCCGGCCCCCTCGCACCCTCCGATAGTTGTAAAGAAGAAAGTTCTACCC 190        200        210        220        230        240        250        260        270        280
TTTCTGTCAAAATGAAGTGTGATTTTAATTGTAACCATGTTCATTCCGGACTTAAACTGTAAAACTGGAAGACTAGTTTCCTA 290        300        310        320        330        340        350        360        370
CACCCCTGCATATCTGGAAGGTTCCTGTAAAGACTATGAAAGTATGAAAGGCTGTCATGTATTGGTCACCGATTGTGACGCCTAGGATT 380        390        400        410        420        430        440        450        460        470
GTACAACTTGAAACTGAAAGCAAGCCCTTGCATAACAGCAAATCAACATGTGCAACAGACACTTAATAGTACAAATGAAATGAAGCACTAG 480        490        500        510        520        530        540        550        560
AGACCAGTAGACTTATGAAGACAGTGGCTATTCCTCATTTCTCTACAAAGTGGCCTCAGTGAACATGAAGAAGGTAGCCTCCTCGGAGGAGAA 570        580        590        600        610        620        630        640        650
TTTCGGTGACAGTCTACAATCCTGCCTGCTACAAATACAAAGCCCAGACCAATATCCCAACAAAAACTTGCTGCCAGTTCTTCATTTTGAAAAA 660        670        680        690        700        710        720        730        740        750
GTGGTTTGTTCAACATTAAAAAAGAATCAAAACGAAATCCTAAAGTAGATGTCTGAAGGAAATTATACCCAGACGAAATTTTAGAC 760        770        780        790        800        810        820        830        840
TGCAGAATATAATTGGGCAGAAAATGGGCCTAGAATGTGTAGATATTTCAGCGAACTCTTTCGAAGGGACTCAGACATGTCTTAGCAACTAT 850        860        870        880        890        900        910        920        930        940
TTTAGCACAACTCAGTGACATTAATCAATGTCTAAGTGAGCACAACTTGGAAGAAGAATCCTAGAAGAGATGATAACGGGGCATTCCAG
```

FIG.8B

```
       950       960       970       980       990       1000      1010      1020      1030
TTGTACAGTAAAGCAATACAAAGAGTTACCGAAAACAACAATAAATTTTCACCTCATGCTTCAACCAGAGAATATGTTATGTTCAGAACCCCAC 1040      1050      1060      1070      1080      1090      1100      1110      1120
TGGCTTCTGTTCAGAAATCAGCAGCCCAGACTTCTCTCAAAAAAGATGCTCAAACCAAGTTATCCAATCAAGGTGATCAGAAAGGTTCTACTTA 1130      1140      1150      1160      1170      1180      1190      1200      1210      1220
TAGTCGACACAATGAATTCTCTGAGGTTGCCAAGACATTGAAAAAGAACGAAAGCCTCAAAGCCTGTATTCGCTGTAATTCACCTGCAAAATAT 1230      1240      1250      1260      1270      1280      1290      1300      1310
GATTGCTATTTACAACGGCCAACCTGCAAACGAGAAGGCTGTGGATTTGATTATTGTACGAAGTGTCTCTGTAATTATCATACTACTAAAGACT 1320      1330      1340      1350      1360      1370      1380      1390      1400      1410
GTTCAGATGGCAAGCTCCTCAAAGCCAGTTGTAAAATAGGTCCCCTGCCTGGTACAAAGAAAAGCAAAAAGAATTTACGAAGATTGTGATCTCT 1420      1430      1440      1450      1460      1470      1480      1490      1500
TATTAAATCAATTGTTACTGATCATGAATGTTAGTTAGAAAATGTTAGGTTTTAACTTAAAAAAAATTGTATTGTGATTTTCAATTTTATGTTG 1510      1520      1530      1540      1550      1560      1570      1580      1590
AAATCGGTGTAGTATCCTGAGGTTTTTTTCCCCCCAGAAGATAAAGAGGATAGACAACCTCTTAAAATATTTTTACAATTTAATGAGAAAAAGT 1600      1610      1620      1630      1640      1650      1660      1670      1680      1690
TTAAAATTCTCAATACAAATCAAACAATTTAAATATTTTAACAAAAAAGGAAAAGTAGATAGTGATACTGAGGGTAAAAAAAAAAATTGATTCAA 1700      1710      1720      1730      1740      1750      1760      1770      1780
TTTTATGGTAAAGGAAACCCATGCAATTTTACCTAGACAGTCTTAAATATGTCTGGTTTTCCATCTGTTAGCATTTCAGACATTTTATGTTCCT 1790      1800      1810      1820      1830      1840      1850      1860      1870      1880
CTTACTCAATTGATACCAACAGAAATATCAACTTCTGGAGTCTATTAAATGTGTTGTCACCTTTCTAAAGCTTTTTTTTCATTGTGTGTATTTCC 1890      1900      1910      1920      1930      1940      1950      1960      1970
CAAGAAAGTATCCTTTGTAAAAACTTGCTTGTTTTCCTTATTTCTGAAATCTGTTTTAATATTTTTGTATACATGTAAATATTTCTGTATTTTT 1980      1990      2000      2010      2020      2030      2040      2050      2060
TATATGTCAAAGAATATGTCTCTTGTATGTACATATAAAAATAAATTTTGCTCAATAAAATTGTAAGCTTAAAAAAAAAAAAAAAAAAACTCGAG

2070
ACTAGTGC
```

FIG.8C

```
         10        20        30        40        50        60
ARSGASALRRRRVQVWVLSRPPPGGGDSFRTRRPQRGPGPGGSQAMDAPHSKAALDSINE 70        80        90       100       110       120
LPDNILLELFTHVPARQLLLNCRLVCSLWRDLIDLLTLWKRKCLRKGFITKDWDQPVADW 130       140       150       160       170       180
KIFYFLRSLHRNLLRNPCAENDMFAWQIDFNGGDRWKVDSLPGAHGTEFPDPKVKKSFVT 190       200       210       220       230       240
SYELCLKWELVDLLADRYWEELLDTFRPDIVVKDWFAARADCGCTYQLKVQLASADYFVL 250       260       270       280       290       300
ASFEPPPVTIQQWNNATWTEVSYTFSDYPRGVRYILFQHGGRDTQYWAGWYGPRVTNSSI 310       320       330
VVSPKMTRNQASSEAQPGQKHGQEEAAQSPYGAVVQIF
```

FIG.9A

```
         10         20         30         40         50         60         70         80         90
GCGCGTTCGGGAGCTTCCGCCCCTGCGTAGGAGGCGGGTGCAGGTGTGCTGAGCCGGCCCCTGAGGGGAGACAGCTTCAGGACAC 100        110        120        130        140        150        160        170        180
GCAGGCCCCAGCGAGGGCCCCGGGGGATCCCCACAGCCCCACTCCAAAGCAGCCCTGGACGCATTAACGAGCTGCCCGA 190        200        210        220        230        240        250        260        270        280
TAACATCCTGCTGGAGCTGTTCACGCACGTGCCCCCAGCTGCTGCCCCTGGTCTGCTGCAGGCCCTCTGCGGGGACCTCATCGAC 290        300        310        320        330        340        350        360        370
CTCCTGACCCTCTGAAACGCAAGTGCCTGCGAAAGGGCTTCATCACCAAGGACTGGGACCAGCCCCGTGCCCGACTGAAAATCTCTCTACTTCC 380        390        400        410        420        430        440        450        460        470
TACGGAGCCTGCATAGGAACCTCTGCGCAACCGTGTGCTGAAAACGATATGTTTGCATGGCAAATTGATTTCAATGTGGGGACCGCTGAA 480        490        500        510        520        530        540        550        560
GGTGGATAGCCTCCCTGGAGCCCACGGGACAGAATTTCCTGACCCAAAGTCAAGAAGTCTTTGTCACATCCTACAACTGTGCCTCAAGTGG 570        580        590        600        610        620        630        640        650
GAGCTGCTGGACCTTCTAGCCGACCTACTGGGAGGAGCTACTAGACACATTCCGGCCCGACACTGTGCTTAAGGACTGGTTTGCTGCAGAG 660        670        680        690        700        710        720        730        740        750
CCGACTGTGGCTGCACCTACCAACTCAAAGTGCAGCTGCCTCGGCTGACTACTTCGTGTTGGCCTCCTTCGAGCCCCCACCTGTGACCATCCA 760        770        780        790        800        810        820        830        840
ACAGTGGAAACAATGCCACATGGACTGGGCTGTCCTACAGAGGTCTCCTACACCTTCTCAGACTACACCTCCTCTTCCAGCATGGGGCAGG 850        860        870        880        890        900        910        920        930        940
GACACCCAGTACTGGGCAGGCTGGTATGGGCCCCGAGTGCTCAACAGCAGCATTGTCGTCAGCCCCAAGATGACCAAGGAACCAGGCCTCGTCCG
```

FIG.9B

```
                                                                          1020      1030
          950       960       970       980       990      1000     1010
AGGCTCAGCCTGGGCAGAAGCATGACAGGAGGAGCTGCCCAATCGCCCTACGGAGCTGTTGTCCAGAGCTGTCCATCCTGTG 1040      1050      1060      1070      1080      1090      1100      1110      1120
TCTGGGTCAGCCAGAGGTTCCTCCAGGACTCAGCCAGGCATGGGTGGGCAGTGAGGTCCCTGTACCAGCGACTCCTGCCCGGTTCAACCCTA 1130      1140      1150      1160      1170      1180      1190      1200      1210      1220
CCAGCTTGTGTAACTTACTGTCACATAGCTCTGACCTTTTGTTGTAATAAAATGTTTTCAGCCCGCCCACTGTGGCTCACGCCTGTAATCCCAG 1230      1240      1250      1260      1270      1280      1290      1300      1310
CACTTTGGGAGACCAGGCAGGTGGATCACGAGGTCAGGAGACAGAGACCATCCTGGCCAACACGGTGAAACCCTGTCTCTACTAAAAATACAA 1320      1330      1340      1350      1360      1370      1380      1390      1400      1410
AAAATTAGCCGGGCGTGGTGGGGGGCCTGTAGTCCCAGCTACTCGGGAGGCTGATGCAGAAGAATGGCGTGAACCCGGAAGGCAGAGCTTGC 1420      1430      1440      1450      1460      1470      1480      1490      1500
AGTGAGCCGAGATCACGCCACTGCACTCCAGCCTGGGTGACAGAGCGAGACTCTGTCTCATAAAATAATAATAATAAATAAATAAAAAATA 1510      1520      1530
AATGGTTTTCAGTAAAAAAAAAAAAAAAA
```

FIG.9C

```
          10        20        30        40        50        60
MSNTRFTITLNYKDPLTGDEETLASYGIVSGDLICLILHDDIPPPNIPSSTDSEHSSLQN 70        80        90       100       110       120
NEQPSLATSSNQTSIQDEQPSDSFQGQAAQSGVWNDDSMLGPSQNFEAESIQDNAHMAEG 130       140       150       160       170       180
TGFYPSEPLLCSESVEGQVPHSLETLYQSADCSDANDALIVLIHLLMLESGYIPQGTEAK 190       200       210       220       230       240
ALSLPEKWKLSGVYKLQYMHHLCEGSSATLTCVPLGNLIVVNATLKINNEIRSVKRLQLL 250       260       270       280       290       300
PESFICKEKLGENVANIYKDLQKLSRLFKDQLVYPLLAFTRQALNLPNVFGLVVLPLELK 310       320       330       340       350       360
LRIFRLLDVRSVLSLSAVCRDLFTASNDPLLWRFLYLRDFRDNTVRVQDTDWKELYRKRH 370       380       390       400       410       420
IQRKESPKGRFVLLLPSSTHTIPFYPNPLHPRPFPSSRLPPGIIGGEYDQRPTLPYVGDP 430       440       450       460       470       480
ISSLIPGPGETPSQLPPLRPRFDPVGPLPGPNPILPGRGGPNDRFPFRPSRGRPTDGRLS
FM
```

FIG. 10A

```
        10         20         30         40         50         60         70         80         90
TGGAATTCCCATGGACCATGTCTAATACCGGATTTACAATTGAACTACAAGGATCCCCTCACTGGAGATGAAGAGACCTTGGCTTCATA 100        110        120        130        140        150        160        170        180
TGGGATTGTTTCTGGGGACTTGATATGTTTGATTCTTCACGATGACATTCCACCGCCTAATATACCTTCATCCACAGATTCAGAGCATTCTTCA 190        200        210        220        230        240        250        260        270        280
CTCCAGAACAATGAGCAACCCTCTTTGGCCACCAGCTCCAATCAGACTAGACATACAGGATGAACAACCAGTGATTCATTCCAAGGACAGGCAG 290        300        310        320        330        340        350        360        370
CCCAGTCTGGTGTTTGGAATGACGACAGTATGTTAGGGCCTAGTCAAATTTGAAGCTGAGTCAATTCAAGATAATGCCATATGCCAGAGGG 380        390        400        410        420        430        440        450        460        470
CACAGGTTTCTATCCCTCAGAACCCTGCTCTGTAGTGAATCGGTGAAGCCAAGTGCCACATTCATTAGAGACCTTGTATCAATCAGCTGAC 480        490        500        510        520        530        540        550        560
TGTTCTGATGCCAATGATGGTTGATAGTGTTGATACATCTCTCATGTTGAGAGTCAGGTTACATACCTCAGGGCACGAAGCCAAAGCACTGT 570        580        590        600        610        620        630        640        650
CCCTGCCGGAGAAGTGGAAGTTGAGCGGGGTGTATAAGCTGCAGTACATGCATCATCTCTGCGAGGGCAGCTCCGCTACTCTCCACCGTGTGCC 660        670        680        690        700        710        720        730        740        750
TTTGGAAACCTGATTGTTGTAAATGCTACACTAAAATCAACAATGAGATTAGAAGTGAAAAGATTGCCAGCTGCTACCAGAATCTTTATT 760        770        780        790        800        810        820        830        840
TGCAAAGAGAAACTAGGGGAAAATGTAGCCAACATATACAAAGATCTTCAGAAACTCTCTCGCCTCTTTAAAGACCTGGTGTATCCTCTC 850        860        870        880        890        900        910        920        930        940
TGGCTTTTACCGGACAAGCACTGAACCTACCAAATGTATTGGGTTGGTTCGTCCTCCCATTGGAACTGAAACTACGGATCTCCGACTTCTGA
```

FIG. 10B

```
       950       960       970       980       990      1000      1010      1020      1030
TGTTCGTTCCGTCTTGTCTTTGTCTGCGGTTTGTGTGTGACCTCTTTACTGTCTTCAAATGACCCACTCCTCCTGTGGAGGTTTTTATATCTGCGTGAT 1040      1050      1060      1070      1080      1090      1100      1110      1120
TTTCGAGACAATACTGTCAGAGTTCAAGACACAGATTGGAAGAACTGTACAGGAAGAGGCACATACAAAGAAAAGAATCCCGAAAGGGCGGT 1130      1140      1150      1160      1170      1180      1190      1200      1210      1220
TTGTGCTGCTCCTGCCATCGTCAACCCACACCATTCCATTCTATCCCAACCCCTTGCACCCTAGGCCATTTCCTAGCTCCCGCCTTCCTCCAGG 1230      1240      1250      1260      1270      1280      1290      1300      1310
AATTATCGGGGTGAATATGACCAAAGACCAAACACTTCCTATGTGTTGGAGAGACCAATCAGTTCACTCATTCCTGGTCTGGGGAGACGCCCAGC 1320      1330      1340      1350      1360      1370      1380      1390      1400      1410
CAGTTACCTCCACTGAGAGATCCGGCCTTTGATCCAGTTGGCCCACTTCCCAGGACCTAACCCCCATCTTGCCAGGGCGAGGGCGCCCAATGACAGAT 1420      1430      1440      1450      1460      1470      1480      1490      1500
TTCCCTTTAGACCCAGGAGGGGTCGGCCAACTGATGGCCCGGCCCTGTCATTCATGTGATTGATTGTAATTTCATTTCTGGAGCTCCATTTGTTTT 1510      1520      1530      1540      1550      1560      1570      1580      1590
TGTTTCTAAACTACAGATGTCCACTCCTTGGCGTCCTGAGTCTCGAGTGTATTTTCTGAGTGTTGAGAGTTGCACTCCCAGAAACCTTTT 1600      1610      1620      1630      1640      1650      1660      1670      1680      1690
AAGAGATACATTTATAGCCCTAGGGGTGGTATGACCCAAAGGTTCCTCGTGACAAGGTTGGCCTTGGGAATAGTTGGCTGCCAATCCCCTGC 1700      1710      1720      1730      1740      1750      1760
TCTTGGTTCTCTCTCTAGATTGAAGTTTGTTTTTCTGATGCGTGTTCTTACCAGATTAAAAAAAGTGTAAATT
```

FIG.10C

```
          10        20        30        40        50        60
ETSKLG*SAVLAPAAGGTLSSEGRSAVSGILIAVTSTGVDK*SLNQLLHGLGTSSRLSHF
          70        80        90       100       110       120
PFG*KSPPRGQFVAAAVEIAGRSGLQMGQGLWRVVRNQQLQQEGYSEQGYLTREQSRRMA
         130       140       150       160       170       180
ASNISNTNHRKQVQGGIDIYHLLKARKSKEQEGFINLEMLPPELSFTILSYLNATDLCLA
         190       200       210       220       230       240
SCVWQDLANDELLWQGLCKSTWGHCSIYNKNPPLGFSFRKXYMQLDEGSLTFNANPDEGV
         250       260       270       280       290       300
NYFMSKGILDDSPKEIAKFIFCTRTLNWKKLRIYLDERRDVLDDLVTLHNFRNQFLPNAL
         310       320       330       340       350       360
REFFRHIHAPEERGEYLETLITKFSHRFCACNPDLMRELGLSPDAVYVLCYSLILLSIDL
         370       380       390       400       410       420
TSPHVKNKMSKREFIRNTRRAAQNISEDFVGHLYDNIYLIGHVAA*KAQLLGLQFLLQTK
         430       440       450       460       470       480
ATQGLSRYGGYISAGHCSLSIQSSFSVQPFFLLPFSILVISLGN*IILQNFS*FCLSRFA
         490       500       510       520       530       540
QSRATV*HSC*RMIN*HYTLKDGVFVH*ICLKNFIHFHSLYKYHVMCTYLTKEIYSHNYF
         550       560       570       580       590       600
IVKILTKVFPFLSN*VLKFI*F*SETIVXVKVRSDFRQKPIPASFSFKL*RVLICYYITM
         610       620       630       640       650
QNWQLFL*YKFII*FFILKTGLIKSR*VL*TI*DF*NIKIYDLHS*E*NKIXLELW
```

FIG. 11A

```
  10         20         30         40         50         60         70         80         90
GGAAACGTCAAAATTGGGATAGTCGGCAGTTCTCTGCCCCTGAGCTGAGGTACCCTGAGTTCTGAGCGGTCCTAGTGCTGCTGTTTCTGGTATTCTC 100        110        120        130        140        150        160        170        180
ATCGCGGTCACCTCTACCGGTGTGGACAAGTAAAGTTTGAATCAGCTTCTCCATGGCCTCGGCACCAGTTCCCGGCTGAGCCATTTTCCTTTG 190        200        210        220        230        240        250        260        270        280
GCTAAAACGTCCCCGCCCAGAGCGCCAATTCGTCGCGCGGCGGTGGAGATCGCAGGTGCTCACGCTTGCAGATGGGTCAAGGGTTGTGGAGAGT 290        300        310        320        330        340        350        360        370
GGTCAGAAACCAGCAGCTGCAACAAGAGGCTACAGTGAGCAAGGCTACCTCACGAGACGAGAGAATGCTGCGAGCAACATTCT 380        390        400        410        420        430        440        450        460        470
AACACCCATCATCGTAAACAAGTCCAAGGAGGCATTGACATATCATCTTTTGAAGGCAAGGAAATCGAAAGAACAGGAAGGATTCATTAATT 480        490        500        510        520        530        540        550        560
TGGAAATGTTGCCCTCCTGAGCTAAGCTTTACCATCTGTCCTACCTGAAATGCAACTGACCTTTGCTTGCCTTCATGTGTTGCCAGGACCTTGC 570        580        590        600        610        620        630        640        650
GAATGATGAACTTCTCGGCAAGGGTTGTGCAAATCCACTTGGGGTCACTGTTCCATATACAATAAGAACCCACCTTTAGGATTTTCTTTTAGA 660        670        680        690        700        710        720        730        740        750
AAAKTGTATATGCAGCTGGATGAAGGCAGCCTCACCTTTAATGCCAACCCAGATGAGGGAGTGAACTACTTTATGTCCAAGGGTATCCTGGATC 760        770        780        790        800        810        820        830        840
ATTCGCCAAAGGAAATAGCAAAGTTTATCTTCTGTACAAGAACACTACAATTGGAAAAAACTGAGAAGTCATCTTGATGAAGGAGAGATGCTT 850        860        870        880        890        900        910        920        930        940
GGATGACCTTGTAACATTGCATAATTTTAGAAATCAGTTCTTGCCAAATGCACTGAGAGAATTTTTCGTCATATCCATGCCCTGAAGAGGCGT
```

FIG. 11B

```
     950       960       970       980       990      1000      1010      1020      1030
GGAGAGTATCTGAAACTCTTATAACAAAGTTCTCACATAGATTCTGTGCTTGCAACCTGATTAATGCGAGAACTTGGCCTTAGTCCTGATG 1040      1050      1060      1070      1080      1090      1100      1110      1120
CTGTCTATGTACTGTGCTACTCTTTGATTCTACTTTCCATTGACCTCACTAGCCCTCATGTGAAGAATAAAATGTCAAAAGGGAATTTATTCG 1130      1140      1150      1160      1170      1180      1190      1200      1210      1220
AAATACCCGTGCGCTGCTCAAAATATTAGTGAAGATTTGTAGGGCATCTTTATGACAATATCTACCTTATTGCCATGTGGCTGCATAAAAA 1230      1240      1250      1260      1270      1280      1290      1300      1310
CCACAATTCCTAGCACTTCAGTTTTTTACTTCAGACTAAAACTACCAAGGACTTACCACAGATATGGGTTACATCAGTCGTCATTGTAGCC 1320      1330      1340      1350      1360      1370      1380      1390      1400      1410
TGAGTATACAATCAAGTTCAGTGTGCAACCTTTTTTCTTTTTGCCATTTCTATTTTAGTAATTTCCTGGGAACTAAATAATTTTGCAGAA 1420      1430      1440      1450      1460      1470      1480      1490      1500
TTTTTCCTAATTTTGTTTATCACGTTTTATGCACAAAGCAGAGCCACTGTCTAACAGCTGTTAACGAATGATAAACTGACATTATACTCTAAA 1510      1520      1530      1540      1550      1560      1570      1580      1590
GATGGTGTATTGTGCATTAGATTGCCTGAAAAACTTTATCCATTTCATTCCATTCTTTATACAAATACCATGTAATGTGTACATATTTAACTAAAG 1600      1610      1620      1630      1640      1650      1660      1670      1680      1690
AGATTTATAGTCATAATTATTTATTGTAAAGATTTTAACTAAAGTTTTTCCTTTCTCAAACTGAGTTCTGAAATTTATTTGATTCTGATC

FIG. 11C
```

```
       1700      1710      1720      1730      1740      1750      1760      1770      1780
TGAAACTATTGTCTYCGTAAAAGTTAGATCTGACTTCAGRCAGAAAACCAATACCAGCTTCCTTTCCTTAAACTTTGAAGACTGTTGATTTCT 1790      1800      1810      1820      1830      1840      1850      1860      1870      1880
TACTATATTACTATGCAAAACTGCCAGTTATTTTTTATAATAAATTTATAATTTGATTTTTTTATTTAAAAACTGGTTAATCAACTCTCGGT 1890      1900      1910      1920      1930      1940      1950      1960      1970
AAGTCCCTTTAAAACCATTAGGATTTTAAAACATCAAAATTTATGATTTACATTCATACGAATAAAAATATYATTAGAACTCTCGGT
```

FIG. 11D

```
         10        20        30        40        50        60
MAAAAVDSAMEVVPALAEEAAPEVAGLSCLVNLPGEVLEYILCCGSLTAADIGRVSSTCR 70        80        90       100       110       120
RLRELCQSSGKVWKEQFRVRWPSLMKHYSPTDYVNWLEEYKVRQKAGLEARKIVASFSKR 130       140       150       160       170       180
FFSEHVPCNGFSDIENLEGPEIFFEDELVCILNMEGRKALTWKYYAKKILYYLRQQKILN 190       200       210       220       230       240
NLKAFLQQPDDYESYLEGAVYIDQYCNPLSDISLKDIQAQIDSIVELVCKTLRGINSRHP 250       260       270       280       290       300
SLAFKAGESSMIMEIELQSQVLDAMNYVLYDQLKFKGNRMDYYNALNLYMHQVLIRRTGI 310       320       330       340       350       360
PISMSLLYLTIARQLGVPLEPVNFPSHFLLRWCQGAEGATLDIFDYIYIDAFGKGKQLTV 370       380       390       400       410       420
KECEYLIGQHVTAALYGVVNVKKVLQRMVGNLLSLGKREGIDQSYQLLRDSLDLYLAMYP 430       440       450       460       470       480
DQVQLLLLQARLYFHLGIWPEKVLDILQHIQTLDPGQHGAVGYLVQHTLEHIERKKEEVG 490       500       510       520       530       540
VEVKLRSDEKHRDVCYSIGLIMKHKRYGYNCVIYGWDPTCMMGHEWIRNMNVHSLPHGHH 550       560       570       580       590       600
QPFYNVLVEDGSCRYAAQENLEYNVEPQEISHPDVGRYFSEFTGTHYIPNAELEIRYPED 610       620
LEFVYETVQNIYSAKKENIDE
```

FIG. 12A

FIG.12B

```
      1400       1410       1420       1430       1440       1450       1460       1470       1480       1490       1500       1510       1520
CTGGTGCAGCACACTCTAGAGCACATTGAGCCCAACAAAAGGAGGAGCTGGGCTAGAGGTGAAGCTGGGCTCCGATGAGAAGCACAGAGATGTCTGCTACTCCATGGGCTCATTATGAAGCATAAGAGGTATGGCTATA 1530       1540       1550       1560       1570       1580       1590       1600       1610       1620       1630       1640       1650       1660
ACTGTGATCTACCGGCTGGGACCCCACCTGCTGGACATGAACGTGGATCCGGAACAGTGGACATGACGGACCGGAAACGGAATCCAGCCTTTCTATAACGTGCTGGTGAGGACGGCTCCTGTGCATAAGC 1670       1680       1690       1700       1710       1720       1730       1740       1750       1760       1770       1780       1790       1800
AGCCCAAGAAAACTTGGAATATAACGTGGAGCCTGCAGCAAATCTCACACCCCTGAGCTGGGAGCCGGCTATTCTCAGAGCTTTACTGGCACTCACTACATCCCAAACGCAGAGTCCGAGATCCGTATCCAGAAGATCTGGAG 1810       1820       1830       1840       1850       1860       1870       1880       1890       1900       1910       1920       1930       1940
TTGTCTATGAAACGTCCAGAATATTACAGTGCAAAGAAACGAGAACATAGTGAGTGACACATTGCCACTCTTTGCTGCTGCTCTATCTTCCAAGAGAACGGGACTCCCGAAGAGACGTCTCCACC 1950       1960       1970       1980       1990       2000       2010       2020       2030       2040       2050       2060       2070       2080
GACCCCTCCGGACCCTGCTGCAGGAAAGCCACTCCACCACTGCTGGTGCCTCCTACTAAGTTAAATACCCTGCAAAGACAATCTTGCTCTCCCAGCTGCAAGACTACTAGTAATAATCGA 2090       2100       2110       2120       2130       2140       2150       2160       2170       2180       2190       2200       2210       2220
AAGGCACTGTGTCAGTGCCATGGCATCGTCTGTATCGTCTGTGGTGACAGTTGTGACACATCTGTCTCTCAGATGAGTCTCATGACTCGAAGCACCTGAATCATTGTATTCACTCACTGTCTGTGTCTGCATT 2230       2240       2250       2260       2270       2280       2290       2300       2310       2320       2330       2340       2350       2360
GTCTCAGAACATTCCTTGGCTGACACAATGGGGTTATGCATTGCAATAATTCCTCTGCGATTCCTCTGCGAATAATTCCTTCGAAGCACTGTCTGCTCTTTTACCCTGAAGTTAGTTGCATATTCAGAGG 2370       2380       2390       2400       2410       2420       2430       2440       2450       2460       2470       2480       2490       2500
GTCTCAGAACATTCCTTGGCTGCTATCTTGGCAGCATCTTAGAGATCTTAACAAGCTAATGCATTGAATTTGAATATATGAAACACAGATTTCAAGTGTTTATCTGTTTTTTTTTAAATTTA 2510       2520       2530       2540       2550       2560       2570       2580       2590       2600       2610       2620       2630       2640
TAAAGTTGTGTCGTATCTTCCATTGCCACATCTCCTCTCTCTCCATATTCCCTATATAAATCATTATTTTCTATTTCATTTATTACATAAAATCTTTATTACATAAAATAGTGAACTTGTGAAATGCAATTTTC 2650       2660       2670       2680       2690       2700       2710       2720       2730       2740       2750       2760       2770       2780
AATGGGAATATAACACAGTTTCCCTCCATATTCCCTCTCTCTGCAGTTTATGCACATCTCTATAAATCATTATTTTTAAAAAAATCTACTCTTCAGTCATGAGTAGTCTTACATCATCAGTGATGGGTCTTTTTCTAGTCACATACAAATCGATGCTTTTC

2780
CATACTCATCTACAGTACTTTAAATGACTACTTTATTTTTAATTTAAAAATCTACTCTTCAGTCATGAGTAGTCTTACATCATCAGTGATGGGTCTTTTTCTAGTCACATACAAATCGATGCTTAATGT
```

FIG.12C

```
     2790      2800      2810      2820      2830      2840      2850      2860      2870      2880      2890      2900      2910
TTGCTCTTAGAAGTCATACTCCATGCTCTTCAAACACCAAAAATCAGGTTTTCCCTTTGTAATCAGGAAAAAAAAATTAATGAACCTTAAAAAAAAAAGGTTTGAAGGGAAAAAAGTGGTTTCACACCT 2920      2930      2940      2950      2960      2970      2980      2990      3000      3010      3020      3030      3040      3050
CTTGTTATTCCTTAGAGTCACTTCAAGGCCTGCAGGCCTGCCAGGTTAGAACAGAGAGAATGTCTTTCATTTGAAAGCAGAGAGAATGTCTCGACTTGGACTCTGAAAGCAGCTCGCCGTGTTGGAATCTGCTTTTCAAGCCCCAG 3060      3070      3080      3090      3100      3110      3120      3130      3140      3150      3160      3170      3180      3190
GCTCCTGACGGCCACGAGCACCAAGCCTGTCTGCGGCTCTTCTGGGCTCTTCTGGGCTCTTCGGCCGTGTGTTCGGACGGCACTGGCTCCTTTCCGAAGCCTGAGCCCAGAGTAACTGAGACGCCTTTGTGCAGCTCTGA 3200      3210      3220      3230      3240      3250      3260      3270      3280      3290      3300      3310      3320      3330
GCTCACCAACTCTCGGCCTGCCAGTTCTCCAAGCCAGCTAATCTCTGCATTAATCGATAGAAGCTAACTTCCGAAGTTAGGACCCTAGTTACTTTGCTCTCAACATTTAAAATAATGCAGTTGCTCTAGTGAATGGGGCG 3340      3350      3360      3370      3380      3390      3400      3410      3420      3430      3440      3450      3460      3470
TTAGGGCCCTGTCTGTCTGACCTGTGTCTGCCATCTGCATGCAGTATTCTCACCCATGTGAATGCCTGCTGCTGCTGTTTACCCTTTGGAAAGCCCTGGGGTGACCAAGCGTTTGGAAAGCCACCTGAGACCACTTCATAGCAA 3480      3490      3500      3510      3520      3530      3540      3550      3560      3570      3580      3590      3600      3610
CGGAAGGCTTAACCAGTTACTAGAAAGAGAATGGGAGTTCGCCCCTGCCCTCCTCCACCCTGAATCATCAGTGCCTATTTAATCCTCAGTGTCCATCCAGTCAAATCAAATCAGTCAGTCAAAGTCAAAGGATTCAAACTGCCATCTGGAA 3620      3630      3640      3650      3660      3670      3680      3690      3700      3710      3720      3730      3740      3750
ACGTAACCACTCACAGCACCTGGCCCGCCAAGGTTGGGAGGATTGTACTACTCTTTCATTTAAAGGGGAAAGTTGATAATACGGAAATTAATTAATGAATGAGATGCATTAATAAGAACCTGAATGCATGCTAGAGTT 3760      3770      3780      3790      3800      3810      3820      3830      3840      3850      3860      3870      3880      3890
GCAATTGTTGGTTTCTGGTTTGATTGATTCATTCCTTTTTCTTAGACACATCAAAGTCAAGAAGATGGTTTTACCTTTACTGACCCACTGTACATATGTATCTAGACTGTATCTAGACTGTTTAAATGTCTTTCTTGATGAATGCTT 3900      3910      3920      3930      3940      3950      3960      3970      3980      3990      4000      4010      4020      4030
GCCAATTGTGTTGGTTTCTGGTTTGATTGATTCATTCCTTTTTCTTAGACACATCAAAGTCAAGAAGATGGTTTTACCTTTACTGACCCACTGTACATATGTATCTAGACTGTTTAAATGTCTTTCTTGATGAATGCTT 4040      4050      4060      4070      4080      4090      4100      4110      4120      4130      4140      4150      4160
CATGGGGCTCCAGGAACCTCCAGGAAGCCTGTATCACCTGTGTAAGTGGTATTTGGCCACTTTGGATCCTGTACTCTATAATTTCTAAAAACGTGTTTGGATCCTGTACTCTATAATCATACATTATCATTCTTTAAAAATTTTCAAAACTTTCTCCAT

4160
TTAAAAAGCCCTGTTATAAACGTTGAACTTCACAATGTTAAAATGTAAAATATTTGGATATACCAACTTCTTTCTCTTCAAATGCCAAGCATTTTTTTGTACAATGATTAATAAAATGAACTTATCCAGAG
```

FIG. 12D

```
          10        20        30        40        50        60
RSTGFRRAGEEWSR*XLA*SPGXLRRPAXTFVLSNLAEVVERVLTFLPAKALLRVACVCR
          70        80        90
LWRECVRRVLRTHRSVTWISAGLAEAGHLXGH
```

FIG. 13A

```
          10        20        30        40        50        60
CCGTAGTACTGGNTTCCGGCGGGCTGGTGAGGAATGGAGCCGGTAGNTGCTTGCGGCGAG
          70        80        90       100       110       120
TCCCGGGNTCCTCCGTAGACCCGCGGANACCTTCGTGTTGAGTAACCTGGCGGAGGTGGT
         130       140       150       160       170       180
GGAGCGTGTGCTCACCTTCCTGCCCGCCAAGGCGTTGCTGCGGGTGGCCTGCGTGTGCCG
         190       200       210       220       230       240
CTTATGGAGGGAGTGTGTGCGCAGAGTATTGCGGACCCATCGGAGCGTAACCTGGATCTC
         250       260       270
CGCAGGCCTGGCGGAGGCCGGCCACCTGGNGGGGCATT
```

FIG. 13B

```
         10        20        30        40        50        60
RPRPVQQQQQQPPQQPPPQPPQQQPPQQQPPPPPQQQQQQQPPPPPPPPPPLPQERNNVG
```

```
         70        80        90       100       110       120
ERDDDVPADMVAEESGPGAQNSPYQLRRKTLLPKRTACPTKNSMEGASTSTTENFGHRAK
```

```
        130       140       150       160       170       180
RARVSGKSQDLSAAPAEQYLQEKLPDEVVLKIFSYLLEQDLCRAACVCKRFSELANDPNL
```

```
        190
WKRLYMEVFEYTRPMMH
```

FIG. 14A

```
         10        20        30        40        50        60
GCGGCCGCGCCCGGTGCAGCAACAGCAGCAGCAGCCCCCGCAGCAGCCGCCGCCGCAGCC
```

```
         70        80        90       100       110       120
GCCCCAGCAGCAGCCGCCCCAGCAGCAGCCTCCGCCGCCGCCGCAGCAGCAGCAGCAGCA
```

```
        130       140       150       160       170       180
GCAGCCTCCGCCGCCGCCACCGCCGCCTCCGCCGCTGCCTCAGGAGCGGAACAACGTCGG
```

```
        190       200       210       220       230       240
CGAGCGGGATGATGATGTGCCTGCAGATATGGTTGCAGAAGAATCAGGTCCTGGTGCACA
```

```
        250       260       270       280       290       300
AAATAGTCCATACCAACTTCGTAGAAAAACTCTTTTGCCGAAAAGAACAGCGTGTCCCAC
```

```
        310       320       330       340       350       360
AAAGAACAGTATGGAGGGCGCCTCAACTTCAACTACAGAAAACTTTGGTCATCGTGCAAA
```

```
        370       380       390       400       410       420
ACGTGCAAGAGTGTCTGGAAAATCACAAGATCTATCAGCAGCACCTGCTGAACAGTATCT
```

```
        430       440       450       460       470       480
TCAGGAGAAACTGCCAGATGAAGTGGTTCTAAAAATCTTCTCTTACTTGCTGGAACAGGA
```

```
        490       500       510       520       530       540
TCTTTGTAGAGCAGCTTGTGTATGTAAACGCTTCAGTGAACTTGCTAATGATCCCAATTT
```

```
        550       560       570       580       590
GTGGAAACGATTATATATGGAAGTATTTGAATATACTCGCCCTATGATGCAT
```

FIG. 14B

```
         10        20        30        40        50        60
RPRPGLRGGRAPCEVTMEAGGLPLELWRMILAYLHLPDLGRCSLVCRAWYELILSLDSTR 70        80        90       100       110       120
WRQLCLGCTECRHPNWPNQPDVEPESWREAFKQHYLASKTWTKNALDLESSICFSLFRRR 130       140       150       160       170
RERRTLSVGPGREFDSLGSALAMASLYDRIVLFPGVYEEQGEIILKVPVEIVGQGKLG
```

FIG.15A

```
         10        20        30        40        50        60
GCGGCCGCGGCCCGGACTCCGCGGTGGGCGAGCGCCCTGTGAGGTGACCATGGAGGCTGG 70        80        90       100       110       120
TGGCCTCCCCTTGGAGCTGTGGCGCATGATCTTAGCCTACTTGCACCTTCCCGACCTGGG 130       140       150       160       170       180
CCGCTGCAGCCTGGTATGCAGGGCCTGGTATGAACTGATCCTCAGTCTCGACAGCACCCG 190       200       210       220       230       240
CTGGCGGCAGCTGTGTCTGGGTTGCACCGAGTGCCGCCATCCCAATTGGCCCAACCAGCC 250       260       270       280       290       300
AGATGTGGAGCCTGAGTCTTGGAGAGAAGCCTTCAAGCAGCATTACCTTGCATCCAAGAC 310       320       330       340       350       360
ATGGACCAAGAATGCCTTGGACTTGGAGTCTTCCATCTGCTTTTCTCTATTCCGCCGGAG 370       380       390       400       410       420
GAGGGAACGACGTACCCTGAGTGTTGGGCCAGGCCGTGAGTTTGACAGCCTGGGCAGTGC 430       440       450       460       470       480
CTTGGCCATGGCCAGCCTGTATGACCGAATTGTGCTCTTCCCAGGTGTGTACGAAGAGCA 490       500       510       520       530
AGGTGAAATCATCTTGAAGGTGCCCTGTGGAGATTGTAGGGCAGGGGAAGTTGGGTGA
```

FIG.15B

```
          10         20         30         40         50         60
ETETAPLTLESLPTDPLLLILSFLDYRDLINCCYVSRRLSQLSSHDPLWRRHCKKYWLIS 70         80         90        100        110        120
EEEKTQKNQCWKSLFIDTYSDVGRYIDHYAAIKKASGMISRNIWSPGVLGWVLSLKEGCS 130        140        150        160        170        180
RGRPRCCGSADWAASFLDDYRCSYRIHNGQKLVGSWGYWEAWHCLITIVLKIC*TSIQLP 190        200        210        220        230        240
EIPAETGTEILSPFNFCIHTGLSQYIAVEAAEG*NKNEVFYQCQTVERVFKYGIKMCSDG

250
CINGMH*VFS
```

FIG.16A

```
         10        20        30        40        50        60
GAGACCGAGACGGCGCCGCTGACCCTAGAGTCGCTGCCCACCGATCCCCTGCTCCTCATC 70        80        90       100       110       120
TTATCCTTTTTGGACTATCGGGATCTAATCAACTGTTGTTATGTCAGTCGAAGATTAAGC 130       140       150       160       170       180
CGCTATCAAGTCATGATCCGCTGTGGAGAAGACATTGCAAAAAATACTGGCTGATATCT 190       200       210       220       230       240
GAGGAAGAGAAAACACAGAAGAATCAGTGTTGGAAATCTCTCTTCATAGATACTTACTCT 250       260       270       280       290       300
GATGTAGGAAGATACATTGACCATTATGCTGCTATTAAAAAGGCCTCGGGAATGATCTCA 310       320       330       340       350       360
AGAAATATTTGGAGCCCAGGTGTCCTCGGATGGGTTTTATCTCTGAAAGAGGGGTGCTCG 370       380       390       400       410       420
AGAGGAAGACCTCGATGCTGTGGAAGCGCAGATTGGGCTGCAAGTTTCCTGGACGATTAT 430       440       450       460       470       480
CGATGTTCATACCGAATTCACAATGGACAGAAGTTAGTTGGTTCCTGGGGTTATTGGGAA 490       500       510       520       530       540
GCATGGCACTGTCTAATCACTATCGTTCTGAAGATTTGTTAGACGTCGATACAGCTGCCG 550       560       570       580       590       600
GAGATTCCAGCAGAGACAGGGACTGAAATACTGTCTCCCTTTAACTTTTGCATACATACT 610       620       630       640       650       660
GGTTTGAGTCAGTACATAGCAGTGGAAGCTGCAGAGGGTTGAAACAAAAATGAAGTTTTC 670       680       690       700       710       720
TACCAATGTCAGACAGTAGAACGTGTGTTTAAATATGGCATTAAGATGTGTTCTGATGGT 730       740       750
TGTATAAATGGCATGCATTAGGTATTTTCAG
```

FIG. 16B

```
        10        20        30        40        50        60
GSGFRAGGWPLTMPGKHQHFQEPEVGCCGKYFLFGFNIVFWVLGALFLAIGLWAWGEKGV 70        80        90       100       110       120
LSNISALTDLGGLDPVWLVCGSWRRHVGAGLCWAAIGALRENTFLLKFFXXFLGLIFFLE

LA
```

FIG.17A

```
        10        20        30        40        50        60
GGCTCCGGTTTCCGGGCCGGCGGGTGGCCGCTCACCATGCCCCGGNAAGCACCAGCATTTC 70        80        90       100       110       120
CAGGAACCTGAGGTCGGCTGCTGCGGGAAATACTTCCTGTTTGGCTTCAACATTGTCTTC 130       140       150       160       170       180
TGGGTGCTGGGAGCCCTGTTCCTGGCTATCGGCCTCTGGGCCTGGGGTGAGAAGGGCGTT 190       200       210       220       230       240
CTCTCGAACATCTCAGCGCTGACAGATCTGGGAGGCCTTGACCCCGTGTGGCTTGTTTGT 250       260       270       280       290       300
GGTAGTTGGAGGCGTCATGTCGGTGCTGGGCTTTGCTGGGCTGCAATTGGGGCCCTCCGG 310       320       330       340       350       360
GAGAACACCTTCCTGCTCAAGTTTTTCTNCGNGTTCCTCGGTCTCATCTTCTTCCTGGAG

CTGGCAAC
```

FIG.17B

```
        10        20        30        40        50        60
AAAAAAYLDELPEPLLLRVLAALPAAELVQACRLVCLRWKELVDGAPLWLLKCQQEGLVP 70        80        90       100       110       120
EGGVEEERDHWQQFYFLSKRRRNLLRNPCGEEDLEGWCDVEHGGDGWRVEELPGDSGVEF 130       140       150       160       170       180
THDESVKKYFASSFEWCRKAQVIDLQAEGYWEELLDTTQPAIVVKDWYSGRSDAGCLYEL 190       200       210       220       230       240
TVKLLSEHENVLAEFSSGQVAVPQDSDGGWMEISHTFTDYGPGVRFVRFEHGGQGSVYW

250
KGWFGARVTNSSVWVEP*
```

FIG. 18A

```
        10        20        30        40        50        60
GCGGCGGCCGCCGCCGCGTACCTGGACGAGCTGCCCGAGCCGCTGCTGCTGCGCGTGCTGGCCGCACTG
 70        80        90       100       110       120       130
CCGGCCGCCGAGCTGGTGCAGGCCTGCCGCCTGGTGTGCCTGCGCTGGAAGGAGCTGGTGGACGGCGCC
140       150       160       170       180       190       200
CCGCTGTGGCTGCTCAAGTGCCAGCAGGAGGGGCTGGTGCCCGAGGGCGGCGTGGAGGAGGAGCGCGAC
210       220       230       240       250       260       270
CACTGGCAGCAGTTCTACTTCCTGAGCAAGCGGCGCCGCAACCTTCTGCGTAACCCGTGTGGGGAAGAG
280       290       300       310       320       330       340
GACTTGGAAGGCTGGTGTGACGTGGAGCATGGTGGGGACGGCTGGAGGGTGGAGGAGCTGCCTGGAGAC
350       360       370       380       390       400       410
AGTGGGGTGGAGTTCACCCACGATGAGAGCGTCAAGAAGTACTTCGCCTCCTCCTTTGAGTGGTGTCGC
420       430       440       450       460       470       480
AAAGCACAGGTCATTGACCTGCAGGCTGAGGGCTACTGGGAGGAGCTGCTGGACACGACTCAGCCGGCC
490       500       510       520       530       540       550
ATCGTGGTGAAGGACTGGTACTCGGGCCGCAGCGACGCTGGTTGCCTCTACGAGCTCACCGTTAAGCTA
560       570       580       590       600       610       620
CTGTCCGAGCACGAGAACGTGCTGGCTGAGTTCAGCAGCGGGCAGGTGGCAGTGCCCCAAGCACAGTGAC
630       640       650       660       670       680       690
GGCGGGGGCTGGATGGAGATCTCCCACACCTTCACCGACTACGGGCCGGGCGTCCGCTTCGTCCGCTTC
700       710       720       730       740       750
GAGCACGGGGGGCAGGGCTCCGTCTACTGGAAGGGCTGGTTCGGGGCCCGGGTGACCAACAGCAGCGTG
760       770
TGGGTAGAACCCTGA
```

FIG.18B

```
         10         20         30         40         50         60
MGEKAVPLLRRRRVKRSCPSCGSELGVEEKRGKGNPISIQLFPPELVEHIISFLPVRDLV 70         80         90        100        110        120
ALGQTCRYFHEVCDGEGVWRRICRRLSPRLQDQDTKGLYFQAFGGRRRCLSKSVAPLLAH 130        140        150        160        170        180
GYRRFLPTKDHVFILDYVGTLFFLKNALVSTLGQMQWKRACRYVVLCRGAKDFASDPRCD 190        200        210        220        230        240
TVYRKYLYVLATREPQEVVGTTSSRACDCVEVYLQSSGQRVFKMTFHHSMTFKQIVLVGQ 250        260        270        280        290        300
ETQRALLLLTEEGKIYSLVVNETQLDQPRSYTVQLALRKVSHYLPHLRVACMTSNQSSTL

310
YVTDPILCSWLQPPWPGG
```

FIG. 19A

```
         10        20        30        40        50        60
ATGGGCGAGAAGGCGGTCCCTTTGCTAAGGAGGAGGCGGGTGAAGAGAAGCTGCCCTTCTTGTGGCTCG 70        80        90       100       110       120       130
GAGCTTGGGGTTGAAGAGAAGAGGGGGAAAGGAAATCCGATTTCCATCCAGTTGTTCCCCCCAGAGCTG 140       150       160       170       180       190       200
GTGGAGCATATCATCTCATTCCTCCCAGTCAGAGACCTTGTTGCCCTCGGCCAGACCTGCCGCTACTTC 210       220       230       240       250       260       270
CACGAAGTGTGCGATGGGGAAGGCGTGTGGAGACGCATCTGTCGCAGACTCAGTCCGCGCCTCCAAGAT 280       290       300       310       320       330       340
CAGGACACGAAGGGCCTGTATTTCCAGGCATTTGGAGGCCGCCGCCGATGTCTCAGCAAGAGCGTGGCC 350       360       370       380       390       400       410
CCCTTGCTAGCCCACGGCTACCGCCGCTTCTTGCCCACCAAGGATCACGTCTTCATTCTTGACTACGTG 420       430       440       450       460       470       480
GGGACCCTCTTCTTCCTCAAAAATGCCCTGGTCTCCACCCTCGGCCAGATGCAGTGGAAGCGGGCCTGT 490       500       510       520       530       540       550
CGCTATGTTGTGTTGTGTCGTGGAGCCAAGGATTTTGCCTCGGACCCAAGGTGTGACACAGTTTACCGT 560       570       580       590       600       610       620
AAATACCTCTACGTCTTGGCCACTCGGGAGCCGCAGGAAGTGGTGGGTACCACCAGCAGCCGGGCCTGT 630       640       650       660       670       680       690
GACTGTGTTGAGGTCTATCTGCAGTCTAGTGGGCAGCGGGTCTTCAAGATGACATTCCACCACTCAATG 700       710       720       730       740       750
ACCTTCAAGCAGATCGTGCTGGTTGGTCAGGAGACCCAGCGGGCTCTACTGCTCCTCACAGAGGAAGGA 760       770       780       790       800       810       820
AAGATCTACTCTTTGGTAGTGAATGAGACCCAGCTTGACCAGCCACGCTCCTACACGGTTCAGCTGGCC 830       840       850       860       870       880       890
CTGAGGAAGGTGTCCCACTACCTGCCCTCACCTGCGCGTGGCCTGCATGACTTCCAACCAGAGCAGCACC 900       910       920       930       940       950
CTCTACGTCACAGATCCTATTCTGTGCTCTTGGCTACAACCACCTTGGCCTGGTGGATGA
```

```
          10        20        30        40        50        60
RGGSEGRGRGREKRARGARRKRKQGGREARAADGEGGSGPGAEAGARTRPREEAEGGGSV 70        80        90       100       110       120
EEGARGIIKGDEGSVGAGKEAQGRKYGKEEWRVRARRREGARPGRVQGQGGQVWAYIPGT 130       140       150       160       170       180
GAAMAAAAREEEEEAARESAACPAAGPALWRLPEVLLLHMCSYLDMRALGRLAQVYRWLW 190       200       210       220       230       240
HFTNCDLLRRQIAWASLNSGFTRLGTNLMTSVPVKVSQNWIVGCCREGILLKWRCSQMPW 250       260       270       280       290       300
MQLEDDALYISQANFILAYQFRPDGASLNRQPLGVSAGHDEDVCHFVLATSHIVSAGGDG 310       320       330       340       350       360
KIGLGKIHSTFAAKYWAHEQEVNCVDCKGGIISFGSRDRTAKVWPLASGQLGQCLYTIQT 370       380       390       400       410       420
EDQIWSVAIRPLLSSFVTGTACCGHFSPLKIWDLNSGQLMTHLDRDFPPRAGVLDVIYES 430       440       450       460       470       480
PFALLSCGYDTYVRYWDCRTSVRKCVMEWEEPHNSTLYCLQTDGNHLLATGSSFYSVVRL 490       500       510       520       530
WDRHQRACPHTFPLTSTRLGSPVYCLHLTTKHLYAALSYNLHVLDIQNP*
```

FIG. 20A

```
  10         20         30         40         50         60         70         80         90
CCAGGGGGAAGCGGAAGGAGGGGGAAGAGGAAAAGCCAGCGGAGGAAGCCGAGAGGAGGAAGGCCAAGCCGGGGCCGAAGGAAGCCCGGGCCC
 100        110        120        130        140        150        160        170        180
CAGACGGCGAAGGAGGAGCAGCGGCCCGGGGGCTGAGCCGGAGCCCAAGAGAGACACCCCAAGAGAGGAACAGCAGAGGCGGAAGCGTGGAGGAAGG
 190        200        210        220        230        240        250        260        270        280
GGGCGAGAGGCATCATCAAAGGAGAGATGAGGGGCCAGCCGGGAGCGTAGGGGCCGGGAAAAGAGGCACAAGGAGAAGAAAGTATGGAAGGAGGAATGAGGGTCAGG
 290        300        310        320        330        340        350        360        370
GCTAGGCGGGAGGGCGCCAGGCCGGGAAGAGTACAAGACAAGGAGGTCAGGTTTGGGCCTACATCCGGGACAGGGGCCGGCCATCGCCG
 380        390        400        410        420        430        440        450        460        470
CGGCAGCAGGAGGAGGAGGAGGAGGCCGGAGTCAGCCCCCTGCCCGGCCTCTGGGGCCCAGCGCTCTGGGCCTCTGCGGAAGTGCTGCT
 480        490        500        510        520        530        540        550        560
CGGCACATGTGCTCCTACCTCGACATGCGGGGCCCCTCGGGGCCCCTGGCCCCCAGGTGTACGGCTGGCTGTGGCCACTTCACCAACTGCGACCTGCTC
 570        580        590        600        610        620        630        640        650
CCGGCCCAGATAGCCTGGGGCTCGCTCGGGAGGGGATTCTGCCTGAGAGTGAGTGCCACCAACCTGATGACCAGTCCCAGTGAAGGTGTCTCAGAACT
 660        670        680        690        700        710        720        730        740        750
GGATAGTGGGGTGCTGCCAGAGGGGATTCTGCCTGAAGTGCTTCCCACAGATGTGCCAGCTCAGCCTCAGCCTCGGAGTCTCTCGGAGTCAGATGCTAGAGATGATGCTTTGTACATATC
 760        770        780        790        800        810        820        830        840
CCAGGCTAATTTCATCCTGGCCTACCAGTTCCGTCCAGATGGTGCCAGCTTGAACCGTCAGCAGCCTCGGAGTCTCTCGGAGTCTCTGCTGGGCATGATGAGGAC
 850        860        870        880        890        900        910        920        930        940
GTTTGCCACTTTGTGCTGGCCACCCTCCACATATTGTCAGTGCTTGTAAGATTCACAGCACCACCTTCCGCCTGCTGCCA

FIG. 20B
```

```
       950      960      970      980      990      1000     1010     1020     1030
AGTACTGGGCTCATGAACAGGAGGTGAACTGTGTGGATTGCAAGGGGCATCATATCATTTGGCTCAGGGACAGGACGGCCAAGGTGTGGCC 1040     1050     1060     1070     1080     1090     1100     1110     1120
TTTGGCCTCAGGCCAGCTGGGGCAGTGTTTATACACCATCCAGAGACTGAAGACCAAATCTGGTCTGTTGCTATCAGGCCATTACTCAGCTCTTTT 1130     1140     1150     1160     1170     1180     1190     1200     1210     1220
GTGACAGGGACGGCTTGTTGTGGGCACTTTCTCACCCCTGAAAATCTGGGACCTCAACAGTGGGCAGCTGATGACACACTTGGACAGAGACTTTC 1230     1240     1250     1260     1270     1280     1290     1300     1310
CCCCAAGGGCTGGGGTGCTGGATGTCATATATGAGTCCCCTTTCGCACTGTCTCTCTGTGCTATGACACCTATGTTCGCTACTGGGACTGCCCG 1320     1330     1340     1350     1360     1370     1380     1390     1400     1410
CACCAGTGTCCGGGAAATGTGTCATGAGTGGAGGAGCCCTGCCTGAGCCCTGCAGACAGATGCCAACCACTTGCTTGCCACA 1420     1430     1440     1450     1460     1470     1480     1490     1500
GGTTCCTCCTTCTATAGCGGTTGTACGGCTGTGGGACGGCCACCAAAGGGGCTGCCCCACACCTTCCCGGCTGACGTGCACCCGGCTCGGCAGCC 1510     1520     1530     1540     1550     1560     1570     1580     1590
CTGTGTACTGCCTCACCACCAAGCATCTCAACTCTCTATGCTGGGCTGTCTTACACCTCCAGTCCTCGATATTCAAAACCCGTGA
```

FIG. 20C

```
         10        20        30        40        50        60
LILTSVLLFQRHGYCTLGEAFNRLDFSSAIQDIRTFNYVVKLLQLIAKSQLTSLSGVAQK 70        80        90       100       110       120
NYFNILDKIVQKVLDDHHNPRLIKDLLQDLSSTLCILIRGVGKSVLVGNINIWICRLETI 130       140       150       160       170       180
LAWQQQLQDLQMTKQVNNGLTLSDLPLHMLNNILYRFSDGWDIITLGQVTPTLYMLSEDR 190       200       210       220       230       240
QLWKKLCQYHFAEKQFCRHLILSEKGHIEWKLMYFALQKHYPAKEQYGDTLHFCRHCSIL 250       260       270
FWKDSGHPCTAADPDSCFTPVSPQHFIDLFKF
```

FIG.21A

```
         10         20         30         40         50         60
GCATTGCTATAATTTTACTATACTCTCATCTAAATCTAAAATCAGTCTTCAAAATAAAAACAAATTGTC 70         80         90        100        110        120        130
CTTTGCCAAAAATTTTTTTAATCGCACAATTAATTGACATTAACTGCCAATTCTTTTTGGCTAATTGAC 140        150        160        170        180        190        200
TAATTTTAACTTCTGTGTTGCTTTTCCAGAGGCATGGCTATTGCACCTTGGGAGAAGCCTTTAATCGGT 210        220        230        240        250        260        270
TAGACTTCTCAAGTGCAATTCAAGATATCCGAACGTTCAATTATGTGGTCAAACTGTTGCAGCTAATTG 280        290        300        310        320        330        340
CAAAATCCCAGTTAACTTCATTGAGTGGCGTGGCACAGAAGAATTACTTCAACATTTTGGATAAAATCG 350        360        370        380        390        400        410
TTCAAAAGGTTCTTGATGACCACCACAATCCTCGCTTAATCAAAGATCTTCTGCAAGACCTAAGCTCTA 420        430        440        450        460        470        480
CCCTCTGCATTCTTATTAGAGGAGTAGGGAAGTCTGTATTAGTGGGAAACATCAATATTTGGATTTGCC 490        500        510        520        530        540        550
GATTAGAAACTATTCTCGCCTGGCAACAACAGCTACAGGATCTTCAGATGACTAAGCAAGTGAACAATG 560        570        580        590        600        610        620
GCCTCACCCTCAGTGACCTTCCTCTGCACATGCTGAACAACATCCTATACCGGTTCTCAGACGGATGGG 630        640        650        660        670        680        690
ACATCATCACCTTAGGCCAGGTGACCCCCACGTTGTATATGCTTAGTGAAGACAGACAGCTGTGGAAGA 700        710        720        730        740        750
AGCTTTGTCAGTACCATTTTGCTGAAAAGCAGTTTTGTAGACATTTGATCCTTTCAGAAAAAGGTCATA 760        770        780        790        800        810        820
 TTGAATGGAAGTTGATGTACTTTGCACTTCAGAAACATTACCCAGCGAAGGAGCAGTACGGAGACACAC 830        840        850        860        870        880        890
TGCATTTCTGTCGGCACTGCAGCATTCTCTTTTGGAAGGACTCAGGACACCCCTGCACGGCGGCCGACC 900        910        920        930        940        950        960
CTGACAGCTGCTTCACGCCTGTGTCTCCGCAGCACTTCATCGACCTCTTCAAGTTTTAAGGGCTGCCCC
```

FIG.21B

```
        970       980       990      1000      1010      1020      1030
TGCCATCCCTATTGGAGATTGTGAATCCTGCTGTCTGTGCAGGGCTCATAGTGAGTGTTCTGTGAGGTG 1040      1050      1060      1070      1080      1090      1100
GGTGGAGACTCCTCGGAAGCCCCTGCTTCCAGAAAGCCTGGGAAGAACTGCCCTTCTGCAAAGGGGGGA 1110      1120      1130      1140      1150      1160      1170
CTGCATGGTTGCATTTTCATCACTGAAAGTCAGAGGCCAAGGAAATCATTTCTACTTCTTTAAAAACTC 1180      1190      1200      1210
CTTCTAAGCATATTAAAATGTGAAATTTTGCGTACTCTCTC
```

FIG. 21C

```
         10        20        30        40        50        60
YGSEGKGSSSISSDVSSSTDHTPTKAQKNVATSEDSDLSMRTLSTPSPALICPPNLPGFQ 70        80        90       100       110       120
NGRGSSTSSSSITGETVAMVHSPPPTRLTHPLIRLASRPQKEQASIDRLPDHSMVQIFSF 130       140       150       160       170       180
LPTNQLCRCARVCRRWYNLAWDPRLWRTIRLTGETINVDRALKVLTRRLCQDTPNVCLML 190       200       210       220       230       240
ETVTVSGCRRLTDRGLYTIAQCCPELRRLEVSGCYNISNEAVFDVVSLCPNLEHLDVSGC 250       260       270       280       290       300
SKVTCISLTREASIKLSPLHGKQISIRYLDMTDCFVLEDEGLHTIAAHCTQLTHLYLRRC 310       320       330       340       350       360
VRLTDEGLRYLVIYCASIKELSVSDCRFVSDFGLREIAKLESRLRYLSIAHCGRVTDVGI 370       380       390       400       410       420
RYVAKYCSKLRYLNARGCEGITDHGVEYLAKNCTKLKSLDIGKCPLVSDTGLECLALNCF 430       440       450       460       470       480
NLKRLSLKSCESITGQGLQIVAANCFDLQTLNVQDCEVSVEALRFVKRHCKRCVIEHTNP

AFF
```

FIG.22A

FIG.22B

```
1400       1410       1420       1430       1440       1450       1460       1470       1480       1490       1500       1510       1520
GCGCTTTGTCAAAGGCCCACTGCAAGCGCTGCCTCATCGACACCAACCCGGCCTTTCTTCTGAACGGACAGAGTTCATCCGGCCTTGTATTCACACAAACCTGAACAAGCAAATTTTTTAAAAGCAGCGTATGTAA 1530       1540       1550       1560       1570       1580       1590       1600       1610       1620       1630       1640       1650       1660
GCACCGACACCCACTCAAAACAGCTCTTTCTCCCGGAAGGTTATTAGGAATCGGCCTTTATTTTCTCATTTCTCATGGCAACAGAGCCCAAGAAACGACCAAGCACAAACGGCATTTTGGTCAGC 1670       1680       1690       1700       1710       1720       1730       1740       1750       1760       1770       1780       1790       1800
TCATTTGTAGGCCAGTTTCTTCTCACAAAACATGTACTTAAGCAGCTGATCGCTGTTCCTTGACCAAGCGGCTTACTCTCCCGCTCAGGCCGCTCAGGCGCCCGCCCCTTTCCCTCCGCACACACCAGCCCCACCCACAC 1810       1820       1830       1840       1850       1860       1870       1880       1890       1900       1910       1920       1930       1940
TTCACGCGCCCCCCCAAGGCCACACCCCCCTCCCTCCCAGAGCAGCCAGCGAGGATCCATCAGAATCACAGTGCTCTCCAGACCTCCTCTCAAACTGCTTCATTGACCTAAGTCACTCTCTTCAATCCACACCCA 1950       1960       1970       1980       1990       2000       2010       2020       2030       2040       2050       2060       2070       2080
TGACATTCTTGTCACTCAATACCATAGCACTTTGCATAGGCAAAATACTTTTCAGGCCTTTTTAAAAATTCATTACAGCAAACAGCTCGGGAAGGACATGCAGTCCTCCCCACCTCTGCAATGACTATGACCTT 2090       2100       2110       2120       2130       2140       2150       2160       2170       2180       2190       2200       2210       2220
GGCCAAACCACTTCACTGCTCTCGGGCTGCAGCTTCCAGCACTCAGAATCAGACCCACACAGCCCAAAGATTAGCTTCATGTCCATTATAGCATTGAGGACCAGAATACCCATACACAGAAGCCACCTTGGCATAGACCA 2230       2240       2250       2260       2270       2280       2290       2300       2310       2320       2330       2340       2350       2360
CCCAGGCCATCGACCACTCTCCAGGAGAACTGATTCTGTGGATGGATGCATTCAGGAGATAAGGGTCCTGCTCATGTCCTGTATGCATAAAGGGTCCTGCTCGTTTGGCTCGAAATCACCCACTTCCCTGTTTCAGTC 2370       2380       2390       2400       2410       2420       2430       2440       2450       2460       2470       2480       2490       2500
GGAGAATTTCCTCTCCCACCCCTCACCATCCCTCTTTTGCCAGGCTGGGATCTCTCTGCTGCTCTCGTACACAAATACTTCTGCCATTCCCCCCTCCACACCATCCTACGGAGCAGCACCAGCACCTAATCACAGCAAAGCCCA 2510       2520       2530       2540       2550       2560       2570       2580       2590       2600       2610       2620       2630       2640
GATCCCCCCATCAGTTGCCTTTTACTCAGTGTTTTCAAATAGGAGTAAAGGCCCTTGCAATTTTTAATTAACAAGCAAGGGCCAAGGGCCAAGGGAACACATGTCCTCAAAAGTTTTCTGATCCCTCGGCCTTGCACACCTGGCATG 2650       2660       2670       2680       2690       2700       2710       2720       2730       2740       2750       2760       2770       2780
CATCAGGCACACATGTCCTCCTACAGCTGGCAGAGATGCCGGTTCTTTGTCATTCAGATGCATTGACCTCTCATCATTATTCTTTATACATCCAGACTTCATCACATGAGCCTATTGGGGTTAAGTT
```

FIG.22C

```
2790    2800    2810    2820    2830    2840    2850    2860    2870    2880    2890    2900    2910
TGTAAGTGTTTAATTGTGTCAAAATTGCCACCTCCTGTGTACCTCCTGTGTCTCCTGCGTGTTTTCCACCAAAGAATGCAAAGCACACTTCCAGTGTGTTTAAATTCTGTCACTCAACAATGCCACATGGAATGGAACGACGG 2920    2930    2940    2950    2960    2970    2980    2990    3000    3010    3020    3030    3040    3050
GAACACACTGAGATGACTTAGACTCTCTGGTCCACCACCAGACCCTTGGAAAGGAATACTAAACTCATTACAAGGTATGGATTTTTAAATGAATGAAACTTCAAATTATCTCATTTGGATAACAAGTCTATATTCTAGCCTC 3060    3070    3080    3090    3100    3110    3120    3130    3140    3150    3160    3170    3180    3190
ATTTGCATGAAGTCAGATAGCCAGAAGAAATTCCATTGCTGCTGGTTTCCACGAAATTCACTGTCTCTTTTGCTAATAAACACATGCCCTTTCCCAGATTATTCTAGCCAAGCCCCACCTTGTTACGTTGAAATCCCTC 3200    3210    3220    3230    3240    3250    3260    3270    3280    3290    3300    3310    3320    3330
ATTTATTTCTTCTCAAATGCCCATTATCCCAAATCCAGAAGCCTCTGCATCTCCAAGCCACTCTGCAAACTTAGACACCCTTCAAACTTGCTGAATTTGTCTCAACACCTGAATGCTGAATTTTGTCTCTACTGTCGTCTTC 3340    3350    3360    3370    3380    3390    3400    3410    3420    3430    3440    3450    3460    3470
TGTGGGGATGGAGAGGTTAGTGTGATCAGTGGTGTCTCCCAGGAGGTTTCTTCAAACATCATGCCTCCCATCAATCAACATCATCAATTACAGTGTAATCAAGGCTCTGTGCCATGGGGAAATGAATCAT 3480    3490    3500    3510    3520    3530    3540    3550    3560    3570    3580    3590    3600    3610
TTACCTAGCTAGGGACCCAGGATCTAGTGTAAAGGCCACAGAGAGTTAAAACCATGAAGGCAGCAGATCCTCAGCGCTCCATTGAAGTTTCAGGATTTGGGTGTGACAAACGGATTGTCCCTAATCC 3620    3630    3640    3650    3660    3670    3680    3690    3700    3710    3720    3730    3740    3750
TTGGCCCCTGGGGTCTTCCGAGTGACCTGCTTTAATACTCTGAGAATGACCAGGAGATCCCAGAGAATGAATCCCTGACCGCATCACCTAAACTGTCTCTCCAAACATGTCTCCAAACATGACAAAGCTGACTGTTCACACTGATTGCCCA 3760    3770    3780    3790    3800    3810    3820    3830    3840    3850    3860    3870    3880    3890
GCACATACCCTCTTGCCAGTTCTTCTTCTTTCTCCCAGTCCTCCTGTTCATCCATTCGTTCTCGTTCTCCGTCTGGGGTCGAATCTATGAGGTTACTGCATGGAGGTTACTGGGGAAACAGCTCAGCAGATTTTGAGACCAAAGCTC 3900    3910    3920    3930    3940    3950    3960    3970    3980    3990    4000    4010    4020    4030
ACTAGGAAATTATCTGTTTTAAAACATTGCTTCCTTTCTCCTTCCTTCCTCGGCTCTCTGCTAAATTCAATGCTCTATGTGTGTGTTGTTGTTTTTTAAAATTCTAAGTTCAAATCACTGCGTGCTGATAATGAATGAATGGTC 4040    4050
CTACCAAGAAATAAAGCAATATGTTCGT
```

FIG. 22D

```
         10        20        30        40        50        60
AAAPAPAPAPTPTPEEGPDAGWGDRIPLEILVQIFGLLVAADGPMPFLGRAARVCRRWQE 70        80        90       100       110       120
AASQPALWHTVTLSSPLVGRPAKGGVKAEKKLLASLEWLMPNRFSQLQRLTLIHWKSQVH 130       140       150       160       170       180
PVLKLVGECCPRLTFLKLSGCHGVTADALVMLAKACCQLHSLDLQHSMVESTAVVSFLEE 190       200       210       220       230       240
AGSRMRKLWLTYSSQTTAILGALLGSCCPQLQVLEVSTGINRNSIPLQLPVEALQKGCPQ 250       260       270       280
LQVLRLLNLMWLPKPPGRGVAPGPGFPSLEELCLASSTCNFVS
```

FIG.23A

```
          10        20        30        40        50        60
TGCGGCCGCGCCCGCACCCGCACCGGCACCCACGCCCACGCCCGAGGAAGGGCCCGACGCGGGCTGGGG 70        80        90       100       110       120       130
AGACCGCATTCCCTTGGAAATCCTGGTGCAGATTTTCGGGTTGTTGGTGGCGGCGGACGGCCCCATGCC 140       150       160       170       180       190       200
CTTCCTGGGCAGGGCTGCGCGCGTGTGCCGCCGCTGGCAGGAGGCCGCTTCCCAACCCGCGCTCTGGCA 210       220       230       240       250       260       270
CACCGTGACCCTGTCGTCCCCGCTGGTCGGCCGGCCTGCCAAGGGCGGGGTCAAGGCGGAGAAGAAGCT 280       290       300       310       320       330       340
CCTTGCTTCCCTGGAGTGGCTTATGCCCAATCGGTTTTCACAGCTCCAGAGGCTGACCCTCATCCACTG 350       360       370       380       390       400       410
GAAGTCTCAGGTACACCCCGTGTTGAAGCTGGTAGGTGAGTGCTGTCCTCGGCTCACTTTCCTCAAGCT 420       430       440       450       460       470       480
CTCCGGCTGCCACGGTGTGACTGCTGACGCTCTGGTCATGCTAGCCAAAGCCTGCTGCCAGCTCCATAG 490       500       510       520       530       540       550
CCTGGACCTACAGCACTCCATGGTGGAGTCCACAGCTGTGGTGAGCTTCTTGGAGGAGGCAGGGTCCCG 560       570       580       590       600       610       620
AATGCGCAAGTTGTGGCTGACCTACAGCTCCCAGACGACAGCCATCCTGGGCGCATTGCTGGGCAGCTG 630       640       650       660       670       680       690
CTGCCCCCAGCTCCAGGTCCTGGAGGTGAGCACCGGCATCAACCGTAATAGCATTCCCCTTCAGCTGCC 700       710       720       730       740       750
TGTCGAGGCTCTGCAGAAAGGCTGCCCTCAGCTCCAGGTGCTGCGGCTGTTGAACCTGATGTGGCTGCC 760       770       780       790       800       810       820
CAAGCCTCCGGGACGAGGGGTGGCTCCCGGACCAGGCTTCCCTAGCCTAGAGGAGCTCTGCCTGGCGAG 830       840       850
CTCAACCTGCAACTTTGTGAGC
```

FIG.23B

```
        10         20         30         40         50         60
QHCSQKDTAELLRGLSLWNHAEERQKFFKYSVDEKSDKEAEVSEHSTGITHLPPEVMLSI 70         80         90        100        110        120
FSYLNPQELCRCSQVSMKWSQLTKTGSLWKHLYPVHWARGDWYSGPATELDTEPDDEWVK 130        140        150        160        170        180
NRKDESRAFHEWDEDADIDESEESAEESIAISIAQMEKRLLHGLIHNVLPYVGTSVKTLV 190        200        210        220        230        240
LAYSSAVSSKMVRQILELCPNLEHLDLTQTDISDSAFDSWSWLGCCQSLRHLDLSGCEKI 250        260        270        280        290        300
TDVALEKISRALGILTSHQSGFLKTSTSKITSTAWKNKDITMQSTKQYACLHDLTNKGIG 310        320        330        340        350        360
EEIDNEHPWTKPVSSENFTSPYVWMLDAEDLADIEDTVEWRHRNVESLCVMETASNFSCS 370        380        390        400        410        420
TSGCFSKDIVGLRTSVCWQQHCASPAFAYCGHSFCCTGTALRTMSSLPESSAMCRKAART 430        440        450        460        470        480
RLPRGKDLIYFGSEKSDQETGRVLLFLSLSGCYQITDHGLRVLTLGGGLPYLEHLNLSGC 490        500        510        520        530        540
LTITGAGLQDLVSACPSLNDEYFYYCDNINGPHADTASGCQNLQCGFRACCRSGE*PLTS 550        560        570        580        590
DLCLLHLAEQAFFHALYS*HISCVNHPFLSVTCFGPIXYNFRNLNYQXIVML
```

FIG.24A

```
  10         20         30         40         50         60         70         80         90
ACAACACTGCTCTCAGAAGGATACTGCAGAACTCCTTAGAGGTCTTAGCCTATGGAATCATGCTGAAGAGCCGACAGAATTTTTAAATATTCC 100        110        120        130        140        150        160        170        180
GTGGATGAAAAGTCAGATAAAGAAGCAGAAGTGTCAGAACACTCCAGAGTATAACCCATCTTCCTCCTGAGGTAATGCTGTCAATTTCAGCT 190        200        210        220        230        240        250        260        270        280
ATCTTAATCCTCAAGAGTTATGTCGATGCAGTCAAGTATGCTCAGTCAGTATGAAATGGTCTCAGCTGACAAAAACGGATCGCTTTGGAAACATCTTTACCC 290        300        310        320        330        340        350        360        370
TGTTCATTGGGCCAGAGGTGACTGGTATAGTGGTCCCGCAACTGAACTTGATACTGAACCTGATGATGAATGGTGAAAAATAGGAAAGATGAA 380        390        400        410        420        430        440        450        460        470
AGTCGTGCTCTTTCATGAGTGGGATGAAGATGCTGACATTGATGAATCTGAAGAGTCTGCGGAGGAATCAATTGCTATCAGCATTGCACAAATGG 480        490        500        510        520        530        540        550        560
AAAAACGTTTACTCCATGGCTTAATTCATAACGTTCTCTGTACTTCTGTAAAACCTTAGTATTAGCATACAGCTCTGCAGTTTC 570        580        590        600        610        620        630        640        650
CAGCAAAAATGGTTAGGCAGATTTTAGAGCTTTGTCCTAACCTGGAGCATCTGGATCTGTCTGGTTGTGAGAAATCACAGATCTTACCAGAGACTGACATTCTGCATTGACAGT 660        670        680        690        700        710        720        730        740        750
TGGTCTTGGCTTGGTTGCTGCCAGAGTCTTCGGCATCTTGATCTGTCTGGTTGTGAGAAATCACAGATGTGGCCCTAGAGAAGATTTCCAGAG 760        770        780        790        800        810        820        830        840
CTCTTGGAATTCTGACATCTCATCAAAGTGGCTTTTTGAAAACATCTACAAGCAAAATTACTTCAACTGCCTGAAAAATAAAGACATTACCAT 850        860        870        880        890        900        910        920        930        940
GCAGTCCACCAAGCAGTATGCCTGTGTTTGCACGATTTAACTAACAAGGGCATTGGAGAAGAAATAGATAATGAACACCCCTGGACTAAGCCTAAGCCTGTT
```

FIG. 24B

TCTTCTGAGAATTCACTTCTCTCCTTATGTGTGGATGTTAGATGCTGAAGATGCTGAAGATATTGAAGATACTGTGGAATGGAGACATAGAAATG

TTGAAAGTCTTTGTGTGTAATGGAAACAGCATCCAACTTTAGTTGTTCCACCTCTGGTTGTTTAGTAAGGACACATTGTTGGACTAAGGACTAGTGT

CTGTTGGCAGCAGCATTGTGCTTCTCCAGCTTTGCCTATTGTGGTCACTCATTTGTTGTGTACAGAACAGCTTAAGAACTATGTCATCACTC

CCAGAAATCTTCTGCAATGTGTAGAAAAGCAGCAAGGACTAGATTGCCTAGGGGAAAAGACTTAATTTACTTTGGGAGTGAAAAATCTGATCAAG

AGACTGGAGCTACTTCTGTTCTCAGTTTATCTGGATGTTATCAGATACAGACCATGTCTCAGGGTTTGACTCTGGGAGGAGGGCTGCC

TTATTTGGAGCACCTTAATCTCTCCTGGTCGTTGTCTGTGTCTTACTACTATAACTGGTGAGCCTGCAGGATTTGGTTGTTCAGCATGTCTTCTCTGAATGATGAA

TACTTTTACTACTGTGACAACATTAACGGTCCCTCATGCTGCACTTCATTAGCTGAGCAGGCTTTCTTCTTCATGCACTTTACTCATAGCACATTTCTTGTGT

CTGGCGAATGACCCTGACTTGTTTGGGCCCATNYTTACAACTTCAGAAATCTTAATTACCAGTGRATTGTAATGTTG

FIG. 24C

```
                10         20         30         40         50         60
      RVTSCCGLARCSSAMVFSNNDEGLINKKLPKELLLRIFSFLDIVTLCRCAQISKAWNILA 70         80         90        100        110        120
      LDGSNWQRIDLFNFQIDVEGRVVENISKRCVGFLRKLSLRGCIGVGDSSLKTFAQNCRNI 130        140        150        160        170        180
      EHLNLNGCTKITDSTCYSLSRFCSKLKHLXLTSCVSITNSSLKGISEGCRNLEYLNLSWC 190        200        210        220        230        240
      DQITKDGIEALVRGCRGLKALLLRGCTQLEDEALKHIQNYCHELVSLNLQSCSRITDEGV 250        260        270        280        290        300
      VQICRGCHRLQALCLSGCSNLTDASLTALGLNCPRLQILEAARCSHLTDAGFTLLARNCH 310        320        330        340        350        360
      ELEKMDLEXCILITDSTLIQLSIHCPKLQALSLSHCELIXDDGILHLSNSTCGHERLRVL 370        380        390        400        410        420
      ELDNCLLITDVALXHLENCRGLERLELYDCQQVTRAGIKRMRAQLPHVKVHAYFAPVTPP 430        440        450        460        470        480
      TAVAGSGQRLCRCCVIL*QQLPGPKG**GILSSRRPESS*PTPPSPNLLILHWERHLQFP 490        500        510        520        530        540
      NRHLSRFKNGEDKKGFISNI*HHIVT*NMALT*LVLLLPSSLMSSLTSTHLLL*YL*RLI

550
      ILKTDQTGPASKYINCVQ*
```

FIG.25A

```
         10         20         30         40         50         60         70         80         90
TTTTACTGTACACAGTTGATGATTGATATTTGATGCTGGGCCTGTCTGCTGGTCTGCTCTTGAGGATTATTAACCTTTAGAGGTATCAGAGAAGCAAATGGG 100        110        120        130        140        150        160        170        180
TACTGGTGAGGCTGCTCATTAGGGAAGAGGGCAAAGGAGCACTAGCTAGGTCAGAGCCATGTTCAGTCACAATGTGATGTCAGATGTTGCT 190        200        210        220        230        240        250        260        270        280
TATAAATCCTTTCTGCTTGCCATTCTTAAATCTTGATAGGTGCCTGTGGCAAACTGTAAATGCCTTTCCCAATGCAGAATCAACAGATTG 290        300        310        320        330        340        350        360        370
GGTGATGGTCGAGTCGGTCACGAAGACTCAGGTCTTCTAGAGAAGAAGATGCCTCATCACCCCTTNGGCCCAGGCAGCTGCTGTCAGAGAATGA 380        390        400        410        420        430        440        450        460        470
CACAGCACCTGCACAGTCGCCTGTCCACTTCCTGCCACTGCCTGTCGGTCGGTGACGGGACCAAAGTAGGCGTGGACTTTGACATGAGGCAGCTG 480        490        500        510        520        530        540        550        560
AGCCCGCATCCGGTGATGCCTGCACGGGTAACCTGCTGGCCAGTCGTACAGACTCGGAGGCCCTCCAGGCCTCGGCAGTTCTCTAGGTGTYCCAGG 570        580        590        600        610        620        630        640        650
GCCACATCAGTCAGTGATGAGGAGGCAGTTGTCCAACTCCAGTACCCGCAGCCTCATGGCCACAGTACTGTTGCTCAGGTGCAGGATCCCATCAT 660        670        680        690        700        710        720        730        740        750
CTGKGATGAGTTCACAGTGGACAGGCTCAGGGCCTTGCAGTTTAGGACAGTGAATGGAGAGCTGGATGAGTGCTGTCGGTTATCAGGATGCA 760        770        780        790        800        810        820        830        840
WTCTTCAAGATCCATCTTCTCCAATTCGTGCCAATTCGTGGCAATGGCTAAAAGTGTAAAACTCGCTCAGTCAAATGGAGCATCGGGAGCAGCCTCCAAA

FIG.25B
```

```
850      860        870        880        890        900        910        920        930        940
ATTTGCAGTCGCGGGACAGTTCAAACCCAGGCGTGTAAGAGAGGCATCTGTGAGGTTGCTGCAACCCGAAAGGCAGAGAGCCTGTAGCCGGTGAC 950        960        970        980        990       1000       1010       1020       1030
AGCCCCTGCATATCTGCACACACCTTCATCCGTGATACGTGAGCAGGACTGCAAGTTGAGGCTCACAAGCTCATGGCAGTAATTCTGAATGTG 1040       1050       1060       1070       1080       1090       1100       1110       1120
TTTCAGAGCTTCATCTCTAACTGTGTGCAGCCCCTCAGGACGCAGGGCTTTCAGGCCTCGACAACCTGCACCAGTCCTCGATGCCATCCTTC 1130       1140       1150       1160       1170       1180       1190       1200       1210       1220
GTGATCTGATCACACCAGAGAGGTTCAGGTACTCCAGGTTTCCGCAGCCCTCACTGATGATCCCTTCAAGGAGCTGTTTGTAATAGACACACGG 1230       1240       1250       1260       1270       1280       1290       1300       1310
AGGTCAGAWCCAGATGTTTCAGGTTCTGTGCAAGGTCTTGGAACAGAATCTGCTAAGGCTATAACACGTGCTGTCAGTGATTTTGTGCATCCATTGAGGTTCAAATG 1320       1330       1340       1350       1360       1370       1380       1390       1400       1410
TTCAATGTTTGGCAGTTCTGTGCAAAGGTCTTCAAGGAGGAATCCCAACACCAATGCAGCCTCGCAAGCTGAGCTTCCTCAGGAATCCAACG 1420       1430       1440       1450       1460       1470       1480       1490       1500
CATCCGCTTCGAGATATTTTCCACCACTGACCCTCTACATCTATTGAAAGTTAAAAAGATCTATTCTTTGCCAGTGTGCTTCATCCAGGGCTA 1510       1520       1530       1540       1550       1560       1570       1580       1590
AGATGTTCCAAGCCTTGGAAATCTGTGCACATGGCACAAAGTTACTATATCCAAGAGGAAAATATTCTTAACAGAAGTTCTTTGGGTAACTT 1600       1610       1620       1630       1640       1650       1660       1670       1680
TTTGTTAATAAGGCCTTCATCATTGTTTGAGAAAACCATGGCCGAGAGCCGGCGAGCCCACAGCCCGAGTCACACGGC
```

FIG.25C

```
         10         20         30         40         50         60
MSPVFPMLTVLTMFYYICLRRRARTATRGEMMNTHRAIESNSQTSPLNAEVVQYAKEVVD 70         80         90        100        110        120
FSSHYGSENSMSYTMWNLAGVPNVFPSSGDFTQTAVFRTYGTWWDQCPSASLPFKRTPPN 130        140        150        160        170        180
FQSQDYVELTFEQQVYPTAVHVLETYHPGAVIRILACSANPYSPNPPAEVRWEILWSERP 190        200        210        220        230        240
TKVNASQARQFKPCIKQINFPTNLIRLEVNSSLLEYYTELDAVVLHGVKDKPVLSLKTSL 250        260        270        280        290        300
IDMNDIEDDAYAEKDGCGMDSLNKKFSSAVLGEGPNNGYFDKLPYELIQLILNHLTLPDL 310        320        330        340        350        360
CRLAQTCKLLSQHCCDPLQYIHLNLQPYWAKLDDTSLEFLQSRCTLVQWLNLSWTGNRGF 370        380        390        400        410        420
ISVAGFSRFLKVCGSELVRLELSCSHFLNETCLEVISEMCPNLQALNLSSCDKLPPQAFN 430        440        450        460        470        480
HIAKLCSLKRLVLYRTKVEQTALLSILNFCSELQHLSLGSCVMIEDYDVIASMIGAKCKK 490        500        510        520        530        540
LRTLDLWRCKNITENGIAELASGCPLLEELDLGWCPTLQSSTGCFTRLAHQLPNLQKLFL 550        560        570        580        590        600
TANRSVCDTDIDELACNCTRLQQLDILGTRMVSPASLRKLLESCKDLSLLDVSFCSQIDN 610        620
RAVLELNASFPKVFIKKSFTQ
```

FIG. 26A

```
         10        20        30        40        50        60        70        80        90
ATGTCACCGGTCTTTCCATGTTAACAGTTCTGACCATGTTTATTATATGCCTTCGGCGCCGAGCCAGACAGCTACAAGAGGAGAAATGA 100       110       120       130       140       150       160       170       180
TGAACACCCATAGAGCTATAGAATCAAACAGCCAGACTTCCCCTCTCAATGCAGAGGTAGTGCCAAAGAAGTAGTGCATTCAGTTC 190      200       210       220       230       240       250       260       270       280
CCATTATGGAAGTGAGAATAGTATGTCCTATACTATGTGGAATTGGCTGGTGTACCAAATGTATTCCCAAGTTCTGGTGACTTACTCAGACA 290       300       310       320       330       340       350       360       370
GCTGTGTTTCGAACTTATGGGACATGGTGGATCAGTGTCCTAGTGCTTCCTTGCCATTCAAGAGGACGGCCACCTAATTTTCAGAGCCAGACT 380      390       400       410       420       430       440       450       460       470
AIGTGGAACTTACTTTTGAACAACAGGTGTATCCTACAGGTGTACATGTTCTAGAAACCTATCATCCCGAGCAGTCATTAGAATTCTGCCTTG 480       490       500       510       520       530       540       550       560
TTCTGCAAATCCTTATTCCCCAAATCCACCAGCTGAAGTAAGAGGAGATTCTTTGGTCAGAGAGACTACGAAGGTGAATGCTTCCAAGCT 570      580       590       600       610       620       630       640       650
CGGCCAGTTTAAACCTTGTATTAAGCAGATAAATTTCCCCACAAATCTTATACGACTGAAGTAAATAGTTCTCTCTGGAATATTACACTGAAT 660      670       680       690       700       710       720       730       740       750
TAGATGCAGTTGTGCTACATGGTGTGAAGGACAGTCTTAACAAAAGTTTAGCAGTGCTGTCCTCGGGGAAGGGCCAAATAATGGGTATTTTGATAAA 760       770       780       790       800       810       820       830       840
TGCAGAAAAGGAGATGGTTGTGTGGAATGGTAGCAGTCTTAACAAAAGTTTAGCAGTGCTGTCTCGGGGAAGGGCCAAATAATGGGTATTTTGATAAA 850      860       870       880       890       900       910       920       930       940
CTACCTTATGAGCTTATTCAGCTGATTCTGAATCATCTTACACTACCAGACCTGTGTAGATTAGCACACGACTTGCAAACTACTGAGCCAGCATT
```

FIG. 26B

```
 950      960      970      980      990      1000     1010     1020     1030
GCTGTGATCCTCTGCAATACATCCACCTCAATCTGCAACCATACTGGGCAAACTAGACACCTTCTCTGGAATTTCTACAGTCTCGCTGCAC 1040     1050     1060     1070     1080     1090     1100     1110     1120
TCTTGTCCAGTGGCTTAATTTATCTTGGACTGCAATAGAGGCTTCATCTCTGTGCAGGATTTAGCAGGTTTCTGAAGGTTTGTGGATCCGAA 1130     1140     1150     1160     1170     1180     1190     1200     1210     1220
TTAGTACGCCCTTGAATTGTCTTGCAGCCACTTCTTAATGAAACTTGCTTAGAAGTTATTTCTGAGATGTGTCCAAATCTACAGGCCTTAAATC 1230     1240     1250     1260     1270     1280     1290     1300     1310
TCTCCTCCTGTGATAAGCTACCACCTCAAGCTTTCAACCACATTGCCAAGTTATGCAGCCTTAAACGACTGTCTCTCTATCGAACAAAAGTAGA 1320     1330     1340     1350     1360     1370     1380     1390     1400     1410
GCAAACAGCACTGCTCAGCATTTTGAACTTCTGTCTTCAGAGCTTAGCACCTCAGTTAGGCAGTTGTGTCATGATTGAAGACTATGATGATA 1420     1430     1440     1450     1460     1470     1480     1490     1500
GCTAGCATGATAGGAGCCAAGTGTAAAAAACTCCGGACCCTGGATCTGTGGAGATGTAAGAATATTACTGAGAATGGAATAGCAGAACTGGCTT 1510     1520     1530     1540     1550     1560     1570     1580     1590
CTGGGTGTCCACTACTGAGGAGCTTGACCTTGGCTGGCTGGTGCCCAACTCTCGAGAGCAGCACCGGGTGCTCTTCACCAGACTGGCCACCAGCTCCC 1600     1610     1620     1630     1640     1650     1660     1670     1680     1690
AAACTTGCAAAAACTCTTCTTACGCTAATAGATCTGTGTGTGACACAGACATTGATGAATTGGCATGTAATTGTACCAGGTTACAGCAGCTG 1700     1710     1720     1730     1740     1750     1760     1770     1780
GACATATTAGGAACAAGAAATGTAGTCCGGCATCCTTAAGGAAATCCTGAATCTTGTAAAGATCTTTCTTTACTTGATGTGTCCTTCTGTT 1790     1800     1810     1820     1830     1840     1850     1860
CCCAGAGATTGATAACAGAGCGCTGTGCTAGAACTGAATGCAAGCTTTCCAAAAGTGTTCATAAAAAGAGCTTTACTCAGTGA
```

FIG.26C

```
            10        20        30        40        50        60
MQLVPDIEFKITYTRSPDGDGVGNSYIEDNDDDSKMADLLSYFQQQLTFQESVLKLCQPE 70        80        90       100       110       120
LESSQIHISVLPMEVLMYIFRWVVSSDLDLRSLEQLSLVCRGFYICARDPEIWRLACLKV 130       140       150       160       170       180
WGRSCIKLVPYTSWREMFLERPRVRFDGVYISKTTYIRQGEQSLDGFYRAWHQVEYYRYI 190       200       210       220       230       240
RFFPDGHVMMLTTPEEPQSIVPRLRTRNTRTDAILLGHYRLSQDTDNQTKVFAVITKKKE 250       260       270       280       290       300
EKPLDYKYRYFRRVPVQEADQSFHVGLQLCSSGHQRFNKLIWIHHSCHITYKSTGETAVS 310       320
AFEIDKMYTPLFFARVRSYTAFSERPL
```

FIG.27A

```
         10        20        30        40        50        60
ATGCAACTTGTACCTGATATAGAGTTCAAGATTACTTATACCCGGTCTCCAGATGGTGATGGCGTTGGA 70        80        90        100       110       120       130
AACAGCTACATTGAAGATAATGATGATGACAGCAAAATGGCAGATCTCTTGTCCTACTTCCAGCAGCAA 140       150       160       170       180       190       200
CTCACATTTCAGGAGTCTGTGCTTAAACTGTGTCAGCCTGAGCTTGAGAGCAGTCAGATTCACATATCA 210       220       230       240       250       260       270
GTGCTGCCAATGGAGGTCCTGATGTACATCTTCCGATGGGTGGTGTCTAGTGACTTGGACCTCAGATCA 280       290       300       310       320       330       340
TTGGAGCAGTTGTCGCTGGTGTGCAGAGGATTCTACATCTGTGCCAGAGACCCTGAAATATGGCGTCTG 350       360       370       380       390       400       410
GCCTGCTTGAAAGTTTGGGGCAGAAGCTGTATTAAACTTGTTCCGTACACGTCCTGGAGAGAGATGTTT 420       430       440       450       460       470       480
TTAGAACGGCCTCGTGTTCGGTTTGATGGCGTGTATATCAGTAAAACCACATATATTCGTCAAGGGGAA 490       500       510       520       530       540       550
CAGTCTCTTGATGGTTTCTATAGAGCCTGGCACCAAGTGGAATATTACAGGTACATAAGATTCTTTCCT 560       570       580       590       600       610       620
GATGGCCATGTGATGATGTTGACAACCCCTGAAGAGCCTCAGTCCATTGTTCCACGTTTAAGAACTAGG 630       640       650       660       670       680       690
AATACCAGGACTGATGCAATTCTACTGGGTCACTATCGCTTGTCACAAGACACAGACAATCAGACCAAA 700       710       720       730       740       750
GTATTTGCTGTAATAACTAAGAAAAAAGAAGAAAAACCACTTGACTATAAATACAGATATTTTCGTCGT 760       770       780       790       800       810       820
 GTCCCTGTACAAGAAGCAGATCAGAGTTTTCATGTGGGCTACAGCTATGTTCCAGTGGTCACCAGAGG 830       840       850       860       870       880       890
TTCAACAAACTCATCTGGATACATCATTCTTGTCACATTACTTACAAATCAACTGGTGAGACTGCAGTC 900       910       920       930       940       950       960
AGTGCTTTTGAGATTGACAAGATGTACACCCCCTTGTTCTTCGCCAGAGTAAGGAGCTACACAGCTTTC 970       980
TCAGAAAGGCCTCTGTAG
```

FIG.27B

```
          10        20        30        40        50        60
AALDPDLENDDFFVRKTGAFHANPYVLRAFEDFRKFSEQDDSVERDIILQCREGELVLPD 70        80        90       100       110       120
LEKDDMIVRRIPAQKKEVPLSGAPDRYHPVPFPEPWTLPPEIQAKFLCVLERTCPSKEKS 130       140       150       160       170       180
NSCRILVPSYRQKKDDMLTRKIQSWKLGTTVPPISFTPGPCSEADLKRWEAIREASRLRH 190       200       210       220       230       240
KKRLMVERLFQKIYGENGSKSMSDVSAEDVQNLRQLRYEEMQKIKSQLKEQDQKWQDDLA

250
KWKDRRKSYTSDLQK
```

FIG. 28A

```
         10        20        30        40        50        60
GCAGCCCTGGATCCTGACTTAGAGAATGATGATTTCTTTGTCAGAAAGACTGGGGCTTTCCATGCAAAT 70        80        90       100       110       120       130
 CCATATGTTCTCCGAGCTTTTGAAGACTTTAGAAAGTTCTCTGAGCAAGATGATTCTGTAGAGCGAGAT 140       150       160       170       180       190       200
 ATAATTTTACAGTGTAGAGAAGGTGAACTTGTACTTCCGGATTTGGAAAAAGATGATATGATTGTTCGC 210       220       230       240       250       260       270
 CGAATCCCAGCACAGAAGAAAGAAGTGCCGCTGTCTGGGGCCCCAGATAGATACCACCCAGTCCCTTTT 280       290       300       310       320       330       340
 CCCGAACCCTGGACTCTTCCTCCAGAAATTCAAGCAAAATTTCTCTGTGTACTTGAAAGGACATGCCCA 350       360       370       380       390       400       410
 TCCAAAGAAAAAAGTAATAGCTGTAGAATATTAGTTCCTTCATATCGGCAGAAGAAAGATGACATGCTG 420       430       440       450       460       470       480
 ACACGTAAGATTCAGTCCTGGAAACTGGGAACTACCGTGCCTCCCATCAGTTTCACNCCTGGCCCCTGC 490       500       510       520       530       540       550
 AGTGAGGCTGACTTGAAGAGATGGGAGGCCATCCGGGAGGCCAGCAGACTCAGGCACAAGAAAAGGCTG 560       570       580       590       600       610       620
 ATGGTGGAGAGACTCTTTCAAAAGATTTATGGTGAGAATGGGAGTAAGTCCATGAGTGATGTCAGCGCA 630       640       650       660       670       680       690
 GAAGATGTTCAAAACTTGCGTCAGCTGCGTTACGAGGAGATGCAGAAAATAAAATCACAATTAAAAGAA 700       710       720       730       740       750
 CAAGATCAGAAATGGCAGGATGACCTTGCAAAATGGAAAGATCGTCGAAAAAGTTACACTTCAGATCTG

760
 CAGAAG
```

FIG.28B

```
   1 MAGPQMGGSA EDHPPRKRHA AEKQKKKTVI YTKCFEFESA
  41 TQRPIDRQRY DENEDLSDVE EIVSVRGFSL EEKLRSQLYQ
  81 GDFVHAMEGK DFNYEYVQRE ALRVPLIFRE KDGLGIKMPD
 121 PDFTVRDVKL LVGSRRLVDV MDVNTQKGTE MSMSQFVRYY
 161 ETPEAQRDKL YNVISLEFSH TKLEHLVKRP TVVDLVDWVD
 201 NMWPQHLKEK QTEATNAIAE MKYPKVKKYC LMSVKGCFTD
 241 FHIDFGGTSV WYHVFRGGKI FWLIPPTLHN LALYEEWVLS
 281 GKQSDIFLGD RVERCQRIEL KQGYTFFIPS GWIHAVYTPV
 321 DSLVFGGNIL HSFNVPMQLR IYEIEDRTRV QPKFRYPFYY
 361 EMCWYVLERY VYCVTQRSHL TQEYQRESML IDAPRKPSID
 401 GFSSDSWLEM EEEACDQQPQ EEEEKDEEGE GRDRAPKPPT
 441 DGSTSPTSTP SEDQEALGKK PKAPALRFLK RTLSNESEES
 481 VKSTTLAVDY PKTPTGSPAT EVSAKWTHLT EFELKGLKAL
 521 VEKLESLPEN KKCVPEGIED PQALLEGVKN VLKEHADDDP
 561 SLAITGVPVV TWPKKTPKNR AVGRPKGKLG PASAVKLAAN
 601 RTTAGARRRR TRCRKCEACL RTECGECHFC KDMKKFGGPG
 641 RMKQSCIMRQ CIAPVLPHTA VCLVCGEAGK EDTVEEEGK
 681 FNLMLMECSI CNEIIHPGCL KIKESEGVVN DELPNCWECP
 721 KCNHAGKTGK QKRGPGFKYA SNLPGSLLKE QKMNRDNKEG
 761 QEPAKRRSEC EEAPRRSDE HSKKVPPDGL LRRKSDDVHL
 801 RKKRKYEKPQ ELSGRKRASS LQTSPGSSSH LSPRPPLGSS
 841 LSPWWRSSLT YFQQQLKPGK EDKLFRKKRR SWKNAEDRMA
 881 LANKPLRRFK QEPEDELPEA PPKTRESDHS RSSSPTAGPS
 921 TEGAEGPEEK KKVKMRRKRR LPNKELSREL SKELNHEIQR
 961 TENSLANENQ QPIKSEPESE GEEPKRPPGI CERPHRFSKG
1001 LNGTPRELRH QLGPSLRSPP RVISRPPSV  SPPKCIQMER
1041 HVIRPPPISP PPDSLPLDDG AAHVMHREVW MAVFSYLSHQ
1081 DLCVCMRVCR TWNRWCCDKR LWTRIDLNHC KSITPLMLSG
1121 IIRRQPVSLD LSWTNISKKQ LSWLINRLPG LRDLVLSGCS
1161 WIAVSALCSS SCPLLRTLDV QWVEGLKDAQ MRDLLSPPTD
1201 NRPGQMDNRS KLRNIVELRL AGLDITDASL RLIIRHMPLL
1241 SKLHLSYCNH VTDQSINLLT AVGTTTRDSL TEINLSDCNK
1281 VTDQCLSFFK RCGNICHIDL RYCKQVTKEG CEQFIAEMSV
1321 SVQFGQVEEK LLQKLS
```

Figure 29A

```
   1 ATGGCGGGTC CGCAAATGGG GGGATCTGCA GAGGATCACC CCCCACGAAA AAGACATGCA
  61 GCAGAAAAGC AAAAAAAGAA AACAGTTATA TATACAAAAT GCTTTGAATT TGAGTCGGCC
 121 ACACAGCGCC CGATTGACCG CCAGCGATAC GACGAGAACG AGGACTTGTC GGACGTGGAG
 181 GAGATCGTCA GCGTCCGCGG CTTCAGCCTG GAGGAGAAGC TTCGCAGCCA GCTGTACCAG
 241 GGGGACTTCG TGCACGCCAT GGAGGGCAAA GATTTCAACT ATGAGTACGT ACAGAGAGAA
 301 GCTCTCAGGG TTCCCCTGAT ATTTCGAGAA AAGGATGGAC TGGGAATTAA GATGCCTGAC
 361 CCTGATTTCA CAGTCCGAGA CGTCAAACTC CTAGTGGGGA GCCGGCGGCT TGTGGACGTG
 421 ATGGATGTGA ACACCCAGAA GGGCACGGAG ATGAGCATGT CCCAGTTTGT GCGTTACTAC
 481 GAGACGCCCG AGGCCCAGCG GGACAAGCTG TACAACGTCA TCAGCCTAGA GTTCAGCCAC
 541 ACCAAGCTGG AGCACTTGGT CAAGCGTCCG ACTGTGGTAG ACCTGGTGGA CTGGGTGGAC
 601 AACATGTGGC CCCAGCATCT GAAGGAGAAG CAGACAGAAG CCACGAACGC CATTGCAGAG
 661 ATGAAGTACC CGAAAGTGAA AAAGTACTGT CTGATGAGCG TGAAAGGTTG TTTCACCGAC
 721 TTCCACATCG ACTTTGGAGG CACTTCCGTT TGGTACCATG TTTTCCGGGG TGGGAAGATT
 781 TTTTGGCTGA TTCCTCCAAC GCTGCACAAT TTGGCGCTGT ACGAGGAGTG GGTGCTGTCA
 841 GGCAAACAGA GTGACATCTT TCTGGGAGAC CGTGTGGAAC GATGCCAAAG AATTGAGCTG
 901 AAGCAGGGCT ACACATTTTT CATCCCTTCC GGTTGGATCC ATGCCGTCTA CACCCTGTA
 961 GACTCTTTGG TGTTCGGCGG AAACATCCTG CACAGCTTTA ACGTGCCCAT GCAGCTGCGG
1021 ATCTACGAGA TCGAGGACAG GACGCGGGTG CAGCCCAAAT TCCGTTACCC CTTCTACTAT
1081 GAGATGTGCT GGTATGTCCT GGAGAGATAC GTGTACTGTG TGACCCAGCG CTCCCACCTC
1141 ACTCAGGAAT ACCAGAGGGA GTCGATGCTT ATTGATGCCC CGAGGAAGCC CAGCATAGAC
1201 GGCTTCTCTT CGGATTCCTG GCTGGAGATG GAGGAGGAGG CCTGTGATCA GCAGCCTCAG
1261 GAGGAGGAGG AGAAGGACGA GGAGGGCGAG GGCAGGGACA GGGCACCCAA ACCGCCCACC
1321 GATGGCTCCA CTTCACCCAC CAGCACGCCC TCTGAGGACC AGGAGGCCCT CGGGAAGAAG
1381 CCCAAAGCAC CTGCCCTGCG ATTCCTCAAA AGGACTTTGT CTAATGAGTC GGAGGAAAGT
1441 GTGAAGTCCA CCACATTGGC CGTAGACTAC CCCAAGACCC CCACCGGCTC TCCCGCCACG
1501 GAGGTCTCTG CCAAATGGAC CCATCTCACT GAGTTTGAAC TGAAGGGCCT GAAAGCTCTG
1561 GTGGAGAAAC TGGAATCCCT CCCGGAGAAC AAGAAGTGTG TCCCCGAGGG CATCGAGGAC
1621 CCCCAGGCAC TCCTGGAGGG TGTGAAGAAC GTCCTGAAGG AGCACGCAGA TGATGACCCT
1681 AGTCTGGCCA TCACTGGGGT CCCTGTGGTG ACTTGGCCAA AGAAGACTCC AAAGAACCGG
1741 GCTGTGGGTC GGCCCAAGGG GAAGCTGGGC CCGGCCTCCG CGGTGAAGTT GGCCGCCAAC
1801 CGGACAACGG CAGGAGCTCG GCGGCGCCGG ACGCGATGCC GCAAGTGCGA GGCCTGCCTG
1861 CGGACCGAGT GCGGAGAGTG CCACTTCTGC AAGGACATGA AGAAGTTCGG GGGCCCCGGG
1921 CGCATGAAGC AGAGCTGCAT CATGCGGCAG TGCATCGCGC CAGTGCTGCC CCACACCGCC
1981 GTGTGCCTTG TGTGTGGCGA GGCGGGGAAG GAAGACACGG TGAAGAGGA GGAAGGCAAG
2041 TTTAACCTCA TGCTCATGGA GTGTCCAATC TGCAATGAAA TCATCCACCC TGGATGCCTT
2101 AAGATTAAGG AGTCAGAGGG TGTGGTCAAC GACGAGCTTC CAAACTGCTG GGAGTGTCCG
2161 AAGTGTAACC ACGCCGGCAA GACCGGGAAA CAAAAGCGTG CCCTGGCTT TAAGTACGCC
2221 TCCAACCTGC CCGGCTCCCT GCTCAAGGAG CAGAAGATGA ACCGGGACAA CAAGGAAGGG
2281 CAGGAACCTG CCAAGCGGAG GAGTGAGTGT GAGGAGGCGC CCCGGCGCAG GTCGGATGAG
2341 CACTCGAAGA AGGTGCCGCC GGACGGCCTT CTGCGCAGAA AGTCTGACGA CGTGCACCTG
2401 AGGAAGAAGC GGAAATACGA GAAGCCCCAG GAGCTGAGTG ACGCAAGCG GGCCTCATCG
2461 CTTCAAACGT CCCCCGGTTC CTCCTCTCAC CTCTCGCCGA GGCCCCCTCT AGGCAGCAGC
2521 CTCAGCCCCT GGTGGAGATC CAGTCTCACT TACTTCCAGC AGCAGCTCAA ACCTGGCAAA
2581 GAAGATAAGC TTTTCAGGAA AAAGCGCGGG TCCTGGAAGA ACGCCGAGGA CCGCATGGCG
2641 CTGGCCAACA AGCCCCTCCG GCGCTTCAAG CAGGAACCCG AGGACGAACT GCCCGAGGCG
2701 CCCCCCAAGA CCAGGGAGAG CGACCACTCC CGCTCCAGCT CCCCCACCGC GGGACCCAGC
2761 ACCGAAGGGG CCGAGGGCCC GGAGGAGAAG AAGAAGGTGA AGATGCGCCG GAAGCGGCGG
2821 CTTCCCAACA AGGAGCTGAG CAGGGAGCTG AGCAAGGAGC TCAACCACGA GATCCAGAGG
2881 ACGGAGAACA GCCTGGCCAA CGAGAACCAG CAGCCCATCA AGTCGGAGCC TGAGAGCGAG
```

Figure 29B(I)

```
2941 GGCGAGGAGC CCAAGCGGCC CCCGGGCATC TGCGAGCGTC CCCACCGCTT CAGCAAGGGG
3001 CTCAACGGCA CCCCCCGGGA GCTGCGGCAC CAGCTGGGGC CCAGCCTGCG CAGCCCGCCC
3061 CGTGTCATCT CCCGGCCCCC ACCCTCCGTG TCCCGCCCCA AGTGTATCCA GATGGAGCGC
3121 CATGTGATCC GGCCACCCCC CATCAGCCCC CCGCCTGACT CGCTACCCCT GGACGATGGG
3181 GCAGCCCACG TCATGCACAG GGAGGTGTGG ATGGCCGTCT TCAGCTACCT CAGCCACCAA
3241 GACCTGTGTG TGTGCATGCG GGTCTGCAGG ACCTGGAACC GCTGGTGCTG CGATAAGCGG
3301 TTGTGGACCC GCATTGACCT GAACCACTGC AAGTCTATCA CACCCCTGAT GCTGAGTGGC
3361 ATCATCCGGC GACAGCCCGT CTCCCTCGAC CTCAGCTGGA CCAATATCTC CAAGAAGCAG
3421 CTGAGCTGGC TCATCAACCG GCTGCCTGGG CTCCGGGACT TGGTGCTGTC AGGCTGCTCA
3481 TGGATCGCGG TCTCGGCCCT TTGCAGCTCC AGTTGTCCGC TGCTCCGGAC CCTGGATGTC
3541 CAGTGGGTGG AGGGACTAAA GGATGCCCAG ATGCGGGATC TCCTGTCCCC GCCCACAGAC
3601 AACAGGCCAG GTCAGATGGA CAATCGGAGC AAGCTCCGGA ACATCGTGGA GCTGCGCCTG
3661 GCAGGCCTGG ACATCACAGA TGCCTCCCTG CGGCTCATCA TCCGCCACAT GCCCCTGCTC
3721 TCCAAGCTCC ACCTCAGTTA CTGTAACCAC GTCACCGACC AGTCTATCAA CCTGCTCACT
3781 GCTGTTGGCA CCACCACCCG AGACTCCTTA ACCGAGATCA ACCTGTCTGA CTGCAATAAG
3841 GTCACTGATC AGTGCCTGTC CTTCTTCAAA CGCTGTGGAA ACATCTGTCA TATTGACCTG
3901 AGGTACTGCA AGCAAGTCAC CAAGGAAGGC TGTGAGCAGT TCATAGCCGA GATGTCTGTG
3961 AGTGTCCAGT TTGGGCAAGT AGAAGAAAAA CTCCTGCAAA AACTGAGTTA G
```

Figure 29B(II)

```
   1 MEPEEERIRY SQRLRGTMRR RYEDDGISDD EIEGKRTFDL
  41 EEKLHTNKYN ANFVTFMEGK DFNVEYIQRG GLRDPLIFKN
  81 SDGLGIKMPD PDFTVNDVKM CVGSRRMVDV MDVNTQKGIE
 121 MTMAQWTRYY ETPEEEREKL YNVISLEFSH TRLENMVQRP
 161 STVDFIDWVD NMWPRHLKES QTESTNAILE MQYPKVQKYC
 201 LMSVRGCYTD FHVDFGGTSV WYHIHQGGKV FWLIPPTAHN
 241 LELYENWLLS GKQGDIFLGD RVSDCQRIEL KQGYTFVIPS
 281 GWIHAVYTPT DTLVFGGNFL HSFNIPMQLK IYNIEDRTRV
 321 PNKFRYPFYY EMCWYVLERY VYCITNRSHL TKEFQKESLS
 361 MDLELNGLES GNGDEEAVDR EPRRLSSRRS VLTSPVANGV
 401 NLDYDGLGKT CRSLPSLKKT LAGDSSSDCS RGSHNGQVWD
 441 PQCAPRKDRQ VHLTHFELEG LRCLVDKLES LPLHKKCVPT
 481 GIEDEDALIA DVKILLEELA NSDPKLALTG VPIVQWPKRD
 521 KLKFPTRPKV RVPTIPITKP HTMKPAPRLT PVRPAAASPI
 561 VSGARRRRVR CRKCKACVQG ECGVCHYCRD MKKFGGPGRM
 601 KQSCVLRQCL APRLPHSVTC SLCGEVDQNE ETQDFEKKLM
 641 ECCICNEIVH PGCLQMDGEG LLNEELPNCW ECPKCYQEDS
 681 SEKAQKRKME ESDEEAVQAK VLRPLRSCDE PLTPPPHSPT
 721 SMLQLIHDPV SPRGMVTRSS PGAGPSDHHS ASRDERFKRR
 761 QLLRLQATER TMVREKENNP SGKKELSEVE KAKIRGSYLT
 801 VTLQRPTKEL HGTSIVPKLQ AITASSANLR HSPRVLVQHC
 841 PARTPQRGDE EGLGGEEEEE EEEEEDDSA EEGGAARLNG
 881 RGSWAQDGDE SWMQREVWMS VFRYLSRREL CECMRVCKTW
 921 YKWCCDKRLW TKIDLSRCKA IVPQALSGII KRQPVSLDLS
 961 WTNISKKQLT WLVNRLPGLK DLLLAGCSWS AVSALSTSSC
1001 PLLRTLDLRW AVGIKDPQIR DLLTPPADKP GQDNRSKLRN
1041 MTDFRLAGLD ITDATLRLII RHMPLLSRLD LSHCSHLTDQ
1081 SSNLLTAVGS STRYSLTELN MAGCNKLTDQ TLIYLRRIAN
1121 VTLIDLRGCK QITRKACEHF ISDLSINSLY CLSDEKLIQK
1161 IS
```

Figure 30A

```
   1 ATGGAACCCG AAGAAGAAAG GATTCGTTAC AGCCAGAGAT TGCGTGGTAC CATGCGACGA
  61 CGCTATGAAG ATGATGGCAT TTCAGATGAT GAAATTGAAG GAAAAAGAAC TTTTGACTTG
 121 GAAGAGAAAC TGCACACCAA CAAATATAAT GCCAATTTTG TTACTTTTAT GGAAGGAAAA
 181 GATTTTAATG TAGAGTATAT TCAGCGGGGT GGCTTGAGAG ATCCTCTGAT TTTCAAGAAT
 241 TCTGATGGAC TCGGAATAAA AATGCCGGAT CCAGACTTCA CTGTGAATGA TGTCAAAATG
 301 TGTGTGGGGA GTCGTCGCAT GGTGGATGTC ATGGACGTGA ACACACAGAA AGGCATTGAA
 361 ATGACCATGG CTCAGTGGAC ACGCTACTAT GAGACCCCAG AGGAGGAGCG AGAGAAACTC
 421 TATAATGTCA TCAGCCTCGA GTTTAGCCAC ACCAGGCTGG AGAATATGGT GCAGAGGCCC
 481 TCCACGGTGG ATTTCATTGA CTGGGTAGAC AACATGTGGC CAAGGCACTT GAAGGAAAGC
 541 CAGACTGAAT CAACAAATGC CATCTTGGAG ATGCAGTACC CTAAAGTGCA GAAGTACTGT
 601 CTAATGAGTG TTCGAGGCTG CTATACTGAC TTCCATGTGG ACTTTGGTGG TACCTCTGTT
 661 TGGTATCACA TCCATCAAGG GGGAAAGGTC TTCTGGCTCA TCCCCCCTAC AGCCCACAAC
 721 CTGGAGCTGT ACGAGAATTG GCTGCTGTCA GGGAAACAGG GAGACATCTT TCTGGGTGAC
 781 CGGGTATCAG ATTGTCAGCG CATTGAGCTC AAGCAGGGCT ATACCTTCGT CATTCCCTCA
 841 GGCTGGATTC ATGCTGTGTA TACTCCTACA GACACATTAG TGTTTGGGGG CAATTTTTTG
 901 CATAGCTTCA ACATCCCTAT GCAGTTAAAA ATATACAACA TTGAAGATCG GACACGGGTT
 961 CCAAATAAGT TTCGCTATCC ATTCTACTAT GAGATGTGTT GGTATGTGTT GGAGCGCTAT
1021 GTGTACTGCA TAACCAACCG TTCCCACCTA ACTAAGGAAT TCAGAAAGA GTCCCTCAGC
1081 ATGGATTTGG AGTTAAATGG GTTGGAGTCT GGGAATGGGG ATGAGGAAGC AGTGGATCGA
1141 GAACCCCGAC GCTTGAGCAG CAGGCGTTCT GTCCTCACTA GCCCTGTAGC GAATGGAGTC
1201 AACCTGGATT ATGATGGACT GGGCAAAACC TGCCGAAGTC TTCCAAGTCT GAAGAAAACT
1261 TTGGCTGGGG ACTCATCTTC TGACTGTAGC CGGGGCTCCC ACAATGGACA AGTGTGGGAT
1321 CCCCAGTGTG CTCCCCGAAA GGACAGGCAA GTGCATCTGA CCCATTTTGA GCTTGAAGGC
1381 CTTCGCTGCC TTGTAGATAA GTTGGAGTCT CTGCCACTGC ACAAGAAATG TGTCCCCACA
1441 GGGATAGAAG ATGAAGATGC TCTCATTGCT GATGTAAAGA TTTTGCTGGA GGAGCTTGCC
1501 AACAGCGATC CAAGTTAGCC CCTCACTGGA GTTCCTATAG TACAGTGGCC AAAAAGGGAT
1561 AAGCTTAAAT TCCCCACTCG GCCAAAGGTG CGGGTTCCTA CCATCCCCAT TACGAAGCCT
1621 CACACTATGA AACCAGCTCC ACGGTTAACA CCTGTGAGGC CAGCTGCTGC CTCCCCGATT
1681 GTGTCAGGAG CCAGACGGAG ACGAGTGCGA TGTCGAAAAT GCAAAGCCTG TGTGCAAGGA
1741 GAGTGTGGTG TTTGCCACTA CTGCAGAGAC ATGAAGAAGT TTGGGGGGCC TGGACGCATG
1801 AAGCAGTCCT GTGTCCTCCG ACAGTGCTTG GCACCCAGAC TGCCTCACTC AGTCACATGT
1861 TCCCTCTGTG GAGAGGTGGA TCGAATGAA GAGACACAAG ACTTTGAGAA GAAACTCATG
1921 GAATGCTGTA TCTGCAATGA GATTGTTCAT CCTGGCTGCC TCCAGATGGA CGGAGAGGGG
1981 TTGCTTAACG AAGAATTGCC AAATTGCTGG GAATGTCCAA AGTGCTACCA GGAGGACAGC
2041 TCGGAGAAAG CCCAGAAGCG GAAAATGGAA GAGAGTGACG AAGAAGCTGT GCAAGCCAAA
2101 GTCCTGCGGC CCCTGCGGAG CTGCGATGAG CCTCTCACGC CCCGCCTCA TTCACCCACT
2161 TCCATGCTGC AGCTCATCCA TGACCCGGTT TCCCCCGGG GTATGGTGAC TCGGTCATCC
2221 CCTGGGGCTG GCCCCAGCGA CCACCACAGT GCCAGCCGCG ATGAGCGCTT CAAACGGCGG
2281 CAGTTGCTGC GGCTGCAGGC CACAGAGCGC ACCATGGTAC GGGAAAAGGA GAACAATCCC
2341 AGCGGCAAAA AGGAGCTGTC TGAAGTTGAG AAAGCCAAGA TCCGGGGATC GTACCTCACT
2401 GTCACGCTAC AGAGGCCCAC CAAAGAGCTC ACGGGACAT CCATTGTGCC CAAGCTGCAG
2461 GCCATCACGG CCTCCTCTGC CAACCTTCGC CATTCCCCC GTGTGCTAGT GCAGCACTGC
2521 CCAGCCCGAA CCCCCAGCG TGGGGATGAG GAGGGGCTGG GGGAGAGGA GGAGGAAGAG
2581 GAGGAGGAGG AGGAGGAAGA TGACAGTGCA GAGGAGGGG GTGCAGCCAG GCTGAATGGC
2641 CGGGGCAGTT GGGCTCAGGA TGGAGACGAA AGCTGGATGC AGCGGGAGGT CTGGATGTCT
2701 GTCTTCCGCT ACCTCAGCCG CAGAGAACTT TGTGAATGTA TGCGAGTGTG CAAGACGTGG
2761 TATAAATGGT GCTGCGACAA GAGACTTTGG ACAAAAATTG ACTTGAGTAG GTGTAAGGCC
2821 ATTGTGCCCC AGGCCCTCAG TGGCATCATC AAGAGGCAGC CAGTCAGCCT TGACCTCAGT
2881 TGGACCAACA TCTCTAAAAA GCAACTGACA TGGCTCGTCA ATAGGCTGCC AGGACTGAAA
2941 GACCTCCTCC TAGCAGGCTG CTCCTGGTCT GCAGTCTCTG CCCTCAGCAC CTCCAGCTGC
3001 CCCCTTCTCA GGACCCTTGA TCTTCGGTGG CAGTAGGAA TCAAGGACCC TCAAATTCGG
3061 GACTTGCTTA CTCCACCGGC TGATAAACCA GGTCAGGACA ATCGCAGCAA GCTCCGGAAC
3121 ATGACCGACT TCCGGCTGGC AGGCCTTGAC ATCACAGATG CCACGCTTCG CCTCATAATT
3181 CGCCACATGC CCTCCTGTC TCGACTCGAC CTCAGTCACT GCAGCCACCT TACAGATCAG
3241 TCCTCCAATC TACTCACTGC TGTCGGGTCT TCCACTCGCT ACTCTCTCAC AGAGCTCAAT
3301 ATGGCAGGTT GCAATAAATT GACAGACCAG ACCCTGATCT ACCTACGGCG CATTGCCAAC
3361 GTCACCTTGA TCGACCTTCG AGGATGCAAG CAGATCACTC GAAAAGCCTG CGAGCACTTC
3421 ATCTCAGACT TGTCCATCAA CAGCCTCTAC TGCCTGTCTG ACGAGAAGCT GATACAGAAG
3481 ATCAGCTAA
```

Figure 30B

```
  1 MATLVELPDS  VLLEIFSYLP  VRDRIRISRV  CHRWKRLVDD
 41 RWLWRHVDLT  LYTMRPKVMW  HLLRRYMASR  LHSLRMGGYL
 81 FSGSQAPQLS  PALLRALGQK  CPNLKRLCLH  VADLSMVPIT
121 SLPSTLRTLE  LHSCEISMAW  LHKQQDPTVL  PLLECIVLDR
161 VPAFRDEHLQ  GLTRFRALRS  LVLGGTYRVT  ETGLDAGLQE
201 LSYLQRLEVL  GCTLSADSTL  LAISRHLRDV  RKIRLTVRGL
241 SAPGLAVLEG  MPALESLCLQ  GPLVTPEMPS  PTEILSSCLT
281 MPKLRVLELQ  GLGWEGQEAE  KILCKGLPHC  MVIVRACPKE
321 SMDWWM
```

Figure 31A

```
  1 ATGGCGACTT TGGTCGAACT GCCGGACTCG GTCCTGCTCG AGATCTTCTC TTACCTCCCG
 61 GTACGGGACC GGATCCGCAT CTCCAGGGTC TGTCACCGCT GGAAGAGGCT GGTGGACGAC
121 CGGTGGCTGT GGCGACATGT CGACCTGACG CTCTACACGA TGCGACCTAA AGTCATGTGG
181 CACCTCCTTC GAAGGTACAT GGCATCCGG CTCCATTCCC TGCGGATGGG TGGCTACCTG
241 TTCTCTGGCT CCCAGGCCCC CCAGTTGTCC CCTGCTCTGT TGAGAGCCCT GGGCCAGAAG
301 TGCCCCAACC TGAAGCGCCT CTGCCTGCAC GTGGCCGACC TGAGCATGGT GCCCATCACC
361 AGCCTGCCCA GCACCTTGAG GACCCTGGAG CTGCACAGCT GCGAGATCTC CATGGCCTGG
421 CTCCACAAGC AGCAGGACCC CACCGTGCTG CCCCTGCTTG AATGCATCGT GCTGGACCGC
481 GTCCCCGCCT TCCGTGACGA GCACCTGCAG GGCCTGACGC GCTTCCGGGC CTTGCGCTCG
541 CTGGTGCTGG GTGGTACCTA CCGTGTGACC GAGACAGGGC TGGATGCTGG CCTGCAGGAG
601 CTCAGCTATC TGCAGAGGCT TGAGGTGCTG GCTGCACCC TGTCTGCCGA CAGCACCCTG
661 CTGGCCATCA GCCGCCACCT CCGAGATGTG CGCAAGATCC GGCTGACCGT GAGGGGCCTC
721 TCTGCCCCTG GCCTGGCTGT GCTGGAGGGA ATGCCGGCCC TGGAGAGTCT GTGCCTGCAG
781 GGTCCCCTCG TCACCCCAGA AATGCCCTCC CCCACTGAAA TCCTCTCCTC CTGCCTCACT
841 ATGCCCAAGC TCAGAGTCCT TGAGCTGCAG GGGCTGGGGT GGGAGGGTCA GGAGGCGGAG
901 AAGATCCTGT GTAAGGGGCT GCCCCACTGT ATGGTCATCG TCAGGGCTTG CCCCAAAGAG
961 TCTATGGACT GGTGGATGTA A
```

Figure 31B

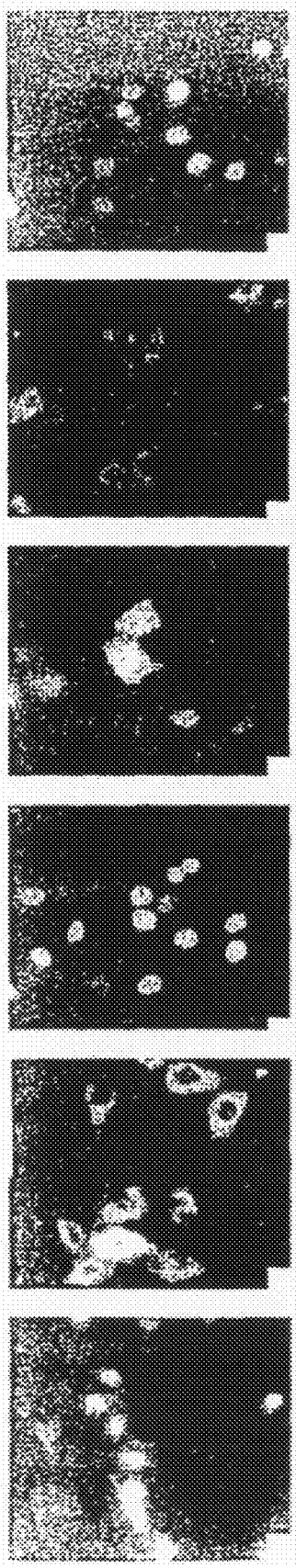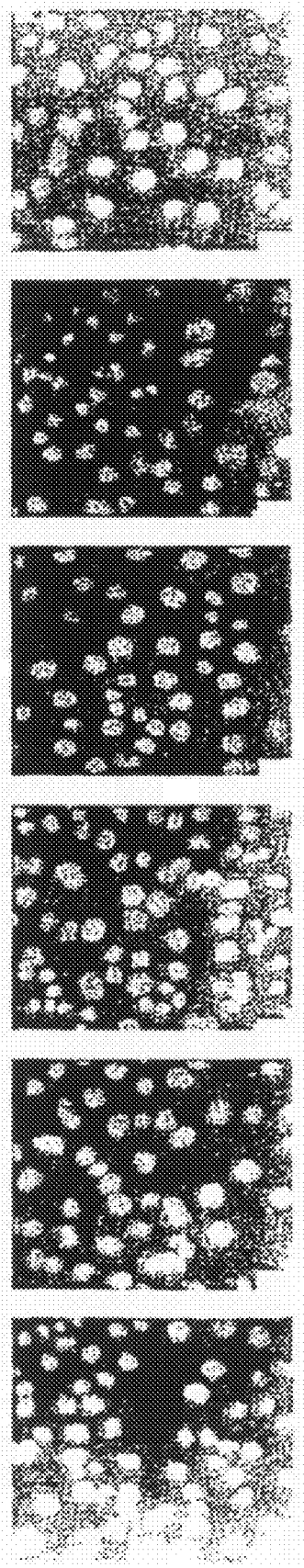

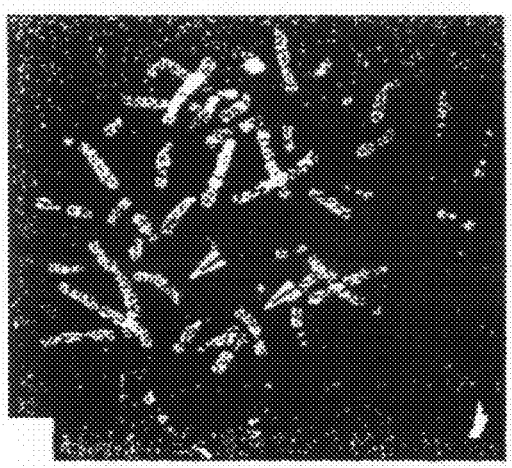 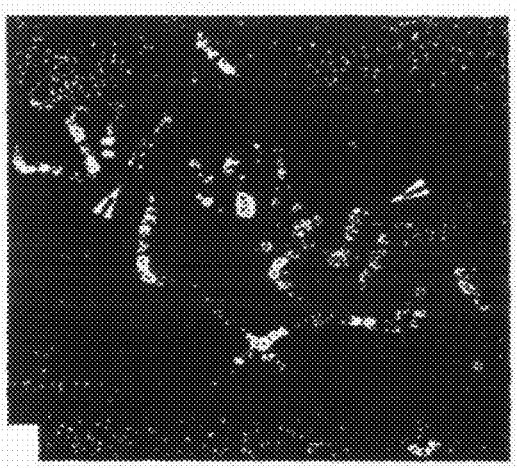
FIG. 37A    FIG. 37B
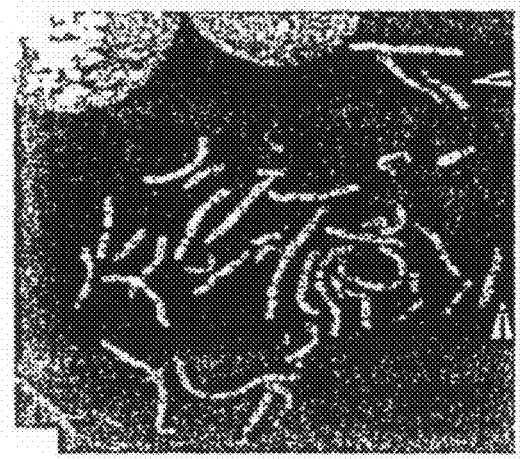 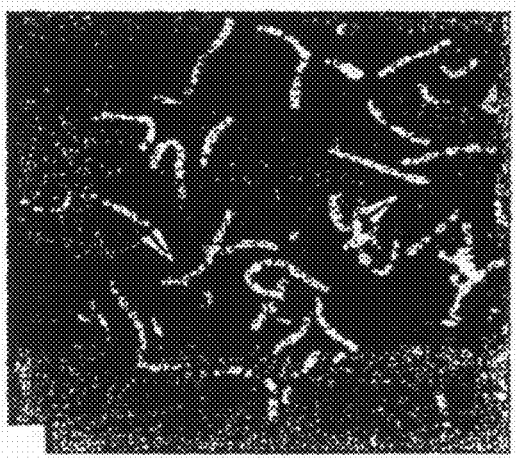
FIG. 37C    FIG. 37D
FIG. 37E

SEQUENCE LISTING

```
<160> NUMBER OF SEQ ID NOS: 99

<210> SEQ ID NO 1
<211> LENGTH: 2151
<212> TYPE: DNA
<213> ORGANISM: Homo sapiens

<400> SEQUENCE: 1
tgcgttggct gcggcctggc accaaagggg cggccccggc ggagagcgga cccagtggcc        60
tcggcgatta tggacccggc cgaggcggtg ctgcaagaga aggcactcaa gtttatgaat       120
```

```
tcctcagaga gagaagactg taataatggc gaaccccta ggaagataat accagagaag      180
aattcactta gacagacata caacagctgt gccagactct gcttaaacca agaaacagta      240
tgtttagcaa gcactgctat gaagactgag aattgtgtgg ccaaaacaaa acttgccaat      300
ggcacttcca gtatgattgt gcccaagcaa cggaaactct cagcaagcta tgaaaaggaa      360
aaggaactgt gtgtcaaata ctttgagcag tggtcagagt cagatcaagt ggaatttgtg      420
gaacatctta tatcccaaat gtgtcattac caacatgggc acataaactc gtatcttaaa      480
cctatgttgc agagagattt cataactgct ctgccagctc ggggattgga tcatatcgct      540
gagaacattc tgtcatacct ggatgccaaa tcactatgtg ctgctgaact tgtgtgcaag      600
gaatggtacc gagtgacctc tgatggcatg ctgtggaaga agcttatcga gaatggtc        660 aggacagatt ctctgtggag aggcctggca gaacgaagag gatggggaca gtatttattc      720
aaaaacaaac ctcctgacgg gaatgctcct cccaactctt tttatagagc actttatcct      780
aaaattatac aagacattga gacaatagaa tctaattgga gatgtggaag acatagttta      840
cagagaattc actgccgaag tgaaacaagc aaaggagttt actgtttaca gtatgatgat      900
cagaaaatag taagcggcct tcgagacaac acaatcaaga tctgggataa aaacacattg      960
gaatgcaagc gaattctcac aggccataca ggttcagtcc tctgtctcca gtatgatgag     1020
agagtgatca taacaggatc atcggattcc acggtcagag tgtgggatgt aaatacaggt     1080
gaaatgctaa acacgttgat tcaccattgt gaagcagttc tgcacttgcg tttcaataat     1140
ggcatgatgg tgacctgctc caaagatcgt tccattgctg tatgggatat ggcctccca     1200 actgacatta ccctccggag ggtgctggtc ggacaccgag ctgctgtcaa tgttgtagac     1260
tttgatgaca gtacattgt ttctgcatct ggggatagaa ctataaaggt atggaacaca     1320
agtacttgtg aatttgtaag gaccttaaat ggacacaaac gaggcattgc ctgtttgcag     1380
tacagggaca ggctggtagt gagtggctca tctgacaaca ctatcagatt atgggacata     1440
gaatgtggtg catgtttacg agtgttagaa ggccatgagg aattggtgcg ttgtattcga     1500
tttgataaca agaggatagt cagtggggcc tatgatggaa aaattaaagt gtgggatctt     1560
gtggctgctt tggaccccg tgctcctgca gggacactct gtctacggac ccttgtggag     1620
cattccggaa gagttttcg actacagttt gatgaattcc agattgtcag tagttcacat     1680
gatgacacaa tcctcatctg ggacttccta aatgatccag ctgcccaagc tgaacccccc     1740
cgttcccctt ctcgaacata cacctacatc tccagataaa taaccataca ctgacctcat     1800
acttgcccag gacccattaa agttgcggta tttaacgtat ctgccaatac caggatgagc     1860
aacaacagta acaatcaaac tactgcccag tttccctgga ctagccgagg agcagggctt     1920
tgagactcct gttgggacac agttggtctg cagtcggccc aggacggtct actcagcaca     1980
actgactgct tcagtgctgc tatcagaaga tgtcttctat caattgtgaa tgattggaac     2040 ttttaaaccct cccctcctct cctccttca cctctgcacc tagtttttc ccattggttc     2100 cagacaaagg tgacttataa atatatttag tgttttgcca gaaaaaaaa a                2151
```

<210> SEQ ID NO 2
<211> LENGTH: 569
<212> TYPE: PRT
<213> ORGANISM: Homo sapiens

<400> SEQUENCE: 2

```
Met Asp Pro Ala Glu Ala Val Leu Gln Glu Lys Ala Leu Lys Phe Met
 1               5                  10                  15
```

```
Asn Ser Ser Glu Arg Glu Asp Cys Asn Asn Gly Glu Pro Pro Arg Lys
            20                  25                  30

Ile Ile Pro Glu Lys Asn Ser Leu Arg Gln Thr Tyr Asn Ser Cys Ala
        35                  40                  45

Arg Leu Cys Leu Asn Gln Glu Thr Val Cys Leu Ala Ser Thr Ala Met
    50                  55                  60

Lys Thr Glu Asn Cys Val Ala Lys Thr Lys Leu Ala Asn Gly Thr Ser
65                  70                  75                  80

Ser Met Ile Val Pro Lys Gln Arg Lys Leu Ser Ala Ser Tyr Glu Lys
                85                  90                  95

Glu Lys Glu Leu Cys Val Lys Tyr Phe Glu Gln Trp Ser Glu Ser Asp
            100                 105                 110

Gln Val Glu Phe Val Glu His Leu Ile Ser Gln Met Cys His Tyr Gln
        115                 120                 125

His Gly His Ile Asn Ser Tyr Leu Lys Pro Met Leu Gln Arg Asp Phe
    130                 135                 140

Ile Thr Ala Leu Pro Ala Arg Gly Leu Asp His Ile Ala Glu Asn Ile
145                 150                 155                 160

Leu Ser Tyr Leu Asp Ala Lys Ser Leu Cys Ala Ala Glu Leu Val Cys
                165                 170                 175

Lys Glu Trp Tyr Arg Val Thr Ser Asp Gly Met Leu Trp Lys Lys Leu
            180                 185                 190

Ile Glu Arg Met Val Arg Thr Asp Ser Leu Trp Arg Gly Leu Ala Glu
        195                 200                 205

Arg Arg Gly Trp Gly Gln Tyr Leu Phe Lys Asn Lys Pro Pro Asp Gly
    210                 215                 220

Asn Ala Pro Pro Asn Ser Phe Tyr Arg Ala Leu Tyr Pro Lys Ile Ile
225                 230                 235                 240

Gln Asp Ile Glu Thr Ile Glu Ser Asn Trp Arg Cys Gly Arg His Ser
                245                 250                 255

Leu Gln Arg Ile His Cys Arg Ser Glu Thr Ser Lys Gly Val Tyr Cys
            260                 265                 270

Leu Gln Tyr Asp Asp Gln Lys Ile Val Ser Gly Leu Arg Asp Asn Thr
        275                 280                 285

Ile Lys Ile Trp Asp Lys Asn Thr Leu Glu Cys Lys Arg Ile Leu Thr
    290                 295                 300

Gly His Thr Gly Ser Val Leu Cys Leu Gln Tyr Asp Glu Arg Val Ile
305                 310                 315                 320

Ile Thr Gly Ser Ser Asp Ser Thr Val Arg Val Trp Asp Val Asn Thr
                325                 330                 335

Gly Glu Met Leu Asn Thr Leu Ile His His Cys Glu Ala Val Leu His
            340                 345                 350

Leu Arg Phe Asn Asn Gly Met Met Val Thr Cys Ser Lys Asp Arg Ser
        355                 360                 365

Ile Ala Val Trp Asp Met Ala Ser Pro Thr Asp Ile Thr Leu Arg Arg
    370                 375                 380

Val Leu Val Gly His Arg Ala Val Asn Val Val Asp Phe Asp Asp
385                 390                 395                 400

Lys Tyr Ile Val Ser Ala Ser Gly Asp Arg Thr Ile Lys Val Trp Asn
                405                 410                 415

Thr Ser Thr Cys Glu Phe Val Arg Thr Leu Asn Gly His Lys Arg Gly
            420                 425                 430

Ile Ala Cys Leu Gln Tyr Arg Asp Arg Leu Val Val Ser Gly Ser Ser
        435                 440                 445
```

```
Asp Asn Thr Ile Arg Leu Trp Asp Ile Glu Cys Gly Ala Cys Leu Arg
    450                 455                 460

Val Leu Glu Gly His Glu Glu Leu Val Arg Cys Ile Arg Phe Asp Asn
465                 470                 475                 480

Lys Arg Ile Val Ser Gly Ala Tyr Asp Gly Lys Ile Lys Val Trp Asp
                485                 490                 495

Leu Val Ala Ala Leu Asp Pro Arg Ala Pro Ala Gly Thr Leu Cys Leu
            500                 505                 510

Arg Thr Leu Val Glu His Ser Gly Arg Val Phe Arg Leu Gln Phe Asp
            515                 520                 525

Glu Phe Gln Ile Val Ser Ser His Asp Asp Thr Ile Leu Ile Trp
    530                 535                 540

Asp Phe Leu Asn Asp Pro Ala Ala Gln Ala Glu Pro Pro Arg Ser Pro
545                 550                 555                 560

Ser Arg Thr Tyr Thr Tyr Ile Ser Arg
                565

<210> SEQ ID NO 3
<211> LENGTH: 1476
<212> TYPE: DNA
<213> ORGANISM: Homo sapiens

<400> SEQUENCE: 3
atggagagaa aggactttga gacatggctt gataacattt ctgttacatt tctttctctg      60
acggacttgc agaaaaatga aactctggat caccctgatta gtctgagtgg ggcagtccag    120
ctcaggcatc tctccaataa cctagagact ctcctcaagc gggacttcct caaactcctt    180
cccctggagc tcagtttta tttgttaaaa tggctcgatc ctcagacttt actcacatgc     240
tgcctcgtct ctaaacagtg gaataaggtg ataagtgcct gtacagaggt gtggcagact    300
gcatgtaaaa atttgggctg cagatagat gattctgttc aggacgcttt gcactggaag     360
aaggtttatt tgaaggctat tttgagaatg aagcaactgg aggaccatga agcctttgaa    420
acctcgtcat taattggaca cagtgccaga gtgtatgcac tttactacaa agatggactt    480
ctctgtacag ggtcagatga cttgtctgca aagctgtggg atgtgagcac agggcagtgc    540
gtttatggca tccagaccca cacttgtgca gcggtgaagt ttgatgaaca gaagcttgtg    600
acaggctcct ttgacaacac tgtggcttgc tgggaatgga gttccggagc caggacccag    660
cactttcggg ggcacacggg ggcggtattt agcgtggact acaatgatga actggatatc    720
ttggtgagcg gctctgcaga cttcactgtg aaagtatggg ctttatctgc tgggacatgc    780
ctgaacacac tcaccgggca cacggaatgg gtcaccaagg tagttttgca gaagtgcaaa    840
gtcaagtctc tcttgcacag tcctggagac tacatcctct taagtgcaga caaatatgag    900
attaagattt ggccaattgg gagagaaatc aactgtaagt gcttaaagac attgtctgtc    960
tctgaggata aagtatctg cctgcagcca agacttcatt ttgatggcaa atacattgtc   1020
tgtagttcag cacttggtct ctaccagtgg gactttgcca gttatgatat tctcagggtc   1080
atcaagactc ctgagatagc aaacttggcc ttgcttggct tggagatat ctttgccctg   1140 ctgtttgaca accgctacct gtacatcatg gacttgcgga cagagagcct gattagtcgc   1200
tggcctctgc cagagtacag ggaatcaaag agaggctcaa gcttcctggc aggcgaacat   1260
cctggctgaa tggactggat gggcacaatg acacgggctt ggtctttgcc accagcatgc   1320
ctgaccacag tattcacctg gtgttgtgga aggagcacgg ctgacaccat gagccaccac   1380
cgctgactga cttggggtgc cggggctgcg ggttttgggt gcacctctgc ggcacgcgac   1440
```
tgcatgaacc aaagttctca cctaatggta tcatca 1476

<210> SEQ ID NO 4
<211> LENGTH: 422
<212> TYPE: PRT
<213> ORGANISM: Homo sapiens

<400> SEQUENCE: 4

| Met | Glu | Arg | Lys | Asp | Phe | Glu | Thr | Trp | Leu | Asp | Asn | Ile | Ser | Val | Thr |
|---|---|---|---|---|---|---|---|---|---|---|---|---|---|---|---|
| 1 | | | | 5 | | | | | 10 | | | | | 15 | |

| Phe | Leu | Ser | Leu | Thr | Asp | Leu | Gln | Lys | Asn | Glu | Thr | Leu | Asp | His | Leu |
| | | | 20 | | | | | 25 | | | | | 30 | | |

| Ile | Ser | Leu | Ser | Gly | Ala | Val | Gln | Leu | Arg | His | Leu | Ser | Asn | Asn | Leu |
| | | 35 | | | | | 40 | | | | | 45 | | | |

| Glu | Thr | Leu | Leu | Lys | Arg | Asp | Phe | Leu | Lys | Leu | Pro | Leu | Glu | Leu |
| | 50 | | | | | 55 | | | | | 60 | | | | |

Ser Phe Tyr Leu Leu Lys Trp Leu Asp Pro Gln Thr Leu Leu Thr Cys
65                  70                  75                  80

Cys Leu Val Ser Lys Gln Trp Asn Lys Val Ile Ser Ala Cys Thr Glu
                85                  90                  95

Val Trp Gln Thr Ala Cys Lys Asn Leu Gly Trp Gln Ile Asp Asp Ser
            100                 105                 110

Val Gln Asp Ala Leu His Trp Lys Lys Val Tyr Leu Lys Ala Ile Leu
        115                 120                 125

Arg Met Lys Gln Leu Glu Asp His Glu Ala Phe Glu Thr Ser Ser Leu
    130                 135                 140

Ile Gly His Ser Ala Arg Val Tyr Ala Leu Tyr Tyr Lys Asp Gly Leu
145                 150                 155                 160

Leu Cys Thr Gly Ser Asp Asp Leu Ser Ala Lys Leu Trp Asp Val Ser
                165                 170                 175

Thr Gly Gln Cys Val Tyr Gly Ile Gln Thr His Thr Cys Ala Ala Val
            180                 185                 190

Lys Phe Asp Glu Gln Lys Leu Val Thr Gly Ser Phe Asp Asn Thr Val
        195                 200                 205

Ala Cys Trp Glu Trp Ser Ser Gly Ala Arg Thr Gln His Phe Arg Gly
    210                 215                 220

His Thr Gly Ala Val Phe Ser Val Asp Tyr Asn Asp Glu Leu Asp Ile
225                 230                 235                 240

Leu Val Ser Gly Ser Ala Asp Phe Thr Val Lys Val Trp Ala Leu Ser
                245                 250                 255

Ala Gly Thr Cys Leu Asn Thr Leu Thr Gly His Thr Glu Trp Val Thr
            260                 265                 270

Lys Val Val Leu Gln Lys Cys Lys Val Lys Ser Leu Leu His Ser Pro
        275                 280                 285

Gly Asp Tyr Ile Leu Leu Ser Ala Asp Lys Tyr Glu Ile Lys Ile Trp
    290                 295                 300

Pro Ile Gly Arg Glu Ile Asn Cys Lys Cys Leu Lys Thr Leu Ser Val
305                 310                 315                 320

Ser Glu Asp Arg Ser Ile Cys Leu Gln Pro Arg Leu His Phe Asp Gly
                325                 330                 335

Lys Tyr Ile Val Cys Ser Ser Ala Leu Gly Leu Tyr Gln Trp Asp Phe
            340                 345                 350

Ala Ser Tyr Asp Ile Leu Arg Val Ile Lys Thr Pro Glu Ile Ala Asn
        355                 360                 365

Leu Ala Leu Leu Gly Phe Gly Asp Ile Phe Ala Leu Leu Phe Asp Asn
        370                 375                 380

Arg Tyr Leu Tyr Ile Met Asp Leu Arg Thr Glu Ser Leu Ile Ser Arg
385                 390                 395                 400

Trp Pro Leu Pro Glu Tyr Arg Glu Ser Lys Arg Gly Ser Ser Phe Leu
                405                 410                 415

Ala Gly Glu His Pro Gly
            420

<210> SEQ ID NO 5
<211> LENGTH: 1407
<212> TYPE: DNA
<213> ORGANISM: Homo sapiens

<400> SEQUENCE: 5

| | | |
|---|---|---|
| cggggtggtg tgtgggggaa gccgcccccg gcagcaggat gaaacgagga ggaagagata | 60 |
| gtgaccgtaa ttcatcagaa gaaggaactg cagagaaatc caagaaactg aggactacaa | 120 |
| atgagcattc tcagacttgt gattggggta atctccttca ggacattatt ctccaagtat | 180 |
| ttaaatattt gcctcttctt gaccgggctc atgcttcaca gtttgccgc aactggaacc | 240 |
| aggtatttca catgcctgac ttgtggagat gttttgaatt tgaactgaat cagccagcta | 300 |
| catcttattt gaaagctacc catccagagc tgatcaaaca gattattaaa agacattcaa | 360 |
| accatctaca atatgtcagc ttcaaggtgg acagcagcaa ggaatcagct gaagcagctt | 420 |
| gtgatatact atcgcaactt gtgaattgct ctttaaaaac acttggactt atttcaactg | 480 |
| ctcgaccaag ctttatggat ttaccaaagt ctcactttat ctctgcactg acagttgtgt | 540 |
| tcgtaaactc caaatccctg tcttcgctta agatagatga tactccagta gatgatccat | 600 |
| ctctcaaagt actagtggcc aacaatagtg atacactcaa gctgttgaaa atgagcagct | 660 |
| gtcctcatgt ctctccagca ggtatccttt gtgtggctga tcagtgtcac ggcttaagag | 720 |
| aactagcccct gaactaccac ttattgagtg atgagttgtt acttgcattg tcttctgaaa | 780 |
| aacatgttcg attagaacat ttgcgcattg atgtagtcag tgagaatcct ggacagacac | 840 |
| acttccatac tattcagaag agtagctggg atgctttcat cagacattca cccaaagtga | 900 |
| acttagtgat gtattttttt ttatatgaag aagaatttga ccccttcttt cgctatgaaa | 960 |
| tacctgccac ccatctgtac tttgggagat cagtaagcaa agatgtgctt ggccgtgtgg | 1020 |
| gaatgacatg ccctagactg gttgaactag tagtgtgtgc aaatggatta cggccacttg | 1080 |
| atgaagagtt aattcgcatt gcagaacgtt gcaaaaattt gtcagctatt ggactagggg | 1140 |
| aatgtgaagt ctcatgtagt gcctttgttg agtttgtgaa gatgtgtggt ggccgcctat | 1200 |
| ctcaattatc cattatggaa gaagtactaa ttcctgacca aaagtatagt ttggagcaga | 1260 |
| ttcactggga agtgtccaag catcttggta gggtgtggtt tcccgacatg atgcccactt | 1320 |
| ggtaaaaact gcatgatgaa tagcacctta atttcaagca aatgtattat aattaaagtt | 1380 |
| ttatttgctg taaaaaaaaa aaaaaaa | 1407 |

<210> SEQ ID NO 6
<211> LENGTH: 428
<212> TYPE: PRT
<213> ORGANISM: Homo sapiens

<400> SEQUENCE: 6

Met Lys Arg Gly Gly Arg Asp Ser Asp Arg Asn Ser Ser Glu Glu Gly
1               5                   10                  15

Thr Ala Glu Lys Ser Lys Lys Leu Arg Thr Thr Asn Glu His Ser Gln

```
                    20                  25                  30
Thr Cys Asp Trp Gly Asn Leu Leu Gln Asp Ile Ile Leu Gln Val Phe
                35                  40                  45

Lys Tyr Leu Pro Leu Leu Asp Arg Ala His Ala Ser Gln Val Cys Arg
        50                  55                  60

Asn Trp Asn Gln Val Phe His Met Pro Asp Leu Trp Arg Cys Phe Glu
65                  70                  75                  80

Phe Glu Leu Asn Gln Pro Ala Thr Ser Tyr Leu Lys Ala Thr His Pro
                85                  90                  95

Glu Leu Ile Lys Gln Ile Ile Lys Arg His Ser Asn His Leu Gln Tyr
            100                 105                 110

Val Ser Phe Lys Val Asp Ser Ser Lys Glu Ser Ala Glu Ala Ala Cys
        115                 120                 125

Asp Ile Leu Ser Gln Leu Val Asn Cys Ser Leu Lys Thr Leu Gly Leu
    130                 135                 140

Ile Ser Thr Ala Arg Pro Ser Phe Met Asp Leu Pro Lys Ser His Phe
145                 150                 155                 160

Ile Ser Ala Leu Thr Val Val Phe Val Asn Ser Lys Ser Leu Ser Ser
                165                 170                 175

Leu Lys Ile Asp Asp Thr Pro Val Asp Pro Ser Leu Lys Val Leu
            180                 185                 190

Val Ala Asn Asn Ser Asp Thr Leu Lys Leu Leu Lys Met Ser Ser Cys
        195                 200                 205

Pro His Val Ser Pro Ala Gly Ile Leu Cys Val Ala Asp Gln Cys His
    210                 215                 220

Gly Leu Arg Glu Leu Ala Leu Asn Tyr His Leu Leu Ser Asp Glu Leu
225                 230                 235                 240

Leu Leu Ala Leu Ser Ser Glu Lys His Val Arg Leu Glu His Leu Arg
                245                 250                 255

Ile Asp Val Val Ser Glu Asn Pro Gly Gln Thr His Phe His Thr Ile
            260                 265                 270

Gln Lys Ser Ser Trp Asp Ala Phe Ile Arg His Ser Pro Lys Val Asn
        275                 280                 285

Leu Val Met Tyr Phe Phe Leu Tyr Glu Glu Glu Phe Asp Pro Phe Phe
    290                 295                 300

Arg Tyr Glu Ile Pro Ala Thr His Leu Tyr Phe Gly Arg Ser Val Ser
305                 310                 315                 320

Lys Asp Val Leu Gly Arg Val Gly Met Thr Cys Pro Arg Leu Val Glu
                325                 330                 335

Leu Val Val Cys Ala Asn Gly Leu Arg Pro Leu Asp Glu Glu Leu Ile
            340                 345                 350

Arg Ile Ala Glu Arg Cys Lys Asn Leu Ser Ala Ile Gly Leu Gly Glu
        355                 360                 365

Cys Glu Val Ser Cys Ser Ala Phe Val Glu Phe Val Lys Met Cys Gly
    370                 375                 380

Gly Arg Leu Ser Gln Leu Ser Ile Met Glu Glu Val Leu Ile Pro Asp
385                 390                 395                 400

Gln Lys Tyr Ser Leu Glu Gln Ile His Trp Glu Val Ser Lys His Leu
                405                 410                 415

Gly Arg Val Trp Phe Pro Asp Met Met Pro Thr Trp
            420                 425
```

<210> SEQ ID NO 7
<211> LENGTH: 1444

```
<212> TYPE: DNA
<213> ORGANISM: Homo sapiens

<400> SEQUENCE: 7
atggcgggaa gcgagccgcg cagcggaaca aattcgccgc cgccgccctt cagcgactgg     60
ggccgcctgg aggcggccat cctcagcggc tggaagacct tctggcagtc agtgagcaag    120
gatagggtgg cgcgtacgac ctcccgggag gaggtggatg aggcggccag caccctgacg    180
cggctgccga ttgatgtaca gctatatatt ttgtcctttc tttcacctca tgatctgtgt    240
cagttgggaa gtacaaatca ttattggaat gaaactgtaa gaaatccaat tctgtggaga    300 tacttttgt tgagggatct tccttcttgg tcttctgttg actggaagtc tcttccatat    360
ctacaaatct taaaaaagcc tatatctgag gtctctgatg gtgcattttt tgactacatg    420
gcagtctatc taatgtgctg tccatacaca agaagagctt caaaatccag ccgtcctatg    480
tatggagctg tcacttcttt tttacactcc ctgatcattc ccaatgaacc tcgatttgct    540
ctgtttggac cacgtttgga acaattgaat acctctttgg tgttgagctt gctgtcttca    600
gaggaacttt gcccaacagc tggtttgcct cagaggcaga ttgatggtat tggatcagga    660
gtcaattttc agttgaacaa ccaacataaa ttcaacattc taatcttata ttcaactacc    720
agaaaggaaa gagatagagc aagggaagag catacaagtg cagttaacaa gatgttcagt    780
cgacacaatg aaggtgatga tcgaccagga agccggtaca gtgtgattcc acagattcaa    840
aaactgtgtg aagttgtaga tgggttcatc tatgttgcaa atgctgaagc tcataaaaga    900
catgaatggc aagatgaatt ttctcatatt atggcaatga cagatccagc ctttgggtct    960
tcgggaagac cattgttggt tttatcttgt atttctcaag gggatgtaaa agaatgccc   1020 tgttttatt tggctcatga gctgcatctg aatcttctaa atcacccatg ctggtccag    1080 gatacagagg ctgaaactct gactggtttt ttgaatggca ttgagtggat tcttgaagaa    1140
gtggaatcta gcgtgcaag atgattctct tttcagatct tgggaactga accatttga    1200 aatttattac taaggtcgtg atgtgaatat ttgctcagtc agcccacctt gtcctgcctt    1260
tttgcagata ggctttcatt tggacagcta taactgctgt gttttttata ttatttttac    1320
tttttaccat aaatcaatta caagaaaaga gtttcagtcc tagtatttag ccccaaaatg    1380
aacctttaaa cattttttg gtaattttta tattttctgt cttttaaaa atattaaatt    1440 ttgg                                                                1444

<210> SEQ ID NO 8
<211> LENGTH: 387
<212> TYPE: PRT
<213> ORGANISM: Homo sapiens

<400> SEQUENCE: 8

Met Ala Gly Ser Glu Pro Arg Ser Gly Thr Asn Ser Pro Pro Pro Pro
1               5                   10                  15

Phe Ser Asp Trp Gly Arg Leu Glu Ala Ala Ile Leu Ser Gly Trp Lys
            20                  25                  30

Thr Phe Trp Gln Ser Val Ser Lys Asp Arg Val Ala Arg Thr Thr Ser
        35                  40                  45

Arg Glu Glu Val Asp Glu Ala Ala Ser Thr Leu Thr Arg Leu Pro Ile
    50                  55                  60

Asp Val Gln Leu Tyr Ile Leu Ser Phe Leu Ser Pro His Asp Leu Cys
65                  70                  75                  80

Gln Leu Gly Ser Thr Asn His Tyr Trp Asn Glu Thr Val Arg Asn Pro
                85                  90                  95
```

```
Ile Leu Trp Arg Tyr Phe Leu Leu Arg Asp Leu Pro Ser Trp Ser Ser
            100                 105                 110

Val Asp Trp Lys Ser Leu Pro Tyr Leu Gln Ile Leu Lys Lys Pro Ile
        115                 120                 125

Ser Glu Val Ser Asp Gly Ala Phe Phe Asp Tyr Met Ala Val Tyr Leu
130                 135                 140

Met Cys Cys Pro Tyr Thr Arg Arg Ala Ser Lys Ser Ser Arg Pro Met
145                 150                 155                 160

Tyr Gly Ala Val Thr Ser Phe Leu His Ser Leu Ile Ile Pro Asn Glu
                165                 170                 175

Pro Arg Phe Ala Leu Phe Gly Pro Arg Leu Glu Gln Leu Asn Thr Ser
            180                 185                 190

Leu Val Leu Ser Leu Leu Ser Ser Glu Glu Leu Cys Pro Thr Ala Gly
        195                 200                 205

Leu Pro Gln Arg Gln Ile Asp Gly Ile Gly Ser Gly Val Asn Phe Gln
210                 215                 220

Leu Asn Asn Gln His Lys Phe Asn Ile Leu Ile Leu Tyr Ser Thr Thr
225                 230                 235                 240

Arg Lys Glu Arg Asp Arg Ala Arg Glu Glu His Thr Ser Ala Val Asn
                245                 250                 255

Lys Met Phe Ser Arg His Asn Glu Gly Asp Asp Arg Pro Gly Ser Arg
            260                 265                 270

Tyr Ser Val Ile Pro Gln Ile Gln Lys Leu Cys Glu Val Val Asp Gly
        275                 280                 285

Phe Ile Tyr Val Ala Asn Ala Glu Ala His Lys Arg His Glu Trp Gln
290                 295                 300

Asp Glu Phe Ser His Ile Met Ala Met Thr Asp Pro Ala Phe Gly Ser
305                 310                 315                 320

Ser Gly Arg Pro Leu Leu Val Leu Ser Cys Ile Ser Gln Gly Asp Val
                325                 330                 335

Lys Arg Met Pro Cys Phe Tyr Leu Ala His Glu Leu His Leu Asn Leu
            340                 345                 350

Leu Asn His Pro Trp Leu Val Gln Asp Thr Glu Ala Glu Thr Leu Thr
        355                 360                 365

Gly Phe Leu Asn Gly Ile Glu Trp Ile Leu Glu Glu Val Glu Ser Lys
370                 375                 380

Arg Ala Arg
385

<210> SEQ ID NO 9
<211> LENGTH: 2076
<212> TYPE: DNA
<213> ORGANISM: Homo sapiens

<400> SEQUENCE: 9
aggttgctca gctgcccccg gagcggttcc tccacctgag gcagacacca cctcggttgg      60
catgagccgg cgcccctgca gctgcgccct acggccaccc cgctgctcct gcagcgccag     120
ccccagcgca gtgacagccg ccgggcgccc tcgaccctcg gatagttgta agaagaaag      180 ttctaccctt tctgtcaaaa tgaagtgtga ttttaattgt aaccatgttc attccggact     240
taaactggta aaacctgatg acattggaag actagttcc tacacccctg catatctgga      300
aggttcctgt aaagactgca ttaaagacta gaaggctg tcatgtattg ggtcaccgat       360
tgtgagccct aggattgtac aacttgaaac tgaaagcaag cgcttgcata acaaggaaaa     420
```

```
tcaacatgtg caacagacac ttaatagtac aaatgaaata gaagcactag agaccagtag    480
actttatgaa gacagtggct attcctcatt ttctctacaa agtggcctca gtgaacatga    540
agaaggtagc ctcctggagg agaatttcgg tgacagtcta caatcctgcc tgctacaaat    600
acaaagccca gaccaatatc ccaacaaaaa cttgctgcca gttcttcatt ttgaaaaagt    660
ggtttgttca acattaaaaa agaatgcaaa acgaaatcct aaagtagatc gggagatgct    720
gaaggaaatt atagccagag gaaattttag actgcagaat ataattggca gaaaaatggg    780
cctagaatgt gtagatattc tcagcgaact cttttcgaagg ggactcagac atgtcttagc    840
aactatttta gcacaactca gtgacatgga cttaatcaat gtgtctaaag tgagcacaac    900
ttggaagaag atcctagaag atgataaggg ggcattccag ttgtacagta aagcaataca    960
aagagttacc gaaacaaca ataaattttc acctcatgct caaccagag aatatgttat     1020
gttcagaacc ccactggctt ctgttcagaa atcagcagcc cagacttctc tcaaaaaaga   1080
tgctcaaacc aagttatcca atcaaggtga tcagaaaggt tctacttata gtcgacacaa   1140
tgaattctct gaggttgcca agacattgaa aaagaacgaa agcctcaaag cctgtattcg   1200
ctgtaattca cctgcaaaat atgattgcta tttacaacgg gcaacctgca acgagaagg    1260
ctgtggattt gattattgta cgaagtgtct ctgtaattat catactacta aagactgttc   1320
agatggcaag ctcctcaaag ccagttgtaa aataggtccc ctgcctggta caaagaaaag   1380
caaaaagaat ttacgaagat tgtgatctct tattaaatca attgttactg atcatgaatg   1440
ttagttagaa aatgttaggt tttaacttaa aaaaaattgt attgtgattt tcaattttat   1500
gttgaaatcg gtgtagtatc ctgaggtttt tttccccca gaagataaag aggatagaca   1560
acctcttaaa atattttac aatttaatga gaaaagttt aaaattctca atacaaatca     1620
aacaatttaa atattttaag aaaaaaggaa aagtagatag tgatactgag ggtaaaaaaa   1680
aaattgattc aattttatgg taaaggaaac ccatgcaatt ttacctagac agtcttaaat   1740
atgtctggtt ttccatctgt tagcatttca gacattttat gttcctctta ctcaattgat   1800
accaacagaa atatcaactt ctggagtcta ttaaatgtgt tgtcaccttt ctaaagcttt   1860
ttttcattgt gtgtatttcc caagaaagta tcctttgtaa aaacttgctt gttttcctta   1920
tttctgaaat ctgttttaat attttgtat acatgtaaat atttctgtat tttttatatg    1980
tcaaagaata tgtctcttgt atgtacatat aaaaataaat tttgctcaat aaaattgtaa   2040
gcttaaaaaa aaaaaaaaaa aactcgagac tagtgc                             2076
```

<210> SEQ ID NO 10
<211> LENGTH: 447
<212> TYPE: PRT
<213> ORGANISM: Homo sapiens

<400> SEQUENCE: 10

```
Met Ser Arg Arg Pro Cys Ser Cys Ala Leu Arg Pro Pro Arg Cys Ser
 1               5                  10                  15

Cys Ser Ala Ser Pro Ser Ala Val Thr Ala Ala Gly Arg Pro Arg Pro
            20                  25                  30

Ser Asp Ser Cys Lys Glu Glu Ser Ser Thr Leu Ser Val Lys Met Lys
        35                  40                  45

Cys Asp Phe Asn Cys Asn His Val His Ser Gly Leu Lys Leu Val Lys
    50                  55                  60

Pro Asp Asp Ile Gly Arg Leu Val Ser Tyr Thr Pro Ala Tyr Leu Glu
65                  70                  75                  80

Gly Ser Cys Lys Asp Cys Ile Lys Asp Tyr Glu Arg Leu Ser Cys Ile
```

|   |   | 85 |   |   |   | 90 |   |   |   | 95 |   |
|---|---|---|---|---|---|---|---|---|---|---|---|

Gly Ser Pro Ile Val Ser Pro Arg Ile Val Gln Leu Glu Thr Glu Ser
                 100                 105                 110

Lys Arg Leu His Asn Lys Glu Asn Gln His Val Gln Gln Thr Leu Asn
            115                 120                 125

Ser Thr Asn Glu Ile Glu Ala Leu Glu Thr Ser Arg Leu Tyr Glu Asp
        130                 135                 140

Ser Gly Tyr Ser Ser Phe Ser Leu Gln Ser Gly Leu Ser Glu His Glu
145                 150                 155                 160

Glu Gly Ser Leu Leu Glu Glu Asn Phe Gly Asp Ser Leu Gln Ser Cys
                165                 170                 175

Leu Leu Gln Ile Gln Ser Pro Asp Gln Tyr Pro Asn Lys Asn Leu Leu
            180                 185                 190

Pro Val Leu His Phe Glu Lys Val Val Cys Ser Thr Leu Lys Lys Asn
        195                 200                 205

Ala Lys Arg Asn Pro Lys Val Asp Arg Glu Met Leu Lys Glu Ile Ile
    210                 215                 220

Ala Arg Gly Asn Phe Arg Leu Gln Asn Ile Ile Gly Arg Lys Met Gly
225                 230                 235                 240

Leu Glu Cys Val Asp Ile Leu Ser Glu Leu Phe Arg Arg Gly Leu Arg
                245                 250                 255

His Val Leu Ala Thr Ile Leu Ala Gln Leu Ser Asp Met Asp Leu Ile
            260                 265                 270

Asn Val Ser Lys Val Ser Thr Thr Trp Lys Lys Ile Leu Glu Asp Asp
        275                 280                 285

Lys Gly Ala Phe Gln Leu Tyr Ser Lys Ala Ile Gln Arg Val Thr Glu
    290                 295                 300

Asn Asn Asn Lys Phe Ser Pro His Ala Ser Thr Arg Glu Tyr Val Met
305                 310                 315                 320

Phe Arg Thr Pro Leu Ala Ser Val Gln Lys Ser Ala Ala Gln Thr Ser
                325                 330                 335

Leu Lys Lys Asp Ala Gln Thr Lys Leu Ser Asn Gln Gly Asp Gln Lys
            340                 345                 350

Gly Ser Thr Tyr Ser Arg His Asn Glu Phe Ser Glu Val Ala Lys Thr
        355                 360                 365

Leu Lys Lys Asn Glu Ser Leu Lys Ala Cys Ile Arg Cys Asn Ser Pro
    370                 375                 380

Ala Lys Tyr Asp Cys Tyr Leu Gln Arg Ala Thr Cys Lys Arg Glu Gly
385                 390                 395                 400

Cys Gly Phe Asp Tyr Cys Thr Lys Cys Leu Cys Asn Tyr His Thr Thr
                405                 410                 415

Lys Asp Cys Ser Asp Gly Lys Leu Leu Lys Ala Ser Cys Lys Ile Gly
            420                 425                 430

Pro Leu Pro Gly Thr Lys Lys Ser Lys Lys Asn Leu Arg Arg Leu
        435                 440                 445

<210> SEQ ID NO 11
<211> LENGTH: 1535
<212> TYPE: DNA
<213> ORGANISM: Homo sapiens

<400> SEQUENCE: 11
gcgcgttcgg gagcttcggc cctgcgtagg aggcgggtgc aggtgtgggt gctgagccgc    60
ccgccgcctg gaggggagac agcttcagg acacgcaggc cgcagcgagg gcccgggccc   120

```
gggggatccc aggccatgga cgctccccac tccaaagcag ccctggacag cattaacgag    180
ctgcccgata acatcctgct ggagctgttc acgcacgtgc ccgcccgcca gctgctgctg    240
aactgccgcc tggtctgcag cctctggcgg gacctcatcg acctcctgac cctctggaaa    300
cgcaagtgcc tgcgaaaggg cttcatcacc aaggactggg accagcccgt ggccgactgg    360
aaaatcttct acttcctacg gagcctgcat aggaacctcc tgcgcaaccc gtgtgctgaa    420
aacgatatgt ttgcatggca aattgatttc aatggtgggg accgctggaa ggtggatagc    480
ctccctggag cccacgggac agaatttcct gaccccaaag tcaagaagtc ttttgtcaca    540
tcctacgaac tgtgcctcaa gtgggagctg gtggaccttc tagccgaccg ctactgggag    600
gagctactag acacattccg gccggacatc gtggttaagg actggtttgc tgccagagcc    660
gactgtggct gcacctacca actcaaagtg cagctggcct cggctgacta cttcgtgttg    720
gcctccttcg agcccccacc tgtgaccatc aacagtgga acaatgccac atggacagag     780
gtctcctaca ccttctcaga ctaccccgg ggtgtccgct acatcctctt ccagcatggg      840
ggcagggaca cccagtactg ggcaggctgg tatgggcccc gagtcaccaa cagcagcatt    900
gtcgtcagcc ccaagatgac caggaaccag gcctcgtccg aggctcagcc tgggcagaag    960
catggacagg aggaggctgc ccaatcgccc tacggagctg ttgtccagat ttctgacag     1020
ctgtccatcc tgtgtctggg tcagccagag gttcctccag gcaggagctg agcatggggt   1080
gggcagtgag gtccctgtac cagcgactcc tgccccggtt caaccctacc agcttgtggt   1140
aacttactgt cacatagctc tgacgttttg ttgtaataaa tgttttcagg ccgggcactg   1200
tggctcacgc ctgtaatccc agcactttgg gagaccgagg caggtggatc acgaggtcag   1260
gagacagaga ccatcctggc caacacggtg aaaccctgtc tctactaaaa atacaaaaaa   1320
ttagccgggc gtggtggcgg cgcctgtag tcccagctac tcgggaggct gatgcagaag    1380
aatggcgtga acccggaagg cagagcttgc agtgagccga gatcacgcca ctgcactcca   1440
gcctgggtga cagagcgaga ctctggctca taaaataata ataataataa ataaataaaa   1500
aataaatggt tttcagtaaa aaaaaaaaa aaaaa                                1535
```

<210> SEQ ID NO 12
<211> LENGTH: 338
<212> TYPE: PRT
<213> ORGANISM: Homo sapiens

<400> SEQUENCE: 12

```
Ala Arg Ser Gly Ala Ser Ala Leu Arg Arg Arg Val Gln Val Trp
 1               5                   10                  15

Val Leu Ser Arg Pro Pro Gly Gly Gly Asp Ser Phe Arg Thr Arg
                20                  25                  30

Arg Pro Gln Arg Gly Pro Gly Pro Gly Ser Gln Ala Met Asp Ala
                35                  40                  45

Pro His Ser Lys Ala Ala Leu Asp Ser Ile Asn Glu Leu Pro Asp Asn
                50                  55                  60

Ile Leu Leu Glu Leu Phe Thr His Val Pro Ala Arg Gln Leu Leu
 65                  70                  75                  80

Asn Cys Arg Leu Val Cys Ser Leu Trp Arg Asp Leu Ile Asp Leu Leu
                     85                  90                  95

Thr Leu Trp Lys Arg Lys Cys Leu Arg Lys Gly Phe Ile Thr Lys Asp
            100                 105                 110

Trp Asp Gln Pro Val Ala Asp Trp Lys Ile Phe Tyr Phe Leu Arg Ser
            115                 120                 125
```

```
Leu His Arg Asn Leu Leu Arg Asn Pro Cys Ala Glu Asn Asp Met Phe
        130                 135                 140

Ala Trp Gln Ile Asp Phe Asn Gly Gly Asp Arg Trp Lys Val Asp Ser
145                 150                 155                 160

Leu Pro Gly Ala His Gly Thr Glu Phe Pro Asp Pro Lys Val Lys Lys
                165                 170                 175

Ser Phe Val Thr Ser Tyr Glu Leu Cys Leu Lys Trp Glu Leu Val Asp
                180                 185                 190

Leu Leu Ala Asp Arg Tyr Trp Glu Glu Leu Leu Asp Thr Phe Arg Pro
        195                 200                 205

Asp Ile Val Val Lys Asp Trp Phe Ala Ala Arg Ala Asp Cys Gly Cys
        210                 215                 220

Thr Tyr Gln Leu Lys Val Gln Leu Ala Ser Ala Asp Tyr Phe Val Leu
225                 230                 235                 240

Ala Ser Phe Glu Pro Pro Val Thr Ile Gln Gln Trp Asn Asn Ala
                245                 250                 255

Thr Trp Thr Glu Val Ser Tyr Thr Phe Ser Asp Tyr Pro Arg Gly Val
                260                 265                 270

Arg Tyr Ile Leu Phe Gln His Gly Gly Arg Asp Thr Gln Tyr Trp Ala
                275                 280                 285

Gly Trp Tyr Gly Pro Arg Val Thr Asn Ser Ser Ile Val Val Ser Pro
        290                 295                 300

Lys Met Thr Arg Asn Gln Ala Ser Ser Glu Ala Gln Pro Gly Gln Lys
305                 310                 315                 320

His Gly Gln Glu Glu Ala Ala Gln Ser Pro Tyr Gly Ala Val Val Gln
                325                 330                 335

Ile Phe

<210> SEQ ID NO 13
<211> LENGTH: 1763
<212> TYPE: DNA
<213> ORGANISM: Homo sapiens

<400> SEQUENCE: 13
tggaattccc atggaccatg tctaataccc gatttacaat tacattgaac tacaaggatc    60
ccctcactgg agatgaagag accttggctt catatgggat tgtttctggg gacttgatat   120
gtttgattct tcacgatgac attccaccgc ctaatatacc ttcatccaca gattcagagc   180
attcttcact ccagaacaat gagcaaccct ctttggccac cagctccaat cagactagca   240
tacaggatga acaaccaagt gattcattcc aaggacaggc agcccagtct ggtgtttgga   300
atgacgacag tatgttaggg cctagtcaaa attttgaagc tgagtcaatt caagataatg   360
cgcatatggc agagggcaca ggtttctatc cctcagaacc cctgctctgt agtgaatcgg   420
tggaagggca agtgccacat tcattagaga ccttgtatca atcagctgac tgttctgatg   480
ccaatgatgc gttgatagtg ttgatacatc ttctcatgtt ggagtcaggt tacatacctc   540
agggcaccga agccaaagca ctgtccctgc ggagaagtg gaagttgagc ggggtgtata   600
agctgcagta catgcatcat ctctgcgagg gcagctccgc tactctcacc tgtgtgcctt   660
tgggaaacct gattgttgta aatgctacac taaaaatcaa caatgagatt agaagtgtga   720
aaagattgca gctgctacca gaatcttta tttgcaaaga gaaactaggg gaaaatgtag   780
ccaacatata caaagatctt cagaaactct ctcgcctctt taaagaccag ctggtgtatc   840
ctcttctggc ttttacccga caagcactga acctaccaaa tgtatttggg ttggtcgtcc   900
tcccattgga actgaaacta cggatcttcc gacttctgga tgttcgttcc gtcttgtctt   960
```

-continued

```
tgtctgcggt tgtcgtgac ctctttactg cttcaaatga cccactcctg tggaggtttt    1020
tatatctgcg tgattttcga dacaatactg tcagagttca agacacagat tggaaagaac    1080
tgtacaggaa gaggcacata caaagaaaag aatccccgaa agggcggttt gtgctgctcc    1140
tgccatcgtc aacccacacc attccattct atcccaaccc cttgcaccct aggccatttc    1200
ctagctcccg ccttcctcca ggaattatcg ggggtgaata tgaccaaaga ccaacacttc    1260
cctatgttgg agacccaatc agttcactca ttcctggtcc tggggagacg cccagccagt    1320
tacctccact gagaccacgc tttgatccag ttggcccact tccaggacct aaccccatct    1380
tgccagggcg aggcggcccc aatgacagat ttcccttag acccagcagg ggtcggccaa    1440
ctgatggccg cctgtcattc atgtgattga tttgtaattt catttctgga gctccatttg    1500
tttttgtttc taaactacag atgtcactcc ttggggtgct gatctcgagt gttatttct    1560 gattgtggtg ttgagagttg cactcccaga aaccttttaa gagatacatt tatagcccta    1620
ggggtggtat gacccaaagg ttcctctgtg acaaggttgg ccttgggaat agttggctgc    1680
caatctccct gctcttggtt ctcctctaga ttgaagtttg ttttctgatg ctgttcttac    1740
cagattaaaa aaagtgtaa att                                             1763
```

<210> SEQ ID NO 14
<211> LENGTH: 482
<212> TYPE: PRT
<213> ORGANISM: Homo sapiens

<400> SEQUENCE: 14

```
Met Ser Asn Thr Arg Phe Thr Ile Thr Leu Asn Tyr Lys Asp Pro Leu
 1               5                  10                  15

Thr Gly Asp Glu Glu Thr Leu Ala Ser Tyr Gly Ile Val Ser Gly Asp
                20                  25                  30

Leu Ile Cys Leu Ile Leu His Asp Asp Ile Pro Pro Asn Ile Pro
            35                  40                  45

Ser Ser Thr Asp Ser Glu His Ser Ser Leu Gln Asn Asn Glu Gln Pro
        50                  55                  60

Ser Leu Ala Thr Ser Ser Asn Gln Thr Ser Ile Gln Asp Glu Gln Pro
 65                  70                  75                  80

Ser Asp Ser Phe Gln Gly Gln Ala Ala Gln Ser Gly Val Trp Asn Asp
                85                  90                  95

Asp Ser Met Leu Gly Pro Ser Gln Asn Phe Glu Ala Glu Ser Ile Gln
            100                 105                 110

Asp Asn Ala His Met Ala Glu Gly Thr Gly Phe Tyr Pro Ser Glu Pro
        115                 120                 125

Leu Leu Cys Ser Glu Ser Val Glu Gly Gln Val Pro His Ser Leu Glu
    130                 135                 140

Thr Leu Tyr Gln Ser Ala Asp Cys Ser Asp Ala Asn Asp Ala Leu Ile
145                 150                 155                 160

Val Leu Ile His Leu Leu Met Leu Glu Ser Gly Tyr Ile Pro Gln Gly
                165                 170                 175

Thr Glu Ala Lys Ala Leu Ser Leu Pro Glu Lys Trp Lys Leu Ser Gly
            180                 185                 190

Val Tyr Lys Leu Gln Tyr Met His His Leu Cys Glu Gly Ser Ser Ala
        195                 200                 205

Thr Leu Thr Cys Val Pro Leu Gly Asn Leu Ile Val Val Asn Ala Thr
    210                 215                 220

Leu Lys Ile Asn Asn Glu Ile Arg Ser Val Lys Arg Leu Gln Leu Leu
```

```
              225                 230                 235                 240
    Pro Glu Ser Phe Ile Cys Lys Glu Lys Leu Gly Glu Asn Val Ala Asn
                    245                 250                 255
    Ile Tyr Lys Asp Leu Gln Lys Leu Ser Arg Leu Phe Lys Asp Gln Leu
                    260                 265                 270
    Val Tyr Pro Leu Leu Ala Phe Thr Arg Gln Ala Leu Asn Leu Pro Asn
                    275                 280                 285
    Val Phe Gly Leu Val Val Leu Pro Leu Glu Leu Lys Leu Arg Ile Phe
                    290                 295                 300
    Arg Leu Leu Asp Val Arg Ser Val Leu Ser Leu Ser Ala Val Cys Arg
    305                 310                 315                 320
    Asp Leu Phe Thr Ala Ser Asn Asp Pro Leu Leu Trp Arg Phe Leu Tyr
                    325                 330                 335
    Leu Arg Asp Phe Arg Asp Asn Thr Val Arg Val Gln Asp Thr Asp Trp
                    340                 345                 350
    Lys Glu Leu Tyr Arg Lys Arg His Ile Gln Arg Lys Glu Ser Pro Lys
                    355                 360                 365
    Gly Arg Phe Val Leu Leu Leu Pro Ser Ser Thr His Thr Ile Pro Phe
                    370                 375                 380
    Tyr Pro Asn Pro Leu His Pro Arg Pro Phe Pro Ser Ser Arg Leu Pro
    385                 390                 395                 400
    Pro Gly Ile Ile Gly Gly Glu Tyr Asp Gln Arg Pro Thr Leu Pro Tyr
                    405                 410                 415
    Val Gly Asp Pro Ile Ser Ser Leu Ile Pro Gly Pro Gly Glu Thr Pro
                    420                 425                 430
    Ser Gln Leu Pro Pro Leu Arg Pro Arg Phe Asp Pro Val Gly Pro Leu
                    435                 440                 445
    Pro Gly Pro Asn Pro Ile Leu Pro Gly Arg Gly Pro Asn Asp Arg
                    450                 455                 460
    Phe Pro Phe Arg Pro Ser Arg Gly Arg Pro Thr Asp Gly Arg Leu Ser
    465                 470                 475                 480
    Phe Met

<210> SEQ ID NO 15
<211> LENGTH: 43
<212> TYPE: PRT
<213> ORGANISM: Homo sapiens

<400> SEQUENCE: 15

Leu Pro Ala Arg Gly Leu Asp His Ile Ala Glu Asn Ile Leu Ser Tyr
    1               5                   10                  15
    Leu Asp Ala Lys Ser Leu Cys Ala Ala Glu Leu Val Cys Lys Glu Trp
                    20                  25                  30
    Tyr Arg Val Thr Ser Asp Gly Met Leu Trp Lys
                    35                  40

<210> SEQ ID NO 16
<211> LENGTH: 40
<212> TYPE: PRT
<213> ORGANISM: Homo sapiens

<400> SEQUENCE: 16

Leu Pro Leu Glu Leu Ser Phe Tyr Leu Leu Lys Trp Leu Asp Pro Gln
    1               5                   10                  15
    Thr Leu Leu Thr Cys Cys Leu Val Ser Lys Gln Trp Asn Lys Val Ile
                    20                  25                  30
```

```
Ser Ala Cys Thr Glu Val Trp Gln
        35                  40

<210> SEQ ID NO 17
<211> LENGTH: 39
<212> TYPE: PRT
<213> ORGANISM: Homo sapiens

<400> SEQUENCE: 17

Leu Leu Gln Asp Ile Ile Leu Gln Val Phe Lys Tyr Leu Pro Leu Leu
 1               5                  10                  15

Asp Arg Ala His Ala Ser Gln Val Cys Arg Asn Trp Asn Gln Val Phe
            20                  25                  30

His Met Pro Asp Leu Trp Arg
        35

<210> SEQ ID NO 18
<211> LENGTH: 39
<212> TYPE: PRT
<213> ORGANISM: Homo sapiens

<400> SEQUENCE: 18

Leu Pro Ile Asp Val Gln Leu Tyr Ile Leu Ser Phe Leu Ser Pro His
 1               5                  10                  15

Asp Leu Cys Gln Leu Gly Ser Thr Asn His Tyr Trp Asn Glu Thr Val
            20                  25                  30

Arg Asn Pro Ile Leu Trp Arg
        35

<210> SEQ ID NO 19
<211> LENGTH: 39
<212> TYPE: PRT
<213> ORGANISM: Homo sapiens

<400> SEQUENCE: 19

Leu Arg His Val Leu Ala Thr Ile Leu Ala Gln Leu Ser Asp Met Asp
 1               5                  10                  15

Leu Ile Asn Val Ser Lys Val Ser Thr Thr Trp Lys Lys Ile Leu Glu
            20                  25                  30

Asp Asp Lys Gly Ala Phe Gln
        35

<210> SEQ ID NO 20
<211> LENGTH: 40
<212> TYPE: PRT
<213> ORGANISM: Homo sapiens

<400> SEQUENCE: 20

Leu Pro Asp Asn Ile Leu Leu Glu Leu Phe Thr His Val Pro Ala Arg
 1               5                  10                  15

Gln Leu Leu Leu Asn Cys Arg Leu Val Cys Ser Leu Trp Arg Asp Leu
            20                  25                  30

Ile Asp Leu Leu Thr Leu Trp Lys
        35                  40

<210> SEQ ID NO 21
<211> LENGTH: 39
<212> TYPE: PRT
<213> ORGANISM: Homo sapiens

<400> SEQUENCE: 21

Leu Pro Leu Glu Leu Lys Leu Arg Ile Phe Arg Leu Leu Asp Val Arg
```

```
                1               5                  10                 15
        Ser Val Leu Ser Leu Ser Ala Val Cys Arg Asp Leu Phe Thr Ala Ser
                            20                  25                  30

Asn Asp Pro Leu Leu Trp Arg
                    35

<210> SEQ ID NO 22
<211> LENGTH: 39
<212> TYPE: PRT
<213> ORGANISM: Homo sapiens

<400> SEQUENCE: 22

Leu Pro Asp Glu Leu Leu Leu Gly Ile Phe Ser Cys Leu Cys Leu Pro
         1               5                  10                  15

Glu Leu Leu Lys Val Ser Gly Val Cys Lys Arg Trp Tyr Arg Leu Ala
                            20                  25                  30

Ser Asp Glu Ser Leu Trp Gln
                    35

<210> SEQ ID NO 23
<211> LENGTH: 1323
<212> TYPE: DNA
<213> ORGANISM: Homo sapiens

<400> SEQUENCE: 23
acattttcta atgtttacag aatgaagagg aacagtttat ctgttgagaa taaaattgtc      60
cagttgtcag gagcagcgaa acagccaaaa gttgggttct actcttctct caaccagact     120
catacacaca cggttcttct agactggggg agtttgcctc accatgtagt attacaaatt     180
tttcagtatc ttcctttact agatcgggcc tgtgcatctt ctgtatgtag gaggtggaat     240 gaagttttc atatttctga cctttggaga agtttgaat ttgaactgaa ccagtcagct      300
acttcatctt ttaagtccac tcatcctgat ctcattcagc agatcattaa aaagcatttt     360
gctcatcttc agtatgtcag ctttaaggtt gacagtagcg ctgagtcagc agaagctgcc     420
tgtgatatac tctctcagct ggtaaattgt tccatccaga ccttgggctt gatttcaaca     480
gccaagccaa gtttcatgaa tgtgtcggag tctcattttg tgtcagcact tacagttgtt     540
tttatcaact caaaatcatt atcatcaatc aaaattgaag atacaccagt ggatgatcct     600
tcattgaaga ttcttgtggc caataatagt gacactctaa gactcccaaa gatgagtagc     660
tgtcctcatg tttcatctga tggaattctt tgtgtagctg accgttgtca aggccttaga     720
gaactggcgt tgaattatta catcctaact gatgaacttt tccttgcact ctcaagcgag     780
actcatgtta accttgaaca tcttcgaatt gatgttgtga gtgaaaatcc tggacagatt     840
aaatttcatg ctgttaaaaa acacagttgg gatgcactta ttaaacattc ccctagagtt     900
aatgttgtta tgcacttctt tctatatgaa gaggaattcg agacgttctt caaagaagaa     960 accctgtta ctcaccttta ttttggtcgt tcagtcagca agtggttttt aggacgggta     1020
ggtctcaact gtcctcgact gattgagtta gtggtgtgtg ctaatgatct tcagcctctt     1080
gataatgaac ttatttgtat tgctgaacac tgtacaaacc taacagcctt gggcctcagc     1140
aaatgtgaag ttagctgcag tgccttcatc aggtttgtaa gactgtgtga gagaaggtta     1200
acacagctct ctgtaatgga ggaagttttg atccctgatg aggattatag cctagatgaa     1260
attcacactg aagtctccaa atacctggga agagtatggt tccctgatgt gatgcctctc     1320
tgg                                                                    1323
```

<210> SEQ ID NO 24
<211> LENGTH: 434
<212> TYPE: PRT
<213> ORGANISM: Homo sapiens

<400> SEQUENCE: 24

```
Met Lys Arg Asn Ser Leu Ser Val Glu Asn Lys Ile Val Gln Leu Ser
 1               5                  10                  15

Gly Ala Ala Lys Gln Pro Lys Val Gly Phe Tyr Ser Ser Leu Asn Gln
                20                  25                  30

Thr His Thr His Thr Val Leu Leu Asp Trp Gly Ser Leu Pro His His
            35                  40                  45

Val Val Leu Gln Ile Phe Gln Tyr Leu Pro Leu Leu Asp Arg Ala Cys
     50                  55                  60

Ala Ser Ser Val Cys Arg Arg Trp Asn Glu Val Phe His Ile Ser Asp
 65                  70                  75                  80

Leu Trp Arg Lys Phe Glu Phe Glu Leu Asn Gln Ser Ala Thr Ser Ser
                85                  90                  95

Phe Lys Ser Thr His Pro Asp Leu Ile Gln Gln Ile Ile Lys Lys His
               100                 105                 110

Phe Ala His Leu Gln Tyr Val Ser Phe Lys Val Asp Ser Ser Ala Glu
            115                 120                 125

Ser Ala Glu Ala Ala Cys Asp Ile Leu Ser Gln Leu Val Asn Cys Ser
    130                 135                 140

Ile Gln Thr Leu Gly Leu Ile Ser Thr Ala Lys Pro Ser Phe Met Asn
145                 150                 155                 160

Val Ser Glu Ser His Phe Val Ser Ala Leu Thr Val Val Phe Ile Asn
                165                 170                 175

Ser Lys Ser Leu Ser Ser Ile Lys Ile Glu Asp Thr Pro Val Asp Asp
            180                 185                 190

Pro Ser Leu Lys Ile Leu Val Ala Asn Asn Ser Asp Thr Leu Arg Leu
        195                 200                 205

Pro Lys Met Ser Ser Cys Pro His Val Ser Ser Asp Gly Ile Leu Cys
    210                 215                 220

Val Ala Asp Arg Cys Gln Gly Leu Arg Glu Leu Ala Leu Asn Tyr Tyr
225                 230                 235                 240

Ile Leu Thr Asp Glu Leu Phe Leu Ala Leu Ser Ser Glu Thr His Val
                245                 250                 255

Asn Leu Glu His Leu Arg Ile Asp Val Val Ser Glu Asn Pro Gly Gln
            260                 265                 270

Ile Lys Phe His Ala Val Lys Lys His Ser Trp Asp Ala Leu Ile Lys
        275                 280                 285

His Ser Pro Arg Val Asn Val Val Met His Phe Phe Leu Tyr Glu Glu
    290                 295                 300

Glu Phe Glu Thr Phe Phe Lys Glu Glu Thr Pro Val Thr His Leu Tyr
305                 310                 315                 320

Phe Gly Arg Ser Val Ser Lys Val Val Leu Gly Arg Val Gly Leu Asn
                325                 330                 335

Cys Pro Arg Leu Ile Glu Leu Val Val Cys Ala Asn Asp Leu Gln Pro
            340                 345                 350

Leu Asp Asn Glu Leu Ile Cys Ile Ala Glu His Cys Thr Asn Leu Thr
        355                 360                 365

Ala Leu Gly Leu Ser Lys Cys Glu Val Ser Cys Ser Ala Phe Ile Arg
    370                 375                 380

Phe Val Arg Leu Cys Glu Arg Arg Leu Thr Gln Leu Ser Val Met Glu
```

```
       385                 390                 395                 400
Glu Val Leu Ile Pro Asp Glu Asp Tyr Ser Leu Asp Glu Ile His Thr
                    405                 410                 415

Glu Val Ser Lys Tyr Leu Gly Arg Val Trp Phe Pro Asp Val Met Pro
                420                 425                 430

Leu Trp

<210> SEQ ID NO 25
<211> LENGTH: 1970
<212> TYPE: DNA
<213> ORGANISM: Homo sapiens

<400> SEQUENCE: 25
```

| | | | | | |
|---|---|---|---|---|---|
| ggaaacgtca | aaattgggat | agtcggcagt | tctggcccct | gcagctggag | gtaccctgag | 60 |
| ttctgagggt | cgtagtgctg | tttctggtat | tctcatcgcg | gtcacctcta | ccggtgtgga | 120 |
| caagtaaagt | ttgaatcagc | ttctccatgg | cctgggcacc | agttcccggc | tgagccattt | 180 |
| tcctttggc | taaaagtccc | cgcccagagg | ccaattcgtc | gcggcggcgg | tggagatcgc | 240 |
| aggtcgctca | ggcttgcaga | tgggtcaagg | gttgtggaga | gtggtcagaa | accagcagct | 300 |
| gcaacaagaa | ggctacagtg | agcaaggcta | cctcaccaga | gagcagagca | ggagaatggc | 360 |
| tgcgagcaac | atttctaaca | ccaatcatcg | taaacaagtc | caaggaggca | ttgacatata | 420 |
| tcatcttttg | aaggcaagga | atcgaaaga | acaggaagga | ttcattaatt | tggaaatgtt | 480 |
| gcctcctgag | ctaagcttta | ccatcttgtc | ctacctgaat | gcaactgacc | tttgcttggc | 540 |
| ttcatgtgtt | tggcaggacc | ttgcgaatga | tgaacttctc | tggcaagggt | tgtgcaaatc | 600 |
| cacttggggt | cactgttcca | tatacaataa | gaacccacct | ttaggatttt | cttttagaaa | 660 |
| aktgtatatg | cagctggatg | aaggcagcct | cacctttaat | gccaacccag | atgagggagt | 720 |
| gaactacttt | atgtccaagg | gtatcctgga | tgattcgcca | aggaaatag | caaagtttat | 780 |
| cttctgtaca | agaacactaa | attggaaaaa | actgagaatc | tatcttgatg | aaaggagaga | 840 |
| tgtcttggat | gaccttgtaa | cattgcataa | ttttagaaat | cagttcttgc | caaatgcact | 900 |
| gagagaattt | tttcgtcata | tccatgcccc | tgaagagcgt | ggagagtatc | ttgaaactct | 960 |
| tataacaaag | ttctcacata | gattctgtgc | ttgcaaccct | gatttaatgc | gagaacttgg | 1020 |
| ccttagtcct | gatgctgtct | atgtactgtg | ctactctttg | attctacttt | ccattgacct | 1080 |
| cactagccct | catgtgaaga | ataaaatgtc | aaaagggaa | tttattcgaa | atacccgtcg | 1140 |
| cgctgctcaa | atattagtg | aagatttgt | agggcatctt | tatgacaata | tctaccttat | 1200 |
| tggccatgtg | gctgcataaa | aagcacaatt | gctaggactt | cagttttac | ttcagactaa | 1260 |
| agctacccaa | ggacttagca | gatatggggg | ttacatcagt | gctggtcatt | gtagcctgag | 1320 |
| tatacaatca | agcttcagtg | tgcaaccttt | ttttcttttg | ccatttcta | ttttagtaat | 1380 |
| ttccttgggg | aactaaataa | ttttgcagaa | ttttttcctaa | ttttgtttat | cacgttttgc | 1440 |
| acaaagcaga | gccactgtct | aacacagctg | ttaacgaatg | ataaactgac | attatactct | 1500 |
| aaaagatggt | gtatttgtgc | attagatttg | cctgaaaaac | tttatccatt | tccattcttt | 1560 |
| atacaaatac | catgtaatgt | gtacatattt | aactaaagag | atttatagtc | ataattattt | 1620 |
| tattgtaaag | attttaacta | aagttttttcc | ttttctctca | aactgagttc | tgaaatttat | 1680 |
| ttgattctga | tctgaaacta | ttgtctycgt | aaaagttaga | tctgacttca | grcagaaacc | 1740 |
| aataccagct | tccttttcct | ttaaactttg | aagagtgttg | atttgttact | atattactat | 1800 |
| gcaaaactgg | cagttatttt | tataatataa | atttataatt | tgatttttta | ttttaaaaac | 1860 |

```
tgggttaatc aagtctcggt aagtccttta aaccatttag gatttttaaa acatcaaaat   1920
ttatgattta cattcatagg aataaaataa aatatyatta gaactctggt              1970
```

<210> SEQ ID NO 26
<211> LENGTH: 341
<212> TYPE: PRT
<213> ORGANISM: Homo sapiens
<220> FEATURE:
<221> NAME/KEY: VARIANT
<222> LOCATION: 157
<223> OTHER INFORMATION: Xaa = Any Amino Acid

<400> SEQUENCE: 26

```
Lys Ser Pro Pro Arg Gly Gln Phe Val Ala Ala Val Glu Ile Ala
  1               5                  10                  15

Gly Arg Ser Gly Leu Gln Met Gly Gln Gly Leu Trp Arg Val Arg
                 20                  25                  30

Asn Gln Gln Leu Gln Gln Glu Gly Tyr Ser Glu Gln Gly Tyr Leu Thr
                 35                  40                  45

Arg Glu Gln Ser Arg Arg Met Ala Ala Ser Asn Ile Ser Asn Thr Asn
             50                  55                  60

His Arg Lys Gln Val Gln Gly Gly Ile Asp Ile Tyr His Leu Leu Lys
 65                  70                  75                  80

Ala Arg Lys Ser Lys Glu Gln Glu Gly Phe Ile Asn Leu Glu Met Leu
                 85                  90                  95

Pro Pro Glu Leu Ser Phe Thr Ile Leu Ser Tyr Leu Asn Ala Thr Asp
                100                 105                 110

Leu Cys Leu Ala Ser Cys Val Trp Gln Asp Leu Ala Asn Asp Glu Leu
            115                 120                 125

Leu Trp Gln Gly Leu Cys Lys Ser Thr Trp Gly His Cys Ser Ile Tyr
        130                 135                 140

Asn Lys Asn Pro Pro Leu Gly Phe Ser Phe Arg Lys Xaa Tyr Met Gln
145                 150                 155                 160

Leu Asp Glu Gly Ser Leu Thr Phe Asn Ala Asn Pro Asp Glu Gly Val
                165                 170                 175

Asn Tyr Phe Met Ser Lys Gly Ile Leu Asp Asp Ser Pro Lys Glu Ile
                180                 185                 190

Ala Lys Phe Ile Phe Cys Thr Arg Thr Leu Asn Trp Lys Lys Leu Arg
            195                 200                 205

Ile Tyr Leu Asp Glu Arg Arg Asp Val Leu Asp Leu Val Thr Leu
        210                 215                 220

His Asn Phe Arg Asn Gln Phe Leu Pro Asn Ala Leu Arg Glu Phe Phe
225                 230                 235                 240

Arg His Ile His Ala Pro Glu Glu Arg Gly Glu Tyr Leu Glu Thr Leu
                245                 250                 255

Ile Thr Lys Phe Ser His Arg Phe Cys Ala Cys Asn Pro Asp Leu Met
                260                 265                 270

Arg Glu Leu Gly Leu Ser Pro Asp Ala Val Tyr Val Leu Cys Tyr Ser
            275                 280                 285

Leu Ile Leu Leu Ser Ile Asp Leu Thr Ser Pro His Val Lys Asn Lys
        290                 295                 300

Met Ser Lys Arg Glu Phe Ile Arg Asn Thr Arg Arg Ala Ala Gln Asn
305                 310                 315                 320

Ile Ser Glu Asp Phe Val Gly His Leu Tyr Asp Asn Ile Tyr Leu Ile
                325                 330                 335

Gly His Val Ala Ala
```

<210> SEQ ID NO 27
<211> LENGTH: 4168
<212> TYPE: DNA
<213> ORGANISM: Homo sapiens

<400> SEQUENCE: 27

```
gatggcggcg gcagcagtcg acagcgcgat ggaggtggtg ccggcgctgg cggaggaggc      60
cgcgccggag gtagcgggcc tcagctgcct cgtcaacctg ccgggtgagg tgctggagta     120
catcctgtgc tgcggctcgc tgacggccgc cgacatcggc cgtgtctcca gcacctgccg     180
gcggctgcgc gagctgtgcc agagcagcgg gaaggtgtgg aaggagcagt tccgggtgag     240
gtggccttcc cttatgaaac actacagccc caccgactac gtcaattggt tggaagagta     300
taaagttcgg caaaaagctg ggttagaagc gcggaagatt gtagcctcgt tctcaaagag     360
gttcttttca gagcacgttc cttgtaatgg cttcagtgac attgagaacc ttgaaggacc     420
agagattttt tttgaggatg aactggtgtg tatcctaaat atggaaggaa gaaaagcttt     480
gacctggaaa tactacgcaa aaaaaattct ttactacctg cggcaacaga agatcttaaa     540
taatcttaag gccttttcttc agcagccaga tgactatgag tcgtatcttg aaggtgctgt     600
atatattgac cagtactgca atcctctctc cgacatcagc ctcaaagaca tccaggccca     660
aattgacagc atcgtggagc ttgtttgcaa acccttcgg ggcataaaca gtcgccaccc     720
cagcttggcc ttcaaggcag gtgaatcatc catgataatg gaaatagaac tccagagcca     780
ggtgctggat gccatgaact atgtcccttta cgaccaactg aagttcaagg ggaatcgaat     840
ggattactat aatgccctca acttatatat gcatcaggtt ttgattcgca gaacaggaat     900
cccaatcagc atgtctctgc tctatttgac aattgctcgg cagttgggag tcccactgga     960
gcctgtcaac ttcccaagtc acttcttatt aaggtggtgc aaggcgcag aaggggcgac    1020
cctggacatc tttgactaca tctacataga tgcttttggg aaaggcaagc agctgacagt    1080
gaaagaatgc gagtacttga tcggccagca cgtgactgca gcactgtatg ggtggtcaa    1140
tgtcaagaag gtgttacaga aatggtggg aaacctgtta agcctgggga agcgggaagg    1200
catcgaccag tcataccagc tcctgagaga ctcgctggat ctctatctgg caatgtaccc    1260
ggaccaggtg cagcttctcc tcctccaagc caggctttac ttccacctgg aatctggcc    1320
agagaaggtg cttgacatcc tccagcacat ccaaacccta cccgggggc agcacggggc    1380
ggtgggctac ctggtgcagc acactctaga gcacattgag cgcaaaaagg aggaggtggg    1440
cgtagaggtg aagctgcgct ccgatgagaa gcacagagat gtctgctact ccatcgggct    1500
cattatgaag cataagaggt atggctataa ctgtgtgatc tacggctggg accccacctg    1560
catgatggga cacgagtgga tccggaacat gaacgtccac agcctgccgc acggccacca    1620
ccagccttc tataacgtgc tggtggagga cggctcctgt cgatacgcag cccaagaaaa    1680
cttggaatat aacgtggagc tcaagaaat ctcacaccct gacgtgggac gctatttctc    1740
agagtttact ggcactcact acatccccaa cgcagagctg gagatccggt atccagaaga    1800
tctggagttt gtctatgaaa cggtgcagaa tatttacagt gcaagaaaag agaacataga    1860
tgagtaaagt ctagagagga cattgcacct ttgctgctgc tgctatcttc caagagaacg    1920
ggactccgga agaagacgtc tccacggagc cctcgggacc tgctgcacca ggaaagccac    1980
tccaccagta gtgctggttg cctcctacta agtttaaata ccgtgtgctc ttccccagct    2040
gcaaagacaa tgttgctctc cgcctacact agtgaattaa tctgaaaggc actgtgtcag    2100
```

-continued

```
tggcatggct tgtatgcttg tcctgtggtg acagtttgtg acattctgtc ttcatgaggt    2160
ctcacagtcg acgctcctgt aatcattctt tgtattcact ccattcccct gtctgtctgc    2220
atttgtctca gaacatttcc ttggctggac agatggggtt atgcatttgc aataatttcc    2280
ttctgatttc tctgtggaac gtgttcggtc ccgagtgagg actgtgtgtc ttttttaccct   2340 gaagttagtt gcatattcag aggtaaagtt gtgtgctatc ttggcagcat cttagagatg    2400
gagacattaa caagctaatg gtaattagaa tcatttgaat ttattttttt ctaatatgtg    2460
aaacacagat ttcaagtgtt ttatcttttt tttttaaatt taaatgggaa tataacacag    2520
ttttcccttc catattcctc tcttgagttt atgcacatct ctataaatca ttagttttct    2580
attttattac ataaaattct tttagaaaat gcaaatagtg aactttgtga atggattttt    2640
ccatactcat ctacaattcc tccattttaa atgactactt ttattttta atttaaaaaa     2700 tctacttcag tatcatgagt aggtcttaca tcagtgatgg gttctttttg tagtgagaca    2760
tacaaatctg atgttaatgt ttgctcttag aagtcatact ccatggtctt caaagaccaa    2820
aaaatgaggt tttgcctttg taatcaggaa aaaaaaaaat taatgaacct taaaaaaaaa    2880
aaaaaaggtt ttgaagggaa aaaaagtggt ttcacacctc ttgttattcc ttagagtcac    2940
ttcaaggcct gtttgaatgt ggcaggttag aaagagagag aatgtctttc atttgaagag    3000
tgttggactt gtgtgaaagg agatgtgcgt gttggaatct gcttttccaa gccgccaggg    3060
tcctgacggc agcaggacga agcctgttgt ggcgtcttct gggaaagcct gaccgtgtgt    3120
tcggacggca ctggctcctt tccgaagttc tcagtaactg agcccagagt aactgcacgc    3180 cttttgtgcag ctctggagct ccaccaactc tcggcctgcc agttctcaag cgagctaatc    3240
ttgtcattaa tcgatagaag ctaacttccg aagttaggac ctagttactt tgctctcaac    3300
atttaaaata atgcagttgc tctagtgaat ggggcgttag gggcctgtct ctgcacctgt    3360
ctgtccatct gcatgcagta ttctcaccca tgttgaatgc ctgctgcttg tttacccttt    3420
ggaaaccctg gggtgaccaa ggtttggaaa gccacctgag accacttcat agcaagggaa    3480
ggctttaagc agttactaga aagagatggg gatttggccc ctggctcctc cagcctgaat    3540
gagctattta atccactgtc catgttcctc atcagtcaaa tccaaagtca aaggatttga    3600
acctgcatct ggaaacgtaa ccactcacag cacctggccc gccaaggttg ggaggattgt    3660
acactacttt catttaaagg ggaaagtttg ataatacgga attaattaat atgaatgaga    3720
tgcattaata agaacctgag catgctgaga gttgcaattg ttggttttct ggtttgattg    3780
attttccttt tcttagaca catcaaagtc aagaaagatg gttttacctt tactgaccca     3840
gctgtacata tgtatctaga ctgttttaa atgtctttct tcatgaatgc ttcatggggc     3900
tccaggaagc ctgtatcacc tgtgtaagtt ggtatttggg cactttatat ttttctaaaa    3960
acgtgttttg gatcctgtac tctaataaat cataagtttc tttttaaaaa ttttccaaaa    4020
cttttctcca tttttaaaaag ccctgttata aacgttgaac tttcacaatg ttaaaatgtt    4080
aaatatttgg atatagcaac ttcttttctc ttcaaatgaa tgccaagatt ttttttgtaca    4140 atgattaata aatggaactt atccagag                                      4168
```

<210> SEQ ID NO 28
<211> LENGTH: 621
<212> TYPE: PRT
<213> ORGANISM: Homo sapiens

<400> SEQUENCE: 28

Met Ala Ala Ala Ala Val Asp Ser Ala Met Glu Val Val Pro Ala Leu
1               5                   10                  15

Ala Glu Glu Ala Ala Pro Glu Val Ala Gly Leu Ser Cys Leu Val Asn
            20                  25                  30

Leu Pro Gly Glu Val Leu Glu Tyr Ile Leu Cys Cys Gly Ser Leu Thr
        35                  40                  45

Ala Ala Asp Ile Gly Arg Val Ser Ser Thr Cys Arg Arg Leu Arg Glu
    50                  55                  60

Leu Cys Gln Ser Ser Gly Lys Val Trp Lys Glu Gln Phe Arg Val Arg
65                  70                  75                  80

Trp Pro Ser Leu Met Lys His Tyr Ser Pro Thr Asp Tyr Val Asn Trp
                85                  90                  95

Leu Glu Glu Tyr Lys Val Arg Gln Lys Ala Gly Leu Glu Ala Arg Lys
            100                 105                 110

Ile Val Ala Ser Phe Ser Lys Arg Phe Phe Ser Glu His Val Pro Cys
        115                 120                 125

Asn Gly Phe Ser Asp Ile Glu Asn Leu Glu Gly Pro Glu Ile Phe Phe
    130                 135                 140

Glu Asp Glu Leu Val Cys Ile Leu Asn Met Glu Gly Arg Lys Ala Leu
145                 150                 155                 160

Thr Trp Lys Tyr Tyr Ala Lys Lys Ile Leu Tyr Tyr Leu Arg Gln Gln
                165                 170                 175

Lys Ile Leu Asn Asn Leu Lys Ala Phe Leu Gln Gln Pro Asp Asp Tyr
            180                 185                 190

Glu Ser Tyr Leu Glu Gly Ala Val Tyr Ile Asp Gln Tyr Cys Asn Pro
        195                 200                 205

Leu Ser Asp Ile Ser Leu Lys Asp Ile Gln Ala Gln Ile Asp Ser Ile
    210                 215                 220

Val Glu Leu Val Cys Lys Thr Leu Arg Gly Ile Asn Ser Arg His Pro
225                 230                 235                 240

Ser Leu Ala Phe Lys Ala Gly Glu Ser Ser Met Ile Met Glu Ile Glu
                245                 250                 255

Leu Gln Ser Gln Val Leu Asp Ala Met Asn Tyr Val Leu Tyr Asp Gln
            260                 265                 270

Leu Lys Phe Lys Gly Asn Arg Met Asp Tyr Tyr Asn Ala Leu Asn Leu
        275                 280                 285

Tyr Met His Gln Val Leu Ile Arg Arg Thr Gly Ile Pro Ile Ser Met
    290                 295                 300

Ser Leu Leu Tyr Leu Thr Ile Ala Arg Gln Leu Gly Val Pro Leu Glu
305                 310                 315                 320

Pro Val Asn Phe Pro Ser His Phe Leu Leu Arg Trp Cys Gln Gly Ala
                325                 330                 335

Glu Gly Ala Thr Leu Asp Ile Phe Asp Tyr Ile Tyr Ile Asp Ala Phe
            340                 345                 350

Gly Lys Gly Lys Gln Leu Thr Val Lys Glu Cys Glu Tyr Leu Ile Gly
        355                 360                 365

Gln His Val Thr Ala Ala Leu Tyr Gly Val Asn Val Lys Lys Val
    370                 375                 380

Leu Gln Arg Met Val Gly Asn Leu Leu Ser Leu Gly Lys Arg Glu Gly
385                 390                 395                 400

Ile Asp Gln Ser Tyr Gln Leu Leu Arg Asp Ser Leu Asp Leu Tyr Leu
                405                 410                 415

Ala Met Tyr Pro Asp Gln Val Gln Leu Leu Leu Gln Ala Arg Leu
            420                 425                 430

Tyr Phe His Leu Gly Ile Trp Pro Glu Lys Val Leu Asp Ile Leu Gln

```
                435              440             445
His Ile Gln Thr Leu Asp Pro Gly Gln His Gly Ala Val Gly Tyr Leu
    450                 455                 460

Val Gln His Thr Leu Glu His Ile Glu Arg Lys Lys Glu Glu Val Gly
465                 470                 475                 480

Val Glu Val Lys Leu Arg Ser Asp Glu Lys His Arg Asp Val Cys Tyr
                485                 490                 495

Ser Ile Gly Leu Ile Met Lys His Lys Arg Tyr Gly Tyr Asn Cys Val
            500                 505                 510

Ile Tyr Gly Trp Asp Pro Thr Cys Met Met Gly His Glu Trp Ile Arg
        515                 520                 525

Asn Met Asn Val His Ser Leu Pro His Gly His His Gln Pro Phe Tyr
530                 535                 540

Asn Val Leu Val Glu Asp Gly Ser Cys Arg Tyr Ala Ala Gln Glu Asn
545                 550                 555                 560

Leu Glu Tyr Asn Val Glu Pro Gln Glu Ile Ser His Pro Asp Val Gly
                565                 570                 575

Arg Tyr Phe Ser Glu Phe Thr Gly Thr His Tyr Ile Pro Asn Ala Glu
            580                 585                 590

Leu Glu Ile Arg Tyr Pro Glu Asp Leu Glu Phe Val Tyr Glu Thr Val
        595                 600                 605

Gln Asn Ile Tyr Ser Ala Lys Lys Glu Asn Ile Asp Glu
610                 615                 620

<210> SEQ ID NO 29
<211> LENGTH: 278
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 29
ccgtagtact ggnttccggc gggctggtga ggaatggagc cggtagntgc ttgcggcgag      60
tcccgggntc ctccgtagac ccgcgganac cttcgtgttg agtaacctgg cggaggtggt     120
ggagcgtgtg ctcaccttcc tgcccgccaa ggcgttgctg cgggtggcct gcgtgtgccg     180
cttatggagg gagtgtgtgc gcagagtatt gcggacccat cggagcgtaa cctggatctc     240
cgcaggcctg gcggaggccg gccacctggn ggggcatt                             278

<210> SEQ ID NO 30
<211> LENGTH: 77
<212> TYPE: PRT
<213> ORGANISM: Homo sapiens
<220> FEATURE:
<221> NAME/KEY: VARIANT
<222> LOCATION: 1, 8, 14, 75
<223> OTHER INFORMATION: Xaa = Any Amino Acid

<400> SEQUENCE: 30

Xaa Leu Ala Ala Ser Pro Gly Xaa Leu Arg Arg Pro Ala Xaa Thr Phe
  1               5                  10                  15

Val Leu Ser Asn Leu Ala Glu Val Val Glu Arg Val Leu Thr Phe Leu
                20                  25                  30

Pro Ala Lys Ala Leu Leu Arg Val Ala Cys Val Cys Arg Leu Trp Arg
            35                  40                  45

Glu Cys Val Arg Arg Val Leu Arg Thr His Arg Ser Val Thr Trp Ile
        50                  55                  60
```

Ser Ala Gly Leu Ala Glu Ala Gly His Leu Xaa Gly His
65                  70                  75

<210> SEQ ID NO 31
<211> LENGTH: 592
<212> TYPE: DNA
<213> ORGANISM: Homo sapiens

<400> SEQUENCE: 31
gcggccgcgc ccggtgcagc aacagcagca gcagccccccg cagcagccgc cgccgcagcc    60
gccccagcag cagccgcccc agcagcagcc tccgccgccg ccgcagcagc agcagcagca   120
gcagcctccg ccgccgccac cgccgcctcc gccgctgcct caggagcgga caacgtcgg   180
cgagcgggat gatgatgtgc ctgcagatat ggttgcagaa gaatcaggtc ctggtgcaca   240
aaatagtcca taccaacttc gtagaaaaac tcttttgccg aaaagaacag cgtgtcccac   300
aaagaacagt atggagggcg cctcaacttc aactacagaa aactttggtc atcgtgcaaa   360
acgtgcaaga gtgtctggaa atcacaagat ctatcagca gcacctgctg aacagtatct   420
tcaggagaaa ctgccagatg aagtggttct aaaaatcttc tcttacttgc tggaacagga   480
tctttgtaga gcagcttgtg tatgtaaacg cttcagtgaa cttgctaatg atcccaattt   540
gtggaaacga ttatatatgg aagtatttga atatactcgc cctatgatgc at           592

<210> SEQ ID NO 32
<211> LENGTH: 197
<212> TYPE: PRT
<213> ORGANISM: Homo sapiens

<400> SEQUENCE: 32

Arg Pro Arg Pro Val Gln Gln Gln Gln Gln Pro Pro Gln Gln Pro
 1               5                  10                  15

Pro Pro Gln Pro Pro Gln Gln Gln Pro Pro Gln Gln Gln Pro Pro Pro
                20                  25                  30

Pro Pro Gln Gln Gln Gln Gln Gln Gln Pro Pro Pro Pro Pro
             35                  40                  45

Pro Pro Pro Leu Pro Gln Glu Arg Asn Asn Val Gly Glu Arg Asp Asp
 50                  55                  60

Asp Val Pro Ala Asp Met Val Ala Glu Glu Ser Gly Pro Gly Ala Gln
 65                  70                  75                  80

Asn Ser Pro Tyr Gln Leu Arg Arg Lys Thr Leu Leu Pro Lys Arg Thr
                 85                  90                  95

Ala Cys Pro Thr Lys Asn Ser Met Glu Gly Ala Ser Thr Ser Thr Thr
            100                 105                 110

Glu Asn Phe Gly His Arg Ala Lys Arg Ala Arg Val Ser Gly Lys Ser
        115                 120                 125

Gln Asp Leu Ser Ala Ala Pro Ala Glu Gln Tyr Leu Gln Glu Lys Leu
130                 135                 140

Pro Asp Glu Val Val Leu Lys Ile Phe Ser Tyr Leu Leu Glu Gln Asp
145                 150                 155                 160

Leu Cys Arg Ala Ala Cys Val Cys Lys Arg Phe Ser Glu Leu Ala Asn
                165                 170                 175

Asp Pro Asn Leu Trp Lys Arg Leu Tyr Met Glu Val Phe Glu Tyr Thr
            180                 185                 190

Arg Pro Met Met His
        195

-continued

<210> SEQ ID NO 33
<211> LENGTH: 537
<212> TYPE: DNA
<213> ORGANISM: Homo sapiens

<400> SEQUENCE: 33

| | |
|---|---|
| gcggccgcgg cccggactcc gcggtgggcg agcgccctgt gaggtgacca tggaggctgg | 60 |
| tggcctcccc ttggagctgt ggcgcatgat cttagcctac ttgcaccttc ccgacctggg | 120 |
| ccgctgcagc ctggtatgca gggcctggta tgaactgatc ctcagtctcg acagcacccg | 180 |
| ctggcggcag ctgtgtctgg gttgcaccga gtgccgccat cccaattggc ccaaccagcc | 240 |
| agatgtggag cctgagtctt ggagagaagc cttcaagcag cattaccttg catccaagac | 300 |
| atggaccaag aatgccttgg acttggagtc ttccatctgc ttttctctat tccgccggag | 360 |
| gagggaacga cgtaccctga gtgttgggcc aggccgtgag tttgacagcc tgggcagtgc | 420 |
| cttggccatg ccagcctgt atgaccgaat tgtgctcttc ccaggtgtgt acgaagagca | 480 |
| aggtgaaatc atcttgaagg tgcctgtgga gattgtaggg caggggaagt tgggtga | 537 |

<210> SEQ ID NO 34
<211> LENGTH: 178
<212> TYPE: PRT
<213> ORGANISM: Homo sapiens

<400> SEQUENCE: 34

Arg Pro Arg Pro Gly Leu Arg Gly Gly Arg Ala Pro Cys Glu Val Thr
1               5                   10                  15

Met Glu Ala Gly Gly Leu Pro Leu Glu Leu Trp Arg Met Ile Leu Ala
            20                  25                  30

Tyr Leu His Leu Pro Asp Leu Gly Arg Cys Ser Leu Val Cys Arg Ala
        35                  40                  45

Trp Tyr Glu Leu Ile Leu Ser Leu Asp Ser Thr Arg Trp Arg Gln Leu
    50                  55                  60

Cys Leu Gly Cys Thr Glu Cys Arg His Pro Asn Trp Pro Asn Gln Pro
65                  70                  75                  80

Asp Val Glu Pro Glu Ser Trp Arg Glu Ala Phe Lys Gln His Tyr Leu
                85                  90                  95

Ala Ser Lys Thr Trp Thr Lys Asn Ala Leu Asp Leu Glu Ser Ser Ile
            100                 105                 110

Cys Phe Ser Leu Phe Arg Arg Arg Glu Arg Arg Thr Leu Ser Val
        115                 120                 125

Gly Pro Gly Arg Glu Phe Asp Ser Leu Gly Ser Leu Ala Met Ala
    130                 135                 140

Ser Leu Tyr Asp Arg Ile Val Leu Phe Pro Gly Val Tyr Glu Glu Gln
145                 150                 155                 160

Gly Glu Ile Ile Leu Lys Val Pro Val Glu Ile Val Gly Gln Gly Lys
                165                 170                 175

Leu Gly

<210> SEQ ID NO 35
<211> LENGTH: 751
<212> TYPE: DNA
<213> ORGANISM: Homo sapiens

<400> SEQUENCE: 35

| | |
|---|---|
| gagaccgaga cggcgccgct gaccctagag tcgctgccca ccgatcccct gctcctcatc | 60 |
| ttatcctttt tggactatcg ggatctaatc aactgttgtt atgtcagtcg aagattaagc | 120 |

```
cagctatcaa gtcatgatcc gctgtggaga agacattgca aaaaatactg gctgatatct    180
gaggaagaga aaacacagaa gaatcagtgt tggaaatctc tcttcataga tacttactct    240
gatgtaggaa gatacattga ccattatgct gctattaaaa aggcctcggg aatgatctca    300
agaaatattt ggagcccagg tgtcctcgga tgggttttat ctctgaaaga ggggtgctcg    360
agaggaagac ctcgatgctg tggaagcgca gattgggctg caagtttcct ggacgattat    420
cgatgttcat accgaattca caatggacag aagttagttg gttcctgggg ttattgggaa    480
gcatggcact gtctaatcac tatcgttctg aagatttgtt agacgtcgat acagctgccg    540
gagattccag cagagacagg gactgaaata ctgtctccct ttaacttttg catacatact    600
ggtttgagtc agtacatagc agtggaagct gcagagggtt gaaacaaaaa tgaagttttc    660
taccaatgtc agacagtaga acgtgtgttt aaatatggca ttaagatgtg ttctgatggt    720
tgtataaatg gcatgcatta ggtattttca g                                  751

<210> SEQ ID NO 36
<211> LENGTH: 173
<212> TYPE: PRT
<213> ORGANISM: Homo sapiens

<400> SEQUENCE: 36

Glu Thr Glu Thr Ala Pro Leu Thr Leu Glu Ser Leu Pro Thr Asp Pro
 1               5                  10                  15

Leu Leu Leu Ile Leu Ser Phe Leu Asp Tyr Arg Asp Leu Ile Asn Cys
            20                  25                  30

Cys Tyr Val Ser Arg Arg Leu Ser Gln Leu Ser Ser His Asp Pro Leu
        35                  40                  45

Trp Arg Arg His Cys Lys Lys Tyr Trp Leu Ile Ser Glu Glu Glu Lys
    50                  55                  60

Thr Gln Lys Asn Gln Cys Trp Lys Ser Leu Phe Ile Asp Thr Tyr Ser
65                  70                  75                  80

Asp Val Gly Arg Tyr Ile Asp His Tyr Ala Ala Ile Lys Lys Ala Ser
                85                  90                  95

Gly Met Ile Ser Arg Asn Ile Trp Ser Pro Gly Val Leu Gly Trp Val
            100                 105                 110

Leu Ser Leu Lys Glu Gly Cys Ser Arg Gly Arg Pro Arg Cys Cys Gly
        115                 120                 125

Ser Ala Asp Trp Ala Ala Ser Phe Leu Asp Asp Tyr Arg Cys Ser Tyr
    130                 135                 140

Arg Ile His Asn Gly Gln Lys Leu Val Gly Ser Trp Gly Tyr Trp Glu
145                 150                 155                 160

Ala Trp His Cys Leu Ile Thr Ile Val Leu Lys Ile Cys
                165                 170

<210> SEQ ID NO 37
<211> LENGTH: 368
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 37
ggctccggtt tccgggccgg cgggtggccg ctcaccatgc ccggnaagca ccagcatttc     60
caggaacctg aggtcggctg ctgcgggaaa tacttcctgt ttggcttcaa cattgtcttc    120
tgggtgctgg agccctgtt cctggctatc ggcctctggg cctggggtga aagggcgtt     180
```

-continued

```
ctctcgaaca tctcagcgct gacagatctg ggaggccttg accccgtgtg gcttgtttgt    240
ggtagttgga ggcgtcatgt cggtgctggg ctttgctggg ctgcaattgg ggccctccgg    300
gagaacacct tcctgctcaa gttttctnc gngttcctcg gtctcatctt cttcctggag    360
ctggcaac                                                              368
```

<210> SEQ ID NO 38
<211> LENGTH: 122
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 38

```
Gly Ser Gly Phe Arg Ala Gly Gly Trp Pro Leu Thr Met Pro Gly Lys
  1               5                  10                  15

His Gln His Phe Gln Glu Pro Glu Val Gly Cys Cys Gly Lys Tyr Phe
             20                  25                  30

Leu Phe Gly Phe Asn Ile Val Phe Trp Val Leu Gly Ala Leu Phe Leu
         35                  40                  45

Ala Ile Gly Leu Trp Ala Trp Gly Glu Lys Gly Val Leu Ser Asn Ile
     50                  55                  60

Ser Ala Leu Thr Asp Leu Gly Gly Leu Asp Pro Val Trp Leu Val Cys
 65                  70                  75                  80

Gly Ser Trp Arg Arg His Val Gly Ala Gly Leu Cys Trp Ala Ala Ile
             85                  90                  95

Gly Ala Leu Arg Glu Asn Thr Phe Leu Leu Lys Phe Phe Xaa Xaa Phe
            100                 105                 110

Leu Gly Leu Ile Phe Phe Leu Glu Leu Ala
            115                 120
```

<210> SEQ ID NO 39
<211> LENGTH: 774
<212> TYPE: DNA
<213> ORGANISM: Homo sapiens

<400> SEQUENCE: 39

```
gcggcggccg ccgccgcgta cctggacgag ctgcccgagc cgctgctgct gcgcgtgctg     60
gccgcactgc cggccgccga gctggtgcag gcctgccgcc tggtgtgcct gcgctggaag    120
gagctggtgg acggcgcccc gctgtggctg ctcaagtgcc agcaggaggg gctggtgccc    180
gagggcggcg tggaggagga gcgcgaccac tggcagcagt tctacttcct gagcaagcgg    240
cgccgcaacc ttctgcgtaa cccgtgtggg aagaggact tggaaggctg gtgtgacgtg    300
gagcatggtg gggacggctg gagggtggag gagctgcctg gagacagtgg ggtggagttc    360
acccacgatg agagcgtcaa gaagtacttc gcctcctcct ttgagtggtg tcgcaaagca    420
caggtcattg acctgcaggc tgagggctac tgggaggagc tgctggacac gactcagccg    480
gccatcgtgg tgaaggactg gtactcgggc cgcagcgacg ctggttgcct ctacgagctc    540
accgttaagc tactgtccga gcacgagaac gtgctggctg agttcagcag cgggcaggtg    600
gcagtgcccc aagacagtga cggcggggc tggatggaga tctcccacac cttcaccgac    660
tacgggccgg gcgtccgctt cgtccgcttc gagcacgggg ggcagggctc cgtctactgg    720
aagggctggt tcggggcccg ggtgaccaac agcagcgtgt gggtagaacc ctga          774
```

<210> SEQ ID NO 40
<211> LENGTH: 257
<212> TYPE: PRT
<213> ORGANISM: Homo sapiens

<400> SEQUENCE: 40

Ala Ala Ala Ala Ala Tyr Leu Asp Glu Leu Pro Glu Pro Leu Leu
1               5                   10                  15

Leu Arg Val Leu Ala Ala Leu Pro Ala Ala Glu Leu Val Gln Ala Cys
            20                  25                  30

Arg Leu Val Cys Leu Arg Trp Lys Glu Leu Val Asp Gly Ala Pro Leu
        35                  40                  45

Trp Leu Leu Lys Cys Gln Gln Glu Gly Leu Val Pro Glu Gly Gly Val
    50                  55                  60

Glu Glu Glu Arg Asp His Trp Gln Gln Phe Tyr Phe Leu Ser Lys Arg
65                  70                  75                  80

Arg Arg Asn Leu Leu Arg Asn Pro Cys Gly Glu Glu Asp Leu Glu Gly
                85                  90                  95

Trp Cys Asp Val Glu His Gly Gly Asp Gly Trp Arg Val Glu Glu Leu
            100                 105                 110

Pro Gly Asp Ser Gly Val Glu Phe Thr His Asp Glu Ser Val Lys Lys
        115                 120                 125

Tyr Phe Ala Ser Ser Phe Glu Trp Cys Arg Lys Ala Gln Val Ile Asp
    130                 135                 140

Leu Gln Ala Glu Gly Tyr Trp Glu Glu Leu Leu Asp Thr Thr Gln Pro
145                 150                 155                 160

Ala Ile Val Val Lys Asp Trp Tyr Ser Gly Arg Ser Asp Ala Gly Cys
                165                 170                 175

Leu Tyr Glu Leu Thr Val Lys Leu Leu Ser Glu His Glu Asn Val Leu
            180                 185                 190

Ala Glu Phe Ser Ser Gly Gln Val Ala Val Pro Gln Asp Ser Asp Gly
        195                 200                 205

Gly Gly Trp Met Glu Ile Ser His Thr Phe Thr Asp Tyr Gly Pro Gly
    210                 215                 220

Val Arg Phe Val Arg Phe Glu His Gly Gly Gln Gly Ser Val Tyr Trp
225                 230                 235                 240

Lys Gly Trp Phe Gly Ala Arg Val Thr Asn Ser Ser Val Trp Val Glu
                245                 250                 255

Pro

<210> SEQ ID NO 41
<211> LENGTH: 957
<212> TYPE: DNA
<213> ORGANISM: Homo sapiens

<400> SEQUENCE: 41
atgggcgaga aggcggtccc tttgctaagg aggaggcggg tgaagagaag ctgcccttct      60
tgtggctcgg agcttggggt tgaagagaag aggggaaag gaaatccgat ttccatccag      120
ttgttccccc cagagctggt ggagcatatc atctcattcc tcccagtcag agaccttgtt     180
gccctcggcc agacctgccg ctacttccac gaagtgtgcg atggggaagg cgtgtggaga     240
cgcatctgtc gcagactcag tccgcgcctc caagatcagg acacgaaggg cctgtatttc     300
caggcatttg gaggccgccg ccgatgtctc agcaagagcg tggccccctt gctagcccac     360
ggctaccgcc gcttcttgcc caccaaggat cacgtcttca ttcttgacta cgtggggacc     420
ctcttcttcc tcaaaaatgc cctggtctcc accctcggcc agatgcagtg gaagcgggcc     480

```
tgtcgctatg ttgtgttgtg tcgtggagcc aaggattttg cctcggaccc aaggtgtgac    540
acagtttacc gtaaatacct ctacgtcttg gccactcggg agccgcagga agtggtgggt    600
accaccagca gccgggcctg tgactgtgtt gaggtctatc tgcagtctag tgggcagcgg    660
gtcttcaaga tgacattcca ccactcaatg accttcaagc agatcgtgct ggttggtcag    720
gagacccagc gggctctact gctcctcaca gaggaaggaa agatctactc tttggtagtg    780
aatgagaccc agcttgacca gccacgctcc tacacggttc agctggccct gaggaaggtg    840
tcccactacc tgcctcacct gcgcgtggcc tgcatgactt ccaaccagag cagcaccctc    900
tacgtcacag atcctattct gtgctcttgg ctacaaccac cttggcctgg tggatga       957
```

<210> SEQ ID NO 42
<211> LENGTH: 318
<212> TYPE: PRT
<213> ORGANISM: Homo sapiens

<400> SEQUENCE: 42

```
Met Gly Glu Lys Ala Val Pro Leu Leu Arg Arg Arg Val Lys Arg
 1               5                  10                  15

Ser Cys Pro Ser Cys Gly Ser Glu Leu Gly Val Glu Glu Lys Arg Gly
                20                  25                  30

Lys Gly Asn Pro Ile Ser Ile Gln Leu Phe Pro Pro Glu Leu Val Glu
            35                  40                  45

His Ile Ile Ser Phe Leu Pro Val Arg Asp Leu Val Ala Leu Gly Gln
        50                  55                  60

Thr Cys Arg Tyr Phe His Glu Val Cys Asp Gly Glu Gly Val Trp Arg
 65                  70                  75                  80

Arg Ile Cys Arg Arg Leu Ser Pro Arg Leu Gln Asp Gln Asp Thr Lys
                    85                  90                  95

Gly Leu Tyr Phe Gln Ala Phe Gly Gly Arg Arg Arg Cys Leu Ser Lys
                100                 105                 110

Ser Val Ala Pro Leu Leu Ala His Gly Tyr Arg Arg Phe Leu Pro Thr
            115                 120                 125

Lys Asp His Val Phe Ile Leu Asp Tyr Val Gly Thr Leu Phe Phe Leu
        130                 135                 140

Lys Asn Ala Leu Val Ser Thr Leu Gly Gln Met Gln Trp Lys Arg Ala
145                 150                 155                 160

Cys Arg Tyr Val Val Leu Cys Arg Gly Ala Lys Asp Phe Ala Ser Asp
                165                 170                 175

Pro Arg Cys Asp Thr Val Tyr Arg Lys Tyr Leu Tyr Val Leu Ala Thr
            180                 185                 190

Arg Glu Pro Gln Glu Val Val Gly Thr Thr Ser Arg Ala Cys Asp
        195                 200                 205

Cys Val Glu Val Tyr Leu Gln Ser Ser Gly Gln Arg Val Phe Lys Met
    210                 215                 220

Thr Phe His His Ser Met Thr Phe Lys Gln Ile Val Leu Val Gly Gln
225                 230                 235                 240

Glu Thr Gln Arg Ala Leu Leu Leu Leu Thr Glu Glu Gly Lys Ile Tyr
                245                 250                 255

Ser Leu Val Val Asn Glu Thr Gln Leu Asp Gln Pro Arg Ser Tyr Thr
            260                 265                 270

Val Gln Leu Ala Leu Arg Lys Val Ser His Tyr Leu Pro His Leu Arg
        275                 280                 285

Val Ala Cys Met Thr Ser Asn Gln Ser Ser Thr Leu Tyr Val Thr Asp
```

```
                290                 295                 300
Pro Ile Leu Cys Ser Trp Leu Gln Pro Pro Trp Pro Gly Gly
305                 310                 315
```

<210> SEQ ID NO 43
<211> LENGTH: 1590
<212> TYPE: DNA
<213> ORGANISM: Homo sapiens

<400> SEQUENCE: 43

| | | | | | |
|---|---|---|---|---|---|
| cgaggggaa | gcgaaggaag | gggaagagga | agggaaaagc | gagcgagagg | ggcaaggcgg | 60 |
| aagaggaagc | agggcggaag | ggaagcccgg | gccgcagacg | gcgaaggagg | cagcgggccg | 120 |
| ggggctgagg | cggagcgag | gacacgccca | agagaggaag | cagagggagg | cggaagcgtg | 180 |
| gaggaagggg | cgagaggcat | catcaaagga | gatgagggga | gcgtagggc | cgggaaagag | 240 |
| gcacaaggaa | gaaagtatgg | gaaggaggaa | tggagggtca | gggctaggcg | gcggagggc | 300 |
| gccaggccgg | gaagagtaca | aggacaagga | ggtcaggttt | gggcctacat | cccggggaca | 360 |
| ggggcggcca | tggcggcggc | agccaggag | gaggaggagg | aggcggctcg | ggagtcagcc | 420 |
| gcctgcccgg | ctgcggggcc | agcgctctgg | cgcctgccgg | aagtgctgct | gctgcacatg | 480 |
| tgctcctacc | tcgacatgcg | ggccctcggc | cgcctggccc | aggtgtaccg | ctggctgtgg | 540 |
| cacttcacca | actgcgacct | gctccggcgc | cagatagcct | gggcctcgct | caactccggc | 600 |
| ttcacgcggc | tcggcaccaa | cctgatgacc | agtgtcccag | tgaaggtgtc | tcagaactgg | 660 |
| atagtggggt | gctgccgaga | ggggattctg | ctgaagtgga | gatgcagtca | gatgccctgg | 720 |
| atgcagctag | aggatgatgc | tttgtacata | tcccaggcta | atttcatcct | ggcctaccag | 780 |
| ttccgtccag | atggtgccag | cttgaaccgt | cagcctctgg | gagtctctgc | tgggcatgat | 840 |
| gaggacgttt | gccactttgt | gctggccacc | tcgcatattg | tcagtgcagg | aggagatggg | 900 |
| aagattggcc | ttggtaagat | tcacagcacc | ttcgctgcca | agtactgggc | tcatgaacag | 960 |
| gaggtgaact | gtgtggattg | caaagggggc | atcatatcat | ttggctccag | ggacaggacg | 1020 |
| gccaaggtgt | ggccttggc | ctcaggccag | ctggggcagt | gtttatacac | catccagact | 1080 |
| gaagaccaaa | tctggtctgt | tgctatcagg | ccattactca | gctcttttgt | gacagggacg | 1140 |
| gcttgttgtg | ggcacttctc | acccctgaaa | atctgggacc | tcaacagtgg | gcagctgatg | 1200 |
| acacacttgg | acagagactt | tccccaagg | gctggggtgc | tggatgtcat | atatgagtcc | 1260 |
| cctttcgcac | tgctctcctg | tggctatgac | acctatgttc | gctactggga | ctgccgcacc | 1320 |
| agtgtccgga | aatgtgtcat | ggagtgggag | gagccccaca | acagcaccct | gtactgcctg | 1380 |
| cagacagatg | gcaaccactt | gcttgccaca | ggttcctcct | tctatagcgt | tgtacggctg | 1440 |
| tgggaccggc | accaaagggc | ctgcccgcac | accttcccgc | tgacgtcgac | ccgcctcggc | 1500 |
| agccctgtgt | actgcctgca | tctcaccacc | aagcatctct | atgctgcgct | gtcttacaac | 1560 |
| ctccacgtcc | tggatattca | aaacccgtga | | | | 1590 |

<210> SEQ ID NO 44
<211> LENGTH: 529
<212> TYPE: PRT
<213> ORGANISM: Homo sapiens

<400> SEQUENCE: 44

```
Arg Gly Gly Ser Glu Gly Arg Gly Arg Gly Arg Glu Lys Arg Ala Arg
 1               5                  10                  15

Gly Ala Arg Arg Lys Arg Lys Gln Gly Gly Arg Glu Ala Arg Ala Ala
            20                  25                  30
```

Asp Gly Glu Gly Gly Ser Gly Pro Gly Ala Glu Ala Gly Ala Arg Thr
        35                  40                  45

Arg Pro Arg Glu Glu Ala Glu Gly Gly Gly Ser Val Glu Glu Gly Ala
        50                  55                  60

Arg Gly Ile Ile Lys Gly Asp Glu Gly Ser Val Gly Ala Gly Lys Glu
65                  70                  75                  80

Ala Gln Gly Arg Lys Tyr Gly Lys Glu Glu Trp Arg Val Arg Ala Arg
                85                  90                  95

Arg Arg Glu Gly Ala Arg Pro Gly Arg Val Gln Gly Gln Gly Gly Gln
            100                 105                 110

Val Trp Ala Tyr Ile Pro Gly Thr Gly Ala Ala Met Ala Ala Ala Ala
            115                 120                 125

Arg Glu Glu Glu Glu Ala Ala Arg Glu Ser Ala Ala Cys Pro Ala
            130                 135                 140

Ala Gly Pro Ala Leu Trp Arg Leu Pro Glu Val Leu Leu Leu His Met
145                 150                 155                 160

Cys Ser Tyr Leu Asp Met Arg Ala Leu Gly Arg Leu Ala Gln Val Tyr
                165                 170                 175

Arg Trp Leu Trp His Phe Thr Asn Cys Asp Leu Leu Arg Arg Gln Ile
            180                 185                 190

Ala Trp Ala Ser Leu Asn Ser Gly Phe Thr Arg Leu Gly Thr Asn Leu
            195                 200                 205

Met Thr Ser Val Pro Val Lys Val Ser Gln Asn Trp Ile Val Gly Cys
210                 215                 220

Cys Arg Glu Gly Ile Leu Leu Lys Trp Arg Cys Ser Gln Met Pro Trp
225                 230                 235                 240

Met Gln Leu Glu Asp Asp Ala Leu Tyr Ile Ser Gln Ala Asn Phe Ile
                245                 250                 255

Leu Ala Tyr Gln Phe Arg Pro Asp Gly Ala Ser Leu Asn Arg Gln Pro
            260                 265                 270

Leu Gly Val Ser Ala Gly His Asp Glu Asp Val Cys His Phe Val Leu
            275                 280                 285

Ala Thr Ser His Ile Val Ser Ala Gly Gly Asp Gly Lys Ile Gly Leu
            290                 295                 300

Gly Lys Ile His Ser Thr Phe Ala Ala Lys Tyr Trp Ala His Glu Gln
305                 310                 315                 320

Glu Val Asn Cys Val Asp Cys Lys Gly Gly Ile Ile Ser Phe Gly Ser
                325                 330                 335

Arg Asp Arg Thr Ala Lys Val Trp Pro Leu Ala Ser Gly Gln Leu Gly
            340                 345                 350

Gln Cys Leu Tyr Thr Ile Gln Thr Glu Asp Gln Ile Trp Ser Val Ala
            355                 360                 365

Ile Arg Pro Leu Leu Ser Ser Phe Val Thr Gly Thr Ala Cys Cys Gly
370                 375                 380

His Phe Ser Pro Leu Lys Ile Trp Asp Leu Asn Ser Gly Gln Leu Met
385                 390                 395                 400

Thr His Leu Asp Arg Asp Phe Pro Arg Ala Gly Val Leu Asp Val
                405                 410                 415

Ile Tyr Glu Ser Pro Phe Ala Leu Leu Ser Cys Gly Tyr Asp Thr Tyr
            420                 425                 430

Val Arg Tyr Trp Asp Cys Arg Thr Ser Val Arg Lys Cys Val Met Glu
            435                 440                 445

Trp Glu Glu Pro His Asn Ser Thr Leu Tyr Cys Leu Gln Thr Asp Gly

```
                450               455               460
Asn His Leu Leu Ala Thr Gly Ser Ser Phe Tyr Ser Val Val Arg Leu
465                 470                 475                 480

Trp Asp Arg His Gln Arg Ala Cys Pro His Thr Phe Pro Leu Thr Ser
                485                 490                 495

Thr Arg Leu Gly Ser Pro Val Tyr Cys Leu His Leu Thr Thr Lys His
            500                 505                 510

Leu Tyr Ala Ala Leu Ser Tyr Asn Leu His Val Leu Asp Ile Gln Asn
        515                 520                 525

Pro

<210> SEQ ID NO 45
<211> LENGTH: 1214
<212> TYPE: DNA
<213> ORGANISM: Homo sapiens

<400> SEQUENCE: 45
gcattgctat aattttacta tactctcatc taaatctaaa atcagtcttc aaaataaaaa      60
caaattgtcc tttgccaaaa attttttttaa tcgcacaatt aattgacatt aactgccaat    120 tcttttttggc taattgacta attttaactt ctgtgttgct tttccagagg catggctatt    180 gcacttggg agaagccttt aatcggttag acttctcaag tgcaattcaa gatatccgaa     240
cgttcaatta tgtggtcaaa ctgttgcagc taattgcaaa atcccagtta acttcattga    300
gtggcgtggc acagaagaat tacttcaaca ttttggataa aatcgttcaa aaggttcttg    360
atgaccacca caatcctcgc ttaatcaaag atcttctgca agacctaagc tctaccctct    420
gcattcttat tagaggagta gggaagtctg tattagtggg aaacatcaat atttggattt    480
gccgattaga aactattctc gcctggcaac aacagctaca ggatcttcag atgactaagc    540
aagtgaacaa tggcctcacc ctcagtgacc ttcctctgca catgctgaac aacatcctat    600
accggttctc agacggatgg gacatcatca ccttaggcca ggtgaccccc acgttgtata    660
tgcttagtga agacagacag ctgtggaaga agctttgtca gtaccatttt gctgaaaagc    720
agttttgtag acatttgatc ctttcagaaa aaggtcatat tgaatggaag ttgatgtact    780
ttgcacttca gaaacattac ccagcgaagg agcagtacgg agacacactg catttctgtc    840
ggcactgcag cattctcttt tggaaggact caggacaccc ctgcacggcg gccgaccctg    900
acagctgctt cacgcctgtg tctccgcagc acttcatcga cctcttcaag ttttaagggc    960
tgcccctgcc atccctattg gagattgtga atcctgctgt ctgtgcaggg ctcatagtga   1020
gtgttctgtg aggtgggtgg agactcctcg gaagcccctg cttccagaaa gcctgggaag   1080
aactgccctt ctgcaaaggg gggactgcat ggttgcattt tcatcactga aagtcagagg   1140
ccaaggaaat catttctact tctttaaaaa ctccttctaa gcatattaaa atgtgaaatt   1200
ttgcgtactc tctc                                                      1214

<210> SEQ ID NO 46
<211> LENGTH: 272
<212> TYPE: PRT
<213> ORGANISM: Homo sapiens

<400> SEQUENCE: 46

Leu Ile Leu Thr Ser Val Leu Leu Phe Gln Arg His Gly Tyr Cys Thr
1               5                   10                  15

Leu Gly Glu Ala Phe Asn Arg Leu Asp Phe Ser Ser Ala Ile Gln Asp
            20                  25                  30
```

-continued

| | | | | | | | | | | | | | |
|---|---|---|---|---|---|---|---|---|---|---|---|---|---|
|Ile|Arg|Thr|Phe|Asn|Tyr|Val|Val|Lys|Leu|Leu|Gln|Leu|Ile|Ala|Lys
| | |35| | | |40| | | |45| | | |

Ser Gln Leu Thr Ser Leu Ser Gly Val Ala Gln Lys Asn Tyr Phe Asn
    50              55              60

Ile Leu Asp Lys Ile Val Gln Lys Val Leu Asp Asp His His Asn Pro
65              70              75              80

Arg Leu Ile Lys Asp Leu Leu Gln Asp Leu Ser Ser Thr Leu Cys Ile
                85              90              95

Leu Ile Arg Gly Val Gly Lys Ser Val Leu Val Gly Asn Ile Asn Ile
            100             105             110

Trp Ile Cys Arg Leu Glu Thr Ile Leu Ala Trp Gln Gln Leu Gln
        115             120             125

Asp Leu Gln Met Thr Lys Gln Val Asn Asn Gly Leu Thr Leu Ser Asp
130             135             140

Leu Pro Leu His Met Leu Asn Asn Ile Leu Tyr Arg Phe Ser Asp Gly
145             150             155             160

Trp Asp Ile Ile Thr Leu Gly Gln Val Thr Pro Thr Leu Tyr Met Leu
                165             170             175

Ser Glu Asp Arg Gln Leu Trp Lys Lys Leu Cys Gln Tyr His Phe Ala
            180             185             190

Glu Lys Gln Phe Cys Arg His Leu Ile Leu Ser Glu Lys Gly His Ile
195             200             205

Glu Trp Lys Leu Met Tyr Phe Ala Leu Gln Lys His Tyr Pro Ala Lys
210             215             220

Glu Gln Tyr Gly Asp Thr Leu His Phe Cys Arg His Cys Ser Ile Leu
225             230             235             240

Phe Trp Lys Asp Ser Gly His Pro Cys Thr Ala Ala Asp Pro Asp Ser
                245             250             255

Cys Phe Thr Pro Val Ser Pro Gln His Phe Ile Asp Leu Phe Lys Phe
            260             265             270

<210> SEQ ID NO 47
<211> LENGTH: 4059
<212> TYPE: DNA
<213> ORGANISM: Homo sapiens

<400> SEQUENCE: 47

```
agtacggcag tgagggcaaa ggcagctcga gcatctcatc tgacgtgagt tcaagtacag      60
atcacacgcc cactaaagcc cagaagaatg tggctaccag cgaagactcc gacctgagca     120
tgcgcacact gagcacgccc agcccagccc tgatatgtcc accgaatctc ccaggatttc     180
agaatggaag gggctcgtcc acctcctcgt cctccatcac cggggagacg gtggccatgg     240
tgcactcccc gccccgacc cgcctcacac accgctcat ccggctcgcc tccagacccc       300
agaaggagca ggccagcata gaccggctcc cggaccactc catggtgcag atcttctcct     360
tcctgccac caaccagctg tgccgctgcg cgcgagtgtg ccgccgctgg tacaacctgg      420
cctgggaccc gcggctctgg aggactatcc gcctgacggg cgagaccatc aacgtggacc     480
gcgccctcaa ggtgctgacc cgcagactct gccaggacac cccaacgtg tgtctcatgc      540
tggaaaccgt aactgtcagt ggctgcaggc ggctcacaga ccgagggctg tacaccatcg     600
cccagtgctg cccgaactg aggcgactgg aagtctcagg ctgttacaat atctccaacg      660
aggccgtctt tgatgtggtg tccctctgcc ctaatctgga gcacctggat gtgtcaggat     720
gctccaaagt gacctgcatc agcttgaccc gggaggcctc cattaaactg tcacccttgc     780
atggcaaaca gatttccatc cgctacctgg acatgacgga ctgcttcgtg ctggaggacg     840
```

```
aaggcctgca caccatcgcg gcgcactgca cgcagctcac ccacctctac ctgcgccgct    900
gcgtccgcct gaccgacgaa ggcctgcgct acctggtgat ctactgcgcc tccatcaagg    960
agctgagcgt cagcgactgc cgcttcgtca gcgacttcgg cctgcgggag atcgccaagc   1020
tggagtcccg cctgcggtac ctgagcatcg cgcactgcgg ccgggtcacc gacgtgggca   1080
tccgctacgt ggccaagtac tgcagcaagc tgcgctacct caacgcgagg ggctgcgagg   1140
gcatcacgga ccacggtgtg gagtacctcg ccaagaactg caccaaactc aaatccctgg   1200
atatcggcaa atgccctttg gtatccgaca cgggcctgga gtgcctggcc ctgaactgct   1260
tcaacctcaa gcggctcagc ctcaagtcct gcgagagcat caccggccag ggcttgcaga   1320
tcgtggccgc caactgcttt gacctccaga cgctgaatgt ccaggactgc gaggtctccg   1380
tggaggccct gcgctttgtc aaacgccact gcaagcgctg cgtcatcgag cacaccaacc   1440
cggctttctt ctgaagggac agagttcatc cggcgttgta ttcacacaaa cctgaacaaa   1500
gcaaattttt ttaaaagcag cgtatgtaag caccgacacc cactcaaaac agctctttct   1560
tccgggaagg ttattaggaa tctggccttt attttcctc atttctcatg gcaacagag     1620 gccaaagaaa cgaagcaaga caaacagcaa acaggcattt tggtcaggtc atttgtaggc   1680
agtttctctt ctcacaaaag atgtacttaa gcaggctgat cgctgttcct tgagcaaggc   1740
gcttactctc ctccgctcag gcccccaagg ccgccctttc cctcgcacac aggccccacc   1800
cccacagttc cacgccccc cccaaggcc acaccctccc tccctagagc agcagcgagg     1860
atccatcatc agaatcacag tgctctccag acctcctctc taaactgctt cattgaccta   1920
agtcactctc ttcaatccca cacccatgga cattcttgtc aactcaatac catagcactt   1980
tgcataggca aaatactttt caggcctttt taaaaaattc attacagcaa acagctgggg   2040
aaggacatgc agtcctcccc cagctctgtc aatgactatg accttggcca agcacttca    2100 ctgctctggg ctgcagcttc cagcactgaa tcagaggcca cacagcccaa agattagctt   2160
catgtccatt atagcattga gggagcagag atacccatac acagaagcac cttggcatag   2220
agcacccagg catcgacctc ttccaggaga actgattctg tggatggatg tgatttcagg   2280
agattgtgca gtgccagcat cagtgcataa agggtcctgt atgtcctttg gctgcaaatc   2340
acccacttcc ctgtgtttca gtgggagaat ttcctctccc acctcctcac atcctctttt   2400
gccaggctgg atgctgtcgt ctctgtacac aaatactttc tgcattcccc cctccacacc   2460
atcctagcga ggcaccagca cacctaatca cagcaaagcc cagatccccc catcagttgc   2520
ttttactcag tgttttcaaa taggagtaaa ggcccttgca attttaatt aacaagcaag    2580 gcccaaggga acacatgtcc tcaaaagttt ttctgatccc tcgccttgca cacctggcat   2640
gcatcaggca catctgtcct acagctggca gagacagatg cctcggttct tgtcattca    2700 gattgcattt gacctcttct catctattta tttctttata catccagact tcatcacatg   2760
aagcctattg gggttaagtt tgtaagtgtt taattgtgca aattgccacc ctgtgtacct   2820
cctccatgtc tgtctgcgtg ttttccacca aagaatgcaa agcagacttc caggtgttta   2880
aattctgttc actcaacaat gccagatgaa tggaagaggg aacacactga gatgacttag   2940
actctggtcc accaaccaga cccttggaaa ggaatactaa aatcattaca aggtatggat   3000
tttaaatgga tgaaacttca aattatctta tttggataga agtctatatt ctagcctcat   3060
ttgcatgaag tcagatagcc agaagaaatt ccattgctgg ttttcacgaa attcacttgt   3120
cttttgctaa taaacacatg gcccctttccc agattattct ctagccaagc cccacctttg   3180
ttacgttgaa atccctcatt tattttcttc tcaaaatgcc cattatccaa atgcagaacc   3240
```

```
tctgcatctc caagccagtt atgctgaatt tgtcaaactt agacacccct gacaactgca    3300
ctcctactgt aggctcctgt gcatactgtc gtcttctgtg ggggatggag aggttagtgt    3360
gatgaggtgg tgtctgccca ggaggtttct ttcaaacatc atggcctccc atccaatcaa    3420
catcatcaaa ttacatgtgt aatcaaggct ctgtgccatg ggggaaatga atcatttagc    3480
taggccagga tctagtgaaa gccacagagt ttaaaaccat gaagaagtt gaaggcagca    3540 ttcctcagct ctgtgacttg tgaccctatt tgaagtttca ggatttgggt gtcacaaagg    3600
attgtcccta atccttggcc ctggggtctt ccgagtgagc tggtttaata ctctgagaat    3660
gagcagggag atccagagaa tgaatccctg accgcatcac ctaaactgtc ttccaaacat    3720
gagacaaagc tgactgttca cactgattgc ccagcacata ccgtcttgcc agtttcttct    3780
tttctcccag tctcctgttc atccattctg ttctcccttg gggtgggaat ctatgatgga    3840
ggttactggg gaaacagctc agcagatttt tggagaccaa accaaaggtc tcactaggaa    3900
atttatctgt tttaaaacat tgcttccttc ctggctctgc taaattgaat gctcattgtt    3960
tgttgttgtt gttttttaat tctaatgttc aaatcactgc gtgctgtatg aatctagaaa    4020
gccttaattt actaccaaga aataaagcaa tatgttcgt                           4059
```

<210> SEQ ID NO 48
<211> LENGTH: 483
<212> TYPE: PRT
<213> ORGANISM: Homo sapiens

<400> SEQUENCE: 48

```
Tyr Gly Ser Glu Gly Lys Gly Ser Ser Ile Ser Ser Asp Val Ser
 1               5                  10                  15

Ser Ser Thr Asp His Thr Pro Thr Lys Ala Gln Lys Asn Val Ala Thr
            20                  25                  30

Ser Glu Asp Ser Asp Leu Ser Met Arg Thr Leu Ser Thr Pro Ser Pro
        35                  40                  45

Ala Leu Ile Cys Pro Pro Asn Leu Pro Gly Phe Gln Asn Gly Arg Gly
    50                  55                  60

Ser Ser Thr Ser Ser Ser Ser Ile Thr Gly Glu Thr Val Ala Met Val
65                  70                  75                  80

His Ser Pro Pro Thr Arg Leu Thr His Pro Leu Ile Arg Leu Ala
                85                  90                  95

Ser Arg Pro Gln Lys Glu Gln Ala Ser Ile Asp Arg Leu Pro Asp His
            100                 105                 110

Ser Met Val Gln Ile Phe Ser Phe Leu Pro Thr Asn Gln Leu Cys Arg
        115                 120                 125

Cys Ala Arg Val Cys Arg Arg Trp Tyr Asn Leu Ala Trp Asp Pro Arg
    130                 135                 140

Leu Trp Arg Thr Ile Arg Leu Thr Gly Glu Thr Ile Asn Val Asp Arg
145                 150                 155                 160

Ala Leu Lys Val Leu Thr Arg Arg Leu Cys Gln Asp Thr Pro Asn Val
                165                 170                 175

Cys Leu Met Leu Glu Thr Val Thr Val Ser Gly Cys Arg Arg Leu Thr
        180                 185                 190

Asp Arg Gly Leu Tyr Thr Ile Ala Gln Cys Cys Pro Glu Leu Arg Arg
    195                 200                 205

Leu Glu Val Ser Gly Cys Tyr Asn Ile Ser Asn Glu Ala Val Phe Asp
    210                 215                 220

Val Val Ser Leu Cys Pro Asn Leu Glu His Leu Asp Val Ser Gly Cys
```

```
              225                 230                 235                 240
Ser Lys Val Thr Cys Ile Ser Leu Thr Arg Glu Ala Ser Ile Lys Leu
              245                 250                 255

Ser Pro Leu His Gly Lys Gln Ile Ser Ile Arg Tyr Leu Asp Met Thr
              260                 265                 270

Asp Cys Phe Val Leu Glu Asp Glu Gly Leu His Thr Ile Ala Ala His
              275                 280                 285

Cys Thr Gln Leu Thr His Leu Tyr Leu Arg Arg Cys Val Arg Leu Thr
              290                 295                 300

Asp Glu Gly Leu Arg Tyr Leu Val Ile Tyr Cys Ala Ser Ile Lys Glu
305                 310                 315                 320

Leu Ser Val Ser Asp Cys Arg Phe Val Ser Asp Phe Gly Leu Arg Glu
              325                 330                 335

Ile Ala Lys Leu Glu Ser Arg Leu Arg Tyr Leu Ser Ile Ala His Cys
              340                 345                 350

Gly Arg Val Thr Asp Val Gly Ile Arg Tyr Val Ala Lys Tyr Cys Ser
              355                 360                 365

Lys Leu Arg Tyr Leu Asn Ala Arg Gly Cys Glu Gly Ile Thr Asp His
              370                 375                 380

Gly Val Glu Tyr Leu Ala Lys Asn Cys Thr Lys Leu Lys Ser Leu Asp
385                 390                 395                 400

Ile Gly Lys Cys Pro Leu Val Ser Asp Thr Gly Leu Glu Cys Leu Ala
              405                 410                 415

Leu Asn Cys Phe Asn Leu Lys Arg Leu Ser Leu Ser Lys Cys Glu Ser
              420                 425                 430

Ile Thr Gly Gln Gly Leu Gln Ile Val Ala Ala Asn Cys Phe Asp Leu
              435                 440                 445

Gln Thr Leu Asn Val Gln Asp Cys Glu Val Ser Val Glu Ala Leu Arg
              450                 455                 460

Phe Val Lys Arg His Cys Lys Arg Cys Val Ile Glu His Thr Asn Pro
465                 470                 475                 480

Ala Phe Phe

<210> SEQ ID NO 49
<211> LENGTH: 850
<212> TYPE: DNA
<213> ORGANISM: Homo sapiens

<400> SEQUENCE: 49
tgcggccgcg cccgcacccg caccggcacc cacgcccacg cccgaggaag ggcccgacgc      60
gggctgggga gaccgcattc ccttggaaat cctggtgcag attttcgggt tgttggtggc     120
ggcggacggc cccatgccct tcctgggcag ggctgcgcgc gtgtgccgcc gctggcagga     180
ggccgcttcc caacccgcgc tctggcacac cgtgaccctg tcgtcccgc tggtcggccg      240 gcctgccaag ggcggggtca aggcggagaa gaagctcctt gcttccctgg agtggcttat     300
gcccaatcgg ttttcacagc tccagaggct gaccctcatc cactggaagt ctcaggtaca     360
ccccgtgttg aagctggtag gtgagtgctg tcctcggctc actttcctca agctctccgg     420
ctgccacggt gtgactgctg acgctctggt catgctagcc aaagcctgct gccagctcca     480
tagcctggac ctacagcact ccatggtgga gtccacagct gtggtgagct tcttggagga     540
ggcagggtcc cgaatgcgca agttgtggct gacctacagc tcccagacga cagccatcct     600
gggcgcattg ctgggcagct gctgcccca gctccaggtc ctgaggtga gcaccggcat       660 caaccgtaat agcattcccc ttcagctgcc tgtcgaggct ctgcagaaag gctgccctca     720
```

-continued

```
gctccaggtg ctgcggctgt tgaacctgat gtggctgccc aagcctccgg gacgaggggt    780 ggctccccgga ccaggcttcc ctagcctaga ggagctctgc ctggcgagct caacctgcaa    840
ctttgtgagc                                                             850
```

<210> SEQ ID NO 50
<211> LENGTH: 283
<212> TYPE: PRT
<213> ORGANISM: Homo sapiens

<400> SEQUENCE: 50

```
Ala Ala Ala Pro Ala Pro Ala Pro Ala Pro Thr Pro Thr Pro Glu Glu
  1               5                  10                  15

Gly Pro Asp Ala Gly Trp Gly Asp Arg Ile Pro Leu Glu Ile Leu Val
                 20                  25                  30

Gln Ile Phe Gly Leu Leu Val Ala Ala Asp Gly Pro Met Pro Phe Leu
             35                  40                  45

Gly Arg Ala Ala Arg Val Cys Arg Arg Trp Gln Glu Ala Ala Ser Gln
         50                  55                  60

Pro Ala Leu Trp His Thr Val Thr Leu Ser Ser Pro Leu Val Gly Arg
 65                  70                  75                  80

Pro Ala Lys Gly Gly Val Lys Ala Glu Lys Lys Leu Leu Ala Ser Leu
                 85                  90                  95

Glu Trp Leu Met Pro Asn Arg Phe Ser Gln Leu Gln Arg Leu Thr Leu
                100                 105                 110

Ile His Trp Lys Ser Gln Val His Pro Val Leu Lys Leu Val Gly Glu
            115                 120                 125

Cys Cys Pro Arg Leu Thr Phe Leu Lys Leu Ser Gly Cys His Gly Val
        130                 135                 140

Thr Ala Asp Ala Leu Val Met Leu Ala Lys Ala Cys Cys Gln Leu His
145                 150                 155                 160

Ser Leu Asp Leu Gln His Ser Met Val Glu Ser Thr Ala Val Val Ser
                165                 170                 175

Phe Leu Glu Glu Ala Gly Ser Arg Met Arg Lys Leu Trp Leu Thr Tyr
            180                 185                 190

Ser Ser Gln Thr Thr Ala Ile Leu Gly Ala Leu Leu Gly Ser Cys Cys
        195                 200                 205

Pro Gln Leu Gln Val Leu Glu Val Ser Thr Gly Ile Asn Arg Asn Ser
    210                 215                 220

Ile Pro Leu Gln Leu Pro Val Glu Ala Leu Gln Lys Gly Cys Pro Gln
225                 230                 235                 240

Leu Gln Val Leu Arg Leu Leu Asn Leu Met Trp Leu Pro Lys Pro Pro
                245                 250                 255

Gly Arg Gly Val Ala Pro Gly Pro Phe Pro Ser Leu Glu Glu Leu
            260                 265                 270

Cys Leu Ala Ser Ser Thr Cys Asn Phe Val Ser
        275                 280
```

<210> SEQ ID NO 51
<211> LENGTH: 1777
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 51

```
acaacactgc tctcagaagg atactgcaga actccttaga ggtcttagcc tatggaatca    60
tgctgaagag cgacagaart ttttttaaata ttccgtggat gaaaagtcag ataaagaagc   120
agaagtgtca gaacactcca caggtataac ccatcttcct cctgaggtaa tgctgtcaat   180
tttcagctat cttaatcctc aagagttatg tcgatgcagt caagtaagca tgaaatggtc   240
tcagctgaca aaaacgggat cgcttttgaa acatctttac cctgttcatt gggccagagg   300
tgactggtat agtggtcccg caactgaact tgatactgaa cctgatgatg aatgggtgaa   360
aaataggaaa gatgaaagtc gtgcttttca tgagtgggat gaagatgctg acattgatga   420
atctgaagag tctgcggagg aatcaattgc tatcagcatt gcacaaatgg aaaaacgttt   480
actccatggc ttaattcata cgttctacc atatgttggt acttctgtaa aaaccttagt   540
attagcatac agctctgcag tttccagcaa aatggttagg cagattttag agctttgtcc   600
taacctggag catctggatc ttacccagac tgacatttca gattctgcat ttgacagttg   660
gtcttggctt ggttgctgcc agagtcttcg gcatcttgat ctgtctggtt gtgagaaaat   720
cacagatgtg gccctagaga agatttccag agctcttgga attctgacat ctcatcaaag   780 tggcttttg aaaacatcta caagcaaaat tacttcaact gcgtggaaaa ataagacat   840 taccatgcag tccaccaagc agtatgcctg tttgcacgat ttaactaaca agggcattgg   900
agaagaaata gataatgaac acccctggac taagcctgtt tcttctgaga atttcacttc   960
tccttatgtg tggatgttag atgctgaaga tttggctgat attgaagata ctgtggaatg  1020
gagacataga aatgttgaaa gtctttgtgt aatggaaaca gcatccaact ttagttgttc  1080
cacctctggt tgttttagta aggacattgt tggactaagg actagtgtct gttggcagca  1140
gcattgtgct ctccagcct ttgcgtattg tggtcactca ttttgttgta caggaacagc  1200
tttaagaact atgtcatcac tcccagaatc ttctgcaatg tgtagaaaag cagcaaggac  1260
tagattgcct aggggaaaag acttaattta cttttgggagt gaaaaatctg atcaagagac  1320
tggacgtgta cttctgtttc tcagtttatc tggatgttat cagatcacag accatggtct  1380
cagggttttg actctgggag gagggctgcc ttatttggag caccttaatc tctctggttg  1440
tcttactata actggtgcag gcctgcagga tttggtttca gcatgtcctt ctctgaatga  1500
tgaatacttt tactactgtg acaacattaa cggtcctcat gctgataccg ccagtggatg  1560
ccagaatttg cagtgtggtt ttcgagcctg ctgccgctct ggcgaatgac ccttgacttc  1620
tgatctttgt ctacttcatt tagctgagca ggctttcttt catgcacttt actcatagca  1680
catttcttgt gttaaccatc cctttttgag cgtgacttgt tttgggccca ttnyttacaa  1740
cttcagaaat cttaattacc agtgrattgt aatgttg                           1777
```

<210> SEQ ID NO 52
<211> LENGTH: 535
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 52

Gln His Cys Ser Gln Lys Asp Thr Ala Glu Leu Leu Arg Gly Leu Ser
 1               5                  10                  15

Leu Trp Asn His Ala Glu Glu Arg Gln Lys Phe Phe Lys Tyr Ser Val
             20                  25                  30

Asp Glu Lys Ser Asp Lys Glu Ala Glu Val Ser Glu His Ser Thr Gly

-continued

```
                35                  40                  45
Ile Thr His Leu Pro Pro Glu Val Met Leu Ser Ile Phe Ser Tyr Leu
     50                  55                  60
Asn Pro Gln Glu Leu Cys Arg Cys Ser Gln Val Ser Met Lys Trp Ser
 65                  70                  75                  80
Gln Leu Thr Lys Thr Gly Ser Leu Trp Lys His Leu Tyr Pro Val His
                 85                  90                  95
Trp Ala Arg Gly Asp Trp Tyr Ser Gly Pro Ala Thr Glu Leu Asp Thr
                100                 105                 110
Glu Pro Asp Asp Glu Trp Val Lys Asn Arg Lys Asp Glu Ser Arg Ala
                115                 120                 125
Phe His Glu Trp Asp Glu Asp Ala Asp Ile Asp Glu Ser Glu Glu Ser
                130                 135                 140
Ala Glu Glu Ser Ile Ala Ile Ser Ile Ala Gln Met Glu Lys Arg Leu
145                 150                 155                 160
Leu His Gly Leu Ile His Asn Val Leu Pro Tyr Val Gly Thr Ser Val
                165                 170                 175
Lys Thr Leu Val Leu Ala Tyr Ser Ser Ala Val Ser Ser Lys Met Val
                180                 185                 190
Arg Gln Ile Leu Glu Leu Cys Pro Asn Leu Glu His Leu Asp Leu Thr
                195                 200                 205
Gln Thr Asp Ile Ser Asp Ser Ala Phe Asp Ser Trp Ser Trp Leu Gly
                210                 215                 220
Cys Cys Gln Ser Leu Arg His Leu Asp Leu Ser Gly Cys Glu Lys Ile
225                 230                 235                 240
Thr Asp Val Ala Leu Glu Lys Ile Ser Arg Ala Leu Gly Ile Leu Thr
                245                 250                 255
Ser His Gln Ser Gly Phe Leu Lys Thr Ser Thr Ser Lys Ile Thr Ser
                260                 265                 270
Thr Ala Trp Lys Asn Lys Asp Ile Thr Met Gln Ser Thr Lys Gln Tyr
                275                 280                 285
Ala Cys Leu His Asp Leu Thr Asn Lys Gly Ile Gly Glu Glu Ile Asp
                290                 295                 300
Asn Glu His Pro Trp Thr Lys Pro Val Ser Ser Glu Asn Phe Thr Ser
305                 310                 315                 320
Pro Tyr Val Trp Met Leu Asp Ala Glu Asp Leu Ala Asp Ile Glu Asp
                325                 330                 335
Thr Val Glu Trp Arg His Arg Asn Val Glu Ser Leu Cys Val Met Glu
                340                 345                 350
Thr Ala Ser Asn Phe Ser Cys Ser Thr Ser Gly Cys Phe Ser Lys Asp
                355                 360                 365
Ile Val Gly Leu Arg Thr Ser Val Cys Trp Gln Gln His Cys Ala Ser
                370                 375                 380
Pro Ala Phe Ala Tyr Cys Gly His Ser Phe Cys Cys Thr Gly Thr Ala
385                 390                 395                 400
Leu Arg Thr Met Ser Ser Leu Pro Glu Ser Ser Ala Met Cys Arg Lys
                405                 410                 415
Ala Ala Arg Thr Arg Leu Pro Arg Gly Lys Asp Leu Ile Tyr Phe Gly
                420                 425                 430
Ser Glu Lys Ser Asp Gln Glu Thr Gly Arg Val Leu Leu Phe Leu Ser
                435                 440                 445
Leu Ser Gly Cys Tyr Gln Ile Thr Asp His Gly Leu Arg Val Leu Thr
                450                 455                 460
```

Leu Gly Gly Gly Leu Pro Tyr Leu Glu His Leu Asn Leu Ser Gly Cys
465                 470                 475                 480

Leu Thr Ile Thr Gly Ala Gly Leu Gln Asp Leu Val Ser Ala Cys Pro
            485                 490                 495

Ser Leu Asn Asp Glu Tyr Phe Tyr Tyr Cys Asp Asn Ile Asn Gly Pro
        500                 505                 510

His Ala Asp Thr Ala Ser Gly Cys Gln Asn Leu Gln Cys Gly Phe Arg
        515                 520                 525

Ala Cys Cys Arg Ser Gly Glu
        530                 535

<210> SEQ ID NO 53
<211> LENGTH: 1681
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 53
ttttactgta cacagttgat gtattttgat gctgggcctg tctggtctgt cttgaggatt      60
attaaccttt agaggtatca gagaagcaaa tgggtactgg tgaggctgct cattagggaa     120
gagggcaaaa ggagcactag ctaggtcaga gccatgtttc aggtcacaat gtgatgtcag     180
atgttgctta taaatccttt cttgtcttcg ccattcttaa atcttgatag gtgcctgttg     240
ggaaactgta aatgcctttc ccaatggaga atcaacagat tgggtgatgg tggagtcggt     300
caggaagact caggtcttct agaggaaagg atgcctcatc accccttngg cccaggcagc     360
tgctgtcaga gaatgacaca gcacctgcac agtcgctgtc cacttcctgc cactgctgtc     420
ggtggggtga cgggagcaaa gtaggcgtgg actttgacat gagggagctg agcccgcatc     480
cgcttgatgc ctgcacgggt aacctgctgg cagtcgtaca gctcgaggcg ctccaggcct     540
cggcagttct ctaggtgtyc cagggccaca tcagtgatga ggaggcagtt gtccaactcc     600
agtacccgca gcctctcatg gccacaggta ctgttgctca ggtgcaggat ccatcatct      660 gkgatgagtt cacagtggga caggctcagg gcttgcagtt taggacagtg aatggagagc     720
tggatgagtg tgctgtcggt tatcaggatg cawtcttcaa gatccatctt ctccaattcg     780
tggcaattcc gagctaaaag tgtaaaacct gcgtcagtca aatgggagca tcgggcagcc     840
tccaaaattt gcagtcgcgg acagttcaaa cccagggctg taagagaggc atctgtgagg     900
ttgctgcaac ccgaaaggca gagagcctgt agccggtgac agcccctgca tatctgcacc     960
acaccttcat ccgtgatacg tgagcaggac tgcaagttga ggctcacaag ctcatggcag    1020
taattctgaa tgtgtttcag agcttcatct tctaactgtg tgcagcccct caggagcagg    1080
gctttcaggc ctcgacaacc tcgcaccagt gcctcgatgc catccttcgt gatctgatca    1140
caccaagaga ggttcaggta ctccaggttt cggcagccct cactgatccc cttcaaggag    1200
ctgtttgtaa tagacacaca ggaggtcaga wccagatgtt tcagcttgga acagaatctg    1260
ctaaggctat aacacgtgct gtcagtgatt tttgtgcatc cattgaggtt caaatgttca    1320
atgtttcggc agttctgtgc aaaggtcttc aaggaggaat ccccaacacc aatgcagcct    1380
cgcaagctga gcttcctcag gaatccaacg catcgcttcg agatattttc caccactcga    1440
ccctctacat ctatttgaaa gttaaaaaga tctattcttt gccagttgct tccatccagg    1500
gctaagatgt tccaagcctt ggaaatctgt gcacatcggc acaaagttac tatatccaag    1560
aaggaaaata ttcttaacag aagttctttg ggtaactttt tgttaataag gccttcatca    1620

```
ttgtttgaga aaaccatggc cgaagagccg cgagcgagcc cacagcccga agtcacacgg    1680
c                                                                    1681
```

<210> SEQ ID NO 54
<211> LENGTH: 437
<212> TYPE: PRT
<213> ORGANISM: Homo sapiens
<220> FEATURE:
<221> NAME/KEY: SITE
<222> LOCATION: all Xaa positions
<223> OTHER INFORMATION: Xaa=unknown amino acid residue

<400> SEQUENCE: 54

```
Arg Val Thr Ser Gly Cys Gly Leu Ala Arg Gly Ser Ser Ala Met Val
  1               5                  10                  15

Phe Ser Asn Asn Asp Glu Gly Leu Ile Asn Lys Lys Leu Pro Lys Glu
                 20                  25                  30

Leu Leu Leu Arg Ile Phe Ser Phe Leu Asp Ile Val Thr Leu Cys Arg
             35                  40                  45

Cys Ala Gln Ile Ser Lys Ala Trp Asn Ile Leu Ala Leu Asp Gly Ser
         50                  55                  60

Asn Trp Gln Arg Ile Asp Leu Phe Asn Phe Gln Ile Asp Val Glu Gly
 65                  70                  75                  80

Arg Val Val Glu Asn Ile Ser Lys Arg Cys Val Gly Phe Leu Arg Lys
                 85                  90                  95

Leu Ser Leu Arg Gly Cys Ile Gly Val Gly Asp Ser Ser Leu Lys Thr
            100                 105                 110

Phe Ala Gln Asn Cys Arg Asn Ile Glu His Leu Asn Leu Asn Gly Cys
        115                 120                 125

Thr Lys Ile Thr Asp Ser Thr Cys Tyr Ser Leu Ser Arg Phe Cys Ser
130                 135                 140

Lys Leu Lys His Leu Xaa Leu Thr Ser Cys Val Ser Ile Thr Asn Ser
145                 150                 155                 160

Ser Leu Lys Gly Ile Ser Glu Gly Cys Arg Asn Leu Glu Tyr Leu Asn
                165                 170                 175

Leu Ser Trp Cys Asp Gln Ile Thr Lys Asp Gly Ile Glu Ala Leu Val
            180                 185                 190

Arg Gly Cys Arg Gly Leu Lys Ala Leu Leu Leu Arg Gly Cys Thr Gln
        195                 200                 205

Leu Glu Asp Glu Ala Leu Lys His Ile Gln Asn Tyr Cys His Glu Leu
210                 215                 220

Val Ser Leu Asn Leu Gln Ser Cys Ser Arg Ile Thr Asp Glu Gly Val
225                 230                 235                 240

Val Gln Ile Cys Arg Gly Cys His Arg Leu Gln Ala Leu Cys Leu Ser
                245                 250                 255

Gly Cys Ser Asn Leu Thr Asp Ala Ser Leu Thr Ala Leu Gly Leu Asn
            260                 265                 270

Cys Pro Arg Leu Gln Ile Leu Glu Ala Ala Arg Cys Ser His Leu Thr
        275                 280                 285

Asp Ala Gly Phe Thr Leu Leu Ala Arg Asn Cys His Glu Leu Glu Lys
290                 295                 300

Met Asp Leu Glu Xaa Cys Ile Leu Ile Thr Asp Ser Thr Leu Ile Gln
305                 310                 315                 320

Leu Ser Ile His Cys Pro Lys Leu Gln Ala Leu Ser Leu Ser His Cys
                325                 330                 335
```

```
Glu Leu Ile Xaa Asp Asp Gly Ile Leu His Leu Ser Asn Ser Thr Cys
            340                 345                 350

Gly His Glu Arg Leu Arg Val Leu Glu Leu Asp Asn Cys Leu Leu Ile
        355                 360                 365

Thr Asp Val Ala Leu Xaa His Leu Glu Asn Cys Arg Gly Leu Glu Arg
    370                 375                 380

Leu Glu Leu Tyr Asp Cys Gln Gln Val Thr Arg Ala Gly Ile Lys Arg
385                 390                 395                 400

Met Arg Ala Gln Leu Pro His Val Lys Val His Ala Tyr Phe Ala Pro
                405                 410                 415

Val Thr Pro Pro Thr Ala Val Ala Gly Ser Gly Gln Arg Leu Cys Arg
            420                 425                 430

Cys Cys Val Ile Leu
            435

<210> SEQ ID NO 55
<211> LENGTH: 1866
<212> TYPE: DNA
<213> ORGANISM: Homo sapiens

<400> SEQUENCE: 55
atgtcaccgg tctttcccat gttaacagtt ctgaccatgt tttattatat atgccttcgg    60
cgccgagcca ggacagctac aagaggagaa atgatgaaca cccatagagc tatagaatca   120
aacagccaga cttcccctct caatgcagag gtagtccagt atgccaaaga agtagtggat   180
ttcagttccc attatggaag tgagaatagt atgtcctata ctatgtggaa tttggctggt   240
gtaccaaatg tattcccaag ttctggtgac tttactcaga cagctgtgtt tcgaacttat   300
gggacatggt gggatcagtg tcctagtgct tccttgccat tcaagaggac gccacctaat   360
tttcagagcc aggactatgt ggaacttact tttgaacaac aggtgtatcc tacagctgta   420
catgttctag aaacctatca tcccggagca gtcattagaa ttctcgcttg ttctgcaaat   480
ccttattccc caaatccacc agctgaagta agatgggaga ttctttggtc agagagacct   540
acgaaggtga atgcttccca agctcgccag tttaaacctt gtattaagca gataaatttc   600
cccacaaatc ttatacgact ggaagtaaat agttctcttc tggaatatta cactgaatta   660
gatgcagttg tgctacatgg tgtgaaggac aagccagtgc tttctctcaa gacttcactt   720
attgacatga atgatataga agatgatgcc tatgcagaaa aggatggttg tggaatggac   780
agtcttaaca aaaagtttag cagtgctgtc ctcggggaag ggccaaataa tgggtatttt   840
gataaactac cttatgagct tattcagctg attctgaatc atcttacact accagacctg   900
tgtagattag cacagacttg caaactactg agccagcatt gctgtgatcc tctgcaatac   960
atccacctca atctgcaacc atactgggca aaactagatg acacttctct ggaatttcta  1020
cagtctcgct gcactcttgt ccagtggctt aatttatctt ggactggcaa tagaggcttc  1080
atctctgttg caggatttag caggtttctg aaggtttgtg atccgaatt agtacgcctt  1140 gaattgtctt gcagccactt tcttaatgaa acttgcttag aagttatttc tgagatgtgt  1200
ccaaatctac aggccttaaa tctctcctcc tgtgataagc taccacctca agctttcaac  1260
cacattgcca agttatgcag ccttaaacga cttgttctct atcgaacaaa agtagagcaa  1320
acagcactgc tcagcatttt gaacttctgt tcagagcttc agcacctcag tttaggcagt  1380
tgtgtcatga ttgaagacta tgatgtgata gctagcatga taggagccaa gtgtaaaaaa  1440
ctccggaccc tggatctgtg gagatgtaag aatattactg agaatggaat agcagaactg  1500
gcttctgggt gtccactact ggaggagctt gaccttggct ggtgcccaac tctgcagagc  1560
```

```
agcaccgggt gcttcaccag actggcacac cagctcccaa acttgcaaaa actctttctt   1620
acagctaata gatctgtgtg tgacacagac attgatgaat tggcatgtaa ttgtaccagg   1680
ttacagcagc tggacatatt aggaacaaga atggtaagtc cggcatcctt aagaaaactc   1740
ctggaatctt gtaaagatct ttctttactt gatgtgtcct tctgttcgca gattgataac   1800
agagctgtgc tagaactgaa tgcaagcttt ccaaaagtgt tcataaaaaa gagctttact   1860
cagtga                                                              1866

<210> SEQ ID NO 56
<211> LENGTH: 621
<212> TYPE: PRT
<213> ORGANISM: Homo sapiens

<400> SEQUENCE: 56

Met Ser Pro Val Phe Pro Met Leu Thr Val Leu Thr Met Phe Tyr Tyr
  1               5                  10                  15

Ile Cys Leu Arg Arg Ala Arg Thr Ala Thr Arg Gly Glu Met Met
                 20                  25                  30

Asn Thr His Arg Ala Ile Glu Ser Asn Ser Gln Thr Ser Pro Leu Asn
                 35                  40                  45

Ala Glu Val Val Gln Tyr Ala Lys Glu Val Val Asp Phe Ser Ser His
             50                  55                  60

Tyr Gly Ser Glu Asn Ser Met Ser Tyr Thr Met Trp Asn Leu Ala Gly
 65                  70                  75                  80

Val Pro Asn Val Phe Pro Ser Ser Gly Asp Phe Thr Gln Thr Ala Val
                 85                  90                  95

Phe Arg Thr Tyr Gly Thr Trp Trp Asp Gln Cys Pro Ser Ala Ser Leu
                100                 105                 110

Pro Phe Lys Arg Thr Pro Pro Asn Phe Gln Ser Gln Asp Tyr Val Glu
                115                 120                 125

Leu Thr Phe Glu Gln Gln Val Tyr Pro Thr Ala Val His Val Leu Glu
            130                 135                 140

Thr Tyr His Pro Gly Ala Val Ile Arg Ile Leu Ala Cys Ser Ala Asn
145                 150                 155                 160

Pro Tyr Ser Pro Asn Pro Pro Ala Glu Val Arg Trp Glu Ile Leu Trp
                165                 170                 175

Ser Glu Arg Pro Thr Lys Val Asn Ala Ser Gln Ala Arg Gln Phe Lys
                180                 185                 190

Pro Cys Ile Lys Gln Ile Asn Phe Pro Thr Asn Leu Ile Arg Leu Glu
                195                 200                 205

Val Asn Ser Ser Leu Leu Glu Tyr Tyr Thr Gly Leu Asp Ala Val Val
            210                 215                 220

Leu His Gly Val Lys Asp Lys Pro Val Leu Ser Leu Lys Thr Ser Leu
225                 230                 235                 240

Ile Asp Met Asn Asp Ile Glu Asp Ala Tyr Ala Glu Lys Asp Gly
                245                 250                 255

Cys Gly Met Asp Ser Leu Asn Lys Lys Phe Ser Ala Val Leu Gly
                260                 265                 270

Glu Gly Pro Asn Asn Gly Tyr Phe Asp Lys Leu Pro Tyr Glu Leu Ile
            275                 280                 285

Gln Leu Ile Leu Asn His Leu Thr Leu Pro Asp Leu Cys Arg Leu Ala
        290                 295                 300

Gln Thr Cys Lys Leu Leu Ser Gln His Cys Cys Asp Pro Leu Gln Tyr
305                 310                 315                 320
```

```
Ile His Leu Asn Leu Gln Pro Tyr Trp Ala Lys Leu Asp Asp Thr Ser
                325                 330                 335

Leu Glu Phe Leu Gln Ser Arg Cys Thr Leu Val Gln Trp Leu Asn Leu
            340                 345                 350

Ser Trp Thr Gly Asn Arg Gly Phe Ile Ser Val Ala Gly Phe Ser Arg
        355                 360                 365

Phe Leu Lys Val Cys Gly Ser Glu Leu Val Arg Leu Glu Leu Ser Cys
    370                 375                 380

Ser His Phe Leu Asn Glu Thr Cys Leu Glu Val Ile Ser Glu Met Cys
385                 390                 395                 400

Pro Asn Leu Gln Ala Leu Asn Leu Ser Ser Cys Asp Lys Leu Pro Pro
                405                 410                 415

Gln Ala Phe Asn His Ile Ala Lys Leu Cys Ser Leu Lys Arg Leu Val
            420                 425                 430

Leu Tyr Arg Thr Lys Val Glu Gln Thr Ala Leu Leu Ser Ile Leu Asn
        435                 440                 445

Phe Cys Ser Glu Leu Gln His Leu Ser Leu Gly Ser Cys Val Met Ile
    450                 455                 460

Glu Asp Tyr Asp Val Ile Ala Ser Met Ile Gly Ala Lys Cys Lys Lys
465                 470                 475                 480

Leu Arg Thr Leu Asp Leu Trp Arg Cys Lys Asn Ile Thr Glu Asn Gly
                485                 490                 495

Ile Ala Glu Leu Ala Ser Gly Cys Pro Leu Leu Glu Glu Leu Asp Leu
            500                 505                 510

Gly Trp Cys Pro Thr Leu Gln Ser Ser Thr Gly Cys Phe Thr Arg Leu
        515                 520                 525

Ala His Gln Leu Pro Asn Leu Gln Lys Leu Phe Leu Thr Ala Asn Arg
    530                 535                 540

Ser Val Cys Asp Thr Asp Ile Asp Glu Leu Ala Cys Asn Cys Thr Arg
545                 550                 555                 560

Leu Gln Gln Leu Asp Ile Leu Gly Thr Arg Met Val Ser Pro Ala Ser
                565                 570                 575

Leu Arg Lys Leu Leu Glu Ser Cys Lys Asp Leu Ser Leu Leu Asp Val
            580                 585                 590

Ser Phe Cys Ser Gln Ile Asp Asn Arg Ala Val Leu Glu Leu Asn Ala
        595                 600                 605

Ser Phe Pro Lys Val Phe Ile Lys Lys Ser Phe Thr Gln
    610                 615                 620

<210> SEQ ID NO 57
<211> LENGTH: 984
<212> TYPE: DNA
<213> ORGANISM: Homo sapiens

<400> SEQUENCE: 57
atgcaacttg tacctgatat agagttcaag attacttata cccggtctcc agatggtgat      60
ggcgttggaa acagctacat tgaagataat gatgatgaca gcaaaatggc agatctcttg     120
tcctacttcc agcagcaact cacatttcag gagtctgtgc ttaaactgtg tcagcctgag     180
cttgagagca gtcagattca catatcagtg ctgccaatgg aggtcctgat gtacatcttc     240
cgatgggtgg tgtctagtga cttggacctc agatcattgg agcagttgtc gctggtgtgc     300
agaggattct acatctgtgc cagagaccct gaaatatggc gtctggcctg cttgaaagtt     360
tggggcagaa gctgtattaa acttgttccg tacacgtcct ggagagagat gttttagaa      420
```

```
cggcctcgtg ttcggtttga tggcgtgtat atcagtaaaa ccacatatat tcgtcaaggg    480
gaacagtctc ttgatggttt ctatagagcc tggcaccaag tggaatatta caggtacata    540
agattctttc ctgatggcca tgtgatgatg ttgacaaccc ctgaagagcc tcagtccatt    600
gttccacgtt taagaactag gaataccagg actgatgcaa ttctactggg tcactatcgc    660
ttgtcacaag acacagacaa tcagaccaaa gtatttgctg taataactaa gaaaaagaa     720 gaaaaaccac ttgactataa atacagatat tttcgtcgtg tccctgtaca agaagcagat    780
cagagttttc atgtggggct acagctatgt ccagtggtc accagaggtt caacaaactc      840
atctggatac atcattcttg tcacattact tacaaatcaa ctggtgagac tgcagtcagt    900
gcttttgaga ttgacaagat gtacaccccc ttgttcttcg ccagagtaag gagctacaca    960
gctttctcag aaaggcctct gtag                                           984
```

<210> SEQ ID NO 58
<211> LENGTH: 327
<212> TYPE: PRT
<213> ORGANISM: Homo sapiens

<400> SEQUENCE: 58

```
Met Gln Leu Val Pro Asp Ile Glu Phe Lys Ile Thr Tyr Thr Arg Ser
 1               5                  10                  15

Pro Asp Gly Asp Gly Val Gly Asn Ser Tyr Ile Glu Asp Asn Asp Asp
            20                  25                  30

Asp Ser Lys Met Ala Asp Leu Leu Ser Tyr Phe Gln Gln Gln Leu Thr
         35                  40                  45

Phe Gln Glu Ser Val Leu Lys Leu Cys Gln Pro Glu Leu Glu Ser Ser
     50                  55                  60

Gln Ile His Ile Ser Val Leu Pro Met Glu Val Leu Met Tyr Ile Phe
 65                  70                  75                  80

Arg Trp Val Val Ser Ser Asp Leu Asp Leu Arg Ser Leu Glu Gln Leu
                 85                  90                  95

Ser Leu Val Cys Arg Gly Phe Tyr Ile Cys Ala Arg Asp Pro Glu Ile
            100                 105                 110

Trp Arg Leu Ala Cys Leu Lys Val Trp Gly Arg Ser Cys Ile Lys Leu
         115                 120                 125

Val Pro Tyr Thr Ser Trp Arg Glu Met Phe Leu Glu Arg Pro Arg Val
    130                 135                 140

Arg Phe Asp Gly Val Tyr Ile Ser Lys Thr Thr Tyr Ile Arg Gln Gly
145                 150                 155                 160

Glu Gln Ser Leu Asp Gly Phe Tyr Arg Ala Trp His Gln Val Glu Tyr
                165                 170                 175

Tyr Arg Tyr Ile Arg Phe Phe Pro Asp Gly His Val Met Met Leu Thr
            180                 185                 190

Thr Pro Glu Glu Pro Gln Ser Ile Val Pro Arg Leu Arg Thr Arg Asn
        195                 200                 205

Thr Arg Thr Asp Ala Ile Leu Leu Gly His Tyr Arg Leu Ser Gln Asp
    210                 215                 220

Thr Asp Asn Gln Thr Lys Val Phe Ala Val Ile Thr Lys Lys Lys Glu
225                 230                 235                 240

Glu Lys Pro Leu Asp Tyr Lys Tyr Arg Tyr Phe Arg Arg Val Pro Val
                245                 250                 255

Gln Glu Ala Asp Gln Ser Phe His Val Gly Leu Gln Leu Cys Ser Ser
            260                 265                 270

Gly His Gln Arg Phe Asn Lys Leu Ile Trp Ile His His Ser Cys His
```

```
                  275                 280                 285
Ile Thr Tyr Lys Ser Thr Gly Glu Thr Ala Val Ser Ala Phe Glu Ile
        290                 295                 300

Asp Lys Met Tyr Thr Pro Leu Phe Phe Ala Arg Val Arg Ser Tyr Thr
305                 310                 315                 320

Ala Phe Ser Glu Arg Pro Leu
                325

<210> SEQ ID NO 59
<211> LENGTH: 765
<212> TYPE: DNA
<213> ORGANISM: Homo sapiens
<220> FEATURE:
<221> NAME/KEY: modified_base
<222> LOCATION: all n positions
<223> OTHER INFORMATION: n=a, c, g or t

<400> SEQUENCE: 59
gcagccctgg atcctgactt agagaatgat gatttctttg tcagaaagac tggggctttc      60
catgcaaatc catatgttct ccgagctttt gaagacttta gaagttctc  tgagcaagat     120 gattctgtag agcgagatat aattttacag tgtagaaag  gtgaacttgt acttccggat     180
ttggaaaaag atgatatgat tgttcgccga atcccagcac agaagaaaga gtgccgctg     240 tctgggccc  cagatagata ccacccagtc ccttttcccg aaccctggac tcttcctcca     300
gaaattcaag caaaatttct ctgtgtactt gaaaggacat gcccatccaa agaaaaagt     360 aatagctgta gaatattagt tccttcatat cggcagaaga agatgacat  gctgacacgt     420 aagattcagt cctggaaact gggaactacc gtgcctccca tcagtttcac nccctggcccc    480 tgcagtgagc tgacttgaa  gagatgggag gccatccggg aggccagcag actcaggcac     540 aagaaaggc  tgatggtgga gagactcttt caaaagattt atggtgagaa tgggagtaag     600
tccatgagtg atgtcagcgc agaagatgtt caaaacttgc gtcagctgcg ttacgaggag     660
atgcagaaaa taaaatcaca attaaaagaa caagatcaga atggcagga  tgaccttgca     720 aaatggaaag atcgtcgaaa aagttacact tcagatctgc agaag                    765

<210> SEQ ID NO 60
<211> LENGTH: 255
<212> TYPE: PRT
<213> ORGANISM: Homo sapiens

<400> SEQUENCE: 60

Ala Ala Leu Asp Pro Asp Leu Glu Asn Asp Asp Phe Phe Val Arg Lys
 1               5                  10                  15

Thr Gly Ala Phe His Ala Asn Pro Tyr Val Leu Arg Ala Phe Glu Asp
                20                  25                  30

Phe Arg Lys Phe Ser Glu Gln Asp Asp Ser Val Glu Arg Asp Ile Ile
            35                  40                  45

Leu Gln Cys Arg Glu Gly Glu Leu Val Leu Pro Asp Leu Glu Lys Asp
        50                  55                  60

Asp Met Ile Val Arg Arg Ile Pro Ala Gln Lys Lys Glu Val Pro Leu
65                  70                  75                  80

Ser Gly Ala Pro Asp Arg Tyr His Pro Val Pro Phe Pro Glu Pro Trp
                85                  90                  95

Thr Leu Pro Pro Glu Ile Gln Ala Lys Phe Leu Cys Val Leu Glu Arg
            100                 105                 110

Thr Cys Pro Ser Lys Glu Lys Ser Asn Ser Cys Arg Ile Leu Val Pro
        115                 120                 125
```

```
Ser Tyr Arg Gln Lys Lys Asp Asp Met Leu Thr Arg Lys Ile Gln Ser
    130                 135                 140
Trp Lys Leu Gly Thr Thr Val Pro Pro Ile Ser Phe Thr Pro Gly Pro
145                 150                 155                 160
Cys Ser Glu Ala Asp Leu Lys Arg Trp Glu Ala Ile Arg Glu Ala Ser
                165                 170                 175
Arg Leu Arg His Lys Lys Arg Leu Met Val Glu Arg Leu Phe Gln Lys
            180                 185                 190
Ile Tyr Gly Glu Asn Gly Ser Lys Ser Met Ser Asp Val Ser Ala Glu
        195                 200                 205
Asp Val Gln Asn Leu Arg Gln Leu Arg Tyr Glu Glu Met Gln Lys Ile
    210                 215                 220
Lys Ser Gln Leu Lys Glu Gln Asp Gln Lys Trp Gln Asp Asp Leu Ala
225                 230                 235                 240
Lys Trp Lys Asp Arg Arg Lys Ser Tyr Thr Ser Asp Leu Gln Lys
                245                 250                 255

<210> SEQ ID NO 61
<211> LENGTH: 36
<212> TYPE: PRT
<213> ORGANISM: Homo sapiens

<400> SEQUENCE: 61

Leu Pro Pro Glu Leu Ser Phe Thr Ile Leu Ser Tyr Leu Asn Ala Thr
1               5                   10                  15
Asp Leu Cys Leu Ala Ser Cys Val Trp Gln Asp Leu Ala Asn Asp Glu
            20                  25                  30
Leu Leu Trp Gln
        35

<210> SEQ ID NO 62
<211> LENGTH: 42
<212> TYPE: PRT
<213> ORGANISM: Homo sapiens

<400> SEQUENCE: 62

Leu Pro Gly Glu Val Leu Glu Tyr Ile Leu Cys Cys Gly Ser Leu Thr
1               5                   10                  15
Ala Ala Asp Ile Gly Arg Val Ser Ser Thr Cys Arg Arg Leu Arg Glu
            20                  25                  30
Leu Cys Gln Ser Ser Gly Lys Val Trp Lys
        35                  40

<210> SEQ ID NO 63
<211> LENGTH: 44
<212> TYPE: PRT
<213> ORGANISM: Homo sapiens

<400> SEQUENCE: 63

Leu Ala Glu Val Val Glu Arg Val Leu Thr Phe Leu Pro Ala Lys Ala
1               5                   10                  15
Leu Leu Arg Val Ala Cys Val Cys Arg Leu Trp Arg Glu Cys Val Arg
            20                  25                  30
Arg Val Leu Arg Thr His Arg Ser Val Thr Trp Ile
        35                  40

<210> SEQ ID NO 64
<211> LENGTH: 39
<212> TYPE: PRT
```

<213> ORGANISM: Homo sapiens

<400> SEQUENCE: 64

Leu Pro Asp Glu Val Val Leu Lys Ile Phe Ser Tyr Leu Leu Glu Gln
1               5                   10                  15

Asp Leu Cys Arg Ala Ala Cys Val Cys Lys Arg Phe Ser Glu Leu Ala
            20                  25                  30

Asn Asp Pro Asn Leu Trp Lys
        35

<210> SEQ ID NO 65
<211> LENGTH: 41
<212> TYPE: PRT
<213> ORGANISM: Homo sapiens

<400> SEQUENCE: 65

Leu Pro Leu Glu Leu Trp Arg Met Ile Leu Ala Tyr Leu His Leu Pro
1               5                   10                  15

Asp Leu Gly Arg Cys Ser Leu Val Cys Arg Ala Trp Tyr Glu Leu Ile
            20                  25                  30

Leu Ser Leu Asp Ser Thr Arg Trp Arg
        35                  40

<210> SEQ ID NO 66
<211> LENGTH: 39
<212> TYPE: PRT
<213> ORGANISM: Homo sapiens

<400> SEQUENCE: 66

Leu Pro Thr Asp Pro Leu Leu Ile Leu Ser Phe Leu Asp Tyr Arg
1               5                   10                  15

Asp Leu Ile Asn Cys Cys Tyr Val Ser Arg Arg Leu Ser Gln Leu Ser
            20                  25                  30

Ser His Asp Pro Leu Trp Arg
        35

<210> SEQ ID NO 67
<211> LENGTH: 40
<212> TYPE: PRT
<213> ORGANISM: Homo sapiens

<400> SEQUENCE: 67

Leu Pro Glu Pro Leu Leu Leu Arg Val Leu Ala Ala Leu Pro Ala Ala
1               5                   10                  15

Glu Leu Val Gln Ala Cys Arg Leu Val Cys Leu Arg Trp Lys Glu Leu
            20                  25                  30

Val Asp Gly Ala Pro Leu Trp Leu
        35                  40

<210> SEQ ID NO 68
<211> LENGTH: 40
<212> TYPE: PRT
<213> ORGANISM: Homo sapiens

<400> SEQUENCE: 68

Leu Phe Pro Pro Glu Leu Val Glu His Ile Ile Ser Phe Leu Pro Val
1               5                   10                  15

Arg Asp Leu Val Ala Leu Gly Gln Thr Cys Arg Tyr Phe His Glu Val
            20                  25                  30

Cys Asp Gly Glu Gly Val Trp Arg
        35                  40

<210> SEQ ID NO 69
<211> LENGTH: 44
<212> TYPE: PRT
<213> ORGANISM: Homo sapiens

<400> SEQUENCE: 69

Leu Pro Glu Val Leu Leu His Met Cys Ser Tyr Leu Asp Met Arg
1               5                   10                  15

Ala Leu Gly Arg Leu Ala Gln Val Tyr Arg Trp Leu Trp His Phe Thr
            20                  25                  30

Asn Cys Asp Leu Leu Arg Arg Gln Ile Ala Trp Ala
        35                  40

<210> SEQ ID NO 70
<211> LENGTH: 40
<212> TYPE: PRT
<213> ORGANISM: Homo sapiens

<400> SEQUENCE: 70

Leu Pro Leu His Met Leu Asn Asn Ile Leu Tyr Arg Phe Ser Asp Gly
1               5                   10                  15

Trp Asp Ile Ile Thr Leu Gly Gln Val Thr Pro Thr Leu Tyr Met Leu
            20                  25                  30

Ser Glu Asp Arg Gln Leu Trp Lys
        35                  40

<210> SEQ ID NO 71
<211> LENGTH: 39
<212> TYPE: PRT
<213> ORGANISM: Homo sapiens

<400> SEQUENCE: 71

Leu Pro Asp His Ser Met Val Gln Ile Phe Ser Phe Leu Pro Thr Asn
1               5                   10                  15

Gln Leu Cys Arg Cys Ala Arg Val Cys Arg Arg Trp Tyr Asn Leu Ala
            20                  25                  30

Trp Asp Pro Arg Leu Trp Arg
        35

<210> SEQ ID NO 72
<211> LENGTH: 44
<212> TYPE: PRT
<213> ORGANISM: Homo sapiens

<400> SEQUENCE: 72

Ile Pro Leu Glu Ile Leu Val Gln Ile Phe Gly Leu Leu Val Ala Ala
1               5                   10                  15

Asp Gly Pro Met Pro Phe Leu Gly Arg Ala Ala Arg Val Cys Arg Arg
            20                  25                  30

Trp Gln Glu Ala Ala Ser Gln Pro Ala Leu Trp His
        35                  40

<210> SEQ ID NO 73
<211> LENGTH: 39
<212> TYPE: PRT
<213> ORGANISM: Homo sapiens

<400> SEQUENCE: 73

Leu Pro Pro Glu Val Met Leu Ser Ile Phe Ser Tyr Leu Asn Pro Gln
1               5                   10                  15

-continued

```
Glu Leu Cys Arg Cys Ser Gln Val Ser Met Lys Trp Ser Gln Leu Thr
                20                  25                  30

Lys Thr Gly Ser Leu Trp Lys
        35

<210> SEQ ID NO 74
<211> LENGTH: 39
<212> TYPE: PRT
<213> ORGANISM: Homo sapiens

<400> SEQUENCE: 74

Leu Pro Lys Glu Leu Leu Arg Ile Phe Ser Phe Leu Asp Ile Val
 1               5                  10                  15

Thr Leu Cys Arg Cys Ala Gln Ile Ser Lys Ala Trp Asn Ile Leu Ala
                20                  25                  30

Leu Asp Gly Ser Asn Trp Gln
        35

<210> SEQ ID NO 75
<211> LENGTH: 48
<212> TYPE: PRT
<213> ORGANISM: Homo sapiens

<400> SEQUENCE: 75

Leu Pro Tyr Glu Leu Ile Gln Leu Ile Leu Asn His Leu Thr Leu Pro
 1               5                  10                  15

Asp Leu Cys Arg Leu Ala Gln Thr Cys Lys Leu Leu Ser Gln His Cys
                20                  25                  30

Cys Asp Pro Leu Gln Tyr Ile His Leu Asn Leu Gln Pro Tyr Trp Ala
        35                  40                  45

<210> SEQ ID NO 76
<211> LENGTH: 44
<212> TYPE: PRT
<213> ORGANISM: Homo sapiens

<400> SEQUENCE: 76

Leu Pro Met Glu Val Leu Met Tyr Ile Phe Arg Trp Val Val Ser Ser
 1               5                  10                  15

Asp Leu Asp Leu Arg Ser Leu Glu Gln Leu Ser Leu Val Cys Arg Gly
                20                  25                  30

Phe Tyr Ile Cys Ala Arg Asp Pro Glu Ile Trp Arg
        35                  40

<210> SEQ ID NO 77
<211> LENGTH: 49
<212> TYPE: PRT
<213> ORGANISM: Homo sapiens

<400> SEQUENCE: 77

Leu Pro Pro Glu Ile Gln Ala Lys Phe Leu Cys Val Leu Glu Arg Thr
 1               5                  10                  15

Cys Pro Ser Lys Glu Lys Ser Asn Ser Cys Arg Ile Leu Val Pro Ser
                20                  25                  30

Tyr Arg Gln Lys Lys Asp Asp Met Leu Thr Arg Lys Ile Gln Ser Trp
        35                  40                  45

Lys

<210> SEQ ID NO 78
<211> LENGTH: 39
<212> TYPE: PRT
```

<213> ORGANISM: Homo sapiens

<400> SEQUENCE: 78

Leu Pro His His Val Val Leu Gln Ile Phe Gln Tyr Leu Pro Leu Leu
1               5                   10                  15

Asp Arg Ala Cys Ala Ser Ser Val Cys Arg Arg Trp Asn Glu Val Phe
            20                  25                  30

His Ile Ser Asp Leu Trp Arg
        35

<210> SEQ ID NO 79
<211> LENGTH: 43
<212> TYPE: PRT
<213> ORGANISM: Homo sapiens

<400> SEQUENCE: 79

Leu Trp Ala Trp Gly Glu Lys Gly Val Leu Ser Asn Ile Ser Ala Leu
1               5                   10                  15

Thr Asp Leu Gly Gly Leu Asp Pro Val Trp Leu Val Cys Gly Ser Trp
            20                  25                  30

Arg Arg His Val Gly Ala Gly Leu Cys Trp Ala
        35                  40

<210> SEQ ID NO 80
<211> LENGTH: 59
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 80
agtagtaaca aaggtcaaag acagttgact gtatcgtcga ggatgccttc aattaagtt      59

<210> SEQ ID NO 81
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 81
gcggttactt acttagagct cgacgtctta cttacttagc tcacttctct tcacacca       58

<210> SEQ ID NO 82
<211> LENGTH: 12
<212> TYPE: PRT
<213> ORGANISM: Homo sapiens

<400> SEQUENCE: 82

Cys Asp Gly Glu Lys Asp Thr Tyr Ser Tyr Leu Ala
1               5                   10

<210> SEQ ID NO 83
<211> LENGTH: 25
<212> TYPE: PRT
<213> ORGANISM: Homo sapiens

<400> SEQUENCE: 83

Cys Glu Ser Ser Phe Ser Leu Asn Met Asn Phe Ser Ser Lys Arg Thr
1               5                   10                  15

Lys Phe Lys Ile Thr Thr Ser Met Gln
            20                  25

<210> SEQ ID NO 84
<211> LENGTH: 12
<212> TYPE: PRT
<213> ORGANISM: Homo sapiens

<400> SEQUENCE: 84

Cys Glu Glu Ala Gln Val Arg Lys Glu Asn Gln Trp
 1               5                  10

<210> SEQ ID NO 85
<211> LENGTH: 19
<212> TYPE: PRT
<213> ORGANISM: Homo sapiens
<220> FEATURE:
<221> NAME/KEY: Phosphorylation
<222> LOCATION: 8
<223> OTHER INFORMATION: Phosothreonine

<400> SEQUENCE: 85

Asn Ala Gly Ser Val Glu Gln Thr Pro Lys Lys Pro Gly Leu Arg Arg
 1               5                  10                  15

Arg Gln Thr

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 86
cctgggggat gttctca                                                    17

<210> SEQ ID NO 87
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 87
ggcttccggg catttag                                                    17

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 88
catctggcac gattcca                                                    17

<210> SEQ ID NO 89
<211> LENGTH: 17
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 89
ccgctcatcg tatgaca                                                    17

<210> SEQ ID NO 90
<211> LENGTH: 19
<212> TYPE: PRT
<213> ORGANISM: Homo sapiens
<220> FEATURE:
<221> NAME/KEY: Phosphorylation
<222> LOCATION: 8
<223> OTHER INFORMATION: Phosotyrosine

<400> SEQUENCE: 90

Ala Glu Ile Gly Val Gly Ala Tyr Gly Thr Val Tyr Lys Ala Arg Asp
 1               5                  10                  15

Pro His Ser

<210> SEQ ID NO 91
<211> LENGTH: 4011
<212> TYPE: DNA
<213> ORGANISM: Homo sapiens
<220> FEATURE:
<223> OTHER INFORMATION: Human Fbxl 10 protein (NP_115979.3)

<400> SEQUENCE: 91

| | |
|---|---|
| atggcgggtc cgcaaatggg gggatctgca gaggatcacc ccccacgaaa aagacatgca | 60 |
| gcagaaaagc aaaaaaagaa aacagttata tatacaaaat gctttgaatt tgagtcggcc | 120 |
| acacagcgcc cgattgaccg ccagcgatac gacgagaacg aggacttgtc ggacgtggag | 180 |
| gagatcgtca gcgtccgcgg cttcagcctg gaggagaagc ttcgcagcca gctgtaccag | 240 |
| ggggacttcg tgcacgccat ggagggcaaa gatttcaact atgagtacgt acagagagaa | 300 |
| gctctcaggg ttcccctgat atttcgagaa aaggatggac tggaattaa gatgcctgac | 360 |
| cctgatttca cagtccgaga cgtcaaactc ctagtgggga ccggcggct tgtggacgtg | 420 |
| atggatgtga acacccagaa gggcacggag atgagcatgt cccagtttgt gcgttactac | 480 |
| gagacgcccg aggcccagcg ggacaagctg tacaacgtca tcagcctaga gttcagccac | 540 |
| accaagctgg agcacttggt caagcgtccg actgtggtag acctggtgga ctgggtggac | 600 |
| aacatgtggc cccagcatct gaaggagaag cagacagaag ccacgaacgc cattgcagag | 660 |
| atgaagtacc cgaaagtgaa aaagtactgt ctgatgagcg tgaaaggttg tttcaccgac | 720 |
| ttccacatcg acttggagg cacttccgtt tggtaccatg tttccggggt gggaagatt | 780 |
| ttttggctga ttcctccaac gctgcacaat ttggcgctgt acgaggagtg ggtgctgtca | 840 |
| ggcaaacaga gtgacatctt tctgggagac cgtgtggaac gatgccaaag aattgagctg | 900 |
| aagcagggct acacattttt catcccttcc ggttggatcc atgccgtcta caccctgta | 960 |
| gactcttttgg tgttcggcgg aaacatcctg cacagcttta acgtgcccat gcagctgcgg | 1020 |
| atctacgaga tcgaggacag gacgcgggtg cagcccaaat tccgttaccc cttctactat | 1080 |
| gagatgtgct ggtatgtcct ggagagatac gtgtactgtg tgacccagcg ctcccacctc | 1140 |
| actcaggaat accagaggga gtcgatgctt attgatgccc gaggaagcc cagcatagac | 1200 |
| ggcttctctt cggattcctg gctggagatg gaggaggagg cctgtgatca gcagcctcag | 1260 |
| gaggaggagg agaaggacga ggagggcgag ggcagggaca gggcacccaa accgcccacc | 1320 |
| gatggctcca cttcacccac cagcacgccc tctgaggacc aggaggccct cgggaagaag | 1380 |
| cccaaagcac ctgccctgcg attcctcaaa aggactttgt ctaatgagtc ggaggaaagt | 1440 |
| gtgaagtcca ccacattggc cgtagactac cccaagaccc caccggctc tcccgccacg | 1500 |
| gaggtctctg ccaaatggac ccatctcact gagtttgaac tgaagggcct gaaagctctg | 1560 |

```
gtggagaaac tggaatccct cccggagaac aagaagtgtg tccccgaggg catcgaggac      1620
ccccaggcac tcctggaggg tgtgaagaac gtcctgaagg agcacgcaga tgatgaccct      1680
agtctggcca tcactggggt ccctgtggtg acttggccaa agaagactcc aaagaaccgg      1740
gctgtgggtc ggcccaaggg gaagctgggc ccggcctccg cggtgaagtt ggccgccaac      1800
cggacaacgg caggagctcg gcggcgccgg acgcgatgcc gcaagtgcga ggcctgcctg      1860
cggaccgagt gcggagagtg ccacttctgc aaggacatga agaagttcgg ggccccgggg      1920
cgcatgaagc agagctgcat catgcggcag tgcatcgcgc cagtgctgcc ccacaccgcc      1980
gtgtgccttg tgtgtggcga ggcggggaag aagacacgg tggaagagga ggaaggcaag       2040
tttaacctca tgctcatgga gtgctccatc tgcaatgaaa tcatccaccc tggatgcctt      2100
aagattaagg agtcagaggg tgtggtcaac gacgagcttc caaactgctg ggagtgtccg      2160
aagtgtaacc acgccggcaa gacccggaaa caaaagcgtg gccctggctt taagtacgcc      2220
tccaacctgc ccggctccct gctcaaggag cagaagatga accgggacaa caaggaaggg      2280
caggaacctg ccaagcggag gagtgagtgt gaggaggcgc cccggcgcag gtcggatgag      2340
cactcgaaga aggtgccgcc ggacggcctt ctgcgcagaa agtctgacga cgtgcacctg      2400
aggaagaagc ggaaatacga gaagcccag gagctgagtg gacgcaagcg ggcctcatcg       2460
cttcaaacgt ccccggttc ctcctctcac ctctcgccga ggccccctct aggcagcagc       2520
ctcagcccct ggtggagatc cagtctcact tacttccagc agcagctcaa acctggcaaa      2580
gaagataagc ttttcaggaa aaagcggcgg tcctggaaga cgccgaggga ccgcatggcg      2640
ctggccaaca agcccctccg gcgcttcaag caggaacccg aggacgaact gcccgaggcg      2700 cccccaaga ccaggagag cgaccactcc cgctccagct cccccaccgc gggacccagc        2760
accgaagggg ccgagggccc ggaggagaag aagaaggtga agatgcgccg gaagcggcg       2820 cttcccaaca aggagctgag cagggagctg agcaaggagc tcaaccacga gatccagagg      2880
acggagaaca gcctggccaa cgagaaccag cagcccatca gtcggagcc tgagagcgag       2940 ggcgaggagc ccaagcggcc cccgggcatc tgcgagcgtc ccaccgctt cagcaagggg      3000 ctcaacggca ccccccggga gctgcggcac cagctggggc ccagcctgcg cagcccgccc      3060
cgtgtcatct cccggccccc accctccgtg tccccgccca gtgtatcca tggagcgc       3120 catgtgatcc ggccaccccc catcagcccc ccgcctgact cgctacccct ggacgatggg      3180
gcagcccacg tcatgcacag ggaggtgtgg atggccgtct tcagctacct cagccaccaa      3240
gacctgtgtg tgtgcatgcg ggtctgcagg acctggaacc gctggtgctg cgataagcgg      3300
ttgtggaccc gcattgacct gaaccactgc aagtctatca caccctgat gctgagtggc       3360 atcatccggc gacagcccgt ctccctcgac ctcagctgga ccaatatctc caagaagcag      3420
ctgagctggc tcatcaaccg gctgcctggg ctccgggact tggtgctgtc aggctgctca      3480
tggatcgcgc tctcggccct ttgcagctcc agttgtccgc tgctccggac cctggatgtc      3540
cagtgggtgg agggactaaa ggatgcccag atgcgggatc tcctgtcccc gcccacagac      3600
aacaggccag tcagatgga caatcggagc aagctccgga acatcgtgga gctgcgcctg        3660
gcaggcctgg acatcacaga tgcctccctg cggctcatca tccgccacat gcccctgctc      3720
tccaagctcc acctcagtta ctgtaaccac gtcaccgacc agtctatcaa cctgctcact      3780
gctgttggca ccaccacccg agactcctta accgagatca acctgtctga ctgcaataag      3840
gtcactgatc agtgcctgtc cttcttcaaa cgctgtggaa acatctgtca tattgacctg      3900
aggtactgca agcaagtcac caaggaaggc tgtgagcagt tcatagccga gatgtctgtg      3960
```
agtgtccagt ttgggcaagt agaagaaaaa ctcctgcaaa aactgagtta g         4011

<210> SEQ ID NO 92
<211> LENGTH: 1336
<212> TYPE: PRT
<213> ORGANISM: Homo sapiens
<220> FEATURE:
<223> OTHER INFORMATION: Human Fbxl 10 protein (NP_115979.3)

<400> SEQUENCE: 92

Met Ala Gly Pro Gln Met Gly Gly Ser Ala Glu Asp His Pro Pro Arg
1               5                   10                  15

Lys Arg His Ala Ala Glu Lys Gln Lys Lys Thr Val Ile Tyr Thr
            20                  25                  30

Lys Cys Phe Glu Phe Glu Ser Ala Thr Gln Arg Pro Ile Asp Arg Gln
        35                  40                  45

Arg Tyr Asp Glu Asn Glu Asp Leu Ser Asp Val Glu Ile Val Ser
    50                  55                  60

Val Arg Gly Phe Ser Leu Glu Glu Lys Leu Arg Ser Gln Leu Tyr Gln
65                  70                  75                  80

Gly Asp Phe Val His Ala Met Glu Gly Lys Asp Phe Asn Tyr Glu Tyr
                85                  90                  95

Val Gln Arg Glu Ala Leu Arg Val Pro Leu Ile Phe Arg Glu Lys Asp
            100                 105                 110

Gly Leu Gly Ile Lys Met Pro Asp Pro Asp Phe Thr Val Arg Asp Val
        115                 120                 125

Lys Leu Leu Val Gly Ser Arg Arg Leu Val Asp Val Met Asp Val Asn
    130                 135                 140

Thr Gln Lys Gly Thr Glu Met Ser Met Ser Gln Phe Val Arg Tyr Tyr
145                 150                 155                 160

Glu Thr Pro Glu Ala Gln Arg Asp Lys Leu Tyr Asn Val Ile Ser Leu
                165                 170                 175

Glu Phe Ser His Thr Lys Leu Glu His Leu Val Lys Arg Pro Thr Val
            180                 185                 190

Val Asp Leu Val Asp Trp Val Asp Asn Met Trp Pro Gln His Leu Lys
        195                 200                 205

Glu Lys Gln Thr Glu Ala Thr Asn Ala Ile Ala Glu Met Lys Tyr Pro
    210                 215                 220

Lys Val Lys Lys Tyr Cys Leu Met Ser Val Lys Gly Cys Phe Thr Asp
225                 230                 235                 240

Phe His Ile Asp Phe Gly Gly Thr Ser Val Trp Tyr His Val Phe Arg
                245                 250                 255

Gly Gly Lys Ile Phe Trp Leu Ile Pro Pro Thr Leu His Asn Leu Ala
            260                 265                 270

Leu Tyr Glu Glu Trp Val Leu Ser Gly Lys Gln Ser Asp Ile Phe Leu
        275                 280                 285

Gly Asp Arg Val Glu Arg Cys Gln Arg Ile Glu Leu Lys Gln Gly Tyr
    290                 295                 300

Thr Phe Phe Ile Pro Ser Gly Trp Ile His Ala Val Tyr Thr Pro Val
305                 310                 315                 320

Asp Ser Leu Val Phe Gly Gly Asn Ile Leu His Ser Phe Asn Val Pro
                325                 330                 335

Met Gln Leu Arg Ile Tyr Glu Ile Glu Asp Arg Thr Arg Val Gln Pro
            340                 345                 350

Lys Phe Arg Tyr Pro Phe Tyr Tyr Glu Met Cys Trp Tyr Val Leu Glu
        355                 360                 365

```
Arg Tyr Val Tyr Cys Val Thr Gln Arg Ser His Leu Thr Gln Glu Tyr
    370                 375                 380

Gln Arg Glu Ser Met Leu Ile Asp Ala Pro Arg Lys Pro Ser Ile Asp
385                 390                 395                 400

Gly Phe Ser Ser Asp Ser Trp Leu Glu Met Glu Glu Ala Cys Asp
                405                 410                 415

Gln Gln Pro Gln Glu Glu Glu Lys Asp Glu Glu Gly Gly Arg
            420                 425                 430

Asp Arg Ala Pro Lys Pro Pro Thr Asp Gly Ser Thr Ser Pro Thr Ser
        435                 440                 445

Thr Pro Ser Glu Asp Gln Glu Ala Leu Gly Lys Lys Pro Lys Ala Pro
    450                 455                 460

Ala Leu Arg Phe Leu Lys Arg Thr Leu Ser Asn Glu Ser Glu Glu Ser
465                 470                 475                 480

Val Lys Ser Thr Thr Leu Ala Val Asp Tyr Pro Lys Thr Pro Thr Gly
                485                 490                 495

Ser Pro Ala Thr Glu Val Ser Ala Lys Trp Thr His Leu Thr Glu Phe
            500                 505                 510

Glu Leu Lys Gly Leu Lys Ala Leu Val Glu Lys Leu Glu Ser Leu Pro
    515                 520                 525

Glu Asn Lys Lys Cys Val Pro Glu Gly Ile Glu Asp Pro Gln Ala Leu
530                 535                 540

Leu Glu Gly Val Lys Asn Val Leu Lys Glu His Ala Asp Asp Asp Pro
545                 550                 555                 560

Ser Leu Ala Ile Thr Gly Val Pro Val Val Thr Trp Pro Lys Lys Thr
                565                 570                 575

Pro Lys Asn Arg Ala Val Gly Arg Pro Lys Gly Lys Leu Gly Pro Ala
            580                 585                 590

Ser Ala Val Lys Leu Ala Ala Asn Arg Thr Thr Ala Gly Ala Arg Arg
        595                 600                 605

Arg Arg Thr Arg Cys Arg Lys Cys Glu Ala Cys Leu Arg Thr Glu Cys
    610                 615                 620

Gly Glu Cys His Phe Cys Lys Asp Met Lys Lys Phe Gly Gly Pro Gly
625                 630                 635                 640

Arg Met Lys Gln Ser Cys Ile Met Arg Gln Cys Ile Ala Pro Val Leu
                645                 650                 655

Pro His Thr Ala Val Cys Leu Val Cys Gly Glu Ala Gly Lys Glu Asp
            660                 665                 670

Thr Val Glu Glu Glu Gly Lys Phe Asn Leu Met Leu Met Glu Cys
    675                 680                 685

Ser Ile Cys Asn Glu Ile Ile His Pro Gly Cys Leu Lys Ile Lys Glu
    690                 695                 700

Ser Glu Gly Val Val Asn Asp Glu Leu Pro Asn Cys Trp Glu Cys Pro
705                 710                 715                 720

Lys Cys Asn His Ala Gly Lys Thr Gly Lys Gln Lys Arg Gly Pro Gly
                725                 730                 735

Phe Lys Tyr Ala Ser Asn Leu Pro Gly Ser Leu Leu Lys Glu Gln Lys
            740                 745                 750

Met Asn Arg Asp Asn Lys Glu Gly Gln Glu Pro Ala Lys Arg Arg Ser
        755                 760                 765

Glu Cys Glu Glu Ala Pro Arg Arg Ser Asp Glu His Ser Lys Lys
    770                 775                 780

Val Pro Pro Asp Gly Leu Leu Arg Arg Lys Ser Asp Asp Val His Leu
```

```
                785                 790                 795                 800
Arg Lys Lys Arg Lys Tyr Glu Lys Pro Gln Glu Leu Ser Gly Arg Lys
            805                 810                 815

Arg Ala Ser Ser Leu Gln Thr Ser Pro Gly Ser Ser Ser His Leu Ser
            820                 825                 830

Pro Arg Pro Pro Leu Gly Ser Ser Leu Ser Pro Trp Trp Arg Ser Ser
            835                 840                 845

Leu Thr Tyr Phe Gln Gln Gln Leu Lys Pro Gly Lys Glu Asp Lys Leu
            850                 855                 860

Phe Arg Lys Lys Arg Arg Ser Trp Lys Asn Ala Glu Asp Arg Met Ala
865                 870                 875                 880

Leu Ala Asn Lys Pro Leu Arg Arg Phe Lys Gln Glu Pro Glu Asp Glu
            885                 890                 895

Leu Pro Glu Ala Pro Pro Lys Thr Arg Glu Ser Asp His Ser Arg Ser
            900                 905                 910

Ser Ser Pro Thr Ala Gly Pro Ser Thr Glu Gly Ala Glu Gly Pro Glu
            915                 920                 925

Glu Lys Lys Lys Val Lys Met Arg Arg Lys Arg Arg Leu Pro Asn Lys
            930                 935                 940

Glu Leu Ser Arg Glu Leu Ser Lys Glu Leu Asn His Glu Ile Gln Arg
945                 950                 955                 960

Thr Glu Asn Ser Leu Ala Asn Glu Asn Gln Gln Pro Ile Lys Ser Glu
            965                 970                 975

Pro Glu Ser Glu Gly Glu Glu Pro Lys Arg Pro Gly Ile Cys Glu
            980                 985                 990

Arg Pro His Arg Phe Ser Lys Gly Leu Asn Gly Thr Pro Arg Glu Leu
            995                1000                1005

Arg His Gln Leu Gly Pro Ser Leu Arg Ser Pro Pro Arg Val Ile Ser
           1010                1015                1020

Arg Pro Pro Pro Ser Val Ser Pro Pro Lys Cys Ile Gln Met Glu Arg
1025                1030                1035                1040

His Val Ile Arg Pro Pro Pro Ile Ser Pro Pro Pro Asp Ser Leu Pro
           1045                1050                1055

Leu Asp Asp Gly Ala Ala His Val Met His Arg Glu Val Trp Met Ala
           1060                1065                1070

Val Phe Ser Tyr Leu Ser His Gln Asp Leu Cys Val Cys Met Arg Val
           1075                1080                1085

Cys Arg Thr Trp Asn Arg Trp Cys Cys Asp Lys Arg Leu Trp Thr Arg
           1090                1095                1100

Ile Asp Leu Asn His Cys Lys Ser Ile Thr Pro Leu Met Leu Ser Gly
1105                1110                1115                1120

Ile Ile Arg Arg Gln Pro Val Ser Leu Asp Leu Ser Trp Thr Asn Ile
           1125                1130                1135

Ser Lys Lys Gln Leu Ser Trp Leu Ile Asn Arg Leu Pro Gly Leu Arg
           1140                1145                1150

Asp Leu Val Leu Ser Gly Cys Ser Trp Ile Ala Val Ser Ala Leu Cys
           1155                1160                1165

Ser Ser Ser Cys Pro Leu Leu Arg Thr Leu Asp Val Gln Trp Val Glu
           1170                1175                1180

Gly Leu Lys Asp Ala Gln Met Arg Asp Leu Leu Ser Pro Pro Thr Asp
1185                1190                1195                1200

Asn Arg Pro Gly Gln Met Asp Asn Arg Ser Lys Leu Arg Asn Ile Val
           1205                1210                1215
```

```
Glu Leu Arg Leu Ala Gly Leu Asp Ile Thr Asp Ala Ser Leu Arg Leu
        1220                1225                1230

Ile Ile Arg His Met Pro Leu Ser Lys Leu His Leu Ser Tyr Cys
    1235                1240                1245

Asn His Val Thr Asp Gln Ser Ile Asn Leu Leu Thr Ala Val Gly Thr
        1250                1255                1260

Thr Thr Arg Asp Ser Leu Thr Glu Ile Asn Leu Ser Asp Cys Asn Lys
1265                1270                1275                1280

Val Thr Asp Gln Cys Leu Ser Phe Phe Lys Arg Cys Gly Asn Ile Cys
            1285                1290                1295

His Ile Asp Leu Arg Tyr Cys Lys Gln Val Thr Lys Glu Gly Cys Glu
        1300                1305                1310

Gln Phe Ile Ala Glu Met Ser Val Ser Val Gln Phe Gly Gln Val Glu
        1315                1320                1325

Glu Lys Leu Leu Gln Lys Leu Ser
        1330                1335

<210> SEQ ID NO 93
<211> LENGTH: 3489
<212> TYPE: DNA
<213> ORGANISM: Homo sapiens
<220> FEATURE:
<223> OTHER INFORMATION: Human Fbxl 11 protein (NP_036440.1)

<400> SEQUENCE: 93
atggaacccg aagaagaaag gattcgttac agccagagat tgcgtggtac catgcgacga      60
cgctatgaag atgatggcat ttcagatgat gaaattgaag gaaaagaac ttttgacttg     120 gaagagaaac tgcacaccaa caaatataat gccaattttg ttacttttat ggaaggaaaa     180
gattttaatg tagagtatat tcagcggggt ggcttgagag atcctctgat ttcaagaat     240 tctgatggac tcggaataaa aatgccggat ccagacttca ctgtgaatga tgtcaaaatg     300
tgtgtgggga gtcgtcgcat ggtggatgtc atggacgtga acacacagaa aggcattgaa     360
atgaccatgg ctcagtggac acgctactat gagaccccag aggaggagcg agagaaactc     420
tataatgtca tcagcctcga gtttagccac accaggctgg agaatatggt gcagaggccc     480
tccacggtgg atttcattga ctgggtagac aacatgtggc caaggcactt gaaggaaagc     540
cagactgaat caacaaatgc catcttggag atgcagtacc ctaaagtgca gagtactgt      600 ctaatgagtg ttcgaggctg ctatactgac ttccatgtgg actttggtgg tacctctgtt     660
tggtatcaca tccatcaagg gggaaaggtc ttctggctca tccccctac agcccacaac     720 ctggagctgt acgagaattg gctgctgtca gggaaacagg gagacatctt tctgggtgac     780
cgggtatcag attgtcagcg cattgagctc aagcagggct ataccttcgt cattccctca     840
ggctggattc atgctgtgta tactcctaca gacacattag tgttggggg caatttttg      900 catagcttca acatccctat gcagttaaaa atatacaaca ttgaagatcg gacacgggtt     960
ccaaataagt ttcgctatcc attctactat gagatgtgtt ggtatgtgtt ggagcgctat    1020
gtgtactgca taaccaaccg ttcccaccta actaaggaat tcagaaaga gtccctcagc    1080 atggatttgg agttaaatgg gttggagtct gggaatgggg atgaggaagc agtggatcga    1140
gaaccccgac gcttgagcag caggcgttct gtcctcacta gccctgtagc gaatggagtc    1200
aacctggatt atgatggact gggcaaaacc tgccgaagtc ttccaagtct gaagaaaact    1260
ttggctgggg actcatcttc tgactgtagc cggggctccc acaatggaca agtgtgggat    1320
ccccagtgtg ctccccgaaa ggacaggcaa gtgcatctga cccattttga gcttgaaggc    1380
```

-continued

| | |
|---|---|
| cttcgctgcc ttgtagataa gttggagtct ctgccactgc acaagaaatg tgtccccaca | 1440 |
| gggatagaag atgaagatgc tctcattgct gatgtaaaga ttttgctgga ggagcttgcc | 1500 |
| aacagcgatc ccaagttagc cctcactgga gttcctatag tacagtggcc aaaaagggat | 1560 |
| aagcttaaat tccccactcg gccaaaggtg cgggttccta ccatcccat tacgaagcct | 1620 |
| cacactatga aaccagctcc acggttaaca cctgtgaggc cagctgctgc ctccccgatt | 1680 |
| gtgtcaggag ccagacggag acgagtgcga tgtcgaaaat gcaaagcctg tgtgcaagga | 1740 |
| gagtgtggtg tttgccacta ctgcagagac atgaagaagt ttgggggggcc tggacgcatg | 1800 |
| aagcagtcct gtgtcctccg acagtgcttg gcacccagac tgcctcactc agtcacatgt | 1860 |
| tccctctgtg gagaggtgga tcagaatgaa gagacacaag actttgagaa gaaactcatg | 1920 |
| gaatgctgta tctgcaatga gattgttcat cctggctgcc tccagatgga cggagagggg | 1980 |
| ttgcttaacg aagaattgcc aaattgctgg gaatgtccaa agtgctacca ggaggacagc | 2040 |
| tcggagaaag cccagaagcg gaaaatggaa gagagtgacg aagaagctgt gcaagccaaa | 2100 |
| gtcctgcggc ccctgcggag ctgcgatgag cctctcacgc ccccgcctca ttcacccact | 2160 |
| tccatgctgc agctcatcca tgacccggtt tccccccggg gtatggtgac tcggtcatcc | 2220 |
| cctggggctg gccccagcga ccaccacagt gccagccgcg atgagcgctt caaacggcgg | 2280 |
| cagttgctgc ggctgcaggc cacagagcgc accatggtac gggaaaagga gaacaatccc | 2340 |
| agcggcaaaa aggagctgtc tgaagttgag aaagccaaga tccggggatc gtacctcact | 2400 |
| gtcacgctac agaggcccac caaagagctc cacgggacat ccattgtgcc caagctgcag | 2460 |
| gccatcacgg cctcctctgc caaccttcgc cattccccc gtgtgctagt gcagcactgc | 2520 |
| ccagcccgaa ccccccagcg tggggatgag gaggggctgg ggggagagga ggaggaagag | 2580 |
| gaggaggagg aggaggaaga tgacagtgca gaggaggggg gtgcagccag gctgaatggc | 2640 |
| cggggcagtt gggctcagga tggagacgaa agctggatgc agcgggaggt ctggatgtct | 2700 |
| gtcttccgct acctcagccg cagagaactt tgtgaatgta tgcgagtgtg caagacgtgg | 2760 |
| tataaatggt gctgcgacaa gagactttgg acaaaaattg acttgagtag gtgtaaggcc | 2820 |
| attgtgcccc aggccctcag tggcatcatc aagaggcagc cagtcagcct tgacctcagt | 2880 |
| tggaccaaca tctctaaaaa gcaactgaca tggctcgtca ataggctgcc aggactgaaa | 2940 |
| gacctcctcc tagcaggctg ctcctggtct gcagtctctg ccctcagcac ctccagctgc | 3000 |
| ccccttctca ggacccttga tcttcggtgg gcagtaggaa tcaaggaccc tcaaattcgg | 3060 |
| gacttgctta ctccaccggc tgataaacca ggtcaggaca tcgcagcaa gctccggaac | 3120 |
| atgaccgact tccggctggc aggccttgac atcacagatg ccacgcttcg cctcataatt | 3180 |
| cgccacatgc ccctcctgtc tcgactcgac ctcagtcact gcagccacct tacagatcag | 3240 |
| tcctccaatc tactcactgc tgtcgggtct tccactcgct actctctcac agagctcaat | 3300 |
| atggcaggtt gcaataaatt gacagaccag accctgatct acctacggcg cattgccaac | 3360 |
| gtcaccttga tcgaccttcg aggatgcaag cagatcactc gaaaagcctg cgagcacttc | 3420 |
| atctcagact tgtccatcaa cagcctctac tgcctgtctg acgagaagct gatacagaag | 3480 |
| atcagctaa | 3489 |

<210> SEQ ID NO 94
<211> LENGTH: 1162
<212> TYPE: PRT
<213> ORGANISM: Homo sapiens
<220> FEATURE:
<223> OTHER INFORMATION: Human Fbxl 11 protein (NP_036440.1)

<400> SEQUENCE: 94

```
Met Glu Pro Glu Glu Arg Ile Arg Tyr Ser Gln Arg Leu Arg Gly
 1               5                  10                  15

Thr Met Arg Arg Arg Tyr Glu Asp Asp Gly Ile Ser Asp Asp Glu Ile
             20                  25                  30

Glu Gly Lys Arg Thr Phe Asp Leu Glu Glu Lys Leu His Thr Asn Lys
         35                  40                  45

Tyr Asn Ala Asn Phe Val Thr Phe Met Glu Gly Lys Asp Phe Asn Val
 50                  55                  60

Glu Tyr Ile Gln Arg Gly Gly Leu Arg Asp Pro Leu Ile Phe Lys Asn
 65                  70                  75                  80

Ser Asp Gly Leu Gly Ile Lys Met Pro Asp Pro Asp Phe Thr Val Asn
                 85                  90                  95

Asp Val Lys Met Cys Val Gly Ser Arg Arg Met Val Asp Val Met Asp
            100                 105                 110

Val Asn Thr Gln Lys Gly Ile Glu Met Thr Met Ala Gln Trp Thr Arg
        115                 120                 125

Tyr Tyr Glu Thr Pro Glu Glu Arg Glu Lys Leu Tyr Asn Val Ile
130                 135                 140

Ser Leu Glu Phe Ser His Thr Arg Leu Glu Asn Met Val Gln Arg Pro
145                 150                 155                 160

Ser Thr Val Asp Phe Ile Asp Trp Val Asp Asn Met Trp Pro Arg His
                165                 170                 175

Leu Lys Glu Ser Gln Thr Glu Ser Thr Asn Ala Ile Leu Glu Met Gln
            180                 185                 190

Tyr Pro Lys Val Gln Lys Tyr Cys Leu Met Ser Val Arg Gly Cys Tyr
        195                 200                 205

Thr Asp Phe His Val Asp Phe Gly Gly Thr Ser Val Trp Tyr His Ile
    210                 215                 220

His Gln Gly Gly Lys Val Phe Trp Leu Ile Pro Pro Thr Ala His Asn
225                 230                 235                 240

Leu Glu Leu Tyr Glu Asn Trp Leu Leu Ser Gly Lys Gln Gly Asp Ile
                245                 250                 255

Phe Leu Gly Asp Arg Val Ser Asp Cys Gln Arg Ile Glu Leu Lys Gln
            260                 265                 270

Gly Tyr Thr Phe Val Ile Pro Ser Gly Trp Ile His Ala Val Tyr Thr
        275                 280                 285

Pro Thr Asp Thr Leu Val Phe Gly Gly Asn Phe Leu His Ser Phe Asn
    290                 295                 300

Ile Pro Met Gln Leu Lys Ile Tyr Asn Ile Glu Asp Arg Thr Arg Val
305                 310                 315                 320

Pro Asn Lys Phe Arg Tyr Pro Phe Tyr Tyr Glu Met Cys Trp Tyr Val
                325                 330                 335

Leu Glu Arg Tyr Val Tyr Cys Ile Thr Asn Arg Ser His Leu Thr Lys
            340                 345                 350

Glu Phe Gln Lys Glu Ser Leu Ser Met Asp Leu Glu Leu Asn Gly Leu
        355                 360                 365

Glu Ser Gly Asn Gly Asp Glu Glu Ala Val Asp Arg Glu Pro Arg Arg
    370                 375                 380

Leu Ser Ser Arg Arg Ser Val Leu Thr Ser Pro Val Ala Asn Gly Val
385                 390                 395                 400

Asn Leu Asp Tyr Asp Gly Leu Gly Lys Thr Cys Arg Ser Leu Pro Ser
                405                 410                 415
```

-continued

Leu Lys Lys Thr Leu Ala Gly Asp Ser Ser Asp Cys Ser Arg Gly
            420                 425                 430

Ser His Asn Gly Gln Val Trp Asp Pro Gln Cys Ala Pro Arg Lys Asp
            435                 440                 445

Arg Gln Val His Leu Thr His Phe Glu Leu Glu Gly Leu Arg Cys Leu
            450                 455                 460

Val Asp Lys Leu Glu Ser Leu Pro Leu His Lys Lys Cys Val Pro Thr
465                 470                 475                 480

Gly Ile Glu Asp Glu Asp Ala Leu Ile Ala Asp Val Lys Ile Leu Leu
                    485                 490                 495

Glu Glu Leu Ala Asn Ser Asp Pro Lys Leu Ala Leu Thr Gly Val Pro
                500                 505                 510

Ile Val Gln Trp Pro Lys Arg Asp Lys Leu Lys Phe Pro Thr Arg Pro
            515                 520                 525

Lys Val Arg Val Pro Thr Ile Pro Ile Thr Lys Pro His Thr Met Lys
530                 535                 540

Pro Ala Pro Arg Leu Thr Pro Val Arg Pro Ala Ala Ser Pro Ile
545                 550                 555                 560

Val Ser Gly Ala Arg Arg Arg Val Arg Cys Arg Lys Cys Lys Ala
                    565                 570                 575

Cys Val Gln Gly Glu Cys Gly Val Cys His Tyr Cys Arg Asp Met Lys
                580                 585                 590

Lys Phe Gly Gly Pro Gly Arg Met Lys Gln Ser Cys Val Leu Arg Gln
            595                 600                 605

Cys Leu Ala Pro Arg Leu Pro His Ser Val Thr Cys Ser Leu Cys Gly
610                 615                 620

Glu Val Asp Gln Asn Glu Glu Thr Gln Asp Phe Glu Lys Lys Leu Met
625                 630                 635                 640

Glu Cys Cys Ile Cys Asn Glu Ile Val His Pro Gly Cys Leu Gln Met
                    645                 650                 655

Asp Gly Glu Gly Leu Leu Asn Glu Glu Leu Pro Asn Cys Trp Glu Cys
                660                 665                 670

Pro Lys Cys Tyr Gln Glu Asp Ser Ser Glu Lys Ala Gln Lys Arg Lys
            675                 680                 685

Met Glu Glu Ser Asp Glu Glu Ala Val Gln Ala Lys Val Leu Arg Pro
690                 695                 700

Leu Arg Ser Cys Asp Glu Pro Leu Thr Pro Pro His Ser Pro Thr
705                 710                 715                 720

Ser Met Leu Gln Leu Ile His Asp Pro Val Ser Pro Arg Gly Met Val
                    725                 730                 735

Thr Arg Ser Ser Pro Gly Ala Gly Pro Ser Asp His His Ser Ala Ser
                740                 745                 750

Arg Asp Glu Arg Phe Lys Arg Arg Gln Leu Leu Arg Leu Gln Ala Thr
            755                 760                 765

Glu Arg Thr Met Val Arg Glu Lys Glu Asn Asn Pro Ser Gly Lys Lys
770                 775                 780

Glu Leu Ser Glu Val Glu Lys Ala Lys Ile Arg Gly Ser Tyr Leu Thr
785                 790                 795                 800

Val Thr Leu Gln Arg Pro Thr Lys Glu Leu His Gly Thr Ser Ile Val
                    805                 810                 815

Pro Lys Leu Gln Ala Ile Thr Ala Ser Ser Ala Asn Leu Arg His Ser
                820                 825                 830

Pro Arg Val Leu Val Gln His Cys Pro Ala Arg Thr Pro Gln Arg Gly
            835                 840                 845

```
Asp Glu Glu Gly Leu Gly Gly Glu Glu Glu Glu Glu Glu Glu
    850                 855                 860

Glu Glu Asp Asp Ser Ala Glu Gly Gly Ala Ala Arg Leu Asn Gly
865                 870                 875                 880

Arg Gly Ser Trp Ala Gln Asp Gly Asp Glu Ser Trp Met Gln Arg Glu
                885                 890                 895

Val Trp Met Ser Val Phe Arg Tyr Leu Ser Arg Arg Glu Leu Cys Glu
            900                 905                 910

Cys Met Arg Val Cys Lys Thr Trp Tyr Lys Trp Cys Cys Asp Lys Arg
            915                 920                 925

Leu Trp Thr Lys Ile Asp Leu Ser Arg Cys Lys Ala Ile Val Pro Gln
        930                 935                 940

Ala Leu Ser Gly Ile Ile Lys Arg Gln Pro Val Ser Leu Asp Leu Ser
945                 950                 955                 960

Trp Thr Asn Ile Ser Lys Lys Gln Leu Thr Trp Leu Val Asn Arg Leu
                965                 970                 975

Pro Gly Leu Lys Asp Leu Leu Leu Ala Gly Cys Ser Trp Ser Ala Val
            980                 985                 990

Ser Ala Leu Ser Thr Ser Ser Cys Pro Leu Leu Arg Thr Leu Asp Leu
            995                 1000                1005

Arg Trp Ala Val Gly Ile Lys Asp Pro Gln Ile Arg Asp Leu Leu Thr
        1010                1015                1020

Pro Pro Ala Asp Lys Pro Gly Gln Asp Asn Arg Ser Lys Leu Arg Asn
1025                1030                1035                1040

Met Thr Asp Phe Arg Leu Ala Gly Leu Asp Ile Thr Asp Ala Thr Leu
                1045                1050                1055

Arg Leu Ile Ile Arg His Met Pro Leu Leu Ser Arg Leu Asp Leu Ser
            1060                1065                1070

His Cys Ser His Leu Thr Asp Gln Ser Ser Asn Leu Leu Thr Ala Val
        1075                1080                1085

Gly Ser Ser Thr Arg Tyr Ser Leu Thr Glu Leu Asn Met Ala Gly Cys
        1090                1095                1100

Asn Lys Leu Thr Asp Gln Thr Leu Ile Tyr Leu Arg Arg Ile Ala Asn
1105                1110                1115                1120

Val Thr Leu Ile Asp Leu Arg Gly Cys Lys Gln Ile Thr Arg Lys Ala
                1125                1130                1135

Cys Glu His Phe Ile Ser Asp Leu Ser Ile Asn Ser Leu Tyr Cys Leu
            1140                1145                1150

Ser Asp Glu Lys Leu Ile Gln Lys Ile Ser
        1155                1160
```

<210> SEQ ID NO 95
<211> LENGTH: 981
<212> TYPE: DNA
<213> ORGANISM: Homo sapiens
<220> FEATURE:
<223> OTHER INFORMATION: Human Fbxl 12 protein (NP_060173.1)

<400> SEQUENCE: 95

```
atggcgactt tggtcgaact gccggactcg gtcctgctcg agatcttctc ttacctcccg    60
gtacgggacc ggatccgcat ctccagggtc tgtcaccgct ggaagaggct ggtgacgac    120 cggtggctgt ggcgacatgt cgacctgacg ctctacacga tgcgacctaa agtcatgtgg    180
cacctccttc gaaggtacat ggcatcccgg ctccattccc tgcggatggg tggctacctg    240
ttctctggct cccaggcccc ccagttgtcc cctgctctgt tgagagccct gggccagaag    300
```

```
tgccccaacc tgaagcgcct ctgcctgcac gtggccgacc tgagcatggt gcccatcacc    360
agcctgccca gcaccttgag gaccctggag ctgcacagct gcgagatctc catggcctgg    420
ctccacaagc agcaggaccc caccgtgctg cccctgcttg aatgcatcgt gctggaccgc    480
gtccccgcct tccgtgacga gcacctgcag ggcctgacgc gcttccgggc cttgcgctcg    540
ctggtgctgg gtggtaccta ccgtgtgacc gagacagggc tggatgctgg cctgcaggag    600
ctcagctatc tgcagaggct tgaggtgctg ggctgcaccc tgtctgccga cagcaccctg    660
ctggccatca ccgccacct ccgagatgtg cgcaagatcc ggctgaccgt gaggggcctc    720
tctgcccctg gcctggctgt gctggaggga atgccggccc tggagagtct gtgcctgcag    780
ggtcccctcg tcaccccaga aatgccctcc ccactgaaaa tcctctcctc ctgcctcact    840
atgcccaagc tcagagtcct tgagctgcag gggctggggt ggggagggtca ggaggcggag    900 aagatcctgt gtaaggggct gccccactgt atggtcatcg tcagggcttg ccccaaagag    960
tctatggact ggtggatgta a                                              981
```

<210> SEQ ID NO 96
<211> LENGTH: 326
<212> TYPE: PRT
<213> ORGANISM: Homo sapiens
<220> FEATURE:
<223> OTHER INFORMATION: Human Fbxl 12 protein (NP_060173.1)

<400> SEQUENCE: 96

```
Met Ala Thr Leu Val Glu Leu Pro Asp Ser Val Leu Leu Glu Ile Phe
 1               5                  10                  15

Ser Tyr Leu Pro Val Arg Asp Arg Ile Arg Ile Ser Arg Val Cys His
                20                  25                  30

Arg Trp Lys Arg Leu Val Asp Asp Arg Trp Leu Trp Arg His Val Asp
            35                  40                  45

Leu Thr Leu Tyr Thr Met Arg Pro Lys Val Met Trp His Leu Leu Arg
        50                  55                  60

Arg Tyr Met Ala Ser Arg Leu His Ser Leu Arg Met Gly Gly Tyr Leu
     65                  70                  75                  80

Phe Ser Gly Ser Gln Ala Pro Gln Leu Ser Pro Ala Leu Leu Arg Ala
                    85                  90                  95

Leu Gly Gln Lys Cys Pro Asn Leu Lys Arg Leu Cys Leu His Val Ala
                100                 105                 110

Asp Leu Ser Met Val Pro Ile Thr Ser Leu Pro Ser Thr Leu Arg Thr
            115                 120                 125

Leu Glu Leu His Ser Cys Glu Ile Ser Met Ala Trp Leu His Lys Gln
        130                 135                 140

Gln Asp Pro Thr Val Leu Pro Leu Leu Glu Cys Ile Val Leu Asp Arg
145                 150                 155                 160

Val Pro Ala Phe Arg Asp Glu His Leu Gln Gly Leu Thr Arg Phe Arg
                165                 170                 175

Ala Leu Arg Ser Leu Val Leu Gly Gly Thr Tyr Arg Val Thr Glu Thr
            180                 185                 190

Gly Leu Asp Ala Gly Leu Gln Glu Leu Ser Tyr Leu Gln Arg Leu Glu
        195                 200                 205

Val Leu Gly Cys Thr Leu Ser Ala Asp Ser Thr Leu Leu Ala Ile Ser
    210                 215                 220

Arg His Leu Arg Asp Val Arg Lys Ile Arg Leu Thr Val Arg Gly Leu
225                 230                 235                 240
```

```
Ser Ala Pro Gly Leu Ala Val Leu Glu Gly Met Pro Ala Leu Glu Ser
            245                 250                 255

Leu Cys Leu Gln Gly Pro Leu Val Thr Pro Glu Met Pro Ser Pro Thr
            260                 265                 270

Glu Ile Leu Ser Ser Cys Leu Thr Met Pro Lys Leu Arg Val Leu Glu
            275                 280                 285

Leu Gln Gly Leu Gly Trp Glu Gly Gln Glu Ala Glu Lys Ile Leu Cys
            290                 295                 300

Lys Gly Leu Pro His Cys Met Val Ile Val Arg Ala Cys Pro Lys Glu
305                 310                 315                 320

Ser Met Asp Trp Trp Met
            325
```

<210> SEQ ID NO 97
<211> LENGTH: 19
<212> TYPE: PRT
<213> ORGANISM: Artificial Sequence
<220> FEATURE:
<223> OTHER INFORMATION: phospho-peptide (corresponding to the carboxy
      terminus of the human p27 with a phosphothreonine
      at position T)
<220> FEATURE:
<221> NAME/KEY: VARIANT
<222> LOCATION: 8
<223> OTHER INFORMATION: Xaa = phosphothreonine

<400> SEQUENCE: 97

```
Asn Ala Gly Ser Val Glu Gln Xaa Pro Lys Lys Pro Gly Leu Arg Arg
1               5                   10                  15

Arg Gln Thr
```

<210> SEQ ID NO 98
<211> LENGTH: 19
<212> TYPE: PRT
<213> ORGANISM: Artificial Sequence
<220> FEATURE:
<223> OTHER INFORMATION: control phospho-peptide (corresponding to an
      amino terminal peptide of the human Ddk4 with a
      phosphotyrosine at position Y)
<220> FEATURE:
<221> NAME/KEY: VARIANT
<222> LOCATION: 8
<223> OTHER INFORMATION: Xaa = phosphotyrosine

<400> SEQUENCE: 98

```
Ala Glu Ile Gly Val Gly Ala Xaa Gly Thr Val Tyr Lys Ala Arg Asp
1               5                   10                  15

Pro His Ser
```

<210> SEQ ID NO 99
<211> LENGTH: 16
<212> TYPE: PRT
<213> ORGANISM: Artificial Sequence
<220> FEATURE:
<223> OTHER INFORMATION: a tryptic peptide corresponding to amino acid
      residues 5-20 of human Cks1

<400> SEQUENCE: 99

```
Gln Ile Tyr Tyr Ser Asp Lys Tyr Asp Asp Glu Glu Phe Glu Tyr Arg
1               5                   10                  15
```

US 8,119,421 B2

METHODS TO IDENTIFY COMPOUNDS USEFUL FOR THE TREATMENT OF PROLIFERATIVE AND DIFFERENTIATIVE DISORDERS

1. CROSS-REFERENCE TO RELATED APPLICATIONS

This application is a continuation of U.S. patent application Ser. No. 11/106,014, filed Apr. 13, 2005, now abandoned, which is a continuation-in-part of U.S. patent application Ser. No. 10/042,417, filed Jan. 7, 2002, now abandoned, and also U.S. patent application Ser. No. 10/632,150, filed Jul. 30, 2003, now abandoned, which is a divisional of U.S. patent application Ser. No. 09/385,219, filed Aug. 27, 1999, now U.S. Pat. No. 6,720,181, which claims priority under 35 U.S.C. §119 to U.S. Provisional Patent Application No. 60/098,355, filed Aug. 28, 1998, U.S. Provisional Patent Application No. 60/118,568, filed Feb. 3, 1999, and U.S. Provisional Patent Application No. 60/124,449, filed Mar. 15, 1999, each of which is incorporated herein by reference in its entirety.

2. INTRODUCTION

The present invention relates to the discovery, identification and characterization of nucleotide sequences that encode novel substrate-targeting subunits of ubiquitin ligases. The invention encompasses nucleic acid molecules comprising nucleotide sequences encoding novel substrate-targeting subunits of ubiquitin ligases: FBP1, FBP2, FBP3a, FBP3b, FBP4, FBP5, FBP6, FBP7, FBP8, FBP11, FBP12, FBP13, FBP14, FBP15, FBP17, FBP18, FBP20, FBP21, FBP22, FBP23, and FBP25, transgenic mice, knock-out mice, host cell expression systems and proteins encoded by the nucleotides of the present invention. The present invention relates to screening assays to identify potential therapeutic agents such as small molecules, compounds or derivatives and analogues of the novel ubiquitin ligases which modulate activity of the novel ubiquitin ligases for inducing or inhibiting apoptosis and for the treatment of proliferative and differentiative disorders, such as cancer, major opportunistic infections, immune disorders, certain cardiovascular diseases, and inflammatory disorders. The invention further encompasses therapeutic protocols and pharmaceutical compositions designed to target ubiquitin ligases and their substrates for the modulation of apoptosis and for the treatment of proliferative disorders.

3. BACKGROUND OF THE INVENTION 3.1 Cell Cycle Regulatory Proteins

The eukaryotic cell cycle is regulated by a family of serine/threonine protein kinases called cyclin dependent kinases (Cdks) because their activity requires the association with regulatory subunits named Cyclins (Hunter and Pines, 1994, *Cell* 79:573). Cdks also associate with Cdk inhibitors (Ckis) which mediate cell cycle arrest in response to various antiproliferative signals. So far, based on their sequence homology, two families of Ckis have been identified in mammalian cells: the Cip/Kip family, which includes p21, p27 and p57; and the Ink family, which includes p15, p16, p18, and p20 (Sherr and Roberts, 1999, *Genes Dev.* 13: 1501).

3.2 The Ubiquitin Pathway

Ubiquitin-mediated proteolysis is an important pathway of non-lysosomal protein degradation which controls the timed destruction of many cellular regulatory proteins including, p27, p53, p300, cyclins, E2F, STAT-1, c-Myc, c-Jun, EGF receptor, IκBα, NFκB and β-catenin (reviewed in Pagano, 1997, *FASEB J.* 11:1067). Ubiquitin is an evolutionary highly conserved 76-amino acid polypeptide which is abundantly present in all eukaryotic cells. The ubiquitin pathway leads to the covalent attachment of a poly-ubiquitin chain to target substrates which are then degraded by the multi-catalytic proteasome complex (see Pagano, supra, for a recent review). Many of the steps regulating protein ubiquitination are known. Initially the ubiquitin activating enzyme (E1), forms a high energy thioester with ubiquitin which is, in turn, transferred to a reactive cysteine residue of one of many ubiquitin conjugating enzymes (Ubcs or E2s). The final transfer of ubiquitin to an e-amino group of a reactive lysine residue in the target protein occurs in a reaction that may or may not require an ubiquitin ligase (E3) protein. The large number of ubiquitin ligases ensures a high level of substrate specificity.

3.3 The Ubiquitin Pathway and the Regulation of the G1 Phase by F Box Proteins

Genetic and biochemical studies in several organisms have shown that the G1 phase of the cell cycle is regulated by the ubiquitin pathway. Proteolysis of cyclins, Ckis and other G1 regulatory proteins is controlled in yeast by the ubiquitin conjugating enzyme Ubc3 (also called Cdc34) and by an E3 ubiquitin ligase formed by three subunits: Cdc53, Skp1 and one of many F box proteins (reviewed in Patton, et al., 1998, *Trends in Genet.* 14:6). The F box proteins (FBPs) are so called because they contain a motif, the F Box, that was first identified in Cyclin F, and that is necessary for FBP interaction with Skp1 (Bai, et al., 1996, *Cell* 86:263). Cdc53 (also called Cul A) and Skp1 appear to participate in the formation of at least three distinct E3s, each containing a different FBP. Because these ligases are similar protein modules composed of Skp1, Cul A, and an FBP, they have been named SCF. The three SCFs identified so far in *S. cerevisiae* are: SCF$^{Cdc4}$ (which recruits the Ckis Sic1 and Far1, the replication factor Cdc6, and the transcriptional activator Gen4, as substrates through the F-Box protein Cdc4), SCF$^{Grr1}$ (which recruits the G1 cyclins Cln1 and Cln2 as substrates through the F-Box protein GRR1), and SCF$^{Met30}$ (which recruits the G1 cyclin Cln3 as a substrate throughout the F box protein MET30; see Pagano and Patton, supra, for recent reviews).

The interaction of SCF ligase with its substrates occurs via the FBP. FBPs are present in all eukaryotes (at least 54 in mammals; Cenciarelli, et al., 1999, *Current Biol.* 9: 1177; Winston, et al., 1999, *Current Biol.* 9: 1180). In addition to the F Box, many FBPs contain additional domains that facilitate both protein:protein interactions, e.g. WD-40 domains or leucine-rich repeats (LRRs), and protein:DNA interactions, e.g. tankyrase binding domains or HNH domains. Since the substrate specificity of SCF ligases is dictated by different FBPs that act as substrate targeting subunits, the large numbers of FBPs with varying combinations of protein or DNA interaction domains ensure highly specific substrate recognition (Cenciarelli, et al., supra; Winston, et al., supra).

The intracellular level of the human Cki p27, a cell cycle-regulated cyclin-dependent kinase (Cdk) inhibitor, is regulated by ubiquitin-mediated degradation (Pagano, et al., 1995, *Science* 269:682). Similarly, degradation of other human G1 regulatory proteins (Cyclin E, Cyclin D1, p21, E2F, β-catenin) is controlled by the ubiquitin pathway (reviewed in Pagano, et al, supra). Yet, the specific enzymes involved in the degradation of G1 regulatory proteins have not been identified. A family of 6 genes (CUL1, 2, 3, 4a, 4b, and 5) homologous to *S. cerevisiae* cul A have been identified by searching the EST database (Kipreos, et al., 1996, *Cell* 85:829). Human S-phase kinase-associated protein 1 (Skp1), and the F box protein Skp2, associate in vivo with Cyclin A. (Zhang, et al., 1995, *Cell* 82:915). It has been demonstrated that phosphorylated p27 is specifically recognized by Skp2. Skp1 and Skp2 are also found to associate with Cul-1 and ROC1/Rbx1 to form a SCF ubiquitin ligase complex, $SCF^{Skp2}$. While studies establish that p27 is targeted for degradation by $SCF^{Skp2}$, key factors involved in the degradation were unknown. It had been hypothesized that Nedd8, a highly conserved ubiquitin-like protein that is ligated to different cullins, is a necessary component for ligation of p27 (Podust, et al., 2000, *Proc. Natl. Acad. Sci. USA* 97:4579).

The Suc1 (suppressor of Cdc2 mutation)/Cks (cyclin-dependent kinase subunit) family of cell cycle regulatory proteins binds to some cyclin-dependent kinases and phosphorylated proteins and is essential for cell cycle progression. Suc1 (Hayles, et al., 1986, *Mol. Gen. Genet.* 202:291) and Cks1 (Hadwiger, et al., 1989, *Mol. Cell. Biol.* 9:2034) were discovered in fission and budding yeast, respectively, as essential gene products that interact with cyclin-dependent kinases. Homologues from different species share extensive sequence conservation, and the two human homologues can functionally substitute for Cks1 in budding yeast (Richardson, et al. 1990, *Genes Dev.* 4:1332). Crystal structures of the two human homologues and the fission yeast Suc1 have shown that they share a four-stranded β-sheet involved in binding to a Cdk catalytic subunit (Bourne, et al., 1996, *Cell* 84:863; Pines, 1996, *Curr. Biol.* 11:1399). In addition, they share a highly conserved phosphate-binding site, positioned on a surface contiguous to the Cdk catalytic site in the Cks-Cdk complex (Bourne, et al., supra).

Cks proteins are involved in several cell cycle transitions, including the G1 to S-phase transition, entry into mitosis and exit from mitosis (Pines, 1996, supra), but the molecular basis for their different actions is not well understood. With the exception of Cln2/Cln3-Cdk1 complexes from budding yeast being activated by Cks1 (Reynard, et al., 2000, *Mol. Cell. Biol.* 20:5858), Cks proteins do not directly affect the catalytic activity of the cyclin-dependent kinase. However, Cks proteins can promote multi-site phosphorylations of some substrates by cyclin-dependent kinases. It has been proposed that by simultaneously binding to a partially phosphorylated protein and to a Cdk, Cks proteins increase the affinity of the kinase for the substrate and thus accelerate subsequent multiple phosphorylations (Pines, 1996, supra). Indeed, Cks proteins promote Cdk-catalyzed multiple phosphorylations of subunits of the cyclosome/APC (Patra and Dunphy, 1998, *Genes Dev.* 12:2549; Shteinberg and Hershko, 1999, *Biochem. Biophys. Res. Commun.* 257:12), as well as G2/M regulators such as Cdc25, Myt1 and Wee1 (Patra, et al., 1999, *J. Biol. Chem.* 274:36839).

3.4 FBP1, a Mammalian FBP Involved in Regulation of APC/C

Fbp1, the mammalian homolog of *Xenopus* β-TrCP1 (β-transducin repeat containing protein) (Spevak, et al., 1993, *Mol. Cell. Biol.* 8:4953), was identified using Skp1 as a bait in a two-hybrid screen (Cenciarelli, et al., supra). Fbp1 is an F box protein containing seven WD-40 domains (Margottin, et al., 1998, *Mol. Cell.* 1:565), and is involved in the degradation of IκBα family members in response to NFκB activating stimuli (Gonen, et al., 1999, *J. Biol. Chem.* 274:14823; Hatakeyama, et al., 1999, *Proc. Natl. Acad. Sci. USA* 96:3859; Hattori, et al., 1999, *J. Biol. Chem.* 274:29641; Kroll, et al., 1999, *J. Biol. Chem.* 274:7941; Ohta, et al., 1999, *Mol. Cell.* 3:535; Shirane, et al., 1999, *J. Biol. Chem.* 274: 28169; Spencer, et al., 1999, *Genes Dev.* 13:284; Winston, et al., 1999, *Genes Dev.* 13:270; Wu and Ghosh, 1999, *J. Biol. Chem.* 274:29591; Yaron, et al., 1998, *Nature* 396:590). In addition, consistent with the finding that *Xenopus* and *Drosophila* Fbp1 orthologs act as negative regulators of the Wnt/β-catenin signaling pathway (Jiang and Struhl, 1998, *Nature* 391:493; Marikawa and Elinson, 1998, *Mech. Dev.* 77:75), several studies report that human Fbp1 controls β-catenin stability in vitro and in mammalian cultured cells (Hart, et al., 1999, *Curr. Biol.* 9:207; Hatakeyama, et al., supra; Kitagawa, et al., 1999, *EMBO J.* 18:2401; Latres, et al., 1999, *Oncogene* 18:849; Winston, et al., 1999, *Genes Dev.* 13:270).

All well-characterized substrates of mammalian Fbp1 have a common destruction motif, DSGxxS, and are recognized by Fbp1 only upon phosphorylation of the two serine residues present in this motif. There is, however, some recent evidence for additional mammalian substrates of Fbp1 lacking a completely conserved binding domain, such as ATF4 (Lassot, et al., 2001, *Mol. Cell. Biol.* 21:2192), Smad3 (Fukuchi, et al., 2001, *Mol. Biol. Cell* 12:1431), NFκB p105 (Orian, et al., 2000, *EMBO J.* 19:2580) and NFκB p100 (Fong and Sun, 2002, *J. Biol. Chem.* 277:22111). A conserved DSGxxS motif is present not only in Fbp1 substrates but also in certain regulators of Fbp1, such as the HIV protein Vpu, which targets Fbp1 to the non-physiological substrate, CD4, in virally infected cells. (Margottin, et al., supra). The DSGxxS destruction motif may also be found in peptide regulators of Fbp1 termed pseudosubstrates; however, pseudosubstrates escape the normal degradation fate of other FBP target proteins and instead modulate the activity of the FBP, and corresponding Cks, such as cellular localization and substrate targeting. For example, the Fbp1 pseudosubstrate hnRNP-U not only inhibits Fpb1 from targeting inappropriate substrates but also serves to localize Fbp1 to the nucleus (Davis, et al., 2002, *Genes Dev.* 16:439).

A further level of complexity is added by the presence of a Fbp1/β-Trcp1 paralogous gene product, called β-Trcp2 or Fbxw1B (78% identical, 86% similar; Kipreos and Pagano, 2000, *Genome Biology* 1:3002.1). Fbp1 and β-Trcp2 are ubiquitously expressed in adult human tissues (Cenciarelli, et al., supra; Koike, et al., 2000, *Biochem. Biophys. Res. Commun.* 269:103). In addition, β-Trcp2 has biochemical properties similar to Fbp1 in its ability to sustain the ubiquitinylation of both β-catenin and IκBα family members in vitro and to control their degradation in mammalian cultured cells (Fuchs, et al., 1999, *Oncogene* 18:2039; Suzuki, et al., 1999, *Biochem. Biophys. Res. Commun.* 256:127; Tan, et al., 1999, *Mol. Cell.* 3:527). Despite these similarities, Fbp1 localizes to the nucleus and β-Trcp2 mainly to the cytoplasm (Davis, et al., 2002, *Genes Dev.* 16:439). It is not clear whether these two FBPs have overlapping functions in vivo, or if each of them recognizes specific substrates.

3.5 Deregulation of the Ubiquitin Pathway in Cancer and Other Proliferative Disorders Cancer develops when cells multiply too quickly. Cell proliferation is determined by the net balance of positive and negative signals. When positive signals overcome or when negative signals are absent, the cells multiply too quickly and cancer develops.

Ordinarily cells precisely control the amount of any given protein and eliminate the excess or any unwanted protein. To do so, the cell ubiquitinates the undesired protein to tag the protein for proteasome degradation. This mechanism goes awry in tumors, leading to the excessive accumulation of positive signals (oncogenic proteins), or resulting in the abnormal degradation of negative regulators (tumor suppressor proteins). Thus, without tumor suppressor proteins or in the presence of too much oncogenic proteins, cells multiply ceaselessly, forming tumors (reviewed by Ciechanover, 1998, *EMBO J.* 17: 7151; Spataro, 1998, *Br. J. Cancer* 77: 448). For example, abnormal ubiquitin-mediated degradation of the p53 tumor suppressor (reviewed by Brown and Pagano, 1997, *Biochim. Biophys. Acta* 1332:1), the putative oncogene β-catenin (reviewed by Peifer, 1997, *Science* 275:1752) and the Cki p27 (reviewed in Ciechanover, supra; Spataro, supra; Lloyd, 1999, *Am. J. Pathol.* 154: 313) have been correlated with tumorgenesis, opening to the hypothesis that some genes encoding ubiquitinating enzymes may be mutated in tumors.

Initial evidence indicates that human F box proteins play a role in the ubiquitination of G1 regulatory proteins as do their homologues in yeast (see below). Unchecked degradation of cell cycle regulatory proteins has been observed in certain tumors and it is possible that deregulated ubiquitin ligase plays a role in the altered degradation of cell cycle regulators. A well understood example is that of Mdm2, a ubiquitin ligase whose overexpression induces low levels of its substrate, the tumor suppressor p53.

Alternately, F box proteins have been shown to interact directly with DNA regulating proteins or DNA itself (see below). F box proteins in yeast are known to regulate genomic stability and senescence, and recent data has shown that F box inhibition in mammalian cells can lead to the loss of DNA damage checkpoints. The identification of novel F box protein substrates or activity may thus extend the role of F box proteins in tumorigenesis beyond the understood regulation of traditional cell cycle proteins.

4. SUMMARY OF THE INVENTION

The present invention relates to novel F box proteins as well as therapeutic protocols and pharmaceutical compositions designed to target the novel F box proteins and their interactions with substrates for the treatment of proliferative and differentiative disorders.

The present invention also relates to screening assays to identify substrates of the novel F box proteins and to identify agents which modulate or target the novel ubiquitin ligases and interactions with their substrates. The invention further relates to screening assays based on the identification of novel substrates of known F box proteins, such as the two novel substrates of the known F box protein Skp2, E2F and p27. The screening assays of the present invention may be used to identify potential therapeutic agents for the treatment of proliferative or differentiative disorders and other disorders that relate to levels of expression or enzymatic activity of F box proteins.

The invention is based in part, on the Applicants' discovery, identification and characterization of nucleic acids comprising nucleotide sequences that encode novel ubiquitin ligases with F box motifs. These twenty-nine novel substrate-targeting subunits of ubiquitin ligase complexes, FBP1/β-TRCP1, FBP2, FBP3a, FBP3b, FBP4, FBP5/EMI1, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25, described herein, were first identified based on their interaction with components of the ubiquitin ligase complex (FBP1, FBP2, FBP3a, FBP4, FBP5, FBP6 and FBP7) or by sequence comparison of these proteins with nucleotide sequences present in DNA databases (FBP3b, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25). These novel substrate-targeting subunits of ubiquitin ligase complexes each contain an F box motif through which they interact with the other components of the ubiquitin ligase complex. In addition, some of these FBPs contain WD-40 domains and LRRs (which appear to be involved in their interaction with substrates), while other FBPs contain potential protein-protein interaction modules not yet identified in FBPs, such as leucine zippers, ring fingers, helix-loop-helix motifs, proline rich motifs, PHD fingers, tetratricopeptide repeat domains, and SH2 domains. Amino acid sequence analysis has also revealed that some FBPs may interact directly with DNA through potential protein-DNA interaction domains, such as Jumonji-c domains, CXXC-zinc fingers, and HNH domains. The invention is based, in part, on the Applicants' discovery and identification of FBP specific substrates p27 and β-catenin and on methods to identify novel FBP substrates. Some of the genes encoding the novel F box proteins were also mapped to chromosome sites frequently altered in breast, prostate and ovarian cancer, nasopharyngeal and small cell lung carcinomas, gastric hepatocarcinomas, Burkitt's lymphoma and parathyroid adenomas.

The invention encompasses the following nucleotide sequences, host cells expressing such nucleotide sequences, and the expression products of such nucleotide sequences: (a) nucleotide sequences that encode mammalian FBP1/β-TRCP1, FBP2, FBP3a, FBP3b, FBP4, FBP5/EMI1, FBP6, FBP7, FBP8, FBP11, FBP12, FBP13, FBP14, FBP15, FBP17, FBP18, FBP20, FBP21, FBP22, FBP23, and FBP25, including the human nucleotides, and their gene products; (b) nucleotides that encode portions of the novel substrate-targeting subunits of ubiquitin ligase complexes, and the polypeptide products specified by such nucleotide sequences, including but not limited to F box motifs, the substrate binding domains; WD-40 domains; leucine rich repeats, Jumonji-C domains, etc.; (c) nucleotides that encode mutants of the novel ubiquitin ligases in which all or part of the domain is deleted or altered, and the polypeptide products specified by such nucleotide sequences; (d) nucleotides that encode fusion proteins containing the novel ubiquitin ligases or one of its domains fused to another polypeptide.

The invention further encompasses agonists and antagonists of the substrate-targeting subunits of ubiquitin ligase complexes, including small molecules, large molecules, mutants that compete with native F box binding proteins, and antibodies as well as nucleotide sequences that can be used to inhibit ubiquitin ligase gene expression (e.g., antisense and ribozyme molecules, and gene regulatory or replacement constructs) or to enhance ubiquitin ligase gene expression (e.g., expression constructs that place the ubiquitin ligase gene under the control of a strong promoter system), and transgenic animals that express a ubiquitin ligase transgene or knock-outs that do not express the novel ubiquitin ligases.

Further, the present invention also relates to methods for the use of the genes and/or gene products of substrate-targeting subunits of ubiquitin ligase complexes for the identification of compounds which modulate, i.e., act as agonists or antagonists, of ubiquitin ligase activity. Such compounds can be used as agents to control proliferative or differentiative disorders, e.g. cancer. Such compounds can also be used as agents for the treatment of FBP-related disorders, such as infertility. In particular, the present invention encompasses methods to inhibit the interaction between β-catenin and FBP1 or p27 and Skp2. The present invention also encompasses methods to modulate the interaction between FBP1 and FBP5; between FBP24 and its binding proteins, such as endostatin-like protein, BAF57, splice isoform SP100-HMG (P23497 nuclear autoantigen SP100), and H326 protein; and between FBL11 and MCM7. The invention also encompasses methods to modulate the interaction between F box proteins and DNA, such as the interaction of FBP24 and FBL11 with DNA. Agents able to modulate these interactions can be used to modulate cell proliferation, growth and/or apoptosis.

Still further, the invention encompasses screening methods to identify derivatives and analogues of the novel substrate-targeting subunits of ubiquitin ligase complexes which modulate the activity of the novel ligases as potential therapeutics for proliferative or differentiative disorders. The invention provides methods of screening for proteins that interact with components of the ubiquitin ligase complex, including FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, FBP25, FBL10, FBL11, and FBP25, or derivatives, fragments or domains thereof, such as the F box motif. In accordance with the invention, the screening methods may utilize known assays to identify protein-protein interactions including phage display assays or the yeast two-hybrid assay system or variations thereof.

In addition, the present invention is directed to methods that utilize FBP gene sequences and/or FBP gene product sequences for the diagnostic evaluation, genetic testing and/or prognosis of an FBP-related disorder, such as an infertility or proliferative disorder. For example, the invention relates to methods for diagnosing FBP-related disorders, e.g., infertility or proliferative disorders, wherein such methods can comprise measuring FBP gene expression in a patient sample, or detecting an FBP mutation that correlates with the presence or development of such a disorder, in the genome of a mammal suspected of exhibiting such a disorder. In particular, the invention encompasses methods for determining if a subject (e.g., a human patient) is at risk for a disorder characterized by one or more of: (i) a mutation of an FBP gene encoding a protein represented in part A of FIGS. 3-28, or a homologues thereof; (ii) the mis-expression of an FBP gene; (iii) the mis-expression of an FBP protein.

The invention is illustrated by way of working examples which demonstrate the identification and characterization of the novel substrate-targeting subunits of ubiquitin ligase complexes. The working examples of the present invention further demonstrate the identification of the specific interaction of (i) FBP1 with β-catenin and (ii) the known FBP, Skp2, with the cell-cycle regulatory proteins E2F and p27 and the cell cycle protein Cks1. These interactions suggest that β-catenin is a specific substrate of FBP1, while E2F and p27 are substrates of Skp2 and Cks1 is a mediator for Skp2 and p27. In fact, the working examples of the present invention further demonstrate that β-catenin is a specific substrate of FBP1, while p27 is substrates of Skp2 and Cks1 binds to both p27 and Skp2. The identification of proteins interacting with the novel FBPs will be possible using the methods described herein.

The working examples of the present invention also demonstrate (i) that FBP24 specifically interacts with elongation factor 2 (eEF2), BAF57, and SP100-HMG; and (ii) that FBL11 specifically interacts with a human homolog of yeast MCM7. The identification of these interactions using the invention suggest that Fbox proteins are involved in the regulation of both DNA synthesis and protein synthesis (translational elongation). Further, the working examples of the present invention demonstrate that inhibiting FBL11 activity results in a decrease in cellular proliferation. Similarly, the working examples of the present invention demonstrate that inhibition of FBP24 or FBL12 activity results in an inhibition of cell growth and/or an increase in apoptosis. Identification of the ubiquitin ligase or cellular-growth regulatory activity of novel FBPs will be possible using the methods described herein.

The invention encompasses a method for screening compounds that modulate Fbp1-related disorders, comprising contacting a compound with Fbp1 and Fbp5, and measuring the activity of Fbp1. In a specific embodiment, the activity of Fbp1 is measured by measuring the interaction of Fbp1 with Fbp5. In another specific embodiment, the activity of Fbp1 is measured by measuring the levels of protein of Fbp5.

The invention also encompasses a method for screening compounds that modulate Fbp1-related disorders, comprising (a) contacting a compound with a cell or a cell extract expressing Fbp1 and Fbp5, and detecting a change in the activity of Fbp1, and (b) measuring the level of Fbp1 activity in a cell or cell extract in the absence of said compound, such that if the level of Fbp1 activity measured in (b) differs from the level of activity in (a), then a compound that modulates an Fbp1-related disorder is identified. In a specific embodiment, the activity of Fbp1 is measured by measuring the interaction of Fbp1 with Fbp5. In another specific embodiment, the activity of Fbp1 is measured by measuring the levels of protein of Fbp5.

The invention further encompasses a method for screening compounds useful for the treatment of proliferative and differentiative disorders, comprising contacting a compound with a cell or a cell extract expressing both Fbp1 and β-Trcp2, and an Fbp1 target substrate, and detecting a change in the activity of Fbp1 or β-Trcp2. In a specific embodiment, the target substrate is β-catenin. In another specific embodiment, the target substrate is IkBα. In another specific embodiment, the change in the activity of Fbp1 or β-Trcp2 is detected by detecting a change in the interaction of Fbp1 or β-Trcp2 with β-catenin. In a further specific embodiment, the change in the activity of Fbp1 or βTrcp2 is detected by detecting a change in the interaction of Fbp1 or β-Trcp2 with IkBα. In another specific embodiment, the change in the activity of Fbp1 or β-Trcp2 is detected by detecting a change in the levels of protein of β-catenin. In an additional specific embodiment, the change in the activity of Fbp1 or β-Trcp2 is detected by detecting a change in the levels of protein of IkBα.

The invention also encompasses a method for screening compounds useful for the treatment of proliferative and differentiative disorders comprising (a) contacting a compound with a cell or a cell extract expressing Fbp1 and a test compound, and detecting a change in the activity of Fbp1, (b) contacting a compound with a cell or a cell extract expressing β-Trcp2, and a test compound, and detecting a change in the activity of β-Trcp2, and (c) contacting a compound with a cell or a cell extract expressing Fbp1 and β-Trcp2, and the test compound or compounds identified as changing the activity of Fbp1 or β-Trcp2, and detecting a change in the activity of Fbp1 or β-Trcp2. In a specific embodiment, the change in the activity of Fbp1 or β-Trcp2 is detected by detecting a change in the levels of protein of β-catenin. In another specific embodiment, the change in the activity of Fbp1 or β-Trcp2 is detected by detecting a change in the levels of protein of IkBα.

The invention further encompasses a method for screening compounds useful for the treatment of proliferative and differentiative disorders or for inducing or inhibiting apoptosis in a cell, comprising contacting a compound with a cell or a cell extract expressing both Fbp24 and an Fbp24 target substrate, and detecting a change in the activity of Fbp24. In a specific embodiment, the change in activity of FBP24 is detected by detecting a change in the interaction of FPB24 with the target substrate. In a specific embodiment, the target substrate is DNA. In another specific embodiment, the target substrate is Elongation Factor 2. In a further specific embodiment, the target substrate is endostatin-like protein. In an additional specific embodiment, the target substrate is BAF57. In another specific embodiment, the target substrate is splice isoform SP100-HMG (P23497 nuclear autoantigen SP100). In a further specific embodiment, the target substrate is H326 Protein.

The invention further encompasses a method for screening compounds useful for the treatment of proliferative and differentiative disorders or for modulating cell proliferation comprising contacting a compound with a cell or a cell extract expressing both Fbl11 and an Fbl11 target substrate, and detecting a change in the activity of Fbl11. In a specific embodiment, the target substrate is DNA. In another specific embodiment, the target substrate is MCM7. In an additional specific embodiment, the change in the activity of Fbl11 is detected by detecting a change in the interaction of Fbl11 with DNA. In an additional specific embodiment, the change in the activity of Fbl11 is detected by detecting a change in the interaction of Fbl11 with MCM7.

The invention also encompasses a method for screening compounds useful for the treatment of proliferative and differentiative disorders, for modulating cell proliferation, or for sensitizing cells to chemotherapy, comprising contacting a compound with a cell or a cell extract expressing both Fbl2 and an Fbl2 target substrate, and detecting a change in the activity of Fbl2.

4.1 Definitions

As used herein, the term "F-box motif" refers to a stretch of approximately 40 amino acids that was identified as being necessary for the interaction of F-box containing proteins with Skp1. The consensus sequence of an F-box motif is described in Bai et al., 1996, Cell 86:263, incorporated herein by reference in its entirety.

As used herein the term "F-box protein" (FBP) refers to peptide, polypeptide or protein which contains an F-box motif.

Although, FBPs are substrate-targeting subunits of ubiquitin ligase complexes, as used herein the term "ubiquitin ligase" refers to a peptide, polypeptide or protein that contains an F-box motif and interacts with Skp1.

As used herein, the term "functionally equivalent to an FBP gene product" refers to a gene product that exhibits at least one of the biological activities of the endogenous FBP gene product. For example, a functionally equivalent FBP gene product is one that is capable of interacting with Skp1 so as to become associated with a ubiquitin ligase complex. Such a ubiquitin ligase complex may be capable of ubiquitinating a specific cell-cycle regulatory protein, such as a cyclin or cki protein.

As used herein, the term "to target" means to inhibit, block or prevent gene expression, enzymatic activity, or interaction with other cellular factors.

As used herein, the term "therapeutic agent" refers to any molecule, compound or treatment that alleviates or assists in the treatment of a proliferative disorder or related disorder.

As used herein, the term "clinically normal individual" refers to an individual with an absence of symptoms of a particular disorder.

As used herein, the terms "WD-40 domain", "Leucine Rich Repeat", "Leucine Zipper", "Ring finger", "Helix-loop-helix motif", "Proline rich motif", "SH2 domain", "tetratricopeptide repeat domain" ("TPR"), "tankyrase binding domain", and "PHD finger" refer to domains potentially involved in mediating protein-protein interactions. The "WD-40 domain" refers to a consensus sequence of forty amino acid repeats which is rich in tryptophan and aspartic acid residues and is commonly found in the beta subunits of trimeric G proteins (see Neer, et al., 1994, Nature 371:297-300 and references therein, which are incorporated herein by reference in their entirety). An "LRR" or a "Leucine Rich Repeat" is a leucine rich sequence also known to be involved in mediating protein-protein interactions (see Kobe and Deisenhofer, 1994, Trends. Biochem. Sci. 19:415-421 which are incorporated herein by reference in their entirety). A "leucine zipper" domain refers to a domain comprising a stretch of amino acids with a leucine residue in every seventh position which is present in a large family of transcription factors (see Landshultz, et al., 1988, Science 240:1759; see also Sudol, et al., 1996, Trends Biochem. 21:1, and Koch, et al., 1991, Science 252:668). The majority of known "TPR" domains consist of three copies of the helix-turn-helix TPR motif (a degenerate, 34-amino acid repeat) together with a seventh C-terminal helix and function as protein-protein recognition modules in intracellular signalling (see Cliff, et al., 2005, J. Mol. Biol., 346:717 and references therein, which are incorporated herein by reference in their entirety). A "PHD finger" refers to zinc-finger motifs known as plant homeodomains also known to be involved in mediating protein-protein interactions (sec Panchenko, et al., 2004, J. Biol. Chem., 53:56032 and references therein, which are incorporated herein by reference in their entirety).

As used herein, the terms "Jumonji-c domain", "CXXC-zinc finger", and "HNH domain" refer to domains potentially involved in mediating protein-DNA interactions. For example, the "HNH domain" is a conserved 30 amino acid motif originally indentified the subfamily of HNH homing endonucleases and mediates protein-DNA binding (see Ku, et al., 2002, Nucleic Acids Res., 30:1670 and references therein, which are incorporated herein by reference in their entirety).

5. BRIEF DESCRIPTION OF THE FIGURES

Figure 1:
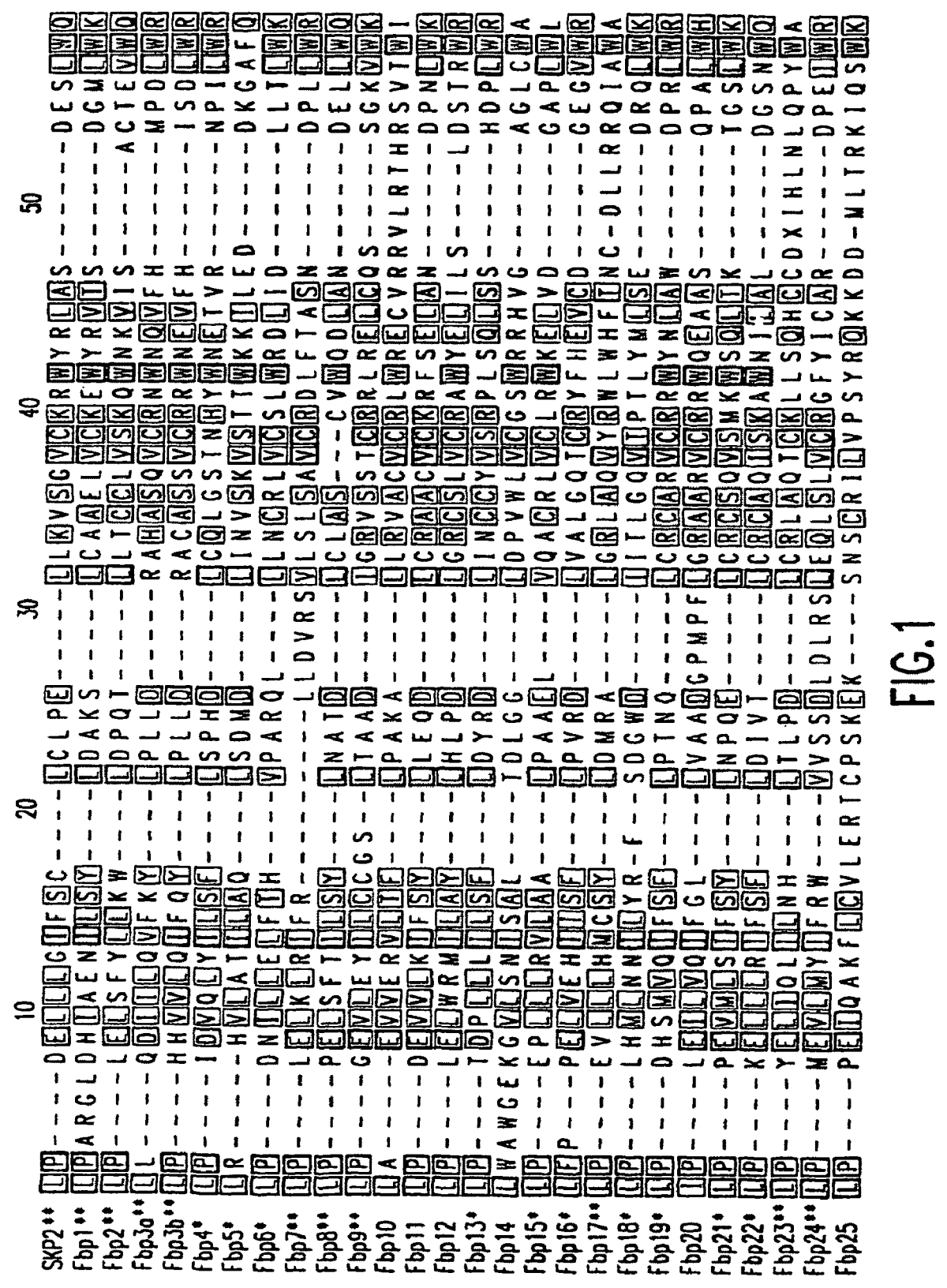

FIG. 1. Alignment of the conserved F-box motif amino acid residues in the human F-box proteins FBP1 (SEQ ID NO:15), FBP2 (SEQ ID NO:16), FBP3a (SEQ ID NO:17), FBP3b (SEQ ID NO:78), FBP4 (SEQ ID NO:18), FBP5 (SEQ ID NO:19), FBP6 (SEQ ID NO:20), FBP7 (SEQ ID NO:21), Skp2 (SEQ ID NO:22), FBP8 (SEQ ID NO:61) FBP9 (SEQ ID NO:62), FBP10 (SEQ ID NO:63), FBP11 (SEQ ID NO:64), FBP12 (SEQ ID NO:65), FBP13 (SEQ ID NO:66); FBP14 (SEQ ID NO:79); FBP15 (SEQ ID NO:67), FBP16 (SEQ ID NO:68), FBP17 (SEQ ID NO:69), FBP18 (SEQ ID NO:70), FBP19 (SEQ ID NO:71), FBP20 (SEQ ID NO:72), FBP21 (SEQ ID NO:73), FBP22 (SEQ ID NO:74), FBP23 (SEQ ID NO:75), FBP24 (SEQ ID NO:76), FBP25 (SEQ ID NO:77). Alignment of the F-boxes of a previously known FBP, Skp2, with the F-boxes of FBPs identified through a two-hybrid screen (designated by the pound symbol) or BLAST searches (designated by a cross) was performed using the Clustal W method (MacVector™) followed by manual re-adjustment. Identical residues in at least 15 F-boxes are shaded in dark gray, while similar residues are shaded in light gray. One asterisk indicates the presence in the cDNA of a STOP codon followed by a polyA tail, while potential full length clones are designated with two asterisks. The asterisks on the bottom of the figure indicate the amino acid residues mutated in FBP3a (see FIG. 29).

FIG. 2. Schematic representation of FBPs. Putative protein-protein interaction domains in human FBPs are represented (see key-box for explanation). FBPs identified by a two-hybrid screen are designated by the pound symbol, FBPs identified through BLAST searches by a cross. The double slash indicates that the corresponding cDNAs are incomplete at the 5' end; the asterisks indicate the presence in the cDNA of a STOP codon followed by a polyA tail.

FIG. 3 A-D. A. Amino acid sequence of human F-box protein FBP1/β-TRCP1 (SEQ ID NO:2). B-D. Corresponding cDNA (SEQ ID NO:1).

FIG. 4 A-C. A. Amino acid sequence of human F-box protein FBP2 (SEQ ID NO:4). B-C. Corresponding cDNA (SEQ ID NO:3).

FIG. 5 A-C. A. Amino acid sequence of human F-box protein FBP3a (SEQ ID NO:6). B-C. Corresponding cDNA (SEQ ID NO:5).

FIG. 6 A-C. A. Amino acid sequence of human F-box protein FBP3b (SEQ ID NO:24). B-C. Corresponding cDNA (SEQ ID NO:23).

FIG. 7 A-C. A. Amino acid sequence of human F-box protein FBP4 (SEQ ID NO:8). B-C. Corresponding cDNA (SEQ ID NO:7).

FIG. 8 A-C. A. Amino acid sequence of human F-box protein FBP5/EMI1 (SEQ ID NO:10). B-C. Corresponding cDNA (SEQ ID NO:9).

FIG. 9 A-C. A. Amino acid sequence of human F-box protein FBP6 (SEQ ID NO:12). B-C. Corresponding cDNA (SEQ ID NO:11).

FIG. 10 A-C. A. Amino acid sequence of human F-box protein FBP7 (SEQ ID NO:14). B-C. Corresponding cDNA (SEQ ID NO:13).

FIG. 11A-D. A. Amino acid sequence of human F-box protein FBP8 (SEQ ID NO:26). B-D. Corresponding cDNA (SEQ ID NO:25).

Figure 12B:
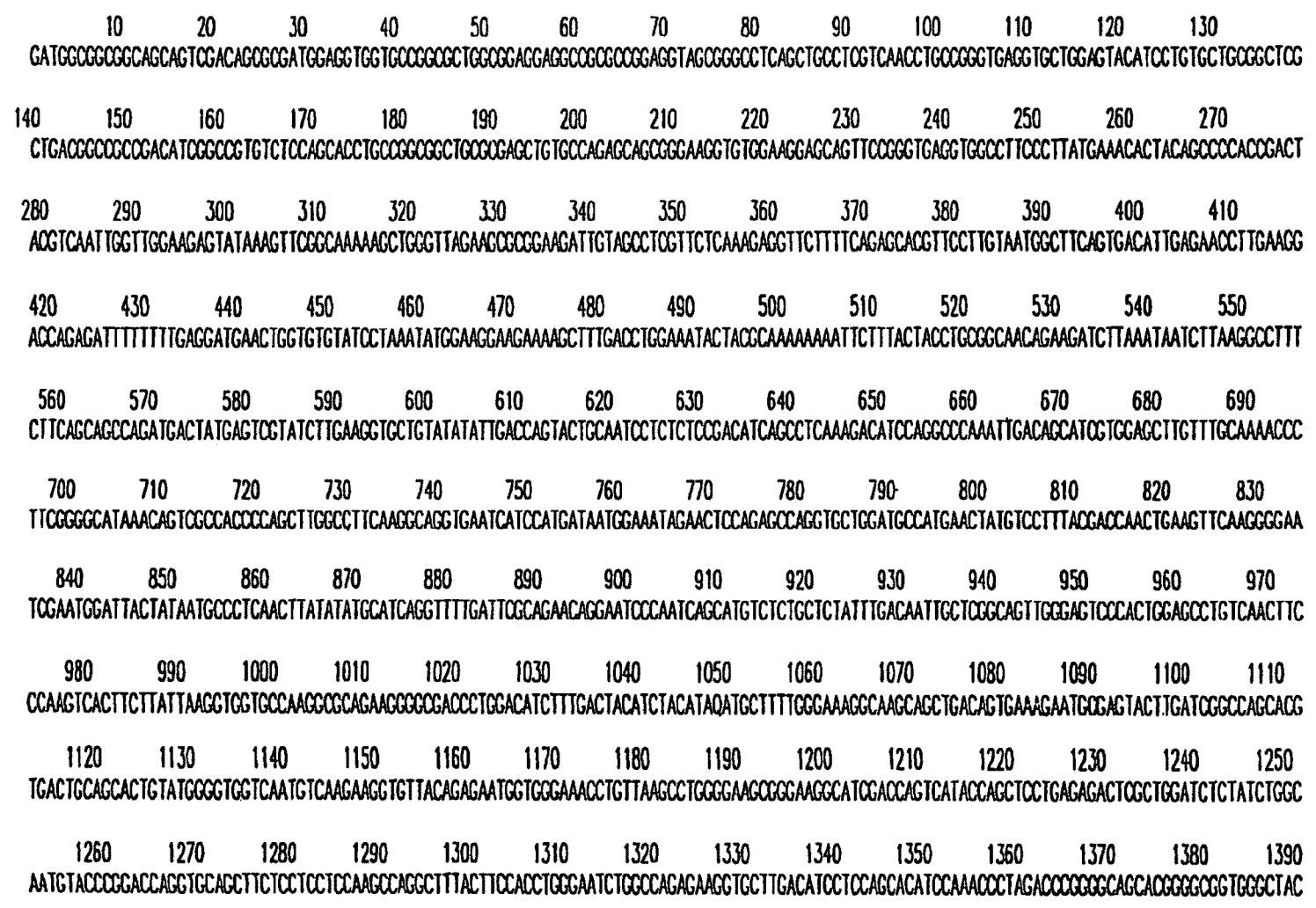

FIG. 12 A-D. A. Amino acid sequence of human F-box protein FBP9 (SEQ ID NO:28). B-D. Corresponding cDNA (SEQ ID NO:27).

FIG. 13 A-B. A. Amino acid sequence of human F-box protein FBP10 (SEQ ID NO: 30). B. Corresponding cDNA (SEQ ID NO:29).

FIG. 14 A-B. A. Amino acid sequence of human F-box protein FBP11 (SEQ ID NO:32). B. Corresponding cDNA (SEQ ID NO:31).

FIG. 15 A-B. A. Amino acid sequence of human F-box protein FBP12 (SEQ ID NO:34). B. Corresponding cDNA (SEQ ID NO:33).

FIG. 16 A-B. A. Amino acid sequence of human F-box protein FBP13 (SEQ ID NO:36). B. Corresponding cDNA (SEQ ID NO:35).

FIG. 17 A-B. A. Amino acid sequence of human F-box protein FBP14 (SEQ ID NO:38). B. Corresponding cDNA (SEQ ID NO:37).

FIG. 18 A-B. A. Amino acid sequence of human F-box protein FBP15 (SEQ ID NO:40). B. Corresponding cDNA (SEQ ID NO:39).

FIG. 19 A-B. A. Amino acid sequence of human F-box protein FBP16 (SEQ ID NO:42). B. Corresponding cDNA (SEQ ID NO:41).

FIG. 20 A-C. A. Amino acid sequence of human F-box protein FBP17 (SEQ ID NO:44). B-C. Corresponding cDNA (SEQ ID NO:43).

FIG. 21A-C. A. Amino acid sequence of human F-box protein FBP18 (SEQ ID NO:46). B-C. Corresponding cDNA (SEQ ID NO:45).

Figure 22B:
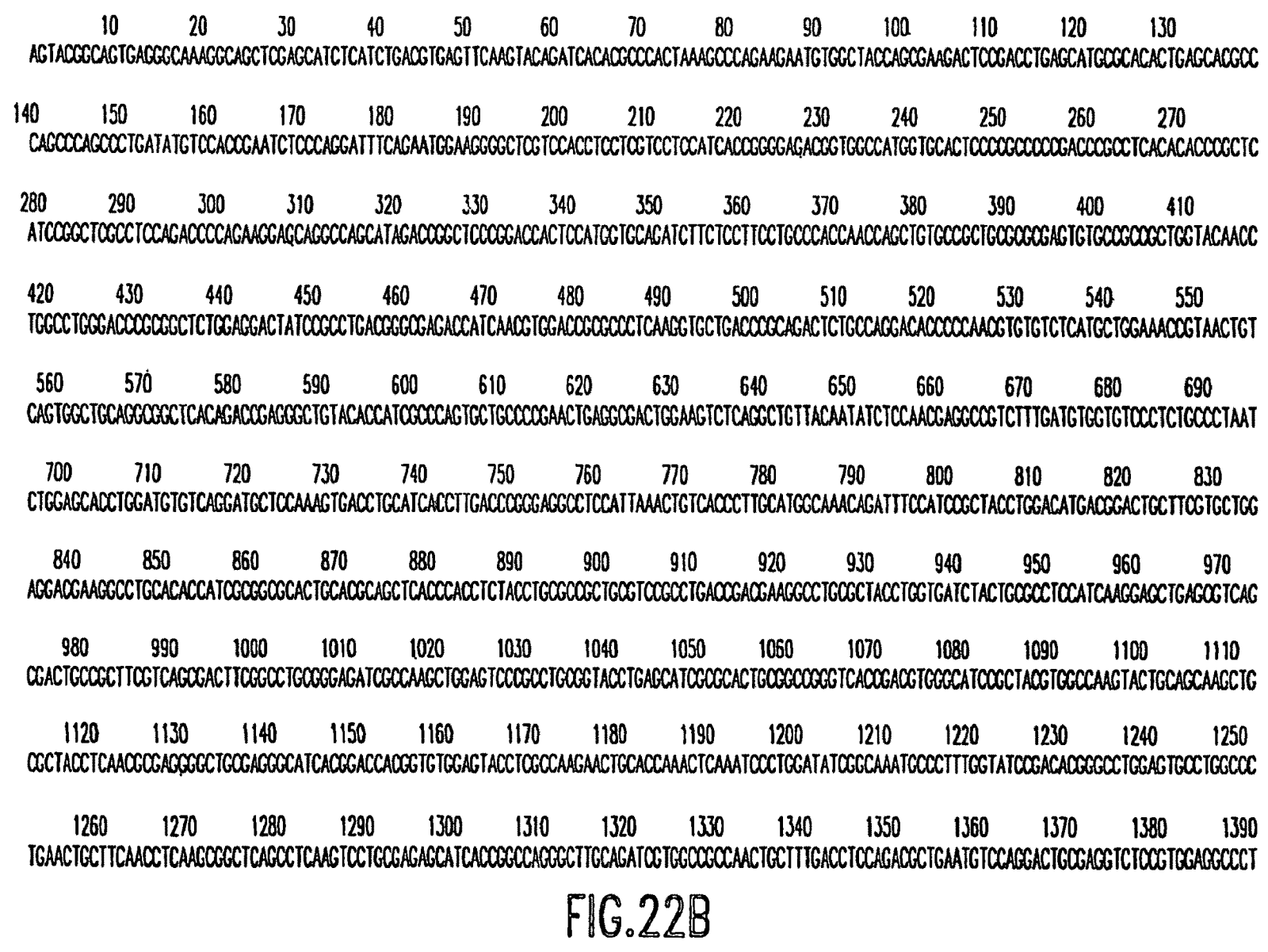

FIG. 22 A-D. A. Amino acid sequence of human F-box protein FBP19 (SEQ ID NO:48). B-D. Corresponding cDNA (SEQ ID NO:47).

FIG. 23 A-B. A. Amino acid sequence of human F-box protein FBP20 (SEQ ID NO:50). B. Corresponding cDNA (SEQ ID NO:49).

FIG. 24 A-C. A. Amino acid sequence of human F-box protein FBP21 (SEQ ID NO:52). B-C. Corresponding cDNA (SEQ ID NO:51).

FIG. 25 A-C. A. Amino acid sequence of human F-box protein FBP22 (SEQ ID NO:54). B-C. Corresponding cDNA (SEQ ID NO:53).

FIG. 26 A-C. A. Amino acid sequence of human F-box protein FBP23 (SEQ ID NO:56). B-C. Corresponding cDNA (SEQ ID NO:55).

FIG. 27 A-B. A. Amino acid sequence of human F-box protein FBP24 (SEQ ID NO:58). B. Corresponding cDNA (SEQ ID NO:57).

FIGS. 28A-B. A. Amino acid sequence of human F-box protein FBP25 (SEQ ID NO:60). B. Corresponding cDNA (SEQ ID NO:59).

FIGS. 29A-B. A. Amino acid sequence of human F-box protein FBL10 (SEQ ID NO:92). B. Corresponding cDNA (SEQ ID NO:91).

FIGS. 30A-B. A. Amino acid sequence of human F-box protein FBL11 (SEQ ID NO:94). B. Corresponding cDNA (SEQ ID NO:93).

FIGS. 31A-B. A. Amino acid sequence of human F-box protein FBL12 (SEQ ID NO:96). B. Corresponding cDNA (SEQ ID NO:95).

Figure 32:
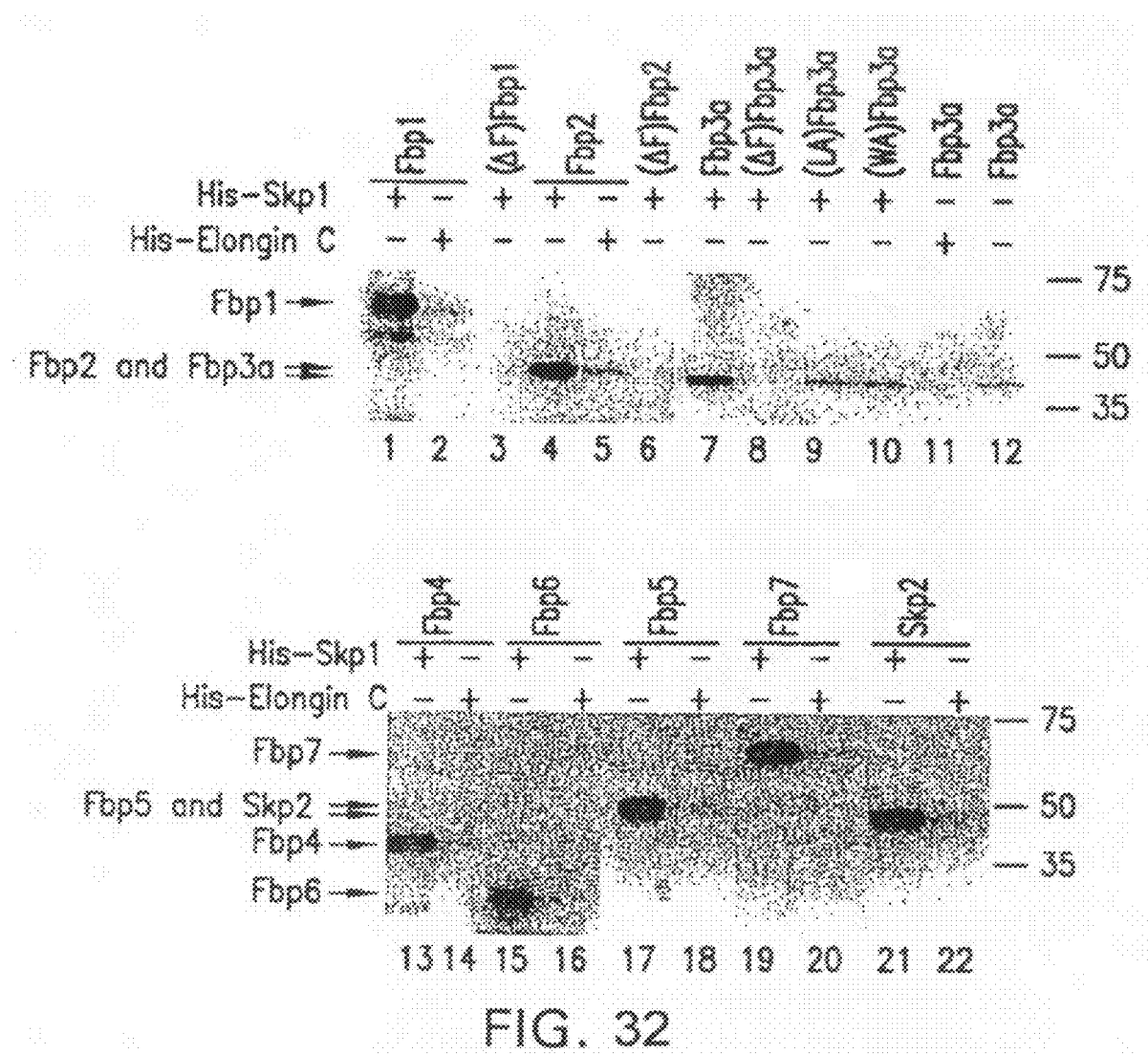

FIG. 32. FBPs interact specifically with Skp1 through their F-box. The cDNAs of FBPs (wild type and mutants) were transcribed and translated in vitro (IVT) in the presence of 35S-methionine. Similar amounts of IVT proteins (indicated at the top of each lane) were subjected to a histidine-tagged pull-down assay using Nickel-agarose beads to which either His-tagged-Skp1 (lanes 1, 3, 4, 6-10, 12, 15, 17, 19 and 21), His-tagged-Elongin C (lanes 2, 5, 11, 14, 16, 18, 19 and 22), or His-tagged p27 (lane 12) were pre-bound. Bound IVT proteins were analyzed by SDS-PAGE and autoradiography. The arrows on the left side of the panels point to the indicated FBPs. The apparent molecular weights of the protein standards are indicated on the right side of the panels.

Figure 33:
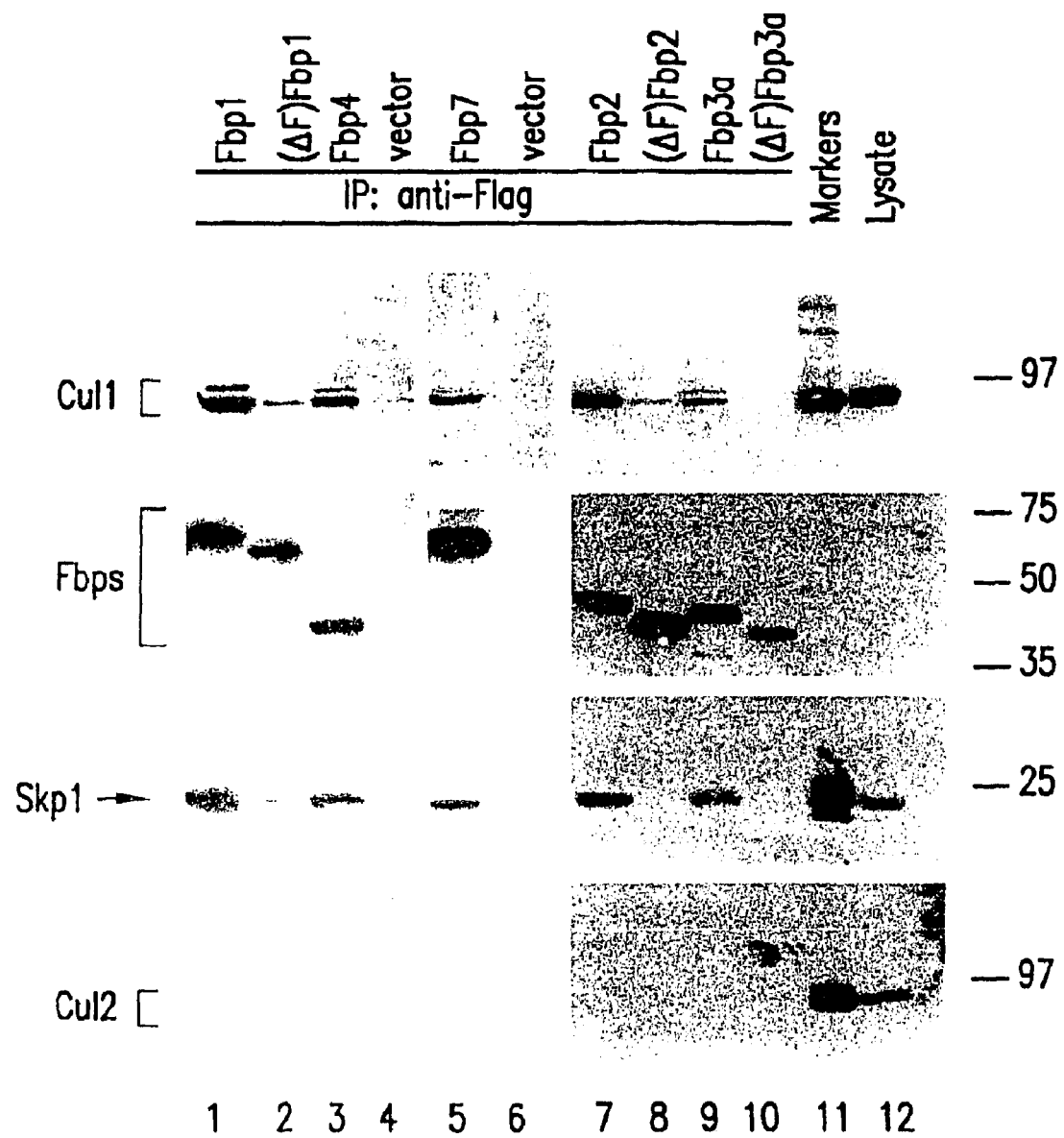

FIG. 33. FBP1, FBP2, FBP3a, FBP4 and FBP7 form novel SCFs with endogenous Skp1 and Cul1 in vivo. HeLa cells were transfected with mammalian expression plasmids encoding Flag-tagged versions of FBP1 (lane 1), (DF)FBP1 (lane 2), FBP4 (lane 3), FBP7 (lane 5), FBP2 (lane 7), (DF) FBP2 (lane 8), FBP3a (lane 9), (DF)FBP3a (lane 10), or with an empty vector (lanes 4 and 6). Cells were lysed and extracts were subjected to immunoprecipitation with a rabbit anti-Flag antibody (lanes 1-8). Immunoprecipitates were then immunoblotted with a mouse anti-Cul1 monoclonal antibody, a rabbit anti-Skp1 polyclonal antibody or a rabbit anti-Cul2 polyclonal antibody, as indicated. The last lane contains 25 µg of extracts from non-transfected HeLa cells; lane 9 contains recombinant Cul1, Skp1, or Cul2 proteins used as markers. The slower migrating bands detected with the antibodies to Cul1 and Cul2 are likely generated by the covalent attachment of a ubiquitin-like molecule to these two cullins, as already described for the yeast cullin Cdc53 and mammalian Cul4a.

Figure 34:
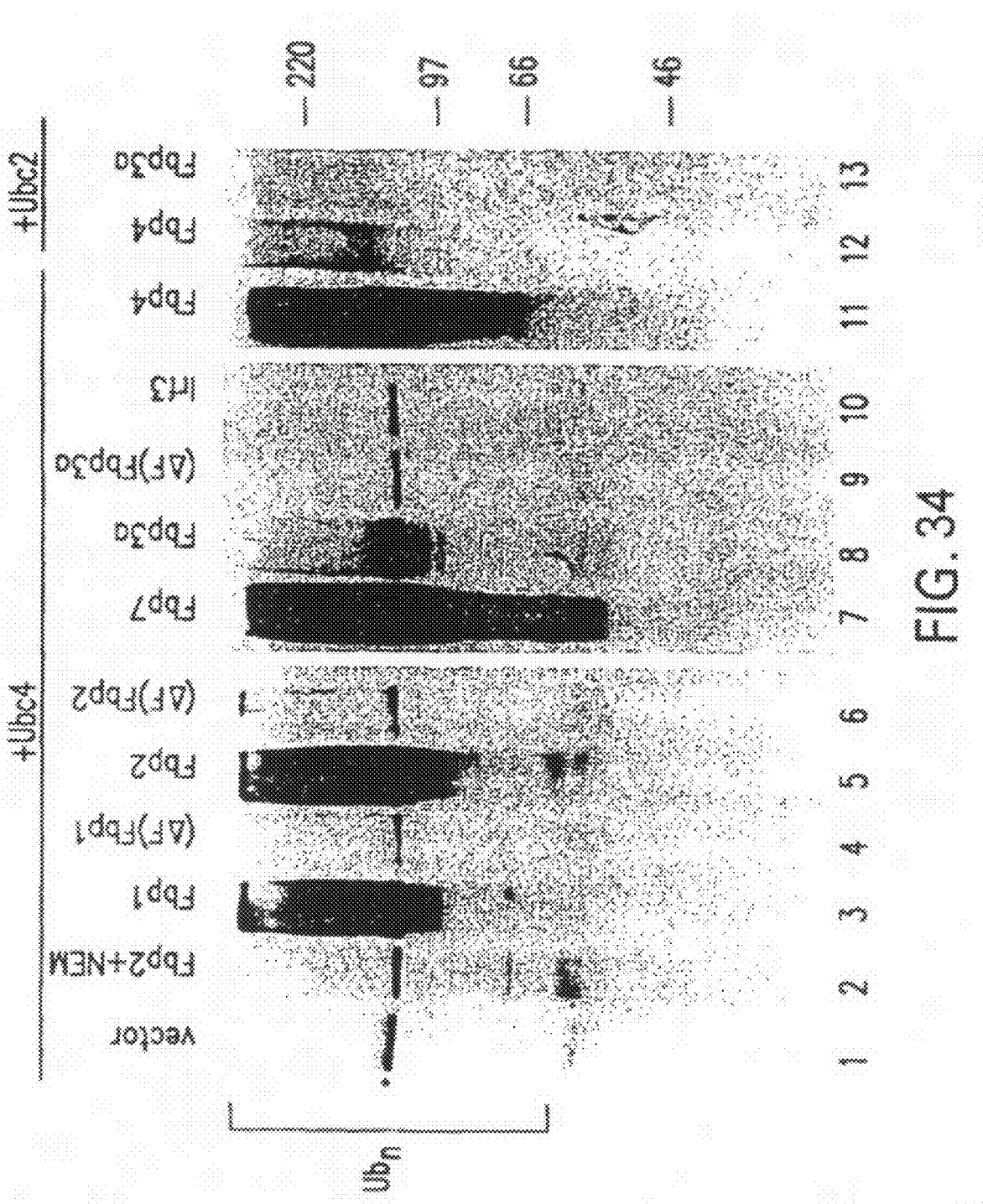

FIG. 34. FBP1, FBP2, FBP3a, FBP4 and FBP7 associate with a ubiquitin ligase activity. HeLa cells were transfected with mammalian expression plasmids encoding human Skp1, Cul1 and Flag-tagged versions of FBP1 (lane 3), (DF)FBP1 (lane 4), FBP2 (lanes 2 and 5), (DF)FBP2 (lane 6), FBP7 (lane 7), FBP3a (lanes 8 and 13), (DF)FBP3a (lane 9), a non relevant Flag-tagged protein (Irf3, lane 10), FBP4 (lanes 11 and 12) or with an empty vector (lane 1). Cells were lysed and extracts were subjected to immunoprecipitation with a rabbit anti-Flag antibody. Immunoprecipitates were incubated in the presence of purified recombinant E1 and Ubc4 (lanes 1-11) or Ubc2 (lanes 12 and 13) and a reaction mix containing biotinylated ubiquitin. Reaction in lane 2 contained also NEM. Ubiquitinated proteins were visualized by blotting with HRP-streptavidin. The bracket on the left side of the panels marks a smear of ubiquitinated proteins produced in the reaction, the asterisk indicates ubiquitin conjugated with E1 that were resistant to boiling.

FIG. 35. Subcellular localization of FBPs. HeLa cells were transfected with mammalian expression plasmids encoding Flag-tagged versions of FBP1 (a-b), FBP2 (c-d), FBP3a (e-f), FBP4 (g-h), (DF)FBP2 (i-j), or (DF)FBP3a (k-l). After 24 hours, cells were subjected to immunofluorescence with a rabbit anti-Flag antibody (a, c, e, g, i, k) to stain FBPs and bisbenzimide (b, d, f, h, j, l) to stain nuclei.

Figure 36:
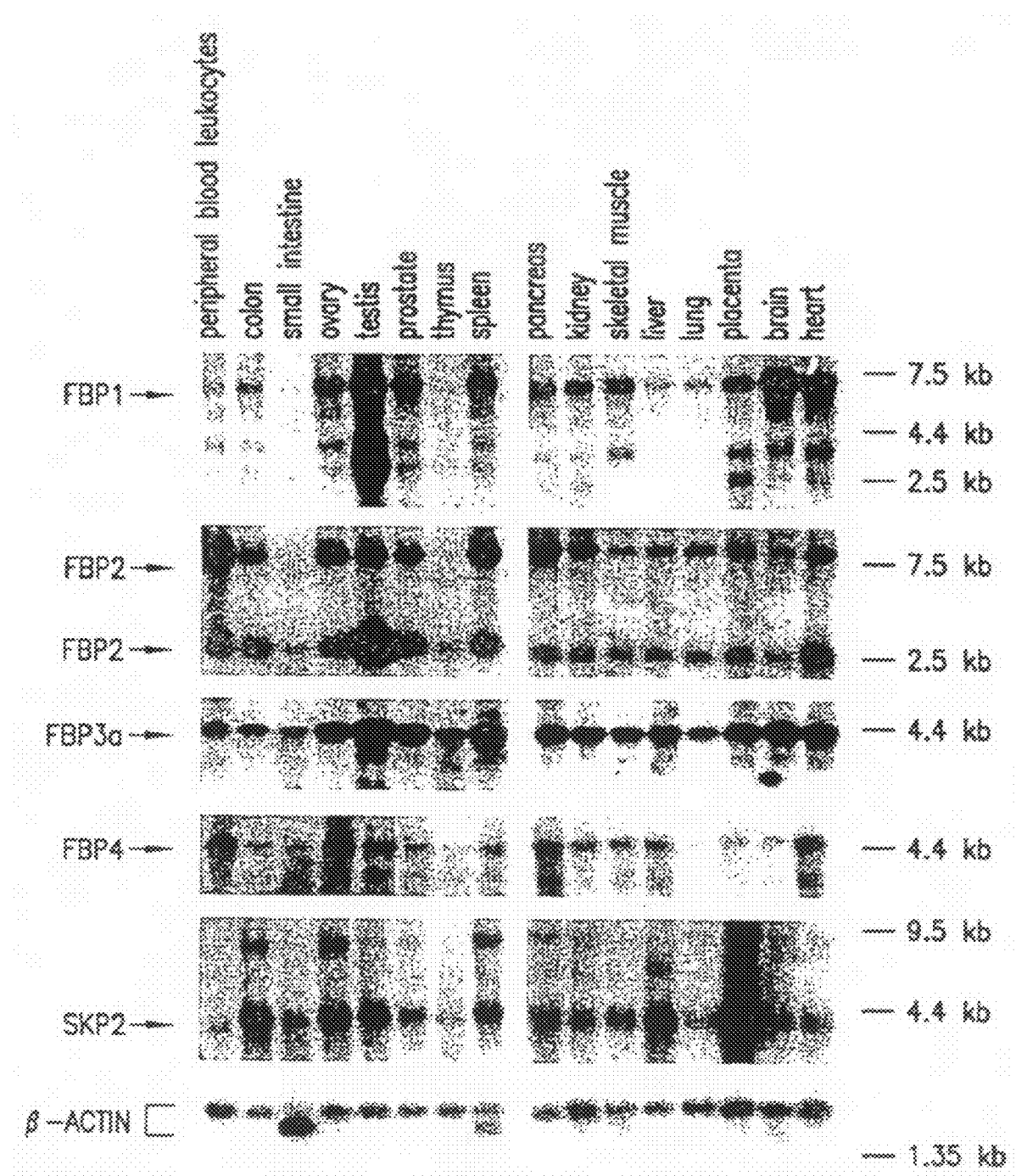

FIG. 36. Abundance of FBP transcripts in human tissues. Membranes containing electrophoretically fractionated poly (A)+ mRNA from different human tissues were hybridized with specific probes prepared form FBP1, FBP2, FBP3a, FBP4, SKP2, and β-ACTIN cDNAs. The arrows on the left side of the figure point to the major transcripts as described in the text.

FIG. 37 A-E. FISH localization of FBP genes. Purified phage DNA containing a genomic probe was labeled with digoxygenin dUTP and detected with Cy3-conjugated antibodies. The signals corresponding to the locus of the genomic probe (red) are seen against the DAPI-Actimomycin D stained normal human chromosomes (blue-white). Panel A shows localization of FBP1 to 10q24, B shows localization of FBP2 to 9q34, C shows localization of FBP3a to 13q22, D shows localization of FBP4 to 5p12, and E shows localization of FBP5 to 6q25-26. Arrows point to FBP-specific FISH signals.

Figure 38A:
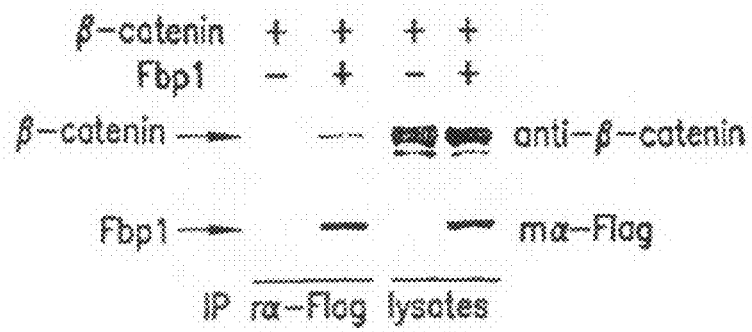
Figure 38B:
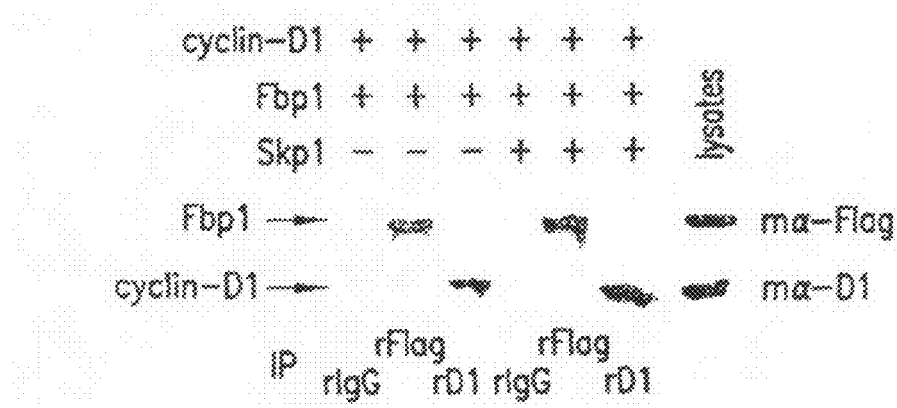
Figure 38C:
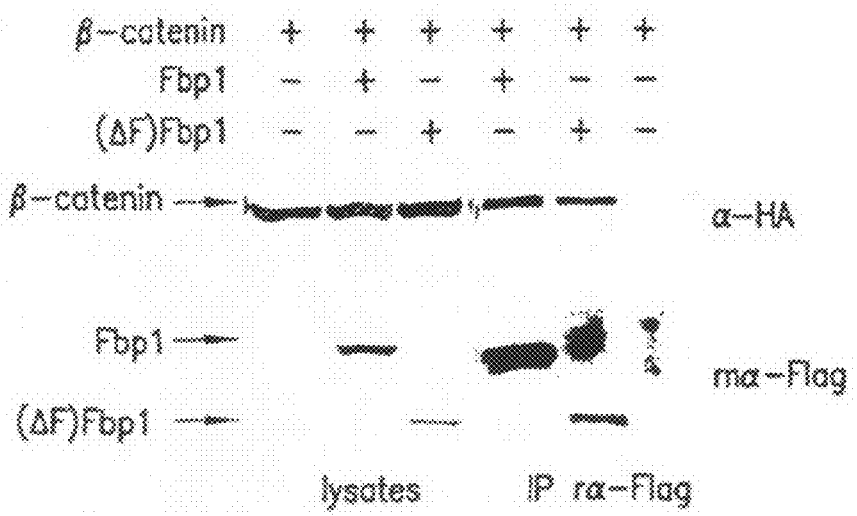

FIGS. 38A-C. FBP1 associates with β-catenin. A. Extracts from baculovirus-infected insect cells expressing either β-catenin alone (lane 1) or in combination with Flag-tagged FBP1 (lane 2) were immunoprecipitated (IP) with a rabbit anti-Flag antibody (rα-Flag), followed by immunoblotting with anti-Flag (mα-Flag) and anti-β-catenin mouse antibodies, as indicated. Lanes 3 and 4 contain 25 μg of extracts from infected insect cells immunoblotted with the same antibodies. B. Extracts from baculovirus-infected insect cells expressing cyclin D1, Flag-FBP1 in the absence (lanes 1-3) or in the presence of Skp1 (lanes 4-6) were immunoprecipitated with normal rabbit IgG (r-IgG, lanes 1 and 4), rabbit anti-Flag Antibody® α-Flag, lanes 2 and 5), or rabbit anti-cyclin D1 Antibody® α-D1, lanes 3 and 6). Immunoprecipitates were then immunoblotted with anti-Flag (mα-Flag) and cyclin D1 (m α-D1) mouse antibodies, as indicated. The last lane contains 25 μg of a representative extract from infected insect cells immunoblotted with the same antibodies. C. 293 cells were transfected with mammalian expression plasmids encoding HA-tagged β-catenin alone or in combination with either Flag-tagged FBP1 or Flag-tagged (DF)FBP1. Cells were lysed and extracts were subjected to immunoprecipitation with a rabbit anti-Flag Antibody® a-Flag, lanes 4-6) and immunoblotted with rat anti-HA (α-HA) and mouse anti-Flag (m α-Flag) antibodies, as indicated. The first three lanes contain 25 μg of extracts from transfected 293 cells immunoblotted with the same antibodies. Transfecting high levels of β-catenin expression vector, the associations of β-catenin with FBP1 and (DF)FBP1 could be determined independently of β-catenin levels.

FIG. 39 A-B. Stabilization of β-catenin by a dominant negative (ΔF)FBP1 mutant. A. Human 293 cells were transfected with mammalian expression plasmids encoding HA-tagged β-catenin alone or in combination with either Flag-tagged (DF)FBP1 or Flag-tagged (DF)FBP2. Cells were lysed and extracts were subjected to immunoblotting with rat anti-HA and rabbit anti-Flag® α-Flag) antibody, as indicated. B. Pulse chase analysis of β-catenin turnover rate. HA-tagged β-catenin in combination with either an empty vector, FBP1, or (DF)FBP1 was co-transfected in 293 cells. 24 hours later cells were labeled with 35S-methionine for 30 minutes and chased with medium for the indicated times. Extracts were then subjected to immunoprecipitation with a rat anti-HA antibody.

Figure 40A:
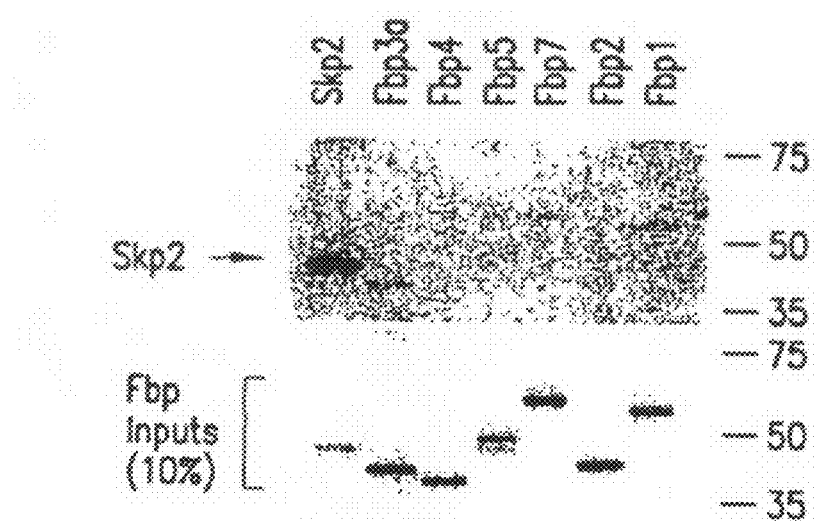
Figure 40B:
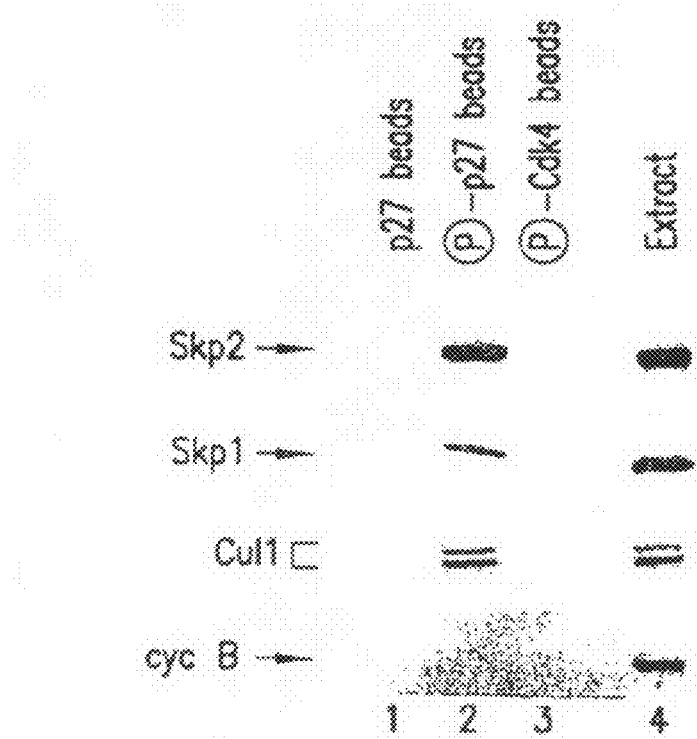
Figure 40C:
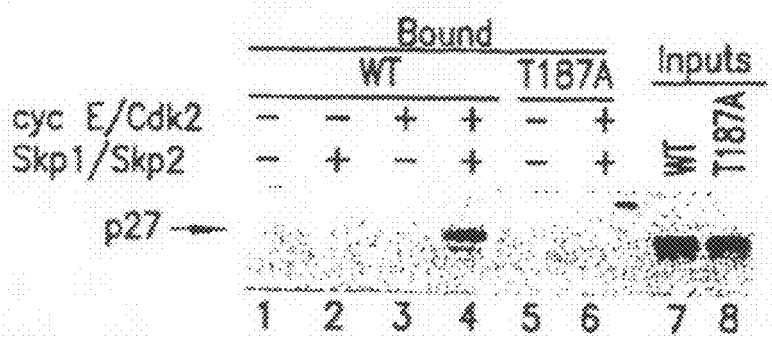

FIGS. 40A-C. Binding of phosphorylated p27 to Skp2. A. A panel of in vitro translated [35S]FBPs were used in binding reactions with beads coupled to the phospho-peptide NAGSVEQT*PICKPGLRRRQT (SEQ ID NO: 97), corresponding to the carboxy terminus of the human p27 with a phosphothreonine at position 187 (T*). Beads were washed with RIPA buffer and bound proteins were eluted and subjected to electrophoresis and autoradiography (Upper Panel). Bottom Panel: 10% of the in vitro translated [35S]FBP inputs. B. HeLa cell extracts were incubated with beads coupled to the phospho-p27 peptide (lane 2), an identical except unphosphorylated p27 peptide (lane 1) or the control phospho-peptide AEIGVGAY*GTVYKARDPHS (SEQ ID NO: 98), corresponding to an amino terminal peptide of human Cdk4 with a phosphotyrosine at position 17 (Y*) (lane 3). Beads were washed with RIPA buffer and bound proteins were immunoblotted with antibodies to the proteins indicated on the left of each panel. A portion of the HeLa extract (25 μg) was used as a control (lane 4). The slower migrating band in Cul1 is likely generated by the covalent attachment of a ubiquitin-like molecule, as already described for other cullins 48. C. One μl of in vitro translated [35S] wild type p27 (WT, lanes 1-4) or p27(T187A) mutant (T187A, lanes 5-6) were incubated for 30 minutes at 30¼ C in 10 μA of kinase buffer. Where indicated, ~2.5 μmol of recombinant purified cyclin E/Cdk2 or ~1 pmole Skp2 (in Skp1/Skp2 complex) were added. Samples were then incubated with 6 μA of Protein-A beads to which antibodies to Skp2 had been covalently linked. Beads were washed with RIPA buffer and bound proteins subjected to electrophoresis and autoradiography. Lanes 1-6: Skp2-bound proteins; Lanes 7 and 8: 7.5% of the in vitro translated [35S] protein inputs.

Figure 41:
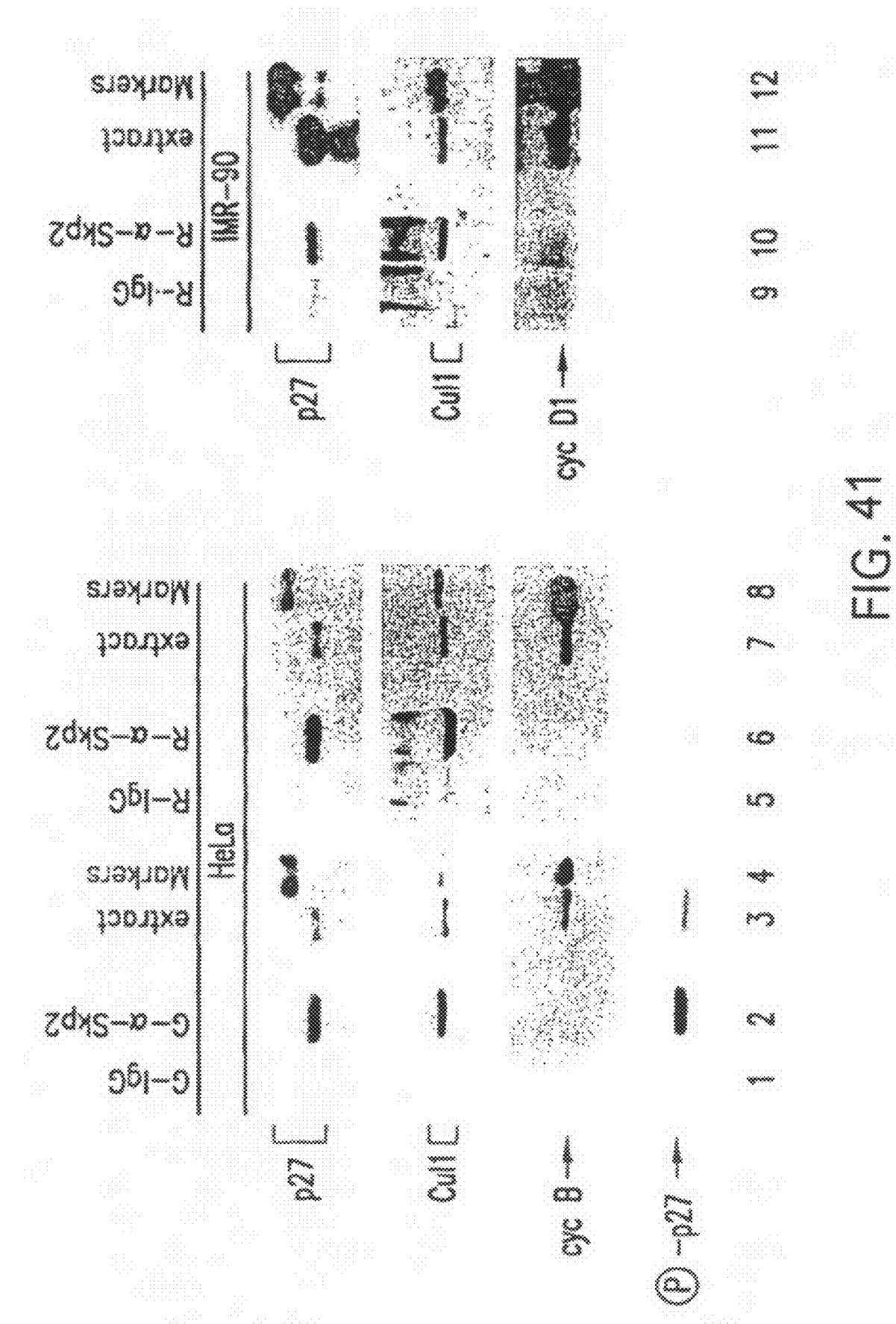

FIG. 41. In vivo binding of Skp2 to p27. Extracts from HeLa cells (lanes 1-2 and 5-6) or IMR90 fibroblasts (lanes 9-10) were immunoprecipitated with different affinity purified (AP) antibodies to Skp2 or with purified control IgG fractions. Lane 1: extract immunoprecipitated with a goat IgG (G-IgG); lane 2: with an AP goat antibody to an N-terminal Skp2 peptide (G-α-Skp2,); lanes 5 and 9: with a rabbit IgG (R-IgG); lanes 6 and 10: with an AP rabbit antibody to Skp2 (R-α-Skp2). Immunoprecipitates were immunoblotted with antibodies to the proteins indicated on the left of each panel. Lanes 1-4 in the bottom panel were immunoblotted with a phospho-site p27 specific antibody. Lanes 3, 7, and 11 contain 25 μg of cell extracts; Lanes 4, 8, and 12 contain the relevant recombinant proteins used as markers. The altered migration of some markers is due to the presence of tags on the recombinant proteins.

Figure 42:
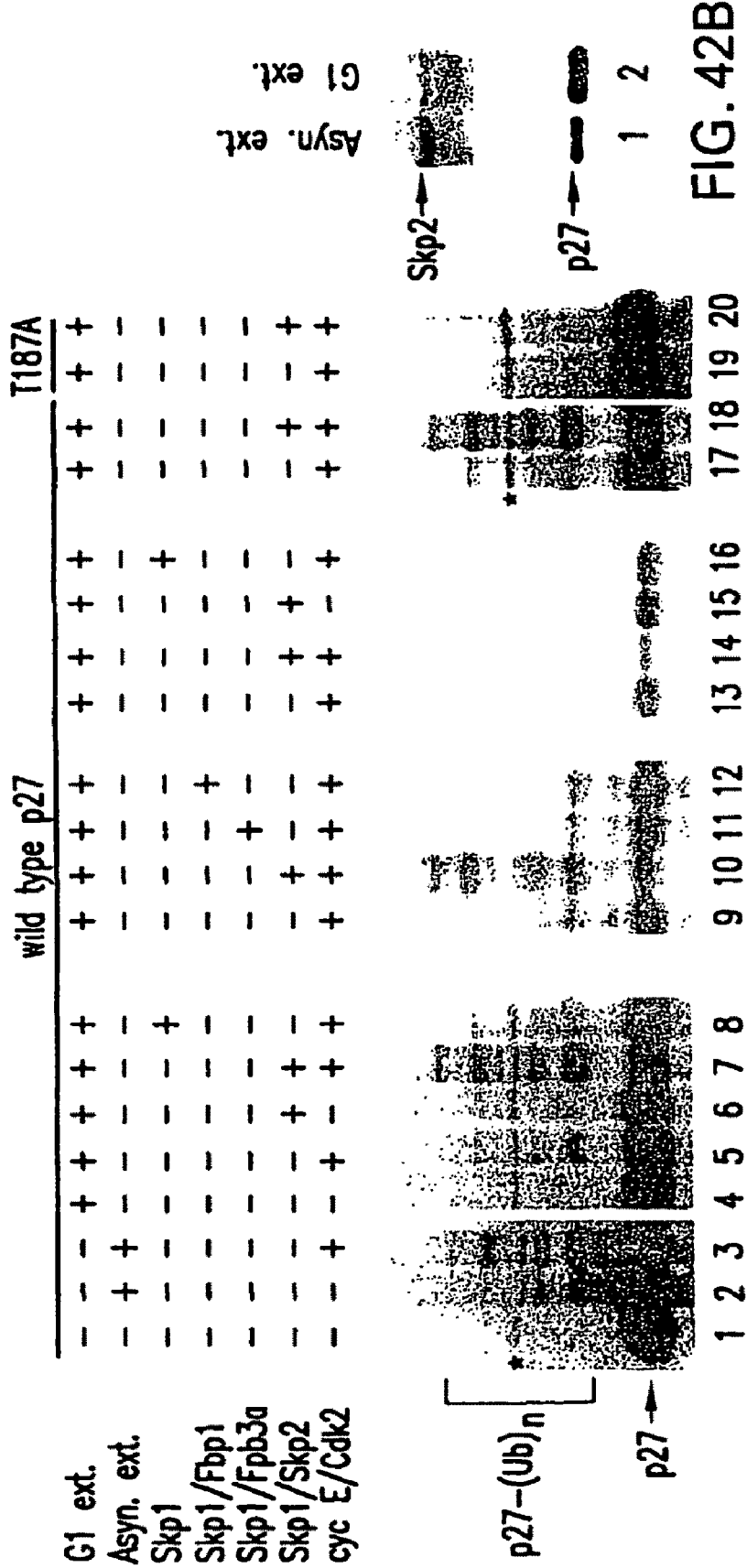

FIG. 42 A-B. Skp2 and cyclin E/Cdk2 complex are rate-limiting for p27 ubiquitination in G1 extracts. A. In vitro ubiquitin ligation (lanes 1-12 and 17-20) and degradation (lanes 13-16) of p27 were carried out with extracts from asynchronously growing (Asyn. ext., lanes 2-3) or G1-arrested (G1 ext., lanes 4-20) HeLa cells. Lane 1 contains no extract. Recombinant purified proteins were supplemented as indicated. Reactions were performed using wild-type p27 (lanes 1-18) or p27(T187A) mutant (T187A, lanes 19-20). Lanes 1-8, 9-12, and 17-20 are from three separate experiments. The bracket on the left side of the panels marks a ladder of bands>27,000 corresponding to polyubiquitinated p27. The asterisk indicates a non-specific band present in most samples. B. Immunoblot analysis of levels of Skp2 and p27 in extracts from asynchronous (lane 1) or G1-arrested (lane 2) HeLa cells.

Figure 43:
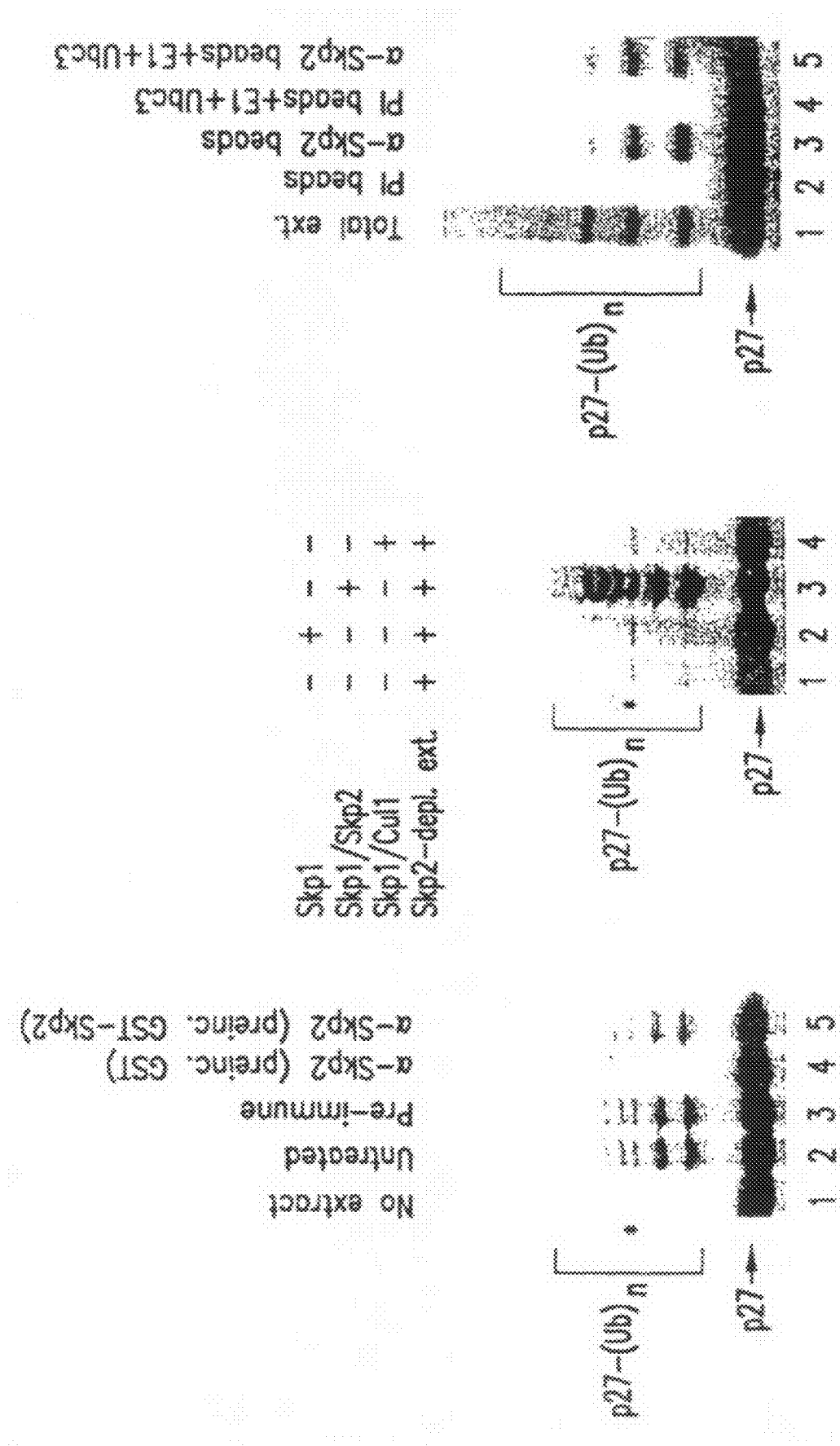

FIG. 43 A-C. Skp2 is required for p27-ubiquitin ligation activity. A. Immunodepletion. Extracts from asynchronous HeLa cells were untreated (lane 2) or immunodepleted with pre-immune serum (lane 3), anti-Skp2 antibody pre-incubated with 2 µg of purified GST (lane 4), or anti-Skp2 antibody pre-incubated with 2 µg of purified GST-Skp2 (lane 5). Lane 1 contains no extract. Samples (30 µg of protein) were assayed for p27 ubiquitination in the presence of cyclin E/Cdk2. The bracket on the left side of the panels marks a ladder of bands>27,000 corresponding to polyubiquitinated p27. The asterisk indicates a non-specific band present in all samples. B. Reconstitution. The restoration of p27 ubiquitination activity in Skp2-immunodepleted extracts was tested by the addition of the indicated purified proteins. All samples contained 30 µg of Skp2-depleted extract (Skp2-depl. ext.) and cyclin E/Cdk2. C. Immunopurification. Extracts from asynchronous HeLa cells were immunoprecipitated with a rabbit anti-Skp2 antibody (lanes 3 and 5) or pre-immune serum (PI, lanes 2 and 4). Total extract (lane 1) and immunobeads (lanes 2-5) were added with p27, recombinant purified cyclin E/Cdk2 and ubiquitination reaction mix. Samples in lanes 4 and 5 were supplemented with recombinant purified E1 and Ubc3. All samples were then assayed for p27 ubiquitination.

Figure 44:

FIG. 44 A-B. In vivo role of Skp2 in p27 degradation. A. Stabilization of p27 by a dominant negative (DF)Skp2 mutant in vivo. NIH-3T3 cells were transfected with mammalian expression vectors encoding human p27 alone (lane 2), p27 in combination with either (DF)Skp2 (lane 3), or (DF)FBP1 (lane 4). Lane 1: untransfected cells. Cells were lysed and extracts were subjected to immunoblotting with antibodies to p27, Skp2 or Flag [to detect Flag-tagged (DF)FBP1]. Exogenous human p27 protein migrates more slowly than the endogenous murine p27. B. Pulse chase analysis of p27 turnover rate. Human p27 in combination with either an empty vector, or (DF)Skp2 was transfected in NIH-3T3 cells. Twenty-four hours later, cells were labeled with [35S]-methionine for 20 minutes and chased with medium for the indicated times. Extracts were then subjected to immunoprecipitation with a mouse anti-p27 antibody.

Figure 45:
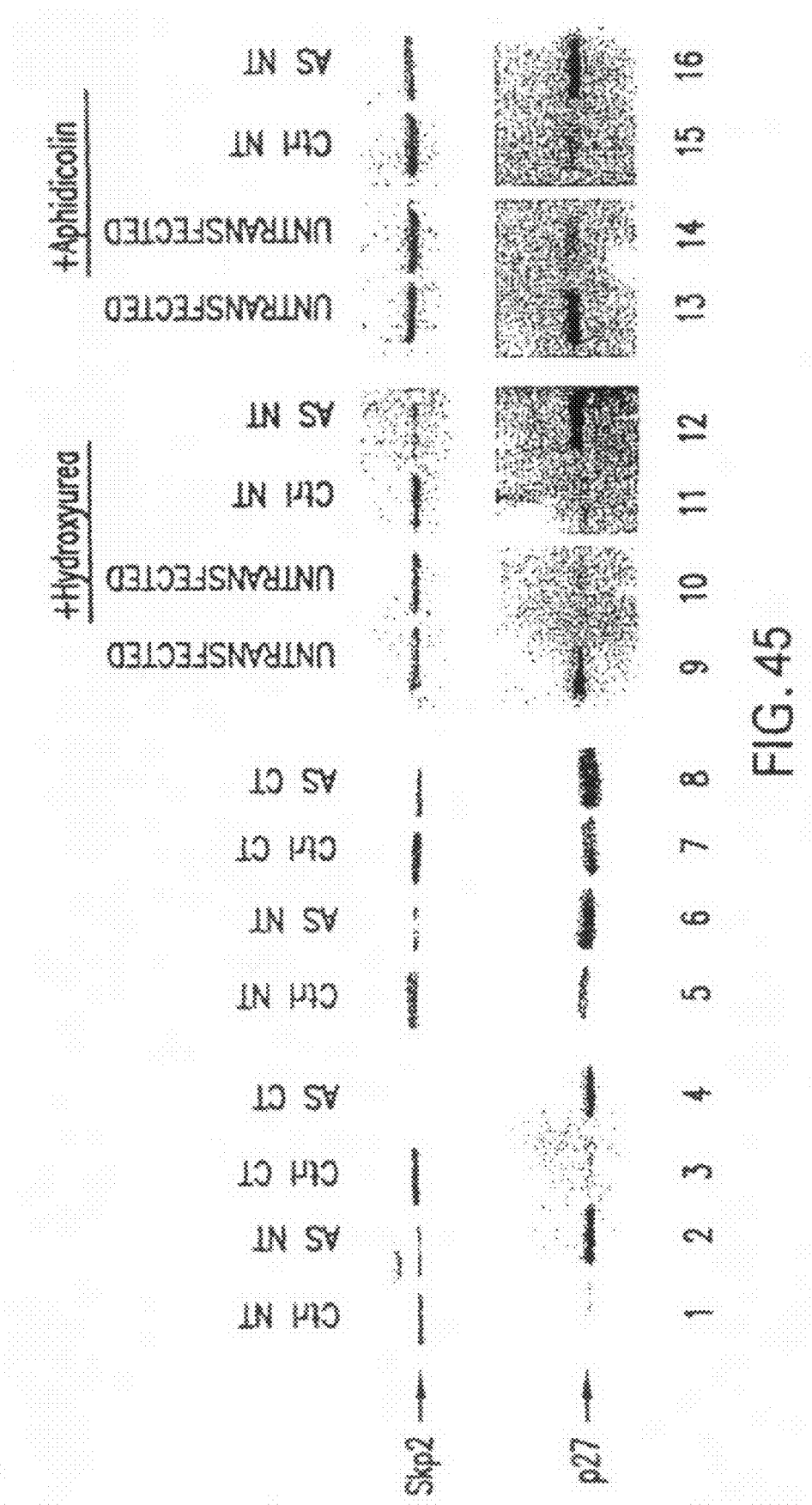

FIG. 45. Stabilization of cellular p27 by antisense oligonucleotides targeting SKP2 mRNA. HeLa cells were treated for 16-18 hours with two different anti-sense oligodeoxynucleotides (AS) targeting two different regions of SKP2 mRNA. Lanes 2, 6, 12 and 16: AS targeting the N-terminal SKP2 region (NT); Lanes 4 and 8: AS targeting the C-terminal SKP2 region (CT); Lanes 1, 3, 5, 7 11 and 15: control oligodeoxynucleotides pairs (Ctrl). Lanes 1-4, and 5-8 are from two separate experiments. Lanes 11-12 and 15-16: HeLa cells were blocked in G1/S with either Hydroxyurea or Aphidicolin treatment respectively, for 24 hours. Cells were then transfected with oligodeoxynucleotides, lysed after 12 hours (before cells had re-entered G1) and immunoblotted with antibodies to Skp2 (top panels) and p27 (bottom panels). Lanes 9 and 13: Untransfected HeLa cells; Lanes 10 and 14: Untransfected HeLa cells treated with drugs as transfected cells.

Figures 46A, 46B, 46C:
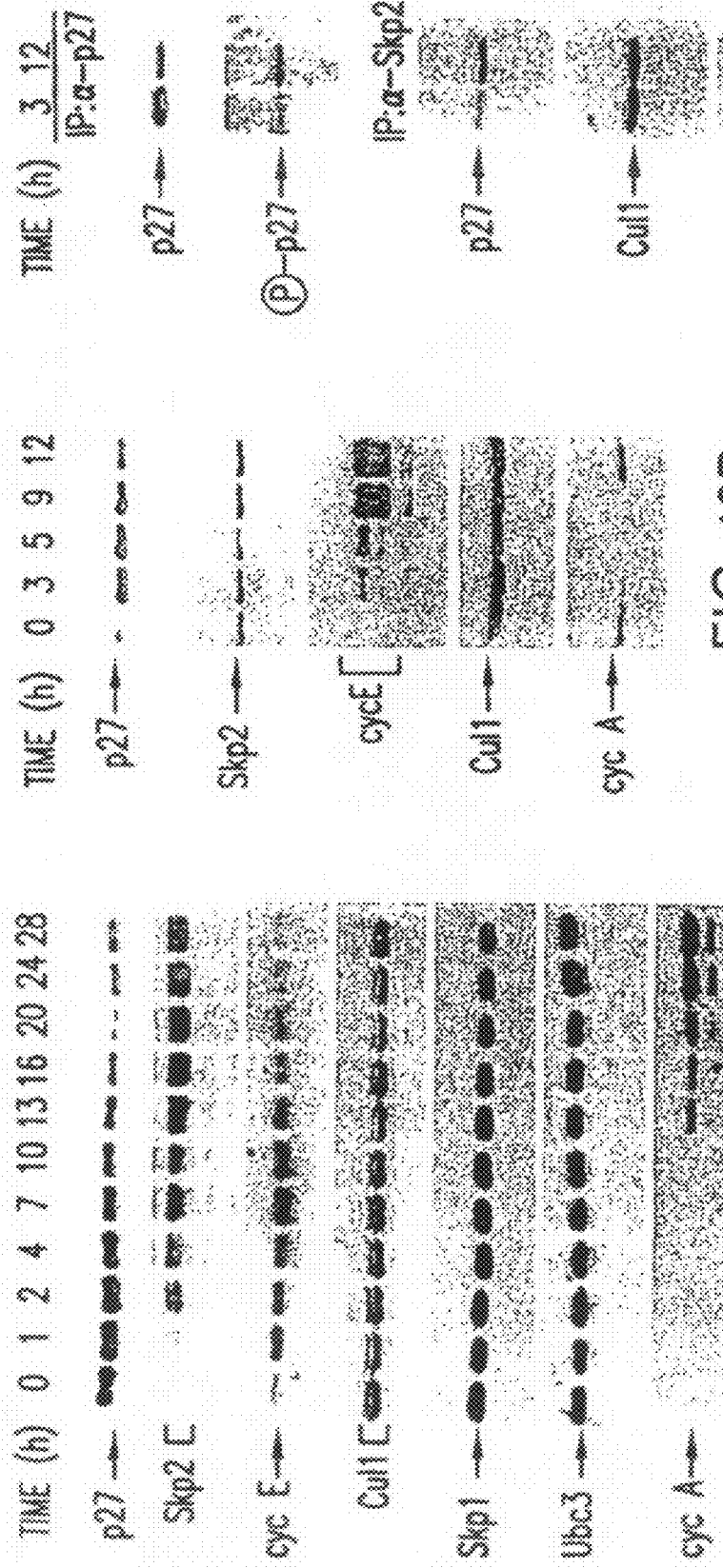

FIG. 46 A-C. Timing of Skp2 action in the process of p27 degradation. A. IMR90 fibroblasts were synchronized in G0/G1 by scrum deprivation, reactivated with serum, and sampled at the indicated intervals. Protein extracts were analyzed by immunoblot with the antibodies to the indicated proteins. The Skp2 doublet was likely generated by phosphorylation since was consistently observed using a 12.5% gel only when cell lysis was performed in the presence of okadaic acid. B. HeLa cells blocked in mitosis with nocodazole were shaken off, released in fresh medium and sampled at the indicated intervals. Protein extracts were analyzed by immunoblotting with the antibodies to the indicated proteins. C. Extracts from G1 (3 hours after release from nocodazole block) (lane 1) and S-phase (12 hours after release from the nocodazole block) (lane 2) HeLa cells were either immunoprecipitated with an anti-p27 antibody (top two panels) or with an anti-Skp2 antibody (bottom three panels) and then immunoblotted with the antibodies to the indicated proteins.

Figure 47:
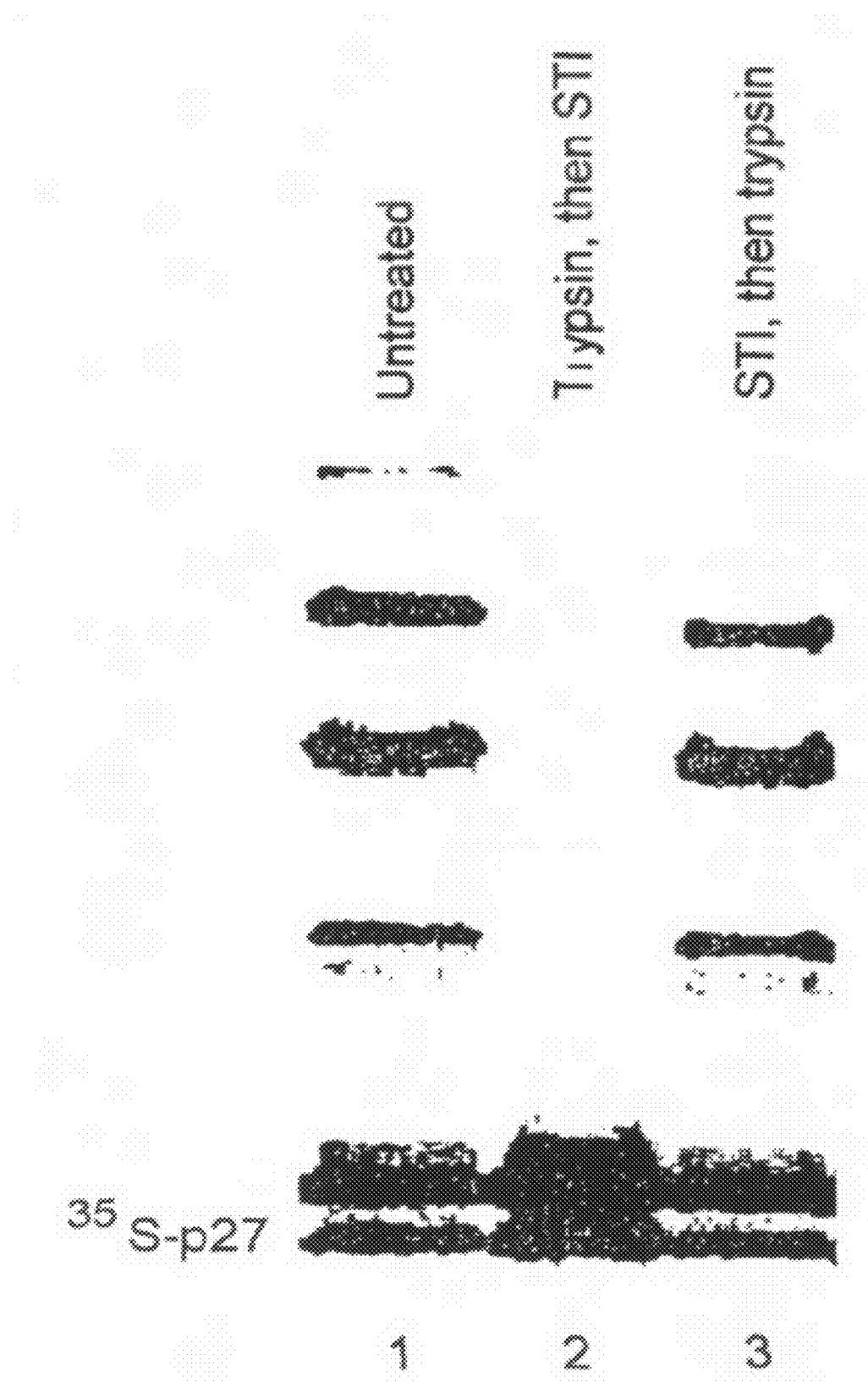

FIG. 47. The heat-stable factor is sensitive to trypsin action. Heat-treated Fraction 1 (~0.1 mg/ml) was incubated at 37° C. for 60 min with 50 mM Tris-HCl (pH 8.0) either in the absence (lane 1) or in the presence of 0.6 mg/ml of TPCK-treated trypsin (Sigma T8642) (lane 2). Trypsin action was terminated by the addition of 2 mg/ml of soybean trypsin inhibitor (STI). In lane 3, STI was added 5 min prior to a similar incubation with trypsin. Subsequently, samples corresponding to ~50 ng of heat-treated Fraction 1 were assayed for the stimulation of p27-ubiquitin ligation.

FIG. 48 A-C. The heat-stable factor is not Nedd8 and is required following the modification of Cul-1 by Nedd8. A. Purified Nedd8 does not replace the factor in the stimulation of p27-ubiquitin ligation. Where indicated, ~50 ng of heat-treated Fraction 1 or 100 ng of purified recombinant human Nedd8 were added to the p27-MeUb ligation assay. B. Ligation of Nedd8 to Cul-1. Cul-1/ROC1 (3 µl) was incubated with Nedd8 (10 µg) and purified Nedd8-conjugating enzymes (20 µl) in a 100-µl reaction mixture containing Tris (pH 7.6), $MgCl_2$, ATP, phosphocreatine, creatine phosphokinase, DTT, glycerol and STI at concentrations similar to those described for the p27-ubiquitin ligation assay. A control preparation of Cul1/ROC1 was incubated under similar conditions, but without Nedd8 conjugating enzymes. Following incubation at 30° C. for 2 hours, samples of control (lane 1) or Nedd8-modified (lane 2) preparations were separated on an 8% polyacrylamide-SDS gel and immunoblotted with an anti-Cul-1 antibody (Zymed). C. $SCF^{Skp2}$ complex containing Nedd8-modified Cul-1 still requires the factor from Fraction 1 for p27-ubiquitin ligation. p27-MeUb ligation was assayed, except that $^{35}S$-labeled p27 was replaced by bacterially expressed purified p27 (20 ng), and Cul-1/ROC1 was replaced by 2 µl of the unmodified or Nedd8-modified Cul-1/ROC1 preparations. Following incubation (30° C., 60 min), samples were separated on a 12.5% polyacrylamide-SDS gel, transferred to nitrocellulose and blotted with an anti-p27 monoclonal antibody (Transduction Laboratories). A cross-reacting protein is labeled by an asterisk.

FIG. 49 A, B. Purification of the factor required for p27-ubiquitin ligation and its identification as Cks1. A. Last step of purification by gel filtration chromatography. The peak of active material from the MonoS step was applied to a Superdex 75 HR 10/30 column (Pharmacia) equilibrated with 20 mM Tris-HCl (pH 7.2), 150 mM NaCl, 1 mM DTT and 01% Brij-35. Samples of 0.5 ml were collected at a flow rate of 0.4 ml/min. Column fractions were concentrated to a volume of 50 µl by centrifuge ultrafiltration (Centricon-10, Amicon). Samples of 0.004 µl of column fractions were assayed for activity to stimulate p27-ubiquitin ligation. Results were quantified by phosphorimager analysis and were expressed as the percentage of $^{35}S$-p27 converted to ubiquitin conjugates. Arrows at top indicate the elution position of molecular mass marker proteins (kDa). B. Silver staining of samples of 2.5 µl from the indicated fractions of the Superdex 75 column, resolved on a 16% polyacrylamide-SDS gel. Numbers on the right indicate the migration position of molecular mass marker proteins (kDa).

Figure 50:
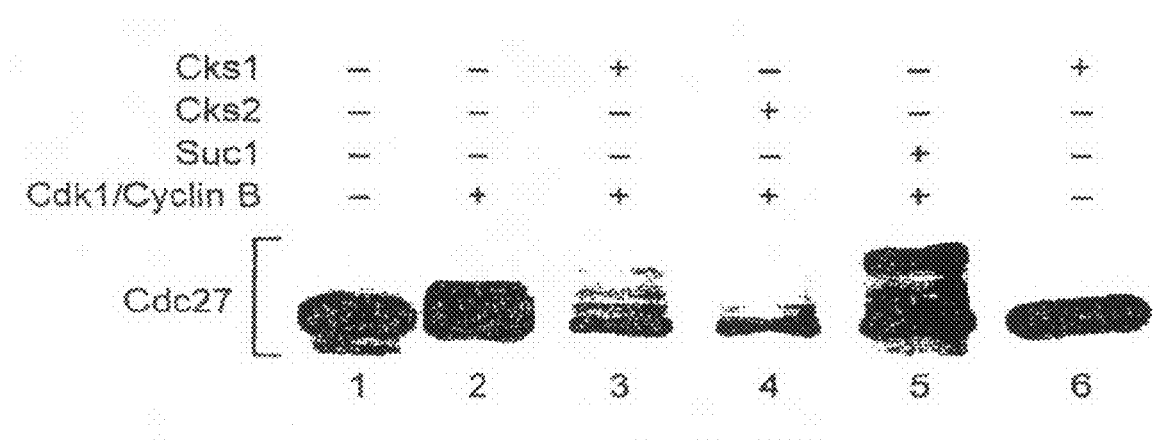

FIG. 50. All bacterially expressed Cks/Suc1 proteins stimulate the multi-phosphorylation of the Cdc27 subunit of the cyclosome/APC. Cyclosomes from S-phase HeLa cells were partially purified and incubated with 500 units of Suc1-free Cdk1/cyclin B (Shteinberg and Hershko, 1999, *Biochem. Biophys. Res. Commun.* 257:12; Yudkovsky, et al., 2000, *Biochem. Biophys. Res. Commun.* 271:299). Where indicated, 10 ng/µl of the corresponding Cks/Suc1 protein was supplemented. The samples were subjected to immunoblotting with a monoclonal antibody directed against human Cdc27 (Transduction Laboratories).

Figure 51A:
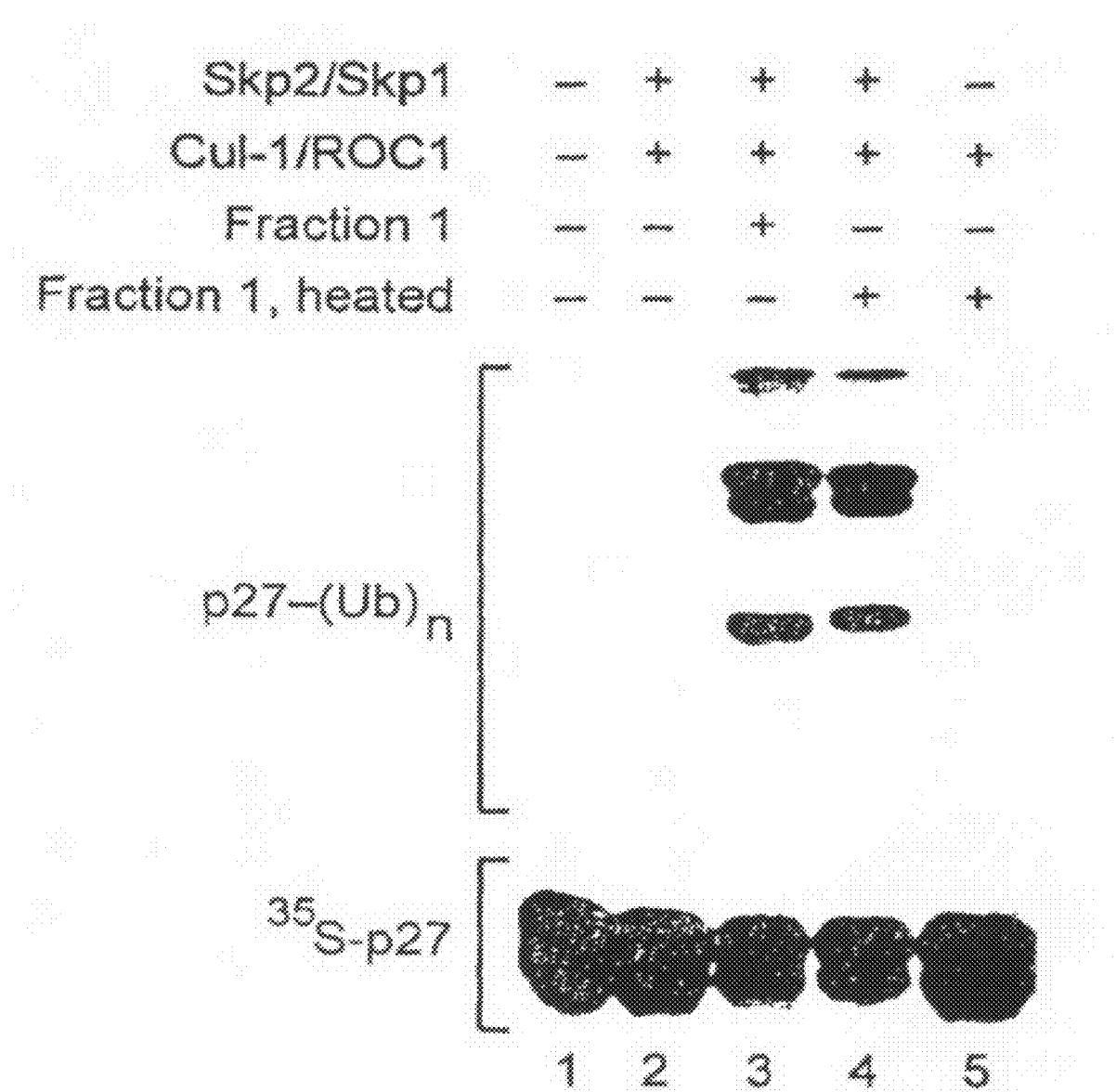

FIG. 51A, B. Identification of the factor required for p27-ubiquitin ligation as Cks1. A. The ligation of $^{35}$S-p27 to MeUb was assayed. Where indicated, Fraction 1 (5 µg protein) or heat-treated Fraction 1 (~50 ng) were added. The bracket on the left side of the panels marks a ladder of bands>27,000 Da corresponding to polyubiquitinated p27. B. Cks1, but not other Cks proteins, is required for p27-ubiquitin ligation. Where indicated, the following proteins were added: "Factor", 0.02 µl of pooled fractions #28-29 from the peak of the Superdex column, which is the last step of purification of the factor required for p27 ubiquitinylation; "Cks1 IVT", 0.3 µl of in-vitro translated Cks1; "Cks2 IVT", 0.3 µl of in vitro-translated Cks2; "Retic. lys.", 0.3 ml of reticulocyte lysate translation mix; Cks1, Cks2 and Suc1, 2 ng of the corresponding bacterially expressed, purified proteins. In vitro-translated $^{35}$S-labeled Cks1 and Cks2 in lanes 3 and 4 are not visible since they migrated off the gel.

FIG. 52 A-D. Cks1 increases the binding of phosphorylated p27 to Skp2. A. Cks1 does not affect the phosphorylation of p27 by Cdk2/cyclin E. Purified p27 was phosphorylated with the only difference that the mixtures were incubated at 20° C. for the time periods indicated. Where indicated, 2 ng of purified Cks1 was added. Samples of 1 µl were taken for SDS-polyacrylamide gel electrophoresis and autoradiography. B. Cks1 acts at a stage subsequent to the phosphorylation of p27. $^{32}$P purified p27 was prepared Where indicated, 0.02 µl of "Factor" (purified as in FIG. 46) or 1 ng of purified recombinant human Cks1 were added. Using this purified system, we have not observed conjugates with MeUb larger than the di-ubiquitinylated form, as opposed to the 4-5 conjugates observed using in vitro-translated $^{35}$S-p27 (compare with FIG. 46). Possibly, ubiquitin is ligated to only two Lys residues in p27, and the larger conjugates may contain short polyubiquitin chains (derived from ubiquitin present in reticulocyte lysates) terminated by MeUb. C. Cks1 increases the binding of p27 to Skp2/Skp1, dependent upon phosphorylation of Thr-187. The binding of $^{35}$S-labeled wild-type (WT) or Thr-187-Ala mutant p27 (T187A) to Skp2/Skp1 was determined. Where indicated, 1 ng of purified Cks1 was added to the incubation. Inputs show 5% of the starting material. D. Cks1 increases the binding of $^{32}$P-p27 to Skp2/Skp1. The experiment was similar to that described in FIG. 48, except that $^{35}$S-p27 was replaced by $^{32}$P-labeled purified p27.

FIG. 53 A-D. Binding of Cks1 to Skp2 and phosphorylated p27. A. Cks1 but not Cks2 binds to Skp2/Skp1. The binding of $^{35}$S-labeled Cks1 or Cks2 to Skp2/Skp1 was assayed by a procedure similar to that described for the binding of p27 to Skp2/Skp1, except that Cdk2/cyclin E, ATP and the ATP-regenerating system were omitted. Where indicated, 1 µl of Skp2/Skp1 was added. Cks1 does not bind to Skp1. The binding of $^{35}$S-Cks 1 to His$_6$-Skp1 or to the Skp2/His$_6$-Skp1 complex (1 µl each) was determined as described in 3a, except that Ni-NTA-agarose beads (Quiagen, 10 µl) were used for precipitation. In both 3a and 3b, inputs show 5% of the starting material. C. Cks 1 stimulates the binding of Skp2 to p27 phosphopeptide. Sepharose beads to which a peptide corresponding to 19 C-terminal amino acid residues of p27 ("p27 beads"), or to a similar peptide containing phosphorylated Thr187 ("P-p27 beads") were prepared as described in Carrano, et al., 1999, *Nat. Cell Biol.* 1:193. In vitro-translated $^{35}$S-Skp2 (3 µl) was mixed with 15 µl of the corresponding beads in the absence (lanes 1 and 3) or in the presence of 10 ng (lane 4) or 100 ng (lanes 2 and 5) of Cks 1. Following rotation at 4° C. for 2 hours, beads were washed 4 times with RIPA buffer. D. Cks1 binds to p27 phosphopeptide. $^{35}$S-Cks1 (2 µl) was mixed with the indicated beads, and beads were treated as in FIG. 3c. Inputs show 10% of the starting material.

Figure 54A:
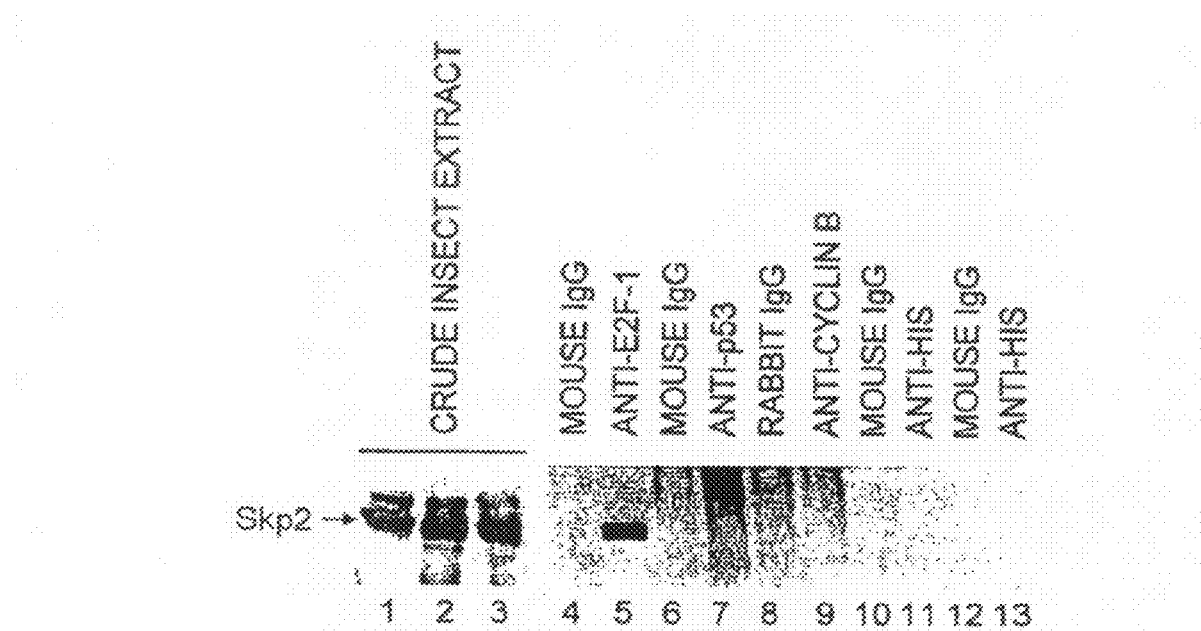

FIG. 54 A-C. Western blot analysis of Skp2/E2F interaction assay. Details of the Western Blot experiments are given in the Example in Section 9.

Figure 55:
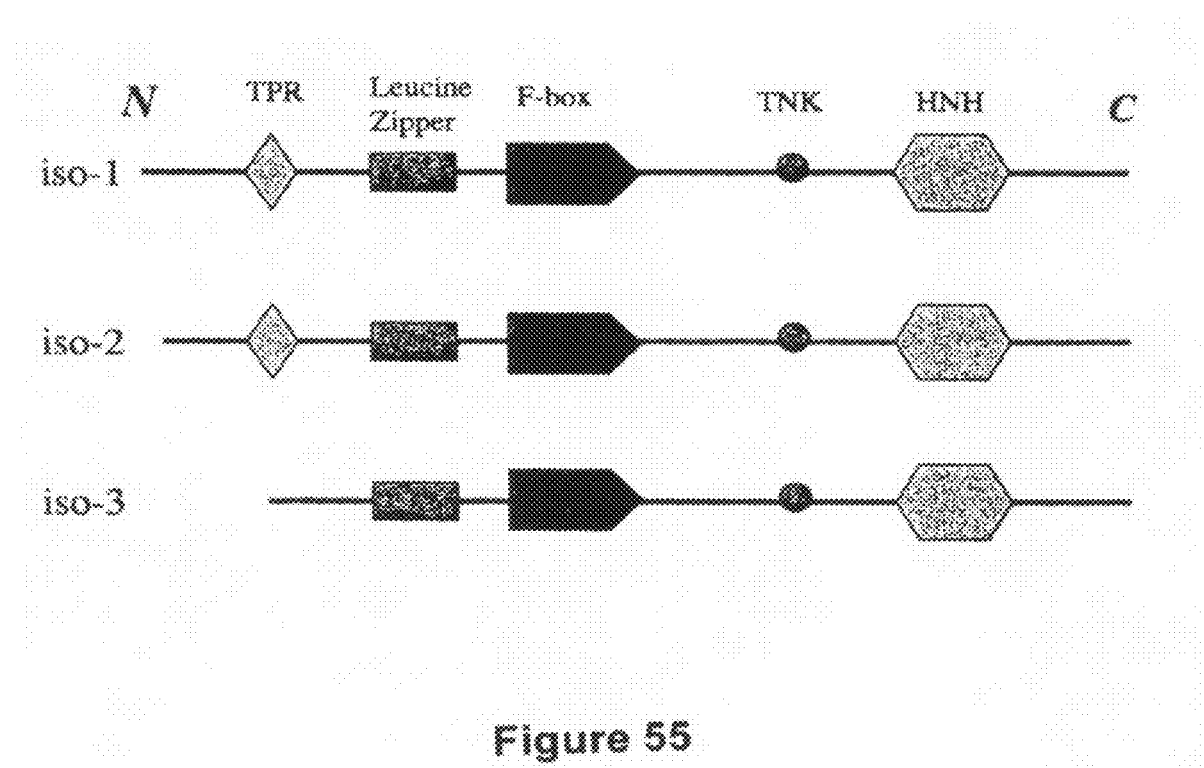

FIG. 55. Schematic representation of three isoforms of Fbx9 containing protein-protein and protein-DNA interaction domains.

Figure 56:
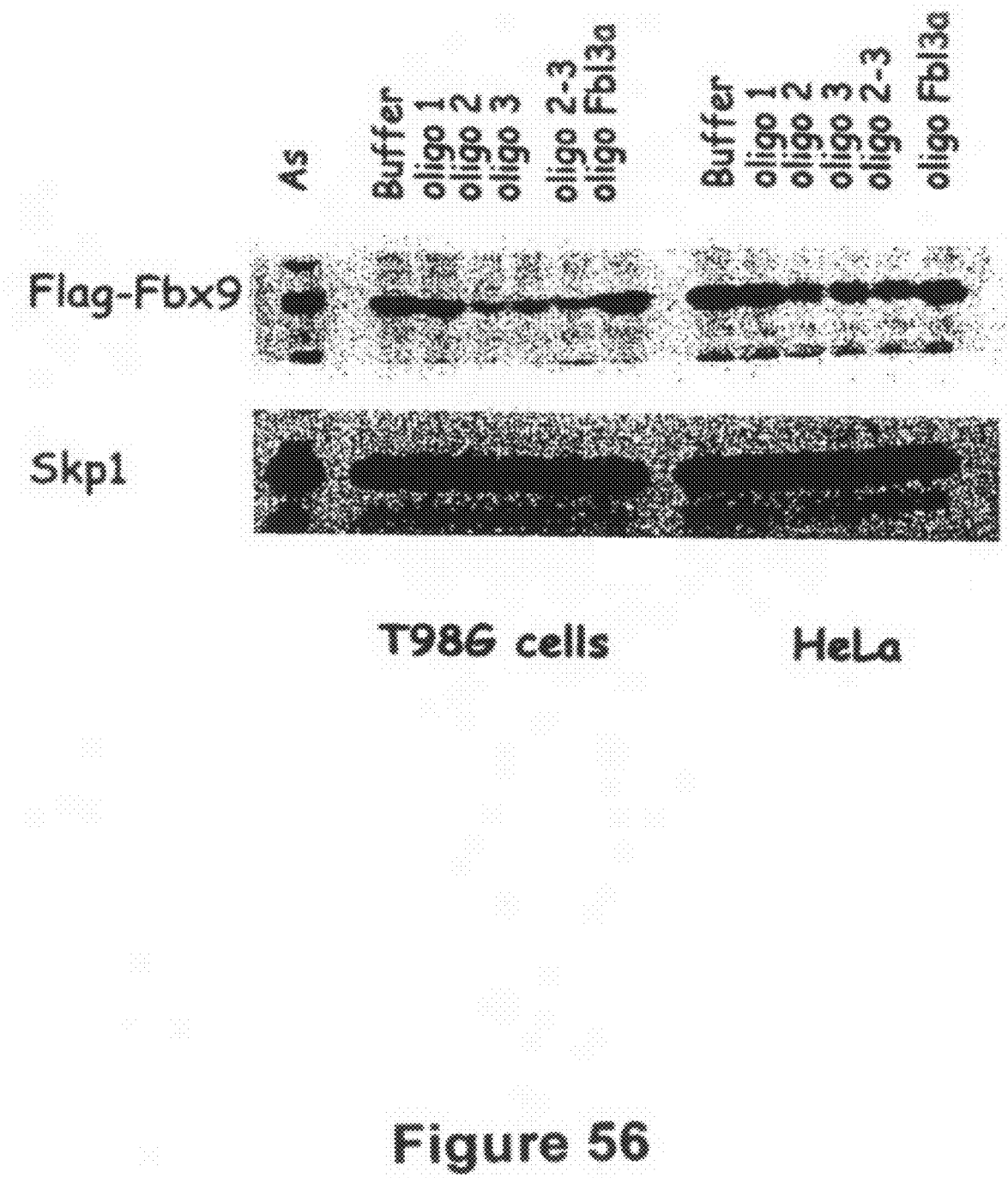

FIG. 56. sRNA silencing of Fbx9. T986 and HeLa cells were transfected with the mammalian expression vector pcDNA3 containing cDNA fragments encoding Flag-tagged Fbx9 as described in section 7.1. Following two transfections with sRNA at 24 and 48 h after replating using Oligofectamine (Invitrogen), whole cell lysates were prepared and analyzed by western blot using anti-Flag antibodies (Sigma). The level of Skp-2 protein in the lysates was similarly analyzed using anti-Skp1 antibody prepared as described in section 7.1 served for comparison.

FIG. 57. Cell cycle analysis of Hela Cells subjected to Fbx9 silencing and UV irradiation. Cell cycle phases were monitored by flow cytometry (FACSCAN, Becton Dickinson) after staining cellular DNA with 50 µg/ml propidium iodide (Sigma) in the presence of 10 µg/ml DNase-free RNase and by BrdU incorporation. Cell monolayers were exposed to UV light in a UVC 515 Ultraviolet Multilinker (245 nm, Ultra Lum).

Figure 58:
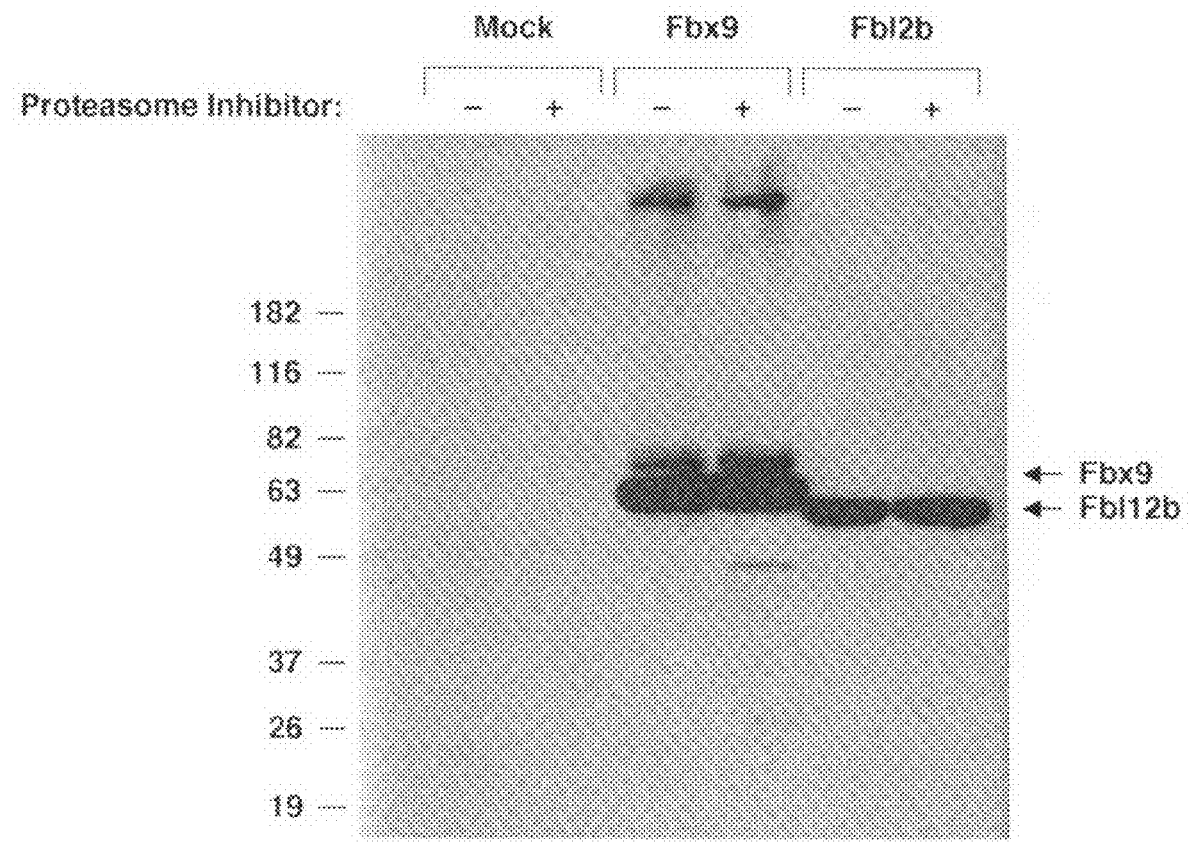

FIG. 58. The protein level of Flag-tagged Fbx9 is not altered by treatment of cells with proteosome inhibitors. HEK293 cells were transiently transfected with an expression vector encoding Flag-tagged Fbx9, Fbl2b, or an empty control (cells were transfected using Lipofectamine 2000 (Invitrogen) according to the manufacturer's directions). Transfected HEK 293 cells were treated with 10 µM proteosome inhibitor, PS341, for 6 hours at 37 C, harvested and whole cell lysate prepared. Lysates were subjected to western blot analysis using anti-Flag antibody (Sigma).

Figure 59:
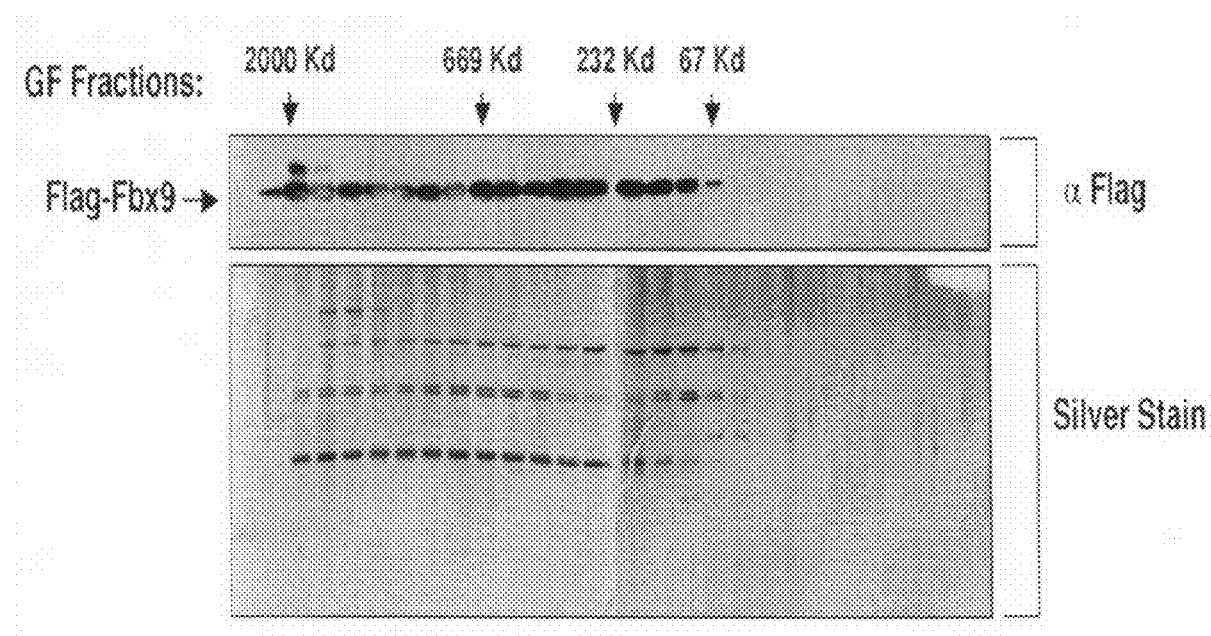

FIG. 59. Fbx9 exists as a higher order complex. Hek 293 cells were transfected with an expression vector encoding Flag-Fbx9 and incubated with PS341 proteosome inhibitor for 6 h at 37 C prior to harvesting to enhance the ability to isolate potential substrates and associated regulatory proteins. Immunoprecipitations were performed on WCEs using anti-Flag antibodies (Sigma). Precipitates were washed with buffer containing 0.5 M urea to remove non-specific binding proteins. The Fbx-9 containing complex was removed from the immunoprecipitate with excess Flag-peptide and fractionated by gel-filtration chromatography. Equal aliquots were analyzed by western blot with anti-Flag antibodies (upper panel) and silver stain (lower panel). Fractions corresponding to ~400 kD MW were pooled and concentrated for mass spectrometric sequencing analysis.

Figure 60:
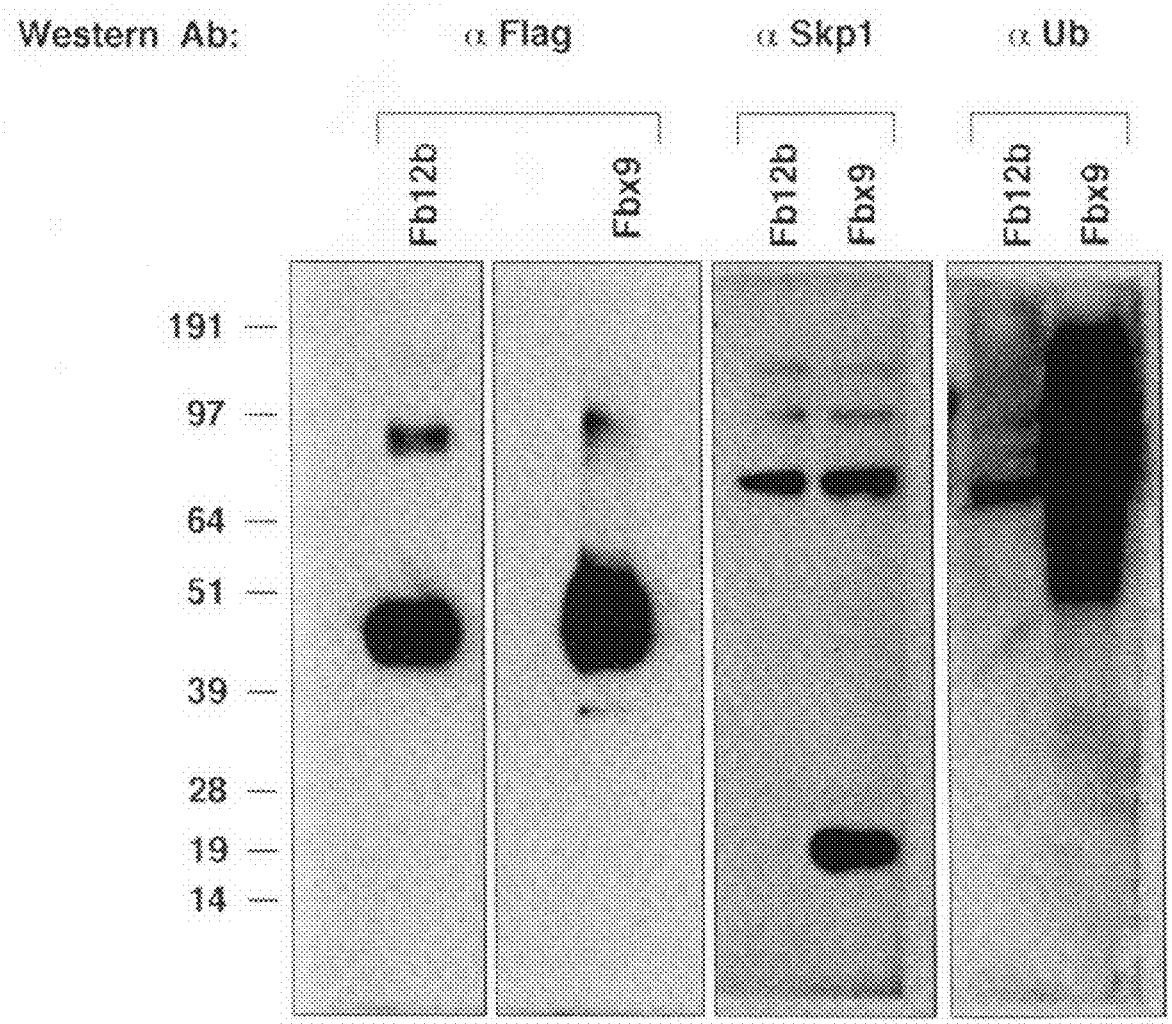

FIG. 60. Identification of Cul1 and Skp1 as Fbx9 binding/associated proteins implies the Fbx9 is a functional E3 ubiquitin ligase. Flag-purified Fbx9 extracts were subjected to western blot analysis using anti-Flag (Sigma, Cat#F3165), anti-Skp1 (Santa Cruz, Cat #SC-52-81) and anti-Ubiquitin (Covance, Cat # MMS-258R) antibodies. The molecular weight markers are indicated to the left of the figure.

Figure 61:
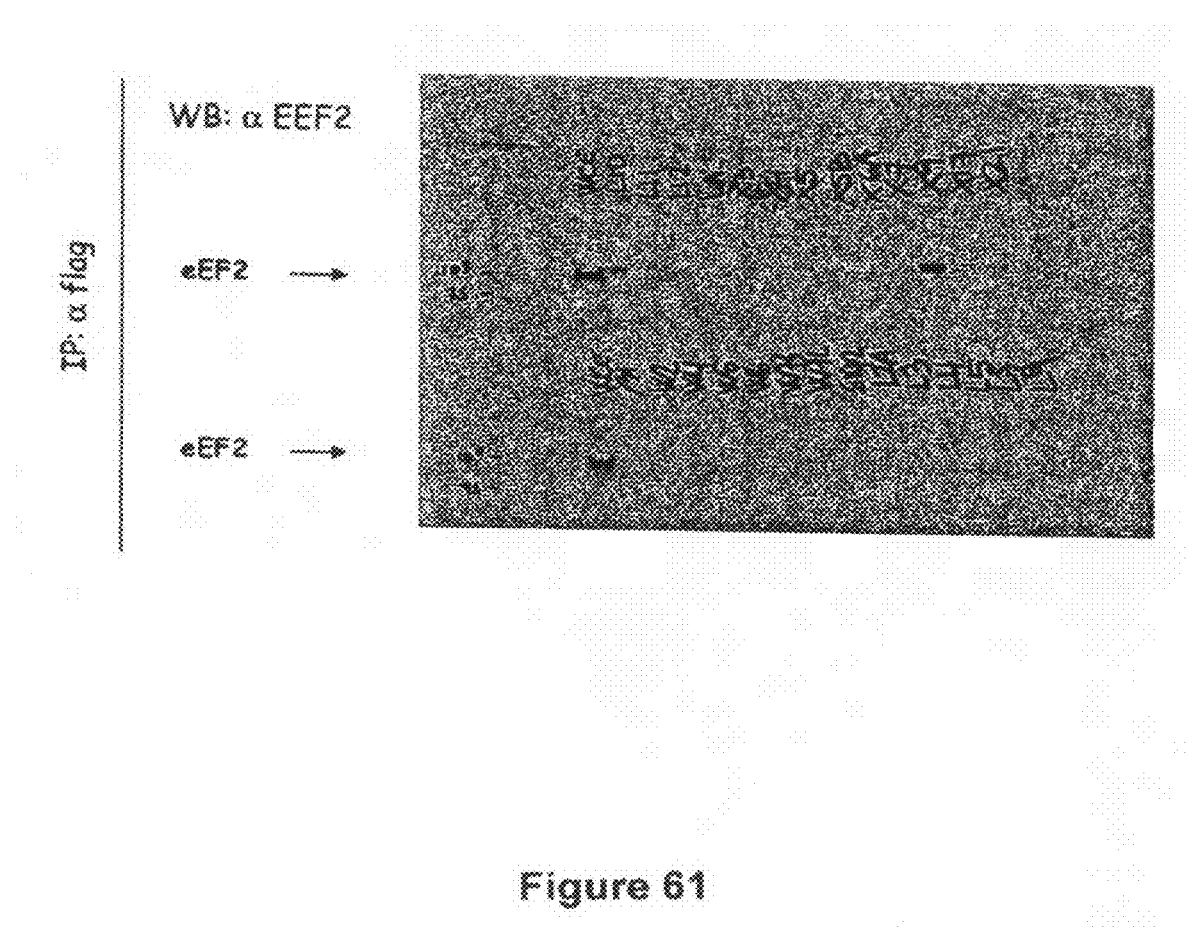

FIG. 61. Identification of eEF2 as an Fbx9 binding/associated protein. Flag-purified Fbx9 extracts were subjected to western blot analysis using anti-Flag (Sigma, Cat#F3165), and anti-eEF2 antibody (Zymed).

Figure 62:
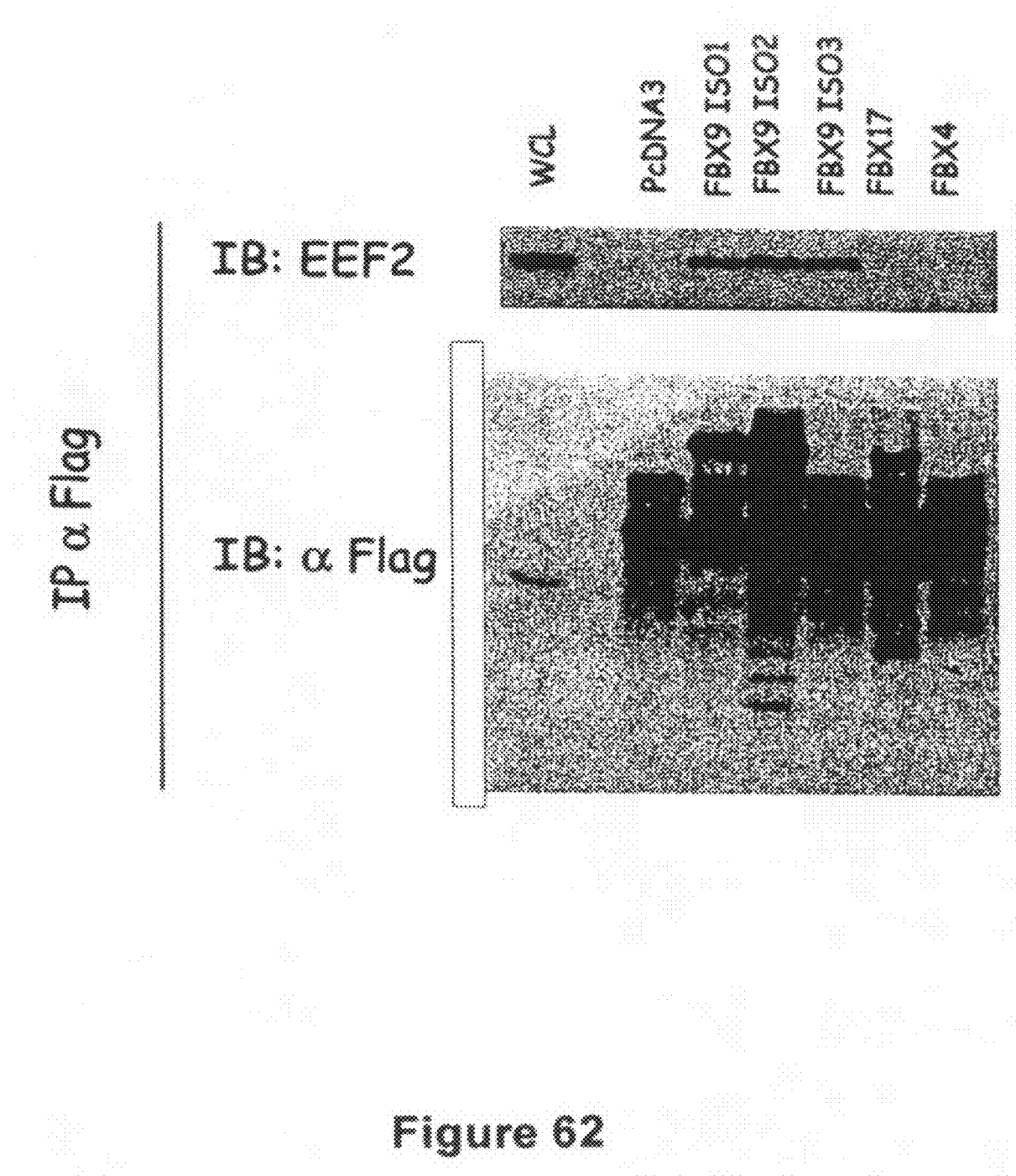

FIG. 62. Identification of eEF2 binding/association protein of 3 isoforms of Fbx9. Flag-purified Fbx9 extracts were subjected to western blot analysis using anti-Flag (Sigma, Cat#F3165), and anti-eEF2 antibody (Zymed).

Figure 63:
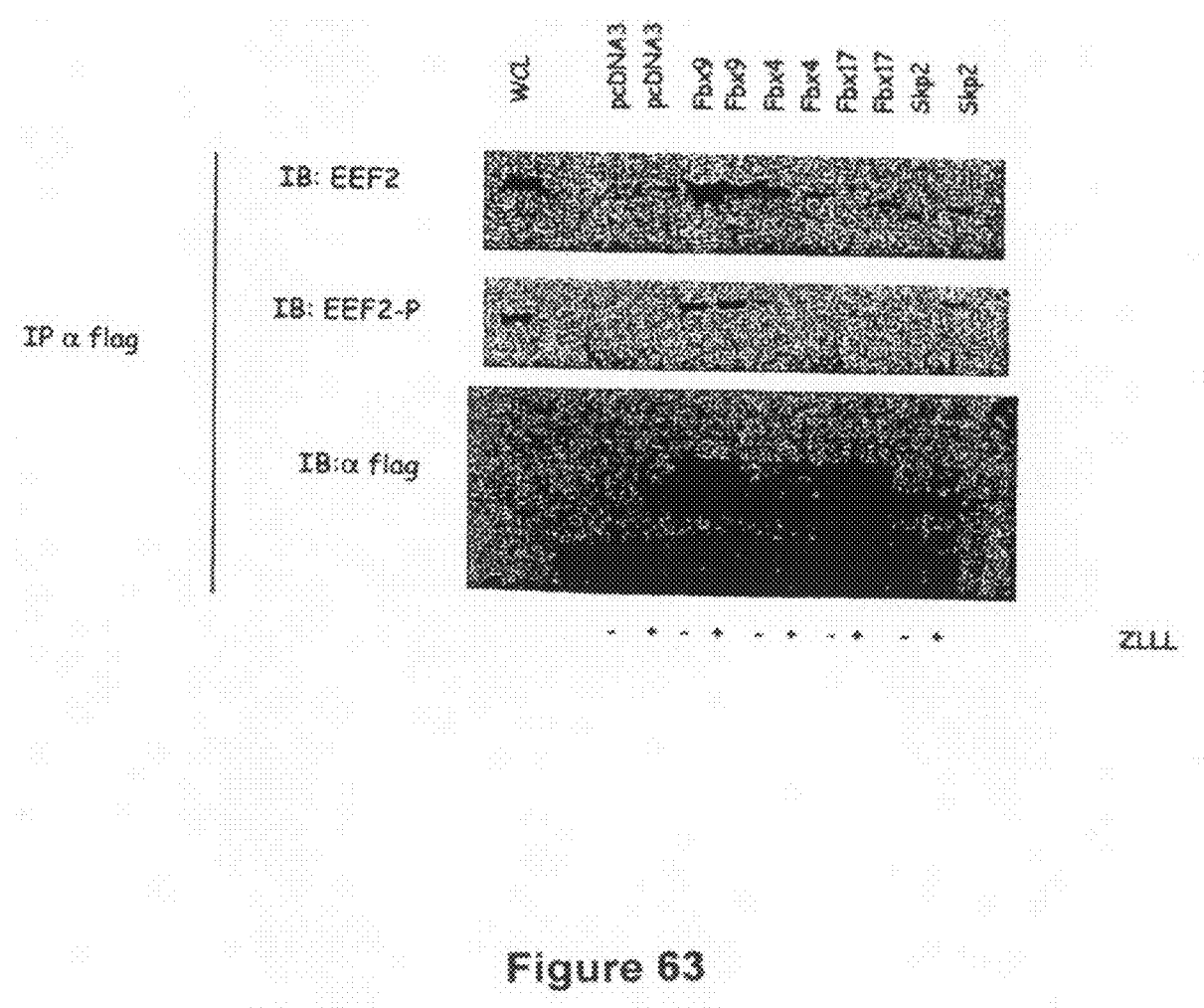

FIG. 63. The protein level of eEF2 in Flag-purified, Flag-Fbx9 expressing WCEs is not altered by treatment of cells with proteosome inhibitors. Flag-purified Flag-Fbx9 extracts were subjected to western blot analysis using anti-Flag (Sigma, Cat#F3165), and anti-eEF2 antibody (Zymed). The constant level expression of eEF2 in row 1 suggests the eEF2 is not a substrate for Fbx9 mediated ubiquitination.

Figure 64A:
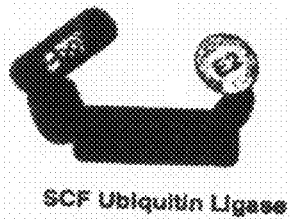
Figure 64B:

FIG. 64 A-B. A. Schematic representation of SCF Ubiquitin Ligase containing Fbl12. B. Schematic representation of Fbl12 containing LRR domain.

Figure 65:
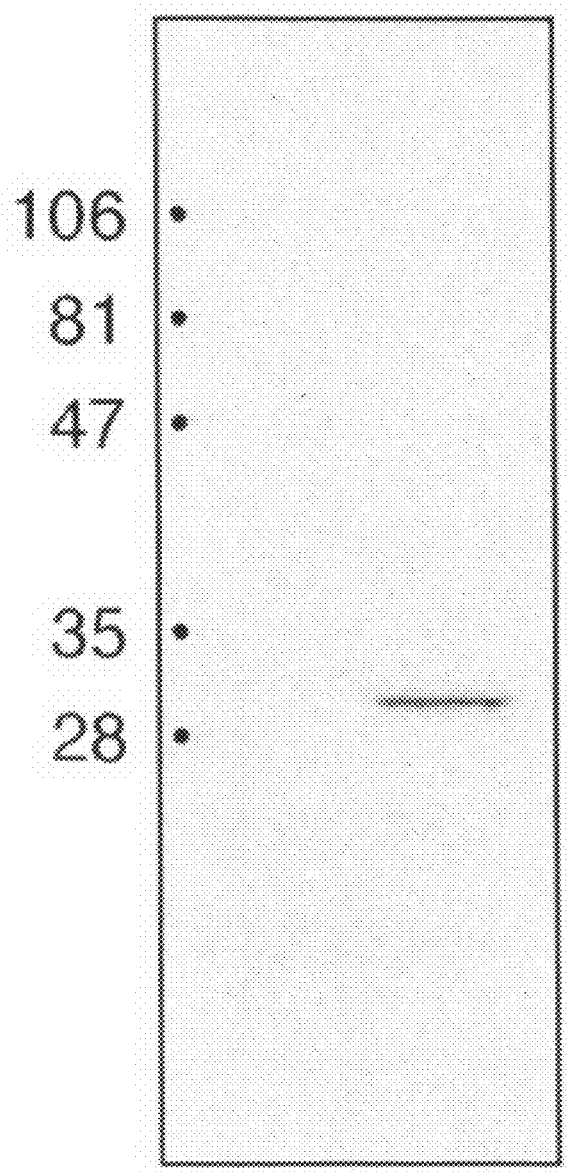

FIG. 65. Expression of a dominant-negative version of Fbl2, Fbl12-ΔFB, in HEK 293 cells. Fbl12-ΔFB retains the putative substrate binding domain, the LRR domain, but lacks the N-terminal F-box domain that is required to recruit the cellular machinery necessary for ubiquitination of the target protein. The cDNA encoding Fbl12-ΔFB was cloned into the pIND/V5-His B mammalian expression vector (Invitrogen). The vector possesses an cedysone/Ponasterone inducible promoter and a V5 epitope tag. HEK 293 cells transfected with the expression vector were treated with Ponasterone A (6 μM) for 6 h and the cells harvested. Cell lysates were prepared and subjected to western-blot analysis with anti-V5 antibody (Invitrogen).

Figure 66:
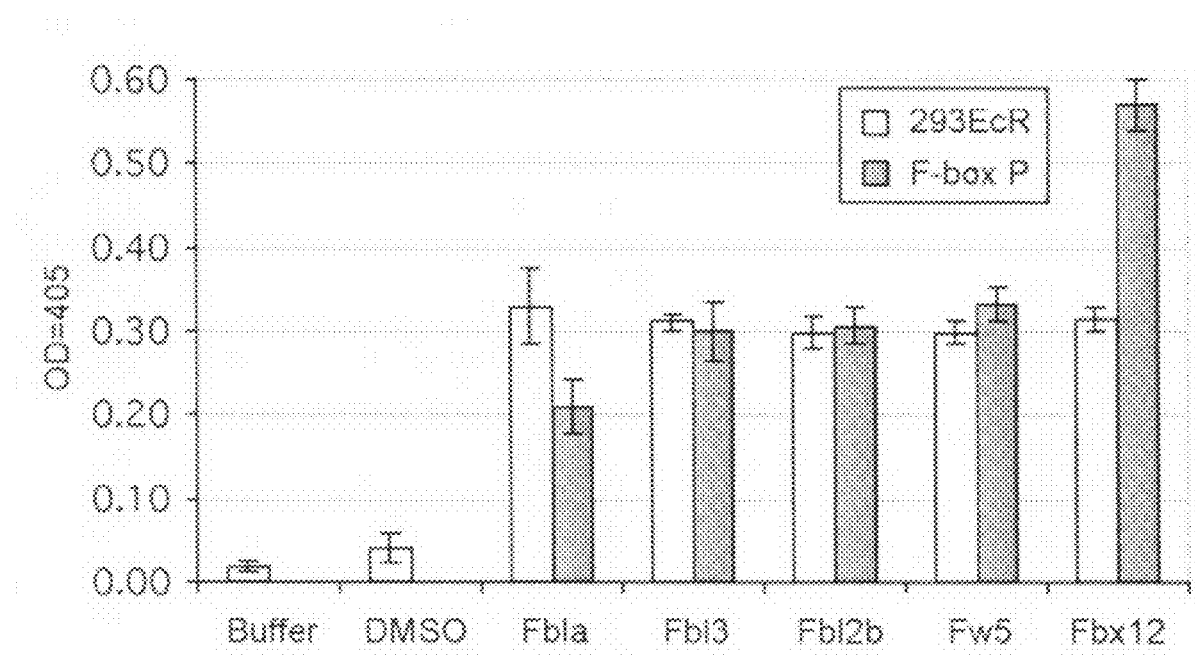

FIG. 66. Expression of Fbl12-ΔFB protein renders HEK 293 cells sensitive to stausporine-induced apoptosis. The control HEK 293 EcR stable cell line was used to establish a stable HEK 293 Fbl12-ΔFB expressing cell line. HEK 293 Fbl12-ΔFB or HEK 293 EcR cells were seeded into a 96 well plate at a density of $2.5 \times 10^3$ cells per well in appropriate medium. Following a 24 h incubation, cells were treated with 6 μM Ponasterone A for 6 h to induce expression of Fbl12-ΔFB. Following the Ponasterone A incubation, 10 nM stauosporine was added to each well and the cultures were incubated for an additional 10 h. Cells were then assayed for apoptosis with an in situ cell death detection kit.

Figure 67:
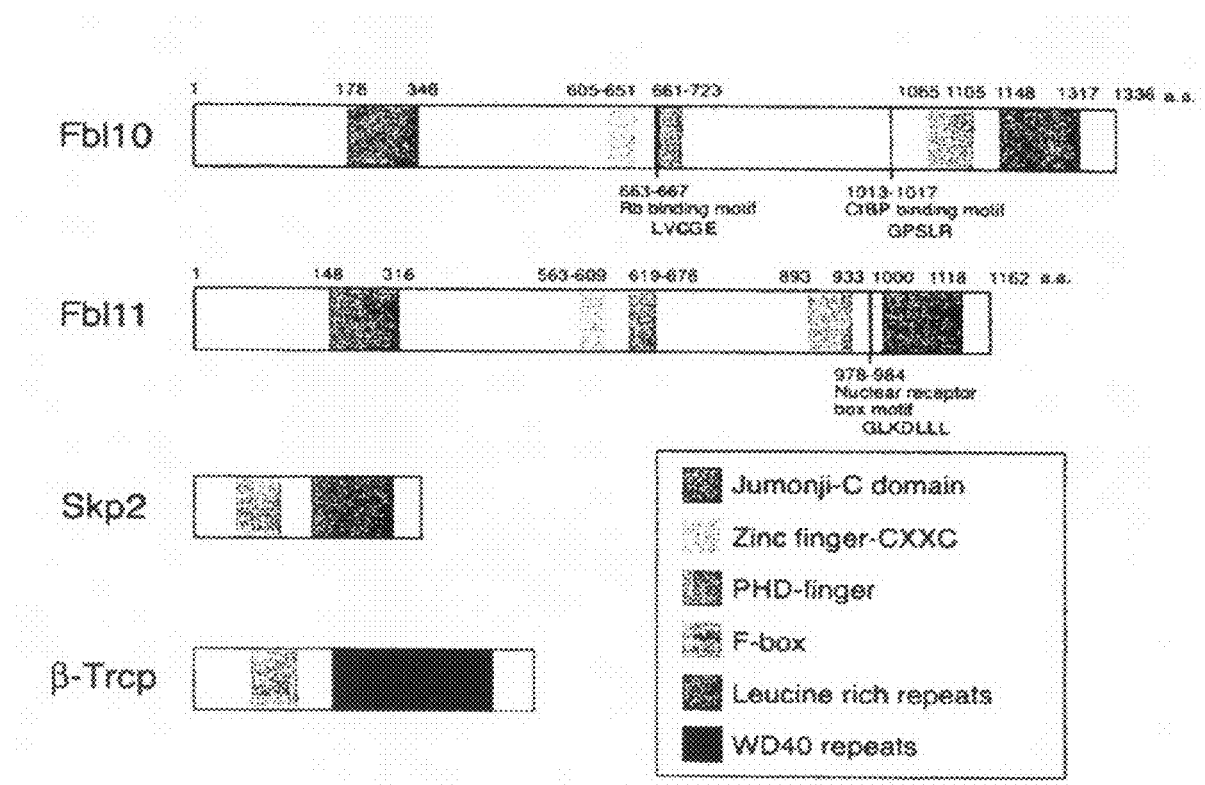

FIG. 67. Schematic representation of Fbl10, FBl11, Skp2 and β-Tcrp containing protein-protein and protein-DNA interaction domains.

Figure 68:
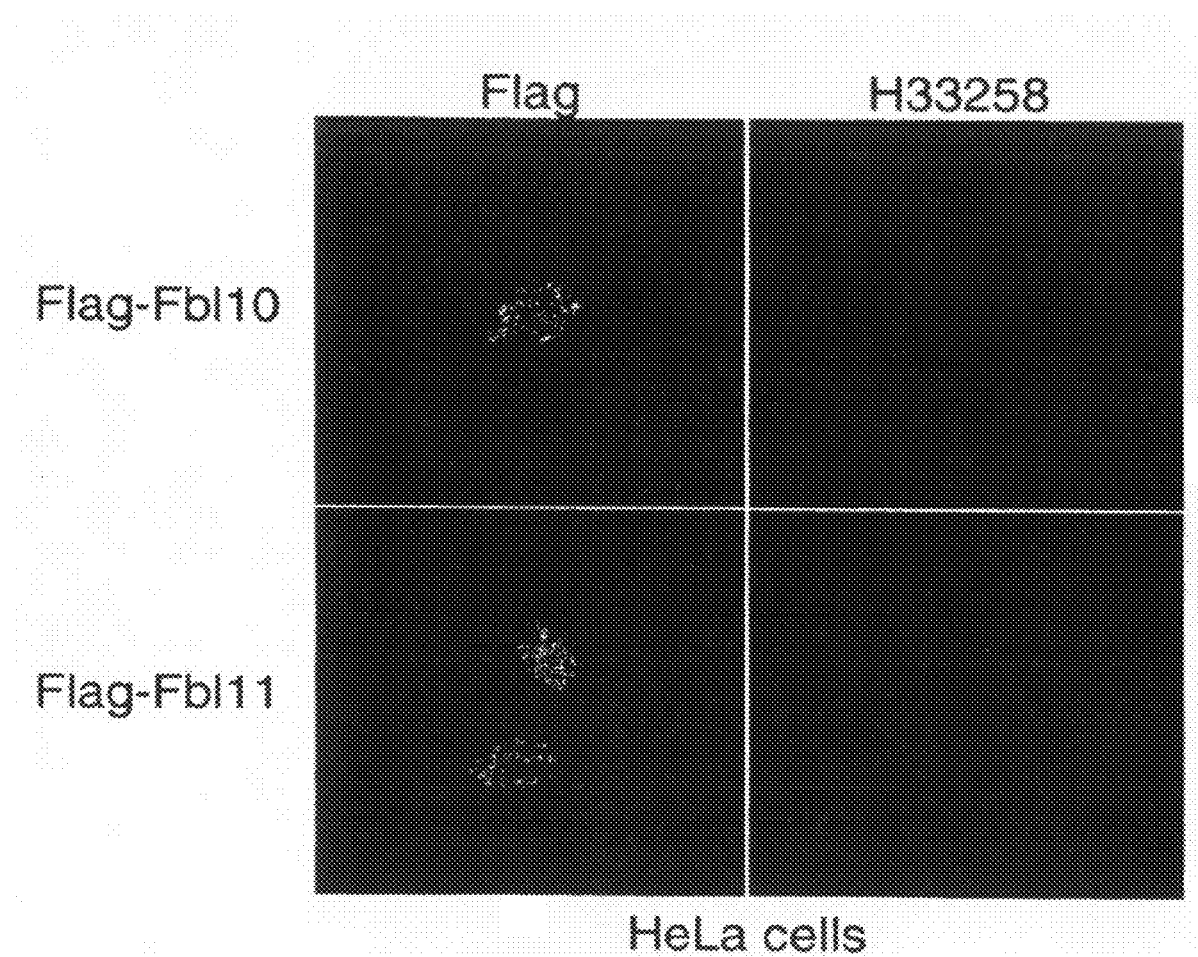

FIG. 68. Immunofluorescence of HeLa cells expressing Flag-tagged FBL10 and Fbl11. Cell monolayers grown on glass coverslips were rinsed in PBS and fixed for 10 min in cold methanol-acetone (1:1). Fixed cells were rehydrated in PBS at room temperature and processed for cell staining. Anti-Flag antibody (Sigma) at 1:100 dilution was used as the primary antibody. Incubation with the primary antibody was carried out for 1 h in a humidified chamber. After three washes in PBS the coverslips were incubated for 30 min with biotinylated horse anti-mouse secondary antibody (Vectron Laboratories, 1:50 dilution). Cell were washed three times with PBS and incubated with FITC-conjugated streptavadin (Vectron Laboratories, 1:50 dilution).

Figure 69:
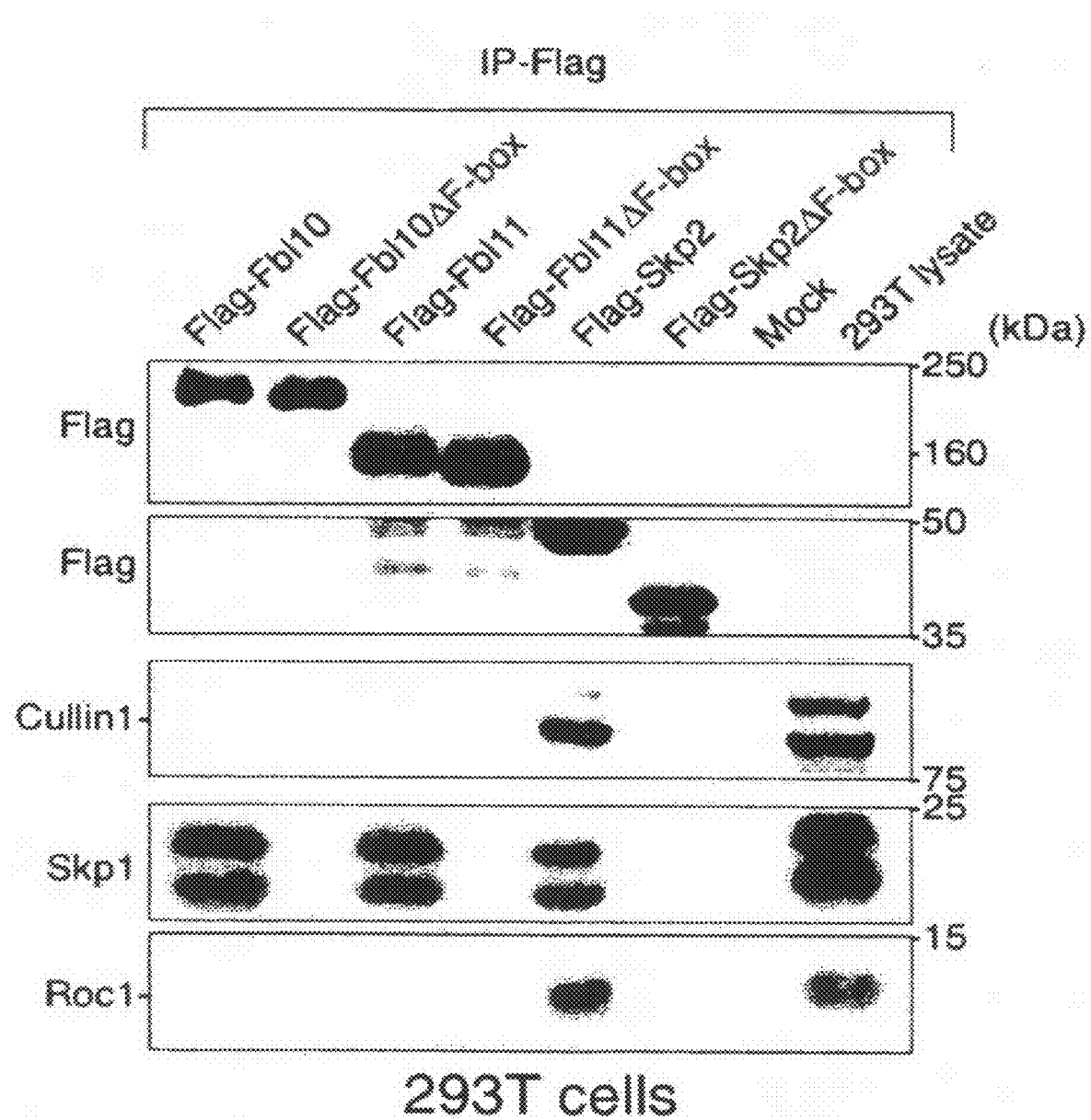

FIG. 69. Identification of Skp1, Cul1, and Roc1 and binding/associated proteins of Fbl10 and Fbl11. Flag-purified extracts of cells expressing Flag-Fbl10, Flag-Fbl11 or Flag-ΔF-box mutants were subjected to western blot analysis using anti-Flag (Sigma, Cat#F3165), anti-Skp1 (Zymed), anti-Cul1 (Zymed), or anti-Roc1 (Zymed) antibodies. Immunoprecipitation of Flag-purified proteins failed to pull down Skp1, Cul1, or Roc1 when ΔF-box mutants were assayed.

Figure 70:
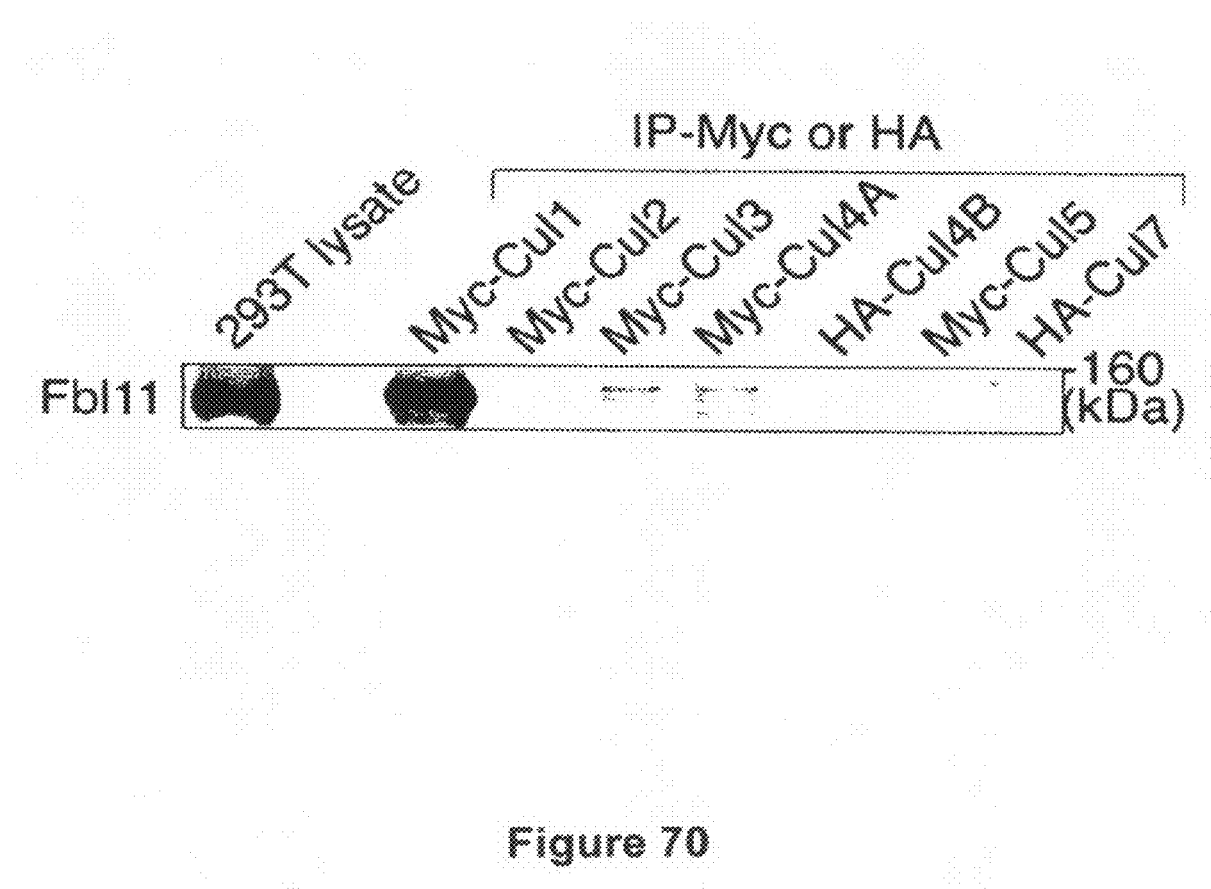

FIG. 70. HEK293 cells were transfected with a mammalian expression vector encoding Cul1. The vector provided the expressed protein with a Myc or HA tag. Whole cell lysates of the transfected cells were immuno purified as described with anti-Myc or anti-HA antibodies. Purified fractions were subjected to gel filtration chromatography and western blot analysis with anti-Fbl11 antibody.

Figure 71:
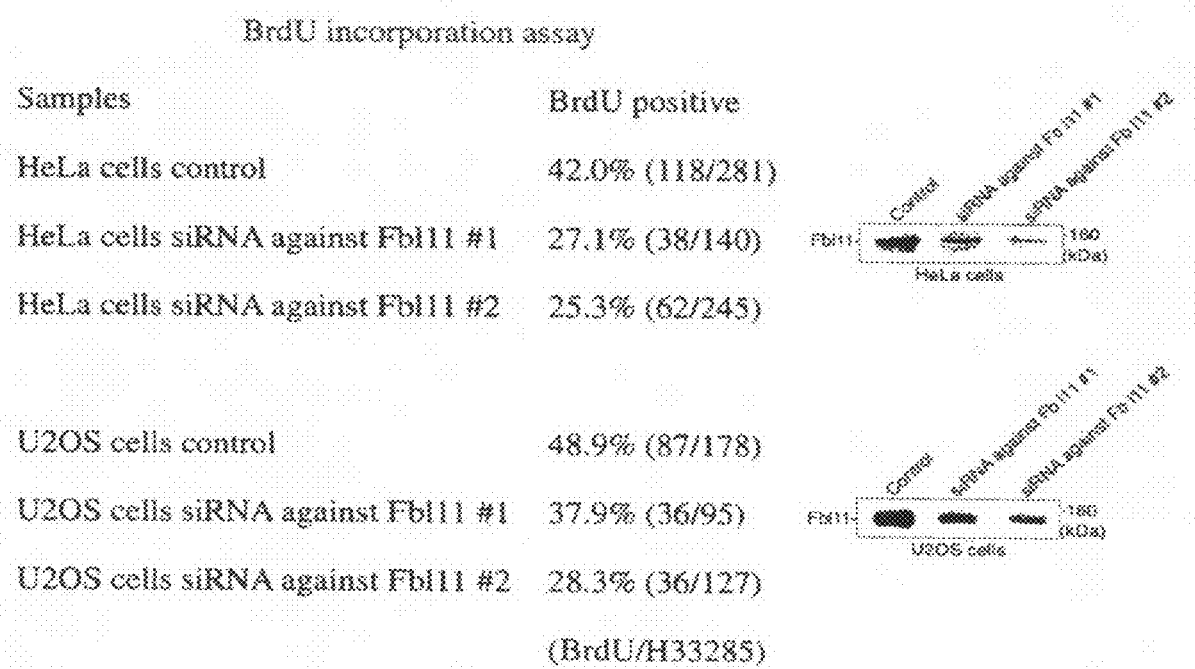

FIG. 71. sRNA silencing of Fbl11. U2OS and HELA cells were transfected with the mammalian expression vector pcDNA3 containing cDNA fragments encoding Flag-tagged Fbl11 as described in section 7.1. Following two transfections with sRNA at 24 and 48 h after replating using Oligofectamine (Invitrogen), whole cell lysates were prepared and analyzed by western blot using anti-Flag antibodies (Sigma).

Figure 72:
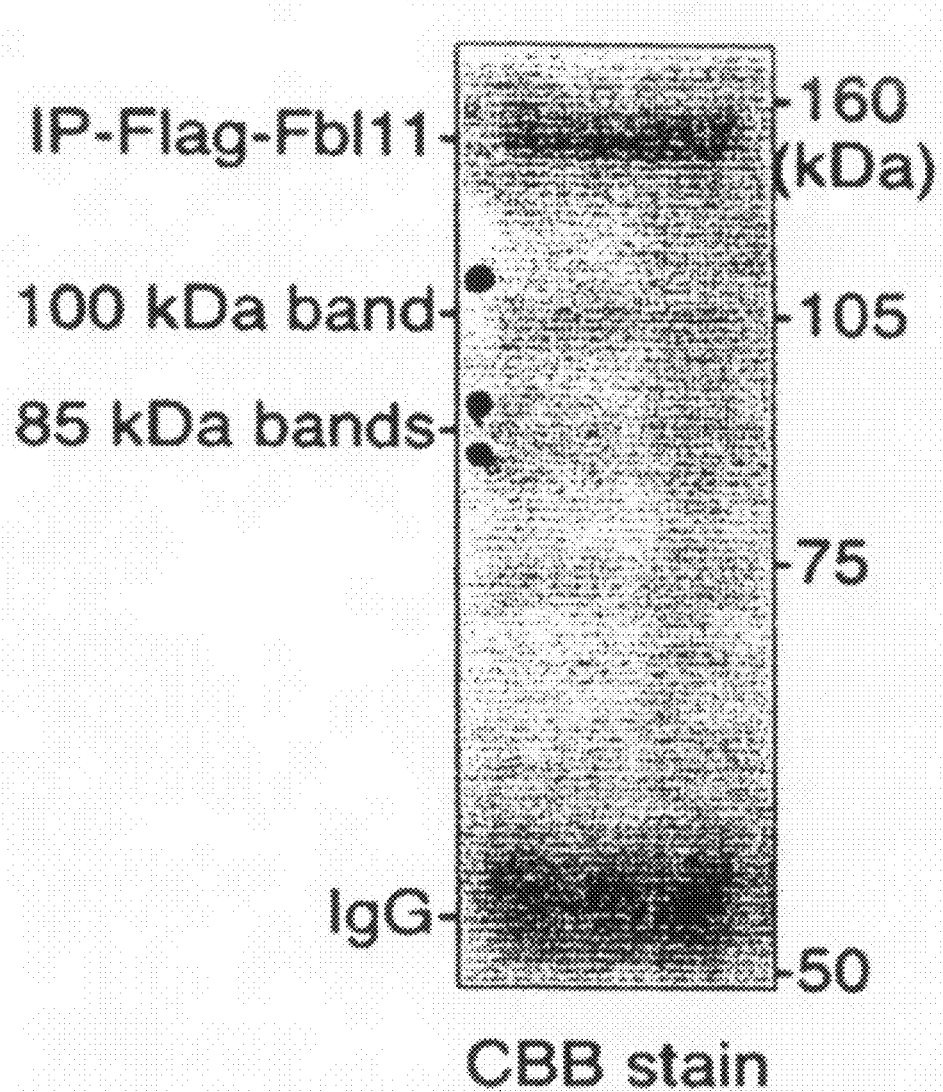

FIG. 72. Associated proteins in Flag-purified, Flag-Fbl11 expressing WCEs of HEK 293 cells. Flag-purified Flag-Fbl11 extracts were subjected to western blot analysis using anti-Flag antibody (Sigma, Cat#F3165).

Figure 73:
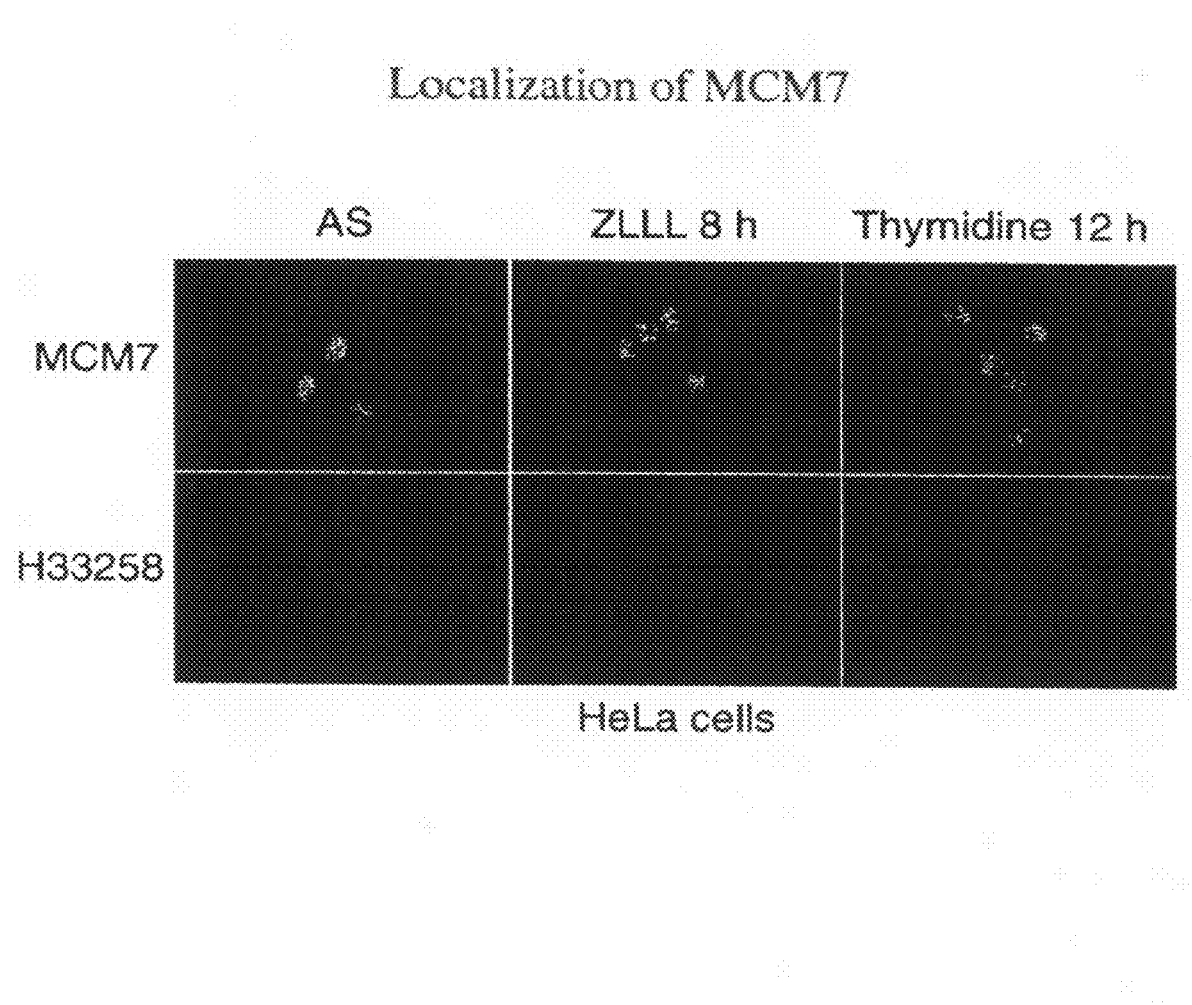

FIG. 73. MCM 7 Immunofluorescence of HeLa cells. Cell monolayers grown on glass coverslips were rinsed in PBS and fixed for 10 min in cold methanol-acetone (1:1). Fixed cells were rehydrated in PBS at room temperature and processed for cell staining. Anti-MCM7 antibody was used as the primary antibody. Incubation with the primary antibody was carried out for 1 h in a humidified chamber. After three washes in PBS the coverslips were incubated for 30 min with biotinylated horse anti-mouse secondary antibody (Vectron Laboratories, 1:50 dilution). Cell were washed three times with PBS and incubated with FITC-conjugated streptavadin (Vectron Laboratories, 1:50 dilution).

Figure 74:
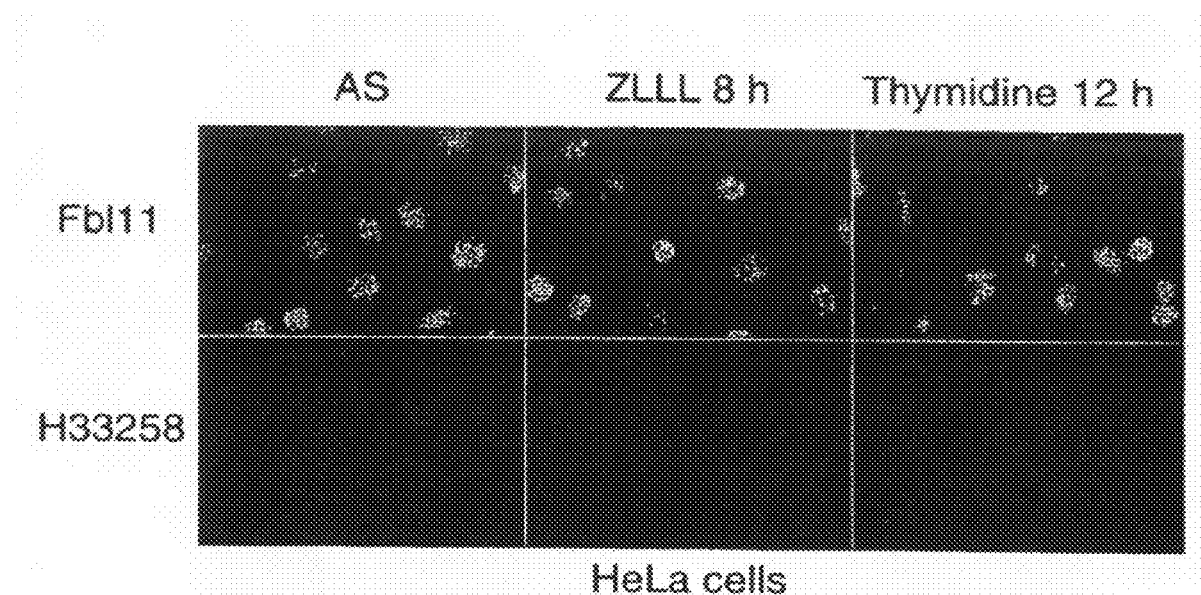

FIG. 74. Immunofluorescence of HeLa cells expressing Flag-tagged FBL11. Cell monolayers grown on glass coverslips were rinsed in PBS and fixed for 10 min in cold methanol-acetone (1:1). Fixed cells were rehydrated in PBS at room temperature and processed for cell staining. Anti-Flag antibody (Sigma) at 1:100 dilution was used as the primary antibody. Incubation with the primary antibody was carried out for 1 h in a humidified chamber. After three washes in PBS the coverslips were incubated for 30 min with biotinylated horse anti-mouse secondary antibody (Vectron Laboratories, 1:50 dilution). Cell were washed three times with PBS and incubated with FITC-conjugated streptavadin (Vectron Laboratories, 1:50 dilution).

Figure 75:
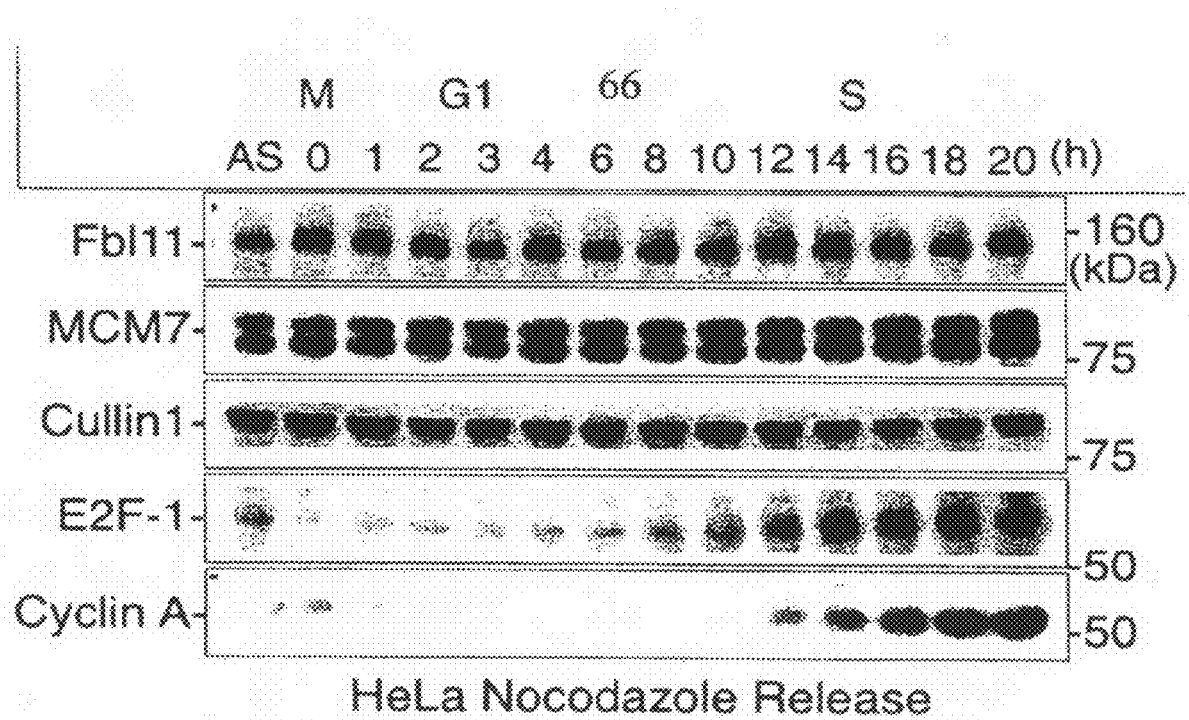

FIG. 75. Correlation of expression levels of Fbl11 with cell cycle. Flag-purified extracts of cells expressing Flag-Fbl11 were subjected to western blot analysis using anti-Flag (Sigma, Cat#F3165), anti-Cul1 (Zymed), anti-MCM7, anti-cyclinA, or anti-E2F1 antibodies.

Figure 76:
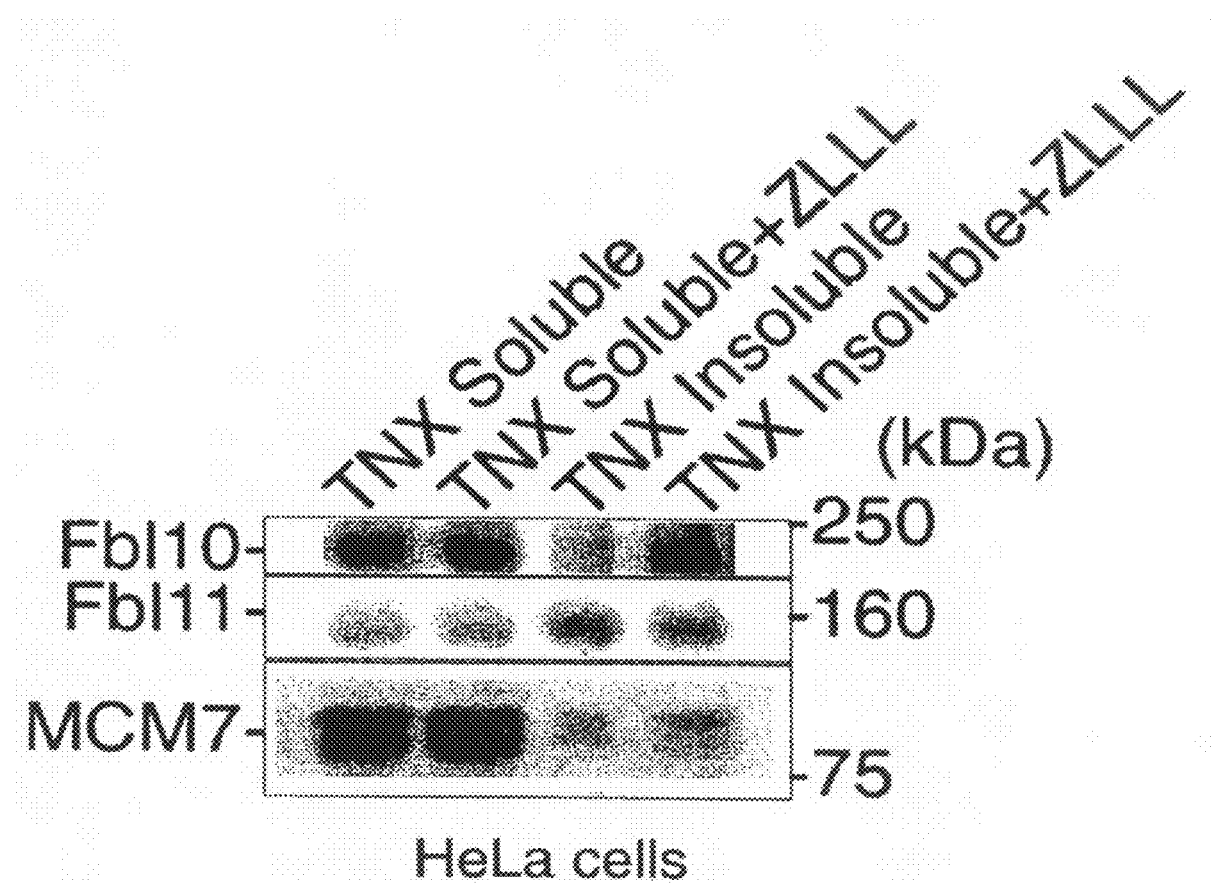

FIG. 76. FBL10 and FBL11 separate into both triton-soluble and triton insoluble phases of WCEs. WCEs of HeLa cells expressing Flag-FBL10 and -Fbl11 were subjected to fractionation based on triton solubility. Soluble and insoluble fractions were separated and subjected to gel filtration chromatography and western blot analysis with anti-Flag (Sigma), and anti-MCM7 antibodies.

Figure 77:
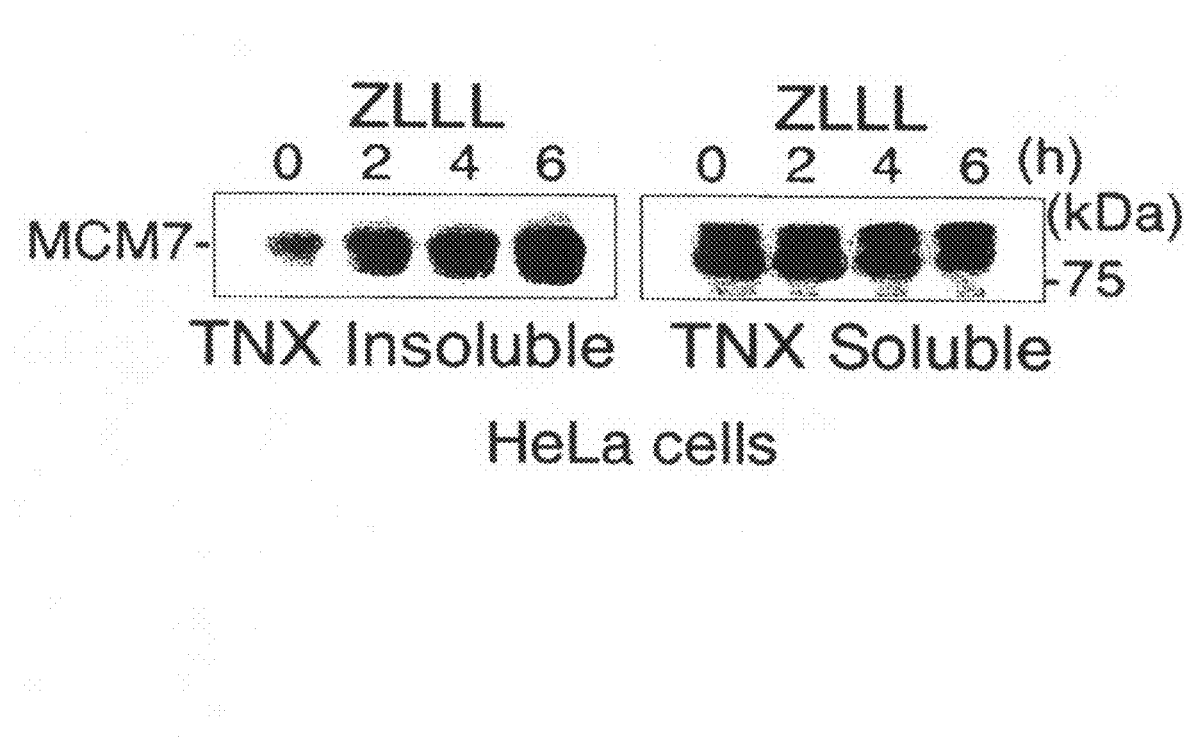

FIG. 77. MCM7 is subject to proteosome dependent degradation in the nucleus. The increasing level of MCM7 expression in the triton insoluble fraction with increasing incubation time of ZLL suggests that MCM7 is normally subjected to proteosome degradation in the nucleus. WCEs of HeLa cells were subjected to fractionation based on triton solubility. Soluble and insoluble fractions were separated and subjected to gel filtration chromatography and western blot analysis with anti-MCM7 antibodies.

Figure 78:
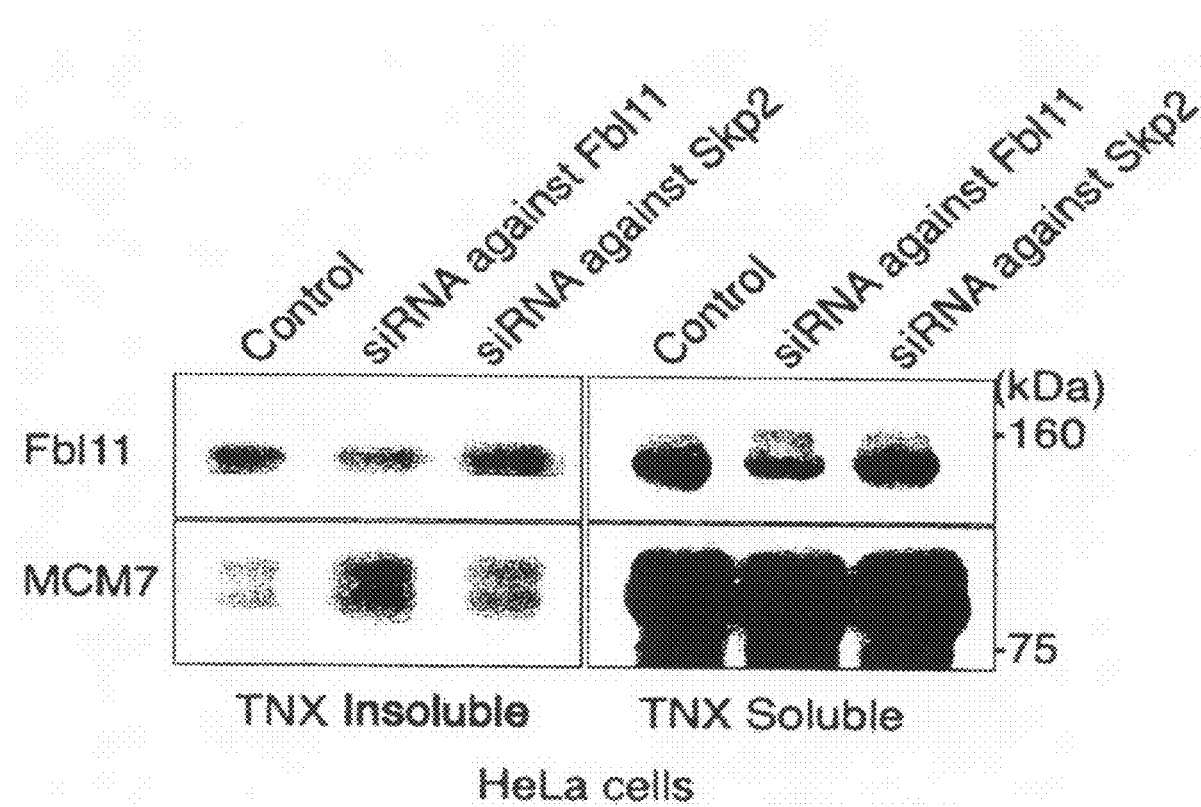

FIG. 78. MCM7 proteosome dependent degradation is dependent on Fbl11. sRNA was used to silence Fbl11. HeLa cells were transfected with the mammalian expression vector pcDNA3 containing cDNA fragments encoding Flag-tagged Fbl11 as described in section 7.1. Following two transfections with sRNA at 24 and 48 h after replating using Oligofectamine (Invitrogen), whole cell lysates were subjected to fractionation based on triton solubility. Soluble and insoluble fractions were separated and subjected to gel filtration chromatography and western blot analysis anti-Flag (Sigma) or anti-MCM7 antibodies.

Figure 79:
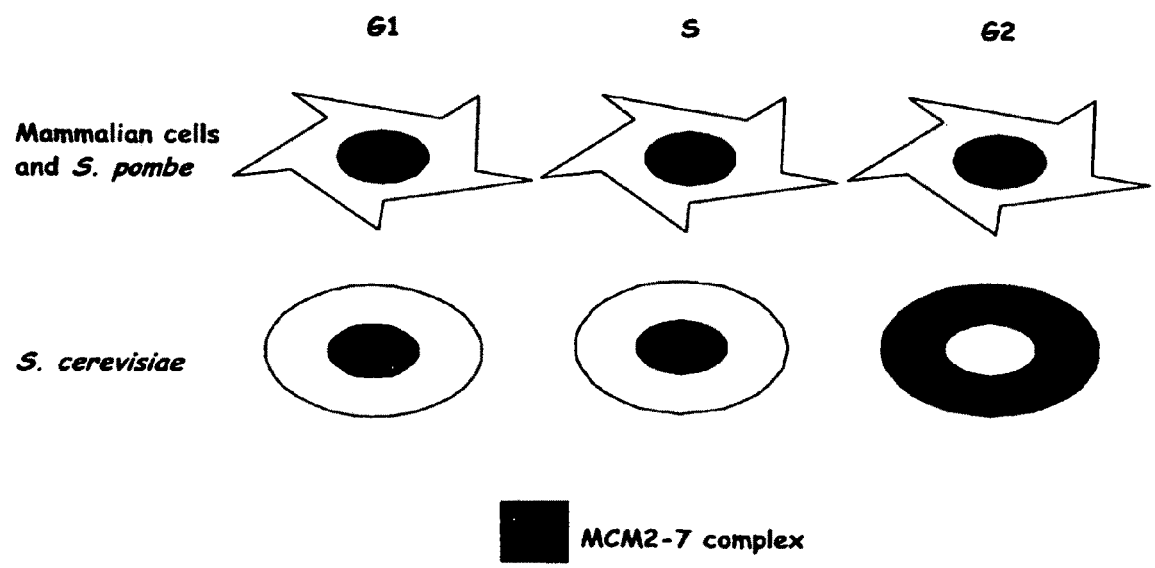

FIG. 79. Schematic representation depicting the exclusion of MCM from the nucleus of S. cerevisiae following the S-phase of the cell cycle.

Figure 81:
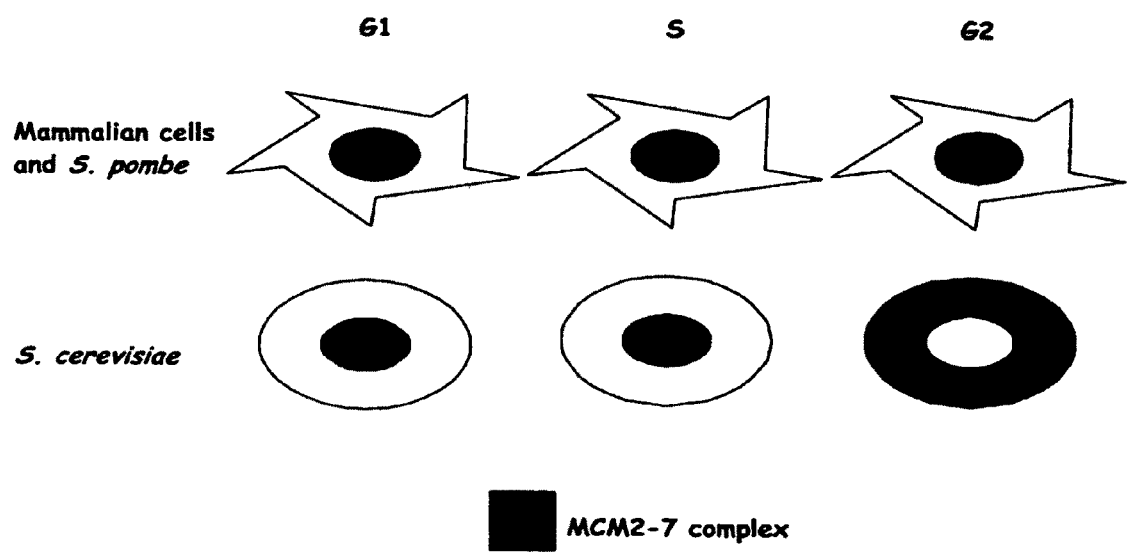

FIG. 81. Schematic representation of the protein-signaling pathway regulating the S-phase of the cell cycle in S. cerevisiae and involving MCM7. Schematic representation depicting the exclusion of MCM from the nucleus of S. cerevisiae following the S-phase of the cell cycle.

Figure 82:
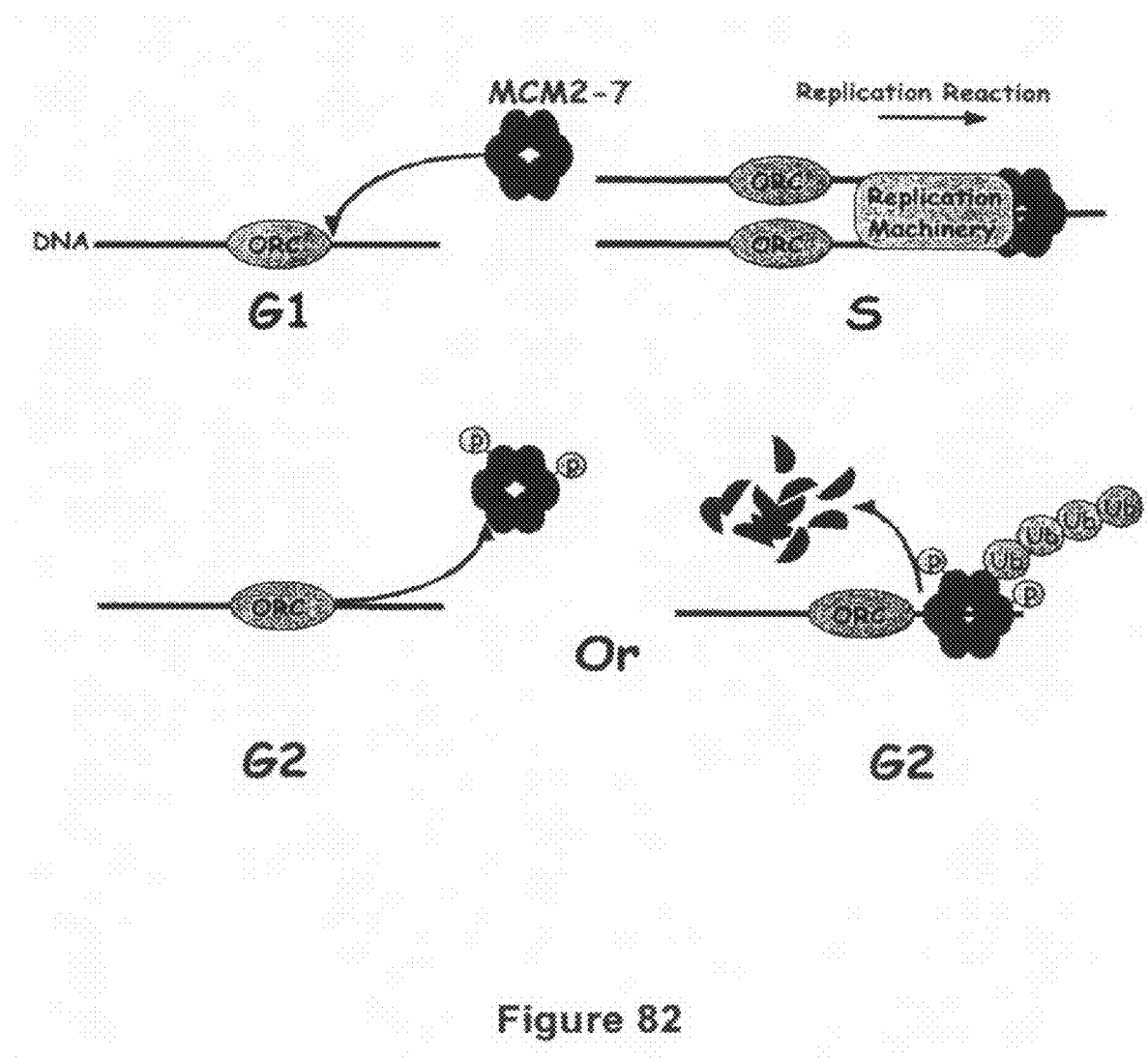

FIG. 82. Schematic representation depicting alternate methods for the inactivation of the MCM complex in the nucleus of mammalian cells.

6. DETAILED DESCRIPTION OF THE INVENTION

The present invention relates to novel F-box proteins and to novel substrates of F-box proteins. The present invention relates to screening assays designed to identify substrates of the F-box proteins and to identify small molecules and compounds which modulate the interaction and/or activity of the F-box proteins and their substrates.

The present invention relates to screening assays to identify substrates of the novel F-box proteins and to identify potential therapeutic agents. The present invention further relates to screening assays based on the identification of novel substrates of both novel and known F-box proteins. The screening assays of the present invention may be used to identify potential therapeutic agents which may be used in protocols and as pharmaceutical compositions designed to target the novel ubiquitin ligases and interactions with their substrates for the treatment of proliferative disorders. In one particular embodiment the present invention relates to screening assays and potential therapeutic agents which target the interaction of FBP with novel substrates β-catenin, p27 and E2F as identified by Applicants.

The invention further encompasses the use of nucleotides encoding the novel F-box proteins, proteins and peptides, as well as antibodies to the novel ubiquitin ligases (which can, for example, act as agonists or antagonists), antagonists that inhibit ubiquitin ligase activity or expression, or agonists that activate ubiquitin ligase activity or increase its expression. In addition, nucleotides encoding the novel ubiquitin ligases and proteins are useful for the identification of compounds which regulate or mimic their activity and therefore are potentially effective in the treatment of cancer and tumorigenesis.

In particular, the invention described in the subsections below encompasses FBP1/β-TRCP1, FBP2, FBP3a, FBP3b, FBP4, FBP5/EMI1, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 polypeptides or peptides corresponding to functional domains of the novel ubiquitin ligases (e.g., the F-box motif, the substrate binding domain, protein-protein interaction domains, and protein-DNA interaction domains), mutated, truncated or deleted (e.g. with one or more functional domains or portions thereof deleted), ubiquitin ligase fusion proteins, nucleotide sequences encoding such products, and host cell expression systems that can produce such ubiquitin ligase products. As used herein, "FBP1" can be considered interchangeable with "β-Trcp1," "FBP5" can be considered interchangeable with "Emi1," and further, "FBP24" can be considered interchangeable with "Fbx9."

The present invention provides methods of screening for peptides and proteins that interact with novel components of the ubiquitin ligase complex, including FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 or derivatives, fragments or analogs thereof. Preferably, the method of screening is a yeast two-hybrid assay system or a variation thereof, as further described below. Derivatives (e.g., fragments) and analogs of a protein can be assayed for binding to a binding partner by any method known in the art, for example, the modified yeast two-hybrid assay system described below, immunoprecipitation with an antibody that binds to the protein in a complex followed by analysis by size fractionation of the immunoprecipitated proteins (e.g., by denaturing or nondenaturing polyacrylamide gel electrophoresis), Western analysis, non-denaturing gel electrophoresis, etc.

The present invention relates to screening assays to identify agents which modulate the activity of the ubiquitin ligases. The invention encompasses both in vivo and in vitro assays to screen small molecules, compounds, recombinant proteins, peptides, nucleic acids, antibodies etc. which modulate the activity of the novel ubiquitin ligases and thus, identify potential therapeutic agents for the treatment of proliferative or differentiative disorders. In one embodiment, the present invention provides methods of screening for proteins that interact with the novel ubiquitin ligases.

The invention also encompasses antibodies and anti-idiotypic antibodies, antagonists and agonists, as well as compounds or nucleotide constructs that inhibit expression of the ubiquitin ligase gene (transcription factor inhibitors, antisense and ribozyme molecules, or gene or regulatory sequence replacement constructs), or promote expression of the ubiquitin ligase (e.g., expression constructs in which ubiquitin ligase coding sequences are operatively associated with expression control elements such as promoters, promoter/enhancers, etc.). The invention also relates to host cells and animals genetically engineered to express the human (or mutants thereof) or to inhibit or "knock-out" expression of the animal's endogenous ubiquitin ligase.

Finally, the ubiquitin ligase protein products and fusion protein products, (i.e., fusions of the proteins or a domain of the protein, e.g., F-box motif), antibodies and anti-idiotypic antibodies (including Fab fragments), antagonists or agonists (including compounds that modulate the ubiquitization pathway can be used for therapy of proliferative or differentiative diseases. Thus, the invention also encompasses pharmaceutical formulations and methods for treating cancer and tumorigenesis.

Various aspects of the invention are described in greater detail in the subsections below.

6.1 FBP Genes

The invention provides nucleic acid molecules comprising seven novel nucleotide sequences, and fragments thereof, FBP1, FBP2, FBP3a, FBP4, FBP5, FBP6, and FBP7, nucleic acids which are novel genes identified by the interaction of their gene products with Skp1, a component of the ubiquitin ligase complex. The invention further provides fourteen novel nucleic acid molecules comprising the nucleotide sequences of FBP1, FBP2, FBP3a, FBP3b, FBP4, FBP5, FBP6, FBP7, FBP8, FBP11, FBP12, FBP13, FBP14, FBP15, FBP17, FBP18, FBP20, FBP21, FBP22, FBP23, FBP24, and FBP25 which Nucleic acid sequences of the identified FBP genes are described herein.

As used herein, "an FBP gene" refers to:

(a) a nucleic acid molecule containing the DNA sequences of FBP1, shown in FIG. 3 (SEQ ID NO:1), the DNA sequences of FBP2, shown in FIG. 4 (SEQ ID NO:3), the DNA sequences of FBP3a, shown in FIG. 5 (SEQ ID NO:5), the DNA sequences of FBP3b, shown in FIG. 6 (SEQ ID NO:23), the DNA sequences of FBP4, shown in FIG. 7 (SEQ ID NO:7), the DNA sequences of FBP5, shown in FIG. 8 (SEQ ID NO:9), the DNA sequences of FBP6, shown in FIG. 9 (SEQ ID NO:11), the DNA sequences of FBP7, shown in FIG. 10 (SEQ ID NO:13), the DNA sequences of FBP8, shown in FIG. 11 (SEQ ID NO:25), the DNA sequences of FBP9, shown in FIG. 12 (SEQ ID NO:27), the DNA sequences of FBP10, shown in FIG. 13 (SEQ ID NO:29), the DNA sequences of FBP11, shown in FIG. 14 (SEQ ID NO:31), the DNA sequences of FBP12, shown in FIG. 15 (SEQ ID NO:33), the DNA sequences of FBP13, shown in FIG. 16 (SEQ ID NO:35), the DNA sequences of FBP14, shown in FIG. 17 (SEQ ID NO:37), the DNA sequences of FBP15, shown in FIG. 18 (SEQ ID NO:39), the DNA sequences of FBP16, shown in FIG. 19 (SEQ ID NO:41), the DNA sequences of FBP17, shown in FIG. 20 (SEQ ID NO:43), the DNA sequences of FBP18, shown in FIG. 21 (SEQ ID NO:45), the DNA sequences of FBP19, shown in FIG. 22 (SEQ ID NO:47), the DNA sequences of FBP20, shown in FIG. 23 (SEQ ID NO:49), the DNA sequences of FBP21, shown in FIG. 24 (SEQ ID NO:51), the DNA sequences of FBP22, shown in FIG. 25 (SEQ ID NO:53), the DNA sequences of FBP23, shown in FIG. 26 (SEQ ID NO:55), the DNA sequences of FBP24, shown in FIG. 27 (SEQ ID NO:57), the DNA sequences of FBP25, shown in FIG. 28 (SEQ ID NO:59), the DNA sequences of FBL10, shown in FIG. 29 (SEQ ID NO:91), the DNA sequences of FBL11, shown in FIG. 30 (SEQ ID NO:93), the DNA sequences of FBL12, shown in FIG. 31 (SEQ ID NO:95).

(b) any DNA sequence that encodes a polypeptide containing: the amino acid sequence of FBP1 shown in FIG. 3A (SEQ ID NO:2), the amino acid sequence of FBP2, shown in FIG. 4A (SEQ ID NO:4), the amino acid sequence of FBP3a shown in FIG. 5A (SEQ ID NO:6), the amino acid sequence of FBP3b shown in FIG. 6A (SEQ ID NO:24), the amino acid sequence of FBP4 shown in FIG. 7A (SEQ ID NO:8), the amino acid sequence of FBP5 shown in FIG. 8A (SEQ ID NO:10), or the amino acid sequence of FBP6 shown in FIG. 9A (SEQ ID NO:12), the amino acid sequences of FBP7, shown in FIG. 10A (SEQ ID NO:14), the amino acid sequences of FBP8, shown in FIG. 11A (SEQ ID NO:26), the amino acid sequences of FBP9, shown in FIG. 12A (SEQ ID NO:28), the amino acid sequences of FBP10, shown in FIG. 13A (SEQ ID NO:30), the amino acid sequences of FBP11, shown in FIG. 14A (SEQ ID NO:32), the amino acid sequences of FBP12, shown in FIG. 15A (SEQ ID NO:34), the amino acid sequences of FBP13, shown in FIG. 16A (SEQ ID NO:36), the amino acid sequences of FBP14, shown in FIG. 17A (SEQ ID NO:38), the amino acid sequences of FBP15, shown in FIG. 18A (SEQ ID NO:40), the amino acid sequences of FBP16, shown in FIG. 19A (SEQ ID NO:42), the amino acid sequences of FBP17, shown in FIG. 20A (SEQ ID NO:44), the amino acid sequences of FBP18, shown in FIG. 21A (SEQ ID NO:46), the amino acid sequences of FBP19, shown in FIG. 22A (SEQ ID NO:48), the amino acid sequences of FBP20, shown in FIG. 23A (SEQ ID NO:50), the amino acid sequences of FBP21, shown in FIG. 24A (SEQ ID NO:52), the amino acid sequences of FBP22, shown in FIG. 25A (SEQ ID NO:54), the amino acid sequences of FBP23, shown in FIG. 26A (SEQ ID NO:56), the amino acid sequences of FBP24, shown in FIG. 27A (SEQ ID NO:58), the amino acid sequences of FBP25, shown in FIG. 28A (SEQ ID NO:60), the amino acid sequences of FBL10, shown in FIG. 29A (SEQ ID NO:92), the amino acid sequences of FBL11, shown in FIG. 30A (SEQ ID NO:94), the amino acid sequences of FBL12, shown in FIG. 31A (SEQ ID NO:96).

(c) any DNA sequence that hybridizes to the complement of the DNA sequences that encode any of the amino acid sequences of (SEQ ID NO: 2, 4, 6, 8, 10, 12 or 14) or FIG. 15 under highly stringent conditions, e.g., hybridization to filter-bound DNA in 0.5 M NaHPO4, 7% sodium dodecyl sulfate (SDS), 1 mM EDTA at 65 C, and washing in 0.1×SSC/0.1% SDS at 68 C (Ausubel, et al., eds., 1989, *Current Protocols in Molecular Biology*, Vol. 1, Green Publishing Associates, Inc., and John Wiley & sons, Inc., New York, at p. 2.10.3); and/or (d) any DNA sequence that hybridizes to the complement of the DNA sequences that encode any of the amino acid sequences in (SEQ ID NO: 2, 4, 6, 8, 10, 12 or 14) or FIG. 15, under less stringent conditions, such as moderately stringent conditions, e.g., washing in 0.2×SSC/0.1% SDS at 42 C (Ausubel, et al., 1989, supra), and encodes a gene product functionally equivalent to an FBP gene product.

It is understood that the FBP gene sequences of the present invention do not encompass the previously described genes encoding other mammalian F-box proteins, Skp2, Elongin A, Cyclin F, mouse Md6, (see Pagano, 1997, supra; Zhang et al., 1995, supra; Bai et al., 1996, supra; Skowyra et al., 1997, supra). It is further understood that the nucleic acid molecules of the invention do not include nucleic acid molecules that consist solely of the nucleotide sequence in GenBank Accession Nos. AC002428, AI457595, AI105408, H66467, T47217, H38755, THC274684, AI750732, AA976979, AI571815, T57296, Z44228, Z45230, N42405, AA018063, AI751015, AI400663, T74432, AA402415, AI826000, AI590138, AF174602, Z45775, AF174599, THC288870, AI017603, AF174598, THC260994, AI475671, AA768343, AF174595, THC240016, N70417, T10511, AF174603, EST04915, AA147429, AI192344, AF174594, AI147207, AI279712, AA593015, AA644633, AA335703, N26196, AF174604, AF053356, AF174606, AA836036, AA853045, AI479142, AA772788, AA039454, AA397652, AA463756, AA007384, AA749085, AI640599, THC253263, AB020647, THC295423, AA434109, AA370939, AA215393, THC271423, AF052097, THC288182, AL049953, CAB37981, AL022395, AL031178, THC197682, THC205131, NM_032590, NM_012308, and NM_017703.

FBP sequences of the present invention are derived from a eukaryotic genome, preferably a mammalian genome, and more preferably a human or murine genome. Thus, the nucleotide sequences of the present invention do not encompass those derived from yeast genomes. In a specific embodiment, the nucleotides of the present invention encompass any DNA sequence derived from a mammalian genome which hybridizes under highly stringent conditions to SEQ ID NO: 1, 3, 5, 7, 9, 11 or 13, or to DNA sequence shown in FIG. 14, encodes a gene product which contains an F-box motif and binds to Skp1. In a specific embodiment, the nucleotides of the present invention encompass any DNA sequence derived from a mammalian genome which hybridize under highly stringent conditions to SEQ ID NO: 1, 3, 5, 7, 9, 11 or 13 encodes a gene product which contains an F-box motif and another domain selected from the group comprising WD-40, leucine rich region, leucine zipper motif, or other protein-protein interaction domain, and binds to Skp-1 and is at least 300 or 400 nucleotides in length.

FBP sequences can include, for example, either eukaryotic genomic DNA (cDNA) or cDNA sequences. When referring to a nucleic acid which encodes a given amino acid sequence, therefore, it is to be understood that the nucleic acid need not only be a cDNA molecule, but can also, for example, refer to a cDNA sequence from which an mRNA species is transcribed that is processed to encode the given amino acid sequence.

As used herein, an FBP gene may also refer to degenerate variants of DNA sequences (a) through (d).

The invention also includes nucleic acid molecules derived from mammalian nucleic acids, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37 C (for 14-base oligos), 48 C (for 17-base oligos), 55 C (for 20-base oligos), and 60 C (for 23-base oligos). These nucleic acid molecules may encode or act as FBP gene antisense molecules, useful, for example, in FBP gene regulation (for and/or as antisense primers in amplification reactions of FBP gene nucleic acid sequences). With respect to FBP gene regulation, such techniques can be used to regulate, for example, an FBP-regulated pathway, in order to block cell proliferation associated with cancer. Further, such sequences may be used as part of ribozyme and/or triple helix sequences, also useful for FBP gene regulation. Still further, such molecules may be used as components of diagnostic methods whereby, for example, the presence of a particular FBP allele responsible for causing an FBP-related disorder, e.g., proliferative or differentiative disorders such as tumorigenesis or cancer, may be detected.

The invention also encompasses:

(a) DNA vectors that contain any of the foregoing FBP coding sequences and/or their complements (i.e., antisense);

(b) DNA expression vectors that contain any of the foregoing FBP coding sequences operatively associated with a regulatory element that directs the expression of the coding sequences; and (c) genetically engineered host cells that contain any of the foregoing FBP coding sequences operatively associated with a regulatory element that directs the expression of the coding sequences in the host cell.

As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast-mating factors.

The invention further includes fragments of any of the DNA sequences disclosed herein.

In one embodiment, the FBP gene sequences of the invention are mammalian gene sequences, with human sequences being preferred.

In yet another embodiment, the FBP gene sequences of the invention are gene sequences encoding FBP gene products containing polypeptide portions corresponding to (that is, polypeptide portions exhibiting amino acid sequence similarity to) the amino acid sequence depicted in FIG. 2, 4-9 or 15, wherein the corresponding portion exhibits greater than about 50% amino acid identity with the depicted sequence, averaged across the FBP gene product's entire length.

In specific embodiments, F-box encoding nucleic acids comprise the cDNA sequences of SEQ ID NOs: 1, 3, 5, 23, 7, 9, 11, 13, 15, 25, 27, 29, 31, 33, 35, 37, 39, 41, 43, 45, 47, 49, 51, 53, 55, 57, 59, 93, 95, 97, nucleotide sequence of FIGS. 3B, 4B, 5B, 6B, 7B, 8B, 9B, 10B, 11B, 12B, 13B, 14B, 15B, 16B, 17B, 18B, 19B, 20B, 21B, 22B, 23B, 24B, 25B, 26B, 27B, 28B, 29B, 30B, and 31B, respectively, or the coding regions thereof, or nucleic acids encoding an F-box protein (e.g., a protein having the sequence of SEQ ID NOs: 2, 4, 6, 24, 8, 10, 12, 14, 26, 28, 30, 32, 34, 36, 38, 40, 42, 44, 46, 48, 50, 52, 54, 56, 68, 60, 94, 96, or 98, or as shown in FIGS. 3A, 4A, 5A, 6A, 7A, 8A, 9A, 10A, 11A, 12A, 13A, 14A, 15A, 16A, 17A, 18A, 19A, 20A, 21A, 22A, 23A, 24A, 25A, 26A, 27A, 28A, 29A, 30A, or 31A, respectively).

The invention further provides nucleotide fragments of nucleotide sequences encoding FBP1, FBP2, FBP3a, FBP4, FBP5, FBP6, or FBP7 (SEQ ID NOs: 1, 3, 5, 7, 9, 11 and 13, respectively) of the invention. Such fragments consist of at least 8 nucleotides (i.e., a hybridizable portion) of an FBP gene sequence; in other embodiments, the nucleic acids consist of at least 25 (continuous) nucleotides, 50 nucleotides, 100 nucleotides, 150 nucleotides, or 200 nucleotides of an F-box sequence, or a full-length F-box coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of an F-box gene.

The invention further relates to the human genomic nucleotide sequences of nucleic acids. In specific embodiments, F-box encoding nucleic acids comprise the genomic sequences of SEQ ID NOs: 1, 3, 5, 7, 9, 11 or 13 or the coding regions thereof, or nucleic acids encoding an FBP protein (e.g., a protein having the sequence of SEQ ID Nos: 2, 4, 6, 8, 10, 12 or 14). The invention provides purified nucleic acids consisting of at least 8 nucleotides (i.e., a hybridizable portion) of an FBP gene sequence; in other embodiments, the nucleic acids consist of at least 25 (continuous) nucleotides, 50 nucleotides, 100 nucleotides, 150 nucleotides, or 200 nucleotides of an FBP gene sequence or a full-length FBP gene coding sequence. In another embodiment, the nucleic acids are smaller than 35, 200 or 500 nucleotides in length. Nucleic acids can be single or double stranded. The invention also relates to nucleic acids hybridizable to or complementary to the foregoing sequences. In specific aspects, nucleic acids are provided which comprise a sequence complementary to at least 10, 25, 50, 100, or 200 nucleotides or the entire coding region of an FBP gene sequence.

In addition to the human FBP nucleotide sequences disclosed herein, other FBP gene sequences can be identified and readily isolated, without undue experimentation, by molecular biological techniques well known in the art, used in conjunction with the FBP gene sequences disclosed herein. For example, additional human FBP gene sequences at the same or at different genetic loci as those disclosed in SEQ ID Nos: 1, 3, 5, 7, 9, 11 or 13 can be isolated readily. There can exist, for example, genes at other genetic or physical loci within the human genome that encode proteins that have extensive homology to one or more domains of the FBP gene products and that encode gene products functionally equivalent to an FBP gene product. Further, homologous FBP gene sequences present in other species can be identified and isolated readily.

The FBP nucleotide sequences of the invention further include nucleotide sequences that encode polypeptides having at least 30%, 35%, 40%, 45%, 50%, 55%, 60%, 65%, 70%, 75%, 80%, 85%, 90%, 95%, 98%, or higher amino acid sequence identity to the polypeptides encoded by the FBP nucleotide sequences of SEQ ID No. 1, 3, 5, 7, 9, 11 or 13.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical overlapping positions/total # of overlapping positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul, et al., 1990, J. Mol. Biol. 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Altschul et al., 1997, supra). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of two sequences is the algorithm of Karlin and Altschul, 1990, Proc. Natl. Acad. Sci. USA 87:2264, modified as in Karlin and Altschul, 1993, Proc. Natl. Acad. Sci. USA 90:5873. Such an algorithm is incorporated into the NBLAST and XBLAST programs of Altschul, et al., 1990, J. Mol. Biol. 215:403. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul, et al., 1997, Nucleic Acids Res. 25:3389. Alternatively, PSI-Blast can be used to perform an iterated search which detects distant relationships between molecules (Altschul, et al., 1997, supra). When utilizing BLAST, Gapped BLAST, and PSI-Blast programs, the default parameters of the respective programs (e.g.,)(BLAST and NBLAST) can be used. Another preferred, non-limiting example of a mathematical algorithm utilized for the comparison of sequences is the algorithm of Myers and Miller, 1988, CABIOS 4:11. Such an algorithm is incorporated into the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

With respect to identification and isolation of FBP gene sequences present at the same genetic or physical locus as those sequences disclosed herein, such sequences can, for example, be obtained readily by utilizing standard sequencing and bacterial artificial chromosome (BAC) technologies.

With respect to the cloning of an FBP gene homologue in human or other species (e.g., mouse), the isolated FBP gene sequences disclosed herein may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., supra. Further, an FBP gene homologue may be isolated from, for example, human nucleic acid, by performing PCR using two degenerate oligonucleotide primer pools designed on the basis of amino acid sequences within any FBP gene product disclosed herein.

The PCR product may be subcloned and sequenced to ensure that the amplified sequences represent the sequences of an FBP gene nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the FBP gene, such as, for example, blood samples or brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., supra.

FBP gene sequences may additionally be used to identify mutant FBP gene alleles. Such mutant alleles may be isolated from individuals either known or proposed to have a genotype that contributes to the symptoms of an FBP gene disorder, such as proliferative or differentiative disorders involved in tumorigenesis or causing cancer, for example. Mutant alleles and mutant allele products may then be utilized in the therapeutic, diagnostic and prognostic systems described below. Additionally, such FBP gene sequences can be used to detect FBP gene regulatory (e.g., promoter) defects which can be associated with an FBP disorder, such as proliferative or differentiative disorders involved in tumorigenesis or causing cancer, for example.

FBP alleles may be identified by single strand conformational polymorphism (SSCP) mutation detection techniques, Southern blot, and/or PCR amplification techniques. Primers can routinely be designed to amplify overlapping regions of the whole FBP sequence including the promoter region. In one embodiment, primers are designed to cover the exon-intron boundaries such that, first, coding regions can be scanned for mutations. Genomic DNA isolated from lymphocytes of normal and affected individuals is used as PCR template. PCR products from normal and affected individuals are compared, either by single strand conformational polymorphism (SSCP) mutation detection techniques and/or by sequencing. SSCP analysis can be performed as follows: 100 ng of genomic DNA is amplified in a 10 μl reaction, adding 10 pmols of each primer, 0.5 U of Taq DNA polymerase (Promega), 1 μCi of α-[32P]dCTP (NEN; specific activity, 3000 Ci/mmol), in 2.5 μM dNTPs (Pharmacia), 10 mM Tris-HCl (pH 8.8), 50 mM KCl, 1 mM MgCl2, 0.01% gelatin, final concentration. Thirty cycles of denaturation (94° C.), annealing (56° C. to 64° C., depending on primer melting temperature), and extension (72° C.) is carried out in a thermal-cycler (MJ Research, Boston, Mass., USA), followed by a 7 min final extension at 72° C. Two microliters of the reaction mixture is diluted in 0.1% SDS, 10 mM EDTA and then mixed 1:1 with a sequencing stop solution containing 20 mM NaOH. Samples are heated at 95 C for 5 min, chilled on ice for 3 min and then 3 l will be loaded onto a 6% acrylamide/TBE gel containing 5% (v/v) glycerol. Gels are run at 8 W for 12-15 h at room temperature. Autoradiography is performed by exposure to film at −70 C with intensifying screens for different periods of time. The mutations responsible for the loss or alteration of function of the mutant FBP gene product can then be ascertained.

Alternatively, a cDNA of a mutant FBP gene may be isolated, for example, using PCR. In this case, the first cDNA strand may be synthesized by hybridizing an oligo-dT oligonucleotide to mRNA isolated from tissue known or suspected to be expressed in an individual putatively carrying the mutant FBP allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant FBP allele to that of the normal FBP allele, the mutation(s) responsible for the loss or alteration of function of the mutant FBP gene product can be ascertained.

Alternatively, a genomic library can be constructed using DNA obtained from an individual suspected of or known to carry a mutant FBP allele, or a cDNA library can be constructed using RNA from a tissue known, or suspected, to express a mutant FBP allele. An unimpaired FBP gene or any suitable fragment thereof may then be labeled and used as a probe to identify the corresponding mutant FBP allele in such libraries. Clones containing the mutant FBP gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant FBP allele in an individual suspected of or known to carry such a mutant allele. In this manner, gene products made by the putatively mutant tissue may be expressed and screened using standard antibody screening techniques in conjunction with antibodies raised against the normal FBP gene product, as described, below, in Section 5.3. (For screening techniques, see, for example, Harlow and Lane, eds., 1988, "Antibodies: A Laboratory Manual", Cold Spring Harbor Press, Cold Spring Harbor.)

Nucleic acids encoding derivatives and analogs of FBP proteins, and FBP antisense nucleic acids can be isolated by the methods recited above. As used herein, a "nucleic acid encoding a fragment or portion of an F-box protein" shall be construed as referring to a nucleic acid encoding only the recited fragment or portion of the FBP and not the other contiguous portions of the FBP protein as a continuous sequence.

Fragments of FBP gene nucleic acids comprising regions conserved between (i.e., with homology to) other FBP gene nucleic acids, of the same or different species, are also provided. Nucleic acids encoding one or more FBP domains can be isolated by the methods recited above.

In cases where an FBP mutation results in an expressed gene product with altered function (e.g., as a result of a missense or a frameshift mutation), a polyclonal set of anti-FBP gene product antibodies are likely to cross-react with the mutant FBP gene product. Library clones detected via their reaction with such labeled antibodies can be purified and subjected to sequence analysis according to methods well known to those of skill in the art.

6.2 Proteins and Polypeptides of FBP Genes

The amino acid sequences depicted in FIGS. 1, 2, and parts B of FIGS. 3 to 28 represent FBP gene products. The FBP1 gene product, sometimes referred to herein as a "FBP1 protein", includes those gene products encoded by the FBP1 gene sequences described in Section 5.1, above. Likewise, the FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, FBP25, FBL10, FBL11, and FBL12 gene products, referred to herein as an FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, FBP25, FBL10, FBL11, and FBL12 proteins, include those gene products encoded by the FBP2, FBP3, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, FBP25, FBL10, FBL11, and FBL12 genes. In accordance with the present invention, the nucleic acid sequences encoding the FBP gene products are derived from eukaryotic genomes, including mammalian genomes. In a preferred embodiment the nucleic acid sequences encoding the FBP gene products are derived from human or murine genomes.

FBP gene products, or peptide fragments thereof, can be prepared for a variety of uses. For example, such gene products, or peptide fragments thereof, can be used for the generation of antibodies, in diagnostic and prognostic assays, or for the identification of other cellular or extracellular gene products involved in the ubiquitination pathway and thereby implicated in the regulation of cell cycle and proliferative disorders.

In addition, FBP gene products of the present invention may include proteins that represent functionally equivalent (see Section 3.1 for a definition) gene products. FBP gene products of the invention do not encompass the previously identified mammalian F-box proteins Skp2, Cyclin F, Elongin A, or mouse Md6 (see Pagano, 1997, supra; Zhang, et al., 1995, supra; Bai, et al., 1996, supra; Skowyra, et al., 1997, supra).

Functionally equivalent FBP gene products may contain deletions, including internal deletions, additions, including additions yielding fusion proteins, or substitutions of amino acid residues within and/or adjacent to the amino acid sequence encoded by the FBP gene sequences described, above, in Section 5.1, but that result in a "silent" change, in that the change produces a functionally equivalent FBP gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered FBP gene products. Such alterations can, for example, alter one or more of the biological functions of the FBP gene product. Further, such alterations can be selected so as to generate FBP gene products that are better suited for expression, scale up, etc. in the host cells chosen. For example, cysteine residues can be deleted or substituted with another amino acid residue in order to eliminate disulfide bridges.

The FBP gene products, peptide fragments thereof and fusion proteins thereof, may be produced by recombinant DNA technology using techniques well known in the art. Thus, methods for preparing the FBP gene polypeptides, peptides, fusion peptide and fusion polypeptides of the invention by expressing nucleic acid containing FBP gene sequences are described herein. Methods that are well known to those skilled in the art can be used to construct expression vectors containing FBP gene product coding sequences and appropriate transcriptional and translational control signals. These methods include, for example, in vitro recombinant DNA techniques, synthetic techniques, and in vivo genetic recombination. See, for example, the techniques described in Sambrook, et al., supra, and Ausubel, et al., supra. Alternatively, RNA capable of encoding FBP gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the FBP gene coding sequences of the invention. Such host-expression systems represent vehicles by which the coding sequences of interest may be produced and subsequently purified, but also represent cells that may, when transformed or transfected with the appropriate nucleotide coding sequences, exhibit the FBP gene product of the invention in situ. These include but are not limited to microorganisms such as bacteria (e.g., *E. coli, B. subtilis*) transformed with recombinant bacteriophage DNA, plasmid DNA or cosmid DNA expression vectors containing FBP gene product coding sequences; yeast (e.g., *Saccharomyces, Pichia*) transformed with recombinant yeast expression vectors containing the FBP gene product coding sequences; insect cell systems infected with recombinant virus expression vectors (e.g., baculovirus) containing the FBP gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing FBP gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the FBP gene product being expressed. For example, when a large quantity of such a protein is to be produced, for the generation of pharmaceutical compositions of FBP protein or for raising antibodies to FBP protein, for example, vectors that direct the expression of high levels of fusion protein products that are readily purified may be desirable. Such vectors include, but are not limited, to the *E. coli* expression vector pUR278 (Ruther, et al., 1983, *EMBO J.* 2:1791), in which the FBP gene product coding sequence may be ligated individually into the vector in frame with the lac Z coding region so that a fusion protein is produced; pIN vectors (Inouye and Inouye, 1985, *Nucleic Acids Res.* 13:3101; Van Heeke and Schuster, 1989, *J. Biol. Chem.* 264:5503-5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhedrosis virus (AcNPV) is used as a vector to express foreign genes. The virus grows in *Spodoptera frugiperda* cells. The FBP gene coding sequence may be cloned individually into non-essential regions (for example the polyhedrin gene) of the virus and placed under control of an AcNPV promoter (for example the polyhedrin promoter). Successful insertion of FBP gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith, et al., 1983, *J. Virol.* 46:584; Smith, U.S. Pat. No. 4,215,051).

In mammalian host cells, a number of viral-based expression systems may be utilized. In cases where an adenovirus is used as an expression vector, the FBP gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing FBP gene product in infected hosts. (e.g., See Logan and Shenk, 1984, *Proc. Natl. Acad. Sci. USA* 81:3655). Specific initiation signals may also be required for efficient translation of inserted FBP gene product coding sequences. These signals include the ATG initiation codon and adjacent sequences. In cases where an entire FBP gene, including its own initiation codon and adjacent sequences, is inserted into the appropriate expression vector, no additional translational control signals may be needed. However, in cases where only a portion of the FBP gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, *Methods in Enzymol.* 153:516).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and W138.

For long-term, high-yield production of recombinant proteins, stable expression is preferred. For example, cell lines that stably express the FBP gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the FBP gene product. Such engineered cell lines may be particularly useful in screening and evaluation of compounds that affect the endogenous activity of the FBP gene product.

A number of selection systems may be used, including but not limited to the herpes simplex virus thymidine kinase (Wigler, et al., 1977, *Cell* 11:223), hypoxanthine-guanine phosphoribosyltransferase (Szybalska and Szybalski, 1962, *Proc. Natl. Acad. Sci. USA* 48:2026), and adenine phosphoribosyltransferase (Lowy, et al., 1980, *Cell* 22:817) genes can be employed in tk-, hgprt- or aprt-cells, respectively. Also, antimetabolite resistance can be used as the basis of selection for the following genes: dhfr, which confers resistance to methotrexate (Wigler, et al., 1980, *Natl. Acad. Sci. USA* 77:3567; O'Hare, et al., 1981, *Proc. Natl. Acad. Sci. USA* 78:1527); gpt, which confers resistance to mycophenolic acid (Mulligan and Berg, 1981, *Proc. Natl. Acad. Sci. USA* 78:2072); neo, which confers resistance to the aminoglycoside G-418 (Colberre-Garapin, et al., 1981, *J. Mol. Biol.* 150:1); and hygro, which confers resistance to hygromycin (Santerre, et al., 1984, *Gene* 30:147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, *Proc. Natl. Acad. Sci. USA* 88:8972). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto Ni2+ nitriloacetic acid-agarose columns and histidine-tagged proteins are selectively eluted with imidazole-containing buffers.

The FBP gene products can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate FBP transgenic animals. The term "transgenic," as used herein, refers to animals expressing FBP gene sequences from a different species (e.g., mice expressing human FBP sequences), as well as animals that have been genetically engineered to overexpress endogenous (i.e., same species) FBP sequences or animals that have been genetically engineered to no longer express endogenous FBP gene sequences (i.e., "knock-out" animals), and their progeny.

In particular, the present invention relates to FBP1 knockout mice. The present invention also relates to transgenic mice which express human wild-type FBP1 and Skp2 gene sequences in addition to mice engineered to express human mutant FBP1 and Skp2 gene sequences deleted of their F-box domains. Any technique known in the art may be used to introduce an FBP gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, *Proc. Natl. Acad. Sci., USA* 82:6148); gene targeting in embryonic stem cells (Thompson, et al., 1989, *Cell* 56:313); electroporation of embryos (Lo, 1983, *Mol. Cell. Biol.* 3:1803); and sperm-mediated gene transfer (Lavitrano et al., 1989, *Cell* 57:717) (For a review of such techniques, see Gordon, 1989, Transgenic Animals, *Intl. Rev. Cytol.* 115:171)

Any technique known in the art may be used to produce transgenic animal clones containing an FBP transgene, for example, nuclear transfer into enucleated oocytes of nuclei from cultured embryonic, fetal or adult cells induced to quiescence (Campbell, et al., 1996, *Nature* 380:64; Wilmut, et al., *Nature* 385:810).

The present invention provides for transgenic animals that carry an FBP transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, *Proc. Natl. Acad. Sci. USA* 89:6232). The regulatory sequences required for such a cell-type specific activation will depend upon the particular cell type of interest, and will be apparent to those of skill in the art. Examples of regulatory sequences that can be used to direct tissue-specific expression of an FBP transgene include, but are not limited to, the elastase I gene control region which is active in pancreatic acinar cells (Swift et al., 1984, Cell 38:639; Ornitz et al., 1986, Cold Spring Harbor Symp. Quant. Biol. 50:399; MacDonald, 1987, Hepatology 7:42 S); the insulin gene control region which is active in pancreatic beta cells (Hanahan, 1985, Nature 315:115); immunoglobulin gene control region which is active in lymphoid cells (Grosschedl, et al., 1984, Cell 38:647; Adams, et al., 1985, Nature 318:533; Alexander, et al., 1987, Mol. Cell. Biol. 7:1436): albumin gene control region which is active in liver (Pinkert, et al., 1987, Genes Dev. 1:268) alpha-fetoprotein gene control region which is active in liver (Krumlauf, et al., 1985, Mol. Cell. Biol. 5:1639; Hammer, et al., 1987, Science 235:53); alpha-1-antitrypsin gene control region which is active in liver (Kelsey, et al., 1987, Genes Dev. 1:161); beta-globin gene control region which is active in myeloid cells (Magram, et al., 1985, Nature 315:338; Kollias, et al., 1986, Cell 46:89); myelin basic protein gene control region which is active in oligodendrocyte cells in the brain (Readhead, et al., 1987, Cell 48:703); myosin light chain-2 gene control region which is active in skeletal muscle (Shani, 1985, Nature 314:283); and gonadotropic releasing hormone gene control region which is active in the hypothalamus (Mason, et al., 1986, Science 234:1372). Promoters isolated from the genome of viruses that grow in mammalian cells, (e.g., vaccinia virus 7.5K, SV40, HSV, adenoviruses MLP, MMTV, LTR and CMV promoters) may be used, as well as promoters produced by recombinant DNA or synthetic techniques.

When it is desired that the FBP gene transgene be integrated into the chromosomal site of the endogenous FBP gene, gene targeting is preferred. Briefly, when such a technique is to be utilized, vectors containing some nucleotide sequences homologous to the endogenous FBP gene are designed for the purpose of integrating, via homologous recombination with chromosomal sequences, into and disrupting the function of the nucleotide sequence of the endogenous FBP gene. The transgene may also be selectively introduced into a particular cell type, thus inactivating the endogenous FBP gene in only that cell type, by following, for example, the teaching of Gu, et al. (Gu, et al., 1994, Science 265:103). The regulatory sequences required for such a cell-type specific inactivation will depend upon the particular cell type of interest, and will be apparent to those of skill in the art.

Once transgenic animals have been generated, the expression of the recombinant FBP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of FBP gene-expressing tissue, may also be evaluated immunocytochemically using antibodies specific for the FBP transgene product.

Transgenic mice harboring tissue-directed transgenes can be used to test the effects of FBP gene expression the intact animal. In one embodiment, transgenic mice harboring a human FBP1 transgene in the mammary gland can be used to assess the role of FBPs in mouse mammary development and tumorigenesis. In another embodiment, transgenic mice can be generated that overexpress the human FBP1 dominant negative mutant form (F-box deleted) in the mammary gland. In a specific embodiment, for example, the MMTV LTR promoter (mouse mammary tumor virus long terminal repeat) can be used to direct integration of the transgene in the mammary gland. An MMTV/FBP1 fusion gene can be constructed by fusing sequences of the MMTV LTR promoter to nucleotide sequences upstream of the first ATG of FBP1 gene. An SV40 polyadenylation region can also be fused to sequences downstream of the FBP1 coding region. Transgenic mice are generated by methods well known in the art (Gordon, 1989, supra). Briefly, immature B6D2F1 female mice are superovulated and mated to CD-1 males. The following morning the females are examined for the presence of vaginal plugs, and fertilized ova are recovered and microinjected with a plasmid vector. Approximately 2000 copies of the material are microinjected into each pronucleus. Screening of founder animals is performed by extraction of DNA from spleen and Southern hybridization using the MMTV/FBP1 as a probe. Screening of offspring is performed by PCR of tail DNA. Once transgenic pedigrees are established, the expression pattern of the transgene is determined by Northern blot and RT-PCR analysis in different organs in order to correlate it with subsequent pathological changes.

The resulting transgenic animals can then be examined for the role of FBP genes in tumorigenesis. In one embodiment, for example, FBP transgenes can be constructed for use as a breast cancer model. Overexpression of FBP1 genes in such mice is expected to increase β-catenin ubiquitination and degradation, resulting in a tumor suppressor phenotype. Conversely, overexpression of the FBP1 deletion mutant is expected to result in stabilization of β-catenin and induce proliferation of mammary gland epithelium.

In another specific embodiment, transgenic mice are generated that express FBP1 transgenes in T-lymphocytes. In this embodiment, a CD2/FBP1 fusion gene is constructed by fusion of the CD2 promoter, which drives expression in both CD4 positive and negative T-cells, to sequences located upstream of the first ATG of an FBP gene, e.g., the wild-type and mutant FBP1 genes. The construct can also contain an SV40 polyadenylation region downstream of the FBP gene. After generation and testing of transgenic mice, as described above, the expression of the FBP transgene is examined. The transgene is expressed in thymus and spleen. Overexpression of wild-type FBP1 is expected to result in a phenotype. For example, possible expected phenotypes of FBP1 transgenic mice include increased degradation of IKBα, increased activation of NFκB, or increased cell proliferation. Conversely, overexpression of the dominant negative mutant, FBP1, lacking the F-box domain, can be expected to have the opposite effect, for example, increased stability of IKBα, decreased activation of NFκB, or decreased cell proliferation. Such transgenic phenotypes can be tested by assays such as those used in Section 5.4 and 5.5.

In another specific embodiment, the SKP2 gene is expressed in T-lymphocytes of transgenic mice. Conversely, the F-box deletion form acts as dominant negative, stabilizing p27 and inhibiting T-cell activation. Construction of the CD2/SKP2 fusion genes and production of transgenic mice are as described above for CD2/FBP fusion genes, using wild-type and mutant SKP2 cDNA, instead of FBP1 cDNA, controlled by the CD2 promoter. Founders and their progeny are analyzed for the presence and expression of the SKP2 transgene and the mutant SKP2 transgene. Expression of the transgene in spleen and thymus is analyzed by Northern blot and RT-PCR In another specific embodiment, transgenic mice are constructed by inactivation of the FBP1 locus in mice. Inactivation of the FBP1 locus in mice by homologous recombination involves four stages: 1) the construction of the targeting vector for FBP1; 2) the generation of ES +/− cells; 3) the production of knock-out mice; and 4) the characterization of the phenotype. A 129 SV mouse genomic phage library is used to identify and isolate the mouse FBP1 gene. Bacteriophages are plated at an appropriate density and an imprint of the pattern of plaques can be obtained by gently layering a nylon membrane onto the surface of agarose dishes. Bacteriophage particles and DNA are transferred to the filter by capillary action in an exact replica of the pattern of plaques. After denaturation, the DNA is bound to the filter by baking and then hybridized with $^{32}$P-labeled-FBP1 cDNA. Excess probe is washed away and the filters were then exposed for autoradiography. Hybridizing plaques, identified by aligning the film with the original agar plate, were picked for a secondary and a tertiary screening to obtain a pure plaque preparation. Using this method, positive phage which span the region of interest, for example, the region encoding the F-box, are isolated. Using PCR, Southern hybridization, restriction mapping, subcloning and DNA sequencing the partial structure of the wild-type FBP1 gene can be determined.

To inactivate the FBP1 locus by homologous recombination, a gene targeting vector is used in which exon 3 in the FBP1 locus is replaced by a selectable marker, for example, the neoR gene, in an antisense orientation can be constructed. Exon 3 encodes the F-box motif which is known to be critical for FBP1 interaction with Skp1. The targeting construct possesses a short and a long arm of homology flanking a selectable marker gene. One of the vector arms is relatively short (2 kb) to ensure efficient amplification since homologous recombinant ES clones will be screened by PCR. The other arm is >6 kb to maximize the frequency of homologous recombination. A thymidine kinase (tk) gene, included at the end of the long homology arm of the vector provides an additional negative selection marker (using gancylovir) against ES clones which randomly integrate the targeting vector. Since homologous recombination occurs frequently using linear DNA, the targeting vector is linearized prior to transfection of ES cells.

Following electroporation and double drug selection of embryonic stem cell clones, PCR and Southern analysis is used to determine whether homologous recombination has occurred at the FBP1 locus. Screening by PCR is advantageous because a larger number of colonies can be analyzed with this method than with Southern analysis. In addition, PCR screening allows rapid elimination of negative clones thus to avoid feeding and subsequently freezing all the clones while recombinants are identified. This PCR strategy for detection of homologous recombinants is based on the use of a primer pair chosen such that one primer anneals to a sequence specific to the targeting construct, e.g., sequences of the neomycin gene or other selectable marker, and not in the endogenous locus, and the other primer anneals to a region outside the construct, but within the endogenous locus. Southern analysis is used to confirm that a homologous recombination event has occurred (both at the short arm of homology and at the long arm of homology) and that no gene duplication events have occurred during the recombination.

Such FBP1 knockout mice can be used to test the role of FBP1 in cellular regulation and control of proliferation. In one embodiment, phenotype of such mice lacking FBP1 is cellular hyperplasia and increased tumor formation. In another embodiment, FBP1 null mice phenotypes include, but are not limited to, increased β-catenin activity, stabilization of β-catenin, increased cellular proliferation, accumulation of IKBα, decreased NF-KB activity, deficient immune response, inflammation, or increased cell death or apoptotic activity. Alternatively, a deletion of the of the FBP1 gene can result in an embryonic lethality. In this case, heterozygous mice at the FBP1 allele can be tested using the above assays, and embryos of null FBP mice can be tested using the assays described above. In an additional embodiment, FBP1 null mice have a phenotype of decreased fertility.

Transgenic mice bearing FBP transgenes can also be used to screen for compounds capable of modulating the expression of the FBP gene and/or the synthesis or activity of the FBP1 gene or gene product. Such compounds and methods for screening are described.

6.3 Generation of Antibodies to F-Box Proteins and their Derivatives

According to the invention, the F-box motif, its fragments or other derivatives, or analogs thereof, may be used as an immunogen to generate antibodies which immunospecifically bind such an immunogen. Such antibodies include but are not limited to polyclonal, monoclonal, chimeric, single chain, Fab fragments, and an Fab expression library. In a specific embodiment, antibodies to a human FBP protein are produced. In another embodiment, antibodies to a domain (e.g., the F-box domain or the substrate-binding domain) of an FBP are produced.

Various procedures known in the art may be used for the production of polyclonal antibodies to an FBP or derivative or analog. In a particular embodiment, rabbit polyclonal antibodies to an epitope of an FBP encoded by a sequence of FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, FBP25, FBL10, FBL11, and FB112, or a subsequence thereof, can be obtained (Pagano, 1995, *Cell Cycle: Materials and Methods*. M. Pagano, ed. Spring-Verlag. 217-281). For the production of antibody, various host animals can be immunized by injection with the native FBP, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward an FBP sequence or analog thereof, any technique which provides for the production of antibody molecules by continuous cell lines in culture may be used. For example, the hybridoma technique originally developed by Kohler and Milstein (Kohler and Milstein, 1975, *Nature* 256:495), as well as the trioma technique, the human B-cell hybridoma technique (Kozbor, et al., 1983, *Immunol. Today* 4:72), and the EBV-hybridoma technique to produce human monoclonal antibodies (Cole, et al., 1985, *Monoclonal Antibodies and Cancer Therapy*, Alan R. Liss, Inc., 77-96). In an additional embodiment of the invention, monoclonal antibodies can be produced in germ-free animals utilizing recent technology (PCT/US90/02545). According to the invention, human antibodies may be used and can be obtained by using human hybridomas (Cote, et al., 1983, *Proc. Natl. Acad. Sci. U.S.A.* 80:2026) or by transforming human B cells with EBV virus in vitro (Cole, et al., supra). In fact, according to the invention, techniques developed for the production of "chimeric antibodies" (Morrison, et al., 1984, *Proc. Natl. Acad. Sci. U.S.A.* 81:6851; Neuberger, et al., 1984, *Nature* 312:604; Takeda, et al., 1985, *Nature* 314:452) by splicing the genes from a mouse antibody molecule specific for FBP together with genes from a human antibody molecule of appropriate biological activity can be used; such antibodies are within the scope of this invention.

According to the invention, techniques described for the production of single chain antibodies (U.S. Pat. No. 4,946,778) can be adapted to produce FBP-specific single chain antibodies. An additional embodiment of the invention utilizes the techniques described for the construction of Fab expression libraries (Huse, et al., 1989, *Science* 246:1275) to allow rapid and easy identification of monoclonal Fab fragments with the desired specificity for FBPs, derivatives, or analogs.

Antibody fragments which contain the idiotype of the molecule can be generated by known techniques. For example, such fragments include but are not limited to: the F(ab')2 fragment which can be produced by pepsin digestion of the antibody molecule; the Fab' fragments which can be generated by reducing the disulfide bridges of the F(ab')2 fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific domain of an FBP, one may assay generated hybridomas for a product which binds to an FBP fragment containing such domain. For selection of an antibody that specifically binds a first FBP homolog but which does not specifically bind a different FBP homolog, one can select on the basis of positive binding to the first FBP homolog and a lack of binding to the second FBP homolog.

Antibodies specific to a domain of an FBP are also provided, such as an F-box motif.

The foregoing antibodies can be used in methods known in the art relating to the localization and activity of the FBP sequences of the invention, e.g., for imaging these proteins, measuring levels thereof in appropriate physiological samples, in diagnostic methods, etc.

In another embodiment of the invention (see infra), anti-FBP antibodies and fragments thereof containing the binding domain are used as therapeutics.

6.4 Screening Assays for the Identification of Agents that Interact with F-Box Proteins and/or Interfere with their Enzymatic Activities Novel components of the ubiquitin ligase complex, including FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, and FBP25 interact with cellular proteins to regulate cellular proliferation. One aspect of the present invention provides methods for assaying and screening fragments, derivatives and analogs of the novel components to identify polypeptides or peptides or other compounds that interact with the novel ubiquitin ligases such as potential substrates of ubiquitin ligase activity. The present invention also provides screening assays to identify compounds that modulate or inhibit the interaction of the novel FBPs with other subunits or numbers of the ubiquitin ligase complex, such as Skp1, or ubiquitinating enzymes with which the novel FBPs interact.

In yet another embodiment, the assays of the present invention may be used to identify polypeptides or peptides or other compounds which inhibit or modulate the interaction between the novel ubiquitin ligases or known (e.g., Skp1) components of the ubiquitin ligase complex with novel or known substrates. By way of example, but not by limitation, the screening assays described herein may be used to identify peptides or proteins that interfere with the interaction between known ubiquitin ligase component, Skp2, and its novel substrate, p27. In another example, compounds that interfere with the interaction between FBP1/β-Trcp1 and its novel substrate, β-catenin, are identified using the screening assay. In another example, compounds that interfere with the interaction between FBP1 and its novel substrate FBP5/Emi1 are identified using the screening assay. In another example, compounds that interfere with the interaction between Skp2 and another putative substrate, E2F, are identified using the screening assay. In yet another example, compounds that interfere with the interaction between FBP1 and another putative substrate, IκBα, are identified using the screening assay. In an additional example, compounds that interfere with the interaction between the FBP1 isoforms FBP1/β-Trcp1 and FBX1B/β-Trcp2, and their substrate β-catenin, are identified using the screening assay. In yet another example, compounds that interfere with the interaction between the FBP1 isoforms FBP1/β-Trcp1 and FBX1μ/β-Trcp2, and their substrate IκBα, are identified using the screening assay.

In yet another embodiment, the assays of the present invention may be used to identify polypeptides or peptides which inhibit or activate the enzymatic activators of the novel FBPs.

6.4.1 Assays for Protein-Protein Interactions

Derivatives, analogs and fragments of proteins that interact with the novel components of the ubiquitin ligase complex of the present invention can be identified by means of a two hybrid assay system. Originally developed in yeast, the two hybrid system has recently been adapted for use in mammalian cells and may be obtained in kit form (Fields and Song, 1989, *Nature* 340:245; U.S. Pat. No. 5,283,173; Dang et al., 1991, *Mol. Cell. Biol.* 11:954; Fearon et al., 1992, *Proc. Natl. Acad. Sci. U.S.A.* 89:7958, and CheckMate Mammalian Two-Hybrid System, Promega Cat. # E2440). When the assay system is implemented in yeast, the intermolecular protein interactions detected in this system occur under physiological conditions that mimic the conditions in mammalian cells (Chien, et al., 1991, *Proc. Natl. Acad. Sci. U.S.A.* 88:9578). If implemented in mammalian cells, the protein:protein interactions can be assayed in the cell line of choice (see Check-Mate Mammalian Two-Hybrid System, Technical Manual #TM049, 2000, Promega).

Identification of interacting proteins by the two hybrid system is based upon the detection of expression of a reporter gene, the transcription of which is dependent upon the reconstitution of a transcriptional regulator by the interaction of two proteins, each fused to one half of the transcriptional regulator. The "bait" (i.e., the novel components of the ubiquitin ligase complex of the present invention or derivatives or analogs thereof) and "prey" (proteins to be tested for ability to interact with the bait) proteins are expressed as fusion proteins to a DNA binding domain, and to a transcriptional regulatory domain, respectively, or vice versa. In various specific embodiments, the prey has a complexity of at least about 50, about 100, about 500, about 1,000, about 5,000, about 10,000, or about 50,000; or has a complexity in the range of about 25 to about 100,000, about 100 to about 100,000, about 50,000 to about 100,000, or about 100,000 to about 500,000. For example, the prey population can be one or more nucleic acids encoding mutants of a protein (e.g., as generated by site-directed mutagenesis or another method of making mutations in a nucleotide sequence). Preferably, the prey populations are proteins encoded by DNA, e.g., cDNA or genomic DNA or synthetically-generated DNA. For example, the populations can be expressed from chimeric genes comprising cDNA sequences from an un-characterized sample of a population of cDNA from mRNA.

In a specific embodiment, recombinant biological libraries expressing random peptides can be used as the source of prey nucleic acids.

In general, proteins of the bait and prey populations are provided as fusion (chimeric) proteins (preferably by recombinant expression of a chimeric coding sequence) comprising each protein contiguous to a pre-selected sequence. For one population, the pre-selected sequence is a DNA binding domain. The DNA binding domain can be any DNA binding domain, as long as it specifically recognizes a DNA sequence within a promoter. For example, the DNA binding domain is of a transcriptional activator or inhibitor. For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably do not detectably interact (so as to avoid false positives in the assay). The assay system further includes a reporter gene operably linked to a promoter that contains a binding site for the DNA binding domain of the transcriptional activator (or inhibitor). Accordingly, in the present method of the present invention, binding of a ubiquitin ligase fusion protein to a prey fusion protein leads to reconstitution of a transcriptional activator (or inhibitor) which activates (or inhibits) expression of the reporter gene. The activation (or inhibition) of transcription of the reporter gene occurs intracellularly, e.g., in prokaryotic or eukaryotic cells, preferably in cell culture.

The promoter that is operably linked to the reporter gene nucleotide sequence can be a native or non-native promoter of the nucleotide sequence, and the DNA binding site(s) that are recognized by the DNA binding domain portion of the fusion protein can be native to the promoter (if the promoter normally contains such binding site(s)) or non-native to the promoter.

Alternatively, the transcriptional activation binding site of the desired gene(s) can be deleted and replaced with GAL4 binding sites (Bartel, et al., 1993, *BioTechniques* 14:920, Chasman, et al., 1989, *Mol. Cell. Biol.* 9:4746). The reporter gene preferably contains the sequence encoding a detectable or selectable marker, the expression of which is regulated by the transcriptional activator, such that the marker is either turned on or off in the cell in response to the presence of a specific interaction. Preferably, the assay is carried out in the absence of background levels of the transcriptional activator (e.g., in a cell that is mutant or otherwise lacking in the transcriptional activator).

The activation domain and DNA binding domain used in the assay can be from a wide variety of transcriptional activator proteins, as long as these transcriptional activators have separable binding and transcriptional activation domains. For example, the GAL4 protein of *S. cerevisiae* (Ma, et al., 1987, *Cell* 48:847), the GCN4 protein of *S. cerevisiae* (Hope and Struhl, 1986, *Cell* 46:885), the ARD1 protein of *S. cerevisiae* (Thukral, et al., 1989, *Mol. Cell. Biol.* 9:2360), and the human estrogen receptor (Kumar, et al., 1987, *Cell* 51:941), have separable DNA binding and activation domains. The DNA binding domain and activation domain that are employed in the fusion proteins need not be from the same transcriptional activator. In a specific embodiment, a GAL4 or LEXA DNA binding domain is employed. In another specific embodiment, a GAL4 or herpes simplex virus VP16 (Triezenberg, et al., 1988, *Genes Dev.* 2:730, and CheckMate Mammalian Two-Hybrid System, Promega Cat #E2440) activation domain is employed. In a specific embodiment, amino acids 1-147 of GAL4 (Ma et al., supra; Ptashne, et al., 1990, *Nature* 346:329) is the DNA binding domain, and amino acids 411-455 of VP16 (Triezenberg, et al., supra; Cress, et al., 1991, *Science* 251:87) comprise the activation domain.

In one embodiment using the yeast two-hybrid assay system, the yeast transcription factor GAL4 is reconstituted by protein-protein interaction and the host strain is mutant for GAL4. In another embodiment, the DNA-binding domain is Ace1N and/or the activation domain is Ace1, the DNA binding and activation domains of the Ace1 protein, respectively. Ace1 is a yeast protein that activates transcription from the CUP1 operon in the presence of divalent copper. CUP1 encodes metallothionein, which chelates copper, and the expression of CUP1 protein allows growth in the presence of copper, which is otherwise toxic to the host cells. The reporter gene can also be a CUP1-lacZ fusion that expresses the enzyme beta-galactosidase (detectable by routine chromogenic assay) upon binding of a reconstituted Ace1N transcriptional activator (see Chaudhuri, et al., 1995, *FEBS Letters* 357:221). In another specific embodiment, the DNA binding domain of the human estrogen receptor is used, with a reporter gene driven by one or three estrogen receptor response elements (Le Douarin, et al., 1995, *Nucl. Acids. Res.* 23:876). The DNA binding domain and the transcriptional activator/inhibitor domain each preferably has a nuclear localization signal (see Ylikomi, et al., 1992, *EMBO J.* 11:3681, Dingwall and Laskey, 1991, *TIBS* 16:479) functional in the cell in which the fusion proteins are to be expressed.

To facilitate isolation of the encoded proteins, the fusion constructs can further contain sequences encoding affinity tags such as glutathione-S-transferase or maltose-binding protein or an epitope of an available antibody, for affinity purification (e.g., binding to glutathione, maltose, or a particular antibody specific for the epitope, respectively) (Allen, et al., 1995, *TIBS* 20:511). In another embodiment, the fusion constructs further comprise bacterial promoter sequences for recombinant production of the fusion protein in bacterial cells.

The host cell in which the interaction assay occurs can be any cell, prokaryotic or eukaryotic, in which transcription of the reporter gene can occur and be detected, including, but not limited to, mammalian (e.g., monkey, mouse, rat, human, bovine), chicken, bacterial, insect cells, or yeast cells. Expression constructs encoding and capable of expressing the binding domain fusion proteins, the transcriptional activation domain fusion proteins, and the reporter gene product(s) are provided within the host cell by cell fusion, transformation, electroporation, microinjection or other suitable method known in the art. For example, in yeast, the expression constructs may be introduced into a host cell by the mating of cells containing the individual expression constructs.

Various vectors and host strains for expression of the two fusion protein populations in yeast are known and can be used (see e.g., U.S. Pat. No. 5,468,614; Bartel, et al., 1993, In: *Cellular Interactions in Development*, Hartley, ed., Practical Approach Series xviii, IRL Press at Oxford University Press, New York, N.Y., 153-179; Fields and Sternglanz, 1994, *Trends In Genetics* 10:286-292).

If not already lacking in endogenous reporter gene activity, cells mutant in the reporter gene may be selected by known methods, or the cells can be made mutant in the target reporter gene by known gene-disruption methods prior to introducing the reporter gene (Rothstein, 1983, *Meth. Enzymol.* 101:202-211).

In a specific embodiment, plasmids encoding the different fusion protein populations can be introduced simultaneously with a plasimid containing the reporter gene construct or introduced into a single host cell already containing one or more reporter genes, by co-transformation, to conduct the assay for protein-protein interactions. If using a kit assay system for mammalian cells, the introduction of the fusion proteins and reporter gene construct will be according to the manufacturer's directions. In mammalian cells, the various plasmids or plasmids may also be introduced into a single cell by cell fusion. In a yeast-based system, the two fusion protein populations may be introduced into a single cell by mating (e.g., for yeast cells). In a mating type assay, conjugation of haploid yeast cells of opposite mating type that have been transformed with a binding domain fusion expression construct (preferably a plasmid) and an activation (or inhibitor) domain fusion expression construct (preferably a plasmid), respectively, will deliver both constructs into the same diploid cell. The mating type of a yeast strain may be manipulated by transformation with the HO gene (Herskowitz and Jensen, 1991, *Meth. Enzymol.* 194:132).

The yeast interaction mating assay is employed using two different types of host cells, strain-type a and alpha of the yeast *Saccharomyces cerevisiae*. The host cell preferably contains at least two reporter genes, each with one or more binding sites for the DNA-binding domain (e.g., of a transcriptional activator). The activator domain and DNA binding domain are each parts of chimeric proteins formed from the two respective populations of proteins. One strain of host cells, for example the a strain, contains fusions of the library of nucleotide sequences with the DNA-binding domain of a transcriptional activator, such as GAL4. The hybrid proteins expressed in this set of host cells are capable of recognizing the DNA-binding site in the promoter or enhancer region in the reporter gene construct. The second set of yeast host cells, for example, the alpha strain, contains nucleotide sequences encoding fusions of a library of DNA sequences fused to the activation domain of a transcriptional activator.

In another embodiment, the fusion constructs are introduced directly into the yeast chromosome via homologous recombination. The homologous recombination for these purposes is mediated through yeast sequences that are not essential for vegetative growth of yeast, e.g., the MER2, MER1, ZIPI, REC102, or ME14 gene.

Bacteriophage vectors can also be used to express the DNA binding domain and/or activation domain fusion proteins. Libraries can generally be prepared faster and more easily from bacteriophage vectors than from plasmid vectors.

In a specific embodiment, the present invention provides a method of detecting one or more protein-protein interactions comprising (a) recombinantly expressing a novel ubiquitin ligase component of the present invention or a derivative or analog thereof in a first population of yeast cells being of a first mating type and comprising a first fusion protein containing the sequence of a novel ubiquitin ligase component of the present invention and a DNA binding domain, wherein said first population of yeast cells contains a first nucleotide sequence operably linked to a promoter driven by one or more DNA binding sites recognized by said DNA binding domain such that an interaction of said first fusion protein with a second fusion protein, said second fusion protein comprising a transcriptional activation domain, results in increased transcription of said first nucleotide sequence; (b) negatively selecting to eliminate those yeast cells in said first population in which said increased transcription of said first nucleotide sequence occurs in the absence of said second fusion protein; (c) recombinantly expressing in a second population of yeast cells of a second mating type different from said first mating type, a plurality of said second fusion proteins, each second fusion protein comprising a sequence of a fragment, derivative or analog of a protein and an activation domain of a transcriptional activator, in which the activation domain is the same in each said second fusion protein; (d) mating said first population of yeast cells with said second population of yeast cells to form a third population of diploid yeast cells, wherein said third population of diploid yeast cells contains a second nucleotide sequence operably linked to a promoter driven by a DNA binding site recognized by said DNA binding domain such that an interaction of a first fusion protein with a second fusion protein results in increased transcription of said second nucleotide sequence, in which the first and second nucleotide sequences can be the same or different; and (e) detecting said increased transcription of said first and/or second nucleotide sequence, thereby detecting an interaction between a first fusion protein and a second fusion protein.

6.4.2 Assays to Identify F-Box Protein Interactions with Known Proteins Including Potential Substrates The cellular abundance of cell-cycle regulatory proteins, such as members of the cyclin family or the Cki inhibitory proteins, is regulated by the ubiquitin pathway. The enzymes responsible for the ubiquitination of mammalian cell cycle regulation are not known. In yeast, SCF complexes represent the ubiquitin ligases for cell cycle regulators. The F-box component of the ubiquitin ligase complexes, such as the novel F-box proteins of the invention, determines the specificity of the target of the ubiquitin ligase complex. The invention therefore provides assays to screen known molecules for specific binding to F-box protein nucleic acids, proteins, or derivatives under conditions conducive to binding, and then molecules that specifically bind to the FBP protein are identified.

In a specific embodiment, the invention provides a method for studying the interaction between the F-box protein Fbp1 and the Cul1/Skp1 complex, and its role in regulating the stability of β-catenin. Protein-protein interactions can be probed in vivo and in vitro using antibodies specific to these proteins, as described in detail in the experiments in Section 7.

In another specific embodiment, methods for detecting the interaction between Skp2 and p27, a cell cycle regulated cyclin-dependent kinase (Cdk) inhibitor, are provided, as described in Section 9. The interaction between Skp2 and p27 may be targeted to identify modulators of Skp2 activity, including its interaction with cell cycle regulators, such as p27. The ubiquitination of Skp2-specific substrates, such as p27 may be used as a means of measuring the ability of a test compound to modulate Skp2 activity. In another embodiment of the screening assays of the present invention, immunodepletion assays, as described in Section 9, can be used to identify modulators of the Skp2/p27 interaction. In particular, Section 9 describes a method for detection of ubiquitination activity in vitro using p27 as a substrate, which can also be used to identify modulators of the Skp2-dependent ubiquitination of p27. In another embodiment of the screening assays of the present invention, antisense oligonucleotides, as described in Section 6.7.1, can be used as inhibitors of the Skp2 activity. Such identified modulators of p27 ubiquitination/degradation and of the Skp2/p27 interaction can be useful in anti-cancer therapies.

In another specific embodiment, methods for detecting the interaction between Skp2 and Cks1 and Skp2, Cks1, and p27 are provided. The interaction between Skp2 and Cks1, and Skp2, Cks1 and p27 may be targeted to identify modulators of Skp2 activity, including its interaction with molecules involved in the cell cycle, such as Cks1 and p27. The ubiquitination of Skp2-specific substrates, such as p27 may be used as a means of measuring the ability of a test compound to modulate Skp2 activity in the presence or absence of Cks1. Section 9 describes another embodiment of the screening assays of the present invention for detection of ubiquitination activity by Skp2 with or without Cks1 in vitro using p27 or a phospho-peptide corresponding to the carboxy terminus of p27 with or without a phosphothreonine at position 187 as a substrate, which can also be used to identify modulators of the Skp2-dependent ubiquitination of p27. In another embodiment of the screening assays of the present invention, antisense oligonucleotides, as described in Section 6.7.1, can be used as inhibitors of the Skp2 activity. Such identified modulators of p27 ubiquitination/degradation and of the Skp2/Cks1/p27 interaction can be useful in anti-cancer therapies.

In another specific embodiment, the invention provides for a method for detecting the interaction between the F-box protein Skp2 and E2F-1, a transcription factor involved in cell cycle progression. Insect cells can be infected with baculoviruses co-expressing Skp2 and E2F-1, and cell extracts can be prepared and analyzed for protein-protein interactions. As described in detail in Section 11, this assay has been used successfully to identify potential targets, such as E2F, for known F-box proteins, such as Skp2. This assay can be used to identify other Skp2 targets, as well as targets for novel F-box proteins.

In another specific embodiment, methods for detecting the interaction between Fbp1 and either of the Fbp1 substrates β-catenin or IκBα, are provided. In another specific embodiment, methods for detecting the interaction between the Fbp1 isoform β-Trcp2 and either of the β-Trcp2 substrates β-catenin or IκBα, are provided. In yet another specific embodiment, compounds that interfere with the interaction between Fbp1 and either of the Fbp1 substrates β-catenin or IκBα, are provided. In another specific embodiment, compounds that interfere with the interaction between β-Trcp2 and either of the β-Trcp2 substrates β-catenin or IκBα, are provided. The interaction of FBP1 or p-Trcp2, with substrates such as β-catenin or IκBα, may be targeted to identify modulators of FBP1 or β-Trcp2. The ubiquitination of FBP1 or β-Trcp2 specific substrates, such as β-catenin or IκBα, may be used as a means of measuring the ability of a test compound to modulate FBP1 or β-Trcp2 activity. In particular, Section 12 describes a method for detection of substrate stabilization in vitro using β-catenin or IκBα as a substrate, which can also be used to identify modulators of FBP1 or β-Trcp2-mediated substrate degradation. In another embodiment of the screening assays of the present invention, antisense oligonucleotides, as described in Section 5.7.1, can be used as inhibitors of FBP1 or β-Trcp2 activity. Such identified modulators of β-catenin or IκBα degradation can be useful in anti-cancer or infertility therapies.

The invention further provides methods for screening ubiquitin ligase complexes having novel F-box proteins (or fragments thereof) as one of their components for ubiquitin ligase activity using known cell-cycle regulatory molecules as potential substrates for ubiquitination. For example, cells engineered to express FBP nucleic acids can be used to recombinantly produce FBP proteins either wild-type or dominant negative mutants in cells that also express a putative ubiquitin-ligase substrate molecule. Such candidates for substrates of the novel FBP of the present invention include, but are not limited to, such potential substrates as IκBα, β-catenin, myc, E2F-1, p27, p21, cyclin A, cyclin B, cycD1, cyclin E and p53. Then the extracts can be used to test the association of F-box proteins with their substrates, (by Western blot immunoassays) and whether the presence of the FBP increases or decreases the level of the potential substrates.

6.5 Assays for the Identification of Compounds that Modulate the Activity of F-Box Proteins The present invention relates to in vitro and in vivo assay systems described in the subsections below, which can be used to identify compounds or compositions that modulate the interaction of known FBPs with novel substrates and novel components of the ubiquitin ligase complex. The screening assays of the present invention may also be used to identify compounds or compositions that modulate the interaction of novel FBPs with their identified substrates and components of the ubiquitin ligase complex.

Methods to screen potential agents for their ability to disrupt or moderate FBP expression and activity can be designed based on the Applicants' discovery of novel FBPs and their interaction with other components of the ubiquitin ligase complex as well as its known and potential substrates. For example, candidate compounds can be screened for their ability to modulate the interaction of an FBP and Skp1, or the specific interactions of Skp2 with E2F-1, Skp2 with Cks 1, Skp2 with Cks 1 and p27, or the FBP1/Cul1/Skp1 complex with β-catenin. In principle, many methods known to those of skill in the art, can be readily adapted in designed the assays of the present invention.

The screening assays of the present invention also encompass high-throughput screens and assays to identify modulators of FBP expression and activity. In accordance with this embodiment, the systems described below may be formulated into kits. To this end, cells expressing FBP and components of the ubiquitination ligase complex and the ubiquitination pathway, or cell lysates, thereof can be packaged in a variety of containers, e.g., vials, tubes, microtitre well plates, bottles, and the like. Other reagents can be included in separate containers and provided with the kit; e.g., positive control samples, negative control samples, buffers, cell culture media, etc.

The invention provides screening methodologies useful in the identification of proteins and other compounds which bind to, or otherwise directly interact with, the FBP genes and their gene products. Screening methodologies are well known in the art (see e.g., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the normal or mutant FBP genes and FBP proteins.

Alternatively, any of a variety of exogenous compounds, both naturally occurring and/or synthetic (e.g., libraries of small molecules or peptides), may be screened for binding capacity. All of these methods comprise the step of mixing an FBP protein or fragment with test compounds, allowing time for any binding to occur, and assaying for any bound complexes. All such methods are enabled by the present disclosure of substantially pure FBP proteins, substantially pure functional domain fragments, fusion proteins, antibodies, and methods of making and using the same.

6.5.1 Assays for F-Box Protein Agonists and Antagonists

FBP nucleic acids, F-box proteins, and derivatives can be used in screening assays to detect molecules that specifically bind to FBP nucleic acids, proteins, or derivatives and thus have potential use as agonists or antagonists of FBPs, in particular, molecules that thus affect cell proliferation. In a preferred embodiment, such assays are performed to screen for molecules with potential utility as anti-cancer drugs or lead compounds for drug development. The invention thus provides assays to detect molecules that specifically bind to FBP nucleic acids, proteins, or derivatives. For example, recombinant cells expressing FBP nucleic acids can be used to recombinantly produce FBP proteins in these assays, to screen for molecules that bind to an FBP protein. Similar methods can be used to screen for molecules that bind to FBP derivatives or nucleic acids. Methods that can be used to carry out the foregoing are commonly known in the art. The assays of the present invention may be first optimized on a small scale (i.e., in test tubes), and then scaled up for high-throughput assays. The screening assays of the present may be performed in vitro, i.e. in test tubes, using purified components or cell lysates. The screening assays of the present invention may also be carried out in intact cells in culture and in animal models. In accordance with the present invention, test compounds which are shown to modulate the activity of the FBP as described herein in vitro, will further be assayed in vivo, including cultured cells and animal models to determine if the test compound has the similar effects in vivo and to determine the effects of the test compound on cell cycle progression, the accumulation or degradation of positive and negative regulators, cellular proliferation etc.

In accordance with the present invention, screening assays may be designed to detect molecules which act as agonists or antagonists of the activity of the novel and known F-box proteins. In accordance with this aspect of the invention, the test compound may be added to an assay system to measure its effect on the activity of the novel or known FBP, i.e., ubiquitination of its substrates, interaction with other components of the ubiquitin ligase complex, etc. These assays should be conducted both in the presence and absence of the test compound.

In accordance with the present invention, ubiquitination activity of a novel or known FBP in the presence or absence of a test compound can be measured in vitro using purified components of the ubiquitination pathway or may be measured using crude cellular extracts obtained from tissue culture cells or tissue samples. In another embodiment of the aspect of the present invention the screening may be performed by adding the test agent to in vitro translation systems such as a rabbit reticulocyte lysate (RRL) system and then proceeding with the established analysis. As another alternative, purified or partially purified components which have been determined to interact with one another by the methods described above can be placed under conditions in which the interaction between them would normally occur, with and without the addition of the test agent, and the procedures previously established to analyze the interaction can be used to assess the impact of the test agent. In this approach, the purified or partially purified components may be prepared by fractionation of extracts of cells expressing the components of the ubiquitin ligase complex and pathway, or they may be obtained by expression of cloned genes or cDNAs or fragments thereof, optionally followed by purification of the expressed material.

Within the broad category of in vitro selection methods, several types of method are likely to be particularly convenient and/or useful for screening test agents. These include but are not limited to methods which measure a binding interaction between two or more components of the ubiquitin ligase complex or interaction with the target substrate, methods which measure the activity of an enzyme which is one of the interacting components, and methods which measure the activity or expression of "reporter" protein, that is, an enzyme or other detectable or selectable protein, which has been placed under the control of one of the components.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

In another embodiment, screening can be carried out by contacting the library members with an FBP protein (or nucleic acid or derivative) immobilized on a solid phase and harvesting those library members that bind to the protein (or nucleic acid or derivative). Examples of such screening methods, termed "panning" techniques are described by way of example in Parmley and Smith, 1988, Gene 73:305; Fowlkes, et al., 1992, BioTechniques 13:422; PCT Publication No. WO 94/18318; and in references cited herein above.

In another embodiment, the two-hybrid system for selecting interacting proteins or peptides in yeast (Fields and Song, 1989, Nature 340:245; Chien, et al., 1991, Proc. Natl. Acad. Sci. USA 88:9578) can be used to identify molecules that specifically bind to an FBP protein or derivative.

Alternatively, test methods may rely on measurements of enzyme activity, such as ubiquitination of the target substrate. Once a substrate of a novel FBP is identified or a novel putative substrate of a known FBP is identified, such as the novel substrates of Skp2, E2F and p27, these components may be used in assays to determine the effect of a test compound on the ubiquitin ligase activity of the ubiquitin ligase complex.

In one embodiment, the screening assays may be conducted with a purified system in the presence and absence of test compound. Purified substrate is incubated together with purified ubiquitin ligase complex, ubiquitin conjugating enzymes, ubiquitin activating enzymes and ubiquitin in the presence or in the absence of test compound. Ubiquitination of the substrate is analyzed by immunoassay (see Pagano et al., 1995, Science 269:682). Briefly, ubiquitination of the substrate can be performed in vitro in reactions containing 50-200 ng of proteins in 50 mM Tris pH 7.5, 5 mM MgCl2, 2 mM ATPγ-S, 0.1 mM DTT and 5 μM of biotinylated ubiquitin. Total reactions (30 μl) can be incubated at 25° C. for up to 3 hours in the presence or absence of test compound and then loaded on an 8% SDS gel or a 4-20% gradient gel for analysis. The gels are run and proteins are electrophoretically transferred to nitrocellulose. Ubiquitination of the substrate can be detected by immunoblotting. Ubiquitinated substrates can be visualized using Extravidin-HRP (Sigma), or by using a substrate-specific antibody, and the ECL detection system (NEN).

In another embodiment, ubiquitination of the substrate may be assayed in intact cells in culture or in animal models in the presence and absence of the test compound. For example, the test compound may be administered directly to an animal model or to crude extracts obtained from animal tissue samples to measure ubiquitination of the substrate in the presence and absence of the test compounds. For these assays, host cells to which the test compound is added may be genetically engineered to express the FBP components of the ubiquitin ligase pathway and the target substrate, the expression of which may be transient, induced or constitutive, or stable. For the purposes of the screening methods of the present invention, a wide variety of host cells may be used including, but not limited to, tissue culture cells, mammalian cells, yeast cells, and bacteria. Each cell type has its own set of advantages and drawbacks. Mammalian cells such as primary cultures of human tissue cells may be a preferred cell type in which to carry out the assays of the present invention, however these cell types are sometimes difficult to cultivate. Bacteria and yeast are relatively easy to cultivate but process proteins differently than mammalian cells. This ubiquitination assay may be conducted as follows: first, the extracts are prepared from human or animal tissue. To prepare animal tissue samples preserving ubiquitinating enzymes, 1 g of tissue can be sectioned and homogenized at 15,000 r.p.m. with a Brinkmann Polytron homogenizer (PT 3000, Westbury, N.Y.) in 1 ml of ice-cold double-distilled water. The sample is frozen and thawed 3 times. The lysate is spun down at 15,000 r.p.m. in a Beckman JA-20.1 rotor (Beckman Instruments, Palo Alto, Calif.) for 45 min at 4° C. The supernatant is retrieved and frozen at −80° C. This method of preparation of total extract preserves ubiquitinating enzymes (Loda, et al. 1997, *Nature Medicine* 3:231, incorporated by reference herein in its entirety).

Purified recombinant substrate is added to the assay system and incubated at 37° C. for different times in 30 µl of ubiquitination mix containing 100 µg of protein tissue homogenates, 50 mM Tris-HCl (pH 8.0), 5 mM MgCl2, and 1 mM DTT, 2 mM ATP, 10 mM creatine phosphokinase, 10 mM creatine phosphate and 5 µM biotinylated ubiquitin. The substrate is then re-purified with antibodies or affinity chromatography. Ubiquitination of the substrate is measured by immunoassays with either antibodies specific to the substrates or with Extravidin-HRP.

In addition, *Drosophila* can be used as a model system in order to detect genes that phenotypically interact with FBP. For example, overexpression of FBP in *Drosophila* eye leads to a smaller and rougher eye. Mutagenesis of the fly genome can be performed, followed by selecting flies in which the mutagenesis has resulted in suppression or enhancement of the small rough eye phenotype; the mutated genes in such flies are likely to encode proteins that interact/bind with FBP. Active compounds identified with methods described above will be tested in cultured cells and/or animal models to test the effect of blocking in vivo FBP activity (e.g. effects on cell proliferation, accumulation of substrates, etc.).

In various other embodiments, screening the can be accomplished by one of many commonly known methods. See, e.g., the following references, which disclose screening of peptide libraries: Parmley and Smith, 1989, *Adv. Exp. Med. Biol.* 251:215; Scott and Smith, 1990, *Science* 249:386; Fowlkes, et al., 1992; *BioTechniques* 13:422; Oldenburg, et al., 1992, *Proc. Natl. Acad. Sci. USA* 89:5393; Yu, et al., 1994, *Cell* 76:933; Staudt, et al., 1988, *Science* 241:577; Bock, et al., 1992, *Nature* 355:564; Tuerk, et al., 1992, *Proc. Natl. Acad. Sci. USA* 89:6988; Ellington, et al., 1992, *Nature* 355:850; U.S. Pat. No. 5,096,815, U.S. Pat. No. 5,223,409, and U.S. Pat. No. 5,198,346, all to Ladner et al.; Rebar and Pabo, 1993, *Science* 263:671; and PCT Publication No. WO 94/18318.

Compounds, peptides, and small molecules can be used in screening assays to identify candidate agonists and antagonists. In one embodiment, peptide libraries may be used to screen for agonists or antagonists of the FBP of the present invention diversity libraries, such as random or combinatorial peptide or non-peptide libraries can be screened for molecules that specifically bind to FBP. Many libraries are known in the art that can be used, e.g., chemically synthesized libraries, recombinant (e.g., phage display libraries), and in vitro translation-based libraries.

Examples of chemically synthesized libraries are described in Fodor, et al., 1991, *Science* 251:767; Houghten, et al., 1991, *Nature* 354:84; Lam, et al., 1991, *Nature* 354:82; Medynski, 1994, *BioTechnology* 12:709; Gallop, et al., 1994, *J. Medicinal Chemistry* 37:1233; Ohlmeyer, et al., 1993, *Proc. Natl. Acad. Sci. USA* 90:10922; Erb, et al., 1994, *Proc. Natl. Acad. Sci. USA* 91:11422; Houghten, et al., 1992, *Biotechniques* 13:412; Jayawickreme, et al., 1994, *Proc. Natl. Acad. Sci. USA* 91:1614; Salmon, et al., 1993, *Proc. Natl. Acad. Sci. USA* 90:11708; PCT Publication No. WO 93/20242; and Brenner and Lerner, 1992, *Proc. Natl. Acad. Sci. USA* 89:5381.

Examples of phage display libraries are described in Scott and Smith, 1990, *Science* 249:386; Devlin, et al., 1990, *Science*, 249:404; Christian, et al., 1992, *J. Mol. Biol.* 227:711; Lenstra, 1992, *J. Immunol. Meth.* 152:149; Kay, et al., 1993, *Gene* 128:59; and PCT Publication No. WO 94/18318 dated Aug. 18, 1994.

In vitro translation-based libraries include but are not limited to those described in PCT Publication No. WO 91/05058 dated Apr. 18, 1991; and Mattheakis, et al., 1994, *Proc. Natl. Acad. Sci. USA* 91:9022.

By way of examples of non-peptide libraries, a benzodiazepine library (see e.g., Bunin et al., 1994, *Proc. Natl. Acad. Sci. USA* 91:4708) can be adapted for use. Peptoid libraries (Simon et al., 1992, *Proc. Natl. Acad. Sci. USA* 89:9367) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138).

6.5.2 Assays for the Identification of Compounds that Modulate the Interaction of F-Box Proteins with Other Proteins Once a substrate or interacting protein is identified, as described in detail in Section 6.4, then one can assay for modulators of the F-box protein interaction with such a protein. The present invention provides for methods of detecting agonists and antagonists of such interactions.

In one embodiment, the invention encompasses methods to identify modulators, such as inhibitors or agonists, of the interaction between the F-box protein Skp2 and E2F-1, identified in Section 11. Such methods comprise both in vivo and in vitro assays for modulator activity. For example, in an in vivo assay, insect cells can be co-infected with baculoviruses co-expressing Skp2 and E2F-1 as well as potential modulators of the Skp2/E2F-1 interaction. The screening methods of the present invention encompass in vitro assays which measure the ability of a test compound to inhibit the enzymatic activity of Skp2 as described above in Section 6.5.1. Cell extracts can be prepared and analyzed for protein-protein interactions by gel electrophoresis and detected by immunoblotting, as described in detail in Section 11. Alternatively, an in vitro protein-protein interaction assay can be used. Recombinant purified Skp2, E2F-1, and putative agonist or antagonist molecules can be incubated together, under conditions that allow binding to occur, such as 37 C for 30 minutes. Protein-protein complex formation can be detected by gel analysis, such as those described herein in Section 7. This assay can be used to identify modulators of interactions of known FBP, such as Skp2 with novel substrates.

In another embodiment, the invention provides for a method for identification of modulators of F-box protein/Skp1 interaction. Such agonist and antagonists can be identified in vivo or in vitro. For example, in an in vitro assay to identify modulators of F-box protein/Skp1 interactions, purified Skp1 and the novel FBP can be incubated together, under conditions that allow binding occur, such as 37 C for 30 minutes. In a parallel reaction, a potential agonist or antagonist, as described above in Section 6.5.1, is added either before or during the box protein/Skp1 incubation. Protein-protein interactions can be detected by gel analysis, such as those described herein in Section 7. Modulators of FBP activities and interactions with other proteins can be used as therapeutics using the methods described herein, in Section 6.7.

In another embodiment, the invention provides for a method for identification of modulators of FBP1-FBP5 interaction. Such agonist and antagonists can be identified in vivo or in vitro. For example, in an in vitro assay to identify modulators of FBP1-FBP5 interactions, purified FBP5 and FBP1 can be incubated together, under conditions that allow binding to occur, such as incubation at 37° C. for 30 minutes. In a parallel reaction, a potential agonist or antagonist, as described above in Section 6.5.1, is added either before or during the FBP1-FBP5 incubation. Protein-protein interactions can be detected by gel analysis, such as those described herein in Section 7. Modulators of FBP activities and interactions with other proteins can be used as therapeutics using the methods described herein, in Section 6.7.

These assays may be carried out utilizing any of the screening methods described herein, including the following in vitro assay. The screening can be performed by adding the test agent to intact cells which express components of the ubiquitin pathway, and then examining the component of interest by whatever procedure has been established. Alternatively, the screening can be performed by adding the test agent to in vitro translation reactions and then proceeding with the established analysis. As another alternative, purified or partially purified components which have been determined to interact with one another by the methods described above can be placed under conditions in which the interaction between them would normally occur, with and without the addition of the test agent, and the procedures previously established to analyze the interaction can be used to assess the impact of the test agent. In this approach, the purified or partially purified components may be prepared by fractionation of extracts of cells expressing the components of the ubiquitin ligase complex and pathway, or they may be obtained by expression of cloned genes or cDNAs or fragments thereof, optionally followed by purification of the expressed material.

Within the broad category of in vitro selection methods, several types of method are likely to be particularly convenient and/or useful for screening test agents. These include but are not limited to methods which measure a binding interaction between two or more components of the ubiquitin ligase complex or interaction with the target substrate, methods which measure the activity of an enzyme which is one of the interacting components, and methods which measure the activity or expression of "reporter" protein, that is, an enzyme or other detectable or selectable protein, which has been placed under the control of one of the components.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

6.6 Methods and Compositions for Diagnostic Use of F-Box Proteins, Derivatives, and Modulators Cell cycle regulators are the products of oncogenes (cyclins, β-catenin, etc.), or tumor suppressor genes (ckis, p53, etc.) The FBPs, part of ubiquitin ligase complexes, might therefore be products of oncogenes or tumor suppressor genes, depending on which cell cycle regulatory proteins for which they regulate cellular abundance.

FBP proteins, analogues, derivatives, and subsequences thereof, FBP nucleic acids (and sequences complementary thereto), anti-FBP antibodies, have uses in diagnostics. The FBP and FBP nucleic acids can be used in assays to detect, prognose, or diagnose infertility or proliferative or differentiative disorders, including tumorigenesis, carcinomas, adenomas etc. The novel FBP nucleic acids of the present invention are located at chromosome sites associated with karyotypic abnormalities and loss of heterozygosity. The FBP1 nucleic acid of the present invention is mapped and localized to chromosome position 10q24, the loss of which has been demonstrated in 10% of human prostate tumors and small cell lung carcinomas (SCLC), suggesting the presence of a tumor suppressor gene at this location. In addition, up to 7% of childhood acute T-cell leukemia is accompanied by a translocation involving 10q24 as a breakpoint, either t(10;14)(q24;q11) or t(7;10)(q35;q24). 9q34 region (where FBP2 is located) has been shown to be a site of loss of heterozygosity (LOH) in human ovarian and bladder cancers. The FBP2 nucleic acid of the present invention is mapped and localized to chromosome position 9q34 which has been shown to be a site of loss of heterozygosity (LOH) in human ovarian and bladder cancers. The FBP3 nucleic acid of the present invention is mapped and localized to chromosome position 13q22, a region known to contain a putative tumor suppressor gene with loss of heterozygosity in approx. 75% of human SCLC. The FBP4 nucleic acid of the present invention is mapped and localized to chromosome position 5p12, a region shown to be a site of karyotypic abnormalities in a variety of tumors, including human breast cancer and nasopharyngeal carcinomas. The FBP5 nucleic acid of the present invention is mapped and localized to chromosome position 6q25-26, a region shown to be a site of loss of heterozygosity in human ovarian, breast and gastric cancers hepatocarcinomas, Burkitt's lymphomas, gliomas, and parathyroid adenomas. The FBP7 nucleic acid of the present invention is mapped and localized to chromosome position 15q15 a region which contains a tumor suppressor gene associated with progression to a metastatic stage in breast and colon cancers and a loss of heterozygosity in parathyroid adenomas.

The molecules of the present invention can be used in assays, such as immunoassays, to detect, prognose, diagnose, or monitor various conditions, diseases, and disorders affecting FBP expression, or monitor the treatment thereof. In particular, such an immunoassay is carried out by a method comprising contacting a sample derived from a patient with an anti-FBP antibody under conditions such that immunospecific binding can occur, and detecting or measuring the amount of any immunospecific binding by the antibody. In a specific aspect, such binding of antibody, in tissue sections, can be used to detect aberrant FBP localization or aberrant (e.g., low or absent) levels of FBP. In a specific embodiment, antibody to FBP can be used to assay a patient tissue or serum sample for the presence of FBP where an aberrant level of FBP is an indication of a diseased condition. By "aberrant levels," is meant increased or decreased levels relative to that present, or a standard level representing that present, in an analogous sample from a portion of the body or from a subject not having the disorder.

The immunoassays which can be used include but are not limited to competitive and non-competitive assay systems using techniques such as western blots, immunohisto-chemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

FBP genes and related nucleic acid sequences and subsequences, including complementary sequences, can also be used in hybridization assays. FBP nucleic acid sequences, or subsequences thereof comprising about at least 8 nucleotides, can be used as hybridization probes. Hybridization assays can be used to detect, prognose, diagnose, or monitor conditions, disorders, or disease states associated with aberrant changes in FBP expression and/or activity as described supra. In particular, such a hybridization assay is carried out by a method comprising contacting a sample containing nucleic acid with a nucleic acid probe capable of hybridizing to FBP DNA or RNA, under conditions such that hybridization can occur, and detecting or measuring any resulting hybridization.

In specific embodiments, diseases and disorders involving overproliferation of cells can be diagnosed, or their suspected presence can be screened for, or a predisposition to develop such disorders can be detected, by detecting decreased levels of FBP protein, FBP RNA, or FBP functional activity (e.g., ubiquitin ligase target binding activity, F-box domain binding activity, ubiquitin ligase activity etc.), or by detecting mutations in FBP RNA, DNA or FBP protein (e.g., translocations in FBP nucleic acids, truncations in the FBP gene or protein, changes in nucleotide or amino acid sequence relative to wild-type FBP) that cause decreased expression or activity of FBP. Such diseases and disorders include but are not limited to those described in Section 6.7.3. By way of example, levels of FBP protein can be detected by immunoassay, levels of FBP RNA can be detected by hybridization assays (e.g., Northern blots, in situ-hybridization), FBP activity can be assayed by measuring ubiquitin ligase activity in E3 ubiquitin ligase complexes formed in vivo or in vitro, F-box domain binding activity can be assayed by measuring binding to Skp1 protein by binding assays commonly known in the art, translocations, deletions and point mutations in FBP nucleic acids can be detected by Southern blotting, FISH, RFLP analysis, SSCP, PCR using primers that preferably generate a fragment spanning at least most of the FBP gene, sequencing of FBP genomic DNA or cDNA obtained from the patient, etc.

In a preferred embodiment, levels of FBP mRNA or protein in a patient sample are detected or measured, in which decreased levels indicate that the subject has, or has a predisposition to developing, a malignancy or hyperproliferative disorder; in which the decreased levels are relative to the levels present in an analogous sample from a portion of the body or from a subject not having the malignancy or hyperproliferative disorder, as the case may be.

In another specific embodiment, levels of FBP mRNA or protein in a patient sample, such as germ cells, are detected or measured, in which decreased levels indicate that the subject has, or has a predisposition to developing, an infertility disorder; in which the decreased levels are relative to the levels present in an analogous sample from another portion of the body, or from a "clinically normal individual", defined in this case as an individual not having the infertility disorder.

In another specific embodiment, diseases and disorders involving a deficiency in cell proliferation or in which cell proliferation is desirable for treatment, are diagnosed, or their suspected presence can be screened for, or a predisposition to develop such disorders can be detected, by detecting increased levels of FBP protein, FBP RNA, or FBP functional activity (e.g., ubiquitin ligase activity, Skp1 binding activity, etc.), or by detecting mutations in FBP RNA, DNA or protein (e.g., translocations in FBP nucleic acids, truncations in the gene or protein, changes in nucleotide or amino acid sequence relative to wild-type FBP) that cause increased expression or activity of FBP. Such diseases and disorders include but are not limited to those described in Section 6.7.3. By way of example, levels of FBP protein, levels of FBP RNA, ubiquitin ligase activity, FBP binding activity, and the presence of translocations or point mutations can be determined as described above.

In a specific embodiment, levels of FBP mRNA or protein in a patient sample are detected or measured, in which increased levels indicate that the subject has, or has a predisposition to developing, a growth deficiency or degenerative or hypoproliferative disorder, or an infertility disorder; in which the increased levels are relative to the levels present in an analogous sample from a portion of the body or from a subject not having the growth deficiency, degenerative, or hypoproliferative or infertility disorder, as the case may be.

Kits for diagnostic use are also provided, that comprise in one or more containers an anti-FBP antibody, and, optionally, a labeled binding partner to the antibody. Alternatively, the anti-FBP antibody can be labeled (with a detectable marker, e.g., a chemiluminescent, enzymatic, fluorescent, or radioactive moiety). A kit is also provided that comprises in one or more containers a nucleic acid probe capable of hybridizing to FBP RNA. In a specific embodiment, a kit can comprise in one or more containers a pair of primers (e.g., each in the size range of 6-30 nucleotides) that are capable of priming amplification [e.g., by polymerase chain reaction (see e.g., Innis, et al., 1990, *PCR Protocols*, Academic Press, Inc., San Diego, Calif.), ligase chain reaction (see EP 320,308) use of Q replicase, cyclic probe reaction, or other methods known in the art] under appropriate reaction conditions of at least a portion of a FBP nucleic acid. A kit can optionally further comprise in a container a predetermined amount of a purified FBP protein or nucleic acid, e.g., for use as a standard or control.

6.7 Methods and Compositions for Therapeutic Use of F-Box Proteins, Derivatives, and Modulators Described below are methods and compositions for the use of F-box proteins in the treatment of proliferative disorders, infertility disorders, or oncogenic disease symptoms which may be ameliorated by compounds that activate or enhance FBP activity, and whereby proliferative or infertility disorders or cancer may be ameliorated.

In certain instances, compounds and methods that increase or enhance the activity of an FBP can be used to treat proliferative, infertile, and oncogenic disease symptoms. Such a case may involve, for example, a proliferative or infertility disorder that is brought about, at least in part, by a reduced level of FBP gene expression, or an aberrant level of an FBP gene product's activity. For example, decreased activity or under-expression of an FBP component of a ubiquitin ligase complex whose substrate is a positive cell-cycle regulator, such as a member of the Cyclin family, will result in increased cell proliferation. As such, an increase in the level of gene expression and/or the activity of such FBP gene products would bring about the amelioration of proliferative disease symptoms.

In another instance, compounds that increase or enhance the activity of an FBP can be used to treat proliferative, infertile, and oncogenic disease symptoms resulting from defects in the expression or activity of other genes and gene products involved in cell cycle control, such as FBP substrate molecules. For example, an increase in the expression or activity of a positive cell-cycle positive molecule, such as a member of the Cyclin family, may result in its over-activity and thereby lead to increased cell proliferation. Compounds that increase the expression or activity of the FBP component of a ubiquitin ligase complex whose substrate is such a cell-cycle positive regulator will lead to ubiquitination of the defective molecule, and thereby result in an increase in its degradation. Disease symptoms resulting from such a defect may be ameliorated by compounds that compensate the disorder by increased FBP activity. Techniques for increasing FBP gene expression levels or gene product activity levels are discussed in Section 6.7, below.

Alternatively, compounds and methods that reduce or inactivate FBP activity may be used therapeutically to ameliorate proliferative, infertile, or oncogenic disease symptoms. For example, a proliferative disorder may be caused, at least in part, by a defective FBP gene or gene product that leads to its overactivity. Where such a defective gene product is a component of a ubiquitin ligase complex whose target is a cell-cycle inhibitor molecule, such as a Cki, an overactive FBP will lead to a decrease in the level of cell-cycle molecule and therefore an increase in cell proliferation. In such an instance, compounds and methods that reduce or inactivate FBP function may be used to treat the disease symptoms.

In another instance, compounds and methods that reduce the activity of an FBP can be used to treat disorders resulting from defects in the expression or activity of other genes and gene products involved in cell cycle control, such as FBP substrate molecules. For example, a defect in the expression or activity of a cell-cycle negative regulatory molecule, such as a Cki, may lead to its under-activity and thereby result in increased cell proliferation. Reduction in the level and/or activity of an FBP component whose substrate was such molecule would decrease the ubiquitination and thereby increase the level of such a defective molecule. Therefore, compounds and methods aimed at reducing the expression and/or activity of such FBP molecules could thereby be used in the treatment of disease symptoms by compensating for the defective gene or gene product.

Techniques for the reduction of target gene expression levels or target gene product activity levels are discussed in Section 6.7 below.

6.7.1 Therapeutic Use of Inhibitory Antisense, Ribozyme and Triple Helix Molecules and Identified Agonists and Antagonists In another embodiment, symptoms of certain FBP disorders, such as such as proliferative or differentiative disorders causing tumorigenesis or cancer, or meiotic disorders causing infertility, may be ameliorated by decreasing the level of FBP gene expression and/or FBP gene product activity by using FBP gene sequences in conjunction with well-known antisense, gene "knock-out" ribozyme and/or triple helix methods to decrease the level of FBP gene expression. Among the compounds that may exhibit the ability to modulate the activity, expression or synthesis of the FBP gene, including the ability to ameliorate the symptoms of an FBP disorder, such as cancer, are antisense, ribozyme, and triple helix molecules. Such molecules may be designed to reduce or inhibit either unimpaired, or if appropriate, mutant target gene activity. Techniques for the production and use of such molecules are well known to those of skill in the art. For example, antisense targeting of SKP2 mRNA stabilizes the Skp2-substrate p27, as described in Section 9 (FIG. 45).

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the FBP gene could be used in an antisense approach to inhibit translation of endogenous FBP mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

In an embodiment of the present invention, oligonucleotides complementary to the nucleic acids encoding the F-box motif are indicated in FIGS. 2 and 4-9.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, *Proc. Natl. Acad. Sci. U.S.A.* 86:6553; Lemaitre, et al., 1987, *Proc. Natl. Acad. Sci. U.S.A.* 84:648; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol, et al., 1988, *Bio Techniques* 6:958-976) or intercalating agents (see, e.g., Zon, 1988, *Pharm. Res.* 5:539). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate (S-ODNs), a phosphorodithioate, a phosphoramidothioate, a phosphoramidate, a phosphordiamidate, a methylphosphonate, an alkyl phosphotriester, and a formacctal or analog thereof.

In yet another embodiment, the antisense oligonucleotide is an -anomeric oligonucleotide. An -anomeric oligonucleotide forms specific double-stranded hybrids with complementary RNA in which, contrary to the usual -units, the strands run parallel to each other (Gautier, et al., 1987, *Nucl. Acids Res.* 15:6625). The oligonucleotide is a 2-0-methylribonucleotide (Inoue, et al., 1987, *Nucl. Acids Res.* 15:6131), or a chimeric RNA-DNA analogue (Inoue, et al., 1987, *FEBS Lett.* 215:327).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein, et al. (1988, *Nucl. Acids Res.* 16:3209), methylphosphonate oligonucleotides can be prepared by use of controlled pore glass polymer supports (Sarin, et al., 1988, *Proc. Natl. Acad. Sci. U.S.A.* 85:7448), etc.

While antisense nucleotides complementary to the target gene coding region sequence could be used, those complementary to the transcribed, untranslated region are most preferred.

In one embodiment of the present invention, gene expression downregulation is achieved because specific target mRNAs are digested by RNAse H after they have hybridized with the antisense phosphorothioate oligonucleotides (S-ODNs). Since no rules exist to predict which antisense S-ODNs will be more successful, the best strategy is completely empirical and consists of trying several antisense S-ODNs. Antisense phosphorothioate oligonucleotides (S-ODNs) will be designed to target specific regions of mRNAs of interest. Control S-ODNs consisting of scrambled sequences of the antisense S-ODNs will also be designed to assure identical nucleotide content and minimize differences potentially attributable to nucleic acid content. All S-ODNs will be synthesized by Oligos Etc. (Wilsonville, Oreg.). In order to test the effectiveness of the antisense molecules when applied to cells in culture, such as assays for research purposes or ex vivo gene therapy protocols, cells will be grown to 60-80% confluence on 100 mm tissue culture plates, rinsed with PBS and overlaid with lipofection mix consisting of 8 ml Opti-MEM, 52.8 l Lipofectin, and a final concentration of 200 nM S-ODNs. Lipofections will be carried out using Lipofectin Reagent and Opti-MEM (Gibco BRL). Cells will be incubated in the presence of the lipofection mix for 5 hours. Following incubation the medium will be replaced with complete DMEM. Cells will be harvested at different time points post-lipofection and protein levels will be analyzed by Western blot.

Antisense molecules should be targeted to cells that express the target gene, either directly to the subject in vivo or to cells in culture, such as in ex vivo gene therapy protocols. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304), the promoter contained in the 3 long terminal repeat of Rous sarcoma virus (Yamamoto, et al., 1980, *Cell* 22:787), the herpes thymidine kinase promoter (Wagner, et al., 1981, *Proc. Natl. Acad. Sci. U.S.A.* 78:1441), the regulatory sequences of the metallothionein gene (Brinster, et al., 1982, *Nature* 296:39), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product (see, e.g., PCT International Publication WO90/11364, published Oct. 4, 1990; Sarver, et al., 1990, *Science* 247:1222). In an embodiment of the present invention, oligonucleotides which hybridize to the FBP gene are designed to be complementary to the nucleic acids encoding the F-box motif as indicated in FIGS. 2 and 4-9.

Ribozymes are enzymatic RNA molecules capable of catalyzing the specific cleavage of RNA. (For a review, see Rossi, 1994, *Current Biology* 4:469). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff and Gerlach, 1988, *Nature*, 334:585, which is incorporated herein by reference in its entirety. Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al., 1984, *Science*, 224:574; Zaug and Cech, 1986, *Science*, 231:470; Zaug, et al., 1986, *Nature*, 324:429; published International patent application No. WO 88/04300 by University Patents Inc.; Been and Cech, 1986, *Cell*, 47:207). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, *Nature* 317:230; Thomas and Capecchi, 1987, *Cell* 51:503; Thompson, et al., 1989, *Cell* 5:313; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, *Anticancer Drug Des.*, 6: 569; Helene, et al., 1992, *Ann. N.Y. Acad. Sci.*, 660:27; and Maher, 1992, *Bioassays* 14: 807).

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.7.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

6.7.2 Gene Replacement Therapy

With respect to an increase in the level of normal FBP gene expression and/or FBP gene product activity, FBP gene nucleic acid sequences, described, above, in Section 5.1 can, for example, be utilized for the treatment of proliferative disorders such as cancer or meiosis-related disorders such as infertility. Such treatment can be administered, for example, in the form of gene replacement therapy. Specifically, one or more copies of a normal FBP gene or a portion of the FBP gene that directs the production of an FBP gene product exhibiting normal FBP gene function, may be inserted into the appropriate cells within a patient, using vectors that include, but are not limited to adenovirus, adeno-associated virus, and retrovirus vectors, in addition to other particles that introduce DNA into cells, such as liposomes.

For FBP genes that are expressed in all tissues or are preferentially expressed, such as FBP1 gene is expressed preferably in the brain, such gene replacement therapy techniques should be capable of delivering FBP gene sequences to these cell types within patients. Thus, in one embodiment, techniques that are well known to those of skill in the art (see, e.g., PCT Publication No. WO89/10134, published Apr. 25, 1988) can be used to enable FBP gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such FBP gene sequences to the site of the cells in which the FBP gene sequences are to be expressed.

Additional methods that may be utilized to increase the overall level of FBP gene expression and/or FBP gene product activity include the introduction of appropriate FBP-expressing cells, preferably autologous cells, into a patient at positions and in numbers that are sufficient to ameliorate the symptoms of an FBP disorder. Such cells may be either recombinant or non-recombinant.

Among the cells that can be administered to increase the overall level of FBP gene expression in a patient are cells that normally express the FBP gene.

Alternatively, cells, preferably autologous cells, can be engineered to express FBP gene sequences, and may then be introduced into a patient in positions appropriate for the amelioration of the symptoms of an FBP disorder or a proliferative or differentiative disorders, e.g., cancer and tumorigenesis. Alternately, cells that express an unimpaired FBP gene and that are from a MHC matched individual can be utilized, and may include, for example, brain cells. The expression of the FBP gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 6.5, that are capable of modulating FBP gene product activity can be administered using standard techniques that are well known to those of skill in the art. In instances in which the compounds to be administered are to involve an interaction with brain cells, the administration techniques should include well known ones that allow for a crossing of the blood-brain barrier.

6.7.3 Target Proliferative Cell Disorders

With respect to specific proliferative and oncogenic disease associated with ubiquitin ligase activity, the diseases that can be treated or prevented by the methods of the present invention include but are not limited to: infertility, human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pincaloma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease.

Diseases and disorders involving a deficiency in cell proliferation or in which cell proliferation is desired for treatment or prevention, and that can be treated or prevented by inhibiting FBP function, include but are not limited to degenerative disorders, growth deficiencies, hypoproliferative disorders, physical trauma, lesions, and wounds; for example, to promote wound healing, or to promote regeneration in degenerated, lesioned or injured tissues, etc. In a specific embodiment, nervous system disorders are treated. In another specific embodiment, a disorder that is not of the nervous system is treated.

6.8 Pharmaceutical Preparations and Methods of Administration

The compounds that are determined to affect FBP gene expression or gene product activity can be administered to a patient at therapeutically effective doses to treat or ameliorate a cell proliferative disorder. A therapeutically effective dose refers to that amount of the compound sufficient to result in amelioration of symptoms of such a disorder.

6.8.1 Effective Dose

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6.8.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

7. EXAMPLE

Identification and Characterization of Novel Ubiquitin Ligase F-Box Proteins and Genes The following studies were carried out to identify novel F-box proteins which may act to recruit novel specific substrates to the ubiquitination pathway. Studies involving several organisms have shown that some FBPs play a crucial role in the controlled degradation of important cellular regulatory proteins (e.g., cyclins, cdk-inhibitors, β-catenin, IκBα, etc.). These FBPs are subunits of ubiquitin protein SCF ligases formed by three basic subunits: a cullin subunit (called Cdc53 in S. cerevisiae and Cul1 in humans); Skp1; and one of many FBPs. SCF ligases target ubiquitin conjugating enzymes (either Ubc3 or Ubc4) to specific substrates which are recruited by different FBPs. Schematically, the Ubc is bound to the ligase through the cullin subunit while the substrate interacts with the FBP subunit. Although FBPs can bind the cullin subunit directly, the presence of fourth subunit, Skp1, which simultaneously can bind the cullin-terminus and the F-box of the FBP, stabilizes the complex. Thus, the substrate specificity of the ubiquitin ligase complex is provided by the F-box subunit.

7.1 Materials and Methods Used for the Identification and Characterization of Novel F-Box Genes Yeast Two-Hybrid Screening In order to clone the human genes encoding F-box proteins, proteins associated with Skp1 were identified using a modified yeast 2-hybrid system (Vidal, et al., 1996, *Proc. Natl. Acad. Sci. U.S.A.*, 93:10315; Vidal, et al., 1996, *Proc. Natl. Acad. Sci. U.S.A.*, 93:10321). This modified system takes advantage of using three reporter genes expressed from three different Gal4 binding site promoters, thereby decreasing the number of false positive interactions. This multiple reporter gene assay facilitates identification of true interactors.

Human Skp1 was used as a bait to search for proteins that interact with Skp1, such as novel F-box proteins and the putative human homolog of Cdc4. The plasmids pPC97-CYH2 and pPC86 plasmids, encoding the DNA binding domain (DB, aa 1-147) and the transcriptional activation domain (AD, aa 768-881) of yeast GAL4, and containing LEU2 and TRP1 as selectable markers, respectively, were used (Chevray and Nathans, 1992, *Proc. Natl. Acad. Sci. U.S.A.*, 89:5789; Vidal, et al., supra).

An in-frame fusion between Skp1 and DB was obtained by homologous recombination of the PCR product described below. The following 2 oligonucleotides were designed and obtained as purified primers from Gene Link Inc.: 5'-AGT-AGT-AAC-AAA-GGT-CAA-AGA-CAG-TTG-ACT-GTA-TCG-TCG-AGG-ATG-CCT-TCA-ATT-AAG-TT (SEQ ID NO: 80); 3'-GCG-GTT-ACT-TAC-TTA-GAG-CTC-GAC-GTC-TTA-CTT-ACT-TAG-CTC-ACT-TCT-CTT-CAC-ACC-A (SEQ ID NO: 81). The 5' primer corresponds to a sequence located in the DB of the pPC97-CYH2 plasmid (underlined) flanked by the 5' sequence of the skp1 gene. The 3' primer corresponds to a sequence located by polylinker of the pPC97-CYH2 plasmid (underlined) flanked by the 3' sequence of the skp1 gene. These primers were used in a PCR reaction containing the following components: 100 ng DNA template (skp1 pET plasmid), 1 µM of each primer, 0.2 mM dNTP, 2 mM MgCl$_2$, 10 mM KCl, 20 mM TrisCl pH 8.0, 0.1% Triton X-100, 6 mM (NH$_4$)$_2$SO$_4$, 10 µg/ml nuclease-free BSA, 1 unit of Pfu DNA polymerase (4' at 94° C., 1' at 50 C, 10' at 72° C. for 28 cycles). Approximately 100 ng of PCR product were transformed into yeast cells (MaV103 strain; Vidal et al., 1996, *Proc. Natl. Acad. Sci. U.S.A.* 93:10315; Vidal et al., 1996, Proc. Natl. Acad. Sci. U.S.A. 93:10321) in the presence or in the absence of 100 ng of pPC97-CYH2 plasmid previously digested with BglII and SalI. As a result of the homologous recombination, only yeast cells containing the pPC97-CYH2 plasmid homologously recombined with skp1 cDNA, grew in the absence of leucine. Six colonies were isolated and analyzed by immunoblotting for the expression of Skp1, as described (Vidal et al., supra). All 6 colonies, but not control colonies, expressed a Mr 36,000 fusion-protein that was recognized by our affinity purified anti-Skp1 antibody.

The AD fusions were generated by cloning cDNA fragments in the frame downstream of the AD domains and constructs were confirmed by sequencing, immunoblot, and interaction with Skp1. The pPC86-Skp2s (pPC86) include: pPC86-Skp2, and pPC86-Skp2-CT (aa 181-435 of Skp2). The first fusion represents our positive control since Skp2 is a known interactor of Skp1 (Zhang, et al, 1995, *Cell* 82: 915); the latter fusion was used as a negative control since it lacked the F-box required for the interaction with Skp1.

MaV103 strain harboring the DB-skp1 fusions was transformed with an activated T-cell cDNA library (Alala 2; Hu, et al., *Genes Dev.* 11: 2701) in pPC86 using the standard lithium acetate method. Transformants were first plated onto synthetic complete (SC)-Leu-Trp plates, followed by replica plating onto (SC)-Leu-Trp-His plates containing 20 mM 3-aminotriazole (3-AT) after 2 days. Yeast colonies grown out after additional 3-4 days of incubation were picked as primary positives and further tested in three reporter assays: i) growth on SC-Leu-Trp-His plates supplemented with 20 mM 3-AT; ii)-galactosidase activity; and iii) URA3 activation on SC-Leu-Trp plates containing 0.2% 5-fluoroortic acid, as a counterselection method. Of the 3×10$^6$ yeast transformants screened AD plasmids were rescued from the fifteen selected positive colonies after all three. MaV103 cells were re-transformed with either rescued AD plasmids and the DBskp1 fusion or rescued AD plasmid and the pPC97-CYH2 vector without a cDNA insert as control. Eleven AD plasmids from colonies that repeatedly tested positive in all three reporter assays (very strong interactors) and four additional AD plasmids from clones that were positive on some but not all three reporter assays (strong interactors) were recovered and sequenced with the automated ABI 373 DNA sequencing system.

Cloning of full length FBPs Two of the clones encoding FBP4 and FBP5 appeared to be full-length, while full length clones of 4 other cDNAs encoding FBP1, FBP2, FBP3 and FBP7 were obtained with RACE using Marathon-Ready cDNA libraries (Clonetec, cat. #7406, 7445, 7402) according to the manufacturer's instructions. A full-length clone encoding FBP6 was not obtained. Criteria for full length clones included at least two of the following: i) the identification of an ORF yielding a sequence related to known F-box proteins; ii) the presence of a consensus Kozak translation initiation sequence at a putative initiator methionine codon; iii) the identification of a stop codon in the same reading frame but upstream of the putative initiation codon; iv) the inability to further increase the size of the clone by RACE using three different cDNA libraries.

Analysis by Immunoblotting of Protein from Yeast Extracts Yeast cells were grown to mid-logarithmic phase, harvested, washed and resuspended in buffer (50 mM Tris pH 8.0, 20% glycerol, 1 mM EDTA, 0.1% Triton X-100, 5 mM MgCl2, 10 mM Li-mercaptoethanol, 1 mM PMSF, 1 mg/ml Leupeptin, 1 mg/ml Pepstatin) at a cell density of about 10$^9$ cells/ml. Cells were disrupted by vortexing in the presence of glass beads for 10 min at 40 C. Debris was pelleted by centrifugation at 12,000 RPM for 15 min at 40 C. Approximately 50 g of proteins were subjected to immunoblot analysis as described (Vidal et al., 1996a, supra; Vidal et al., 1996b, supra).

DNA database searches and analysis of protein motifs. ESTs (expressed sequence tags) with homology to FBP genes were identified using BLAST, PSI-BLAST and TGI Sequence Search. ESTs that overlapped more than 95% in at least 100 bps were assembled into novel contiguous ORFS using Sequencher 3.0. Protein domains were identified with ProfileScan Server, BLOCKS Sercher and IMB Jena.

Construction of F-box mutants. Delta-F-box mutants [(ΔF) FBP1, residues 32-179; (ΔF)FBP2, residues 60-101; (ΔF) FBP3a, residues 40-76; (ΔF)FBP4, residues 55-98] were obtained by deletion with the appropriate restriction enzymes with conservation of the reading frame. (ΔF)Skp2 mutant was obtained by removing a DNA fragment (nucleotides 338-997) with BspEI and XbaI restriction enzymes, and replacing it with a PCR fragment containing nucleotides 457 to 997. The final construct encoded a protein lacking residues 113-152. The leucine 51-to-alanine FBP3a mutant [FBP3a(L5 IA)] and the tryptophan 76-to-alanine FBP3a mutant [FBP3a (W76A)] were generated by oligonucleotide-directed mutagenesis using the polymerase chain reaction of the QuikChange site-directed mutagenesis kit (Stratagene). All mutants were sequenced in their entirety.

Recombinant proteins cDNA fragments encoding the following human proteins: Flag-tagged FBP1, Flag-tagged (ΔF) FBP1, Flag-tagged FBP3a, Skp2, HA-tagged Cul1, HA-tagged Cul2, (β-catenin, His-tagged cyclin D1, Skp1, His-tagged Skp1, His-tagged Elongin C were inserted into the baculovirus expression vector pBacpak-8 (Clonetech) and cotransfected into SP) cells with linearized baculovirus DNA using the BaculoGold transfection kit (Pharmingen). Recombinant viruses were used to infect 5B cells and assayed for expression of their encoded protein by immunoblotting as described above. His-proteins were purified with Nickel-agarose (Invitrogen) according to the manufacturer's instructions.

Antibodies. Anti-Cul1 antibodies was generated by injecting rabbits and mice with the following amino acid peptide: (C)DGEKDTYSYLA (SEQ ID NO: 82). This peptide corresponds to the carboxy-terminus of human Cul1 and is not conserved in other cullins. Anti-Cult antibodies was generated by injecting rabbits with the following amino acid peptide: (C)ESSFSLNMNFSSKRTKFKITTSMQ (SEQ ID NO: 83). This peptide is located 87 amino acids from the carboxy-terminus of human Cul2 and is not conserved in other cullins. The anti-Skp1 antibody was generated by injecting rabbits with the peptide (C)EEAQVRKENQW (SEQ ID NO: 84), corresponding to the carboxy-terminus of human Skp1. The cysteine residues (C) were added in order to couple the peptides to keyhole limpet hemocyanin (KLH). All of the antibodies were generated, affinity-purified (AP) and characterized as described (Pagano, M., ed., 1995, "From Peptide to Purified Antibody", in *Cell Cycle Materials and Methods*, Spring-Verlag, 217-281). Briefly, peptides whose sequence showed high antigenic index (high hydrophilicity, good surface probability, good flexibility, and good secondary structure) were chosen. Rabbits and mice were injected with peptide-KLH mixed with complete Freund's adjuvant. Subsequently they were injected with the peptide in incomplete Freund's adjuvant, every 2 weeks, until a significant immunoreactivity was detected by immunoprecipitation of 35S-methionine labeled HeLa extract. These antisera recognized bands at the predicted size in both human extracts and a extracts containing recombinant proteins.

Monoclonal antibody (Mab) to Ubc3 was generated and characterized in collaboration with Zymed Inc. Mab to cyclin B (cat #sc-245) was from Santa Cruz; Mabs to p21 (cat #C24420) and p27 (cat #K25020) from Transduction lab. (Mabs) cyclin E, (Faha, 1993, *J. of Virology* 67: 2456); AP rabbit antibodies to human p27, Skp2, Cdk2, and cyclin A (Pagano, 1992, *EMBO J.* 11: 761), and phospho-site p27 specific antibody, were obtained or generated by standard methods. Where indicated, an AP goat antibody to an N-terminal Skp2 peptide (Santa Cruz, cat #se-1567) was used. Rat anti-HA antibody was from Boehringer Mannheim (cat. #1867423), rabbit anti-HA antibody was from Santa Cruz (cat. # sc-805), mouse anti-Flag antibody was from Kodak (cat. # IBI3010), rabbit anti-Flag antibody was from Zymed (cat. #71-5400), anti-Skp1 and anti-(β-catenin mouse antibodies were from Transduction Laboratories (cat. # C19220 and P46020, respectively). The preparation, purification and characterization of a Mab to human cyclin D I (clone AM29, cat. #33-2500) was performed in collaboration with Zymed Inc. Antiserum to human cyclin D1 was produced as described (Ohtsubo, et al., 1995, *Mol. Cell. Biol.*, 15:2612).

Extract preparation and cell synchronization Protein extraction was performed as previously described (Pagano, 1993, *J. Cell Biol.* 121:101) with the only difference that 1 okadaic acid was present in the lysis buffer. Human lung fibroblasts IMR-90 were synchronized in G0/G1 by serum starvation for 48 hours and the restimulated to re-enter the cell cycle by scrum readdition. HeLa cells were synchronized by mitotic shake-off as described (Pagano, 1992, *EMBO J.* 11: 761). Synchronization was monitored by flow cytometry. For in vitro ubiquitination and degradation assays, G1 HeLa cells were obtained with a 48-hour lovastatin treatment and protein extraction performed as described below.

Immunoprecipitation and Immunoblotting. Cell extracts were prepared by addition of 3-5 volumes of standard lysis buffers (Pagano, et al., 1992, *Science* 255:1144), and conditions for immunoprecipitation were as described (Jenkins and Xiong, 1995 supra; Pagano, et al., 1992, *Science* 255:1144). Proteins were transferred from gel to a nitrocellulose membrance (Novex) by wet blotting as described (Tam, et al., 1994, *Oncogene* 9:2663). Filters were subjected to immunoblotting using a chemiluminescence (DuPont-NEN) detection system according to the manufacturer's instructions Protein extraction for in vitro ubiquitination assay Logarithmically growing, HeLa-S3 cells were collected at a density of 6×10$^5$ cells/ml. Approx. 4 ml of HeLa S3 cell pellet were suspended in 6 ml of ice-cold buffer consisting of 20 mM Tris-HCl (pH 7.2), 2 mM DTT, 0.25 mM EDTA, 10 μg/ml leupeptin, and 10 μg/ml pepstatin. The suspension was transferred to a cell nitrogen-disruption bomb (Parr, Moline, Ill., cat #4639) that had been rinsed thoroughly and chilled on ice before use. The bomb chamber was connected to a nitrogen tank and the pressure was brought slowly to 1000 psi. The chamber was left on ice under the same pressure for 30 minutes and then the pressure was released slowly. The material was transferred to an Eppendorf tube and centrifuged in a microcentrifuge at 10,000 g for 10 minutes. The supernatant (S-10) was divided into smaller samples and frozen at −80° C.

In vitro ubiquitination The ubiquitination assay was performed as described (Lyapina, 1998, *Proc Natl Acad Sci USA*, 95: 7451). Briefly, immuno-beads containing Flag-tagged FBPs immunoprecipitated with anti-Flag antibody were added with purified recombinant human E1 and E2 enzymes (Ubc2, Ubc3 or Ubc4) to a reaction mix containing biotinylated-ubiquitin. Samples were then analyzed by blotting with HRP-streptavidin. E1 and E2 enzymes and biotinylated-ubiquitin were produced as described (Pagano, 1995, *Science* 269:682).

Transient transfections cDNA fragments encoding the following human proteins: FBP1, (ΔF)FBP1, FBP2, (ΔF)FBP2, FBP3a, (ΔF)FBP3a, FBP3a(L51A), FBP3a(W76A), FBP4, (ΔF)FBP4, Skp2, (ΔF)Skp2, HA-tagged β-catenin, untagged β-catenin, Skp1, cyclin D1 were inserted into the mammalian expression vector pcDNA3 (Invitrogen) in frame with a Flag-tag at their C-terminus. Cells were transfected with FuGENE transfection reagent (Boehringer, cat. #1-814-443) according to the manufacture's instruction.

Immunofluorescence Transfected cell monolayers growing on glass coverslips were rinsed in PBS and fixed with 4% paraformaldehyde in PBS for 10 minutes at 4° C. followed by permeabilization for 10 minutes with 0.25% Triton X-100 in PBS. Other fixation protocols gave comparable results. Immunofluorescence stainings were performed using 1 µg/ml rabbit anti-Flag antibody as described (Pagano, 1994, *Genes Dev.*, 8:1627).

Northern Blot Analysis Northern blots were performed using human multiple-tissue mRNAs from Clontech Inc. Probes were radiolabeled with [alpha-32P] dCTP (Amersham Inc.) using a random primer DNA labeling kit (Gibco BRL) (2×106 cpm/ml). Washes were performed with 0.2× SSC, 0.1% SDS, at 55-60° C. FBP1 and FBP3a probes were two HindIII restriction fragments (nucleotides 1-571 and 1-450, respectively), FBP2, FBP4, and FBP1 probes were their respective full-length cDNAs, and 13-ACTIN probe was from Clontech Inc.

Fluorescence in situ hybridixation (FISH) Genomic clones were isolated by high-stringency screening (65° C., 0.2×SSC, 0.1% SDS wash) of a λFIX II placenta human genomic library (Stratagem) with cDNA probes obtained from the 2-hybrid screening. Phage clones were confirmed by high-stringency Southern hybridization and partial sequence analysis. Purified whole phage DNA was labeled and FISH was performed as described (M. Pagano., ed., 1994, *in Cell Cycle: Materials and Methods*, 29).

7.2 Results 7.2.1 Characterization of Novel F-Box Proteins and their Activity In Vivo An improved version of the yeast two-hybrid system was used to search for interactors of human Skp1. The MaV103 yeast strain harboring the Gal4 DB-Skp1 fusion protein as bait was transformed with an activated T-cell cDNA library expressing Gal4 AD fusion proteins as prey. After initial selection and re-transformation steps, 3 different reporter assays were used to obtain 13 positive clones that specifically interact with human Skp1. After sequence analysis, the 13 rescued cDNAs were found to be derived from 7 different open reading frames all encoding FBPs. These novel FBPs were named as follows: FBP1, shown in FIG. 3 (SEQ ID NO:1); FBP2, shown in FIG. 4 (SEQ ID NO:3), FBP3a, shown in FIG. 5 (SEQ ID NO:5), FBP4, shown in FIG. 7 (SEQ ID NO:7), FBP5, shown in FIG. 8 (SEQ ID NO:9), FBP6, shown in FIG. 9 (SEQ ID NO:11), FBP7, shown in FIG. 10 (SEQ ID NO:13). One of the seven FBPs, FBP1 (SEQ ID NO:1) was also identified by others while our screen was in progress (Margottin et al., 1998, *Molecular Cell*, 1:565-74).

BLAST programs were used to search for predicted human proteins containing an F-box in databases available through the National Center for Biotechnology Information and The Institute for Genomic Research. The alignment of the F-box motifs from these predicted human FBPs is shown in FIG. 1. Nineteen previously uncharacterized human FBPs were identified by aligning available sequences (GenBank Accession Nos. AC002428, AI457595, AI105408, H66467, T47217, H38755, THC274684, AI750732, AA976979, AI571815, T57296, Z44228, Z45230, N42405, AA018063, AI751015, AI400663, T74432, AA402415, AI826000, AI590138, AF174602, Z45775, AF174599, THC288870, AI017603, AF174598, THC260994, AI475671, AA768343, AF174595, THC240016, N70417, T10511, AF174603, EST04915, AA147429, AI192344, AF174594, AI147207, AI279712, AA593015, AA644633, AA335703, N26196, AF174604, AF053356, AF174606, AA836036, AA853045, AI479142, AA772788, AA039454, AA397652, AA463756, AA007384, AA749085, AI640599, THC253263, AB020647, THC295423, AA434109, AA370939, AA215393, THC271423, AF052097, THC288182, AL049953, CAB37981, AL022395, AL031178, THC197682, and THC205131), with the nucleotide sequences derived from the F-box proteins disclosed above.

The nineteen previously uncharacterized FBP nucleotide sequences thus identified were named as follows: FBP3b, shown in FIG. 6 (SEQ ID NO:23); FBP8, shown in FIG. 11 (SEQ ID NO:25); FBP9, shown in FIG. 12 (SEQ ID NO:27); FBP10, shown in FIG. 13 (SEQ ID NO:29); FBP11, shown in FIG. 14 (SEQ ID NO:31); FBP12, shown in FIG. 15 (SEQ ID NO:33); FBP13, shown in FIG. 16 (SEQ ID NO:35); FBP14, shown in FIG. 17 (SEQ ID NO:37); FBP15, shown in FIG. 18 (SEQ ID NO:39); FBP16, shown in FIG. 19 (SEQ ID NO:41); FBP17, shown in FIG. 20 (SEQ ID NO:43); FBP18, shown in FIG. 21 (SEQ ID NO:45); FBP19, shown in FIG. 22 (SEQ ID NO:47); FBP20, shown in FIG. 23 (SEQ ID NO:49); FBP21, shown in FIG. 24 (SEQ ID NO:51); FBP22, shown in FIG. 25 (SEQ ID NO:53); FBP23, shown in FIG. 26 (SEQ ID NO:55); FBP24, shown in FIG. 27 (SEQ ID NO:57); and FBP25, shown in FIG. 28 (SEQ ID NO:59). The alignment of the F-box motifs from these predicted human FBPs is shown in FIG. 1A. Of these sequences, the nucleotide sequences of fourteen identified FBPs, FBP3b (SEQ ID NO:23), FBP8 (SEQ ID NO:25), FBP11 (SEQ ID NO:31), FBP12 (SEQ ID NO:33), FBP13 (SEQ ID NO:35), FBP14 (SEQ ID NO:37), FBP15 (SEQ ID NO:39), FBP17 (SEQ ID NO:43), FBP18 (SEQ ID NO:45), FBP20 (SEQ ID NO:49), FBP21 (SEQ ID NO:51), FBP22 (SEQ ID NO:53), FBP23 (SEQ ID NO:55), and FBP25 (SEQ ID NO:59) were not previously assembled and represent novel nucleic acid molecules. The five remaining sequences, FBP9 (SEQ ID NO:27), FBP10 (SEQ ID NO:29), FBP16 (SEQ ID NO:41), FBP19 (SEQ ID NO:47), and FBP24 (SEQ ID NO:57) were previously assembled and disclosed in the database, but were not previously recognized as F-box proteins.

Computer analysis of human FBPs revealed several interesting features (see the schematic representation of FBPs in FIG. 2. Three FBPs contain WD-40 domains; seven FBPs contain LRRs, and six FBPs contain other potential protein-protein interaction modules not yet identified in FBPs, such as leucine zippers, ring fingers, helix-loop-helix domains, proline rich motifs and SH2 domains.

As examples of the human FBP family, a more detailed characterization of some FBPs was performed. To confirm the specificity of interaction between the novel FBPs and human Skp1, eight in vitro translated FBPs were tested for binding to His-tagged-Skp1 pre-bound to Nickel-agarose beads. As a control Elongin C was used, the only known human Skp1 homolog. All 7 FBPs were able to bind His-Skp1 beads but not to His-tagged-Elongin C beads (FIG. 32). The small amount of FBPs that bound to His-tagged-Elongin C beads very likely represents non-specific binding since it was also present when a non-relevant protein (His-tagged-p27) bound to Nickel-agarose beads was used in pull-down assays (see as an example, FIG. 32, lane 12).

F-box deletion mutants, (ΔF)FBP1, (ΔF)FBP2, (ΔF) FBP3a, and mutants containing single point mutations in conserved amino acid residues of the F-box, FBP3a(L51A) and FBP3a(W76A) were constructed. Mutants lacking the F-box and those with point mutations lost their ability to bind Skp1 (FIG. 32), confirming that human FBPs require the integrity of their F-box to specifically bind Skp1.

In order to determine whether FBP1, FBP2, FBP3a, FBP4 and FBP7 interact with human Skp1 and Cul 1 in vivo (as Skp2 is known to do), flag-tagged-FBP1, -(ΔF)FBP1, —FBP2, -(ΔF)FBP2, —FBP3a, -(ΔF)FBP3a, -FBP4 and -FBP7 were expressed in HeLa cells from which cell extracts were made and subjected to immunoprecipitation with an anti-Flag antibody. As detected in immunoblots with specific antibodies to Cul1, Cul2 (another human cullin), and Skp1, the anti-Flag antibody co-precipitated Cul1 and Skp1, but not Cul2, exclusively in extracts from cells expressing wild-type FBPs (FIG. 32 and data not shown). These data indicate that as in yeast, the human Skp1/cullin complex forms a scaffold for many FBPs.

The binding of FBPs to the Skp1/Cul1 complex is consistent with the possibility that FBPs associate with a ubiquitin ligation activity. To test this possibility, Flag-tagged FBPs were expressed in HeLa cells, together with human Skp1 and Cul1. Extracts were subjected to immunoprecipitation with an anti-Flag antibody and assayed for ubiquitin ligase activity in the presence of the human ubiquitin-activating enzyme (E1) and a human Ubc. All of the wild type FBPs tested, but not FBP mutants, associated with a ubiquitin ligase activity which produced a high molecular weight smear characteristic of ubiquitinated proteins (FIG. 33). The ligase activity was N-ethylmaleimide (NEM) sensitive (FIG. 33, lane 2) and required the presence of both Ubc4 and E1. Results similar to those with Ubc4 were obtained using human Ubc3, whereas Ubc2 was unable to sustain the ubiquitin ligase activity of these SCFs (FIG. 33, lanes 12, 13).

Using indirect immunofluorescence techniques, the subcellular distribution of FBP1, FBP2, FBP3a, FBP4 and FBP7 was studied in human cells. Flag-tagged-versions of these proteins were expressed in HeLa, U2OS, and 293T cells and subjected to immunofluorescent staining with an anti-Flag antibody. FBP1, FBP4 and FBP7 were found to be distributed both in the cytoplasm and in the nucleus, while FBP2 was detected mainly in the cytoplasm and FBP3a mainly in the nucleus. FIG. 35 shows, as an example, the subcellular localization of FBP1, FBP2, FBP3a, FBP4 observed in HeLa cells. The localization of (ΔF)FBP1, (ΔF)FBP2, (ΔF)FBP3a mutants was identical to those of the respective wild-type proteins (FIG. 35) demonstrating that the F-box and the F-box-dependent binding to Skp1 do not determine the subcellular localization of FBPs. Immunofluorescence stainings were in agreement with the results of biochemical subcellular fractionation.

7.2.2 Northern Blot Analysis of Novel Ubiquitin Ligase Gene Transcripts

RNA blot analysis was performed on poly(A)+ mRNA from multiple normal human tissues (heart, brain, placenta, lung, liver, skeletal, muscle, kidney, pancreas, spleen, thymus, prostate, testis, ovary, small intestine, colon, peripheral blood leukocytes, see FIG. 36). FBP1 mRNA transcripts (a major band of ~7-kb and two minor bands of ~3.5- and ~2.5 kb) were expressed in all of the 16 human tissues tested but were more prevalent in brain and testis. Testis was the only tissue expressing the smaller FBP1 mRNA forms in amounts equal to, if not in excess of, the 7 kb form. FBP2 transcripts (~7.7-kb and ~2.4-kb) were expressed in all tissues tested, yet the ratio of the FBP2 transcripts displayed some tissue differences. An approximately 4 kb FBP3a transcript was present in all tissues tested and two minor FBP3a forms of approximately 3 kb and 2 kb became visible, upon longer exposure, especially in the testis. An approximately 4.8 kb FBP4 transcript was expressed in all normal human tissues tested, but was particularly abundant in heart and pancreas. Finally, the pattern of expression of the new FBPs was compared to that of FBP1 whose mRNA species (a major band of ~4 kb and a minor band of ~8.5 kb) were found in all tissues but was particularly abundant in placenta.

7.2.3 Chromosomal Location of the Human FBP Genes

Unchecked degradation of cellular regulatory proteins (e.g., p53, p27, (β-catenin) has been observed in certain tumors, suggesting the hypothesis that deregulated ubiquitin ligases play a role in this altered degradation (reviewed in Ciechanover, 1998, *EMBO J*, 17:7151). A well understood example is that of MDM2, a proto-oncogene encoding a ubiquitin ligase whose overexpression destabilize its substrate, the tumor suppressor p53 (reviewed by Brown and Pagano, 1997, *Biochim Biophys Acta*, 1332:1). To map the chromosomal localization of the human FBP genes and to determine if these positions coincided with loci known to be altered in tumors or in inherited disease, fluorescence in situ hybridization (FISH) was used. The FBP1 gene was mapped and localized to 10q24 (FIG. 37A), FBP2 to 9q34 (FIG. 37B), FBP3a to 13q22 (FIG. 37C), FBP4 to 5p12 (FIG. 37D) and FBP5 to 6q25-26 (FIG. 37E). FBP genes (particularly FBP1, FBP3a, and FBP5) are localized to chromosomal loci frequently altered in tumors (for references and details see Online Mendelian Inheritance in Man database,). In particular, loss of 10q24 (where FBP1 is located) has been demonstrated in approx. 10% of human prostate tumors and small cell lung carcinomas (SCLC), suggesting the presence of a tumor suppressor gene at this location. In addition, up to 7% of childhood acute T-cell leukemia is accompanied by a translocation involving 10q24 as a breakpoint, either t(10;14)(q24;q11) or t(7;10)(q35;q24). Although rarely, the 9q34 region (where FBP2 is located) has been shown to be a site of loss of heterozygosity (LOH) in human ovarian and bladder cancers. LOH is also observed in the region. Finally, 6q25-26 (where FBP5 is located) has been shown to be a site of loss of heterozygosity in human ovarian, breast and gastric cancers hepatocarcinomas, Burkitt's lymphomas, and parathyroid adenomas.

8. EXAMPLE

FBP1 Regulates the Stability of B-Catenin

Deregulation of β-catenin proteolysis is associated with malignant transformation. *Xenopus* Slimb and *Drosophila* FBP1 negatively regulate the Wnt/β-catenin signaling pathway (Jiang and Struhl, 1998, supra; Marikawa and Elinson, 1998, supra). Since ubiquitin ligase complexes physically associate with their substrates, the studies in this Example were designed to determine whether FBP1 can interact with β-catenin. The results show that FBP1 forms a novel ubiquitin ligase complex that regulates the in vivo stability of β-catenin. Thus, the identification of FBP1 as a component of the novel ubiquitin ligase complex that ubiquitinates β-catenin, provides new targets that can be used in screens for agonists, antagonists, ligands, and novel substrates using the methods of the present invention. Molecules identified by these assays are potentially useful drugs as therapeutic agents against cancer and proliferative disorders.

8.1 Materials and Methods for Identification of FBP1 Function

Recombinant proteins, Construction of F-box mutants, Antibodies, Transient transfections, Immunoprecipitation, Immunoblotting, Cell culture and Extract preparation Details of the methods are described in Section 7.1, supra.

8.2 Results 8.2.1 Human FBP1 Interacts with B-Catenin

Flag-tagged FBP1 and β-catenin viruses were used to co-infect insect cells, and extracts were analyzed by immunoprecipitation followed by immunoblotting. β-catenin was co-immunoprecipitated by an anti-Flag antibody (FIG. 38A), indicating that in intact cells O-catenin and FBP1 physically interact. It has been shown that binding of the yeast FBP Cdc4 to its substrate Sic1 is stabilized by the presence of Skp1 (Skowyra, et al., 1997, *Cell*, 91:209). Simultaneous expression of human Skp1 had no effect on the strength of the interaction between FBP1 and β-catenin. To test the specificity of the FBP1/β-catenin interaction, cells were co-infected with human FBP1 and FBP1 viruses. The choice of this cyclin was dictated by the fact that human cyclin D1 can form a complex with the Skp2 ubiquitin ligase complex (Skp1-Cul1-Skp2; Yu, et al., 1998, *Proc. Natl. Acad. Sci. U.S.A*, 95:11324). Under the same conditions used to demonstrate the formation of the FBP1/β-catenin complex, cyclin D1 could not be co-immunoprecipitated with Flag-tagged FBP1, and anti-cyclin D1 antibodies were unable to co-immunoprecipitate FBP1 (FIG. 38B, lanes 1-3). Co-expression of Skp1 (FIG. 38B, lanes 4-6) or Cdk4 with FBP1 and cyclin D1 did not stimulate the association of cyclin D1 with FBP1.

Mammalian expression plasmids carrying HA-tagged β-catenin and Flag-tagged FBP1 (wild type or mutant) were then co-transfected in human 293 cells. β-catenin was detected in anti-Flag immunoprecipitates when co-expressed with either wild type or (ΔF)FBP1 mutant (FIG. 38C, lanes 4-6), confirming the presence of a complex formed between β-catenin and FBP1 in human cells.

8.2.2 F-Box Deleted FBP1 Mutant Stabilizes β-Catenin In Vivo

Figures 39A, 39B:
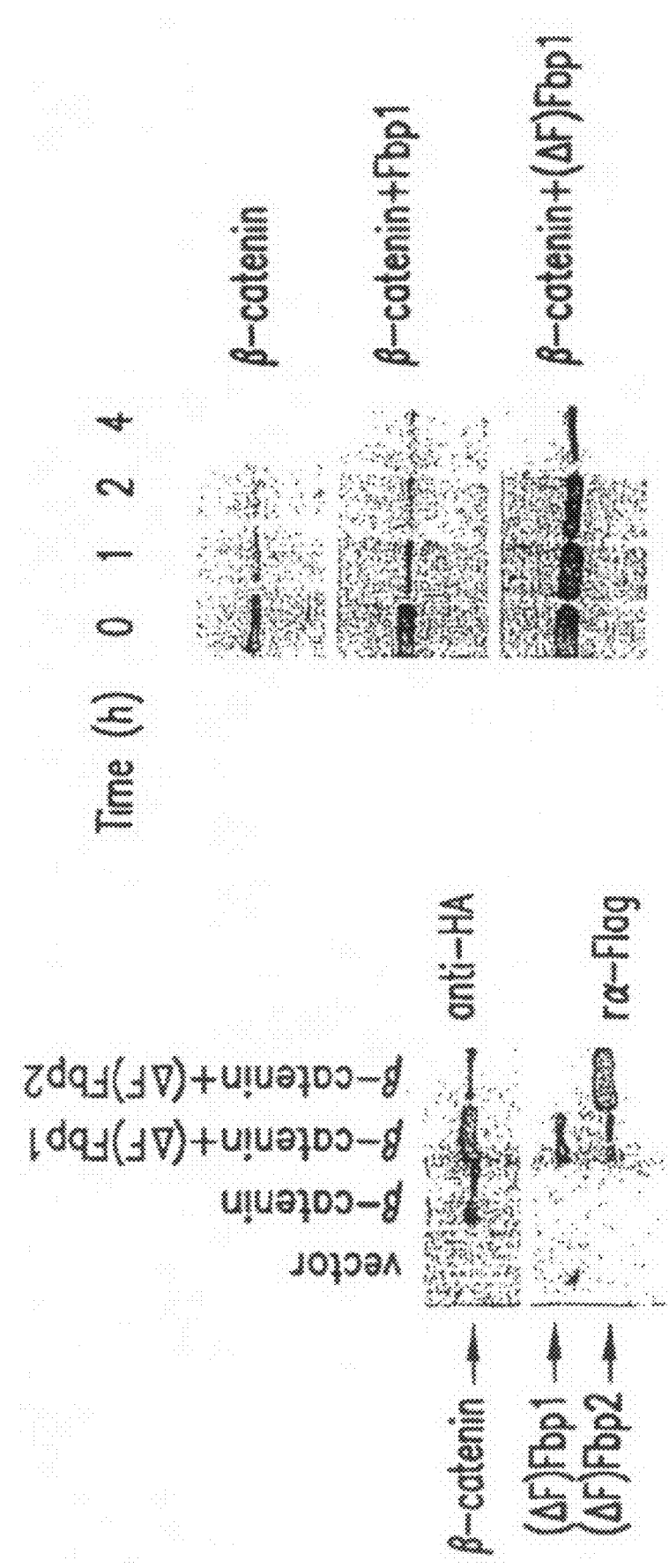

The association of (ΔF)FBP1 to β-catenin suggested that (ΔF)FBP1 might act as a dominant negative mutant in vivo by being unable to bind Skp1/Cul1 complex, on the one hand, while retaining the ability to bind β-catenin, on the other. HA-tagged β-catenin was co-expressed together with Flag-tagged (ΔF)FBP1 or with another F-box deleted FBP, (ΔF) FBP2. FBP2 was also obtained with our screening for Skp1-interactors; and, like FBP1, contains several WD-40 domains. The presence of (ΔF)FBP1 specifically led to the accumulation of higher quantities of β-catenin (FIG. 39A). To determine whether this accumulation was due to an increase in β-catenin stability, we measured the half-life of β-catenin using pulse chase analysis. Human 293 cells were transfected with HA-tagged β-catenin alone or in combination with the wild type or mutant FBP1. While wild type Fpb1 had little effect on the degradation of β-catenin, the F-box deletion mutant prolonged the half life of β-catenin from 1 to 4 hours (FIG. 39B).

FBP1 is also involved in CD4 degradation induced by the HIV-1 Vpu protein (Margottin, et al., supra). It has been shown that Vpu recruits FBP1 to DC4 and (ΔF)FBP1 inhibits Vpu-mediated CD4 regulation. In addition, FBP1-ubiquitin ligase complex also controls the stability of IKBα (Yaron, et al., 1998, *Nature*, 396:590). Thus, the interactions between FBP1 and β-catenin, Vpu protein, CD4, and IKBα are potential targets that can be used to screen for agonists, antagonists, ligands, and novel substrates using the methods of the present invention.

9. EXAMPLE

Methods for Identifying P27 as a Substrate of the FBP SKP2

Degradation of the mammalian G1 cyclin-dependent kinase (Cdk) inhibitor p27 is required for the cellular transition from quiescence to the proliferative state. The ubiquitination and degradation of p27 depend upon its phosphorylation by cyclin/Cdk complexes. Skp2, an F-box protein essential for entry into S phase, specifically recognizes p27 in a phosphorylation-dependent manner. Furthermore, both in vivo and in vitro, Skp2 is a rate-limiting component of the machinery that ubiquitinates and degrades phosphorylated p27. Thus, p27 degradation is subject to dual control by the accumulation of both Skp2 and cyclins following mitogenic stimulation.

This Example discloses novel assays that have been used to identify the interaction of Skp2 and p27 in vitro. First, an in vitro ubiquitination assay performed using p27 as a substrate is described. Second, Skp2 is depleted from cell extracts using anti-Skp2 antibody, and the effect on p27 ubiquitin ligase activity is assayed. Purified Skp2 is added back to such immunodepleted extracts to restore p27 ubiquitination and degradation. Also disclosed is the use of a dominant negative mutant, (ΔF)Skp2, which interferes with p27 ubiquitination and degradation.

The assays described herein can be used to test for compounds that inhibit cell proliferation. The assays can be carried out in the presence or absence of molecules, compounds, peptides, or other agents described in Section 6.5. Agents that either enhance or inhibit the interactions or the ubiquitination activity can be identified by an increase or decrease the formation of a final product are identified. Such agents can be used, for example, to inhibit Skp2-regulated p27 ubiquitination and degradation in vivo. Molecules identified by these assays are potentially useful drugs as therapeutic agents against cancer and proliferative disorders.

Dominant negative mutants, for example the mutant (ΔF) Skp2, and antisense oligos targeting SKP2, mRNA interfere with p27 ubiquitination and degradation, and can be used in gene therapies against cancer. The assays described herein can also be used to identify novel substrates of the novel FBP proteins, as well as modulators of novel ubiquitin ligase complex-substrate interactions and activities.

9.1 Materials and Methods for Identification of P27 as a SKP2 Substrate

Protein extraction for in vitro ubiquitination assay Approx. 4 ml of HeLa S3 cell pellet were suspended in 6 ml of ice-cold buffer consisting of 20 mM Tris-HCl (pH 7.2), 2 mM DTT, 0.25 mM EDTA, 10 μg/ml leupeptin, and 10 μg/ml pepstatin. The suspension was transferred to a cell nitrogen-disruption bomb (Parr, Moline, Ill., cat #4639) that had been rinsed thoroughly and chilled on ice before use. The bomb chamber was connected to a nitrogen tank and the pressure was brought slowly to 1000 psi. The chamber was left on ice under the same pressure for 30 minutes and then the pressure was released slowly. The material was transferred to an Eppendorf tube and centrifuged in a microcentrifuge at 10,000 g for 10 minutes. The supernatant (S-10) was divided into smaller samples and frozen at −80° C. This method of extract preparation based on the use of a cell nitrogen-disruption bomb extract preserves the activity to in vitro ubiquitinate p27 better than the method previously described (Pagano et al., 1995, Science 269:682-685).

Reagents and antibodies Ubiquitin aldehyde (Hershko & Rose, 1987, Proc. Natl. Acad. Sci. USA 84:1829-33), methylubiquitin (Hershko & Heller, 1985, Biochem. Biophys. Res. Commun. 128:1079-86) and p13 beads (Brizuela et al., 1987, EMBO J. 6:3507-3514) were prepared as described. β,γ-imidoadenosine-50-triphosphate (AMP-PNP), staurosporine, hexokinase, and deoxy-glucose were from Sigma; lovastatine obtained from Merck; flavopiridol obtained from Hoechst Marion Roussel. The phospho-site p27 specific antibody was generated in collaboration with Zymed Inc. by injecting rabbits with the phospho-peptide NAGSVEQT*PKKPGLRRRQT (SEQ ID NO: 85), corresponding to the carboxy terminus of the human p27 with a phosphothreonine at position 187 (T*). The antibody was then purified from serum with two rounds of affinity chromatography using both phospho- and nonphospho-peptide chromatography. All the other antibodies are described in Section 6.1.

Immunodepletion Assays For immunodepletion assays, 3 µl of an Skp2 antiserum was adsorbed to 15 µl Affi-Prep Protein-A beads (BioRad), at 4° C. for 90 min. The beads were washed and then mixed (4° C., 2 hours) with 40 µl of HeLa extract (approximately 400 µg of protein). Beads were removed by centrifugation and supernatants were filtered through a 0.45-µMicrospin filter (Millipore). Immunoprecipitations and immunoblots were performed as described (Pagano, et al., 1995, supra). Rabbit polyclonal antibody against purified GST-Skp2 was generated, affinity-purified (AP) and characterized as described (M. Pagano, in Cell Cycle-Materials and Methods, M. Pagano Ed. (Springer, N.Y., 1995), chap. 24; E. Harlow and D. Lane, in Using antibodies. A Laboratory Manual (Cold Spring Harbor Laboratory, Cold Spring Harbor, N.Y., 1998), in collaboration with Zymed Inc. (cat #51-1900). Monoclonal antibodies (Mabs) to human Cul1, and cyclin E, (Faha, et al., 1993, J. of Virology 67:2456); AP rabbit antibodies to human p27, Skp1 (Latres, et al., 1999, Oncogene 18:849), Cdk2 (Pagano, et al., 1992, Science 255:1144) and phospho-site p27 specific antibody. Mab to cyclin B was from Santa Cruz (cat #sc-245); Mabs to p21 (cat #C24420) and p27 (cat #K25020) Transduction lab; anti-Flag rabbit antibody from Zymed (cat #71-5400). An AP goat antibody to an N-terminal Skp2 peptide (Santa Cruz, cat #sc-1567) was used.

Construction of Skp2 F-box mutant (ΔF)Skp2 mutant was obtained by removing a DNA fragment (nucleotides 338-997) with BspEI and XbaI restriction enzymes, and replacing it with a PCR fragment containing nucleotides 457 to 997. The final construct encoded a protein lacking residues 113-152.

Recombinant proteins cDNA fragments encoding the following human proteins: Flag-tagged FBP1, Flag-tagged (ΔF) FBP1, Flag-tagged FBP3a, Skp2, HA-tagged Cul1, HA-tagged Cul2,β-catenin, His-tagged cyclin D1, Skp1, His-tagged Skp1, His-tagged Elongin C were inserted into the baculovirus expression vector pBacpak-8 (Clonetech) and cotransfected into Sf9 cells with linearized baculovirus DNA using the BaculoGold transfection kit (Pharmingen). Baculoviruses expressing human His-tagged cyclin E and HA-tagged Cdk2 were supplied by D. Morgan (Desai, 1992, Mol. Biol. Cell 3:571). Recombinant viruses were used to infect 5B cells and assayed for expression of their encoded protein by immunoblotting as described above. His-proteins were purified with Nickel-agarose (Invitrogen) according to the manufacturer's instructions. The different complexes were formed by co-expression of the appropriate baculoviruses and purified by nickel-agarose chromatography, using the His tag at the 5' of Skp1 and cyclin E. Unless otherwise stated, recombinant proteins were added to incubations at the following amounts: cyclin E/Cdk2, ~0.5 µmol; Skp1, ~0.5 µmol; Skp2, ~0.1 µmol; FBP1, ~0.1 µmol; FBP3a, ~0.1 µmol, Cul1, ~0.1 µmol. The molar ratio of Skp1/Skp2, Skp1/FBP1, Skp1/FBP3a, and Skp1/Cul1 in the purified preparations was ~5.

Extract preparation and cell synchronization, Transient transfections, Immunoprecipitation and Immunoblotting Methods were carried out as described in Section 6.1, supra.

9.2 Results 9.2.1 P27 In Vitro Ubiquitination Assay

In an exemplary in vitro ubiquitination assay, logarithmically growing, HeLa-S3 cells were collected at a density of $6 \times 10^5$ cells/ml. Cells are arrested in G1 by 48-hour treatment with 70 µM lovastatin as described (O'Connor and Jackman, 1995, in Cell Cycle-Materials and Methods, M. Pagano, ed., Springer, N.Y., chap. 6). 1 µl of in vitro translated [35S]p27 is incubated at 30° C. for different times (0-75 minutes) in 10 µl of ubiquitination mix containing: 40 mM Tris pH 7.6, 5 mM $MgCl_2$, 1 mM DTT, 10% glycerol, 1 µM ubiquitin aldehyde, 1 mg/ml methyl ubiquitin, 10 mM creatine phosphate, 0.1 mg/ml creatine phosphokinase, 0.5 mM ATP, 1 µM okadaic acid, 20-30 µg HeLa cell extract. Ubiquitin aldehyde can be added to the ubiquitination reaction to inhibit the isopeptidases that would remove the chains of ubiquitin from p27. Addition of methyl ubiquitin competes with the ubiquitin present in the cellular extracts and terminates p27 ubiquitin chains. Such chains appear as discrete bands instead of a high molecular smear. These shorter polyubiquitin chains have lower affinity for the proteasome and therefore are more stable. Reactions are terminated with Laemmli sample buffer containing β-mercaptoethanol and the products can be analyzed on protein gels under denaturing conditions.

Polyubiquitinated p27 forms are identified by autoradiography. p27 degradation assay is performed in a similar manner, except that (i) Methylated ubiquitin and ubiquitin aldehyde were omitted; (ii) The concentration of HeLa extract is approximately 7 µg/µl; (iii) Extracts are prepared by hypotonic lysis (Pagano, et al., 1995, Science 269:682), which preserves proteasome activity better than the nitrogen bomb disruption procedure. In the absence of methyl ubiquitin, p27 degradation activity, instead of p27 ubiquitination activity, can be measured.

The samples are immunoprecipitated with an antibody to p27 followed by a subsequent immunoprecipitation with an anti-ubiquitin antibody and run on an 8% SDS gel. The high molecular species as determined by this assay are ubiquitinated. As a control, a p27 mutant lacking all 13 lysines was used. This mutant form of p27 is not ubiquitinated and runs at higher molecular weight on the 8% SDS gel.

9.2.2 P27-Skp2 Interaction Assays and P27-Skp2 Immunodepletion Assay

The recruitment of specific substrates by yeast and human FBPs to Skp1/cullin complexes is phosphorylation-dependent. Accordingly, peptides derived from IκBα and β-catenin bind to FBP1 specifically and in a phosphorylation-dependent manner (Yaron, 1998, Nature 396:590; Winston, et al., 1999, Genes Dev. 13:270). A p27 phospho-peptide with a phosphothreonine at position 187 was assayed for its ability to bind to human FBPs, including Skp2 and the FBP1, FBP2, FBP3a, FBP4, FBP5, FBP6, and FBP7, isolated by using a 2-hybrid screen using Skp1 as bait, as described in Section 6, above. Four of these FBPs contain potential substrate interaction domains, such as WD-40 domains in FBP1 and FBP2, and leucine-rich repeats in Skp2 and FBP3a. The phospho-p27 peptide was immobilized to Sepharose beads and incubated with these seven in vitro translated FBPs (FIG. 40A). Only one FBP, Skp2, was able to bind to the phospho-T187 p27 peptide. Then, beads linked to p27 peptides (in either phosphorylated or unphosphorylated forms) or with an unrelated phospho-peptide were incubated with HeLa cell extracts. Proteins stably associated with the beads were examined by immunoblotting. Skp2 and its associated proteins, Skp1 and Cul1, were readily detected as proteins bound to the phospho-p27 peptide but not to control peptides (FIG. 40B).

To further study p27 association to Skp2, in vitro translated p27 was incubated with either Skp1/Skp2 complex, cyclin E/Cdk2 complex, or the combination of both complexes under conditions in which p27 is phosphorylated on T187 by cyclin E/Cdk2 (Montagnoli, et al., 1999, *Genes Dev.* 13:1181). Samples were then immunoprecipitated with an anti-Skp2 antibody. p27 was co-immunoprecipitated with Skp2 only in the presence of cyclin E/Cdk2 complex (FIG. 40C). Notably, under the same conditions, a T187-to-alanine p27 mutant, p27(T187A), was not co-immunoprecipitated by the anti-Skp2 antibody. Finally, we tested Skp2 and p27 association in vivo. Extracts from HeLa cells and IMR90 human diploid fibroblasts were subjected to immunoprecipitation with two different antibodies to Skp2 and then immunoblotted. p27 and Cul1, but not cyclin D1 and cyclin B1, were specifically detected in Skp2 immunoprecipitates (FIG. 41). Importantly, using a phospho-T187 site p27 specific antibody we demonstrated that the Skp2-bound p27 was phosphorylated on T187 (FIG. 41, lane 2, bottom panel). Furthermore, an anti-peptide p27 antibody specifically co-immunoprecipitated Skp2. These results indicate that the stable interaction of p27 with Skp2 was highly specific and dependent upon phosphorylation of p27 on T187.

A cell-free assay for p27 ubiquitination which faithfully reproduced the cell cycle stage-specific ubiquitination and degradation of p27 has been developed (Montagnoli, et al., supra). Using this assay, a p27-ubiquitin ligation activity is higher in extracts from asynchronously growing cells than in those from G1-arrested cells (FIG. 42A, lanes 2 and 4). In accordance with previous findings (Montagnoli, et al., supra), the addition of cyclin E/Cdk2 stimulated the ubiquitination of p27 in both types of extracts (FIG. 42A, lanes 3 and 5). However, this stimulation was much lower in extracts from G1-arrested cells than in those from growing cells, suggesting that in addition to cyclin E/Cdk2, some other component of the p27-ubiquitin ligation system is rate-limiting in G1. This component could be Skp2 since, in contrast to other SCF subunits, its levels are lower in extracts from G1 cells than in those from asynchronous cells and are inversely correlated with levels of p27 (FIGS. 42B and 46).

Skp2 was thus tested to determine if it is a rate-limiting component of a p27 ubiquitin ligase activity. The addition of recombinant purified Skp1/Skp2 complex alone to G1 extracts did not stimulate p27 ubiquitination significantly (FIG. 42A, lane 6). In contrast, the combined addition of Skp1/Skp2 and cyclin E/Cdk2 complexes strongly stimulated p27 ubiquitination in G1 extracts (FIG. 42A, lane 7). Similarly, the combined addition of Skp1/Skp2 and cyclin E/Cdk2 strongly stimulated p27 proteolysis as measured by a degradation assay (FIG. 42A, lanes 13-16).

Since the Skp1/Skp2 complex used for these experiments was isolated from insect cells co-expressing baculovirus His-tagged-Skp1 and Skp2 (and co-purified by nickel-agarose chromatography), it was possible that an insect-derived F-box protein co-purified with His-Skp1 and was responsible for the stimulation of p27 ubiquitination in G1 extracts. This possibility was eliminated by showing that the addition of a similar amount of His-tagged-Skp1, expressed in the absence of Skp2 in insect cells and purified by the same procedure, did not stimulate p27 ubiquitination in the presence of cyclin E/Cdk2 (FIG. 42A, lane 8). Furthermore, we found that neither FBP1 nor FBP3a could replace Skp2 for the stimulation of p27-ubiquitin ligation in G1 extracts (FIG. 42A, lanes 9-12). Stimulation of p27-ubiquitination in G1 extracts by the combined addition of Skp1/Skp2 and cyclin E/Cdk2 could be observed only with wild-type p27, but not with the p27 (T187A) mutant (lanes 17-20), indicating that phosphorylation of p27 on T187 is required for the Skp2-mediated ubiquitination of p27. These findings indicated that both cyclin E/Cdk2 and Skp1/Skp2 complexes are rate-limiting for p27 ubiquitination and degradation in the G1 phase.

To further investigate the requirement of Skp2 for p27 ubiquitin ligation, Skp2 was specifically removed from extracts of asynchronously growing cells by immunodepletion with an antibody to Skp2. The immunodepletion procedure efficiently removed most of Skp2 from these extracts and caused a drastic reduction of p27-ubiquitin ligation activity (FIG. 43A, lane 4) as well as of p27 degradation activity. This effect was specific as shown by the following observations: (i) Similar treatment with pre-immune serum did not inhibit p27-ubiquitination (FIG. 43A, lane 3); (ii) Pre-incubation of anti-Skp2 antibody with recombinant GST-Skp2 (lane 5), but not with a control protein (lane 4), prevented the immunodepletion of p27-ubiquitination activity from extracts; (iii) p27-ubiquitinating activity could be restored in Skp2-depleted extracts by the addition of His-Skp1/Skp2 complex (FIG. 43B, lane 3) but not His-Skp1 (lane 2), His-Skp I/CuI 1 complex (lane 4), or His-Skp1/FBP1.

We then immunoprecipitated Skp2 from HeLa extracts and tested whether this immunoprecipitate contained a p27 ubiquitinating activity. The anti-Skp2 beads, but not a immunoprecipitate made with a pre-immune (PI) serum, was able to induce p27 ubiquitination in the presence of cyclin E/Cdk2 (FIG. 43C, lanes 2 and 3). The addition of purified recombinant E1 ubiquitin-activating enzyme, and purified recombinant Ubc3 did not greatly increase the ability of the Skp2 immunoprecipitate to sustain p27 ubiquitination, (FIG. 43C, lane 5), likely due to the presence of both proteins in the rabbit reticulocyte lysate used for p27 in vitro translation.

9.2.3 F-Box Deleted SKP2 Mutant Stabilizes P27 in Vivo

Skp2 also targets p27 for ubiquitin-mediated degradation in vivo. The F-box-deleted FBP1 mutant, (ΔF)FBP1, acts in vivo as a dominant negative mutant, most likely because without the F-box is unable to bind Skp1/Cul1 complex but retains the ability to bind its substrates. Therefore, once expressed in cells, (ΔF)Fb sequesters β-catenin and IKBα and causes their stabilization. An F-box deleted Skp2 mutant, (ΔF)Skp2, was constructed. p27 was expressed in murine cells either alone or in combination with (ΔF)Skp2 or (DF) FBP1 (see FIG. 44). The presence of (ΔF)Skp2 led to the accumulation of higher quantities of p27. To determine whether this accumulation was due to an increase in p27 stability, the half-life of p27 was measured using pulse chase analysis (for details, see Section 8, above). Indeed, (ΔF)Skp2 prolonged p27 half-life from less than 1 hour to ~0.3 hours. Since in these experiments the efficiency of transfection was approximately 10%, (ΔF)Skp2 affected only the stability of co-expressed human exogenous p27, but not of murine endogenous p27.

9.2.4 SKP2 Antisense Experiments

SKP2 mRNA was targeted with antisense oligonucleotides to determine whether a decrease in Skp2 levels would influence the abundance of endogenous p27. Two different antisense oligos, but not control oligodeoxynucleotides induced a decrease in Skp2 protein levels (FIG. 45). Concomitant with the Skp2 decrease, there was a substantial increase in the level of endogenous p27 protein. Similar results were obtained with cells blocked at the G1/S transition with hydroxyurea or aphidicolin treatment (lanes 9-16). Thus, the effect of the SKP2 antisense oligos on p27 was not a secondary consequence of a possible block in G1 due to the decrease in Skp2 levels.

Antisense experiments were performed as described in (Yu, 1998, *Proc. Natl. Acad. Sci. U.S.A.* 95: 11324). Briefly, four oligodeoxynucleotides that contain a phosphorothioate backbone and C-5 propyne pyrimidines were synthesized (Keck Biotechnology Resource Laboratory at Yale University): (1) 5'-CCTGGGGGATGTTCTCA-3' (SEQ ID NO: 86) (the antisense direction of human Skp2 cDNA nucleotides 180-196); (2) 5'-GGCTTCCGGGCATTTAG-3' (SEQ ID NO: 87) [the scrambled control of (1)]; (3) 5'-CATCTG-GCACGATTCCA-3' (SEQ ID NO: 88) (the antisense direction of Skp2 cDNA nucleotides 1137-1153); (4) 5'-CCGCT-CATCGTATGACA-3' (89) [the scrambled control for (3)]. The oligonucleotides were delivered into HeLa cells using Cytofectin GS (Glen Research) according to the manufacturers instructions. The cells were then harvested between 16 and 18 hours postransfection.

10. EXAMPLE

Method for Identifying Cks1 as a Mediator of the FBP Skp2-P27 Interaction

As stated in Example 9, p27 is recognized by Skp2 in a phosphorylation-dependent manner for entry into S phase and Skp2 is a rate-limiting component of the machinery that ubiquitinates and degrades phosphorylated p27. This Example discloses novel assays that have been used to identify the interactions of Cks1 with Skp2 and Cks1 with p27 in vitro and in a purified system. First, extracts of HeLa cells are fractionated and the activity of the fractions to promote the ligation of p27 is tested. Second, identification of Cks1 as the factor required for p27-ubiquitin ligation is confirmed with use of recombinant Cks1. Third, identification of Cks1's involvement in the p27-ubiquitin ligation after p27 is phosphorylated. Fourth, Cks1 increases the binding of Skp2 to p27. Fifth, Cks1 binds to Skp2. Sixth, Cks1 binds to the C-terminus of p27.

The assays described herein can be used to test for compounds that inhibit cell proliferation. The assays can be carried out in the presence or absence of molecules, compounds, peptides, or other agents described in Section 6.5. Agents that either enhance or inhibit the interactions or the ubiquitination activity can be identified by an increase or decrease the formation of a final product are identified. Such agents can be used, for example, to inhibit Skp2-regulated p27 ubiquitination and degradation in vivo. Molecules identified by these assays are potentially useful drugs as therapeutic agents against cancer and proliferative disorders.

Dominant negative mutants and antisense mRNA, oligos targeting the gene for Cks1, interfere with p27 ubiquitination and degradation, and can be used in gene therapies against cancer. The assays described herein can also be used to identify additional novel substrates of the novel FBP proteins, as well as additional modulators of novel ubiquitin ligase complex-substrate interactions and activities.

10.1 Materials and Methods for Identifying Cks1 as a Mediator of the FBP Skp2/P27 Interaction Proteins His$_6$-tagged p27 and Cdc34 were expressed in *E. coli* and purified by nickel-agarose chromatography. Cks2 and p13$^{Sue1}$ were expressed in bacteria and purified by gel filtration chromatography. His$_6$-Skp1/Skp2, His$_6$-Skp1/β-TrCP, His$_6$-cyclin E/Cdk2, and His$_6$-Cul-1/ROC1 were produced by co-infection of 5B insect cells with baculoviruses encoding the corresponding proteins and were purified by nickel-agarose chromatography as described previously (Montagnoli, et al., 1999, Genes & Dev. 13:1501; Carrano, et al., 1999, Nat. Cell Biol. 1:193). The approximate concentrations of recombinant proteins in these preparations were (in pmole/µl): Skp1, 5; Skp2, 0.5; Cul-1, 4; ROC 1,1; cyclin E, 8; Cdk2, 1.5. Purified recombinant human Nedd8 was the generous gift of C. Pickart, and purified recombinant human Cks1 was the generous gift of S. Reed. Purified GST-IκBα (1-154) and its constitutively active kinase IKKβ$^{S177E,S181E}$ were generously provided by Z.-Q. Pan. $^{35}$S-labeled p27, Skp2 and Cks proteins were prepared by in vitro transcription-translation, using the TnT Quick kit (Promega) and $^{35}$S-methionine (Amersham).

Purification of Nedd8-conjugating enzymes Purified recombinant human Nedd8 was the generous gift of C. Pickart. A mixture of Nedd8-conjugating enzymes (E1-like APP-BP1-Uba3 heterodimer and E2-like Ubc12: Osaka, et al., 1998, *Genes Dev.* 12:2263; Gong, L., Yeh, E. T., 1999, J. Biol. Chem. 274:12036) was co-purified from lysates of rabbit reticulocytes by a "covalent affinity" chromatography procedure similar to that used for the purification of E2s (Hershko, et al., 1983, J. Biol. Chem. 258:8206), except that unfractionated reticulocyte lysate was applied to a column of GST-Nedd8-Sepharose (5 mg/ml). Following a wash with 1M KCl, all proteins bound to immobilized Nedd8 by thiolester linkages were co-eluted with a solution containing 20 mM DTT. The DTT eluate was concentrated by ultrafiltration to approx. 1/10 of the original volume of reticulocyte lysate. This preparation had strong activity in the ligation of Nedd8 to Cul-1, without any detectable hydrolase activity that removes Nedd8 from Cul-1.

Purification of the factor required for p27-ubiquitin ligation A frozen pellet from 50 g of HeLa S3 cells (National Cell Culture Center) was disrupted by a nitrogen cell disruption bomb (Parr, Moline, Ill.) as described Montagnoli, et al., 1999, Genes & Dev. 13:1181, except that the buffer also contained 10 µg/ml chymostatin and 5 µg/ml aprotinin. The extract was centrifuged at 15,000×g for 20 min and the supernatants were centrifuged again at 100,000×g for 60 min. The supernatant was subjected to fractionation on DEAE-cellulose as described (Hershko, et al., 1983, J. Biol. Chem. 258: 8206), except that 2,500 mg of protein was loaded on 250 ml of resin. The fraction not adsorbed to the resin (Fraction 1) was collected and was concentrated by centrifuge ultrafiltration to approx. 10 mg/ml. Fraction 1 (100 mg of protein) was subjected to heat-treatment at 90° C. for 10 minutes. The sample was allowed to stay on ice for 30 min, and then the precipitate was removed by centrifugation (10,000×g, 15 min). Approximately 99% of protein was removed by heat-treatment. The supernatant was concentrated by ultrafiltration and then was applied to a MonoS HR 5/5 column (Pharmacia) equilibrated with 50 mM Tris-HCl, 1 mM DTT and 0.1% (w/v) Brij-35 (Boehringer). The column was washed with 15 ml of the above buffer and was then eluted with a gradient of 0-200 mM NaCl. Activity in column fractions was followed by the p27-ubiquitin ligation assay in the presence of purified SCF$^{Skp2}$ components (see below). The peak fractions of activity eluted at around 30-40 mM NaCl. The peak containing factor activity was pooled, concentrated by centrifuge ultrafiltration and was subjected to the final step of gel filtration chromatography on Superdex-75 HR 10/30 column (Pharmacia) equilibrated with 20 mM Tris-HCl (pH 7.2), 150 mM NaCl, 1 mM DTT and 01% Brij-35. Samples of 0.5 ml were collected at a flow rate of 0.4 ml/min. Column fractions were concentrated to a volume of 50 µl by centrifuge ultrafiltration (Centricon-10, Amicon). Samples of 0.004 µl of column fractions were assayed for activity to stimulate p27-ubiquitin ligation. Results were quantified by phosphorimager analysis and were expressed as the percentage of $^{35}$S-p27 converted to ubiquitin conjugates. Arrows at top indicate the elution position of molecular mass marker proteins (kDa).

Mass spectrometric sequencing The 10-kDa protein from the last step of purification was excised and digested in gel as described (Shevchenko, et al., 1996, Anal. Cham. 68:850. Mass spectrometric analysis was performed on a Sciex QSTAR mass spectrometer (MDS-Sciex, Concord, ON, Canada). A tryptic peptide at mass 2163.5 was fragmented from doubly and triply charged species to yield a complete match to residues 5-20 of human Cks1.

Assay of p27-ubiquitin ligation. Unless otherwise stated, the reaction mixture contained in a volume of 10 W: 40 mM Tris-HCl (pH 7.6), 5 mM MgCl$_2$, 1 mM DTT, 10% (v/v) glycerol, 10 mM phosphocreatine, 100 µg/ml creatine phosphokinase, 0.5 mM ATP, 1 mg/ml soybean trypsin inhibitor, 1 µM ubiquitin aldehyde, 1 mg/ml methylated ubiquitin, 1 µmol E1, 50 µmol Cdc34, 0.25 µl Skp2/Skp1, 0.25 µl Cul-1/ROC1, 0.1 µl cyclin E/Cdk2, 0.5 µl of $^{35}$S-p27 and additions as specified. Following incubation at 30° C. for 60 minutes, samples were subjected to SDS-polyacrylamide gel electrophoresis and autoradiography. The ligation of IκBα to ubiquitin was assayed as described (Chen, et al., 2000, J. Biol. Chem. 275:15432), except that baculovirus-expressed, purified Skp1/β-TrCP was used (5 µmol Skp1, ~1 pmol β-TrCP).

Preparation of $^{32}$P labeled purified p27 and assay of its ubiquitinylation. Purified p27 (0.18 µg) was incubated (60 minutes at 30° C.) with Cdk2/cyclin E (0.25 µl) in a reaction mixture containing in a volume of 10 µl: 50 mM Tris-HCl (pH 7.6), 5 mM MgCl$_2$, 1 mM DTT, 10% glycerol, 1 mg/ml soybean trypsin inhibitor, 1 µM okadaic acid and 100 µM [$^{32}$P-γ-]ATP (~0.50 µCi). This preparation is referred to as "$^{32}$P-p27". The ligation of p27 to MeUb was assayed as described above, with the following changes: $^{35}$S-p27 was replaced by $^{32}$P-p27, the concentration of unlabeled ATP was increased to 2 mM (for more complete isotopic dilution of labeled ATP present in the preparation of $^{32}$P-p27) and okadaic acid (1 µM) was added.

Assay of binding of p27 to Skp2/Skp1 The reaction mixture contained, in a volume of 10 µl: 40 mM Tris-HCl (pH 7.6), 2 mg/ml bovine serum albumin, 1 µl $^{35}$S-p27, 1 µl Cdk2/cyclin E, 1 µl Skp2/Skp1, as well as MgCl$_2$, ATP, DTT, phosphocreatine and creatine phosphokinase at concentrations similar to those described above for p27-ubiquitin ligation assay. Following incubation at 30° C. for 30 min, 6 µl of Affi-prep-Protein A beads (BioRad) to which polyclonal rabbit antibody against full length Skp2 (Carrano, et al., 1999, Nat. Cell Biol. 1:193) had been covalently linked by dimethyl pimelimidate (Harlow and Lane, 1998, in *Antibodies. A Laboratory Manual* (eds. Harlow and Lane), Cold Spring Harb. LabPress, Cold Spring Harbor, N.Y.) was added. The samples were rotated with the anti-Skp2-Protein A beads at 4° C. for 2 hours, and then the beads were washed 4 times with 1-ml portions of RIPA buffer (Harlow and Lane, 1998, supra). Following elution with SDS electrophoresis sample buffer, the samples were subjected to SDS-polyacrylamide gel electrophoresis and autoradiography.

10.2 Results 10.2.1 The Factor from Fraction 1 is a Protein

The activity of Fraction 1 is not destroyed by heating at 90° C. However, the active factor is a protein, as indicated by the observation that incubation of heat-treated Fraction 1 with trypsin completely destroyed its activity (FIG. 47, lane 2). Heat-treated Fraction 1 (~0.1 mg/ml) was incubated at 37° C. for 60 min with 50 mM Tris-HCl (pH 8.0) either in the absence (lane 1) or in the presence of 0.6 mg/ml of TPCK-treated trypsin (Sigma T8642) (lane 2). Trypsin action was terminated by the addition of 2 mg/ml of soybean trypsin inhibitor (STI). In lane 3, STI was added 5 min prior to a similar incubation with trypsin. Subsequently, samples corresponding to ~50 ng of heat-treated Fraction 1 were assayed for the stimulation of p27-ubiquitin ligation. Incubation of Fraction 1 with trypsin is terminated by the addition of excess soybean trypsin inhibitor (STI), to prevent proteolytic damage to the other components of the system, added following trypsin treatment. STI indeed efficiently blocks trypsin action as is shown in a control experiment in which STI is added to heated Fraction 1 prior to incubation with trypsin (FIG. 47, lane 3). In this incubation, there is no significant decrease in p27-ubiquitin ligation.

10.2.2 The Factor from Fraction 1 is not Nedd8

Figure 48A:
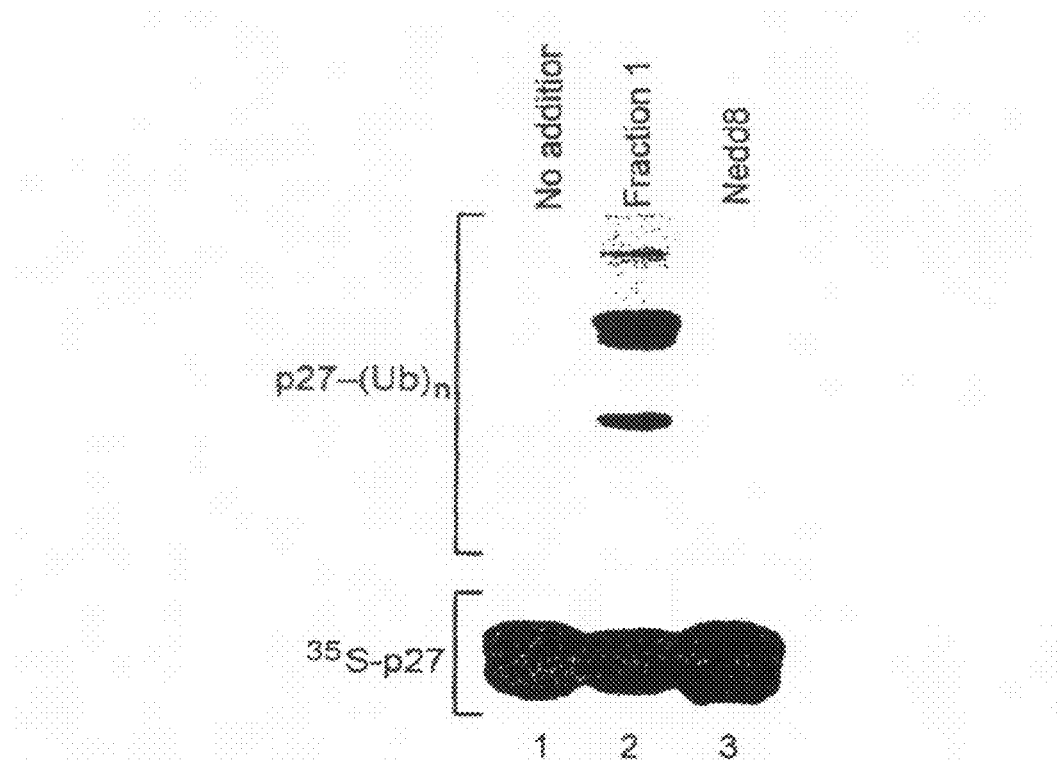

Podust et al. (Podust, et al., 2000, Proc. Natl. Acad. Sci. U.S.A. 97:4579) have reported that the ligation of p27 to ubiquitin requires Fraction 1, and have suggested that Nedd8 is the active component in Fraction 1. Nedd8 (called Rub-1 in yeast) is a highly conserved ubiquitin-like protein that is ligated to different cullins, including Cul-1 (Yeh, et al., 2000, Gene 248:1). The ligation of Nedd8 to Cul-1 has been shown to stimulate, though not to be absolutely required for, the activity of the SCF$^{β-TrCP}$ complex in the ligation of ubiquitin to IκBα (Furukawa, et al., 2000, Mol. Cell. Biol. 20:8185; Read, et al., 2000, Mol. Cell. Biol. 20:2326; Wu, et al., 2000, J. Biol. Chem. 275:32317). Since $^{35}$S-labeled p27 can be produced by in vitro translation in reticulocyte lysates, and since reticulocyte lysates contain the enzymes required for the ligation of Nedd8 to cullins (Osaka, et al., 1998, Genes Dev. 12:2549), it is possible that under these conditions Nedd8 could be ligated to Cul-1. However, recombinant purified Nedd8 does not replace the factor from Fraction 1 in promoting p27-ubiquitin ligation (FIG. 48A). Where indicated, ~50 ng of heat-treated Fraction 1 or 100 ng of purified recombinant human Nedd8 are added to the p27-MeUb ligation assay.

Figure 48B:
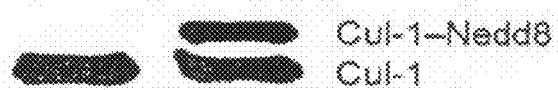

To further examine this problem, the enzymes that ligate Nedd8 to Cul-1 were purified by affinity chromatography on GST-Nedd8-Sepharose. Incubation of Cul-1 with Nedd8 and its purified conjugating enzymes convert about one-half of Cul-1 molecules to Nedd8-conjugated form that migrates slower in SDS-polyacrylamide gel electrophoresis (FIG. 48B). Ligation of Nedd8 to Cul-1. Cul-1/ROC1 (3 µl) is incubated with Nedd8 (10 µg) and purified Nedd8-conjugating enzymes (20 µl) in a 100-µl reaction mixture containing Tris (pH 7.6), MgCl$_2$, ATP, phosphocreatine, creatine phosphokinase, DTT, glycerol and STI at concentrations similar to those described for the p27-ubiquitin ligation assay. A control preparation of Cul1/ROC1 is incubated under similar conditions, but without Nedd8 conjugating enzymes. Following incubation at 30° C. for 2 hours, samples of control or Nedd8-modified preparations are separated on an 8% polyacrylamide-SDS gel and immunoblotted with an anti-Cul-1 antibody (Zymed). The slower migrating form indeed contains Nedd8 as verified by immunoblotting with a specific antibody directed against Nedd8.

Figure 48C:
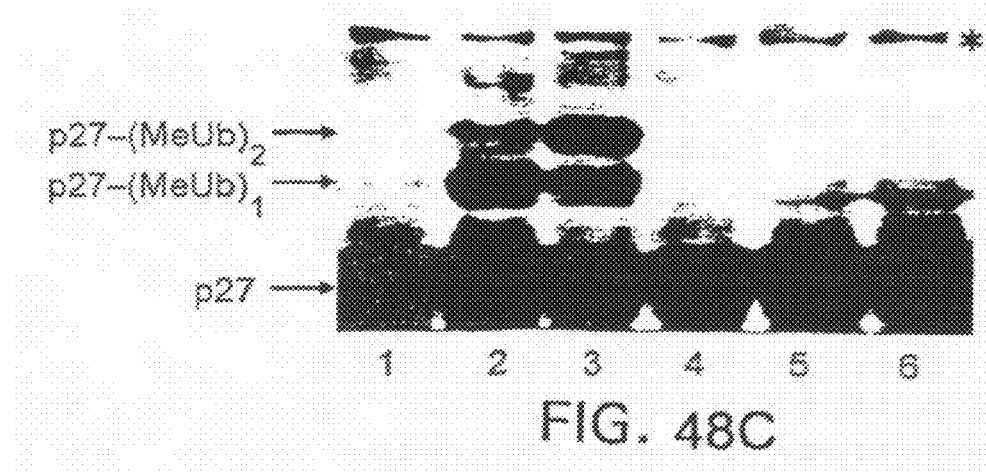

The activity of these preparations of Nedd8-conjugated and unmodified Cul-1 in the p27 ubiquitinylation reaction is measured in the presence or absence of heat-treated Fraction 1. Bacterially expressed, purified p27 (20 ng) is used as the substrate rather than $^{35}$S-labeled p27 translated in reticulocyte lysate, because reticulocyte lysates also contain the enzyme(s) that rapidly cleave(s) the amide linkage between Nedd8 and Cul-1. The ligation of p27 to MeUb occurs at 30° C. for 60 minutes and is followed by separation on a 12.5% polyacrylamide-SDS gel, transfer to nitrocellulose, and immunoblotting with a monoclonal antibody directed against p27 (Transduction Laboratories). Using this purified system and in the presence of heat-treated Fraction 1, significant formation of mono-ubiquitinylated, and less of di-ubiquitinylated derivatives of p27 is promoted by unmodified Cul-1 (FIG. 48C). With the purified system, conjugates with MeUb larger than the di-ubiquitinylated form are not observed, as opposed to the 4-5 conjugates observed with in vitro-translated $^{35}$S-p27 (compare with FIG. 47). With Cul-1 conjugated to Nedd8, a modest stimulation in the ubiquitinylation of p27 is observed, with a special increase in the formation of the di-ubiquitin derivative (FIG. 48, lane 3). In different preparations of Cul-1, Nedd8 ligation increases the overall rate of p27-ubiquitin ligation by 1.5-3 fold.

The basal activity of p27-ubiquitin ligation observed with unmodified Cul-1 is not due to its significant modification by Nedd8 in insect cells, from which baculovirus-expressed Cul-1 was purified, because similar activity is observed with a mutant Cul-1 in which Lys720 at its specific Nedd8-ligation site (Yeh, et al., 2000, *Gene* 248:1) was changed to Arg. Other investigators have also observed that elimination of Nedd8 modification by a similar mutation significantly reduced, but did not abolish the activity of SFC$^{\beta\text{-}TrCP}$ in the ubiqutinylation of IκBα (Furukawa, et al., 2000, *Mol. Cell. Biol.* 20:8185; Read, et al., 2000, *Mol. Cell. Biol.* 20:2326; Wu, et al., 2000, *J. Biol. Chem.* 275:32317). Importantly, the supplementation of Fraction 1 is still required for p27-MeUb ligation even in the presence of Nedd8-modified Cul-1 (FIG. 48, lanes 5 and 6). Similar results are obtained when MeUb is replaced by native ubiquitin, except that in the latter case high molecular weight polyubiquitin derivatives of p27 are formed. Thus, the data does not support the conclusions of Podust et al. (Podust et al., 2000, *Proc. Natl. Acad. Sci. U.S.A.* 97:4579) that the active component in Fraction 1 is Nedd8.

10.2.3 Purification of the Factor and its Identification as Cks1

Figure 49A:
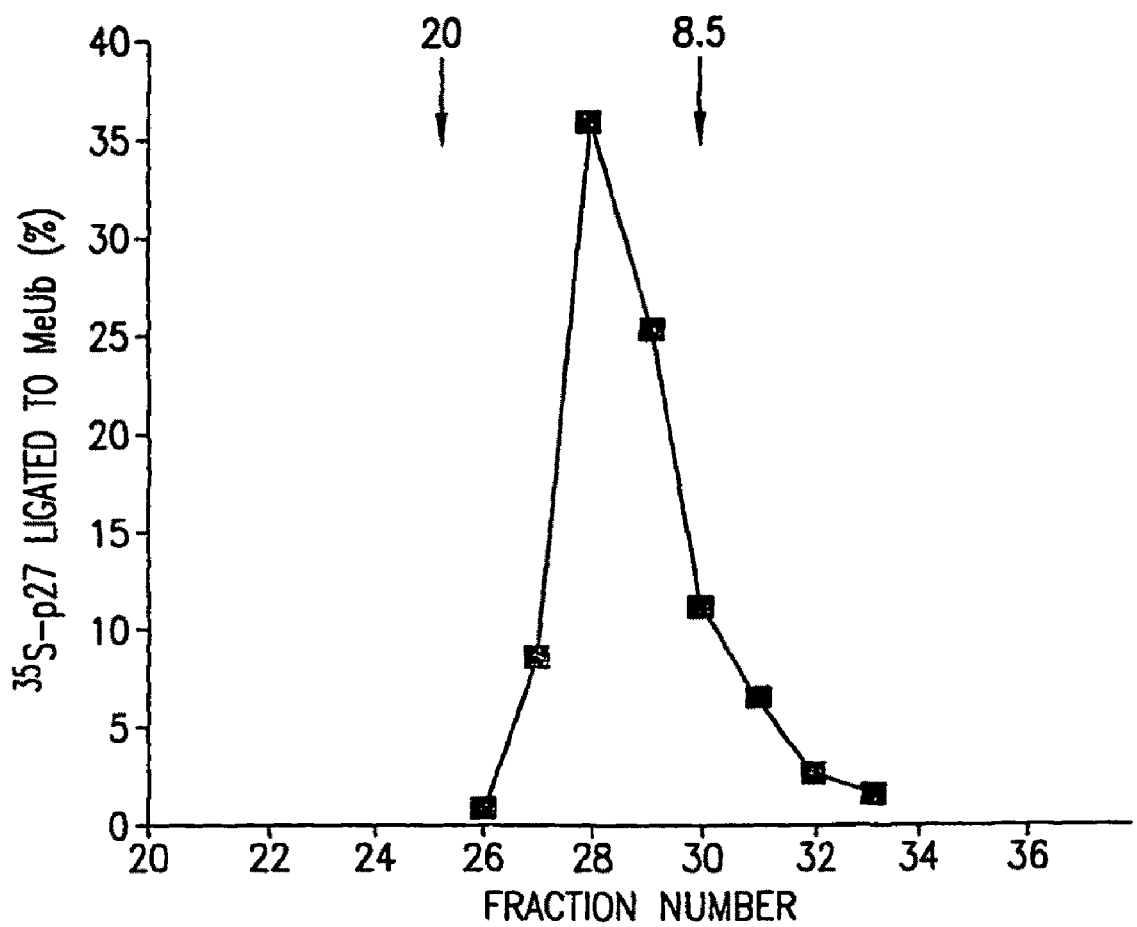
Figure 49B:
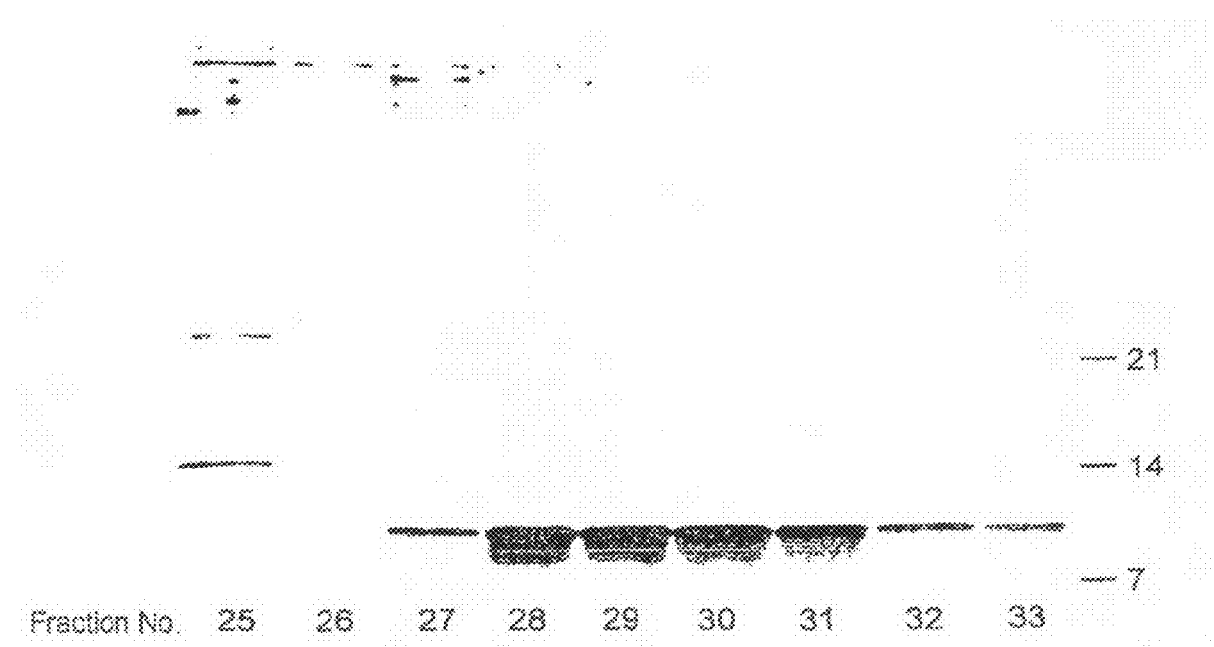

The factor from fraction 1 is purified. FIG. 49A shows the last step of purification on a gel filtration column. The peak of active material from the MonoS step was applied to a Superdex 75 HR 10/30 column (Pharmacia) equilibrated with 20 mM Tris-HCl (pH 7.2), 150 mM NaCl, 1 mM DTT and 01% Brij-35. Samples of 0.5 ml were collected at a flow rate of 0.4 ml/min. Column fractions were concentrated to a volume of 50 µl by centrifuge ultrafiltration (Centricon-10, Amicon). Samples of 0.004 µl of column fractions were assayed for activity to stimulate p27-ubiquitin ligation. Results were quantified by phosphorimager analysis and were expressed as the percentage of $^{35}$S-p27 converted to ubiquitin conjugates. Arrows at top indicate the elution position of molecular mass marker proteins (kDa). Activity eluted as a sharp peak at an apparent molecular mass of approx. 10 kDa. Electrophoresis of samples of 2.5 µl from the indicated fractions of the Superdex 75 column on a 16% polyacrylamide-SDS gel and silver staining of column fractions show a single protein of approx. 10 kDa (FIG. 49B). Numbers on the right indicate the migration position of molecular mass marker proteins (kDa). Elution of the ~10 kDa protein peak coincided with the elution of the peak of activity in fractions 27-28. However, a similar-sized protein continues to be eluted in fractions 30-31, where activity declines markedly. To identify the protein(s), samples from fraction 28 (peak of activity) and fraction 31, subsequent to the peak of activity, are subjected to mass spectrometric sequencing of tryptic peptides. A tryptic peptide of the sequence QIYYSDKYDDEEFEYR (SEQ ID NO:99), corresponding to amino acid residues 5-20 of human Cks1, is detected in the ~10 kDa protein of both fractions. The reason for the difference in the activity of the Cks1 protein in these different fractions is not known. Possibly, the Cks1 protein in fraction 31 is a denatured comformer that may have altered exclusion properties in the gel filtration column.

10.2.4 Activity of Cks1/Suc Proteins

To address whether all Cks/Suc1 proteins used in this study were functional, the action of these proteins in promoting multi-phosphorylation of cyclosome/APC by protein kinase Cdk1/cyclinB was examined (Patra and Dunphy, 1998, *Genes Dev.* 12:2549; Shteinberg and Hershko, 1999, *Biochem. Biophys. Res. Commun.* 257:12). Cyclosomes from S-phase HeLa cells were partially purified (Yudkovsky, et al., 2000, *Biochem. Biophys. Res. Commun.* 271:299) and incubated with 500 units of Suc1-free Cdk1/cyclin B (Shteinberg and Hershko, 1999, supra), as described (Yudkovsky, et al., 2000, supra). Where indicated, 10 ng/µl of the corresponding Cks/Suc1 protein was supplemented. The samples were subjected to immunoblotting with a monoclonal antibody directed against human Cdc27 (Transduction Laboratories). As shown in FIG. 50 the Cdk1-catalyzed hyperphosphorylation of Cdc27, a subunit of the cyclosome/APC, is markedly stimulated by all three recombinant Cks/Suc 1 proteins. This is indicated by the decrease in the unphosphorylated form of Cdc27 and its conversion to several hyperphosphorylated forms that migrate slower in SDS-polyacrylamide gel electrophoresis (FIG. 47, lanes 3-5) This large electrophoretic shift, promoted by all recombinant Cks/Suc1 proteins, requires the action of protein kinase Cdk1/cyclin B (FIG. 50, lane 6). All three bacterially expressed Cks/Suc1 proteins used are at least 95% homogeneous, as indicated by SDS-polyacrylamide gel electrophoresis and Coomassie staining.

10.2.5 Confirmation that the Factor Required for P27-Ubiquitin Ligation is Cks1

Figure 51B:
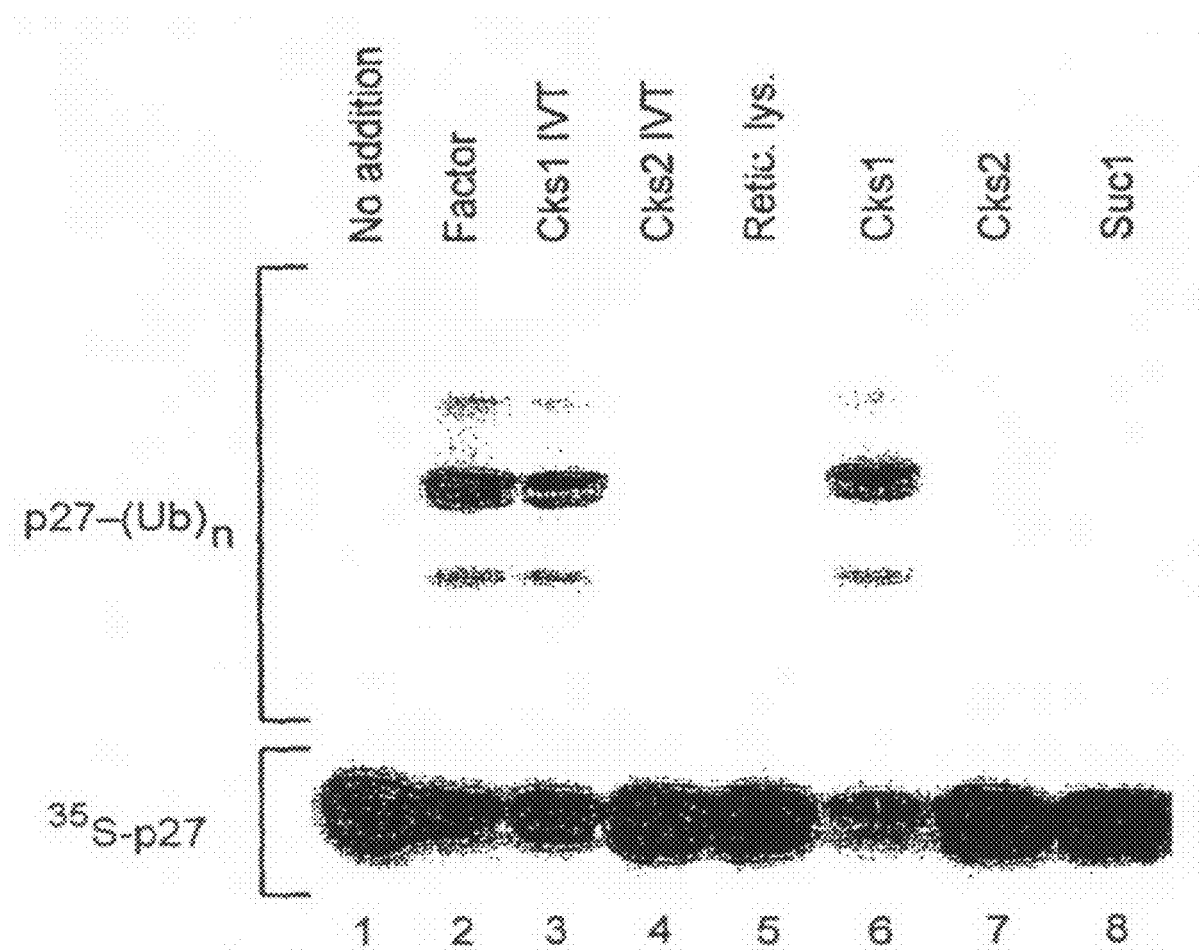

Cks1 produced by in vitro translation (FIG. 51B, lane 3) or bacterially expressed, purified Cks1 (FIG. 51B, lane 6) effectively replaced the factor in this reaction. This action is found to be specific for Cks1 and is not shared by other members of the Cks/Suc1 family of proteins. Human Cks2, which is 81% identical and 90% similar to Cks1, as well as the fission yeast homologue, Suc1, are completely inactive in this reaction, either when produced by in vitro translation (FIG. 51B, lane 4) or as bacterially expressed purified proteins (FIG. 51B, lanes 7 and 8) Purified recombinant Cks2 and Suc1 do not stimulate p27-ubiquitin ligation even when added at up to 50-fold higher concentrations despite their being functional, as demonstrated by their ability to promote the multi-phosphorylation of Cdc27 by Cdk1. The combined evidence thus strongly indicates that the action of Cks1 in p27-ubiquitin ligation is specific and is not shared by other members of this protein family.

10.2.6 Cks1 Promotes the Ligation of Ubiquitin to P27

Cks1 does not seem to be required for the action of all mammalian SCF complexes. In the well-characterized case of SCF$^{\beta\text{-}TrCP}$ the purified complex carries out robust ubiquitinylation of IκB in vitro (Tan, et al., 1999, *Mol. Cell.* 3:527). Furthermore, the addition of Cks1 had no observable influence on the rate of the ligation of ubiquitin to phosphorylated IκBα by purified SCF$^{\beta\text{-}TrCP}$. It seemed more likely that Cks1 is specifically involved either in the action of the SCF$^{Skp2}$ complex or in some other process necessary for p27-ubiquitin ligation. Since p27 has to be phosphorylated on Thr-187 by Cdk2 for recognition by the SCF$^{Skp2}$ complex (Carrano, et al., 1999, *Nat. Cell Biol.* 1:193; Tsvetkov, et al., 1999, *Current Biology* 661) and since Cks proteins may stimulate the protein kinase activity of some, but not all, Cdk/cyclin complexes (Reynard, et al., 2000, *Mol. Cell. Biol.* 20:5858), it seems possible that Cks1 stimulates the phosphorylation of p27 by Cdk2. However, as shown in (FIG. 52A) p27 is rapidly phosphorylated by Cdk2/cyclin E in the absence of Cks1, and the addition of Cks1 has no significant influence on this process. The conclusion that Cks1 acts at a step subsequent to the phosphorylation of p27 is corroborated by the finding that when purified p27 is first phosphorylated by incubation with Cdk2/cyclin E and $^{32}$[P-γ]_ATP, its subsequent ligation to MeUb still requires Cks1 (FIG. 52B) Therefore, Cks1 greatly stimulates the binding of phosphorylated p27 to Skp2.

10.2.7 Cks1 Affects the Binding of Phosphorylated P27 to Skp2

Figure 52A:
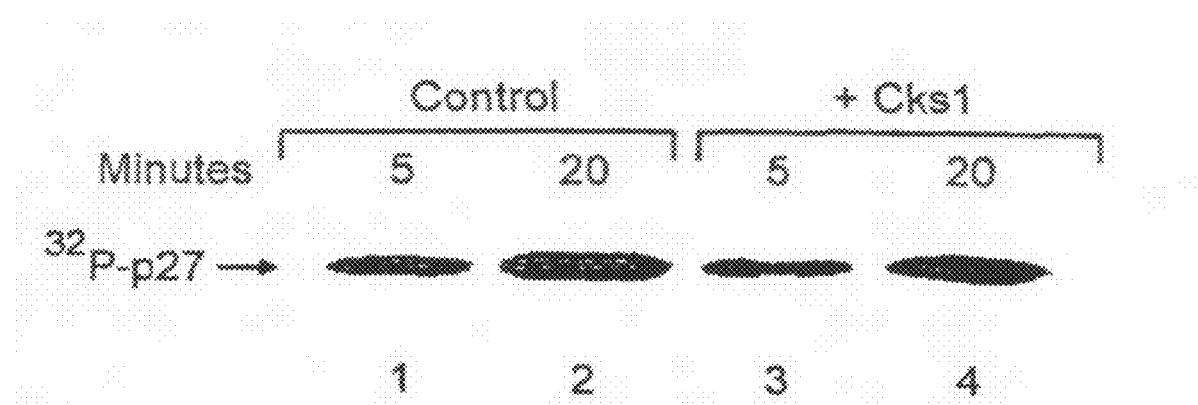
Figure 52B:
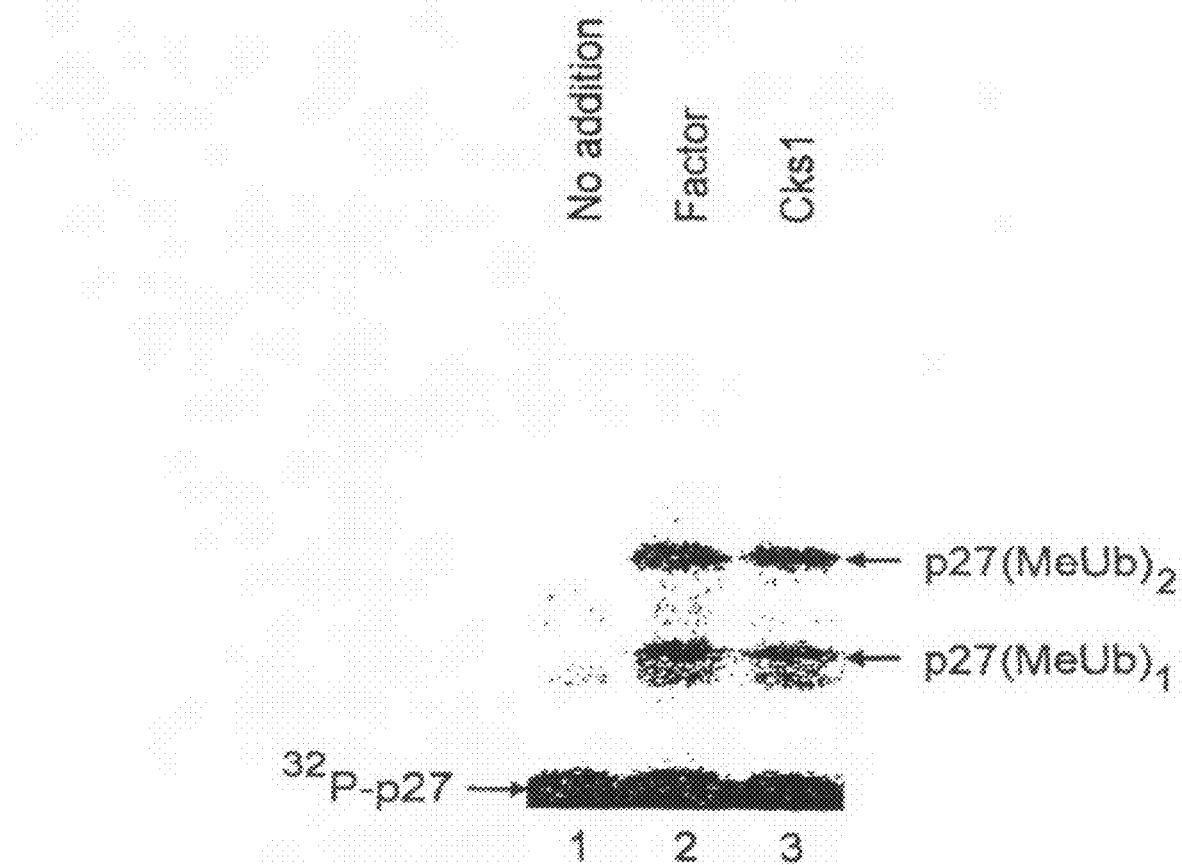
Figure 52C:
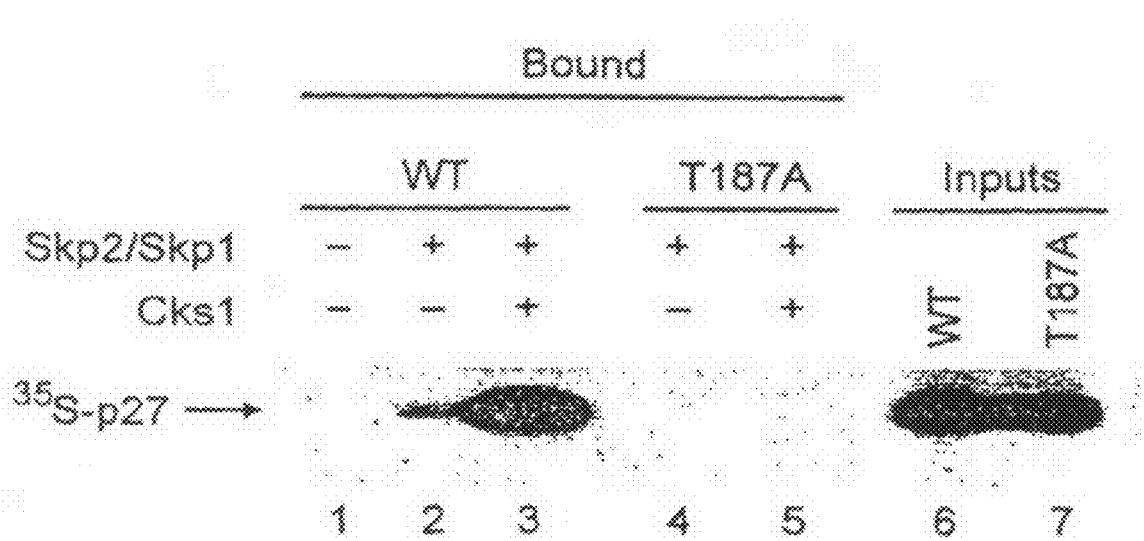
Figure 52D:
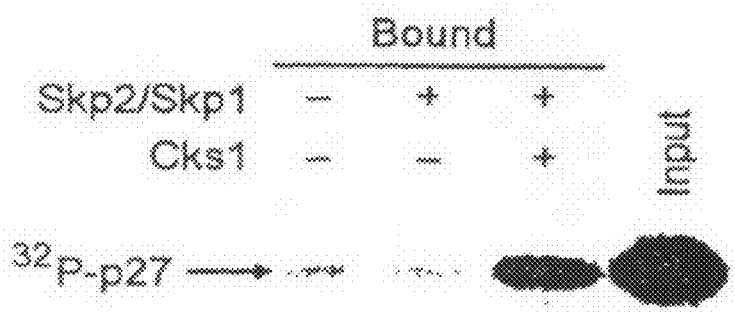

Whether the step affected by Cks1 is the binding of phosphorylated p27 to Skp2 was assessed. Skp2/Skp1 complex was used instead of Skp2, because in the absence of Skp1, recombinant Skp2 is not expressed abundantly in insect cells in a soluble form. Previously small, but significant binding of $^{35}$S-labeled, in vitro-translated p27 to Skp2/Skp1 was detected (by immunoprecipitation with an antibody directed against Skp2), which is dependent upon its phosphorylation on Thr-187 by Cdk2/cyclin E (Carrano, et al., 1999, supra). Using a similar procedure, the binding of p27 to Skp2/Skp1 is greatly stimulated by Cks1 (FIG. 52C, lanes 2 and 3). This action requires the phosphorylation of p27 on Thr-187, since binding of the non-phosphorylatable mutant Thr-187-Ala did not occur even in the presence of Cks1 (FIG. 52C, lanes 4 and 5). To examine whether this action of Cks1 also occurs in a completely purified system devoid of reticulocyte lysate present in preparations of in vitro-translated p27, a similar experiment is performed with bacterially expressed, purified p27 that is phosphorylated by $^{32}$[P-γ] ATP. In this case there is some non-specific binding of phosphorylated p27 to anti-Skp2-Protein A beads in the absence of Skp2. Still, a marked stimulation of the specific binding of $^{32}$P-p27 to Skp2/Skp1 by Cks1 is observed (FIG. 52D) Therefore, Cks1 greatly stimulates the binding of phosphorylated p27 to Skp2.

Figure 53A:
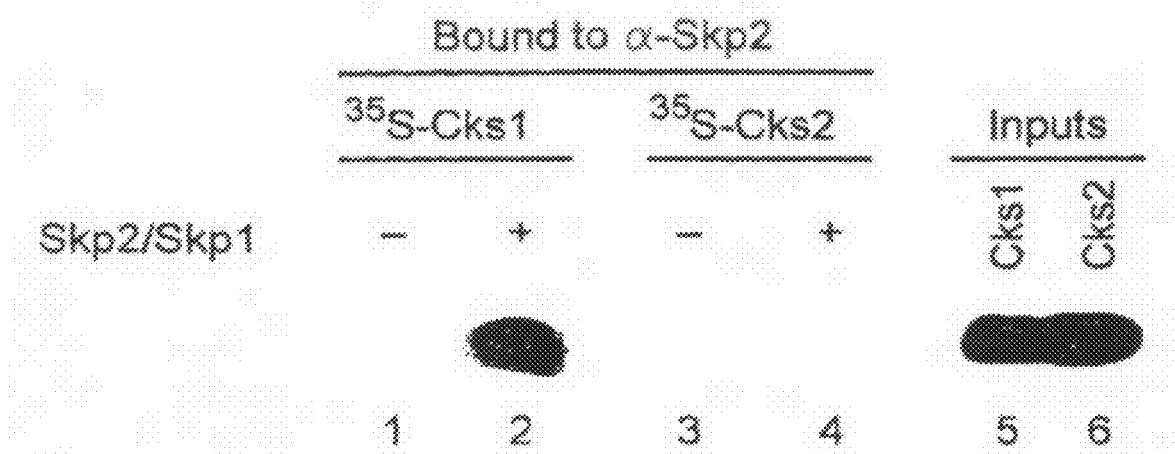
Figure 53B:
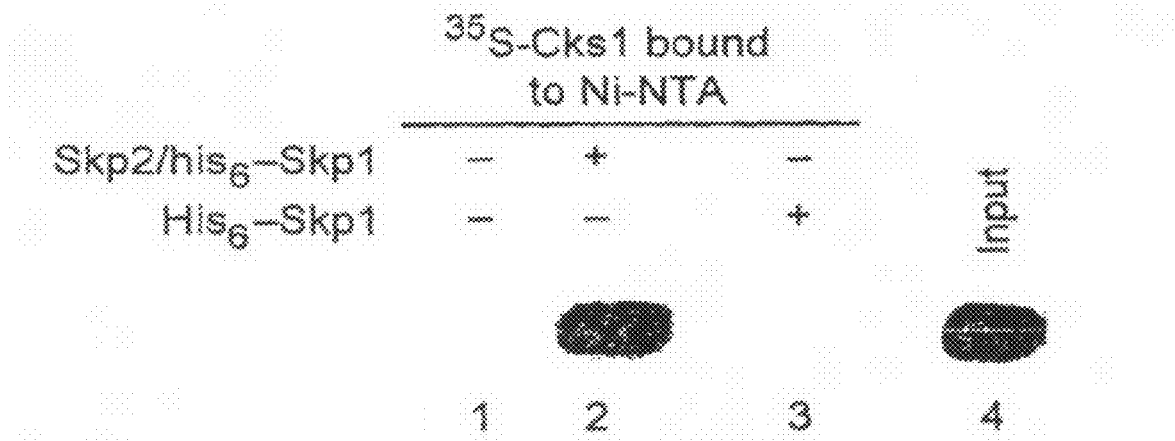

As shown in FIG. 53A, a strong binding of $^{35}$S-Cks1 to the Skp2/Skp1 complex was observed. Under similar conditions, no binding of $^{35}$S-Cks2 to Skp2/Skp1 was seen. Since in these experiments Skp2/Skp1 complex is used (because of the lack of recombinant native Skp2), it is examined whether Cks1 may bind to Skp1 in the absence of Skp2. In the experiment shown in FIG. 53B, $^{35}$S-Cks1 is incubated with either His$_6$-Skp1 or with Skp2/His$_6$-Skp1 complex, and then binding to Ni-NTA-agarose beads is estimated. A strong binding of Cks1 to Skp2/His$_6$-Skp1 but not to His$_6$-Skp1 was observed. Thus, human Cks1 specifically binds to the Skp2/Skp1 complex, likely through the Skp2 protein.

Figure 53C:
Figure 53D:
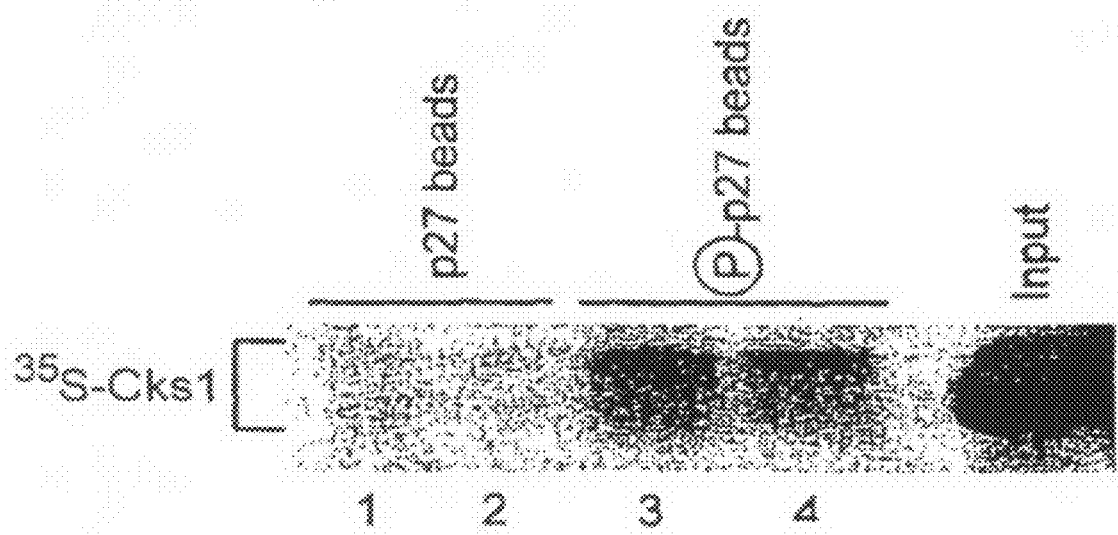

The results presented herein demonstrate that the binding of Skp2 to phosphopeptide-Sepharose beads (but not to control beads that contained an identical but unphosphorylated p27-derived peptide) is greatly increased by Cks1 (FIG. 53C). These findings indicate that binding to this phosphopetide can serve as a valid tool to study Cks1-assisted Skp2-p27 interaction. Using the same p27-derived peptide beads, significant binding of $^{35}$S-Cks1 to phosphorylated p27 peptide, but not to unphosphorylated p27 peptide is observed FIG. 53D. These findings indicate that Cks1 binds directly to phospho-Thr187 of p27 and demonstrate that the presence of Cdk2/cyclin E is not obligatory for the binding of Skp2 to phosphorylated p27.

11. EXAMPLE

Assay to Identify an FBP Interaction with a Cell Cycle Regulatory Protein (e.g., Skp2 with E2F)

The following study was conducted to identify novel substrates of the known FBP, Skp2.

As shown in FIG. 57, E2F-1, but not other substrates of the ubiquitin pathway assayed, including p53 and Cyclin B, physically associates with Skp2. Extracts of insect cells infected with baculoviruses co-expressing Skp2 and E2F-1, (lanes 1, 4 and 5), or Skp2 and hexa-histidine p53 (His-p53) (lanes 2, 6, 7, 10 and 11), or Skp2 and His-Cyclin B (lanes 3, 8, 9, 12, and 13) were either directly immunoblotted with an anti-serum to Skp2 (lanes 1-3) or first subjected to immunoprecipitation with the indicated antibodies and then immunoblotted with an anti-serum to Skp2 (lanes 4-13). Antibodies used in the immunoprecipitations are: normal purified mouse immunoglobulins (IgG) (lane 4, 6, 10 and 12), purified mouse monoclonal anti-E2F-1 antibody (KH-95, from Santa Cruz) (lane 5), purified mouse monoclonal anti-p53 antibody (DO-1, from Oncogene Science) (lane 7), purified rabbit IgG (lane 8), purified rabbit polyclonal anti-Cyclin B antibody (lane 9), purified mouse monoclonal anti-His antibody (clone 34660, from Qiagen) (lanes 11 and 13).

Figure 54B:
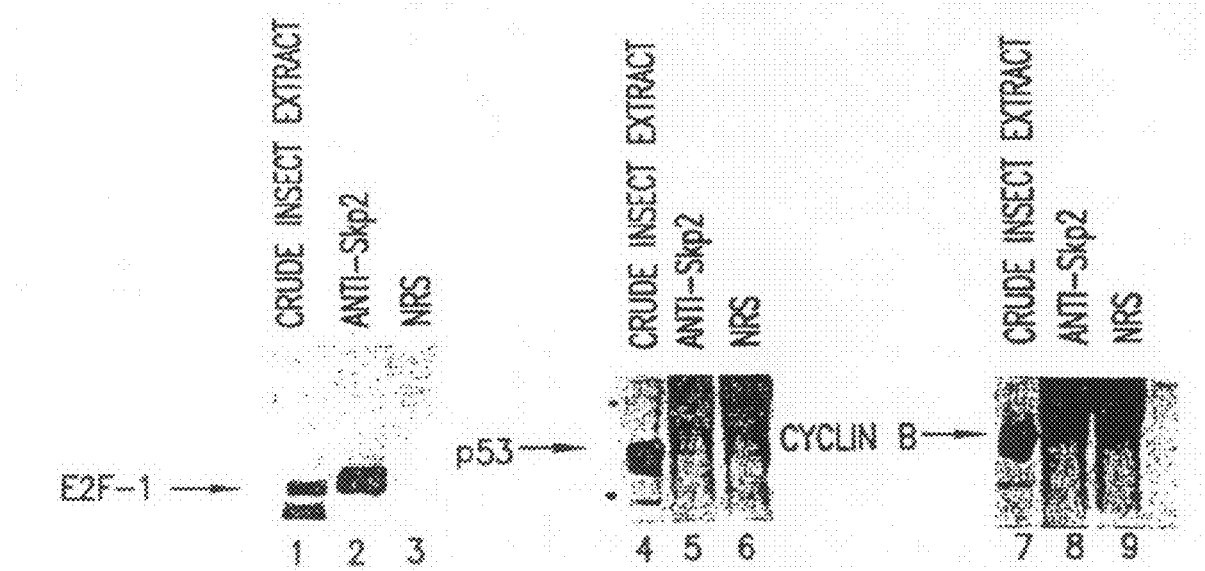

As shown in FIG. 54B, Skp2 physically associates with E2F-1 but not with other substrates of the ubiquitin pathway (p53 and Cyclin B). Extracts of insect cells infected with baculoviruses co-expressing Skp2 and E2F-1 (lanes 1-3), or Skp2 and His-p53 (lanes 4-6), or Skp2 and His-Cyclin B (lanes 7-9) were either directly immunoblotted with antibodies to the indicated proteins (lanes 1, 4 and 7) or first subjected to immunoprecipitation with the indicated anti-sera and then immunoblotted with antibodies to the indicated proteins (lanes 2, 3, 5, 6, 8 and 9). Anti-sera used in the immunoprecipitations are: anti-Skp2 serum (lanes 2, 5 and 8), and normal rabbit serum (NRS) (lane 3, 6 and 9).

Figure 54C:
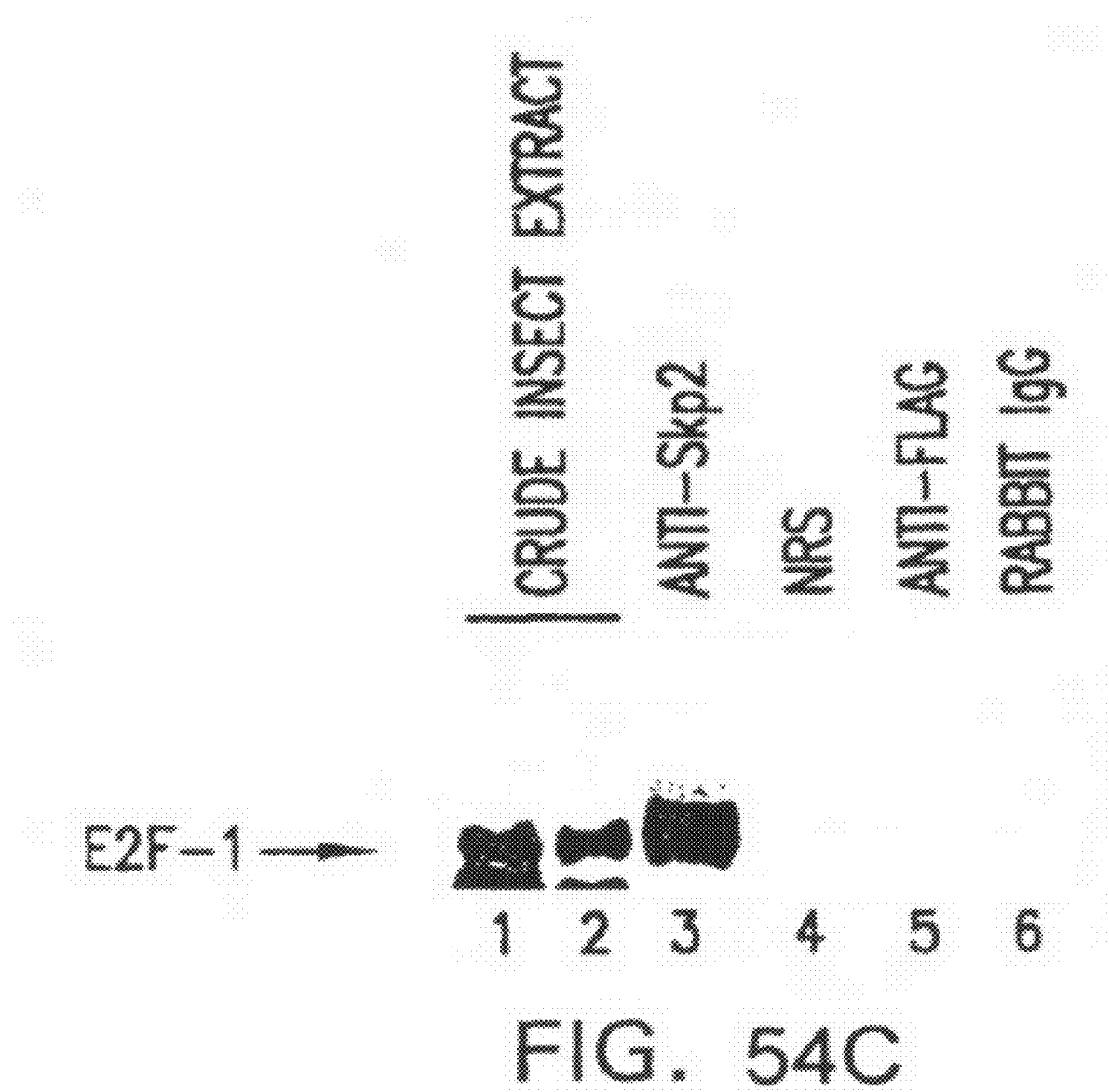

As shown in FIG. 54C, E2F-1 physically associates with Skp2 but not with another F-box protein (FBP1). Extracts of insect cells infected with baculoviruses co-expressing Skp2 and E2F-1 (lanes 1, 3 and 4), or Flag-tagged-FBP1 and E2F-1 (lanes 2, 5 and 6) were either directly immunoblotted with a mouse monoclonal anti-E2F-1 antibody (lanes 1 and 2) or first subjected to immunoprecipitation with the indicated antibodies and then immunoblotted with a mouse monoclonal anti-E2F-1 antibody (lanes 3-6). Antibodies used in the immunoprecipitations are: anti-Skp2 serum (lanes 3), NRS (lane 4), purified rabbit polyclonal anti-Flag (lane 5), purified rabbit IgG (lane 6).

The methodology used in this example can also be applied to identify novel substrates of any FBP, including, but not limited to, the FBPs of the invention, such as FBP1, FBP2, FBP3a, FBP3b, FBP4, FBP5, FBP6, FBP7, FBP8, FBP9, FBP10, FBP11, FBP12, FBP13, FBP14, FBP15, FBP16, FBP17, FBP18, FBP19, FBP20, FBP21, FBP22, FBP23, FBP24, FBP25, FPL10, FBL11, and FBL12.

12. EXAMPLE

Characterization of F-Box Protein Fbp24 and its Activity In Vivo

Fbp24, also known as Fbx9, has been indicated in the regulation of cell growth and proliferation, specifically replicative senescence, and maintenance of chromatin structure. (Zhang, et al., 2003, *Proc. Natl. Acad. Sci.,* 100:3251-3256). Although the exact mechanism is not known, an analysis of the amino acid sequence of the three isoforms of Fbx9 revealed that each contains the characteristic F-box domain as well as several regions indicative of DNA interaction, including tankyrase-binding domains, tetratricopeptide repeat domains ("TPR"), HNH domains, and leucine zipper motifs (schematically represented in FIG. 55; nomenclature reviewed in Jin, et al., 2004, *Genes & Dev.,* 18:2573-2580).

HNH domains and leucine zipper motifs indicate the potential for direct Fbx9:DNA interaction, while the tankyrase-binding and TPR domains suggest that Fbx9 participates in the cellular signalling pathways regulating genomic stability. TPR domains are characteristic of DNA regulatory proteins, with many TPR containing proteins involved the maintenance of telomeres. The only fission yeast F-box protein containing a TPR, Pof3, is involved in chromatin maintenance, with strains lacking Pof3 displaying shortened telomeres. The only F-box protein in budding yeast containing a TPR, Fcl1, is similarly required for genomic stability. The putative role of Fbx9 in both the ubiquitination and genomic maintenance pathways make the protein an attractive therapeutic target for treatment of proliferative or differentiative disorders.

The studies in this example were designed to investigate the role of Fbx9 in the regulation of cellular proliferation. The results indicate that several Fbx9-binding proteins are critically involved with transcriptional regulation, chromatin remodeling, viral replication, and apoptosis/senesence. Fbx9 inhibition induced increased sensitivity to UV irradiation and cell cycle arrest/apoptosis in HeLa cells. These results suggest that modulation of Fbx9 activity is a viable strategy in the therapy of cancer or proliferative disorders.

12.1 Materials and Methods for the Characterization Of Fbp24 Activity

Methods for Mass Spectrometric Sequencing and Immunofluorescence are described in Section 10.1; Recombinant Protein, Construction of F-box Mutant, Antibodies, Transient Transfection, Immunoprecipitation and Immunoblotting Methods are described in Section 7.1.

Cells, Cell Synchronization, and Cell Cycle Analysis

T-cells (Latres, et al., 2001, *Proc. Natl. Acad. Sci. USA* 98:2515) were isolated according to published protocols. HeLa cells were obtained from ATCC. Hela cells were synchronized in prometaphase with 6-12 hour nocodazole treatment (40 ng/ml) followed by mitotic shake-off as described (Carrano, et al., 1999, *Nat. Cell Biol.* 1:193). Cell cycle synchrony was monitored by flow cytometry and BrdU incorporation as described (Pagano, et al., 1992, *Science* 255:1144).

Immunofluorescence

Cells were plated on glass coverslips that had been coated (O/N at 4° C.) with poly-L-lysine (100 µg/ml in PBS; Sigma), rinsed in PBS and fixed for 10 minutes in 4% paraformaldehyde/PBS at room temperature. For centrosomal staining only, cells were fixed for 10 minutes in −20° C. cold methanol. Fixed cells were permeabilized with PBS/0.1% Triton X-100 for 3 minutes, washed in PBS and blocked with PTB buffer (PBS/0.1% Triton X-100/0.3% BSA) for 30 minutes at room temperature. Incubation with primary antibodies was then carried out for one-three hours in a humidified chamber. After three washes in PBS the coverslips were incubated for 30 minutes with Texas red-conjugated or FITC-conjugated secondary antibody (Vector Laboratories, dilution 1:50). All antibody reactions were carried out at room temperature and dilutions were made in PTB buffer. Samples were mounted in Crystal/mount medium containing DAPI (Vysis Inc. cat #32-804831) to identify all nuclei. The number of centrosomes/cell and the number of mitotic figures were quantified using a fluorescence microscope. At least 300 cells were counted for each sample and each experiment was performed at least 4 times.

Silencing by Small Interfering RNA

Logarithmically growing HeLa cells were seeded at a density of $10^5$ cells/6 cm dish and transfected with oligos twice (at 24 and 48 hr after replating) using Oligofectamine (Invitrogen) as described (Elbashir, et al., 2001, *Nature* 411:494). Forty-eight hours after the last transfection, lysates were prepared and analyzed by SDS-PAGE and immunoblotting.

Cell Cycle Analysis

Cell cycle phases were monitored by flow cytometry (FAC-SCAN, Becton Dickinson) after staining cellular DNA with 50 µg/ml propidium iodide (Sigma) in the presence of 10 µg/ml DNase-free RNase (Boehringer Mannheim) and by BrdU incorporation.

UV Light Irradiation

UV irradiation was performed as described in Toschi and Bravo, 1988, *J. Cell Biol.*, 107:1623. Cells to be exposed to UV irradiation were grown as monolayers on glass coverslips. The monolayers were removed from the growth medium and rinsed in PBS. The cultures were then exposed to UV light in a UVC 515 Ultraviolet Multilinker (245 nm, Ultra Lum). The UV doses were monitored with a UV intensity meter.

Purification of Flag-Tagged Protein

Cells containing expression vectors encoding Flag-tagged proteins were grown as monolayers in 150 mm petri dishes. Individual dishes were rinsed in PBS and the cultures lysed with 10 ml whole cell lyses buffer with additional protease inhibitor. Cell lysis and extract preparation were according to manufacturer's instructions. 20 µg anti-FLAG M2 monoclonal antibody (Sigma) was added per ml of cell extract and incubated for 2 h at 4° C. ProteinG plus-Agarose beads (Oncogene) were prepared according to manufacturer's instructions at added to the anti-FLAG antibody/cell extract mixture at a concentration of 20 beads/ml extract. The beads were processed according to manufacture's directions. Protein was eluted from the beads by incubation with 2 µg Flag-peptide/20 µl beads at 4° C. overnight. Supernatant form the elution reaction was collected and subjected to gel filtration chromatography.

12.2 Results 12.2.1 Fbp24/Fbx9 Inhibition Induces Apoptosis in Hela Cells

Figure 57A:
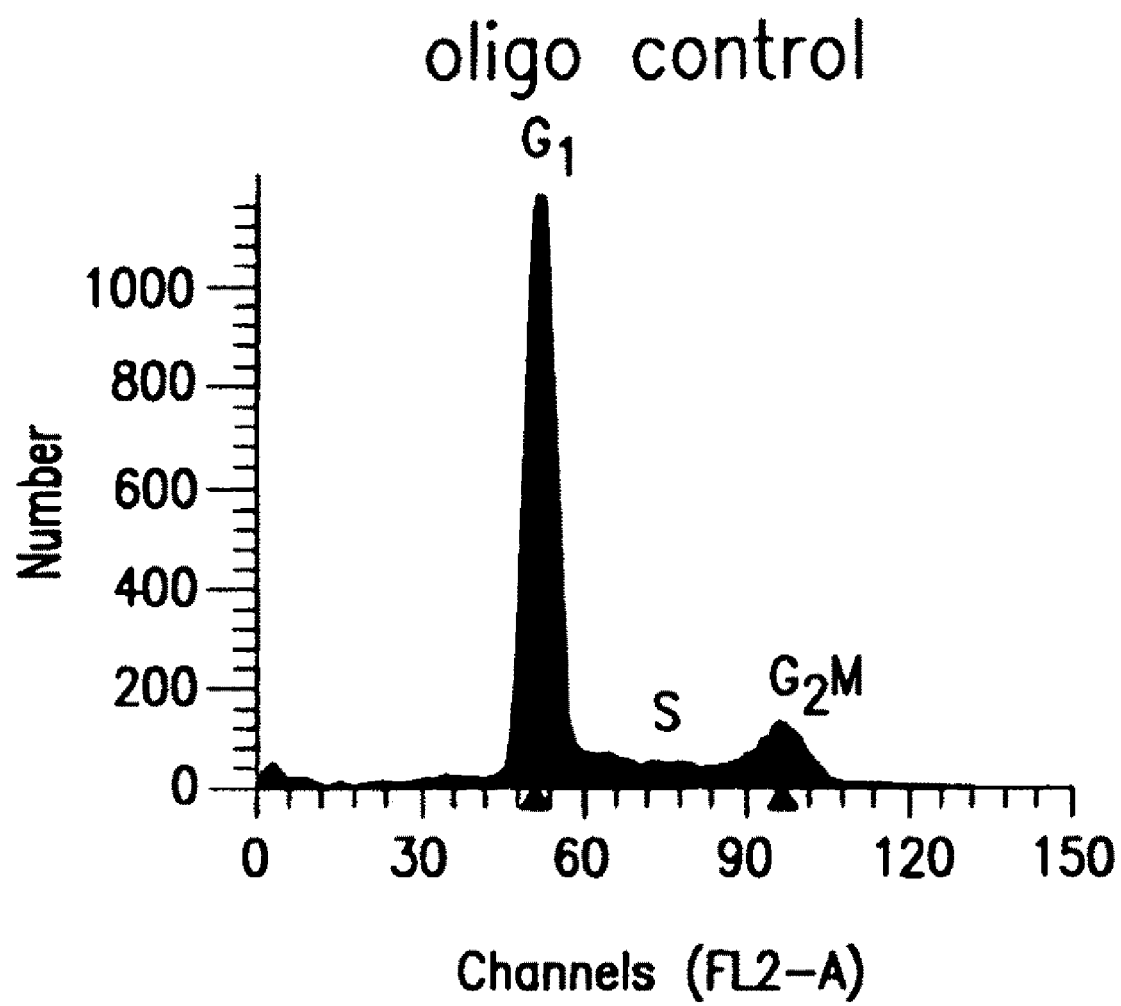
Figure 57B:
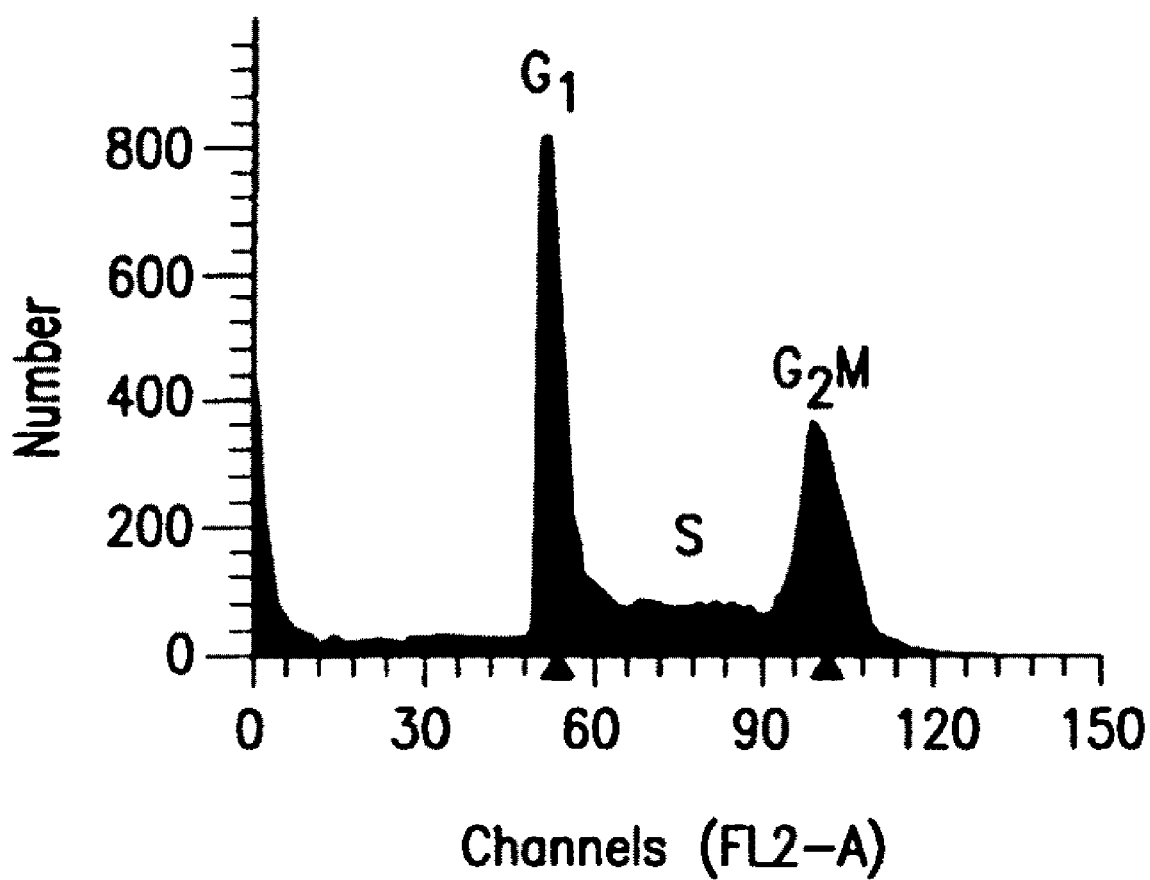
Figure 57C:
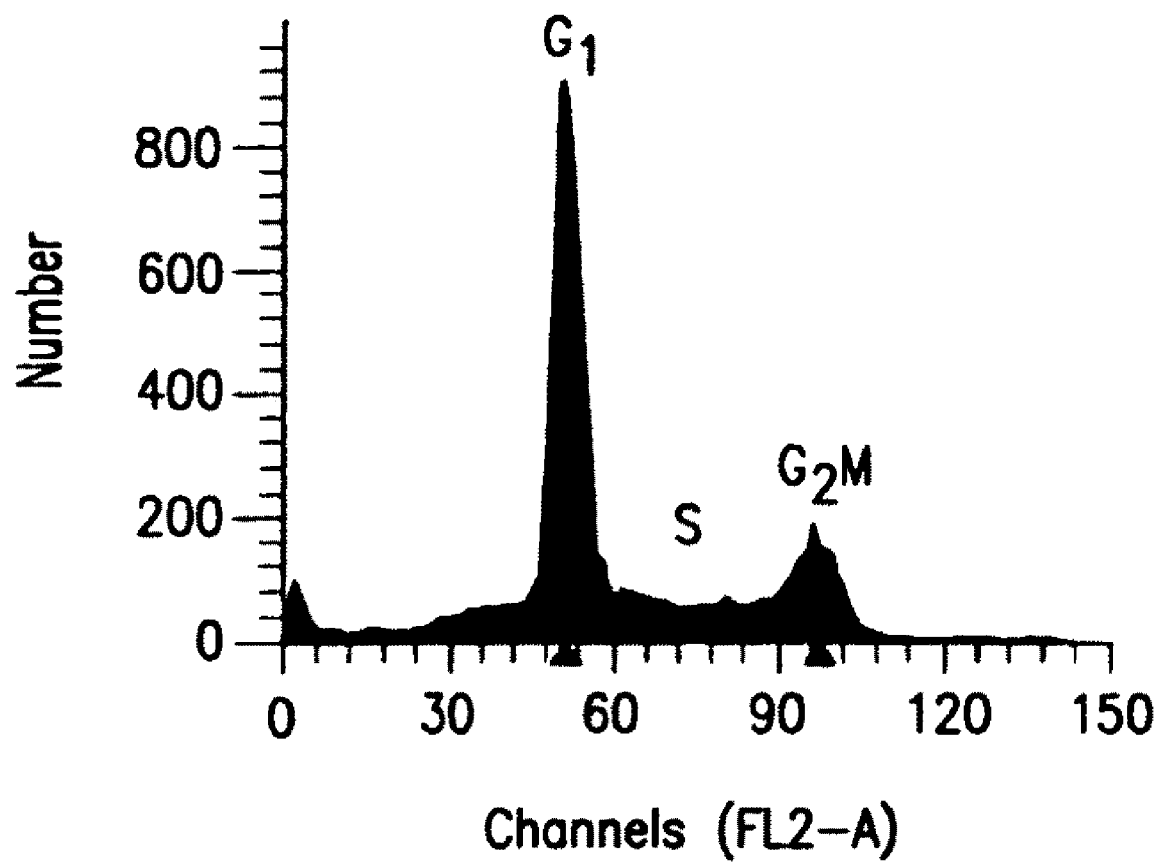
Figure 57D:
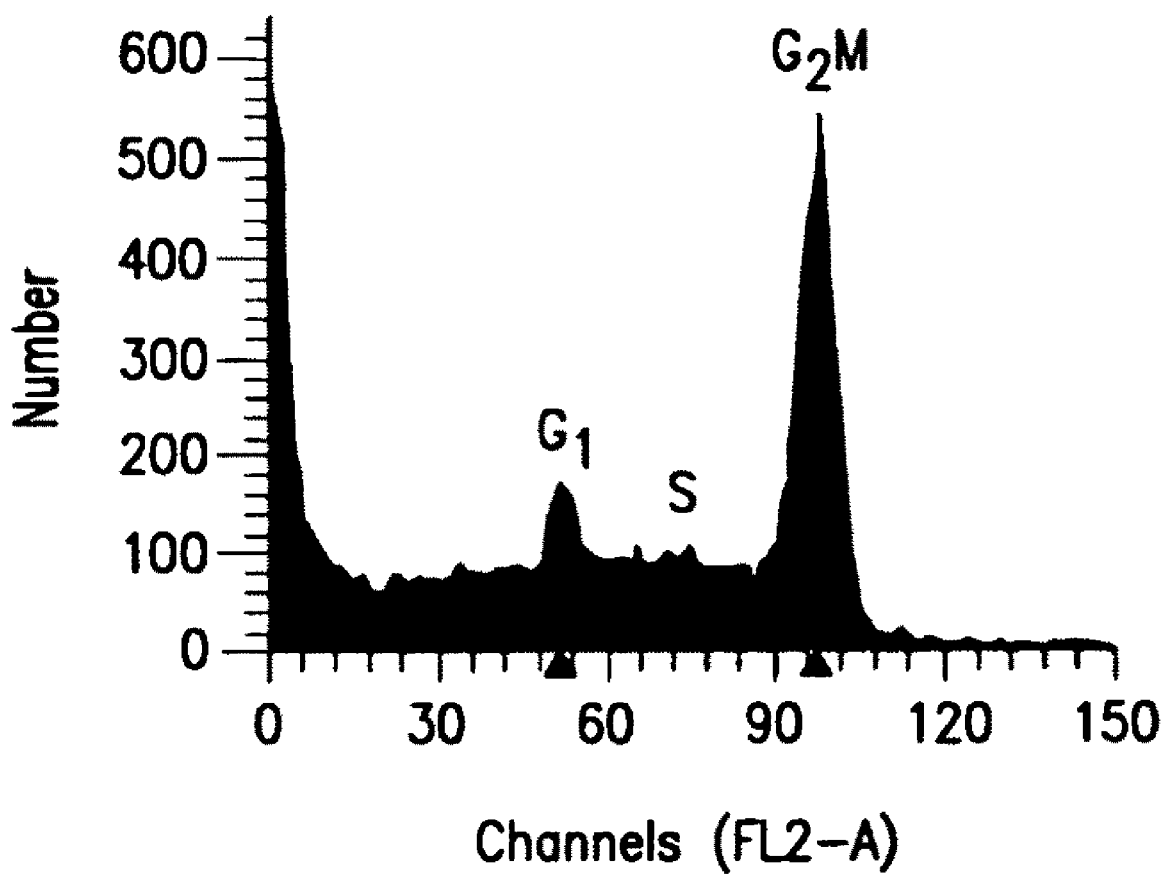

Depletion of Fbx9 in T98G or HeLa cells was effected via siRNA silencing (FIG. 56). In either cell line oligos 1, 2, or 3 (lanes 4, 5, 6, 8 or lanes 12, 13, 14, 15) resulted in decreased expression of Flag-Fbx9 as detected by Western blot. Oligo 2 appeared to produce the greatest suppression of Flag-Fbx9 translation (lanes 5 and 13), a suppression which was not improved when oligos 2 and 3 were combined (lanes 8 and 15). The use of these silencing oligos had no effect on the expression of Skp1. Cells with decreased concentrations of Fbx9 exhibited cell cycle arrest in G2/M and subsequent apoptosis (FIGS. 57A & 57B), as well as hypersensitivity to UV irradiation (FIGS. 57C & 57D). One explanation of the results is that the inhibition of Fbx9 activity critically altered the signaling cascade of a DNA damage checkpoint.

In non-transformed cells, such checkpoints serve as controls to ensure coordinated progression through the cell cycle. Disruption of the control signals can result in uncoordinated cellular events, such as DNA synthesis and mitosis, resulting in the improper expression of regulated genes, the generation of anueploid daughter cells, or malignant transformation. While many anti-cancer efforts have been directed to restoring those checkpoints known to be defective in transformed cells, the results of Fbx9 inhibition on the highly transformed HeLa line suggest that a valid toxic strategy may be to instead disrupt the remaining control pathways. Alternately, the modification of Fbx9 activity may be of benefit in combinatorial therapies. The disruption of a DNA checkpoint could sensitize cells to standard anti-proliferative therapeutics, increasing therapeutic effect and allowing the reduction of the therapeutic dose to better tolerated levels.

12.2.2 Fbx9 Forms a Functional E3 Ubiquitin Ligase with Skp1 and Cul1

In an effort to gain insight into the cellular function of Fbx9, a focused proteomic strategy was used to identify Fbx9 binding or Fbx9 associated proteins. This approach may identify both direct target substrates and regulatory proteins of Fbx9. To this end, 293T cells were transiently transfected with an expression vector encoding flag-tagged Fbx9. To verify Fbx9 activity, transfected cells were treated with an inhibitor of the proteasome, PS341, for 6 h prior to protein harvest. Whole cell extracts (WCEs) were prepared and subjected to western blot analysis; treatment of the cells with the proteasome inhibitor did not affect the level of Fbx9 expression (FIG. 58). Fbx9 complexes were then immunoprecipitated from the WCEs using anti-Flag antibody (Sigma). Precipitates were washed with buffer containing 0.5 M urea to remove non-specific binding proteins. The Fbx-9 containing complex was removed from the immunoprecipitate with excess Flag-peptide and fractionated by gel-filtration chromatography (FIG. 59). Fractions corresponding to the ~40010 MW were concentrated for mass spectrometric sequencing analysis. Several putative Fbx9 binding or Fbx9 associated proteins were identified including Cul1 and Elongation Factor 2 ("cEF2"). Other possible partners included SWI/SNF related, matrix associated, actin dependent regulator of chromatin, subfamily e, member-1 (BAF57); endostatin-like protein; splice isoform SP100-HMG of P23497 nuclear autoantigen SP100; and H326 protein. Interaction with Skp1 was further confirmed by Western blot using anti Skp1 antibody (Santa Cruz) (FIG. 60, lane 4). Identification of both Cul1 and Skp1 as Fbx9 binding/associated proteins implies that Fbx9 is a functional E3 ubiquitin ligase. This is further suggested in that the Flag-purified Fbx9 complex contains significant levels of polyubiquitinated proteins (identified using anti-Ubiquitin antibody (Covance)) (FIG. 60, lane 6). Further examination of the other Fbx9 binding/associated proteins, such as eEF2, endostatin-like protein, BAF57, splice isoform SP100-HMG of P23497 nuclear autoantigen SP100 and H326 protein may provide further insight into Fbx9 function.

12.2.3 Fbx9 Associates with eEF2

The putative association between Fbx9 and eEF2 originally identified by mass spectrometric sequencing was further confirmed with a Western blot. Flag-purified whole cell extracts were tested against an anti-eEF2 antibody (Zymed) (FIG. 61). All three isoforms of Fbx9 were found to associate with eEF2 (FIG. 62, lanes 3-5). The presence or absence of proteosome inhibitors did not affect binding of Fbx9 to eEF2 (FIG. 63, lanes 5 and 6). The apparent constant level of eEF2 expression (FIG. 63, row 1) in these experiments also suggests that eEF2 is not a substrate for Fbx9 mediated ubiquitination.

Elongation factor 2 is a non-ribosomal protein kinase that plays an important role in translational elongation, a process that consumes a high-proportion of metabolic energy in mammalian cells. eEF2 kinase activity is inhibited by phosphorylation an regulated, in part, by the MAP kinase mTOR signaling pathways. The association of Fbx9 with eEF2 suggests a link between the protein synthesis/cellular energy and ubiquitin/proteasome systems and may therefore provide a unique therapeutic target for the control of proliferative disorders.

13. EXAMPLE

Characterization of F-Box Protein Fbl12 and its Activity In-Vivo

The studies in this section were designed to investigate the cellular activity of Fbl12 and its possible role in the regulation of proliferation and/or differentiation. The results reported herein demonstrate that inhibition of Fbl12 activity is associated with slower cellular growth and increased sensitivity to drug-induced apoptosis. Although the total numbers of genes affected by modulation of Fbl12 activity was relatively low, the majority of genes affected are those classically believed to play a role in malignant transformation, for example, those regulating cell migration, angiogenesis, metastasis, hypoxic reaction and apoptosis. The possibility that Fbl12 serves such a relatively specific role suggests that Fbl12 is an attractive candidate as therapeutic target in oncology.

13.1 Materials and Methods for the Characterization of Fbl12 Activity

Recombinant Protein, Construction of F-box Mutant, Antibodies, Transient Transfection, Immunoprecipitation and Immunoblotting Methods are described in Section 7.1.

13.2 Results 13.2.1 Inhibition of Fbl12 Activity is Associated with Slower Cell Growth and Sensitivity to Drug-Induced Apoptosis Analysis of the coding sequence of FBL12 revealed a Leucine Rich Repeat ("LRR") domain in the C-terminal half of the protein (schematically represented in FIG. 64). Several human proteins contain a LRR domain, including the p27 E3 ubiquitin ligase, Skp2. LRR domains are 20-29 residue sequence motifs whose primary function appears to provide a versatile structure framework for the formation of protein-protein interactions. For example, the LRR domain of Skp2 mediates phosphorylation-dependent binding to p27. In an effort to investigate the cellular function of Fbl112, a stable HEK293 cell line was generated that expresses a dominant-negative version of Fbl12, Fbl12-ΔFB, in a tetracycline-inducible manner (FIG. 65). Fbl12-ΔFB retains the putative substrate binding domain, the LRR domain, but lacks the N-terminal F-box domain that is required to recruit the cellular machinery necessary for ubiquitination of the target protein. HEK293 cells expressing Fbl12-ΔFB displayed slower growth as compared to the parental control line, HEK293 EcR. With respect to Fbl12 as a potential novel therapeutic target, the expression of Fbl12-ΔFB rendered cells more sensitive to stauosporine ("SSP")-induced apoptosis (FIG. 66).

An affymetrix microarray analysis was used to identify possible mediators of the Fbl12-ΔFB expressing cell phenotype. The analysis identified a number of genes whose expression was increased (Table 1) or decreased (Table 2) as a function of Fbl12-ΔFB expression.

TABLE 1

| Gene Expression Increased in Fbl12-ΔFB HEK 293 Cells | |
| --- | --- |
| GENE | DESCRIPTION |
| GADD45B, Growth arrest and DNA-damage-inducible 45 beta | a transcriptional co-activator, involved in cell growth inhibition and stimulation of apoptosis, plays a role in the cellular response to stress. Ectopic expression of GADD45 has been demonstrated to sensitize cancer cells to apoptosis induced by genotoxic agents. GADD45B is an effector of TGFbeta-induced apoptosis. |

TABLE 1-continued

Gene Expression Increased in Fbl12-ΔFB HEK 293 Cells

| GENE | DESCRIPTION |
|---|---|
| Dolichyl-phosphate mannosyltransferase subunit 3 (prostin 1). | part of a complex that produces mannosyl donors for glycoconjugate biosynthesis, stabilizes DPM1 and is stabilized by DPM2; expression is associated with a lack of invasive potential in tumors |
| Tetraspan NET-6 protein | member of the tetraspan family, putative integral membrane proteins that are subunits of large molecular complexes that include integrins |
| Succinyl CoA:3-oxoacid CoA transferase | catalyzes the conversion of acetoacetate to CoA in metabolic energy pathways, plays a role in ketone body metabolism in extrahepatic tissues; deficiency is associated with ketoacidosis. May play a role in the motility of sperm |
| Homeo box A9 | a member of the homeodomain-containing family of transcription factors, involved in cell differentiation; chromosomal translocations fusing the HOXA9 gene and the NUP98 gene occur in some acute myeloid leukemias. HOXA9 is expressed in primitive hematopoietic cells, and its prompt downregulation is associated with myelocytic maturation. |
| Spermidine/spermine N1-acetyltransferase (SSAT) | catalyzes the rate limiting step of polyamine catabolism, promotes polyamine homeostasis, involved in oxidative stress and heat shock responses, modulates tumorigenicity and sensitivity to some anticancer drugs. Elevated SSAT has been associated with growth inhibition |
| Protein with very strong similarity to mitogen activated protein binding protein interacting protein (mouse Mapbpip) | binds MAPK scaffold protein MEK partner 1 (mouse Map2k1ip1) and may regulate MAPK signaling, member of the roadblock or LC7 family. LC7 family members may modulate dynein functions, and participate in gliding motility. |

TABLE 2

Gene Expression Decreased in Fbl12-ΔFB HEK 293 Cells

| GENE | DESCRIPTION |
|---|---|
| STRAIT11499/MIG12 | Mig12 binds to Mid1, an E3 ubiquitin ligase, and together function to bundle and stabilize microtubules. The Mid1 complex targets microtubule- associated PP2Ac for degradation through binding to alpha4, a regulatory subunit of PPA-type phosphatases. Studies suggest that Mig12-Mid1 complexes play a role in cellular processes that require microtubule stabilization, such as cell division and migration. |
| Carbonic anhydrase 2 | catalyzes carbon dioxide hydration to form bicarbonate ion and proton, mutations associated with mental retardation, osteopetrosis, renal tubular acidosis, cerebral calcification, autoantibodies detected in colitis, biliary cirrhosis |
| Thymosin beta 4 (X chromosome) | a thymic hormone that sequesters actin monomers thereby inhibiting actin polymerization that has been demonstrated to be involved in metastasis, tumor invasion, apoptosis, and the wounding response. For example, the upregulation of thymosin beta 4 in a wide variety of human carcinomas correlates with the metastatic capacity of the tumor. Kaplan-Meier analysis of NSCLC patients identified thymosin beta 4 as a prognostic marker for metastasis and poor prognosis in early stage NSCLC. In addition, thymosin beta 4 is upregulated hypoxia-acclimatized cells and may contribute to the increased tolerance of tumor cells to hypoxic conditions |
| Monoamine oxidase A | an enzyme involved in degradation of amine neurotransmitters; polymorphisms in the gene are associated with neuropsychiatric disorders, including chronic depression and bipolar disorder, Parkinson disease and Alzheimer disease |
| Neurofilament light polypeptide (68 kD) | a neurofilament protein; gene mutations are linked to the axonal form of Charcot-Marie-Tooth (CMT) disease, decreased expression is linked to Alzheimer |

TABLE 2-continued

Gene Expression Decreased in Fbl12-ΔFB HEK 293 Cells

| GENE | DESCRIPTION |
|---|---|
| | disease, Down syndrome, and amyotrophic lateral sclerosis |
| Hairy enhancer-of-split related with YRPW motif 1 | a transcriptional corepressor of a family of basic helix loop helix (bHLH) proteins, involved in Notch signaling and angiogenesis - HEY family of bHLH transcription factors |
| Cell division cycle 42 | (GTP binding protein 25 kD), Rho GTPase involved in actin cytoskeleton organization, cell migration, cell cycle progression and apoptosis. |
| BNIP3 | HIF-1 regulated protein that induces cell death and is a member of the Bcl2 family of cell death factors expressed in mitochondria, which interacts with survival promoting proteins adenovirus E1B 19 kDa, BCL2 (BCL2), Bcl x L (BCL2L1), and CED 9. Elevated BNIP3 should render cells more sensitive to hypoxia-induced cell death, and the silencing of BNIP3 contributes to adaption of tumor cells to hypoxia. In one study, BNIP3 expression is linked with hypoxia-regulated protein expression and with poor prognosis in non-small cell lung cancer. |
| Glycoprotein M6B | a putative membrane glycoprotein, may play a role in neuronal development, may contribute to oligodendrocyte dysfunction in Pelizaeus Merzbaoher disease |
| HIF-1 responsive RTP801 | a ubiquitously expressed protein whose expression is induced by hypoxia, protects epithelial breast carcinoma MCF-7 cells from hypoxia and H2O2-induced apoptosis. Retinas of RTP801-knockout mice in a 'reinopathy of prematurity (ROP)' model display a significant reduction of retinal neovascularization - study implies a role for RTP801 in the pathogenesis of ROP. Elevated levels of RTP801 might also play important roles in Abeta toxicity and the pathogenesis of Alzheimer's disease. |
| Transketolase | an enzyme that is part of the pentose-phosphate shunt; catalytic activity is significantly decreased in Wernicke Korsakoff syndrome. In one study, elevation of transketolase protein level correlateed with enhanced metastatic capacity of cancer cells. |
| RAN | member of the RAS family of GTP binding proteins, serves in mitotic spindle formation and nucleocytoplasmic transport |
| Asparagine synthase | catalyzes ATP-dependent conversion of aspartate to asparagine, expression is induced upon amino acid and glucose deprivation and induction increases cancer cell resistance to chemotherapy. Studies suggest that down-regulation of Asparagine synthase render cells sensitive to drug-induced apoptosis. |

The number of genes whose expression was altered as a function of Fbl12-ΔFB expression was modest; however, the proportion of genes that play a role in the regulation of cell migration, angiogenesis, metastasis, hypoxia, and apoptosis is striking. The apparent role of Fbl12 in regulating these cellular processes suggests that it is promising therapeutic target in oncology.

14. EXAMPLE

Characterization of F-Box Proteins Fbl10 and Fbl11 and their Activity In-Vivo The studies in this example were designed to investigate the cellular activity of Fbl10 and Fbl11. The results indicate that Fbl10 and Fbl11 are nuclear proteins that are likely involved in cellular proliferation. Interestingly, one putative Fbl11 associated protein was identified as human homolog to Mini Chromosome Maintenance 7 ("MCM7"). Interaction with MCM7 may indicate that Fbl11 participates in the regulation of DNA replication. Analysis of the coding sequence of Fbl10 and Fbl11 revealed several motifs found in nuclear proteins involved in the regulation of transcription and chromatin remodeling (schematically represented in FIG. 67). The functions of the Jumonji-C domain and CXXC-zinc finger are unknown, although the CXXC-zinc finger is thought to bind DNA directly. The PHD-finger is thought to be a protein:protein interaction motif. Additionally, more common protein:protein interaction motifs were identified including (apart from the F-box domain) LRR domains and WD40 repeats.

14.1 Materials and Methods for the Characterization of Fbl10 and Fbl11 Activity

The Methods for Silencing by Small Interfering RNA and Cell Cycle Analysis are described in Section 12.1; Methods for Mass Spectrometric Sequencing and Immunofluorescence are described in Section 10.1; Recombinant Protein, Construction of F-box Mutant, Antibodies, Transient Transfection, Immunoprecipitation and Immunoblotting Methods are described in Section 7.1.

14.2 Results

14.2.1 Fbl10 and Fbl11 are Nuclear Proteins which May Regulate Cell Proliferation HeLa cells containing an expression vector encoding Flag-tagged Fbl10 and Fbl11 were visualized using an nuclear stain H33258 and a fluorescently-labeled anti-Flag antibody (FIG. 68). Fbl10 and Fbl11 were found to localize to the nucleus in strongly staining "nuclear dots."

To gain further insight into the cellular functions of Fbl10 and Fbl11, Flag-tagged Fbl10, Fbl11 and mutant versions of each lacking the respective F-box domain, Fbl10AF-box and Fbl11AF-box, were expressed in 293T cells and immunoprecipitated with an antibody to the Flag-tag. To verify Fbl10 and Fbl11 activity, cells were treated with an inhibitor of the proteasome, PS341, prior to protein harvest. Interaction of Flag-purified protein with Cul1, Skp1 and Roc1 was verified by Western blot. Fbl10 and Fbl11 bind to Skp via their F-box domain (FIG. 69). Cut 1 and Roc 1 were not detectable immunoprecipitated with Flag-tagged FBL10 and Fbl11. This may be due to changes in the conformation of Fbl10 and Fbl11 due to the Flag tag. This observation appears to be limited to this experimental system. Interestingly, when cullins were overexpressed, Cul1 purified whole cell extracts were found to contain Fbl11 (FIG. 70).

Depletion of cellular Fbl10 and Fbl11 was accomplished via siRNA silencing (FIG. 71). In cultures with depleted levels of Fbl11, the percentage of actively cycling cells (BrdU positive) was drastically reduced. This data suggests that Fbl11 plays an important role in DNA replication and cell proliferation.

14.2.2 Fbl11 Associates with a Human Homolog of Yeast MCM7

Flag-purified fractions of the 293T cells described in section 14.2.1, supra, were further purified by gel filtration chromatography. Two distinct bands were identified at 100 kDa and 85 kDa (FIG. 72). These co-immunoprecipitated bands were collected for analysis by mass spectrometric sequencing. The 100 kDa band was determined to contain transcriptional repressor Kap1 and nucleolin, and the 85 kDa band was discovered to contain a human homolog of yeast MCM7.

The intracellular distribution of MCM7 and Fbl11 was investigated using immunofluorescence of intact HeLa cells. Both MCM7 and Fbl11 were found to localize in the nucleus (FIGS. 73 and 74). While the use of proteasome inhibitor, PS341, and an arrest in S-phase using thymidine did not have any effect on the apparent levels of MCM7, both treatments appear to increase the nuclear staining of Fbl11. This increase in Fbl11 was, however, not confirmed with a cell cycle analysis of these two proteins using a Western blot (FIG. 75). The expression levels of Fbl11 (FIG. 75, row 1) in synchronized HeLa cells did not appear to change throughout the cell cycle. MCM7 levels similarly remained steady, although a slight increase was observed in S phase (FIG. 75, row 2). This is perhaps due to an interaction between MCM7 and E2F-1. In yeast, E2F-1 is a transcriptional factor, and drives the production of MCM7 prior to S-phase.

Fbl10, Fbl11 and MCM7 were extracted in both triton soluble and triton-insoluble (DNA-bound) fractions of HeLa cells (FIG. 76). The triton insoluble fraction is typically interpreted as the fraction originally bound to cellular DNA, suggesting that at least a fraction of these proteins are tightly bound to DNA. Although the MCM7 in the triton soluble fraction (cytoplasmic fraction) is stable, MCM7 in the triton insoluble fraction is subject to proteasome dependent degradation as shown by incubating the cells in the proteasome inhibitor ZLL prior to triton fractionation (FIG. 77). This effect is reversed in the triton insoluble fraction by silencing Fbl11 (FIG. 78). Although the exact mechanisms underlying these observations have yet to be proven, an explanation may be offered by comparison to the well-understood yeast system.

Figure 80:
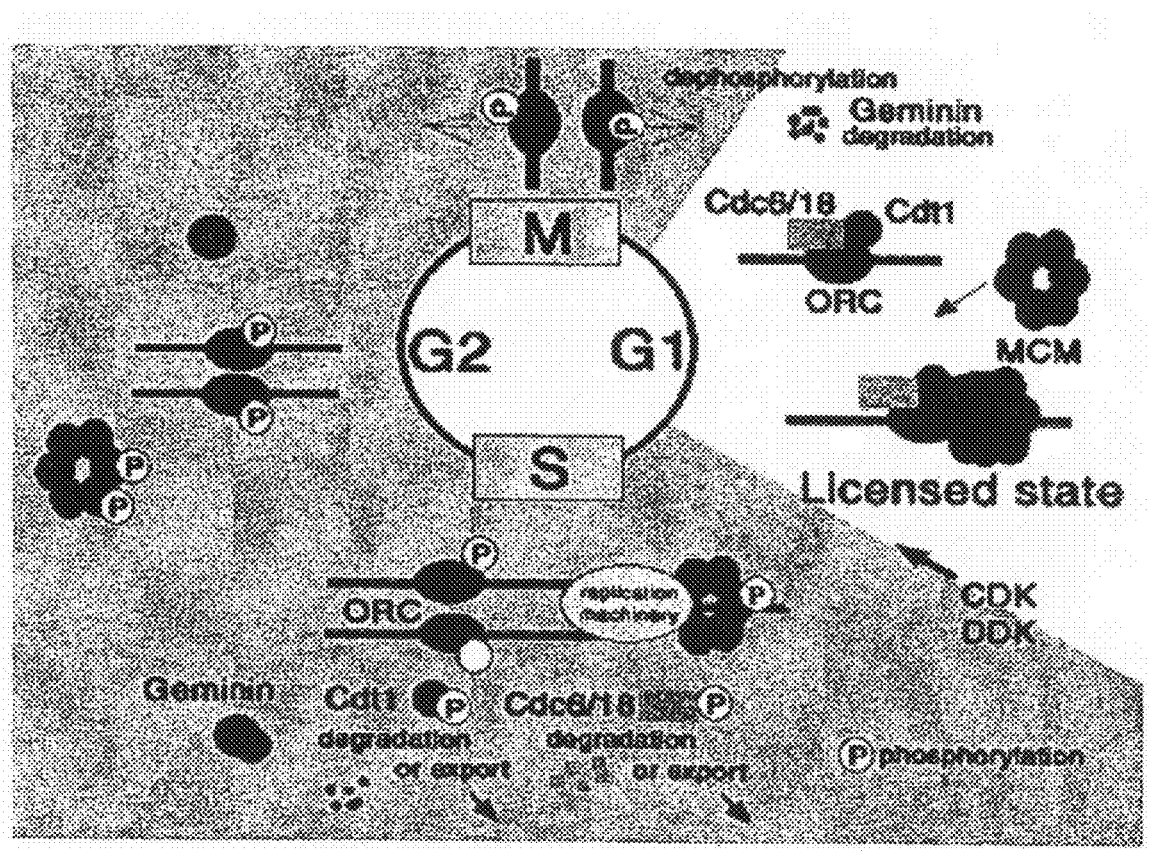

In yeast, the MCM complex is a hexameric protein composed of subunits of MCM2-7 and is required for DNA replication start during S-phase. The complex recognizes the origin region of DNA replication and is thought to have the DNA helicase activity necessary for initial DNA unwinding. After replication start, the MCM complex is no longer necessary required and should be removed for the origin region. In budding yeast this is effected by excluding MCM complex from the nucleus after S-phase (schematically represented in FIG. 79). However, MCM7 complex is retained in the nucleus of mammalian cells even after S-phase had begun. Thus, another method to inactivate MCM complex should be used by mammalian cells. It is known that other DNA machinery licensing factors are degraded by the proteasome after use to avoid overduplication (schematically represented in FIG. 80), and that the mammalian MCM complex becomes phosphorylated during S-phase (schematically represented in FIG. 82). Perhaps then Fbl1 mediates the ubiquitination of phosphorylated MCM7 after S-phase to avoid re-replication. The modulation of Fbl11 cell localization may then offer a means to control proliferation in aberrant cells.

The invention is not to be limited in scope by the specific embodiments described which are intended as single illustrations of individual aspects of the invention. Functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated herein by reference for all purposes.

---

What is claimed is:

1. A method for identifying a compound which modulates the activity of ubiquitin ligases comprising
   a) incubating components comprising the compound, an F-box protein (FBP), or a fragment thereof comprising the F-Box motif, and an FBP target substrate, wherein the incubation is carried out under conditions sufficient to allow the components to interact; and
   b) detecting ubiquitination of the FBP target substrate in the presence and in the absence of the compound, wherein an alteration in ubiquitination of the FBP target substrate in the presence of the compound compared to ubiquitination of the FBP target substrate in the absence of the compound indicates that the compound modulates the activity of ubiquitin ligases.

2. The method of claim 1 wherein the FBP is Fbx9.

3. The method of claim 1 or 2 wherein the incubating components further comprise an FBP-associated protein that is not an FBP target substrate.

4. The method of claim 1 or 2 wherein the FBP target substrate is a component of the ubiquitin pathway.

5. The method of claim 3 wherein the FBP-associated protein is an FPB pseudosubstrate.

6. The method of claim 3 wherein the FBP-associated protein is a protein which regulates the binding of the FBP to the FBP target substrate.

7. The method of claim 1 or 2 wherein the FBP target substrate is Elongation Factor 2.

8. (Previously Present d The method of claim 1 or 2 wherein the FBP target substrate is endostatin-like protein.

9. The method of claim 1 or 2 wherein the FBP target substrate is BAF57.

10. The method of claim 1 or 2 wherein the FBP tar substrate is a splice isoform SP100-HMG of P23497 nuclear autoantigen SP100.

11. The method of claim 1 or 2 wherein the FBP target substrate is H326 protein.

12. The method of claim 3 wherein the FBP-associated protein is Kap1.

13. A method of any one of claim 1 or 2, wherein the compound is selected from the group consisting of a small molecule, a peptide, an antibody, an antisense molecule, or a ribozyme.

* * * * *